US012254961B2

(12) United States Patent
Kotlov et al.

(10) Patent No.: US 12,254,961 B2
(45) Date of Patent: Mar. 18, 2025

(54) HIERARCHICAL MACHINE LEARNING TECHNIQUES FOR IDENTIFYING MOLECULAR CATEGORIES FROM EXPRESSION DATA

(71) Applicant: BostonGene Corporation, Waltham, MA (US)

(72) Inventors: Nikita Kotlov, Moscow (RU); Zoia Antysheva, Moscow (RU); Daria Kiriy, Moscow (RU); Anton Sivkov, Arkhangelsk (RU); Aleksandr Sarachakov, Altai Territory, Biysk District (RU); Viktor Svekolkin, Ulyanovsk (RU); Ivan Kozlov, Moscow (RU)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 17/542,398

(22) Filed: Dec. 4, 2021

(65) Prior Publication Data

US 2022/0180972 A1 Jun. 9, 2022

Related U.S. Application Data

(60) Provisional application No. 63/121,863, filed on Dec. 4, 2020.

(51) Int. Cl.
*G16B 40/00* (2019.01)
*G16B 25/00* (2019.01)
*G16B 30/00* (2019.01)

(52) U.S. Cl.
CPC ............ *G16B 40/00* (2019.02); *G16B 25/00* (2019.02); *G16B 30/00* (2019.02)

(58) Field of Classification Search
CPC ............ C12Q 1/6886; C12Q 2600/158; C12Q 2600/112; C12Q 1/6883; C12Q 2600/118; C12Q 1/68; G16B 20/00; G16B 40/00; G16B 25/10; G16B 40/20; G16B 30/00; G16B 5/20; G16B 50/30; G16B 45/00; G16B 50/00; G16B 5/30; G16B 20/20; G16H 50/20; G16H 50/70; G16H 50/30; G16H 10/60; G16H 50/50; G16H 70/20; G16H 10/40; G16H 70/40; G16H 70/60; G16H 80/00; G16H 70/00; G06F 17/18; G06F 16/285; G06F 16/24578; G06F 17/15; G06F 17/16; G06F 30/27; G06F 18/24323; G06F 18/24; G06F 18/2415; G06N 3/0454; G06N 20/00; G06N 20/20; G06N 3/08; G06N 3/02; G06N 3/045; G06N 3/082; G06N 5/01; G01N 2800/60; G01N 2800/56; G01N 2800/50; G01N 33/5091; G06K 9/6256; G06K 9/6267; G06K 9/6269; G06K 9/6215; G06K 9/6231; G06K 9/6217; G06K 9/628; G06K 9/6284; G06K 9/6298
See application file for complete search history.

(56) References Cited

U.S. PATENT DOCUMENTS

| | | | |
|---|---|---|---|
| 11,398,295 B2 | 7/2022 | Van Laar | |
| 2013/0172203 A1 | 7/2013 | Yeatman et al. | |
| 2017/0233827 A1 | 8/2017 | Moffitt et al. | |
| 2020/0199671 A1* | 6/2020 | Pan | C12N 15/1096 |
| 2020/0365268 A1* | 11/2020 | Michuda | G16B 20/00 |
| 2021/0174899 A1 | 6/2021 | Antysheva et al. | |
| 2022/0093217 A1 | 3/2022 | Abraham et al. | |
| 2023/0073731 A1 | 3/2023 | Antysheva et al. | |

OTHER PUBLICATIONS

Yang, P (2010) A review of ensemble methods in bioinformatics. Current Bioinformatics 5:4 p. 296-308. (Year: 2010).*
Sagi et al. (2018) Ensemble learning, a survey. WIREs data mining and knowledge discovery 8:4 e1249, 18 pages. (Year: 2018).*
Dong et al. (2020) A survey on ensemble learning. Frontiers in computer science 14:2 p. 241-258. (Year: 2020).*
Ma et al. (published online Apr. 16, 2020) Diagnostic classification of cancers using extreme gradient boosting algorithm and multi-omics data. Computers in Biology and Medicine, vol. 121: 10 pages. (Year: 2020).*
Wang 2017 LightGBM: an effective miRNA classification method in Breast cancer patients. ICCB, 2017, Oct. 18-20, 2017, Newark NJ, USA. p. 7-12. (Year: 2017).*
Ramroach et al. 2019 The efficacy of various machine learning models for multi-class classification of RNA-seq expression data. in Arai et al (eds) CompCom 2019, AISC 997, pp. 918-928, 2019. (Year: 2019).*

(Continued)

*Primary Examiner* — Mary K Zeman
(74) *Attorney, Agent, or Firm* — Wolf, Greenfield & Sacks, P.C.

(57) ABSTRACT

Described herein in some embodiments is a method comprising: obtaining expression data previously obtained by processing a biological sample obtained from a subject; processing the expression data using a hierarchy of machine learning classifiers corresponding to a hierarchy of molecular categories to obtain machine learning classifier outputs including a first output and a second output, the hierarchy of molecular categories including a parent molecular category and first and second molecular categories that are children of the parent molecular category in the hierarchy of molecular categories, the hierarchy of machine learning classifiers comprising first and second machine learning classifiers corresponding to the first and second molecular categories; and identifying, using at least some of the machine learning classifier outputs including the first output and the second output, at least one candidate molecular category for the biological sample.

17 Claims, 36 Drawing Sheets

(56) References Cited

OTHER PUBLICATIONS

Hemphill et al. (2014) Feature selection and classifier performance on diverse biological datasets. BMC bioinformatics, 15(Suppl 13):54, 14 pages. (Year: 2014).*
Chen et al. (2018) EGBMMDA: extreme gradient boosting machine for miRNA association prediction. Cell Death and Disease, vol. 9 issue 3, 16 pages. (Year: 2018).*
Li et al 2019 BMC genomics vol. 20: 1021 12 pages (Year: 2019).*
Wikipedia—definition of gradient tree boosting downloaded Jul. 27, 2023 (Year: 2023).*
Wikipedia definition of decision trees, downloaded Jul. 27, 2023 (Year: 2023).*
International Search Report and Written Opinion for International Application No. PCT/US2020/063503 mailed Mar. 18, 2021.
International Search Report and Written Opinion for International Application No. PCT/US2021/061923 mailed Mar. 21, 2022.
[No Author Listed], Non-Hodgkin Lymphoma-Complete. National Cancer Institute Center for Cancer Research. Feb. 20, 2020:2 pages. https://ocg.cancer.gov/programs/cgci/projects/non-hodgkin-lymphoma [last accessed Jan. 19, 2021].
Afsari et al., Rank discriminants for predicting phenotypes from RNA expression. ArXiv preprint arXiv:1401.1490v3. Nov. 21, 2014;3:1-24.
Alizadeh et al., Distinct types of diffuse large B-cell lymphoma identified by gene expression profiling. Nature. Feb. 3, 2000;403(6769):503-11.
Bray et al., Near-optimal RNA-Seq quantification. Nature Biotechnology. May 2016;34(5):525-527.
Chakravarthy et al., Human papillomavirus drives tumor development throughout the head and neck: improved prognosis is associated with an immune response largely restricted to the oropharynx. Journal of Clinical Oncology. Dec. 1, 2016;34(34):4132-4141.
Chapuy et al., Molecular subtypes of diffuse large B cell lymphoma are associated with distinct pathogenic mechanisms and outcomes. Nature medicine. May 2018;24(5):679-90.
Chevrier et al., An immune atlas of clear cell renal cell carcinoma. Cell. May 4, 2017;169(4):736-49.
Ciavarella et al., Dissection of DLBCL microenvironment provides a gene expression-based predictor of survival applicable to formalin-fixed paraffin-embedded tissue. Annals of Oncology. Dec. 1, 2018;29(12):2363-70.
Clozel et al., Mechanism-based epigenetic chemosensitization therapy of diffuse large B-cell lymphoma. Cancer discovery. Sep. 2013;3(9):1002-19.
Dave et al., Molecular Diagnosis of Burkitt's Lymphoma. National Cancer Institute Center for Cancer Research. 2006:1 page. https://llmpp.nih.gov/BL/ [last accessed Jan. 19, 2021].
Ennishi et al., Double-hit gene expression signature defines a distinct subgroup of germinal center B-cell-like diffuse large B-cell lymphoma. Journal of Clinical Oncology. Jan. 20, 2019;37(3):190.
Frontzek et al., Novel insights into the pathogenesis of molecular subtypes of diffuse large B-cell lymphoma and their clinical implications. Expert Review of Clinical Pharmacology. Nov. 2, 2019;12(11):1059-67.
Golub et al., Molecular classification of cancer: class discovery and class prediction by gene expression monitoring. science. Oct. 15, 1999;286(5439):531-7.
Jais et al., The expression of 16 genes related to the cell of origin and immune response predicts survival in elderly patients with diffuse large B-cell lymphoma treated with CHOP and rituximab. Leukemia. Oct. 2008;22(10):1917-24.
Karim et al., OncoNetExplainer: explainable predictions of cancer types based on gene expression data. 2019 IEEE 19th International Conference on Bioinformatics and Bioengineering (BIBE) Oct. 28, 2019:415-422.
Khan et al., Classification and diagnostic prediction of cancers using gene expression profiling and artificial neural networks. Nature medicine. Jun. 2001;7(6):673-9.
Leek, The tspair package for finding top scoring pair classifiers in R. Bioinformatics. May 1, 2009;25(9):1203-4.
Loeffler-Wirth et al., A modular transcriptome map of mature B cell lymphomas. Genome medicine. Dec. 2019;11(1):27.
Monti et al., Molecular profiling of diffuse large B cell lymphoma reveals a novel disease subtype with brisk host inflammatory response and distinct genetic features. Blood. 2005;105(5):1851-61.
Nicholas et al., Tumor microenvironment (TME)-driven immune suppression in B cell malignancy. Biochimica et Biophysica Acta (BBA)-Molecular Cell Research. Mar. 1, 2016;1863(3):471-82.
Pasqualucci et al., The genetic landscape of diffuse large B-cell lymphoma. Seminars in hematology. Apr. 1, 2015;52(2):67-76.
Patil et al., Test set bias affects reproducibility of gene signatures. Bioinformatics. Jul. 15, 2015;31(14):2318-23.
Racle et al., Simultaneous enumeration of cancer and immune cell types from bulk tumor gene expression data. Elife. Nov. 13, 2017;6:e26476.
Rashid et al., Modeling Between-Study Heterogeneity for Improved Reproducibility in Gene Signature Selection and Clinical Prediction. ArXiv preprint arXiv:1708.05508v2. Mar. 26, 2019;2:1-32.
Rashid et al., Purity Independent Subtyping of Tumors (PurIST), A Clinically Robust, Single-sample Classifier for Tumor Subtyping in Pancreatic Cancer. Clinical Cancer Research. Jan. 1, 2020;26(1):82-92.
Reddy et al., Genetic and functional drivers of diffuse large B cell lymphoma. Cell. Oct. 5, 2017;171(2):481-94.
Santiago et al., Changes in Tumor Immune Micro-Environment in Diffuse Large B-Cell Lymphoma (DLBCL): A Comparative Study of Relapsed Versus Diagnostic DLBCL. Blood. Nov. 13, 2019;134:3968.
Schmitz et al., Genetics and pathogenesis of diffuse large B-cell lymphoma. New England Journal of Medicine. Apr. 12, 2018;378(15):1396-407.
Singh et al., Gene expression correlates of clinical prostate cancer behavior. Cancer cell. Mar. 1, 2002;1(2):203-9.
Sotiriou et al., Gene expression profiling in breast cancer: understanding the molecular basis of histologic grade to improve prognosis. Journal of the National Cancer Institute. Feb. 15, 2006;98(4):262-72.
Vose et al., Project International peripheral T-cell and natural killer/T-cell lymphoma study: pathology findings and clinical outcomes, International T-Cell Lymphoma. Journal of clinical oncology. Sep. 1, 2008;26(25):4124-30.
Wright et al., A gene expression-based method to diagnose clinically distinct subgroups of diffuse large B cell lymphoma. Proceedings of the National Academy of Sciences of the United States of America. Aug. 19, 2003;100(17):9991-6.
Wright et al., A Probabilistic Classification Tool for Genetic Subtypes of Diffuse Large B Cell Lymphoma with Therapeutic Implications. Cancer Cell. Apr. 13, 2020;37(4):551-68.
*U.S. Appl. No. 17/113,008, filed Dec. 5, 2020, Antysheva et al.
PCT/US2020/063503, Mar. 18, 2021, International Search Report and Written Opinion.
PCT/US2021/061923, Mar. 21, 2022, International Search Report and Written Opinion.
PCT/US2020/063503, Jun. 16, 2022, Interntional Preliminary Report on Patentability.
International Preliminary Report on Patentability for International Application No. PCT/US2020/063503 mailed Jun. 16, 2022.

* cited by examiner

HIERARCHICAL MACHINE LEARNING TECHNIQUES FOR IDENTIFYING MOLECULAR CATEGORIES FROM EXPRESSION DATA

CROSS-REFERENCE TO RELATED APPLICATIONS

This application claims the benefit of priority under 35 U.S.C. 119(e) of U.S. provisional patent application No. 63/121,863, titled "MACHINE LEARNING TECHNIQUES FOR GENE EXPRESSION DATA AND GENOMIC DATA ANALYSIS", filed on Dec. 4, 2020, which is incorporated by reference herein in its entirety.

FIELD

Aspects of the technology described herein relate to machine learning techniques for analyzing DNA and/or RNA expression data obtained from a biological sample obtained from a subject known to have, suspected of having or at risk of having cancer.

BACKGROUND

Some cancers can be classified by the organ or tissue in which they originated. A "primary tumor" refers to a tumor that forms when a cell or cells undergo oncogenesis in an organ or tissue in which they are present and have not metastasized to that location from another location. The organ or tissue in which the primary tumor forms may be referred to as the "primary site of origin" or the "primary site". Metastasis occurs when cancer cells have spread from the primary site of origin to one or more other parts of the body (e.g., secondary sites). The resulting tumors may be referred to as "metastatic tumors".

SUMMARY

Some embodiments provide for a method for identifying at least one candidate molecular category for a biological sample obtained from a subject. The method comprises using at least one computer hardware processor to perform: obtaining RNA expression data previously obtained by processing the biological sample obtained from the subject, wherein the RNA expression data comprises first RNA expression data for a first set of genes and second RNA expression data for a second set of genes different from the first set of genes; processing the RNA expression data using a hierarchy of RNA-based machine learning classifiers corresponding to a hierarchy of molecular categories to obtain RNA-based machine learning classifier outputs including a first output and a second output, the hierarchy of molecular categories including a parent molecular category and first and second molecular categories that are children of the parent molecular category in the hierarchy of molecular categories, the hierarchy of RNA-based machine learning classifiers comprising first and second RNA-based machine learning classifiers corresponding to the first and second molecular categories, the processing comprising: processing the first RNA expression data using the first RNA-based machine learning classifier to obtain the first output indicative of whether the first molecular category is a candidate molecular category for the biological sample; processing the second RNA expression data using the second RNA-based machine learning classifier to obtain the second output indicative of whether the second molecular category is a candidate molecular category for the biological sample; and identifying, using at least some of the RNA-based machine learning classifier outputs including the first output and the second output, at least one candidate molecular category for the biological sample.

Some embodiments provide for a system, comprising: at least one computer hardware processor; at least one non-transitory computer-readable storage medium storing processor-executable instructions that, when executed by the at least one computer hardware processor, cause the at least one computer hardware processor to perform a method for identifying at least one candidate molecular category for a biological sample obtained from a subject. The method comprises: obtaining RNA expression data previously obtained by processing the biological sample obtained from the subject, wherein the RNA expression data comprises first RNA expression data for a first set of genes and second RNA expression data for a second set of genes different from the first set of genes; processing the RNA expression data using a hierarchy of RNA-based machine learning classifiers corresponding to a hierarchy of molecular categories to obtain RNA-based machine learning classifier outputs including a first output and a second output, the hierarchy of molecular categories including a parent molecular category and first and second molecular categories that are children of the parent molecular category in the hierarchy of molecular categories, the hierarchy of RNA-based machine learning classifiers comprising first and second RNA-based machine learning classifiers corresponding to the first and second molecular categories, the processing comprising: processing the first RNA expression data using the first RNA-based machine learning classifier to obtain the first output indicative of whether the first molecular category is a candidate molecular category for the biological sample; processing the second RNA expression data using the second RNA-based machine learning classifier to obtain the second output indicative of whether the second molecular category is a candidate molecular category for the biological sample; and identifying, using at least some of the RNA-based machine learning classifier outputs including the first output and the second output, at least one candidate molecular category for the biological sample.

Some embodiments provide for at least one non-transitory computer-readable storage medium storing processor-executable instructions that, when executed by at least one computer hardware processor, cause the at least one computer hardware processor to perform a method for identifying at least one candidate molecular category for a biological sample obtained from a subject. The method comprises: obtaining RNA expression data previously obtained by processing the biological sample obtained from the subject, wherein the RNA expression data comprises first RNA expression data for a first set of genes and second RNA expression data for a second set of genes different from the first set of genes; processing the RNA expression data using a hierarchy of RNA-based machine learning classifiers corresponding to a hierarchy of molecular categories to obtain RNA-based machine learning classifier outputs including a first output and a second output, the hierarchy of molecular categories including a parent molecular category and first and second molecular categories that are children of the parent molecular category in the hierarchy of molecular categories, the hierarchy of RNA-based machine learning classifiers comprising first and second RNA-based machine learning classifiers corresponding to the first and second molecular categories, the processing comprising: processing the first RNA expression data using the first RNA-based machine learning classifier to obtain the first output indicative of whether the first molecular category is a candidate molecular category for the biological sample; processing the second RNA expression data using the second RNA-based machine learning classifier to obtain the second output indicative of whether the second molecular category is a candidate molecular category for the biological sample; and identifying, using at least some of the RNA-based machine learning classifier outputs including the first output and the second output, at least one candidate molecular category for the biological sample.

In some embodiments, the RNA expression data further comprises third RNA expression data for a third set of genes different from the first and second sets of genes, the hierarchy of molecular categories further comprises a third molecular category that is a child of the parent molecular category in the hierarchy of molecular categories, the hierarchy of RNA-based machine learning classifiers further comprises a third RNA-based machine learning classifier corresponding to the third molecular category, the processing further comprises processing the third RNA expression data using the third RNA-based machine learning classifier to obtain a third output indicative of whether the third molecular category is a candidate molecular category for the biological sample, and identifying the at least one candidate molecular category for the biological sample is performed using the third output.

In some embodiments, the RNA expression data further comprises fourth RNA expression data for a fourth set of genes different from the first and second sets of genes, the hierarchy of molecular categories further comprises a fourth molecular category that is a child of the first molecular category in the hierarchy of molecular categories, the hierarchy of RNA-based machine learning classifiers further comprises a fourth RNA-based machine learning classifier corresponding to the fourth molecular category, the processing further comprises processing the fourth RNA expression data using the fourth RNA-based machine learning classifier to obtain a fourth output indicative of whether the fourth molecular category is a candidate molecular category for the biological sample, and identifying the at least one candidate molecular category for the biological sample is performed using the fourth output.

In some embodiments, the RNA expression data further comprises fifth RNA expression data for a fifth set of genes different from the first, second, and fourth sets of genes, the hierarchy of molecular categories further comprises a fifth molecular category that is a child of the first molecular category in the hierarchy of molecular categories, the hierarchy of RNA-based machine learning classifiers further comprises a fifth RNA-based machine learning classifier corresponding to the fifth molecular category, wherein the processing further comprises processing the fifth RNA expression data using the fifth RNA-based machine learning classifier to obtain a fifth output indicative of whether the fifth molecular category is a candidate molecular category for the biological sample, and wherein identifying the at least one candidate molecular category for the biological sample is performed using the fifth output.

In some embodiments, the parent molecular category is a solid neoplasm molecular category, the first molecular category is an adenocarcinoma molecular category, and the second molecular category is a sarcoma molecular category.

In some embodiments, the parent molecular category is a breast cancer molecular category, wherein the first molecular category is a basal breast cancer molecular category, and wherein the second molecular category is a non-basal breast cancer molecular category.

In some embodiments, the parent molecular category is a molecular category selected from Table 2, and the first and second molecular categories are children of the parent molecular category in the hierarchy of categories shown in FIGS. 7A-1, 7A-2, and 7A-3.

In some embodiments, processing the first RNA expression data using the first RNA-based machine learning classifier comprises: obtaining first RNA features from the first RNA expression data; and applying the first RNA-based machine learning classifier to the first RNA features to obtain the first output.

In some embodiments, the first RNA expression data comprises first expression levels for the first set of genes, wherein obtaining the first RNA features from the first RNA expression data comprises ranking at least some genes in the first set of genes based on the first expression levels to obtain a first gene ranking, the first gene ranking including values identifying relative ranks of the at least some genes in the gene ranking, wherein the values are different from the first expression levels, and applying the first RNA-based machine learning classifier to the first RNA features comprises applying the first RNA-based machine learning classifier to the first gene ranking to obtain the first output.

In some embodiments, processing the first RNA expression data using the first RNA-based machine learning classifier to obtain the first output comprises processing the first RNA expression data to obtain a first probability that the first molecular category is a first candidate molecular category for the biological sample, and processing the second RNA expression data using the second RNA-based machine learning classifier to obtain the second output comprises processing the second RNA expression data to obtain a second probability that the second molecular category is a second candidate molecular category for the biological sample.

In some embodiments, identifying the at least one candidate molecular category for the biological sample comprises: comparing the first probability to a threshold; and including the first molecular category in the at least one candidate molecular category identified for the biological sample when the first probability exceeds the threshold.

In some embodiments, the method further comprises excluding the first molecular category from the at least one candidate molecular category identified for the biological sample when the first probability does not exceed the threshold.

In some embodiments, identifying the at least one candidate molecular category for the biological sample comprises: comparing the first probability to the second probability; and identifying the first molecular category as a candidate molecular category of the at least one candidate molecular category for the biological sample when the first probability exceeds the second probability.

In some embodiments, the first molecular category is a molecular category selected from molecular categories listed in Table 2. In some embodiments, the first set of genes comprises at least 10 genes listed in at least one of Table 3 corresponding to the first molecular category.

In some embodiments, the first molecular category is associated with at least one international classification of diseases (ICD) code.

In some embodiments, the method further comprises: obtaining DNA expression data previously obtained by processing the biological sample obtained from the subject; and processing the DNA expression data using a hierarchy of DNA-based machine learning classifiers corresponding to the hierarchy of molecular categories to obtain DNA-based machine learning classifier outputs, wherein the hierarchy of DNA-based machine learning classifiers is different from the hierarchy of RNA-based machine learning classifiers, wherein the identifying of the at least one candidate molecular category for the biological sample is performed also using at least some of the DNA-based machine learning classifier outputs.

In some embodiments, processing the DNA expression data comprises: obtaining one or more DNA features using the DNA expression data; and applying at least one DNA-based machine learning classifier of the hierarchy of DNA-based machine learning classifiers to at least some of the DNA features to obtain the DNA-based machine learning classifier outputs.

In some embodiments, the one or more DNA features comprise one or more features indicating, for each gene of a respective set of one or more genes, whether the DNA expression data indicates presence of a pathogenic mutation for the gene. In some embodiments, the one or more DNA features comprise one or more features indicating, for each gene of a respective set of one or more genes, whether the DNA expression data indicates presence of a hotspot mutation for the gene. In some embodiments, the one or more DNA features comprise a feature indicating tumor mutational burden for the biological sample. In some embodiments, the one or more DNA features comprise one or more features indicating a normalized copy number for each chromosome segment of a respective set of one or more chromosome segments for which expression data is included in the DNA expression data. In some embodiments, the one or more DNA features comprise one or more features indicating loss of heterozygosity (LOH) for each chromosome segment of a respective set of one or more chromosome segments for which expression data is included in the DNA expression data. In some embodiments, the one or more DNA features comprise one or more features indicating whether the DNA expression data indicates presence of one or more protein coding genes. In some embodiments, the one or more DNA features comprise one or more features indicating, for each gene of a respective set of one or more genes, whether the DNA expression data indicates presence of a fusion with another gene of the respective plurality of genes. In some embodiments, the one or more DNA features comprises a feature indicating ploidy for the biological sample. In some embodiments, the one or more DNA features comprise a indicating whether the DNA expression data indicates presence of microsatellite instability (MSI). In some embodiments, the one or more DNA features comprise at least ten features listed in Table 5.

In some embodiments, the identifying of the at least one candidate molecular category for the biological sample is performed based on data indicative of a purity of the biological sample and/or data indicative of a site form which the biological sample was obtained.

In some embodiments, the hierarchy of DNA-based machine learning classifiers comprises at least 10 DNA-based machine learning classifiers.

In some embodiments, a first DNA-based machine learning classifier of the hierarchy of DNA-based machine learning classifiers is a gradient-boosted decision tree classifier, a neural network classifier, or a logistic regression classifier. In some embodiments, each DNA-based machine learning classifier of the hierarchy of DNA-based machine learning classifiers is a gradient-boosted decision tree classifier, a neural network classifier, and a logistic regression classifier.

In some embodiments, the method further comprises: receiving an indication of a clinical diagnosis of the biological sample; and determining an accuracy of the clinical diagnosis based on the at least one candidate molecular category identified for the biological sample.

In some embodiments, the method further comprises: generating, using the hierarchy of molecular categories, a graphical user interface (GUI) including a visualization indicating the at least one molecular category identified for the biological sample.

In some embodiments, first molecular category of the hierarchy of molecular categories is one of a neoplasm, hematologic neoplasm, melanoma, sarcoma, mesothelioma, neuroendocrine, squamous cell carcinoma, adenocarcinoma, glioma, testicular germ cell tumor, pheochromocytoma, cervical squamous cell carcinoma, liver neoplasm, lung adenocarcinoma, high grade glioma isocitrate dehydrogenase (IDH) mutant, thyroid neoplasm, squamous cell lung adenocarcinoma, thymoma, prostate adenocarcinoma, urinary bladder urothelial carcinoma, oligodendroglioma, squamous cell carcinoma of the head and neck, gastrointestinal adenocarcinoma, gynecological cancer, renal cell carcinoma, astrocytoma, pancreatic adenocarcinoma, stomach adenocarcinoma, pancreatic adenocarcinoma, breast cancer, ovarian cancer, uterine corpus endometrial carcinoma, non-clear cell carcinoma, clear cell carcinoma, basal breast cancer, non-basal breast cancer, papillary renal cell carcinoma, and chromophobe renal cell carcinoma.

In some embodiments, the hierarchy of RNA-based machine learning classifiers comprises at least 10 RNA-based machine learning classifiers. In some embodiments, the first RNA-based machine learning classifier is a gradient-boosted decision tree classifier, a neural network classifier, or a logistic regression classifier. In some embodiments, each RNA-based machine learning classifier of the hierarchy of RNA-based machine learning classifiers is a gradient-boosted decision tree classifier, a neural network classifier, or a logistic regression classifier.

In some embodiments, the first RNA expression data comprises expression levels for between 20 and 300 genes.

In some embodiments, the subject has, is suspected of having or is at risk for having cancer. In some embodiments, the biological sample is a sample of a cancer of unknown primary (CUP) tumor.

In some embodiments, the method further comprises identifying at least one anti-cancer therapy for the subject based on the identified at least one molecular category. In some embodiments, the method further comprises administering the at least one anti-cancer therapy.

Some embodiments provide for a method for identifying at least one candidate molecular category for a biological sample obtained from a subject. The method comprises using at least one computer hardware processor to perform: obtaining DNA expression data previously obtained by processing the biological sample obtained from the subject, wherein the DNA expression data comprises first DNA expression data and second DNA expression data; processing the DNA expression data using a hierarchy of DNA-based machine learning classifiers corresponding to a hierarchy of molecular categories to obtain DNA-based machine learning classifier outputs including a first output and a second output, the hierarchy of molecular categories including a parent molecular category and first and second molecular categories that are children of the parent molecular category in the hierarchy of molecular categories, the hierarchy of DNA-based machine learning classifiers comprising first and second DNA-based machine learning classifiers corresponding to the first and second molecular categories, the processing comprising: processing the first DNA expression data using the first DNA-based machine learning classifier to obtain the first output indicative of whether the first molecular category is a candidate molecular category for the biological sample; processing the second DNA expression data using the second DNA-based machine learning classifier to obtain the second output indicative of whether the second molecular category is a candidate molecular category for the biological sample; and identifying, using at least some of the DNA-based machine learning classifier outputs including the first output and the second output, at least one candidate molecular category for the biological sample.

Some embodiments provide for a system, comprising at least one computer hardware processor; and at least one non-transitory computer-readable storage medium storing processor-executable instructions that, when executed by the at least one computer hardware processor, cause the at least one computer hardware processor to perform a method for identifying at least one candidate molecular category for a biological sample obtained from a subject. The method comprises: obtaining DNA expression data previously obtained by processing the biological sample obtained from the subject, wherein the DNA expression data comprises first DNA expression data second DNA expression data; processing the DNA expression data using a hierarchy of DNA-based machine learning classifiers corresponding to a hierarchy of molecular categories to obtain DNA-based machine learning classifier outputs including a first output and a second output, the hierarchy of molecular categories including a parent molecular category and first and second molecular categories that are children of the parent molecular category in the hierarchy of molecular categories, the hierarchy of DNA-based machine learning classifiers comprising first and second DNA-based machine learning classifiers corresponding to the first and second molecular categories, the processing comprising: processing the first DNA expression data using the first DNA-based machine learning classifier to obtain the first output indicative of whether the first molecular category is a candidate molecular category for the biological sample; processing the second DNA expression data using the second DNA-based machine learning classifier to obtain the second output indicative of whether the second molecular category is a candidate molecular category for the biological sample; and identifying, using at least some of the DNA-based machine learning classifier outputs including the first output and the second output, at least one candidate molecular category for the biological sample.

Some embodiments provide for at least one non-transitory computer-readable storage medium storing processor-executable instructions that, when executed by at least one computer hardware processor, cause the at least one computer hardware processor to perform a method for identifying at least one candidate molecular category for a biological sample obtained from a subject. The method comprises: obtaining DNA expression data previously obtained by processing the biological sample obtained from the subject, wherein the DNA expression data comprises first DNA expression data and second DNA expression data; processing the DNA expression data using a hierarchy of DNA-based machine learning classifiers corresponding to a hierarchy of molecular categories to obtain DNA-based machine learning classifier outputs including a first output and a second output, the hierarchy of molecular categories including a parent molecular category and first and second molecular categories that are children of the parent molecular category in the hierarchy of molecular categories, the hierarchy of DNA-based machine learning classifiers comprising first and second DNA-based machine learning classifiers corresponding to the first and second molecular categories, the processing comprising: processing the first DNA expression data using the first DNA-based machine learning classifier to obtain the first output indicative of whether the first molecular category is a candidate molecular category for the biological sample; processing the second DNA expression data using the second DNA-based machine learning classifier to obtain the second output indicative of whether the second molecular category is a candidate molecular category for the biological sample; and identifying, using at least some of the DNA-based machine learning classifier outputs including the first output and the second output, at least one candidate molecular category for the biological sample.

In some embodiments, the DNA expression data further comprises third DNA expression data, the hierarchy of molecular categories further comprises a third molecular category that is a child of the parent molecular category in the hierarchy of molecular categories, the hierarchy of DNA-based machine learning classifiers further comprises a third DNA-based machine learning classifier corresponding to the third molecular category, the processing further comprises processing the third DNA expression data using the third DNA-based machine learning classifier to obtain a third output indicative of whether the third molecular category is a candidate molecular category for the biological sample, and identifying the at least one candidate molecular category for the biological sample is performed using the third output.

In some embodiments, the DNA expression data further comprises fourth DNA expression data, the hierarchy of molecular categories further comprises a fourth molecular category that is a child of the first molecular category in the hierarchy of molecular categories, the hierarchy of DNA-based machine learning classifiers further comprises a fourth DNA-based machine learning classifier corresponding to the fourth molecular category, the processing further comprises processing the fourth DNA expression data using the fourth DNA-based machine learning classifier to obtain a fourth output indicative of whether the fourth molecular category is a candidate molecular category for the biological sample, and identifying the at least one candidate molecular category for the biological sample is performed using the fourth output.

In some embodiments, the DNA expression data further comprises fifth DNA expression data, the hierarchy of molecular categories further comprises a fifth molecular category that is a child of the first molecular category in the hierarchy of molecular categories, the hierarchy of DNA-based machine learning classifiers further comprises a fifth DNA-based machine learning classifier corresponding to the fifth molecular category, the processing further comprises processing the fifth DNA expression data using the fifth DNA-based machine learning classifier to obtain a fifth output indicative of whether the fifth molecular category is a candidate molecular category for the biological sample, and identifying the at least one candidate molecular category for the biological sample is performed using the fifth output.

In some embodiments, the parent molecular category is a solid neoplasm molecular category, the first molecular category is an adenocarcinoma molecular category, and the second molecular category is a sarcoma molecular category.

In some embodiments, the parent molecular category is a breast cancer molecular category, the first molecular category is a basal breast cancer molecular category, and the second molecular category is a non-basal molecular category.

In some embodiments, the parent molecular category is a molecular category selected from Table 2, and the first and second molecular categories are children of the parent molecular category in the hierarchy of categories shown in FIGS. 7A-1, 7A-2, and 7A-3.

In some embodiments, processing the first DNA expression data using the first DNA-based machine learning classifier comprises: obtaining one or more first DNA features from the first DNA expression data; and applying the first DNA-based machine learning classifier to the first DNA features to obtain the first output.

In some embodiments, the one or more first DNA features comprise one or more features indicating, for each gene of a respective set of one or more genes, whether the DNA expression data indicates presence of a pathogenic mutation for the gene. In some embodiments, the one or more first DNA features comprise one or more features indicating, for each gene of a respective set of one or more genes, whether the DNA expression data indicates presence of a hotspot mutation for the gene. In some embodiments, the one or more first DNA features comprise a feature indicating tumor mutational burden for the biological sample. In some embodiments, the one or more DNA features comprise one or more features indicating a normalized copy number for each chromosome segment of a respective set of one or more chromosome segments for which expression data is included in the DNA expression data. In some embodiments, the one or more DNA features comprise one or more features indicating loss of heterozygosity (LOH) for each chromosome segment of a respective set of one or more chromosome segments for which expression data is included in the DNA expression data. In some embodiments, the one or more DNA features comprise one or more features indicating whether the DNA expression data indicates presence of one or more protein coding genes. In some embodiments, the one or more DNA features comprise one or more features indicating, for each gene of a respective set of one or more genes, whether the DNA expression data indicates presence of a fusion with another gene of the respective plurality of genes. In some embodiments, the one or more DNA features comprises a feature indicating ploidy for the biological sample. In some embodiments, the one or more DNA features comprise a indicating whether the DNA expression data indicates presence of microsatellite instability (MSI). In some embodiments, the one or more first DNA features comprise at least 10 features listed in Table 5 corresponding to the first molecular category.

In some embodiments, wherein processing the first DNA expression data using the first DNA-based machine learning classifier to obtain the first output comprises processing the first DNA expression data to obtain a first probability that the first molecular category is a first candidate molecular category for the biological sample, and wherein processing the second DNA expression data using the second DNA-based machine learning classifier to obtain the second output comprises processing the second DNA expression data to obtain a second probability that the second molecular category is a second candidate molecular category for the biological sample.

In some embodiments, identifying the at least one candidate molecular category for the biological sample comprises: comparing the first probability to a threshold; and including the first molecular category in the at least one candidate molecular category identified for the biological sample when the first probability exceeds the threshold.

In some embodiments, the method further comprises excluding the first molecular category from the at least one candidate molecular category identified for the biological sample when the first probability does not exceed the threshold.

In some embodiments, identifying the at least one candidate molecular category for the biological sample comprises: comparing the first probability to the second probability; and identifying the first molecular category as a candidate molecular category of the at least one candidate molecular category for the biological sample when the first probability exceeds the second probability.

In some embodiments, the first molecular category is a molecular category selected from molecular categories listed in Table 2.

In some embodiments, the first molecular category is associated with at least one international classification of diseases (ICD) code.

In some embodiments, the method further comprises: obtaining RNA expression data previously obtained by processing the biological sample obtained from the subject; and processing the RNA expression data using a hierarchy of RNA-based machine learning classifiers corresponding to the hierarchy of molecular categories to obtain RNA-based machine learning classifier outputs, wherein the hierarchy of RNA-based machine learning classifiers is different from the hierarchy of DNA-based machine learning classifiers, wherein the identifying of the at least one candidate molecular category for the biological sample is performed also using at least some of the RNA-based machine learning classifier outputs.

In some embodiments, processing the RNA expression data comprises: obtaining RNA features using the RNA expression data; and applying at least one RNA-based machine learning classifier of the hierarchy of RNA-based machine learning classifiers to at least some of the RNA features to obtain the RNA-based machine learning classifier outputs.

In some embodiments, the RNA expression data comprises expression levels for at least one set of genes, obtaining the RNA features using the RNA expression data comprises ranking genes in the at least one set of genes based on the expression levels to obtain at least one gene ranking, the at least one gene ranking including values identifying relative ranks of the genes in the at least one gene ranking, wherein the values are different from the expression levels, and wherein applying the at least one RNA-based machine learning classifier to the at least some of the RNA features comprises applying the RNA-based machine learning classifier to the at least one gene ranking to obtain the RNA-based machine learning classifier outputs.

In some embodiments, identifying of the at least one candidate molecular category for the biological sample is performed based on data indicative of a purity of the biological sample and/or based on data indicative of a site from which the biological sample was obtained.

In some embodiments, the hierarchy of RNA-based machine learning classifiers comprises at least 10 RNA-based machine learning classifiers.

In some embodiments, a first RNA-based machine learning classifier of the hierarchy of RNA-based machine learning classifiers is a gradient-boosted decision tree classifier, a neural network classifier, or a logistic regression classifier. In some embodiments, each RNA-based machine learning classifier of the hierarchy of RNA-based machine learning classifiers is a gradient-boosted decision tree classifier, a neural network classifier, or a logistic regression classifier.

In some embodiments, the RNA expression data comprises expression levels for between 20 and 300 genes.

In some embodiments, the method further comprises: receiving an indication of a clinical diagnosis of the biological sample; and determining an accuracy of the clinical diagnosis based on the at least one candidate molecular category identified for the biological sample.

In some embodiments, the method further comprises generating, using the hierarchy of molecular categories, a graphical user interface (GUI) including a visualization indicating the at least one molecular category identified for the biological sample.

In some embodiments, the first molecular category of the hierarchy of molecular categories is one of neoplasm, hematologic neoplasm, melanoma, sarcoma, mesothelioma, neuroendocrine, squamous cell carcinoma, adenocarcinoma, glioma, testicular germ cell tumor, pheochromocytoma, cervical squamous cell carcinoma, liver neoplasm, lung adenocarcinoma, high grade glioma isocitrate dehydrogenase (IDH) mutant, thyroid neoplasm, squamous cell lung adenocarcinoma, thymoma, prostate adenocarcinoma, urinary bladder urothelial carcinoma, oligodendroglioma, squamous cell carcinoma of the head and neck, gastrointestinal adenocarcinoma, gynecological cancer, renal cell carcinoma, astrocytoma, pancreatic adenocarcinoma, stomach adenocarcinoma, pancreatic adenocarcinoma, breast cancer, ovarian cancer, uterine corpus endometrial carcinoma, non-clear cell carcinoma, clear cell carcinoma, basal breast cancer, non-basal breast cancer, papillary renal cell carcinoma, and chromophobe renal cell carcinoma.

In some embodiments, the hierarchy of DNA-based machine learning classifiers comprises at least 10 DNA-based machine learning classifiers.

In some embodiments, the first DNA-based machine learning classifier is a gradient-boosted decision tree classifier, a neural network classifier, or a logistic regression classifier.

In some embodiments, each DNA-based machine learning classifier of the hierarchy of DNA-based machine learning classifiers is a gradient-boosted decision tree classifier, a neural network classifier, or a logistic regression classifier.

In some embodiments, the subject has, is suspected of having or is at risk for having cancer. In some embodiments, the biological sample is a sample of a cancer of unknown primary (CUP) tumor.

In some embodiments, the method further comprises identifying at least one anti-cancer therapy for the subject based on the identified at least one molecular category. In some embodiments, the method further comprises administering the at least one anti-cancer therapy.

BRIEF DESCRIPTION OF DRAWINGS

FIG. 2B-2 is a diagram depicting an example 230 of illustrative technique 250 for processing expression data to identify a candidate molecular category for a biological sample, according to some embodiments of the technology described herein.

FIG. 5A-1 is an example 500 for processing RNA expression data obtained from a biological sample to identify at least one candidate molecular category for the biological sample, according to some embodiments of the technology described herein.

FIG. 5A-2 is an example 550 for processing DNA expression data obtained from a biological sample to identify at least one candidate molecular category for the biological sample, according to some embodiments of the technology described herein.

FIGS. 7A-1-7A-3 show an example hierarchy 700 of molecular categories, according to some embodiments of the technology described herein.

FIG. 7B-1-7B-5 show an example hierarchy 750 of molecular categories, according to some embodiments of the technology described herein.

DETAILED DESCRIPTION

Figure 1A:
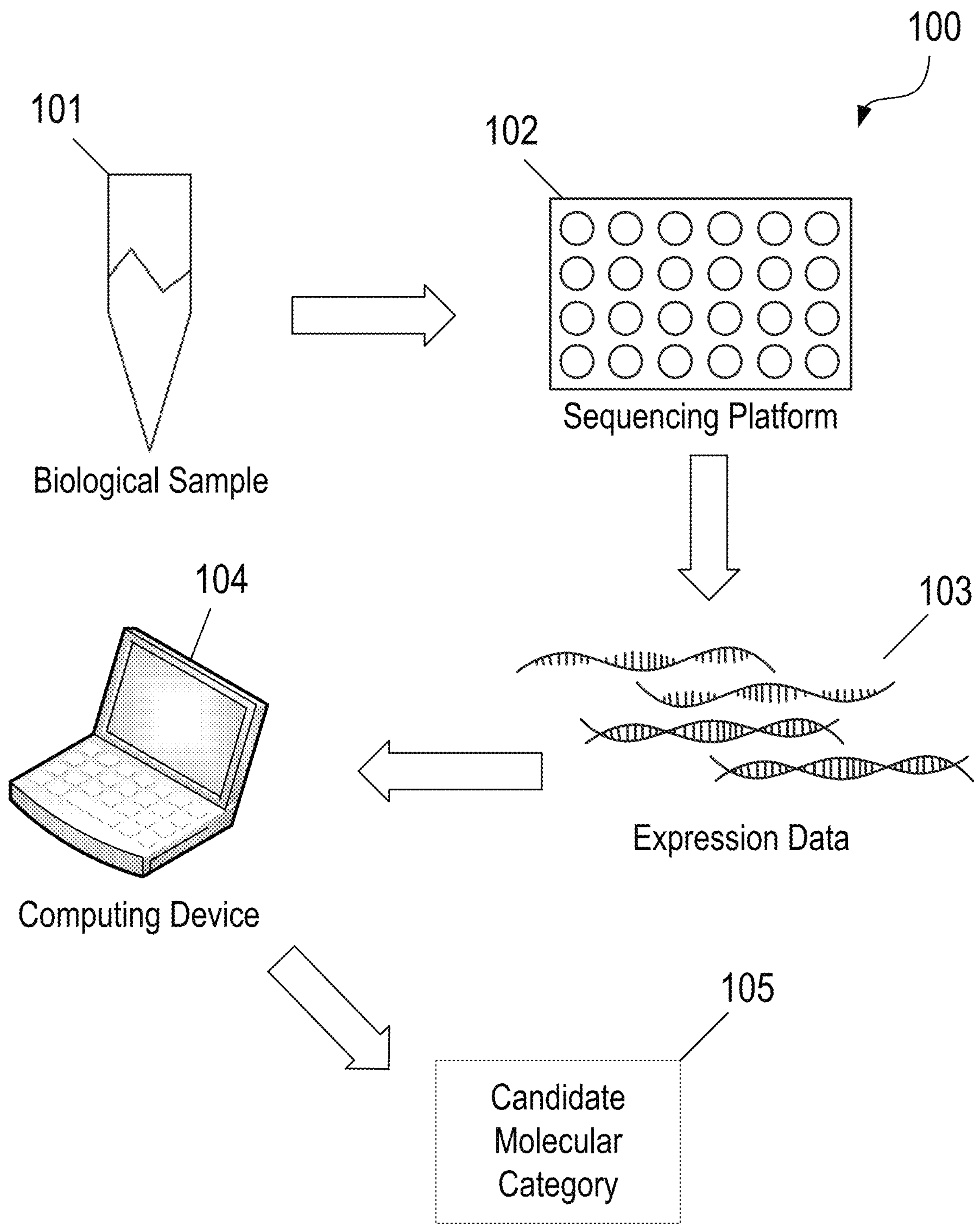
FIG. 1A is a diagram depicting an illustrative technique 100 for identifying a candidate molecular category for a biological sample using a hierarchy of machine learning classifiers, according to some embodiments of the technology described herein.

Aspects of the disclosure relate to machine learning techniques for analyzing expression data obtained from a biological sample obtained from a subject that may have been diagnosed with cancer of unknown primary "CUP" and/or another type of cancer and identifying one or more molecular categories for the biological sample based on results of the machine learning analysis. The machine learning techniques involve processing DNA and/or RNA expression data with a set of hierarchically organized machine learning classifiers, corresponding to a hierarchy of molecular categories, to identify one or more molecular categories for the biological sample. In turn, the identified molecular category or categories may be used for numerous applications including, but not limited to, identifying or facilitating identification of one or more therapeutically effective treatments for the subject (which can subsequently be administered), identifying one or more clinical trials in which the subject may be enrolled, generating a more accurate than previously possible characterization of the tumor's molecular characteristics, and performing one or more quality control processes on the biological sample (e.g., in a laboratory environment the techniques may be used to confirm whether a biological sample labeled with an alleged primary site is in fact a tumor sample that originated at that primary site).

As described above, one important application of the techniques described herein is analyzing expression data obtained from a biological sample obtained from a subject that may have been diagnosed with cancer of unknown primary. "Cancer of unknown primary (CUP)" refers to a group of one or more metastatic tumors for which the primary site of origin cannot be determined at the time of diagnosis of the subject. CUP is quite common and constitutes 3%-5% of all cancer diagnoses, and presents several clinical challenges. For example, CUP tumors are generally aggressive, associated with poor overall survival (OS), and have unpredictable metastatic patterns. Typically, CUP is divided into two categories: about 20% of CUP is characterized as having a good prognosis, and about 80% of CUP is characterized as having a poor prognosis. Treatment of CUP historically comprises either locoregional or systemic administration of platinum-based chemotherapy, or empirical chemotherapy and combinations of platinum or taxane.

Conventional techniques for identifying effective therapies for a CUP tumor involve attempting to identify a primary site for the CUP tumor and then treat the CUP tumor with one or more therapies known to be effective for tumors that originate from the identified primary site. However, such conventional techniques suffer from numerous problems.

First, the lack of differentiation of many CUP tumors makes identification of a primary site of origin challenging. It is difficult to identify the primary site of origin of a CUP tumor because the cells bear little to no resemblance to the normal cells from which they originated, which is the case in a large percentage of CUP cases. (This is also the case in instances of rare malignant cancers, where there is insufficient data to support an identification of the primary site of origin.) Indeed, conventional clinical diagnostic methods, such as blood and biochemical analyses, radiological analyses, and immunohistochemical analysis have had only limited success in characterizing or identifying the origin of CUP tumors, and are often limited to identification of more differentiated CUP tumors. Similarly, tissue of origin classifiers based on genetic information have also been limited in their prognostic value for highly undifferentiated CUP. As such, the conventional approach of identifying an effective therapy for treating a CUP tumor (or another cancer) based on an identified primary site is not possible when the primary site cannot be determined accurately or even at all.

Second, even in cases where it is possible to identify a primary site of origin of the tumor, that identification may not be sufficiently specific to identify an effective treatment for the tumor. A more specific characterization may be needed to identify highly-effective tumor specific therapies. Indeed, there can be important differences between cells originating from the same primary site (e.g., breast cancer cells can be further classified into basal breast cancer cells and non-basal breast cancer cells based on their gene expression) and these differences can impact the selection of the most effective therapy.

Moreover, in some situations, cancer cells originating from different primary sites (e.g., site "A" and site "B") may be, in fact, sufficiently similar to one another such that a treatment for a tumor having primary site "A" may be used, effectively, to treat a tumor having primary site "B". Identifying such treatments for a subject is not possible using conventional primary site identification techniques because they would not identify alternative sites (associated with effective therapies) where tumors with molecular characteristics similar to that of the subject's tumor can originate. As one example, adenocarcinomas of colon and rectum demonstrate similar molecular profiles, although they are associated with different primary sites. Similar tendencies have been observed in various types of gynecological or squamous cell cancers.

The inventors have recognized that in order to address the drawbacks of conventional techniques of identifying treatments based on primary site identification, it is better to instead characterize a tumor sample as belonging to one more "molecular categories", in a hierarchy of such molecular categories, based on the tumor's molecular features (e.g., features derived from DNA and/or RNA expression data obtained from the tumor) and to identify effective treatments for the tumor based on the molecular categories so identified.

A "molecular category" refers to a category or group of biological samples (e.g., tumor samples) that have similar molecular features (e.g., features derived from expression data). Molecular categories may be organized into a hierarchy of molecular categories in which molecular categories at different levels of the hierarchy have differing degrees of specificity—molecular categories at higher levels of the hierarchy are broader categories having lower specificity, while molecular categories at lower levels of the hierarchy are narrower categories having higher specificity. Numerous examples of such hierarchies and their constituent molecular categories are provided herein including with reference to FIGS. 1B, 2A 7A-1-7A-3, and 7B-1-7B-5.

The inventors have developed hierarchies of molecular categories and machine learning techniques for identifying, from DNA and/or RNA expression data obtained from a tumor sample, one or more molecular categories for the tumor in a particular hierarchy of molecular categories. The machine learning techniques involve processing the DNA and/or RNA expression data obtained from a tumor sample with at least one hierarchy of machine learning classifiers that corresponds to a hierarchy of molecular categories and to identify one or more candidate molecular categories for the tumor sample based on output generated by the machine learning classifiers in the hierarchy or hierarchies. As described herein, the identified candidate molecular categories may be used to identify one or more therapies for the subject and have many other uses including, but not limited to, identifying one or more clinical trials in which the subject may enroll, providing a clinician with a graphical user interface (GUI) presenting a visualization of tumor characteristics (e.g., by presenting a visualization of the hierarchy of molecular categories and, among them, visually highlighting the identified molecular category or categories), and performing quality control on biological samples in a laboratory environment.

For example, some embodiments provide for a method for identifying at least one candidate molecular category for a biological sample. The method includes: (a) obtaining expression data (e.g., RNA and/or DNA expression data) previously obtained from a biological sample obtained from a subject, (b) processing the expression data using at least one hierarchy of machine learning classifiers corresponding to a hierarchy of molecular categories to obtain machine learning classifier outputs, and (c) identifying, using the machine learning classifier outputs, at least one candidate molecular category for the biological sample. In some embodiments, the at least one identified candidate molecular category may be used to identify a therapy for the subject, which therapy may then be administered. In some embodiments, processing the expression data using the at least one hierarchy of machine learning classifiers includes processing expression data that is specific to a particular molecular category to determine whether the molecular category should be identified as a candidate molecular category for the biological sample. In some embodiments, a machine learning classifier in the at least one hierarchy of machine learning classifiers is trained to determine whether to identify a particular molecular category as a candidate molecular category for the biological sample based on the specific expression data for that molecular category.

The techniques developed by the inventors and described herein address the above-described shortcomings of conventional methods for identifying therapies for treating a tumor based on identifying a primary site of origin for the tumor.

The techniques described herein identify one or more molecular categories, in a hierarchy of molecular categories, for a tumor based on a tumor's molecular features. As a result, in cases where it is difficult to identify a primary site of origin for a tumor (e.g., when the tumor is undifferentiated), it may nonetheless be possible to identify a molecular category for the tumor (e.g., it may not be possible to identify that the tumor originated in the ovaries, but it may nonetheless be possible to identify that the tumor belongs to the molecular category of gynecological cancers of which ovarian cancer is a subcategory). Even though the molecular category so identified is not limited to tumors from a specific and particular site (e.g., ovaries) and may be broad enough to include multiple different primary sites (e.g., ovaries and uterus), it may nevertheless be sufficient to identify a treatment for the tumor. For example, some therapies may work for both uterine and ovarian cancers because of the molecular similarity among these cancers and, as such, a treatment may be identified using the techniques described herein, whereas using conventional techniques this would not be possible (e.g., because a conventional classifier trained to identify primary sites would fail to identify the primary site with high confidence and its output would be discarded).

On the other hand, there may be cases where the molecular features of a tumor (e.g., of a highly differentiated tumor) may be sufficiently informative so as to identify a histological subtype of a tumor, which enables the identification of treatments that are highly specific to the tumor and have the greatest potential in effectively treating the tumor. For example, a conventional technique may identify, for a differentiated tumor, its primary site as breast tissue and, therefore, that the tumor is breast cancer. However, the techniques described herein may be used to go further and to identify histological subtypes of the tumor (e.g., whether the breast cancer is non-Basal breast cancer or basal breast cancer), which can be used to further tailor the treatment selected.

Consequently, the techniques developed by the inventors provide for more accurate characterization of tumor samples than previously possible using conventional methods. This technology therefore provides an improved diagnostic tool, which can be used to improve the way in which treatments are identified for patients thereby improving clinical outcomes. The techniques described herein allow for the identification of therapies where conventional approaches, based on primary site of origin identification, simply fail to do so. And even where such conventional techniques are able to identify a primary site of origin, the techniques developed by the inventors can go further and identify a histological subtype of the tumor which enables the identification of more tumor-specific treatments than possible merely based on an identified primary site of origin.

In addition to identifying therapies for a subject based on the molecular categories identified using the techniques described herein, one or more clinical trials may be identified for the subject using the identified molecular categories (and, for example, biomarkers associated with the molecular categories; the biomarkers being, for example, the features used as input by the classifiers used to determine that the sample is to be associated with the identified molecular categories).

The techniques described herein may be implemented as part of a software diagnostic tool, which may be used to present medical professionals with information characterizing the molecular features of a patient's tumor. For example, the techniques described herein may be used to identify one or more molecular categories for a patient's tumor (including, for example, with associated probabilities and/or confidences). In turn, the software tool may use this information to generate a visualization of the hierarchy of molecular categories and a visual indication, within the hierarchy, of the molecular categories identified for the tumor (e.g., using color, shading, size, or any other suitable visual cue, as aspects of the technology described herein are not limited in this respect). Additionally, the visualization may include information about confidences of the machine learning classifier(s) used to identify the molecular categories. An example is shown in FIG. 1B, which is further described below.

Additionally or alternatively, the techniques described herein may be utilized in the context of quality control processes in a laboratory environment. For example, a sequencing laboratory may receive a biological sample together with information about the biological sample. Aside from an identifier and/or tracking number, such information may include information about the characteristics of the biological sample (e.g., the tissue source, cancer type, cancer grade, etc.). However, due to errors, it is possible that the biological sample provided does not actually have these characteristics (e.g., due to an error where patient samples are switched, mislabeled, wrong information is provided, etc.). Another application of the techniques described herein is to quality control analysis in a data analysis setting. For example, a patient's sequencing data (e.g., reads, aligned reads, expression levels, etc.) may be provided as input to a data processing pipeline. However, if that sequencing data does not correspond to the alleged source (e.g., it comes from a different patient due to an error), the results of the analysis are likely meaningless.

In some embodiments, quality control may be performed by comparing an asserted characteristic of a biological sample to a predicted characteristic determined using the techniques described herein. When the asserted characteristic and the predicted characteristic match (e.g., are the same or are within a tolerated difference) and/or are consistent with one another, then it may be determined that a quality control check has been satisfied. On the other hand, if the predicted and asserted characteristics do not match, then further action may need to be taken. For example, further analysis of the biological sample may be performed, the biological sample may be rejected, a data processing pipeline may be stopped or not executed (thereby saving valuable and costly computational resources), a laboratory operator and/or other party (e.g., clinician, staff, etc.) may be notified of a potential discrepancy (e.g., by an e-mail alert, a message, a report, an entry in a log-file, etc.).

As one example, the techniques described herein may be used to identify a molecular category from expression data obtained from a sample and that category may be compared with the stated cancer type and/or primary site for the tumor provided with the sample. When the identified molecular category is consistent with the stated cancer type and/or primary site (e.g., the primary site is identified as breast tissue and the molecular category identified is non-basal breast cancer), then this type of quality control check may be passed. On the other hand, when the identified molecular category is inconsistent with the stated cancer type and/or primary site (e.g., the identified molecular category is clear cell carcinoma, but the type of cancer is identified is melanoma), then this type of quality control check may be failed. Further analysis may be performed.

As described herein, the techniques developed by the inventors provide for more accurate characterization of tumor samples than previously possible using conventional methods. Multiple aspects of the developed technology described herein enable this to occur.

Figure 2A:
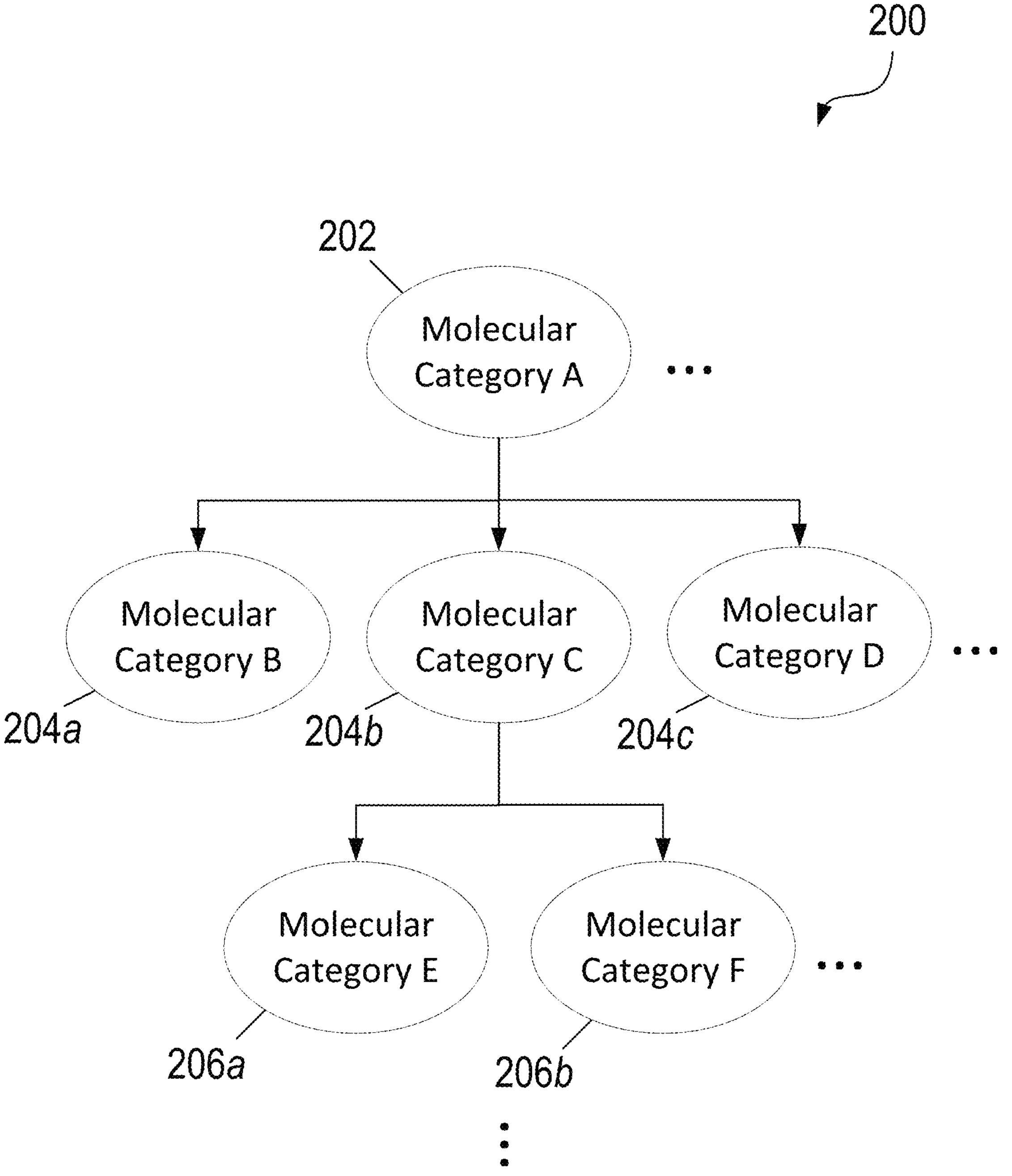
FIG. 2A shows an illustrative hierarchy 200 of molecular categories, according to some embodiments of the technology described herein.
Figures 1, 2B:
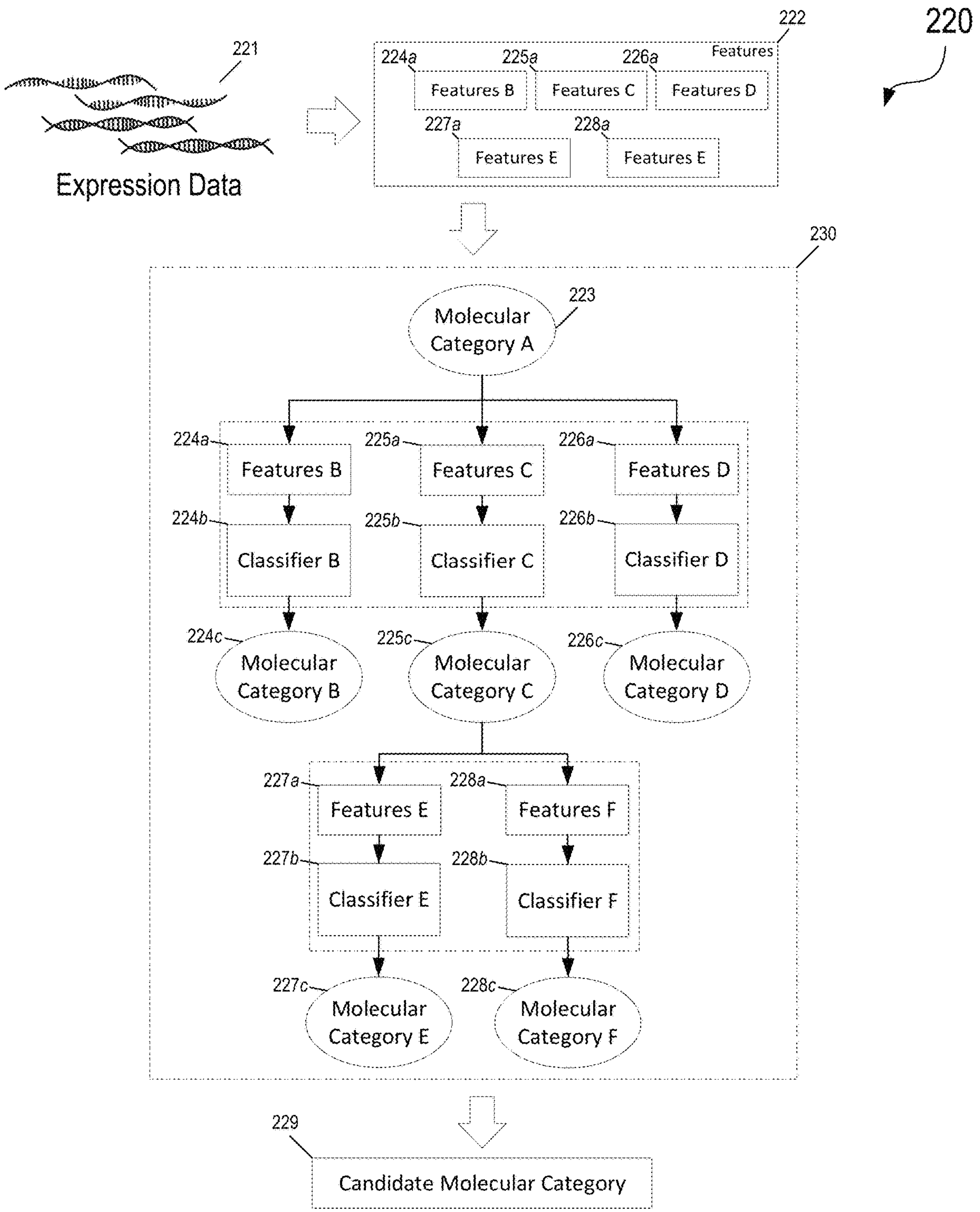
FIG. 2B-1 is a diagram depicting an illustrative technique 220 for processing expression data to identify a candidate molecular category for a biological sample, according to some embodiments of the technology described herein.
Figures 2, 2B:
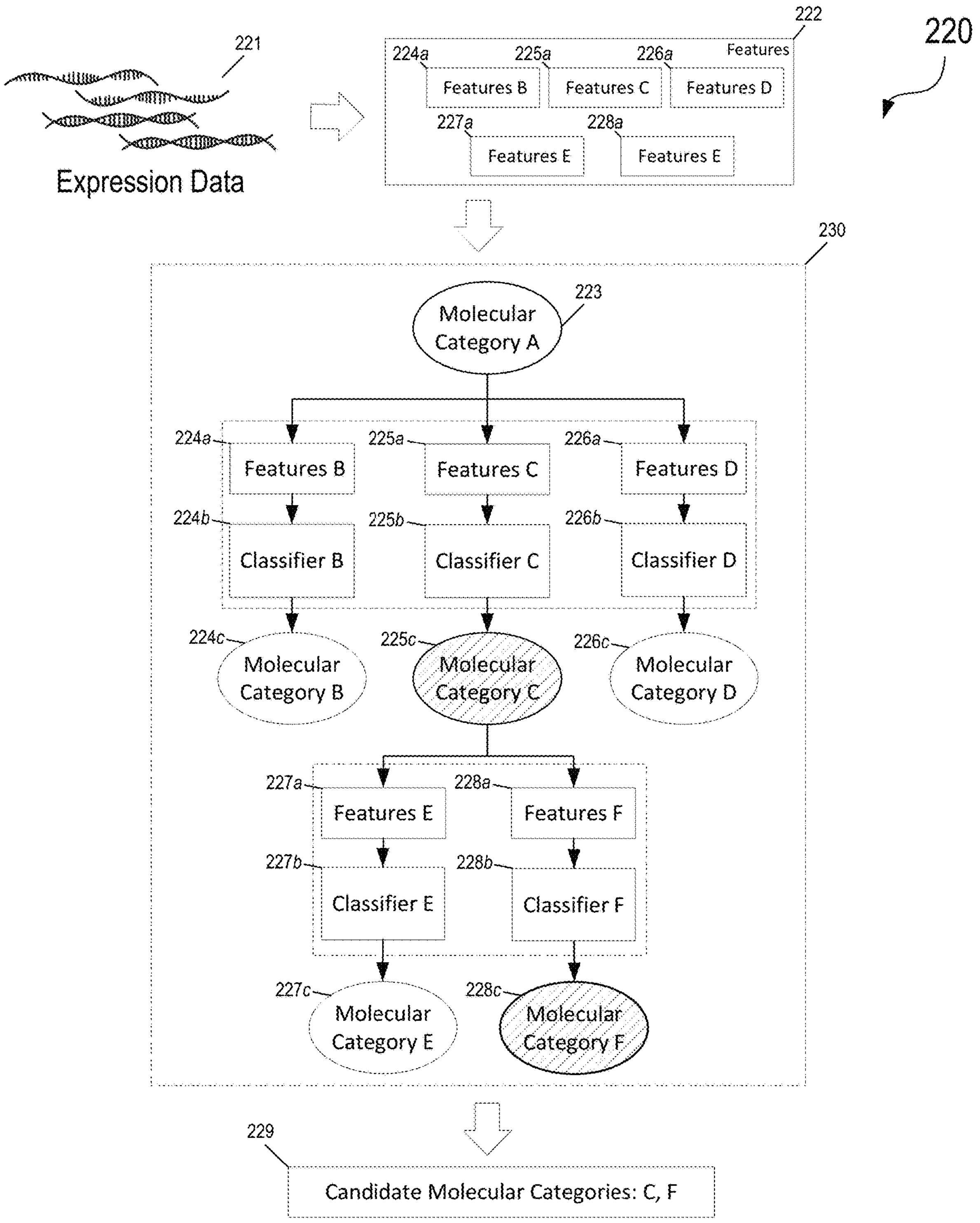

One such aspect is the architecture of the machine learning models used to identify one or more molecular categories for a biological sample. In some embodiments, the techniques involve using a hierarchy of machine learning classifiers that corresponds to the hierarchy of molecular categories. In some embodiments, individual machine learning classifiers in the hierarchy of machine classifiers correspond to respective individual molecular categories in the hierarchy of molecular categories (e.g., as shown in FIGS. 2B-1 and 2B-2 among others). Thus, in some embodiments, a separate machine learning classifier is trained and used to determine whether to identify a particular, respective molecular category for the biological sample, which improves overall accuracy of identification of molecular categories (e.g., as compared to conventional methods that rely on a single multi-class classifier to identify one of a plurality of primary sites from expression data from a sample). The use of a hierarchy of machine learning classifiers allows for the identification of multiple candidate molecular categories of different specificity. Accordingly, molecular categories identified at a general level of the hierarchy may be used to inform identification of molecular categories at a more specific level of the hierarchy, contributing to the accuracy and performance of the techniques described herein.

Relatedly, the use of a hierarchy of machine learning classifiers provides an important computational advantage to using separate, non-hierarchically organized, classifiers for various primary sites and/or categories. The advantage is that decisions made by classifiers at a higher level in the classifier hierarchy may be used to identify a relevant branch in the hierarchy for further processing and, therefore, eliminate the need to invoke and perform any processing using machine learning classifiers in one or more other branches in the hierarchy, thereby saving significant computational resources (e.g., processing resources, network resources utilized by having to transmit expression data, which may be voluminous) and enabling faster processing of the expression data to identify the relevant molecular categories. For example, if the machine learning classifier corresponding to the "Adenocarcinoma" category in FIG. 7A-2 outputs an indication that the tumor is likely an Adenocarcinoma sample and not likely to be anything else, it may not be necessary to invoke machine learning classifiers associated with categories in other branches in the hierarchy (e.g., with the "Glioma", "Squamous Cell Carcinoma", and "Neuroendocrine" branches of the hierarchy of molecular categories).

In some embodiments, the techniques developed by the inventors may utilize multiple hierarchies of machine learning classifiers to identify candidate molecular categories for the biological sample using different types of expression data. For example, a first hierarchy may include RNA-based machine learning classifiers trained to identify candidate molecular categories based on RNA expression data (e.g., using features derived from the RNA expression data and/or the RNA expression data itself) obtained from the biological sample, while a second hierarchy may include DNA-based machine learning classifiers trained to identify candidate molecular categories based on DNA expression data (e.g., using features derived from the RNA expression data and/or the RNA expression data itself) obtained from the biological sample. Using multiple hierarchies of machine learning classifiers allows the techniques to cross-check identified candidate molecular categories and accounts for deficiencies that might be associated with either the RNA expression data or the DNA expression data. Thus, in some embodiments, only one hierarchy of machine learning classifiers may be used (e.g., using only the hierarchy of RNA-based machine learning classifiers or only the hierarchy of DNA-based machine learning classifiers), but not both. In other embodiments, both the RNA-based and DNA-based hierarchies may be used. When both are used, they may be used independently of one another. In such cases their results may be compared with one another for cross-checking purposes. Alternatively, the numerical outputs generated by classifiers in both hierarchies may be combined (sometimes termed "fused") as described herein, including with reference to FIG. 5B.

Another aspect of the approach developed by the inventors that contributes to its accuracy and robustness is the use of features (e.g., features derived from DNA and/or RNA expression data, which features may include the DNA and/or RNA expression data itself, in some embodiments) specified a priori for each molecular category to determine whether to identify the molecular category as a candidate molecular category for the biological sample. For example, RNA expression data for a specific set of genes for a particular molecular category may be processed using a machine learning classifier trained to predict whether a particular molecular category should be identified for the biological sample. The RNA expression data may be first processed to obtain a set of features specified a priori for the particular molecular category (e.g., gene rankings for a set of genes associated with the molecular category, the gene rankings obtained by numerically ranking the expression levels for genes in the set of genes) and this set of features may be provided as input to a specific machine learning classifier for that specific molecular category. As another example, DNA expression data may be used to obtain a specific set of DNA features (e.g., features indicating the presence of gene mutations, presence of genes, copy number alterations, loss of heterozygosity (LOH), ploidy, tumor mutational burden, presence of gene fusions, microsatellite instability (MSI) status, etc.) for a particular molecular category. Then these DNA features may be provided as input to and be processed using a machine learning classifier trained to predict whether the molecular category is a candidate molecular category for the biological sample. In some embodiments, the use of specific features tailored for each particular molecular category allows the techniques developed by the inventors to leverage domain-specific knowledge to distinguish among molecular categories, even when they share similar molecular features, contributing to the success of the techniques described herein. Examples of RNA and DNA features used by RNA-based and DNA-based machine learning classifiers, respectively, are provided herein.

Accordingly, some embodiments provide for computer-implemented techniques for identifying at least one candidate molecular category for a biological sample obtained from a subject. The techniques include: (a) obtaining RNA expression data obtained by processing (e.g., sequencing) the biological sample obtained from the subject, wherein the RNA expression data comprises first RNA expression data (e.g., first RNA expression levels) for a first set of genes and second RNA expression data (e.g., second RNA expression levels) for a second set of genes different from the first set of genes; (b) processing the RNA expression data using a hierarchy of RNA-based machine learning classifiers (e.g., the hierarchy of RNA-based machine learning classifiers 500 shown in FIG. 5A-1) corresponding to a hierarchy of molecular categories (e.g., the hierarchy of molecular categories 200 shown in FIG. 2A) to obtain RNA-based machine learning classifier outputs including a first output and a second output, the hierarchy of molecular categories including a parent molecular category (e.g., represented by node 202 shown in FIG. 2A) and first and second molecular categories (e.g., represented by nodes 204*b* and 204*a* of FIG. 2A) that are children of the parent molecular category in the hierarchy of molecular categories, the hierarchy of RNA-based machine learning classifiers comprising first and second RNA-based machine learning classifiers (e.g., classifiers 513*b* and 514*b* shown in FIG. 5A-1) corresponding to the first and second molecular categories, the processing comprising: (i) processing the first RNA expression data using the first RNA-based machine learning classifier to obtain the first output (e.g., a probability or likelihood or other numerical or categorical value) indicative of whether the first molecular category is a candidate molecular category for the biological sample; (ii) processing the second RNA expression data using the second RNA-based machine learning classifier to obtain the second output (e.g., a probability or likelihood or other numerical or categorical value) indicative of whether the second molecular category is a candidate molecular category for the biological sample; and (c) identifying, using at least some of the RNA-based machine learning classifier outputs (e.g., probabilities 535, 536, and 537 shown in FIG. 5A-1) including the first output and the second output, at least one candidate molecular category.

The at least one candidate molecular category may include one or multiple molecular categories. When multiple molecular category candidates are included, they may include multiple molecular categories at different levels of the hierarchy (e.g., indicating a most likely molecular category and its ancestors—parent, grandparent, etc.—in the hierarchy). Additionally or alternatively, when multiple molecular category candidates are included, they may include multiple molecular categories at the same level in the hierarchy (e.g., indicating multiple potential alternative molecular categories for the biological sample and their respective probabilities, likelihood or other numerical or categorical values).

In some embodiments, the first molecular category is associated with at least one international classification of diseases (ICD) code. For example, the first molecular category may be associated with at least one ICD code, at least two ICD codes, at least five ICD codes, at least 10 ICD codes, or between 1 and 10 ICD codes. Example associations of molecular categories and ICD codes are shown in Table 1 herein.

In some embodiments, the hierarchy of molecular categories may be stored using one or more data structures having one or more fields storing information about the hierarchy of molecular categories. For example, the fields may store information indicating, for each category in the hierarchy, its relationship to one or more other categories in the hierarchy (e.g., indicating a parent molecular category and/or one or more child molecular categories), one or more ICD codes associated with the category, one or more histological cancer subtypes associated with the category, one or more treatments known to be therapeutically effective for the category, and/or any other suitable information, as aspects of the technology described herein are not limited in this respect.

In some embodiments, the hierarchy of machine learning classifiers (e.g., hierarchy of DNA-based machine learning classifiers or the hierarchy of RNA-based machine learning classifiers) may be stored in any suitable way. Each of the machine learning classifiers may comprise program code that, when executed, performs classification using the machine learning classifier's inputs, the machine learning classifier's parameters, the machine learning classifier's hyperparameters, and/or any other suitable configuration information. The hierarchical relationships among the machine learning classifiers may be stored using one or more data structures having one or more fields storing information about the hierarchy. For example, the fields may store information indicating, for each machine learning classifier in the hierarchy, its relationship to one or more other machine learning classifiers in the hierarchy (e.g., indicating a parent machine learning classifier and/or one or more child machine learning classifiers), a respective category in the hierarchy of molecular categories to which the classifier corresponds, and/or any other suitable information, as aspects of the technology described herein are not limited in this respect.

In some embodiments, the RNA expression data further comprises third RNA expression data for a third set of genes different from the first and second sets of genes. In some embodiments, the hierarchy of molecular categories further comprises a third molecular category (e.g., represented by node 204*c*) that is a child of the parent molecular category in the hierarchy of molecular categories. In some embodiments, the hierarchy of RNA-based machine learning classifiers further comprises a third RNA-based machine learning classifier (e.g., RNA-based machine learning classifier 515*c*) corresponding to the third molecular category. In some embodiments, the processing further comprises processing the third RNA expression data using the third RNA-based machine learning classifier (e.g., by processing the third RNA expression data to obtain RNA features 515*a* with RNA classifier 515*b*) to obtain a third output indicative of whether the third molecular category is a candidate molecular category for the biological sample. In some embodiments, identifying the at least one candidate molecular category for the biological sample is performed using the third output.

In some embodiments, the RNA expression data further comprises fourth RNA expression data for a fourth set of genes different from the first and second sets of genes. In some embodiments, the hierarchy of molecular categories further comprises a fourth molecular category (e.g., represented by node 206*a* shown in FIG. 2A) that is a child of the first molecular category (e.g., represented by node 204*b*) in the hierarchy of molecular categories. In some embodiments, the hierarchy of RNA-based machine learning classifiers further comprises a fourth RNA-based machine learning classifier (e.g., RNA-based machine learning classifier 516*b*) corresponding to the fourth molecular category. In some embodiments, the processing further comprises processing the fourth RNA expression data using the fourth RNA-based machine learning classifier (e.g., by processing the fourth RNA expression data to obtain RNA features 516*a* with RNA classifier 516*b*) to obtain a fourth output indicative of whether the fourth molecular category is a candidate molecular category for the biological sample. In some embodiments, identifying the at least one candidate molecular category for the biological sample is performed using the fourth output.

In some embodiments, the RNA expression data further comprises fifth RNA expression data for a fifth set of genes different from the first, second, and fourth sets of genes. In some embodiments, the hierarchy of molecular categories further comprises a fifth molecular category (e.g., represented by node 206*b* shown in FIG. 2A) that is another child of the first molecular category (e.g., represented by node 204*b* shown in FIG. 2A) in the hierarchy of molecular categories. In some embodiments, the hierarchy of RNA-based machine learning classifiers further comprises a fifth RNA-based machine learning classifier (e.g., RNA-based molecular category 517*b*) corresponding to the fifth molecular category. In some embodiments, the processing further comprises processing the fifth RNA expression data using the fifth RNA-based machine learning classifier (e.g., by processing the fifth RNA expression data to obtain RNA features 517*a* with RNA classifier 517*b*) to obtain a fifth output indicative of whether the fifth molecular category is a candidate molecular category for the biological sample. In some embodiments, identifying the at least one candidate molecular category for the biological sample is performed using the fifth output.

In some embodiments, the parent molecular category is a solid neoplasm molecular category, the first molecular category is an adenocarcinoma molecular category, and the second molecular category is a sarcoma molecular category. In some embodiments, the parent molecular category is a breast cancer molecular category, the first molecular category is a basal breast cancer molecular category, and the second molecular category is a non-basal breast cancer molecular category. In some embodiments, the parent molecular category is a category selected from Table 2 (e.g., renal cell carcinoma), and the first and second molecular categories are children of the parent molecular category in the hierarchy of molecular categories shown in FIGS. 7A-1-7B-2 (e.g., non-clear cell carcinoma and clear cell carcinoma show in FIG. 7A-2).

In some embodiments, processing the first RNA expression data using the first RNA-based machine learning classifier comprises: obtaining first RNA features (e.g., a gene ranking obtained by ranking the RNA expression levels for genes associated with the first RNA-based ML classifier) from the first RNA expression data, and applying the first RNA-based machine learning classifier to the first RNA features (e.g., processing the first RNA features using the first RNA-based machine learning classifier) to obtain the first output.

In some embodiments, the first RNA expression data comprises first expression levels (e.g., obtained by RNA sequencing) for the first set of genes. The first RNA expression data may be obtained by accessing RNA sequencing data for a patient's genome and identifying and/or selecting, from this large amount of data, RNA sequencing data for the first set of genes. In some embodiments, the RNA sequencing data may comprise millions of sequencing reads, which may be processed by alignment and/or assembly techniques (using any suitable bioinformatics pipeline) to identify RNA expression levels for the first set of genes. In some embodiments, the first RNA expression data may be stored (and/or manipulated in a computer) using at least one data structure having fields storing RNA expression level values.

In some embodiments, obtaining the first RNA features from the first RNA expression data comprises ranking at least some genes in the first set of genes based on the first expression levels (e.g., rank expression levels in ascending or descending order) to obtain a first gene ranking, the first gene ranking including values (e.g., integers) identifying relative ranks of the at least some genes in the gene ranking, wherein the values are different from the first expression levels. For example, genes [A, B, C], having respective expression levels of 0.01, 0.56, and 0.45, would be ranked [1, 3, 2] if they are to be ranked in ascending order. In some embodiments, a gene ranking may be stored (and/or manipulated in a computer) using at least one data structure having fields storing gene ranking values. In some embodiments, applying the first RNA-based machine learning classifier to the first RNA features comprises applying the first RNA-based machine learning classifier to the first gene ranking to obtain the first output (e.g., processing the gene ranking using the first RNA-based machine learning classifier by providing the gene ranking values as inputs to the first RNA-based machine learning classifier).

In some embodiments, processing the first RNA expression data using the first RNA-based machine learning classifier to obtain the first output comprises processing the first RNA expression data to obtain a first probability (or likelihood or other numerical or categorical value) indicating that the first molecular category is a first candidate molecular category for the biological sample (e.g., relative to the probability that the first molecular category is not a candidate molecular category for the biological sample and/or relative to the probability that the first molecular category is a molecular category for the biological sample). In some embodiments, processing the second RNA expression data using the second RNA-based machine learning classifier to obtain the second output comprises processing the second RNA expression data to obtain a second probability (or likelihood or other numerical or categorical value) indicating that the second molecular category is a second candidate molecular category for the biological sample.

In some embodiments, identifying the at least one candidate molecular category for the biological sample comprises: comparing the first probability to a threshold (e.g., a threshold of at least 0.02, at least 0.05, at least 0.1, or at least 0.5), and including the first molecular category in the at least one candidate molecular category identified for the biological sample when the first probability exceeds the threshold. In some embodiments, identifying the at least one candidate molecular category for the biological sample further comprises excluding the first molecular category from the at least one candidate molecular category identified for the biological sample when the first probability does not exceed the threshold (e.g., the molecular category is not likely a candidate molecular category for the biological sample).

In some embodiments, identifying the at least one candidate molecular category for the biological sample comprises: comparing the first probability to the second probability (e.g., comparing probabilities output by machine learning classifiers at a same level of the hierarchy of machine learning classifiers), and identifying the first molecular category as a candidate molecular category of the at least one candidate molecular category for the biological sample when the first probability exceeds the second probability (e.g., at a level of the hierarchy, identifying the molecular category associated with the machine learning classifier that output the highest probability).

In some embodiments, the first molecular category is a molecular category selected from molecular categories listed in Table 2. For example, the first molecular category is breast cancer, as selected from Table 2.

In some embodiments, the first set of genes comprises at least 10 genes listed in Table 3 corresponding to the first molecular category. For example, the first set of genes may comprise at least 20 genes, at least 40 genes, at least 60 genes, at least 80 genes, at least 100 genes, at least 150 genes, at least 200 genes, at least 300 genes, between 10 and 300 genes, between 10 and 200 genes, between 10 and 100 genes, between 10 and 80 genes, between 20 and 300 genes, between 20 and 100 genes, between 40 and 300 genes, between 40 and 100 genes, between 50 and 300 genes, or between 50 and 100 genes, in each case being selected from the genes listed in Table 3.

In some embodiments, the hierarchy of RNA-based machine learning classifiers comprises at least 10 RNA-based machine learning classifiers. For example, the hierarchy of RNA-based machine learning classifiers may comprise at least 10 RNA-based machine learning classifiers, at least 20 RNA-based machine learning classifiers, at least 30 RNA-based machine learning classifiers, at least 40 RNA-based machine learning classifiers, at least 50 RNA-based machine learning classifiers, at least 60 RNA-based machine learning classifiers, at least 70 RNA-based machine learning classifiers, at least 80 RNA-based machine learning classifiers, between 10 and 50 machine learning classifiers, between 10 and 100 machine learning classifiers, or any other suitable range within these ranges.

In some embodiments, the first RNA-based machine learning classifier is a gradient-boosted decision tree classifier, a neural network classifier, a logistic regression classifier, a support vector machine classifier, a Bayesian classifier, a random forest classifier, any other type of gradient boosted classifier, or any other suitable type of machine learning classifier. In some embodiments, the first classifier may comprise between 10 and 100 parameters, between 100 and 1000 parameters, between 1000 and 10,000 parameters, between 10,000 and 100,000 parameters or more than 100K parameters. Processing input data with a classifier comprises performing calculations using values of the machine learning classifier parameters and the values of the input to the classifier to obtain the corresponding output. Such calculations may involve hundreds, thousands, tens of thousands, hundreds of thousands or more calculations, in some embodiments.

In some embodiments, each RNA-based machine learning classifier of the hierarchy of RNA-based machine learning classifiers is one of a gradient-boosted decision tree classifier, a neural network classifier, a logistic regression classifier, a support vector machine classifier, a Bayesian classifier, a random forest classifier, any other type of gradient boosted classifier, or any other suitable type of machine learning classifier.

In some embodiments, all classifiers in the machine learning classifier hierarchy (whether the hierarchy of RNA-based or DNA-based classifiers) are of a same type (e.g., having different parameters and inputs, but the same architecture, for example, all being gradient boosted decision tree classifiers or all being neural network classifiers). In some embodiments, some of the classifiers in the machine learning classifier hierarchy may be different (e.g., some may be support vector machines and others may be gradient boosted decision tree classifiers).

In some embodiments, the first RNA expression data comprises expression levels for between 20 and 300 genes. For example, the first RNA expression data may comprise expression levels for at least 20 genes, at least 40 genes, at least 60 genes, at least 80 genes, at least 100 genes, at least 150 genes, at least 200 genes, at least 300 genes, between 10 and 300 genes, between 10 and 200 genes, between 10 and 100 genes, between 10 and 80 genes, between 20 and 300 genes, between 20 and 100 genes, between 40 and 300 genes, between 40 and 100 genes, between 50 and 300 genes, or between 50 and 100 genes.

In some embodiments, the hierarchy of machine learning classifiers may include multiple machine learning classifiers, each of which is trained to determine whether to identify a respective molecular category as a candidate molecular category for a biological sample. In some embodiments, the hierarchy of machine learning classifiers include at least 10, at least 20, at least 40, at least 50, at least 60, between 10 and 50, between 25 and 100 machine learning classifiers or any suitable range within these ranges. Thus, in some embodiments, the machine learning classifiers in a hierarchy of machine learning classifiers may be in a one-to-one correspondence with at least some (e.g., all) molecular categories in the hierarchy of molecular categories.

In some embodiments, the computer-implemented techniques for identifying at least one candidate molecular category for a biological sample further involve the use of DNA expression data in addition to (or instead of) the RNA expression data. For example, in some embodiments, the techniques further include obtaining DNA expression data previously obtained by processing the biological sample obtained from the subject (e.g., a patient) and processing the DNA expression data using a hierarchy of DNA-based machine learning classifiers (e.g., hierarchy 550 shown in FIG. 5A-2) corresponding to the hierarchy of molecular categories to obtain DNA-based machine learning classifier outputs (e.g., probabilities 565-567 shown in FIG. 5A-2). The hierarchy of DNA-based machine learning classifiers is a different hierarchy than the hierarchy of RNA-based machine learning classifiers. For example, the hierarchy of DNA-based machine learning classifiers includes machine learning classifiers trained using DNA expression data (e.g., using features derived from the DNA expression data), while the hierarchy of RNA-based machine learning classifiers includes machine learning classifiers trained using RNA expression data (e.g., using features derived from the RNA expression data). In some embodiments, identifying of the at least one candidate molecular category for the biological sample is performed also using at least some of the DNA-based machine learning classifier outputs. For example, by processing the DNA-based machine learning classifier outputs and the RNA-based machine learning classifier outputs using a model or by selecting between the DNA-based machine learning classifier outputs or the RNA-based machine learning classifier outputs. Accordingly, the hierarchy of DNA-based machine learning classifiers may be used together with or instead of the hierarchy of RNA-based machine learning classifiers.

In some embodiments, processing the DNA expression data comprises: obtaining DNA features from the DNA expression data (e.g., by deriving them from the DNA expression data), and applying at least one DNA-based machine learning classifier of the hierarchy of DNA-based machine learning classifiers to at least some of the DNA features (e.g., processing at least some of the DNA features using a classifier of the hierarchy of DNA-based classifiers) to obtain the DNA-based machine learning classifier outputs.

In some embodiments, the DNA features comprise one or more features indicating, for each gene of a respective set of one or more genes, whether the DNA expression data indicates presence of a pathogenic mutation for the gene (e.g., a mutation in DNAH5, as shown in Table 5). A feature providing such an indication may be a binary feature, whereby one value indicates the presence of the pathogenic mutation and the other value indicates its absence.

In some embodiments, the DNA features comprise one or more features indicating, for each gene of a respective set of one or more genes, whether the DNA expression data indicates presence of a hotspot mutation for the gene (e.g., a hotspot mutation in PPP2R1A, as shown in Table 5). A feature providing such an indication may be a binary feature, whereby one value indicates the presence of the hotspot mutation and the other value indicates its absence.

In some embodiments, the DNA features comprise one or more features (e.g., one or more numerical values) indicating tumor mutational burden (e.g., indicative of the number of mutations found in the DNA of cancer cells) for the biological sample.

In some embodiments, the DNA features comprise one or more features (e.g., one or more numerical values) indicating a normalized copy number for each chromosome segment (e.g., a bin, an arm, or a chromosome) of a respective set of one or more chromosome segments for which expression data is included in the DNA expression data.

In some embodiments, the DNA features comprise one or more features (e.g., one or more numerical values) indicating loss of heterozygosity (LOH) for each chromosome segment (e.g., a bin, an arm, or a chromosome) of a respective set of one or more chromosome segments for which expression data is included in the DNA expression data.

In some embodiments, the DNA features comprise one or more features indicating whether the DNA expression data indicates presence of one or more protein coding genes and/or one or more non-protein coding genes. Each such feature may be a binary feature, whereby one value indicates the presence of a protein coding gene and the other value indicates its absence.

In some embodiments, the DNA features comprise one or more features (e.g., one or more binary features) indicating, for each gene of a respective set of one or more genes, whether the DNA expression data indicates presence of a fusion with another gene (e.g., with a specific gene, or with any other gene).

In some embodiments, the DNA features comprise one or more features (e.g., one or more numerical values) indicating ploidy (e.g., the number of chromosomes occurring in the nucleus of the cell) for the biological sample.

In some embodiments, the DNA features comprise one or more features (e.g., one or more binary features) indicating whether the DNA expression data indicates presence of microsatellite instability (MSI) (e.g., a condition of hypermutability that results from impaired DNA mismatch repair).

In some embodiments, the DNA features, provided as input to each DNA-based machine learning classifier in the hierarchy, comprise at least ten features listed in Table 5. For example, the DNA features may comprise at least 20 features, at least 40 features, at least 60 features, at least 80 features, at least 100 features, at least 150 features, at least 200 features, at least 300 features, between 10 and 300 features, between 10 and 200 features, between 10 and 100 features, between 10 and 80 features, between 20 and 300 features, between 20 and 100 features, between 40 and 300 features, between 40 and 100 features, between 50 and 300 features, or between 50 and 100 features.

In some embodiments, the identifying of the at least one candidate molecular category for the biological sample is performed based on data indicative of the purity of the biological sample. For example, the sample purity may affect the data and therefore impact (e.g., invalidate) the predictions output by one or both of the RNA-based and DNA-based machine learning classifiers. Therefore, one or more outputs may be discarded or considered with greater (or lesser) weight when identifying the at least one candidate molecular category.

In some embodiments, the identifying of the at least one candidate molecular category for the biological sample is performed based on data indicative of a site from which the biological sample was obtained. For example, the expression data for the normal tissue from the sample site may be used (e.g., normal lung tissue when the biological sample was obtained from the lung). In some embodiments, at least one machine learning classifier of the hierarchy of RNA-based and DNA-based machine learning classifiers is trained to output an indication of whether the biological sample belongs to the normal tissue.

In some embodiments, the hierarchy of DNA-based machine learning classifiers comprises at least 10 DNA-based machine learning classifiers. For example, the hierarchy of DNA-based machine learning classifiers may comprise at least 10 DNA-based machine learning classifiers, at least 20 DNA-based machine learning classifiers, at least 30 DNA-based machine learning classifiers, at least 40 DNA-based machine learning classifiers, at least 50 DNA-based machine learning classifiers, at least 60 DNA-based machine learning classifiers, at least 70 DNA-based machine learning classifiers, at least 80 DNA-based machine learning classifiers, between 10 and 50 machine learning classifiers, between 10 and 100 machine learning classifiers, or any other suitable range within these ranges.

In some embodiments, the hierarchy of DNA-based machine learning classifiers comprises a first DNA-based machine learning classifier, which is a gradient-boosted decision tree classifier, a neural network classifier, a logistic regression classifier, a support vector machine classifier, a Bayesian classifier, a random forest classifier, any other type of gradient boosted classifier, or any other suitable type of machine learning classifier. In some embodiments, the first DNA based machine learning classifier may comprise between 10 and 100 parameters, between 100 and 1000 parameters, between 1000 and 10,000 parameters, between 10,000 and 100,000 parameters or more than 100K parameters. Processing input data with a classifier comprises performing calculations using values of the machine learning classifier parameters and the values of the input to the classifier to obtain the corresponding output. Such calculations may involve hundreds, thousands, tens of thousands, hundreds of thousands or more calculations, in some embodiments.

In some embodiments, each DNA-based machine learning classifier of the hierarchy of DNA-based machine learning classifiers is one of a gradient-boosted decision tree classifier, a neural network classifier, a logistic regression classifier, a support vector machine classifier, a Bayesian classifier, a random forest classifier, any other type of gradient boosted classifier, or any other suitable type of machine learning classifier. In some embodiments, all classifiers in the machine learning classifier hierarchy are of a same type (e.g., having different parameters and inputs, but the same architecture, for example, all being gradient boosted decision tree classifiers or all being neural network classifiers). In some embodiments, some of the classifiers in the machine learning classifier hierarchy may be different (e.g., some may be support vector machines and others may be gradient boosted decision tree classifiers).

In some embodiments, the techniques involve using the at least one identified candidate molecular category for a sample obtained from a subject to identify at least one therapy to treat the subject. The identified at least one therapy may then be administered to the subject. A molecular category may be used to identify the at least one therapy by identifying any therapies known to be therapeutically effective for the identified molecular category. For example, when a molecular category is associated with one or more ICD codes, the ICD codes may be used to identify (either automatically by software or manually by a clinician) any therapies known to be therapeutically effective for the identified ICD codes. Where the therapies are identified from one or more molecular categories by software, the identified therapy or therapies may be presented to a clinician (e.g., via a graphical user interface generated by the software or in any other suitable way, as aspects of the technology described herein are not limited in this respect). In some embodiments a molecular category may encompass or correspond to a plurality of ICD codes (e.g., 2, 3, 4, 5, . . . ) and that one or more recommended therapies for any one or more of them could be identified (e.g., selected by a clinician, recommended to a clinician) for treatment. The identified therapy or therapies may then be administered to the patient.

In some embodiments, the techniques further include generating, using the hierarchy of molecular categories, a graphical user interface (GUI) (e.g., the screenshot shown in FIG. 1B) including a visualization (e.g., a graph including nodes and edges) indicating the at least one molecular category identified for the biological sample.

In some embodiments, the techniques further include: receiving an indication of a clinical diagnosis of the biological sample (e.g., from a clinician or researcher who analyzed the biological sample) and determining an accuracy of the clinical diagnosis based on the at least one candidate molecular category identified for the biological sample. For example, the techniques described herein may be used to confirm or correct a diagnosis made by a clinician and/or to perform other types of quality control.

In some embodiments, the first molecular category of the hierarchy of molecular categories is one of a neoplasm, hematologic neoplasm, melanoma, sarcoma, mesothelioma, neuroendocrine, squamous cell carcinoma, adenocarcinoma, glioma, testicular germ cell tumor, pheochromocytoma, cervical squamous cell carcinoma, liver neoplasm, lung adenocarcinoma, high grade glioma isocitrate dehydrogenase (IDH) mutant, thyroid neoplasm, squamous cell lung adenocarcinoma, thymoma, prostate adenocarcinoma, urinary bladder urothelial carcinoma, oligodendroglioma, squamous cell carcinoma of the head and neck, gastrointestinal adenocarcinoma, gynecological cancer, renal cell carcinoma, astrocytoma, pancreatic adenocarcinoma, stomach adenocarcinoma, pancreatic adenocarcinoma, breast cancer, ovarian cancer, uterine corpus endometrial carcinoma, non-clear cell carcinoma, clear cell carcinoma, basal breast cancer, non-basal breast cancer, papillary renal cell carcinoma, and chromophobe renal cell carcinoma.

In some embodiments, the first molecular category of the hierarchy of molecular categories is associated with one or more ICD codes. In some embodiments, the first molecular category of the hierarchy of molecular codes is associated with a histological subtype of a cancer.

Some embodiments provide for computer-implemented techniques for identifying at least one candidate molecular category for a biological sample obtained from a subject, the method comprising: (a) obtaining DNA expression data previously obtained by processing (e.g., sequencing) the biological sample obtained from the subject; (b) processing the DNA expression data using a hierarchy of DNA-based machine learning classifiers (e.g., the hierarchy of DNA-based machine learning classifiers 550 shown in FIG. 5A-2) corresponding to a hierarchy of molecular categories (e.g., the hierarchy of molecular categories 200 shown in FIG. 2A) to obtain DNA-based machine learning classifier outputs including a first output and a second output, the hierarchy of molecular categories including a parent molecular category (e.g., represented by node 202 shown in FIG. 2A) and first and second molecular categories (e.g., represented by nodes 204*b* and 204*a* of FIG. 2A) that are children of the parent molecular category in the hierarchy of molecular categories, the hierarchy of DNA-based machine learning classifiers comprising first and second DNA-based machine learning classifiers (e.g., classifiers 553*b* and 554*b* shown in FIG. 5A-2) corresponding to the first and second molecular categories, the processing comprising: (i) processing the first DNA expression data using the first DNA-based machine learning classifier to obtain the first output (e.g., a probability, a likelihood, or other numerical or categorical value) indicative of whether the first molecular category is a candidate molecular category for the biological sample; (ii) processing the second DNA expression data (e.g., using the second DNA-based machine learning classifier to obtain the second output (e.g., a probability, a likelihood, or other numerical or categorical value) indicative of whether the second molecular category is a candidate molecular category for the biological sample; and (c) identifying, using at least some of the DNA-based machine learning classifier outputs (e.g., probabilities 565, 566, and 567 shown in FIG. 5A-2) including the first output and the second output, at least one candidate molecular category (e.g., one more candidate molecular categories corresponding to one or more levels of the hierarchy of DNA-based machine learning classifiers) for the biological sample.

In some embodiments, the DNA expression data further comprises third DNA expression data for a third set of genes different from the first and second sets of genes. In some embodiments, the hierarchy of molecular categories further comprises a third molecular category (e.g., represented by node 204*c*) that is a child of the parent molecular category in the hierarchy of molecular categories. In some embodiments, the hierarchy of DNA-based machine learning classifiers further comprises a third DNA-based machine learning classifier (e.g., DNA-based machine learning classifier 555*b*) corresponding to the third molecular category. In some embodiments, the processing further comprises processing the third DNA expression data using the third DNA-based machine learning classifier (e.g., by processing DNA features 555*a*, obtained from the third DNA expression data, with DNA-based machine learning classifier 555*b*) to obtain a third output indicative of whether the third molecular category is a candidate molecular category for the biological sample. In some embodiments, identifying the at least one candidate molecular category for the biological sample is performed using the third output.

In some embodiments, the DNA expression data further comprises fourth DNA expression data for a fourth set of genes different from the first and second sets of genes. In some embodiments, the hierarchy of molecular categories further comprises a fourth molecular category (e.g., represented by node 206*a* shown in FIG. 2A) that is a child of the first molecular category (e.g., represented by node 204*b*) in the hierarchy of molecular categories. In some embodiments, the hierarchy of DNA-based machine learning classifiers further comprises a fourth DNA-based machine learning classifier (e.g., DNA-based machine learning classifier 556*b*) corresponding to the fourth molecular category. In some embodiments, the processing further comprises processing the fourth DNA expression data using the fourth DNA-based machine learning classifier (e.g., by processing DNA features 556*a*, obtained using the fourth DNA expression data, with DNA-based machine learning classifier 556*b*) to obtain a fourth output indicative of whether the fourth molecular category is a candidate molecular category for the biological sample. In some embodiments, identifying the at least one candidate molecular category for the biological sample is performed using the fourth output.

In some embodiments, the DNA expression data further comprises fifth DNA expression data for a fifth set of genes different from the first, second, and fourth sets of genes. In some embodiments, the hierarchy of molecular categories further comprises a fifth molecular category (e.g., represented by node 206*b* shown in FIG. 2A) that is a child of the first molecular category (e.g., represented by node 204*b* shown in FIG. 2A) in the hierarchy of molecular categories. In some embodiments, the hierarchy of DNA-based machine learning classifiers further comprises a fifth DNA-based machine learning classifier (e.g., DNA-based machine learning classifier 557*b*) corresponding to the fifth molecular category. In some embodiments, the processing further comprises processing the fifth DNA expression data using the fifth DNA-based machine learning classifier to obtain a fifth output indicative of whether the fifth molecular category is a candidate molecular category for the biological sample. In some embodiments, identifying the at least one candidate molecular category for the biological sample is performed using the fifth output.

Molecular Categories

As described above, a "molecular category" refers to a category or group of biological samples (e.g., tumor samples) that have similar molecular features (e.g., features derived from expression data). In some embodiments, a molecular category may be associated with one or more clinical diagnoses. For example, in some embodiments, a molecular category may be associated with one or more International Classification of Diseases (ICD) codes. Examples are provided in Table 1. In some embodiments, a molecular category may be associated with a histological subtype of a cancer. For example, non-basal breast cancer and basal breast cancer are molecular categories, shown in FIG. 7A-2, which are associated with histological subtypes of breast cancer. Other examples are provided herein.

In some embodiments, a molecular category may correspond to a known cancer subtype, for a known histological cancer cell or cancer tissue subtype. However, in other embodiments, a molecular category may be a newly identified category that is clinically relevant and useful for diagnostic, prognostic, and/or therapeutic purposes.

As described herein, molecular categories may be organized into a hierarchy of molecular categories in which molecular categories at different levels of the hierarchy have differing degrees of specificity—molecular categories at higher levels of the hierarchy are broader categories having lower specificity, while molecular categories at lower levels of the hierarchy are narrower categories having higher specificity. In some embodiments, a hierarchy of molecular categories (e.g., hierarchy 200 shown in FIG. 2A) includes nodes, each of which represents a respective molecular category, and edges, which define the hierarchical (e.g., parent-child) relationships between the molecular categories. A parent node (e.g., node 204*b* shown in FIG. 2A) in the hierarchy is a node that is connected by edges to one or more child nodes (e.g., nodes 206*a-b* shown in FIG. 2A). In some embodiments, a parent node represents a molecular category that can be subdivided into more specific molecular categories, which are represented by the child nodes of the parent nodes.

In some embodiments, nodes at different levels of the hierarchy represent molecular categories that have differing degrees of specificity. In some embodiments, a node falling within the upper level(s) of the hierarchy represents a relatively general molecular category, meaning that the molecular category encompasses a broad range of molecular features shared by biological samples associated with multiple different diagnoses associated with multiple different locations in the body. As an example, such a molecular category may encompass molecular features of biological samples that are associated with glioma, testicular germ cell tumor, adenocarcinoma, squamous cell carcinoma, neuroendocrine tumor, mesothelioma, sarcoma, and melanoma. In some embodiments, a node falling within the middle level(s) of the hierarchy represents a molecular category that encompasses molecular features associated with a non-heterogeneous type of cancer. For example, such a molecular category may encompass molecular features of a biological sample associated with ovarian cancer. In some embodiments, a node falling within the bottom level(s) of the hierarchy represents a relatively specific molecular category, meaning that the molecular category encompasses a narrow range of molecular features shared by biological samples associated with a particular histological subtype of cancer (e.g., a molecularly-defined type of cancer). For example, such a molecular category may encompass molecular features of biological samples that are associated with non-basal breast cancer, which is a histological subtype of breast cancer.

Numerous examples of such hierarchies and their constituent molecular categories are provided herein including with reference to FIGS. 1B, 2A 7A-1-7A-3, and 7B-1-7B-5.

TABLE 1

List of ICD codes of disease(s) associated with the molecular categories

| Molecular category | ICD Code |
|---|---|
| Neoplasm | C80 |
| Solid Neoplasm | C76 |
| Hematologic Neoplasm | C96 |
| Melanoma | C43 |
| Sarcoma | C92.3, C47, C48, C47.0-C47.6, C-47.8-C48.2, C48.8, C49, C49.0-49.6, C49.8, C49.9, C22.3, C22.4, C54.2 |
| Mesothelioma | C45 |
| Neuroendocrine | C7A, C7A.0, C7B, C25.4 |
| Squamous Cell Carcinoma | |
| Adenocarcinoma | |
| Glioma | C71.9 |
| Testicular Germ Cell Tumor | C62 |
| Pheochromocytoma | C74.1 |
| Cervical Squamous Cell Carcinoma | C53, C54.9 |
| Liver Neoplasm | C22, C24 |
| Lung Adenocarcinoma | C34 |
| High Grade Glioma IDH Mut | C71.9 |
| Thyroid Neoplasm | C73 |
| Squamous Cell Lung Carcinoma | C34 |
| Thymoma | C37 |
| Prostate Adenocarcinoma | C61 |
| Urinary Bladder Urothelial Carcinoma | C67 |
| Oligodendroglioma | C71.9 |
| Squamous Cell Carcinoma of the Head and Neck | C12, C13, C11, C10 |
| Gastrointestinal Adenocarcinoma | C15-C20 |
| Gynecological | |
| Renal Cell Carcinoma | C64 |
| Astrocytoma | C71.9 |
| Pancreatic Adenocarcinoma | C25 |
| Stomach Adenocarcinoma | C16, C16.9 |
| Pancreatic Adenocarcinoma | C25 |
| Breast Cancer | C50 |
| Ovarian Cancer | C56, C57.0 |
| Uterine Corpus Endometrial Carcinoma | C53, C54, C54.1, C55 |
| Non-Clear Cell Carcinoma | C64 |
| Clear Cell Carcinoma | C64 |
| Basal Breast Cancer | C50 |
| Non-Basal Breast Cancer | C50 |

Following below are more detailed descriptions of various concepts related to, and embodiments of, the systems and methods developed by the inventors for identifying a candidate molecular category for a biological sample. It should be appreciated that various aspects described herein may be implemented in any of numerous ways. Examples of specific implementations are provided herein for illustrative purposes only. In addition, the various aspects described in the embodiments below may be used alone or in any combination and are not limited to the combinations explicitly described herein.

Figure 1B:
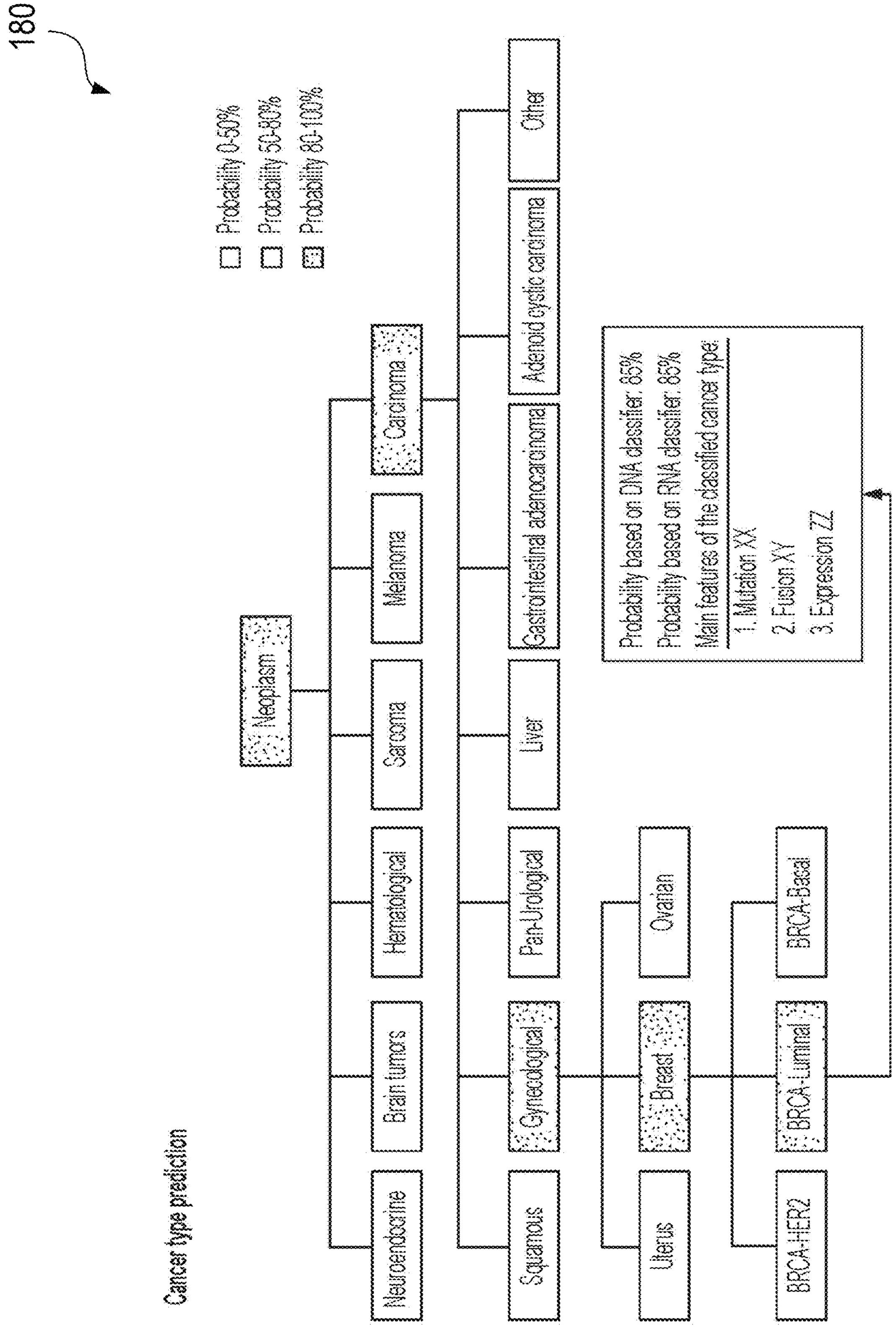
FIG. 1B is a screenshot of an example report indicating candidate molecular categories identified using illustrative technique 100, according to some embodiments of the technology described herein.

FIG. 1A depicts an illustrative technique 100 for identifying a candidate molecular category 105 for a biological sample 101 based on expression data 103 obtained using a sequencing platform 102 to process biological sample 101. The candidate molecular category 105 is identified by processing the expression data 103 using computing device 104.

In some embodiments, the illustrated technique 100 may be implemented in a clinical or laboratory setting. For example, the illustrated technique 100 may be implemented on a computing device 104 that is located within the clinical or laboratory setting. In some embodiments, the computing device 104 may directly obtain the expression data 103 from a sequencing platform 102 located within the clinical or laboratory setting. For example, a computing device 104 included in the sequencing platform 102 may directly obtain the expression data 103 from the sequencing platform 102. In some embodiments, the computing device 104 may indirectly obtain expression data 103 from a sequencing platform 102 that is located within or external to the clinical or laboratory setting. For example, a computing device 104 that is located within the clinical or laboratory setting may obtain expression data 103 via a communication network, such as Internet or any other suitable network, as aspects of the technology described herein are not limited to any particular communication network.

Additionally or alternatively, the illustrated technique 100 may be implemented in a setting that is remote from a clinical or laboratory setting. For example, the illustrated technique 100 may be implemented on a computing device 104 that is located externally from a clinical or laboratory setting. In this case, the computing device 104 may indirectly expression data 103 that is generated using a sequencing platform 102 located within or external to a clinical or laboratory setting. For example, the expression data 103 may be provided to computing device 104 via a communication network, such as Internet or any other suitable network, as aspects of the technology described herein are not limited to any particular communication network.

As shown in FIG. 1A, the technique 100 involves processing a biological sample 101 using a sequencing platform 102, which produces expression data 103. The biological sample 101 may be obtained from a subject having, suspected of having, or at risk of having cancer or any immune-related diseases. The biological sample 101 may be obtained by performing a biopsy or by obtaining a blood sample, a salivary sample, or any other suitable biological sample from the subject. The biological sample 101 may include diseased tissue (e.g., cancerous), and/or healthy tissue. In some embodiments, the origin or preparation methods of the biological sample may include any of the embodiments described herein including with respect to the "Biological Samples" section.

In some embodiments, the sequencing platform 102 may be a next generation sequencing platform (e.g., Illumina™, Roche™, Ion Torrent™, etc.), or any high-throughput or massively parallel sequencing platform. In some embodiments, the sequencing platform 102 may include any suitable sequencing device and/or any sequencing system including one or more devices. In some embodiments, these methods may be automated, in some embodiments, there may be manual intervention. In some embodiments, the expression data 103 may be the result of non-next generation sequencing (e.g., Sanger sequencing, microarrays).

Expression data 103 can include the sequence data generated by a sequencing protocol (e.g., the series of nucleotides in a nucleic acid molecule identified by next-generation sequencing, sanger sequencing, etc.) as well as information contained therein (e.g., information indicative of source, tissue type, etc.) which may also be considered information that can be inferred or determined from the sequence data. In some embodiments, expression data 103 can include information included in a FASTA file, a description and/or quality scores included in a FASTQ file, an aligned position included in a BAM file, and/or any other suitable information obtained from any suitable file.

In some embodiments, the expression data 103 may be generated using a nucleic acid from a sample from a subject. Reference to a nucleic acid may refer to one or more nucleic acid molecules (e.g., a plurality of nucleic acid molecules). In some embodiments, the sequence information may be sequence data indicating a nucleotide sequence of deoxyribonucleic acid (DNA) and/or ribonucleic acid (RNA) from a previously obtained biological sample of a subject having, suspected of having, or at risk of having a disease.

In some embodiments, the nucleic acid is RNA. In some embodiments, sequenced RNA comprises both coding and non-coding transcribed RNA found in a sample. When such RNA is used for sequencing the sequencing is said to be generated from "total RNA" and also can be referred to as whole transcriptome sequencing. Alternatively, the nucleic acids can be prepared such that the coding RNA (e.g., mRNA) is isolated and used for sequencing. This can be done through any means known in the art, for example by isolating or screening the RNA for polyadenylated sequences. This is sometimes referred to as mRNA-Seq.

In some embodiments, the nucleic acid is DNA. In some embodiments, the nucleic acid is prepared such that the whole genome is present in the nucleic acid. In some embodiments, the nucleic acid is processed such that only the protein coding regions of the genome remain (e.g., the exome). When nucleic acids are prepared such that only the exome is sequenced, it is referred to as whole exome sequencing (WES). A variety of methods are known in the art to isolate the exome for sequencing, for example, solution-based isolation wherein tagged probes are used to hybridize the targeted regions (e.g., exons) which can then be further separated from the other regions (e.g., unbound oligonucleotides). These tagged fragments can then be prepared and sequenced.

In some embodiments, expression data 103 may include raw DNA or RNA sequence data, DNA exome sequence data (e.g., from whole exome sequencing (WES), DNA genome sequence data (e.g., from whole genome sequencing (WGS)), RNA expression data, gene expression data, bias-corrected gene expression data, or any other suitable type of sequence data comprising data obtained from the sequencing platform 102 and/or comprising data derived from data obtained from sequencing platform 102. In some embodiments, the origin or preparation of the expression data 103 may include any of the embodiments described with respect to the "Expression Data" and "Obtaining RNA expression data" sections.

Figure 3:
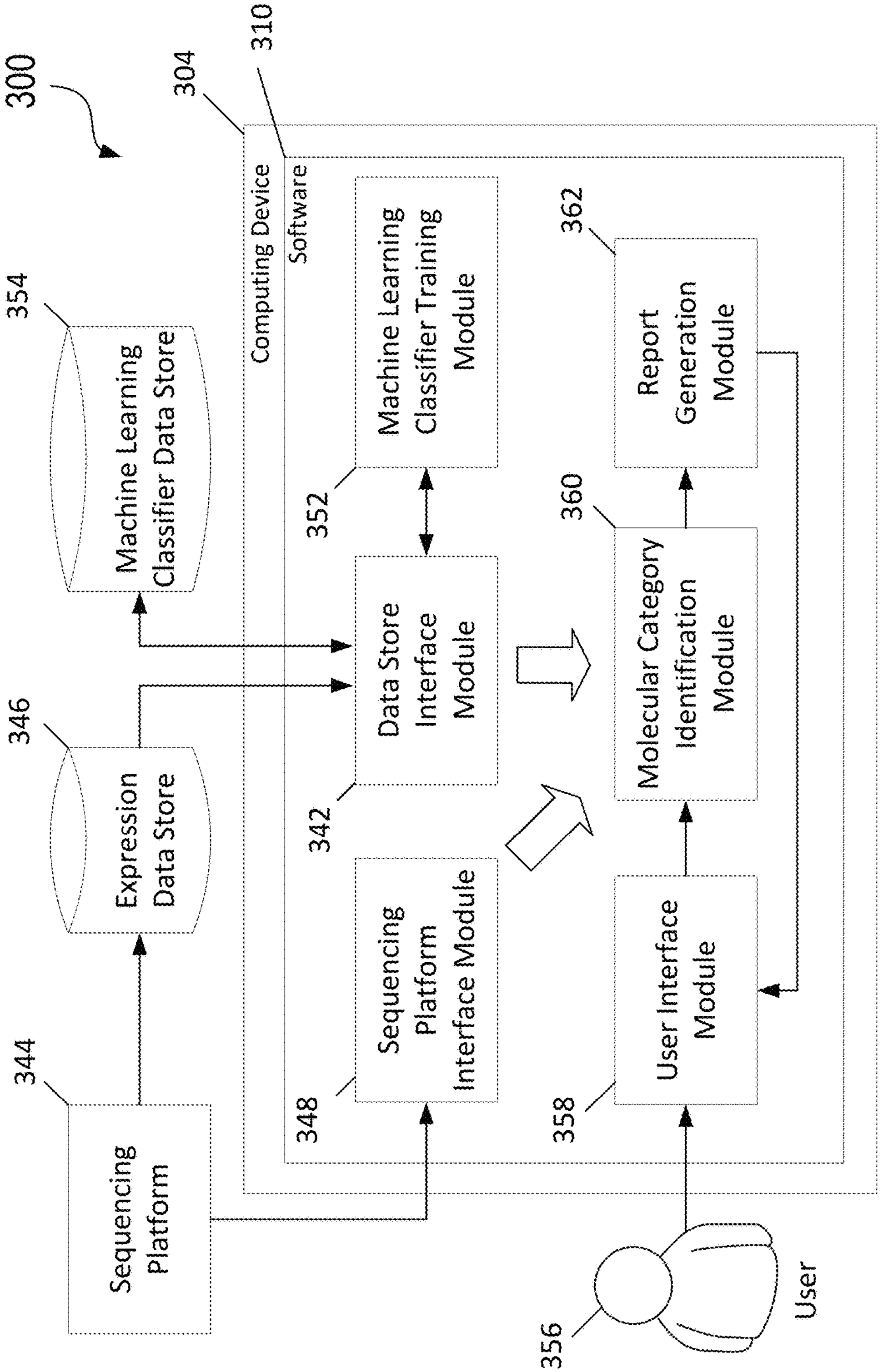
FIG. 3 is a block diagram of a system 300 including example computing device 304 and software 310, according to some embodiments of the technology described herein.

Regardless of the expression data 103 obtained, the expression data 103 is processed using 104. In some embodiments, computing device 104 can be one or multiple computing devices of any suitable type. For example, the computing device 104 may be a portable computing device (e.g., a laptop, a smartphone) or a fixed computing device (e.g., a desktop computer, a server). When computing device 104 includes multiple computing devices, the device(s) may be physically co-located (e.g., in a single room) or distributed across multiple physical locations. In some embodiments, the computing device 104 may be part of a cloud computing infrastructure. In some embodiments, one or more computer(s) 104 may be co-located in a facility operated by an entity (e.g., a hospital, a research institution). In some embodiments, the one or more computing device(s) 104 may be physically co-located with a medical device, such as a sequencing platform 102. For example, a sequencing platform 102 may include computing device 104. FIG. 3 system 300 including example computing device 304 and software 310

In some embodiments, the computing device 104 may be operated by a user such as a doctor, clinician, researcher, patient, or other individual. For example, the user may provide the expression data 103 as input to the computing device 104 (e.g., by uploading a file), and/or may provide user input specifying processing or other methods to be performed using the expression data 103.

In some embodiments, expression data 103 may be processed by one or more software programs running on computing device 104 (e.g., as described herein including at least with respect to FIG. 3). In particular, in some embodiments, the expression data 103 may be processed by a hierarchy of machine learning classifiers that corresponds to a hierarchy of molecular categories. For example, a first machine learning classifier of the hierarchy of machine learning classifiers may be used to process first expression data associated with a first molecular category. The first machine learning classifier may be trained to predict whether the biological sample 101 belongs to the first molecular category in the hierarchy of molecular categories. In some embodiments, such processing may be performed for some, most, or all of the molecular categories included in the hierarchy of molecular categories to obtain machine learning classifier outputs. Illustrative techniques for processing the expression data are described herein including at least with respect to FIG. 2B and FIGS. 4A-4C.

Based on the outputs of the machine learning classifiers, including the output of the first machine learning classifier, in some embodiments, at least one candidate molecular category 105 are identified for the biological sample 101. The at least one candidate molecular category 105 may include one or multiple candidate molecular categories for the biological sample 101. In some embodiments, candidate molecular categories 105 include molecular categories at different levels of the hierarchy of molecular categories. For example, a parent node representing a broad molecular category and one of its child nodes representing a more specific molecular category may be identified for the biological sample. Additionally or alternatively, multiple nodes representing multiple molecular categories at the same level of the hierarchy may be identified for the biological sample. In some embodiments, no candidate molecular categories may be identified for the biological sample.

In some embodiments, the at least one identified candidate molecular category 105 may be provided as output. In some embodiments, for example, the identified candidate molecular categories may be used to generate a report to be output to user (e.g., via a graphical user interface (GUI). FIG. 1B is a screenshot of an example report indicating candidate molecular categories identified using illustrative technique 100. As shown, the example report provides a visualization of the hierarchy of molecular categories. The report 180 also indicates the probability that the biological sample belongs to each particular molecular category, the type of expression data used for candidate molecular category identification, and different features associated with the identified molecular category (e.g., most probable molecular categories). For example, as shown in FIG. 1D, features associated with the identified molecular category include mutations, fusions, and expression of particular genes.

In some embodiments, the at least one candidate molecular category 105 may be used to identify a tumor-specific treatment for the subject from which the biological sample 101 was obtained. For example, as described above, a molecular category may be associated with at least one clinical diagnosis. A treatment known to be effective for tumors of the clinical diagnosis may be identified to treat the biological sample 101.

Additionally or alternatively, the at least one candidate molecular diagnosis may be used to confirm a clinical diagnosis that was previously identified for the biological sample 101. For example, a clinical diagnosis may be received from a clinician. The illustrative techniques 100 may include comparing the clinical diagnosis received from the clinician to the clinical diagnosis associated with at least one candidate molecular category 105 identified for the biological sample 101. If the diagnoses do not match, then the clinical diagnoses associated with the at least one candidate molecular category 105 may be provided to the clinician to inform treatment selection.

Hierarchy of Molecular Categories

In some embodiments, the techniques described herein include using a hierarchy of molecular categories to identify candidate molecular categories for a biological sample. An illustrative hierarchy 230 is shown in FIG. 2A.

In some embodiments, the hierarchy 230 of molecular categories is a directed graph that includes nodes and edges. In some embodiments, a node represents a molecular category, while an edge represents a relationship between molecular categories. For example, as shown in FIG. 2A, node 202 represents molecular category A and node 204*a* represents molecular category B. The edge between node 202 and node 204*a* represents a relationship between those nodes. In particular, node 202 is a parent node of child node 204*a*. Similarly, node 202 is a parent node of nodes 204*b-c*, and node 204*b* is a parent node of child nodes 206*a-b*. It should be appreciated, however, that the hierarchy of molecular categories 200 is not restricted to the nodes shown in FIG. 2A. Rather, any suitable number of nodes representing any suitable number of molecular categories may be included in the hierarchy of molecular categories. For example, the hierarchy of molecular categories 200 may include at least 10 nodes representing 10 molecular categories, at least 20 nodes representing 20 molecular categories, at least 40 nodes representing 40 molecular categories, at least 60 nodes representing 60 molecular categories, or at least 100 nodes representing 100 molecular categories. Additional example hierarchies of molecular categories are provided at least in FIG. 1B, in FIGS. 7A-1-7A-3, and in FIGS. 7B-1-7B-5.

In some embodiments, as described above, node at higher levels of the hierarchy represent molecular categories that are more general, meaning that they encompass a broad range of molecular features shared by biological samples associated with multiple different diagnoses associated with multiple different locations in the body. For example, molecular category A may be a general molecular category, such as neoplasm (e.g., as shown in FIGS. 7A-1-7A-3 and 7B-1-7B-5), which is general molecular category associated with multiple different diagnoses associated with multiple different locations in the body.

In some embodiments, a node falling within the middle levels of the hierarchy represents a molecular category that encompasses molecular features associated with a non-heterogeneous type of cancer. For example, molecular category C, represented by node 204*b*, may represent a molecular category such as ovarian cancer or thymoma (e.g., as shown in FIGS. 7A-1-7A-3 and 7B-1-7B-5), each of which encompasses molecular features associated with a respective non-heterogeneous type of cancer.

In some embodiments, molecular categories at lower levels of the hierarchy of molecular categories are more specific such that they encompass a narrow range of molecular features shared by biological samples associated with a particular histological subtype of cancer (e.g., a molecularly-defined type of cancer). For example, node 206*b* represents a molecular category F at the bottom level of the example hierarchy of molecular classifiers 200. Molecular category F may include, for example, basal breast cancer or non-basal breast cancer (e.g., as shown in FIGS. 7A-1-7A-3 and 7B-1-7B-5), each of which is associated with a molecularly-defined type of cancer.

Identifying Candidate Molecular Categories

FIG. 2B-1 is a diagram depicting an illustrative technique 220 for processing expression data to identify a candidate molecular category for a biological sample, according to some embodiments of the technology described herein. In some embodiments, illustrative technique 220 includes processing expression data 221 to obtain features 222 and apply machine learning techniques 230 to the features 222 to identify at least one candidate molecular category 229 for the biological sample from which the expression data was obtained.

In some embodiments, the expression data 221 may include any suitable expression data, such as the expression data described above with respect to FIG. 1A and described herein including in the section "Expression Data." For example, the expression data 221 may include RNA expression data and/or DNA expression data.

In some embodiments, expression data 221 is processed to obtain features 222 from the expression data 221. In some embodiments, processing the expression data 221 includes generating numeric and/or binary data based on the expression data to obtain the features 222. For example, when the expression data 221 is RNA expression data, processing the expression data 221 may include ranking expression levels of genes in one or more gene sets. Additionally or alternatively, when the expression data 221 is DNA expression data, processing the expression data 221 may include detecting determining copy numbers of genes, detecting the presence or absence of gene mutations, detecting the presence or absence of mutational hotspots, detecting the presence or absence of gene fusion, quantifying copy number alterations, quantifying loss of heterozygosity, quantifying tumor mutational burden, determining ploidy, and/or detecting microsatellite instability (MSI) status. Example RNA and DNA features are described herein in more detail including with respect to FIGS. 6A and 6B.

In some embodiments, features 222 include subsets of features that are each associated with a particular molecular category. For examples, features B 224*a*, features C 225*a*, features D 226*a*, features E 227*a*, and features F 228*a* are associated, respectively, with molecular category B 224*c*, molecular category C 225*c*, molecular category D 226*c*, molecular category E 227*c*, and molecular category F 228*c*.

Figure 8A:
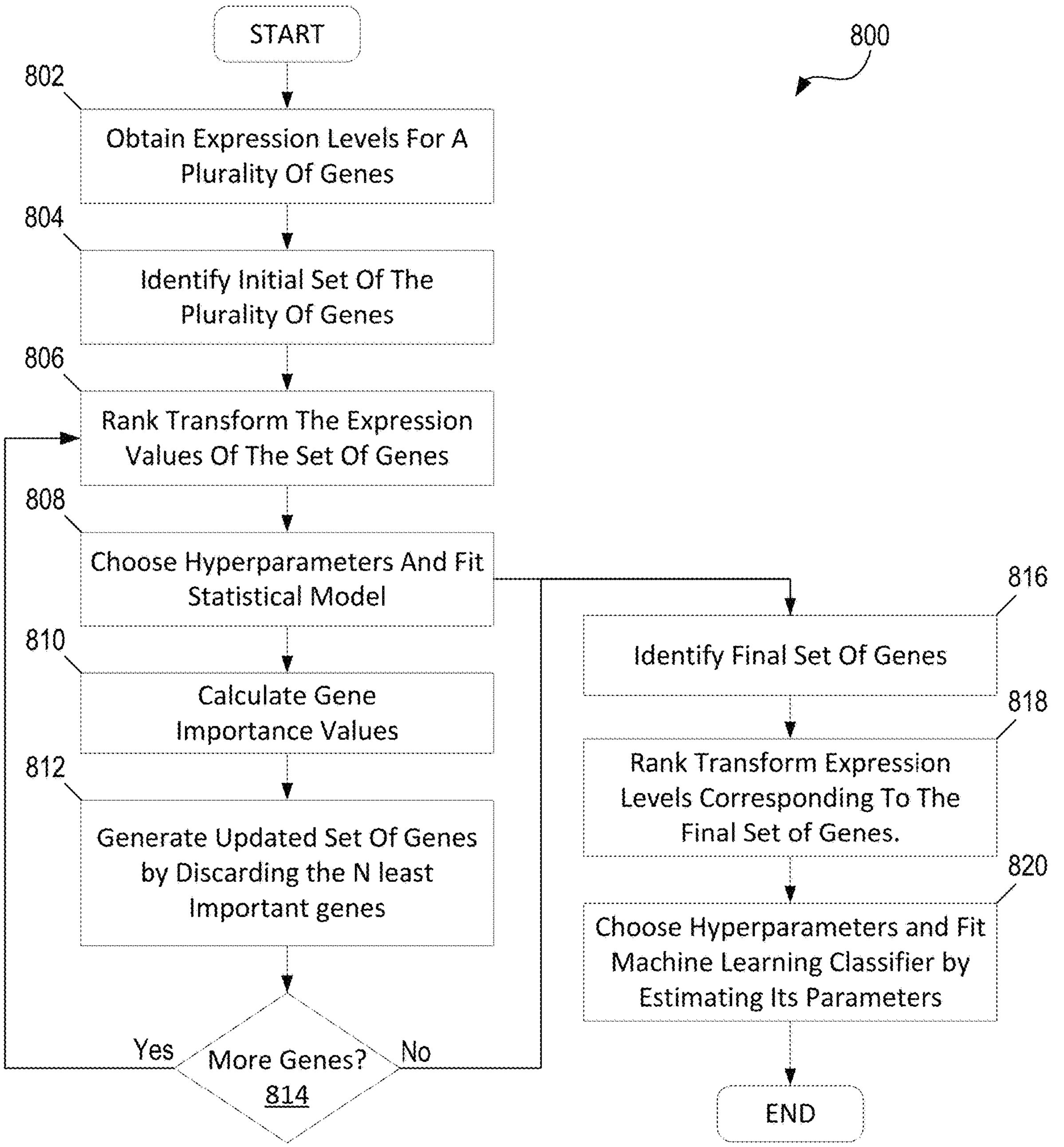
FIG. 8A shows a flowchart of an illustrative process 800 for training an RNA-based machine learning classifier to identify a candidate molecular category for a biological sample, according to some embodiments of the technology described herein.

In some embodiments, a subset of RNA features includes a ranked gene set, where genes in the gene set are specific to the associated molecular category. For example, features E 227*a* may include a ranked set of genes, where genes in the gene set are specific to molecular category E 227*c*. Table 3 lists example genes that are specific to example molecular categories. Techniques for identifying genes that are specific to a molecular category are described herein including at least with respect to FIG. 8A.

Figure 6A:
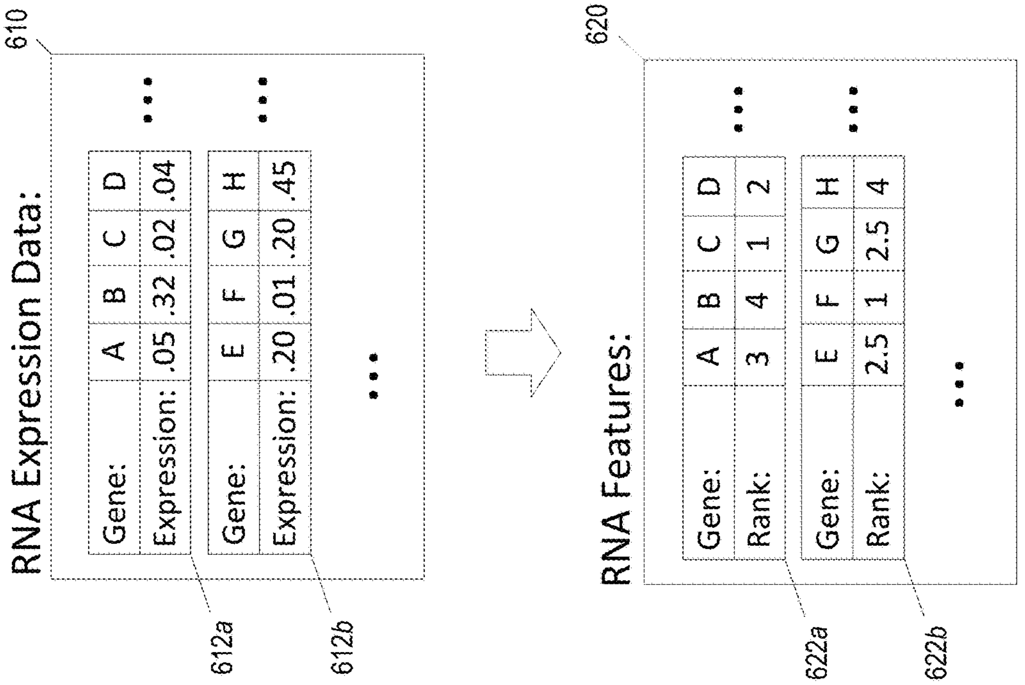
FIG. 6A is a diagram showing example RNA expression data and example RNA features obtained from the RNA expression data, according to some embodiments of the technology described herein.
Figure 6B:
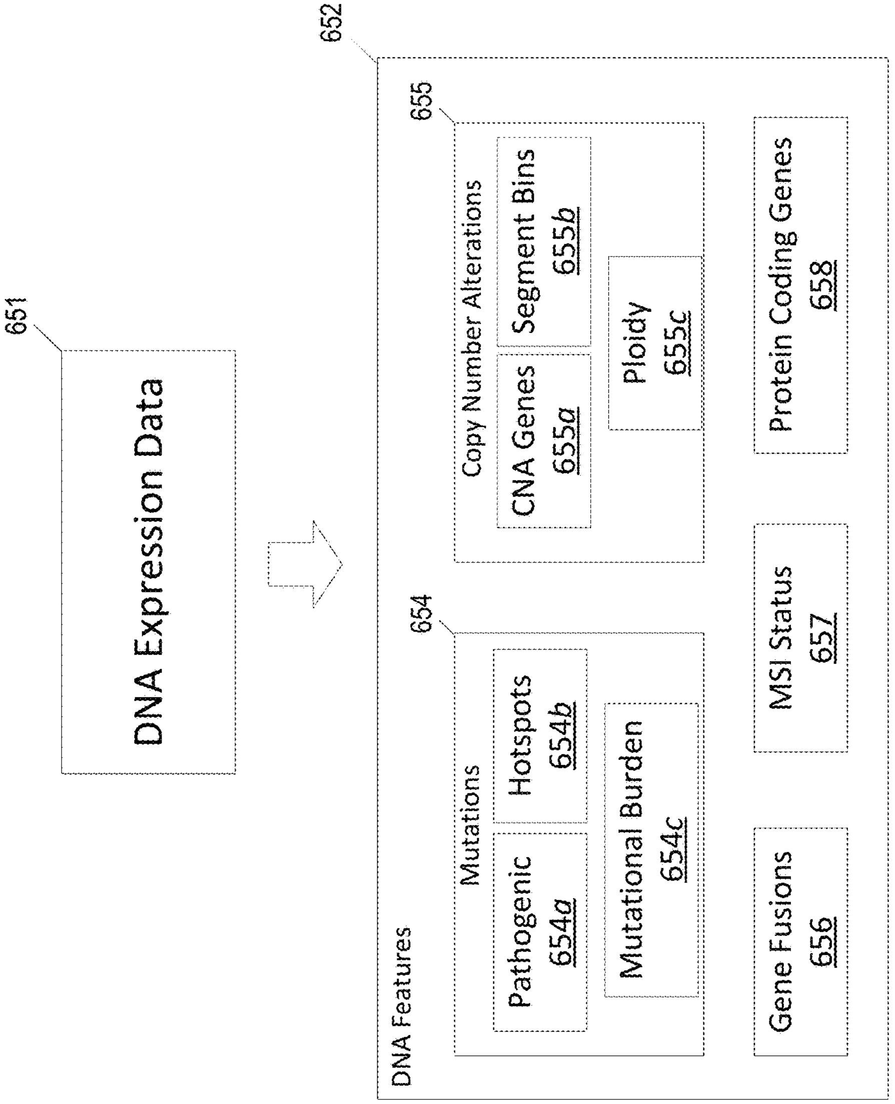
FIG. 6B is a diagram showing example DNA expression data and example DNA features obtained from the DNA expression, according to some embodiments of the technology described herein.
Figure 8B:
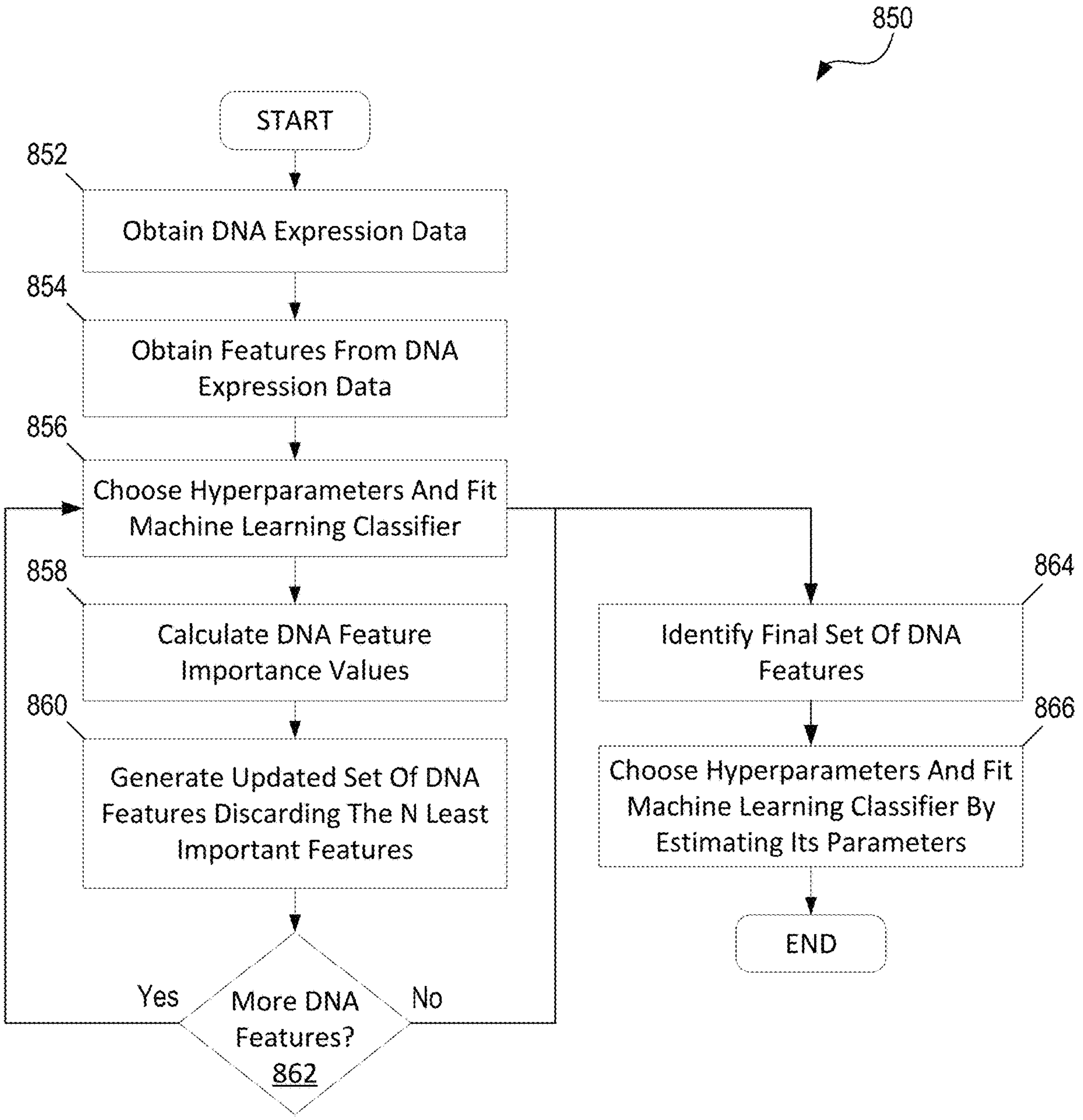
FIG. 8B shows a flowchart of an illustrative process 850 for training a DNA-based machine learning classifier to identify a candidate molecular category for a biological sample, according to some embodiments of the technology described herein.

Additionally or alternatively, a subset of DNA features includes DNA features (e.g., mutational burden, ploidy, and other the features described with respect to FIG. 6B) that are specific to the molecular category. For example, features D 226 may include DNA features that are specific to molecular category E. Table 5 lists example DNA features that are specific to example molecular categories. Techniques for identifying DNA features that are specific to a molecular category are described herein including at least with respect to FIG. 8B.

In some embodiments, the machine learning techniques 230 include processing features 222 using a hierarchy of machine learning classifiers. As shown, the hierarchy of machine learning classifiers includes machine learning classifier B 224*b*, machine learning classifier C 225*b*, machine learning classifier D 226*b*, machine learning classifier E 227*b*, and machine learning classifier F 228*b*. Each machine learning classifier may include any suitable classifier and an illustrative example of such a classifier is described herein including at least with respect to FIG. 2C.

In some embodiments, each of the machine learning classifiers corresponds to a molecular category of a hierarchy of molecular categories (e.g., hierarchy 200 of FIG. 2A), meaning that it is trained to process features associated with the molecular category to determine whether to identify the molecular category as a candidate molecular category for the biological sample. For example, machine learning classifier B 224*c* is trained to process features B 224*a* to determine whether to identify molecular category B 224*c* as a candidate molecular category for the biological sample. Techniques for training machine learning classifiers are described herein including at least with respect to FIGS. 8A-8B.

In some embodiments, at least one candidate molecular category 229 is identified as a result of machine learning techniques 230. In some embodiments, the at least one candidate molecular category includes one or multiple of the molecular categories B-F. For example, a candidate molecular category may be identified at each level of the hierarchy of machine learning classifiers. Additionally or alternatively, multiple candidate molecular categories may be identified at one or more levels of the hierarchy. Additionally or alternatively, no candidate molecular category may be identified for one or more levels of the hierarchy.

FIG. 2B-2 is a diagram depicting an example 230 of illustrative technique 250 for processing expression data to identify a candidate molecular category for a biological sample, according to some embodiments of the technology described herein. As explained above, the machine learning techniques 230 are used to process features 222 obtained from expression data 221 to identify candidate molecular categories 229 for the biological sample.

In some embodiments, the machine learning techniques 230 include determining whether to identify any of the molecular categories (e.g., B, C, and D) descending from molecular category A 223 as a candidate molecular category for the biological sample. In some embodiments, the techniques include processing features B 224*a* using machine learning classifier B 224*b* to determine whether to identify the molecular category B 224*c* as a candidate molecular category, processing features C 225*a* using machine learning classifier C 225*b* to determine whether to identify the molecular category C 225*c* as a candidate molecular category, and processing features D 226*a* using machine learning classifier D 226*b* to determine whether to identify the molecular category D 226*c* as a candidate molecular category.

In some embodiments, the machine learning techniques 230 include determining whether to identify any of the molecular categories (e.g., E and F) descending from molecular category C 225*c* as a candidate molecular category for the biological sample. In some embodiments, the techniques include processing features E 227*a* using machine learning classifier E 227*b* to determine whether to identify the molecular category E 227*c* as a candidate molecular category and processing features F 228*a* using machine learning classifier F 228*b* to determine whether to identify the molecular category C 228*c* as a candidate molecular category.

In some embodiments, the output of each machine learning classifier is indicative of the probability that biological sample belongs to the particular molecular category corresponding to the machine learning classifier. For example, the output of machine learning classifier B 224*b* may indicate the probability that the biological sample belongs to molecular category B 224*c*. Techniques for processing features using a machine learning classifier are described herein including at least with respect to FIG. 2C.

In some embodiments, after processing the features 222 using the machine learning classifiers included in the hierarchy of machine learning classifiers, the techniques include identifying candidate molecular categories 229 for the biological sample. In the example shown in FIG. 2B-2, molecular category C 225*c* and molecular category F 228*c* are identified as candidate molecular categories 229 for the biological sample. Techniques for identifying candidate molecular categories for the biological sample are described herein including at least with respect to FIG. 2D.

Machine Learning Classifier

Figure 2C:
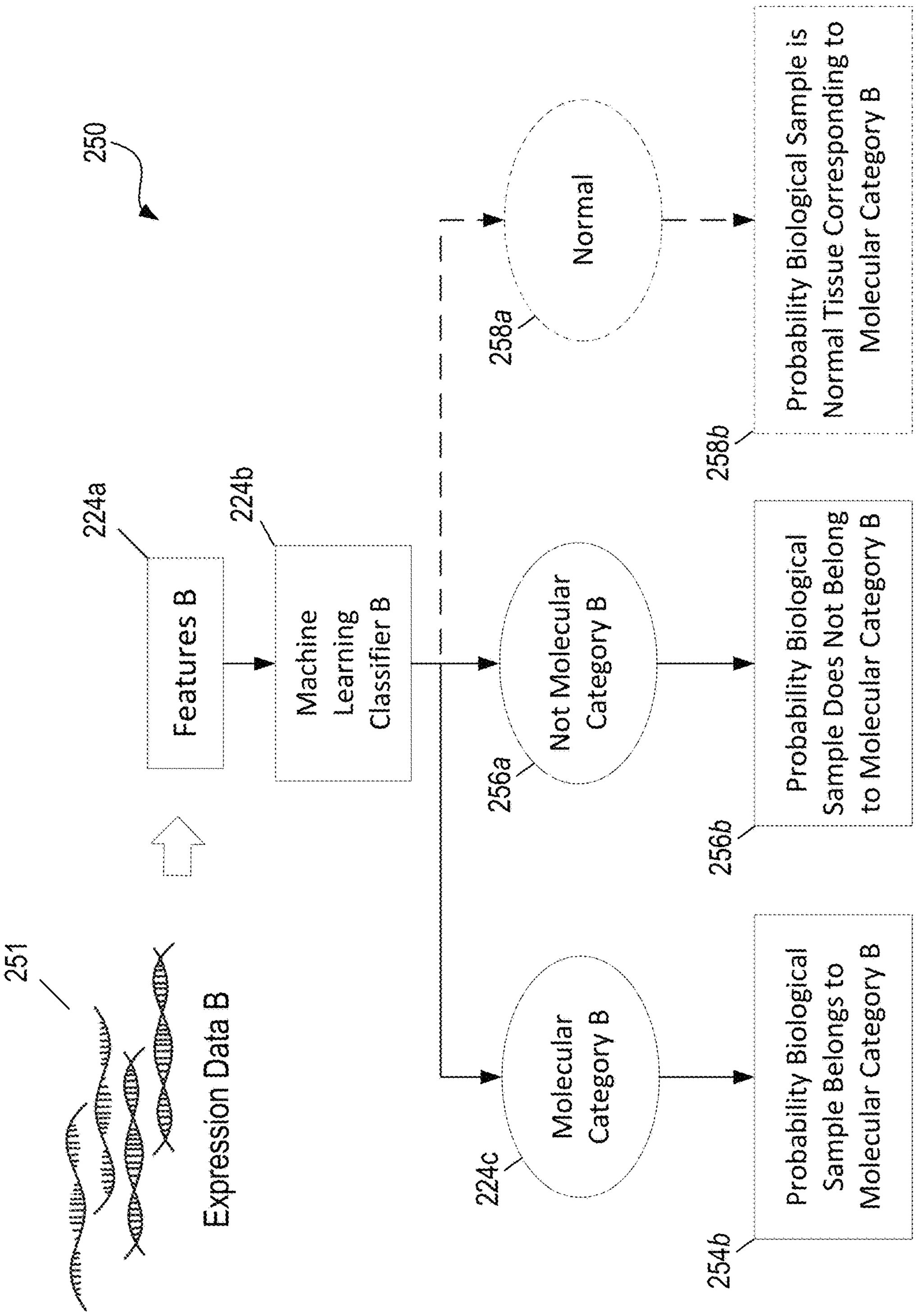
FIG. 2C shows an illustrative diagram 250 of a two-class classifier, optionally a multi-class classifier, used to determine whether a molecular category is a candidate molecular category for a biological sample, according to some embodiments of the technology described herein.

As described above, a hierarchy of machine learning classifiers includes multiple machine learning classifiers used to process features obtained from expression data obtained from the biological sample. FIG. 2C shows an illustrative diagram 250 of a two-class classifier, optionally a multi-class classifier, according to some embodiments of the technology described herein.

In some embodiments, a machine learning classifier included in the hierarchy of machine learning classifiers (e.g., machine learning classifier B 224*b*) can include for example, a gradient boosted tree, a neural network, a logistic regression model, a support vector machine, a Bayesian classifier, a random forest classifier, or any suitable type of machine learning classifier, as aspects of the technology described herein are not limited to any particular type of machine learning classifier In some embodiments, the machine learning classifier B 224*b* is trained to distinguish between two classes: molecular category B 224*c* and not molecular category B 256*a* (e.g., all other molecular categories, not including molecular category B 224*c*). In particular, the machine learning classifier may be trained to predict the probability B 254*b* that the biological sample belongs to molecular category B 224*c* versus the probability 256*b* that the biological sample does not belong to molecular category B 256*a*.

In some embodiments, the machine learning classifier B 224*b* is trained to distinguish between biological samples belonging to molecular category B 224*c* and not molecular category A 376*b* based on features B 224*b* obtained from expression data B 251. As explained above with respect to FIG. 2B-1, in some embodiments, the feature B 224*b* are unique to molecular category B 224*b*. By processing features B 224*b* that are unique to molecular category B 224*c*, it is possible for the machine learning classifier B 224*b* to distinguish between molecular category B 224*c* and not molecular category B 256*a*.

In some embodiments, the sample site from which the biological sample was obtained may affect the accuracy of the results of the machine learning classifier B 224*b* when the machine learning classifier B 224*b* is used to process RNA expression data. Consider, as an example, a tumor sample obtained from the liver that contains normal liver tissue. Since liver neoplasm originates in the liver, the normal tissue from the liver and tumor tissue belonging to the liver neoplasm molecular category may share similar RNA expression profiles. Therefore, a machine learning classifier that receives the tumor sample and is not trained to distinguish between tissue belonging to the liver neoplasm molecular category and normal liver tissue may inaccurately predict a high probability for the liver neoplasm molecular category, even when that is not the case.

To mitigate these biases, in some embodiments, the machine learning classifier B 224*b* may comprise a multi-class classifier trained to distinguish between three classes: normal tissue 258*a* (e.g., tissue from the sample site that is not diseased), molecular category B 224*c*, and molecular category B 254*a*. In this embodiment, the machine learning classifier B 224*b* may be trained to determine probability 356*b* that the biological sample belongs to the normal tissue corresponding to the molecular category B.

Figure 2D:
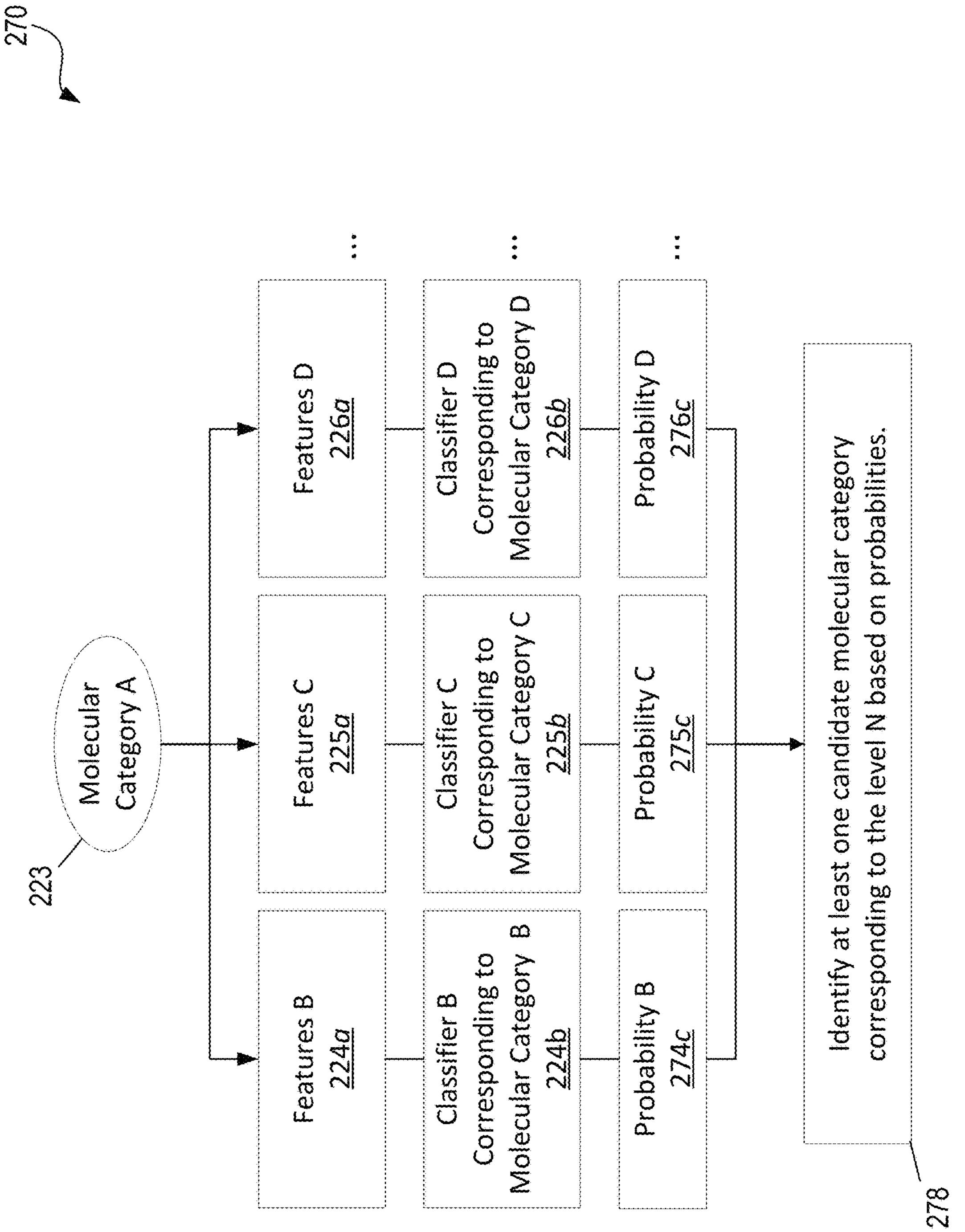
FIG. 2D illustrates identifying a candidate molecular category for a biological sample using machine learning classifiers at the same level of a hierarchy of machine learning classifiers, according to some embodiments of the technology described herein.

FIG. 2D illustrates identifying a candidate molecular category for a biological sample using machine learning classifiers at a same level of a hierarchy of machine learning classifiers, according to some embodiments of the technology described herein.

In some embodiments, classifier B 224*b*, classifier C 225*b*, and classifier D 226*b* are each associated with molecular categories represented by nodes that descend from parent node 223, representing molecular category A. Therefore, classifiers B-D are positioned at a same level (e.g., level N) of the hierarchy of machine learning classifiers as one another.

As described above, the machine learning techniques 230, shown in FIG. 2A, include using a hierarchy of machine learning classifiers to obtain outputs indicating the probability that a biological sample belongs to each molecular category. For example, as shown in FIG. 2D, classifier B 224*a* outputs probability B 274*c*, classifier C 225*a* outputs probability C 275*c*, and classifier D 226*b* outputs probability D 276*c*.

In some embodiments, the probabilities 274*c*, 275*c*, and 276*c* may be used to identify at least one candidate molecular category for the biological sample that corresponds to level N. In some embodiments, the techniques include comparing each of probability B 274*c*, probability C 275*c*, and probability D 276*c* to a threshold. If the probability exceeds the threshold the molecular category may be identified as a candidate molecular category for the biological sample. By contrast, a molecular category corresponding to a classier that output a probability that is below a threshold may be excluded. For example, if the probability exceeds a threshold of at least 0.01, at least 0.05, at least 0.1, at least 0.3, at least 0.5, or at least 0.7 then the molecular category may be identified as a candidate molecular category for the biological sample.

Additionally or alternatively, the probabilities 274*c*, 275*c*, and 276*c* may be compared to one another to identify at least one candidate molecular category for the biological sample. For example, the molecular category or categories corresponding to the highest probability or N highest probabilities at the level of the hierarchy (e.g., level N of the hierarchy) may be identified as a candidate molecular category for the biological sample.

In some embodiments, the techniques 270 are used to identify candidate molecular categories at one or more levels of the hierarchy of machine learning classifiers. For example, the techniques may be used to identify candidate molecular categories at one or multiple levels of the hierarchy.

FIG. 3 is a block diagram of a system 300 including example computing device 304 and software 310, according to some embodiments of the technology described herein.

In some embodiments, computing device 304 includes software 310 configured to perform various functions with respect to the expression data 303. In some embodiments, software 310 includes a plurality of modules. A module may include processor-executable instructions that, when executed by at least one computer hardware processor, cause the at least one computer hardware processor to perform the function(s) of the module. Such modules are sometimes referred to herein as "software modules." each of which includes processor executable instructions configured to perform one or more processes, such as the processes described herein including at least with respect to FIGS. 4A-4C and FIGS. 8A-8B.

For example, as shown in FIG. 3, software 310 includes one or more software modules for processing expression data 303, such as a molecular category identification module 360 and a report generation module 362. In some embodiments, the software 310 additionally includes a user interface module 358, a sequencing platform interface module 348, and/or a data store interface module 342 for obtaining data (e.g., user input, expression data, machine learning classifier(s)). In some embodiments, data is obtained from sequencing platform 344, expression data store 346, and/or machine learning classifier data store 354. In some embodiments, the software 310 further includes machine learning classifier training module 352 for training one or more machine learning classifiers (e.g., stored in machine learning classifier data store 354).

In some embodiments, the molecular category identification module 360 obtains expression data from the expression data store 346 and/or the sequencing platform 344 and obtains machine learning classifiers from the machine learning classifier data store 354.

In some embodiments, the obtained machine learning classifiers include machine learning classifiers that are arranged into one or more hierarchies of machine learning classifiers. In some embodiments, different hierarchies include classifiers trained on different types of data. For example, a hierarchy of RNA-based machine learning classifiers includes classifiers trained using RNA data, while a hierarchy of DNA-based machine learning classifiers includes classifiers trained using DNA data. Regardless of the differences in training data, both hierarchies may be used by the molecular category identification module 360 for the same purpose, as described herein.

In some embodiments, the molecular category identification module 360 processes the obtained expression data using the machine learning classifiers of a first hierarchy of machine learning classifiers (e.g., a hierarchy of RNA-based machine learning classifiers) to identify candidate molecular categories for the biological sample from which the expression data was obtained. For example, the molecular category identification module 360 may process the obtained expression data using machine learning classifiers at a first level of the hierarchy to identify a first candidate molecular category for the biological sample. In some embodiments, the molecular category identification module 360 may process the obtained expression data using machine learning classifiers at a second level of the hierarchy to identify a second candidate molecular category for the biological sample. In some embodiments, the second candidate molecular category may be more specific than the first candidate molecular category. Techniques for using a hierarchy of machine learning classifiers to identify candidate molecular categories for a biological sample are described herein including at least with respect to FIGS. 4A-C.

Additionally or alternatively, the machine learning molecular category identification module 360 processes the obtained expression data using machine learning classifiers of a second hierarchy of machine learning classifiers (e.g., a hierarchy of DNA-based machine learning classifiers) to identify candidate molecular categories for the biological sample. In some embodiments, the results may be used to confirm or take the place the results obtained from the first hierarchy of classifiers.

In some embodiments, the molecular category identification module 360 obtains the expression data and/or the machine learning classifiers via one or more interface modules. In some embodiments, the interface modules include sequencing platform interface module 348 and data store interface module 342. The sequencing platform interface module 348 may be configured to obtain (either pull or be provided) expression data from the sequencing platform 344. The data store interface module may be configured to obtain (either pull or be provided) expression data and/or machine learning classifiers from the expression data store 346 and/or the machine learning classifier data store 354, respectively. The data and/or the machine learning classifiers may be provided via a communication network (not shown), such as Internet or any other suitable network, as aspects of the technology described herein are not limited to any particular communication network.

In some embodiments, expression data store 346 includes any suitable data store, such as a flat file, a data store, a multi-file, or data storage of any suitable type, as aspects of the technology described herein are not limited to any particular type of data store. The expression data store 346 may be part of software 304 (not shown) or excluded from software 304, as shown in FIG. 3.

In some embodiments, expression data store 346 stores expression data obtained from biological sample(s) of one or more subjects. In some embodiments, the expression data may be obtained from sequencing platform 344 and/or from one or more public data stores and/or studies. In some embodiments, a portion of the expression data may be processed by the molecular category identification module 360 to identify candidate molecular categories for a biological sample. In some embodiments, a portion of the expression data may be used to train one or more machine learning classifiers (e.g., with the machine learning classifier training module 364).

In some embodiments, machine learning classifier data store 354 includes any suitable data store, such as a flat file, a data store, a multi-file, or data storage of any suitable type, as aspects of the technology described herein are not limited to any particular type of data store. The machine learning classifier data store 354 may be part of software 304 (not shown) or excluded from software 310, as shown in FIG. 3.

In some embodiments, machine learning classifier data store 354 stores one or more hierarchies of machine learning classifiers used to identify candidate molecular categories for a biological sample. In some embodiments, each hierarchy of machine learning classifiers corresponds to a hierarchy of molecular categories. The relationships between the machine learning classifiers in each hierarchy may be stored in the machine learning classifier data store 354. For example, the machine learning classifier data store 354 may store a relationship between a machine learning classifier trained to determine the probably that the biological sample belongs to a molecular category represented by a parent node and a machine learning classifier trained to determine whether the biological sample belongs to a molecular category represented by a child node of the parent node.

In some embodiments, report identification module 362 processes results obtained from the molecular category identification module 360 to generate one or more reports. An example report is described above including at least with respect to FIG. 1B.

User interface 348 may be a graphical user interface (GUI), a text-based user interface, and/or any other suitable type of interface through which a user may provide input. For example, in some embodiments, the user interface may be a webpage or web application accessible through an Internet browser. In some embodiments, the user interface may be a graphical user interface (GUI) of an app executing on the user's mobile device. In some embodiments, the user interface may include a number of selectable elements through which a user may interact. For example, the user interface may include dropdown lists, checkboxes, text fields, or any other suitable element.

In some embodiments, machine learning classifier training module 352, referred to herein as training module 352, is configured to train the one or more machine learning classifiers used to identify candidate molecular categories for the biological sample. This may include training a machine learning classifier to determine the probability that the biological sample belongs to a particular molecular category. In some embodiments, the training module 352 trains a machine learning classifier using a training set of expression data. For example, the training module 352 may obtain training data via data store interface module 342. In some embodiments, the training module 352 may provide trained machine learning classifiers to the machine learning classifier data store 354 via data store interface module 342. Techniques for training machine learning classifiers are described herein including at least with respect to FIGS. 8A-B.

Figure 4A:
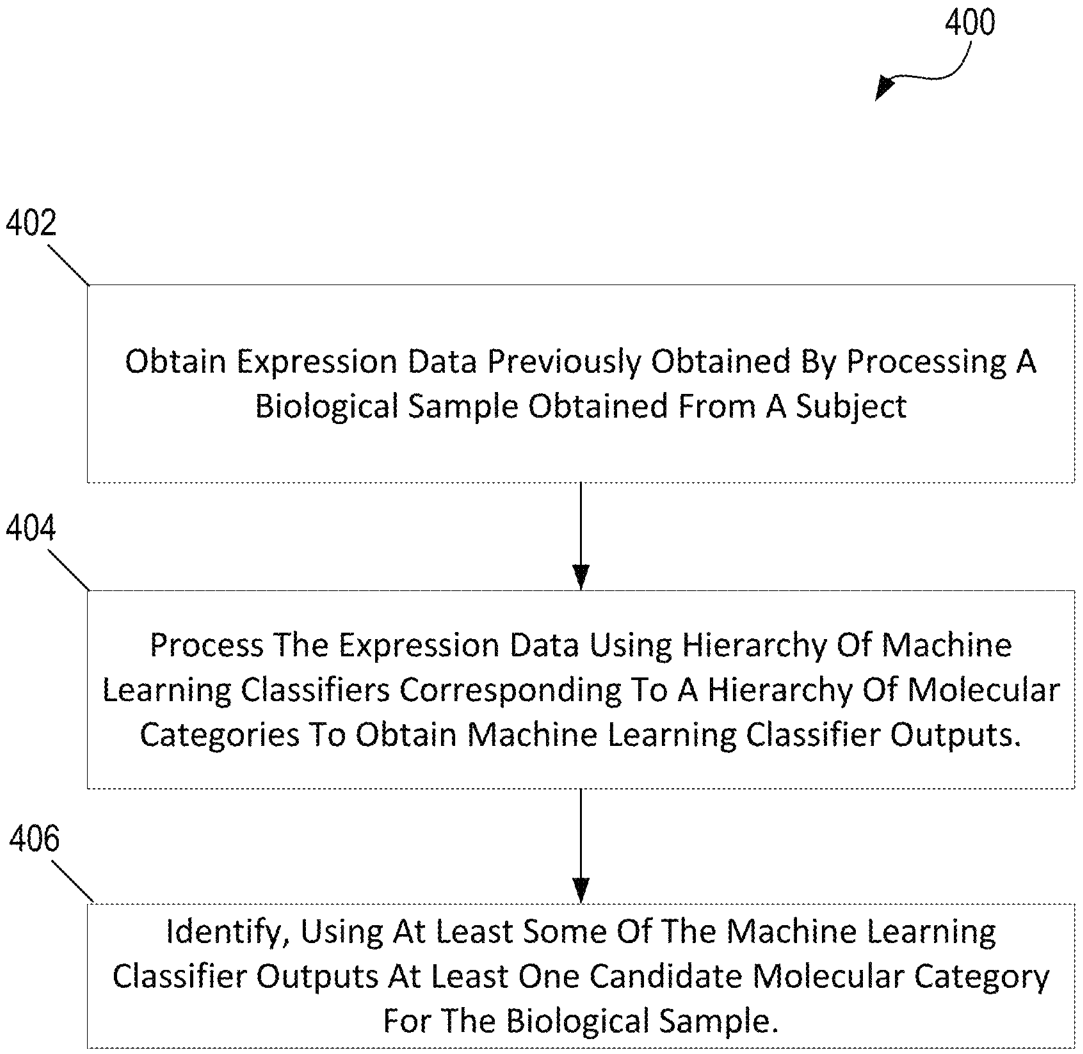
FIG. 4A shows a flowchart of an illustrative process 400 for identifying at least one candidate molecular category for a biological sample using a hierarchy of machine learning classifiers corresponding to a hierarchy of molecular categories, according to some embodiments of the technology described herein.
Figure 4B:
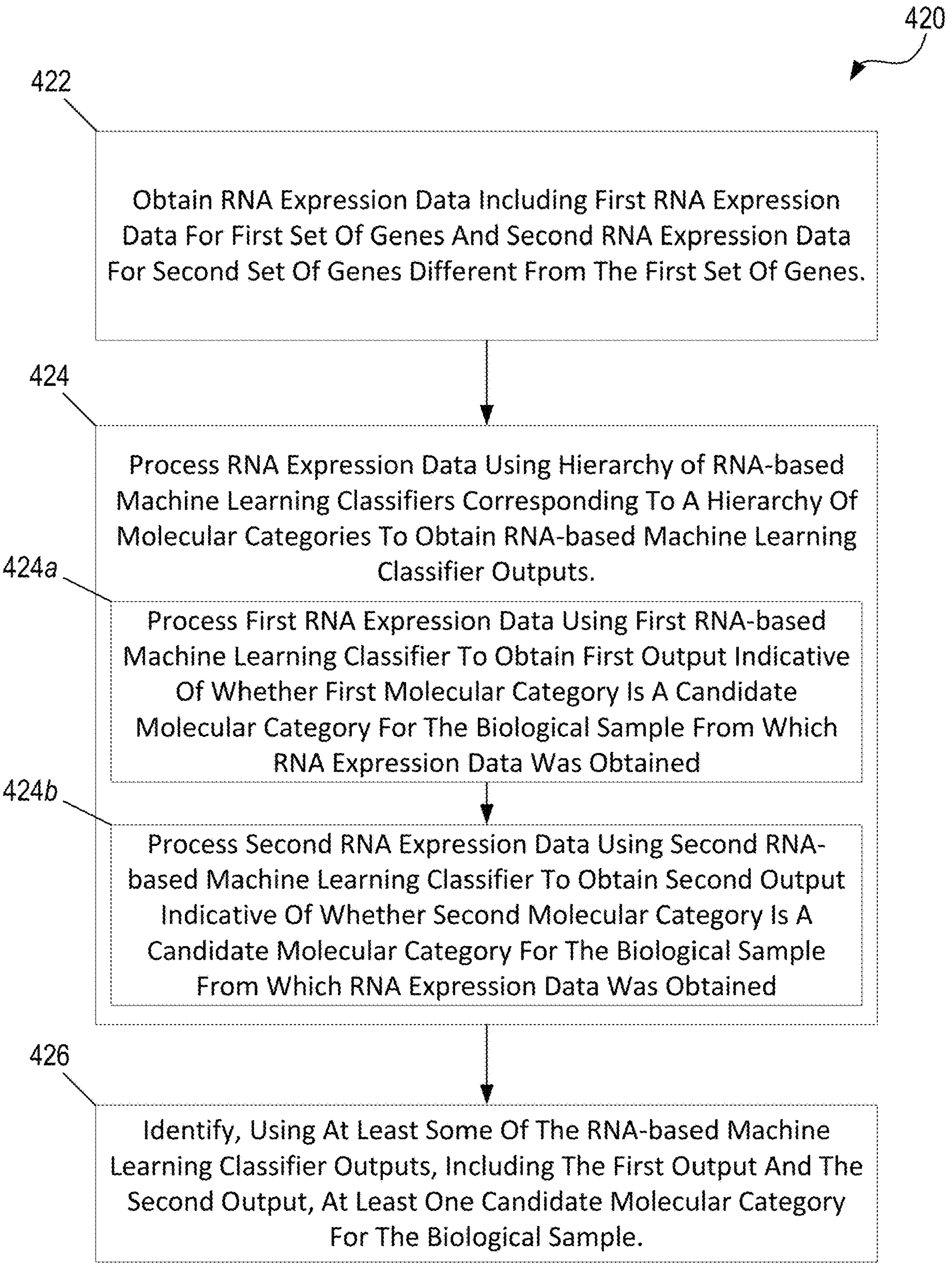
FIG. 4B shows a flowchart of an illustrative process 420 for identifying at least one candidate molecular category for a biological sample using a hierarchy of RNA-based machine learning classifiers corresponding to a hierarchy of molecular categories, according to some embodiments of the technology described herein.
Figure 4C:
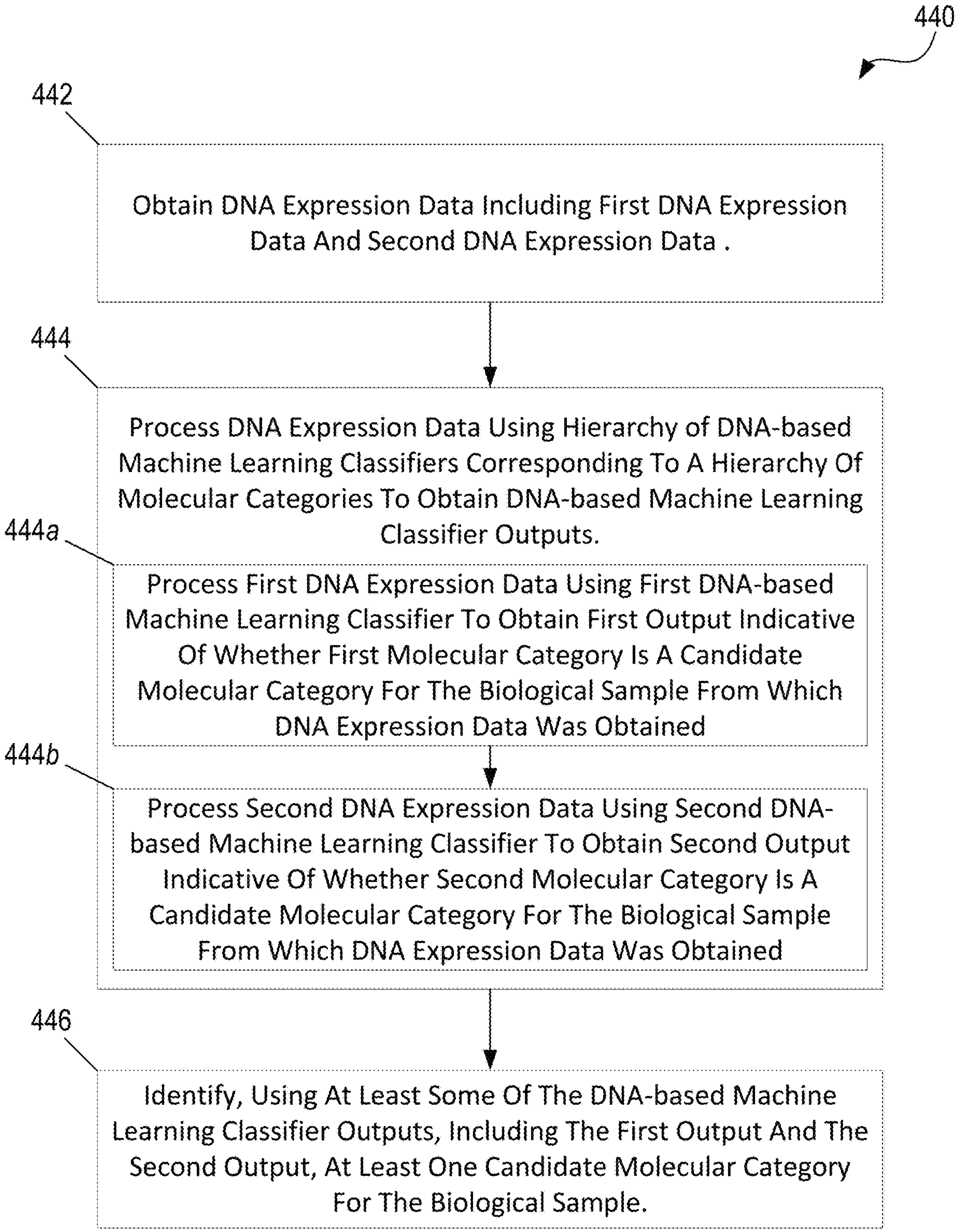
FIG. 4C shows a flowchart of an illustrative process 440 for identifying at least one candidate molecular category for a biological sample using a hierarchy of DNA-based machine learning classifiers corresponding to a hierarchy of molecular categories, according to some embodiments of the technology described herein.

FIGS. 4A-4C show flowcharts of illustrative processes (e.g., processes 400, 420, and 440) for identifying at least one candidate molecular category for a biological sample using a hierarchy of machine learning classifiers corresponding to a hierarchy of molecular categories, according to some embodiments of the technology described herein. The processes may be performed by a laptop computer, a desktop computer, one or more servers, in a cloud computing environment, computing device 104 as described herein with respect to FIG. 1A, computing device 304 as described herein with respect to FIG. 3, computing device 1000 as described herein with respect to FIG. 10, or in any other suitable way.

Shown in FIG. 4A, process 400 begins at act 402 for obtaining expression data previously obtained by processing a biological sample obtained from a subject. In some embodiments, the expression data includes any suitable expression data, such as expression data described herein including at least with respect to FIG. 1A and the section "Expression Data". For example, the expression data may include RNA and/or DNA expression data.

In some embodiments, the expression data is obtained using any suitable techniques from any suitable location. For example, the expression data may be obtained from a data store (e.g., expression data store 346 of FIG. 3). For example, the expression data may have been previously obtained in a remote setting and uploaded to the data store. Additionally or alternatively, the expression data may be obtained directly from a sequencing platform (e.g., sequencing platform 344 of FIG. 3) used to previously obtain the expression data.

At act 404, the process 400 includes processing the expression data using the hierarchy of machine learning classifiers corresponding to a hierarchy of molecular categories to obtain machine learning classifier outputs. In some embodiments, the processing includes processing the expression data to obtain one or more features form the expression data. For example, the features may be derived from and/or inferred from the expression data obtained at act 404. In some embodiments, different features are obtained depending on the type of expression data obtained at act 404. For example, RNA features may be obtained from RNA expression data, while DNA features may be obtained from DNA expression data. Example RNA features and DNA features are described herein including at least with respect to FIGS. 6A-6B.

In some embodiments, the obtained features include a subset of features for a particular molecular category. The subset of features may include features that are unique to the molecular category. For example, as shown in FIG. 2A, feature B includes features unique to molecular category B.

In some embodiments, after obtaining features from the expression data, the processing includes applying at least one machine learning classifier of the hierarchy of machine learning classifiers to the obtained features. In some embodiments, this includes processing the features associated with a particular molecular category using at least one machine learning classifier in the hierarchy of machine learning classifiers to obtain an output indicative of whether to identify the molecular category as a candidate molecular category for the biological sample. For example, as shown in FIG. 2A, machine learning classifier B is used to process features B to determine whether to identify molecular category B as a candidate molecular category for the biological sample.

In some embodiments, as a result of processing the features, a machine learning classifier of the hierarchy of machine learning classifiers outputs a probability that the biological sample belongs to a particular molecular category. Additionally or alternatively, the machine learning classifier outputs a probability that the biological sample does not belong to the particular molecular category and/or a probability that the biological sample includes normal tissue from the site where the biological sample was obtained. For example, FIG. 2C illustrates a diagram of an example machine learning classifier used to predict between "Molecular Category B," "Not Molecular Category B," and (optionally) "Normal."

At act 406, the process 400 includes identifying, using at least some of the machine learning classifier outputs, at least one candidate molecular category for the biological sample. In some embodiments, identifying the at least one candidate molecular category for the biological sample includes evaluating the probabilities indicated by the machine learning classifier outputs. For example, this may include comparing the probabilities to a threshold. In some embodiments, if a probability does not exceed the threshold, then the candidate molecular category associated with the machine learning classifier that output the probability is excluded from the candidate molecular categories identified for the biological sample. Conversely, if the probability does exceed the threshold, then the candidate molecular category associated with the machine learning classifier that output the probability may be included in the candidate molecular categories identified for the biological sample. Additionally or alternatively, in some embodiments, probabilities indicated by the output of machine learning classifiers at a same level of the hierarchy may be compared to one another. In some embodiments, molecular categories associated with machine learning classifiers that output the N (e.g., 1, 2, 3, etc.) greatest probabilities are included are identified as the candidate molecular categories for the biological sample.

FIG. 4B shows a flowchart of an illustrative process 420 for identifying at least one candidate molecular category for a biological sample using a hierarchy of RNA-based machine learning classifiers corresponding to a hierarchy of molecular categories, according to some embodiments of the technology described herein.

Process 420 begins at act 422, which includes obtaining RNA expression data including first RNA expression data for a first set of genes and second RNA expression data for a second set of genes different from the first set of genes. In some embodiments, the RNA expression data includes any suitable RNA expression data, such as the RNA expression data described herein including at least with respect to FIG. 1A and the section "Expression Data".

In some embodiments, the RNA expression data includes expression level values for a number of genes. For example, the first RNA expression data includes first RNA expression level values for a first set of genes and the second RNA expression data includes second RNA expression level values for the second set of genes. In some embodiments, the first set of genes and second set of genes overlap, meaning that they share some of the same genes. In some embodiments, the first and second sets of genes do not overlap, meaning they do not share any of the same genes.

In some embodiments, the RNA expression data is obtained using any suitable techniques from any suitable location. For example, the RNA expression data may be obtained from a data store (e.g., expression data store 346 of FIG. 3). For example, the RNA expression data may have been previously obtained in a remote setting and uploaded to the data store. Additionally or alternatively, the RNA expression data may be obtained directly from a sequencing platform (e.g., sequencing platform 344 of FIG. 3) used to previously obtain the RNA expression data.

At act 424, the techniques include processing the RNA expression data using a hierarchy of RNA-based machine learning classifiers corresponding to a hierarchy of molecular categories to obtain RNA-based machine learning classifier outputs. In some embodiments, the hierarchy molecular categories includes a parent molecular category and first and second molecular categories that are children of the parent molecular category. In some embodiments, the hierarchy of RNA-based machine learning classifiers includes a first RNA-based machine learning classifier used to obtain a first output that indicates whether the first molecular category is a candidate molecular category for the biological sample. In some embodiments, the hierarchy of RNA-based machine learning classifiers includes a second RNA-based machine learning classifier used to obtain a second output that indicates whether the second molecular category is a candidate molecular category for the biological sample.

In some embodiments, act 424 includes sub-act 424*a* and sub-act 424*b*. Sub-act 424*a* includes processing the first RNA expression data using the first RNA-based machine learning classifier to obtain the first output.

In some embodiments, processing the first RNA expression data includes processing the first RNA expression data to obtain a first set of RNA features. In some embodiments, as described herein, this includes ranking genes in the first set of genes based on the RNA expression level values associated with the first set of genes. In some embodiments, genes are ranked in ascending or descending order according to their expression level values. For example, the genes in the first set of genes may be assigned a value (e.g., 1, 2, 3, etc.) based on its expression level value. In some embodiments, the assigned values are different from the expression level values. Techniques for ranking genes are described herein including at least with respect to FIG. 6A.

In some embodiments, the first RNA-based machine learning classifier is applied to the obtained RNA features (e.g., the ranked gene sets). In some embodiments, this includes processing the obtained ranked gene set using the first RNA-based machine learning classifier to obtain the first output. In some embodiments, the first output is indicative of the probability that the biological sample belongs to the first molecular category corresponding to the first RNA-based machine learning classifier.

Sub-act 424*b* includes processing second RNA expression data using the second RNA-based machine learning classifier to obtain the second output indicative of whether second molecular category is a candidate molecular category for the biological sample from which RNA expression data was obtained.

In some embodiments, processing the second RNA expression data includes processing the second RNA expression data to obtain a second set of RNA features. In some embodiments, as described herein, this includes ranking genes in the second set of genes based on the RNA expression level values associated with the second set of genes. In some embodiments, genes are ranked in ascending or descending order according to their expression level values. For example, the genes in the second set of genes may be assigned a value (e.g., 1, 2, 3, etc.) based on its expression level value. In some embodiments, the assigned values are different from the expression level values.

In some embodiments, the second RNA-based machine learning classifier is applied to the obtained RNA features (e.g., the ranked gene sets). In some embodiments, this includes processing the obtained ranked gene set using the second RNA-based machine learning classifier to obtain a second output. In some embodiments, the second output is indicative of the probability that the biological sample belongs to the second molecular category corresponding to the second RNA-based machine learning classifier.

At act 426, process 420 includes identifying, using at least some of the RNA-based machine learning classifier outputs, including the first output and the second output, at least one candidate molecular category for the biological sample. In some embodiments, as described above, including at least with respect to FIG. 4A, identifying the at least one candidate molecular category for the biological sample includes evaluating the probabilities indicated by the RNA-based machine learning classifier outputs. For example, this may include comparing the probabilities to a threshold. In some embodiments, if a probability does not exceed the threshold, then the candidate molecular category associated with the RNA-based machine learning classifier that output the probability is excluded from the candidate molecular categories identified for the biological sample. Conversely, if the probability does exceed the threshold, then the candidate molecular category associated with the RNA-based machine learning classifier that output the probability may be included in the candidate molecular categories identified for the biological sample. Additionally or alternatively, in some embodiments, probabilities indicated by the output of RNA-based machine learning classifiers at a same level of the hierarchy may be compared to one another. For example, this may include comparing the first and second outputs. In some embodiments, molecular categories associated with RNA-based machine learning classifiers that output the N (e.g., 1, 2, 3, etc.) greatest probabilities are included are identified as the candidate molecular categories for the biological sample. For example, one of the first and second molecular categories may be identified for the biological sample based on how they compare to one another.

FIG. 4C shows a flowchart of an illustrative process 440 for identifying at least one candidate molecular category for a biological sample using a hierarchy of DNA-based machine learning classifiers corresponding to a hierarchy of molecular categories, according to some embodiments of the technology described herein.

Process 440 begins at act 442, which includes obtaining DNA expression data including first DNA expression data and second DNA expression data. In some embodiments, the DNA expression data includes any suitable DNA expression data, such as the DNA expression data described herein including at least with respect to FIG. 1A and the section "Expression Data".

In some embodiments, the DNA expression data is obtained using any suitable techniques from any suitable location. For example, the DNA expression data may be obtained from a data store (e.g., expression data store 346 of FIG. 3). For example, the DNA expression data may have been previously obtained in a remote setting and uploaded to the data store. Additionally or alternatively, the DNA expression data may be obtained directly from a sequencing platform (e.g., sequencing platform 344 of FIG. 3) used to previously obtain the DNA expression data.

At act 444, the techniques include processing the DNA expression data using a hierarchy of DNA-based machine learning classifiers corresponding to a hierarchy of molecular categories to obtain DNA-based machine learning classifier outputs. In some embodiments, the hierarchy molecular categories includes a parent molecular category and first and second molecular categories that are children of the parent molecular category. In some embodiments, the hierarchy of DNA-based machine learning classifiers includes a first DNA-based machine learning classifier used to obtain a first output that indicates whether the first molecular category is a candidate molecular category for the biological sample. In some embodiments, the hierarchy of DNA-based machine learning classifiers includes a second DNA-based machine learning classifier used to obtain a second output that indicates whether the second molecular category is a candidate molecular category for the biological sample.

In some embodiments, act 444 includes sub-act 444*a* and sub-act 424*b*. Sub-act 444*a* includes processing the first DNA expression data using a first DNA-based machine learning classifier to obtain the first output indicative of whether first molecular category is a candidate molecular category for the biological sample from which DNA expression data was obtained.

In some embodiments, processing the first DNA expression data includes processing the first DNA expression data to obtain a first set of DNA features. In some embodiments, as described herein, this includes generating numeric and/or binary data that quantifies and/or identifies information contained in the first DNA expression data. Example DNA features are described herein including at least with respect to FIG. 6B.

In some embodiments, the first DNA-based machine learning classifier is applied to the obtained DNA features. In some embodiments, this includes processing the obtained features using the first DNA-based machine learning classifier to obtain the first output. In some embodiments, the first output is indicative of the probability that the biological sample belongs to the first molecular category corresponding to the first DNA-based machine learning classifier.

Sub-act 444*b* includes processing second DNA expression data using second DNA-based machine learning classifier to obtain the second output indicative of whether second molecular category is a candidate molecular category for the biological sample from which DNA expression data was obtained.

In some embodiments, processing the second DNA expression data includes processing the second DNA expression data to obtain a second set of DNA features. In some embodiments, as described herein, this includes generating numeric and/or binary data that quantifies and/or identifies information contained in the second DNA expression data. Example DNA features are described herein including at least with respect to FIG. 6B.

In some embodiments, the second DNA-based machine learning classifier is applied to the obtained DNA features. In some embodiments, this includes processing the obtained features using the second DNA-based machine learning classifier to obtain the second output. In some embodiments, the second output is indicative of the probability that the biological sample belongs to the second molecular category corresponding to the second DNA-based machine learning classifier.

At act 446, process 440 includes identifying, using at least some of the DNA-based machine learning classifier outputs, including the first output and the second output, at least one candidate molecular category for the biological sample. In some embodiments, as described above, including at least with respect to FIG. 4A, identifying the at least one candidate molecular category for the biological sample includes evaluating the probabilities indicated by the DNA-based machine learning classifier outputs. For example, this may include comparing the probabilities to a threshold. In some embodiments, if a probability does not exceed the threshold, then the candidate molecular category associated with the DNA-based machine learning classifier that output the probability is excluded from the candidate molecular categories identified for the biological sample. Conversely, if the probability does exceed the threshold, then the candidate molecular category associated with the DNA-based machine learning classifier that output the probability may be included in the candidate molecular categories identified for the biological sample. Additionally or alternatively, in some embodiments, probabilities indicated by the output of DNA-based machine learning classifiers at a same level of the hierarchy may be compared to one another. For example, this may include comparing the first and second outputs. In some embodiments, molecular categories associated with DNA-based machine learning classifiers that output the N (e.g., 1, 2, 3, etc.) greatest probabilities are included are identified as the candidate molecular categories for the biological sample. For example, one of the first and second molecular categories may be identified for the biological sample based on how they compare to one another.

Figures 1, 5A:
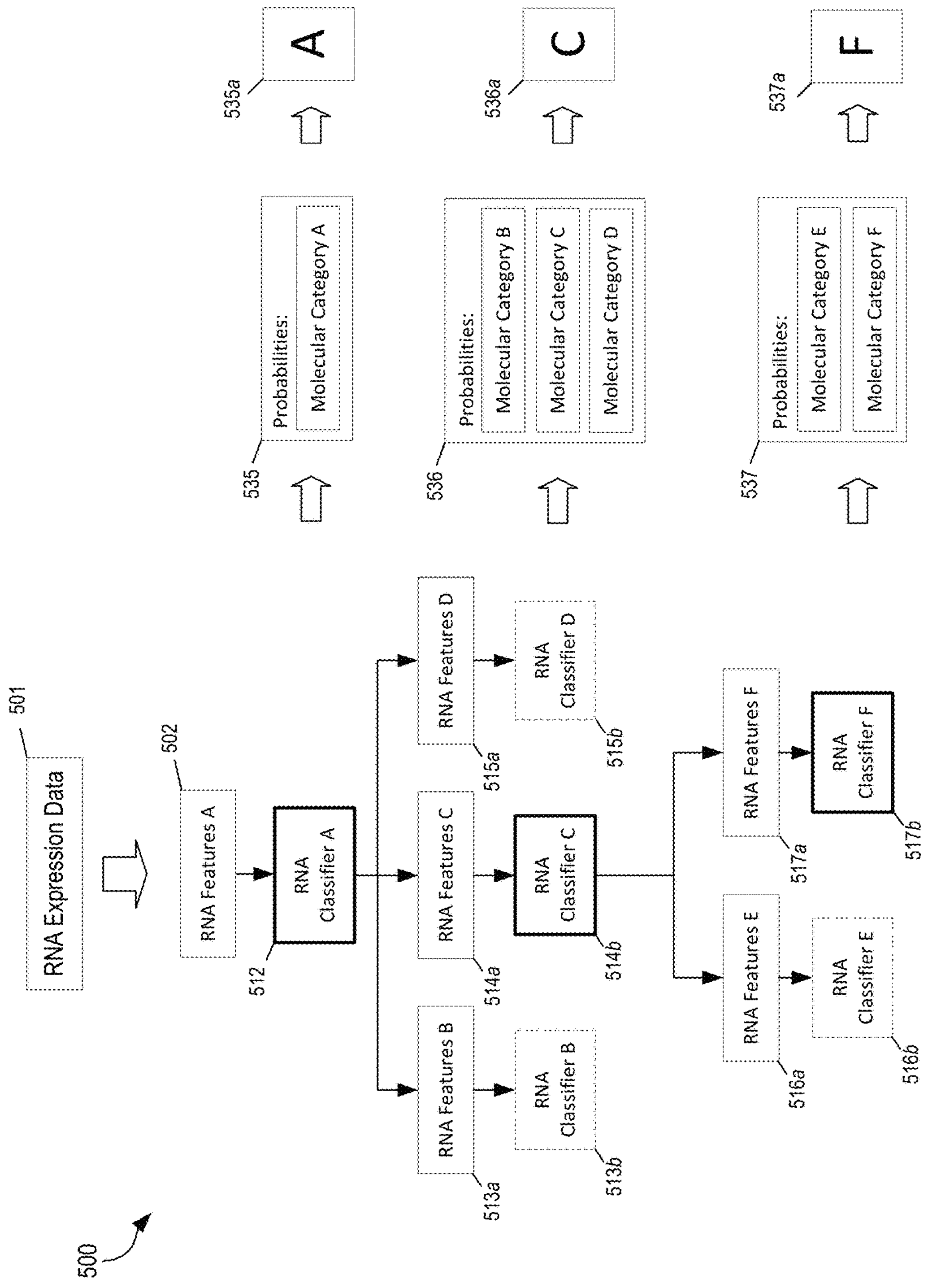
Figures 2, 5A:
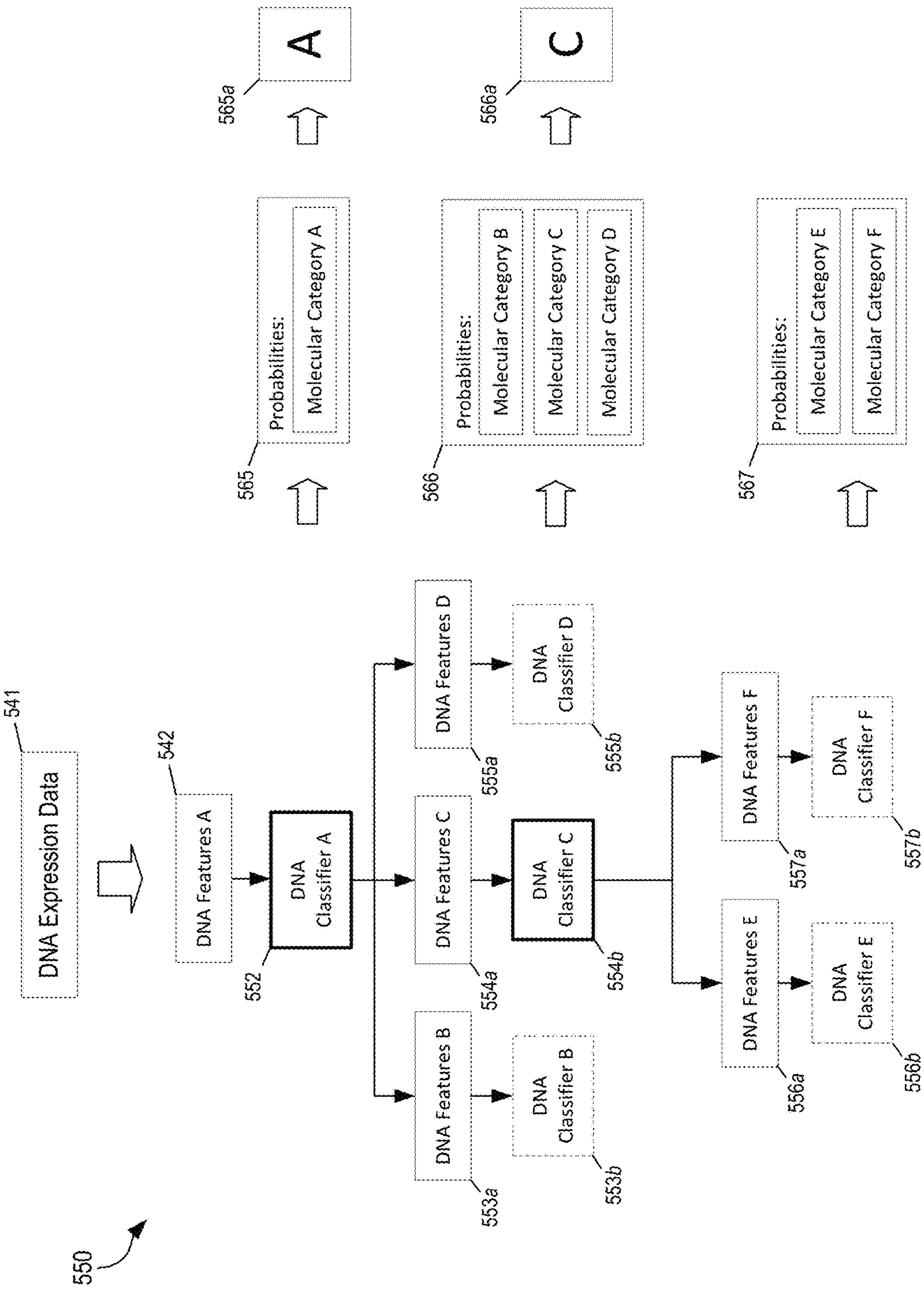

FIG. 5A-1 is an example 500 for processing RNA expression data obtained from a biological sample to identify at least one candidate molecular category for the biological sample, according to some embodiments of the technology described herein.

In some embodiments, the techniques include processing the RNA expression data 501 to obtain RNA features A 502, RNA features B 513*a*, RNA features C 514*a*, RNA features D 515*a*, RNA features E 516*a*, and RNA features F 517*a*. Example RNA features are described herein including at least with respect to FIG. 6A.

In some embodiments, the RNA-based machine learning classifiers of the hierarchy of RNA-based machine learning classifiers are used to process the features to determine whether to identify the molecular category associated with the machine learning classifier as a candidate molecular category for the biological sample. For example, RNA classifier B 513*b* is used to process RNA features B 513*a* to determine whether to identify molecular category B as a candidate molecular category for the biological sample. Similarly, classifier C 514*b*, classifier D 515*b*, classifier E 516*b*, and classifier F 517*b* are each used to process respective features B-F.

In some embodiments, the output of the RNA-based machine learning classifiers indicates the probability 535, 536, and 537 that the biological sample belong to each particular molecular category. As described above, including at least with respect to FIG. 2D, the probabilities at each level may be compared to a threshold and/or compared to one another to determine whether to identify a molecular category as a candidate molecular category for the biological sample.

As shown in FIG. 5A-1, candidate molecular category A 535*a*, candidate molecular category C 536*a*, and candidate molecular category F 537*a* are identified for the biological sample in this example.

FIG. 5A-2 is an example 550 for processing DNA expression data obtained from a biological sample to identify at least one candidate molecular category for the biological sample, according to some embodiments of the technology described herein.

In some embodiments, the techniques include processing the DNA expression data 541 to obtain DNA features A 542, DNA features B 553*a*, DNA features C 554*a*, DNA features D 555*a*, DNA features E 556*a*, and DNA features F 557*a*. Example DNA features are described herein including at least with respect to FIG. 6A.

In some embodiments, the DNA-based machine learning classifiers of the hierarchy of DNA-based machine learning classifiers are used to process the features to determine whether to identify the molecular category associated with the machine learning classifier as a candidate molecular category for the biological sample. For example, DNA classifier B 553*b* is used to process DNA features B 553*a* to determine whether to identify molecular category B as a candidate molecular category for the biological sample. Similarly, classifier C 554*b*, classifier D 555*b*, classifier E 556*b*, and classifier F 557*b* are each used to process respective features B-F.

In some embodiments, the output of the DNA-based machine learning classifiers indicates the probability 565, 566, and 567 that the biological sample belong to each particular molecular category. As described above, including at least with respect to FIG. 2D, the probabilities at each level may be compared to a threshold and/or compared to one another to determine whether to identify a molecular category as a candidate molecular category for the biological sample.

As shown in FIG. 5A-2, candidate molecular category A 565*a* and candidate molecular category C 566*a* are identified for the biological sample in this example.

Combining RNA and DNA Hierarchical Outputs

Figure 5B:
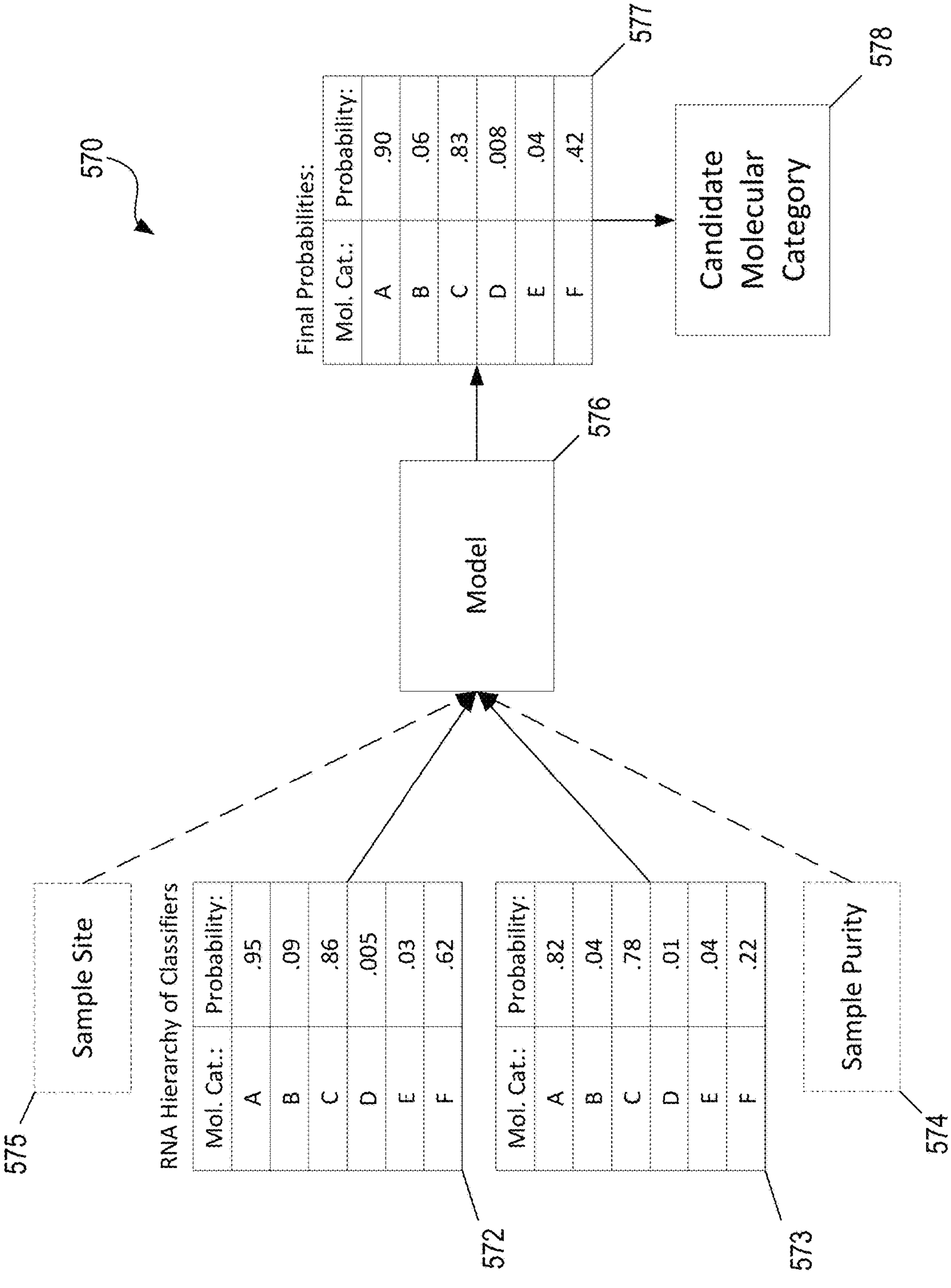
FIG. 5B illustrates an example 570 for combining the output of the hierarchy of RNA-based machine learning classifiers with the output of the hierarchy of DNA-based machine learning classifiers to identify at least one candidate molecular category for the biological sample, according to some embodiments of the technology described herein.

FIG. 5B illustrates an example 570 for using the output of the hierarchy of RNA-based machine learning classifiers and the output of the hierarchy of DNA-based machine learning classifiers to identify at least one candidate molecular category for the biological sample, according to some embodiments of the technology described herein.

As shown in the example of FIGS. 5A-1-5A-2, a hierarchy of RNA-based machine learning classifiers 500 and a hierarchy of DNA-based machine learning classifiers 550 are each used to identify candidate molecular categories for a biological sample. In some embodiments, such as in this example, there may be differences in the molecular categories (e.g., categories "A," "C" and "F" output by the RNA-based hierarchy and categories "A" and "C" output by the DNA-based hierarchy) identified by the two hierarchies.

In some embodiments, such difference between outputs may arise due to differences between the RNA expression data and the DNA expression data processed using the hierarchies. For example, the sample purity may affect the data and therefore affect (e.g., invalidate) the predictions output by one or both of the classifiers. In particular, the sample purity may influence the output of classifiers trained to process RNA expression data. For example, if the sample purity is high, an RNA-based machine learning classifier may yield a more accurate and/or reliable result because the signal is improved. By contrast, if sample purity is low, the RNA-based classifier may yield a less accurate and/or reliable result (and therefore a DNA classifier may be more reliable). Additionally or alternatively, site from which the biological sample was obtained may affect at least the RNA-based machine learning classifier outputs 572. In particular, as explained above including at least with respect to FIG. 2D, the outputs 572 may be biased towards molecular categories that are associated with clinical diagnoses originating from the sample site.

Accordingly, the inventors have developed techniques that account for these discrepancies. As shown in FIG. 5B, in some embodiments, the techniques include identifying final probabilities 577 for the molecular categories based on the RNA-based machine learning classifier outputs 572 and the DNA-based machine learning classifier outputs 573.

In some embodiments, identifying the final probabilities 577 includes processing the RNA-based machine learning classifier outputs 572 and the DNA-based machine learning classifier outputs 573 using model 576. In some embodiments, model 576 is used to combine outputs 572 and outputs 573, such that the final probabilities 577 differ. For example, as shown in FIG. 5B, the final probabilities 577 differ from outputs 572 and 573. In some embodiments, model 576 may implement machine learning techniques to combine outputs 572 and 573. For example, model 576 may include a neural network, a Naïve Bayes model, a linear regression model, or any suitable machine learning model, as aspects of the technology are not limited in this respect. In some embodiments, model 576 may include calculating an average or a weighted average of the outputs 572 and 573.

Additionally or alternatively, in some embodiments, model 576 may select between the RNA-based classifier outputs 572 and the DNA-based classifier outputs 576. For example, this may include selecting either output 572 or output 573 for final probabilities 577. Additionally or alternatively, this may include selectively identifying probabilities from among outputs 572 and 572 to be used as final probabilities 577.

In some embodiments, discrepancies between outputs 572 and 573 arise due to differences between the RNA and DNA expression data processed using the hierarchy of RNA-based and the hierarchy of DNA-based machine learning classifiers, respectively. For example, the sample purity may affect the data and therefore affect (e.g., invalidate) the predictions output by one or both of the classifiers. In particular, the sample purity may influence the output of classifiers trained to process RNA expression data. For example, if the sample purity is high, an RNA-based machine learning classifier may yield a more accurate and/or reliable result because the signal is improved. By contrast, if sample purity is low, the RNA-based classifier may yield a less accurate and/or reliable result (and therefore a DNA classifier may be more reliable). Accordingly, in some embodiments, model 576 may consider sample purity 574 in determining final probabilities 577. For example, the model 576 may apply different weights to probabilities 572 and 573 when the sample purity is high versus when the sample purity is low. In particular, when the sample purity is high, a greater weight may be applied to the RNA-based machine learning classifier outputs 572 (and vice versa). Additionally or alternatively, sample purity 574 can be used to exclude probabilities included in outputs 572 and/or 573 from final probabilities 577.

Figures 1, 7A:
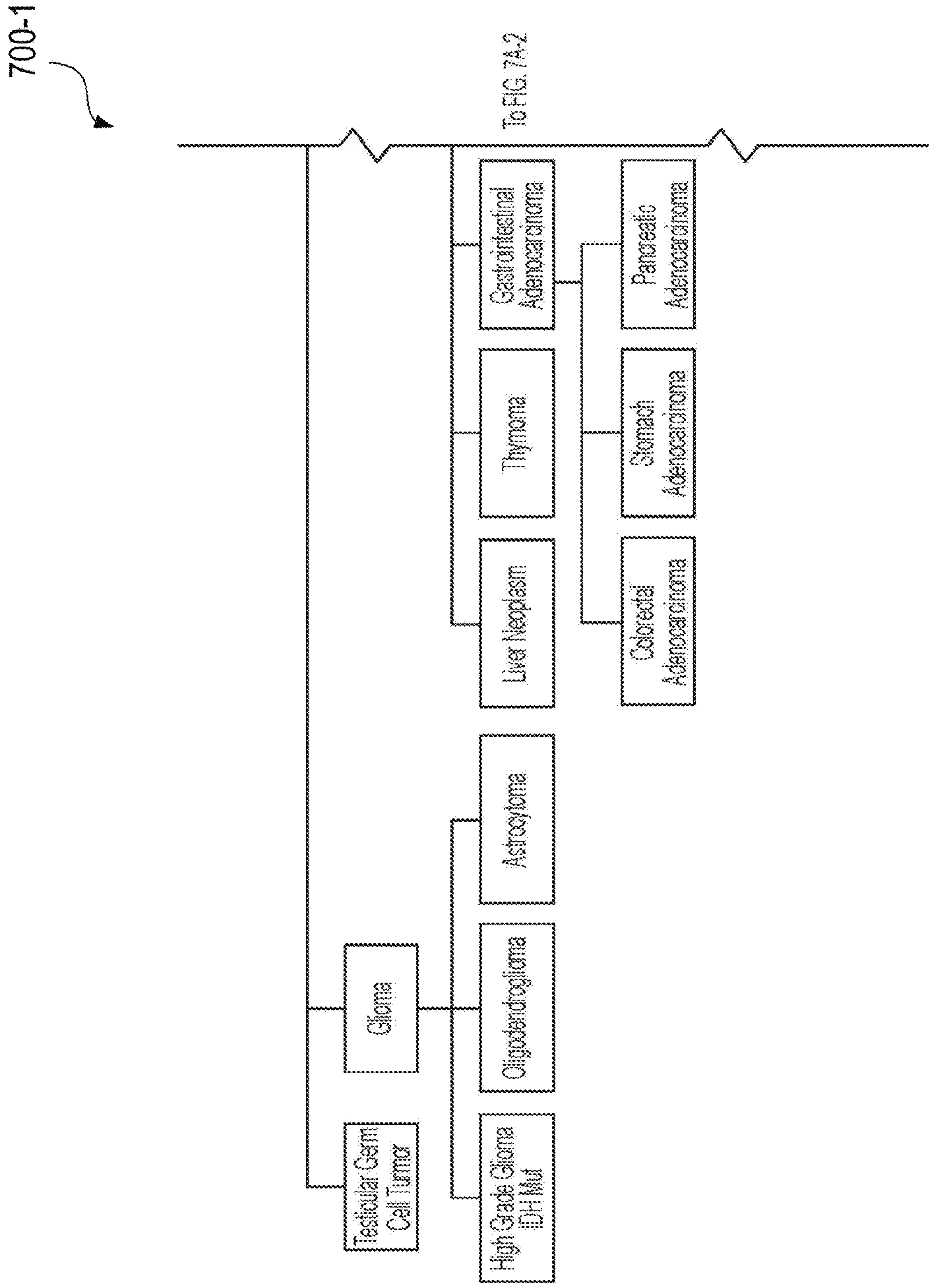
Figures 2, 7A:
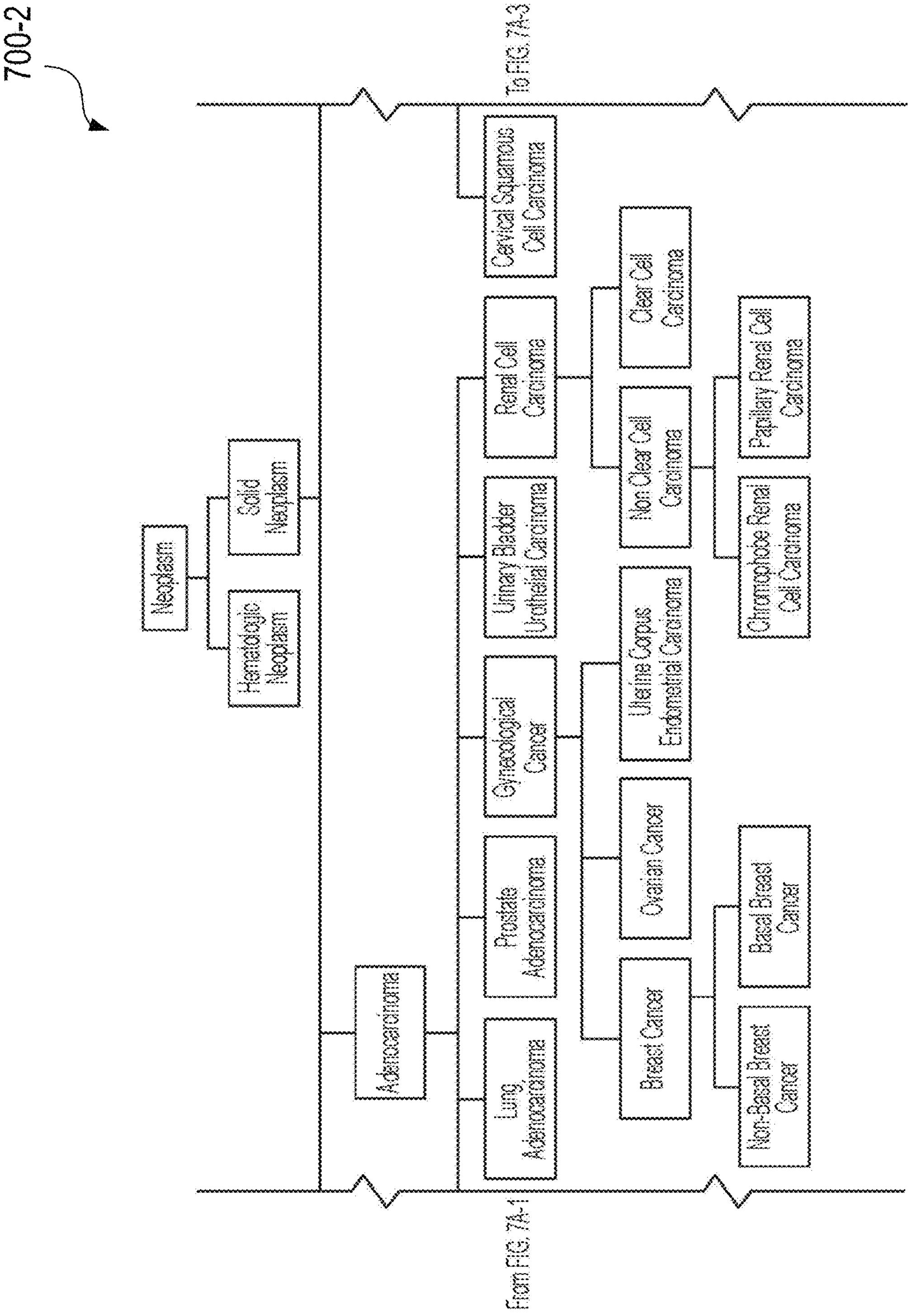
Figures 3, 7A:
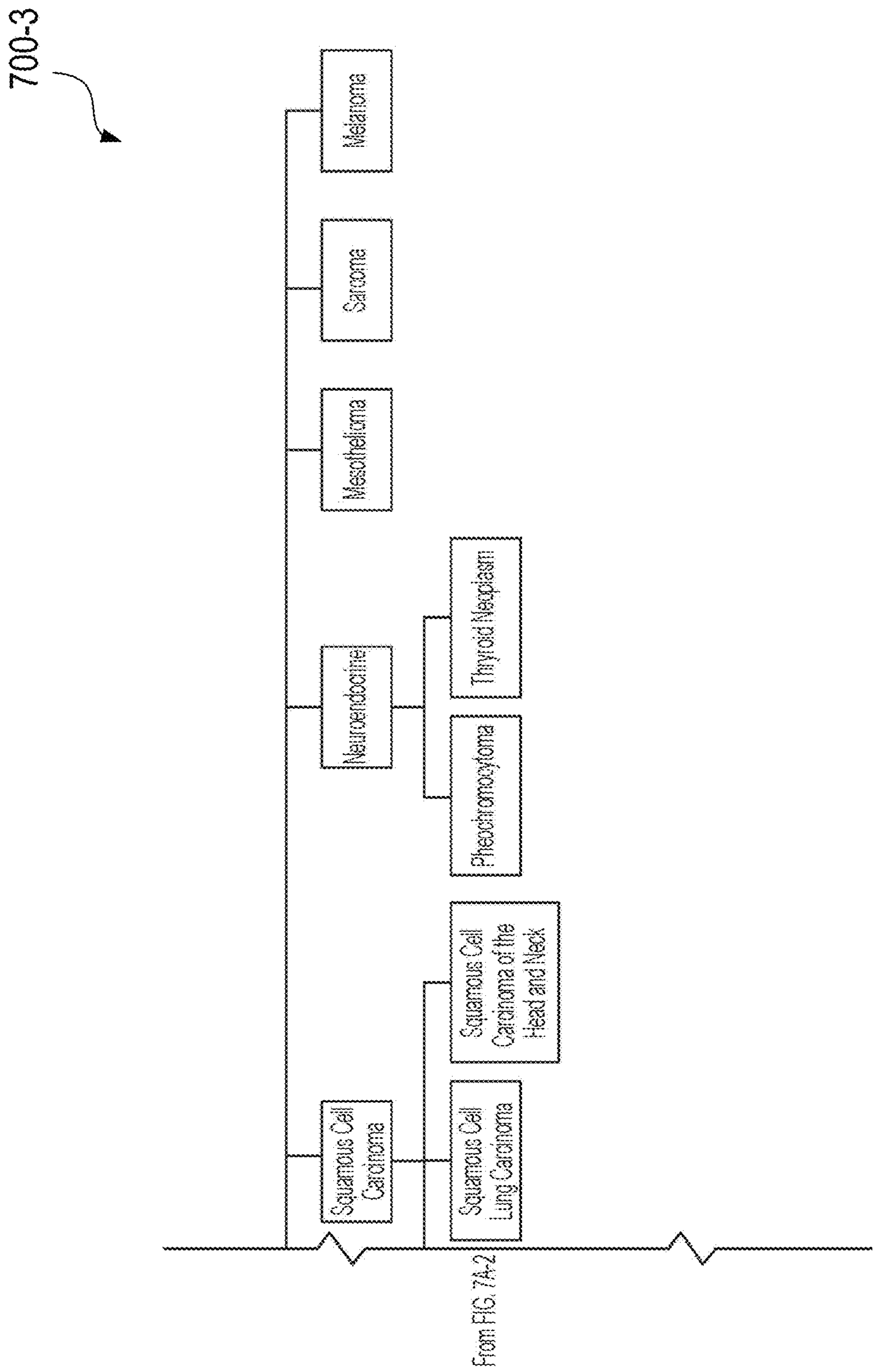

Additionally or alternatively, site from which the biological sample was obtained may affect at least the RNA-based machine learning classifier outputs 572. In particular, as explained above including at least with respect to FIG. 2D, the outputs 572 may be biased towards particular molecular categories that are associated with clinical diagnoses originating from the sample site. Accordingly, in some embodiments, the model 576 considers the sample site 574 in determining final probabilities 577. In some embodiments, the probabilities corresponding to molecular categories that are associated with clinical diagnoses corresponding to the sample site may be considered with less weight. For example, the probabilities corresponding to the molecular category "Lung Neoplasm" (e.g., as shown in FIG. 7A-1) may be considered with less weight when the biological sample is obtained from the lung.

In some embodiments, the final probabilities 577 are used to identify candidate molecular categories 578 (e.g., according to the techniques described herein including at least with respect to FIG. 2D. Additionally or alternatively, the candidate molecular categories 578 are obtained directly from model 576 (e.g., without determining final probabilities 577).

Output Correction Techniques

In some embodiments, as described above, the output of a machine learning classifiers in the hierarchy of machine learning classifiers is indicative of a probability that the biological sample belong to a particular molecular category. In some embodiments, the machine learning classifier accounts for the probability that the biological sample belongs to another molecular category at the same level of the molecular category (e.g., "not molecular category A" as shown in FIG. 2D).

Figure 5C:
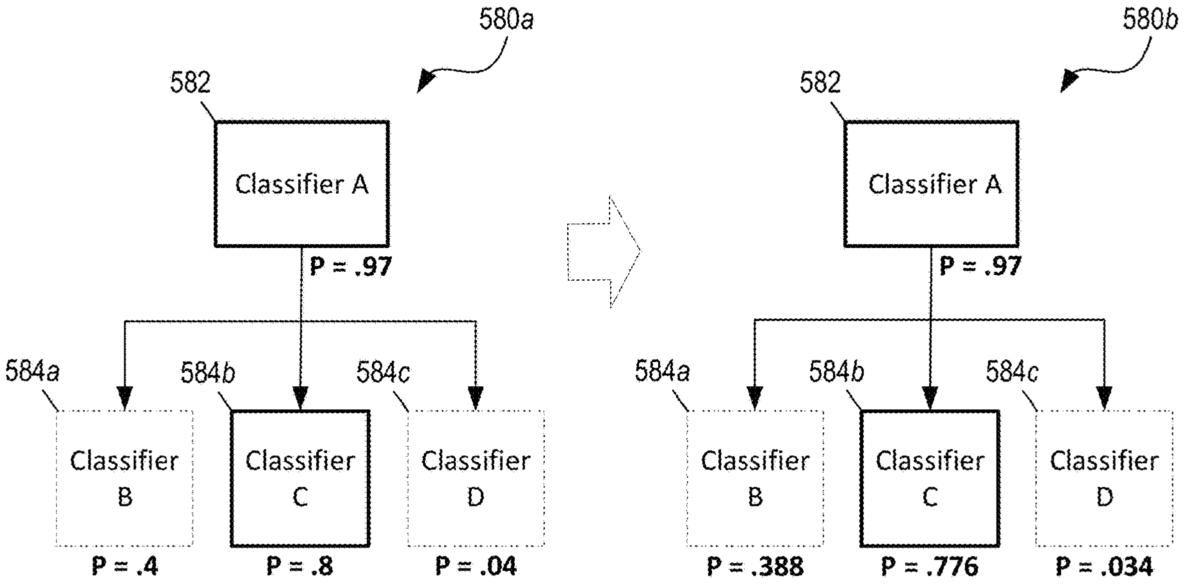
FIGS. 5C-5D shows an example of correcting for probabilities output by machine learning classifiers of the hierarchy of machine learning classifiers, according to some embodiments of the technology described herein.

However, since a machine learning classifier is trained, in some embodiments, to independently predict whether to identify a corresponding molecular category as a candidate molecular category for the biological sample, it does not account for probabilities output by other machine learning classifiers in the hierarchy, resulting in mispredictions. For example, as shown in FIG. 5C, classifier 582 outputs a probability of 0.04, while classifier 584*b* outputs a probability of 0.7. Since classifier 584*b* is corresponds to a molecular category that descends from the molecular category corresponding to classifier 582, it should output a lower probability than the probability output by classifier 582.

Accordingly, one or more correction techniques may be applied to the probabilities output by the classifiers, after at least some of the classifiers have made their predictions. In some embodiments, the techniques include multiplying a probability output by a classifier at a lower level of the hierarchy by a probability output by a classifier at an upper level of the classifier. However, it should be appreciated that any suitable correction technique may be used to correct for mispredictions, as aspects of the technology described herein are not limited to any particular correction technique.

Figure 5D:
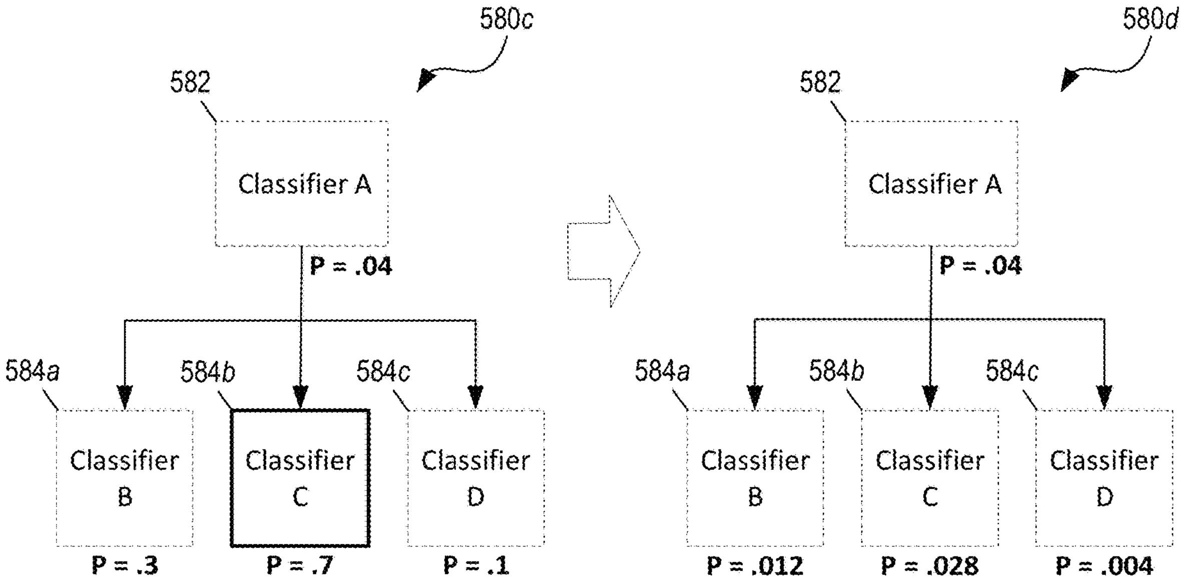

FIGS. 5C-5D shows an example of correcting for probabilities output by machine learning classifiers of the hierarchy of machine learning classifiers.

In the example shown in FIG. 5C, the probabilities output by classifiers 584*a-c*, of hierarchy 580*a*, are each multiplied by the probability output by classifier 582. The results are shown with respect to hierarchy 580*b*. In particular, P=0.4 is multiplied by P=0.97 to obtain P=0.388, P=0.8 is multiplied by P=0.97 to obtain P=0.776, and P=0.04 is multiplied by P=0.97 to obtain P=0.034.

In the example shown in FIG. 5D, the probabilities output by classifiers 584*a-c*, of hierarchy 580*c*, are each multiplied by the probability output by classifier 582. The results are shown with respect to hierarchy 580*d*. In particular, P=0.3 is multiplied by P=0.04 to obtain P=0.012, P=0.7 is multiplied by P=0.04 to obtain P=0.028, and P=0.1 is multiplied by P=0.04 to obtain P=0.004.

As described above, in some embodiments, molecular categories associated with classifiers that output probabilities that exceed a threshold may be identified as a candidate molecular category for the biological sample, while others will be excluded. Here, with respect to hierarchy 580*c*, classifier 584*b* output a probability that exceeded an example threshold of 0.5 before the application of the correction techniques. However, after the application of such techniques, the probability does not exceed the example threshold, and will thus be excluded from further analysis.

Example RNA and DNA Features

FIG. 6A is a diagram showing example RNA expression data 610 and example RNA features obtained from the RNA expression data, according to some embodiments of the technology described herein.

In some embodiments, RNA expression data 610 includes gene expression levels for multiple genes. For example, RNA expression data 610 includes gene expression levels 612*a* for a first set of genes (e.g., genes A-D) and gene expression levels 612*b* for a second set of genes (e.g., genes E-H). However, it should be appreciated that gene sets described herein are not limited to any particular number of genes, as aspects of the technology described herein are not limited in this respect. In some embodiments, different sets of genes may share one or more of the same genes or may not share any of the same genes. Techniques for determining which genes are to be included in a set of genes are described herein including at least with respect to FIG. 8A.

In some embodiments, RNA expression data 610 may be processed to obtain one or more RNA features 620. In some embodiments, processing the RNA expression data includes ranking genes in a gene set (e.g., gene sets A-D) based on the expression levels of the genes. In some embodiments, the genes may be ranked in ascending order, such that genes associated with relatively low expression values are assigned lower ranks, while genes associated with relatively high expression values are assigned higher ranks. However, it should be appreciated that genes could be ranked in descending order, as aspects of the technology are not limited in this respect. Example techniques for ranking genes are described in U.S. patent application Ser. No. 17/113,008, titled "MACHINE LEARNING TECHNIQUES FOR GENE EXPRESSION ANALYSIS", filed on Dec. 5, 2020, which is incorporated by reference herein in its entirety.

FIG. 6A shows an example of ranking genes in based on expression levels 612*a*. As shown, gene C corresponds to the lowest expression level value (e.g., 0.02) out of RNA expression data associated with gene set 612*a*. Therefore, gene C is assigned to a rank of 1, as shown in the rank transformed data 622*a*. By contrast, gene B corresponds to the highest expression level value (e.g., 0.32) out of RNA expression data for gene set 612*a*. Therefore, gene B is assigned a rank of 4, as shown in rank transformed data 622*b*. However, it should be appreciated that genes could be ranked in descending order, as aspects of the technology are not limited in this respect.

In some embodiments, the same expression level value may be measured for different genes. For example, genes E and G share the same expression level value (e.g., 0.20). Such genes may be assigned an average rank of all ranks corresponding to those genes. As shown in the example, genes E and G would correspond to ranks 2 and 3, and the average rank of 2.5 would be applied to both genes.

FIG. 6B is a diagram showing example DNA expression data 651 and example DNA features 652 obtained from the DNA expression data 651, according to some embodiments of the technology described herein.

In some embodiments, DNA expression data 651 is processed to obtain DNA features 652. For example, the DNA features 652 may be derived and/or inferred from the DNA expression data 651 according to any suitable technique, as aspects of the technology are not limited in this respect. For example, one or more bioinformatics software packages may be used to calculate one or more of the DNA features from DNA expression data.

Non-limiting examples of DNA features 652 include one or more features 654 indicative of the presence of one or more mutations, one or more features 655 indicative of copy number alterations (CNA), one or more feature 655*c* indicative of ploidy, one or more features 656 indicative of the presence of one or more gene fusions 656, one or more features 657 indicative of microsatellite instability (MSI) status, one or more features indicative of presence of protein-coding genes, and/or any other suitable features that may be derived and/or inferred from DNA sequence data, as aspects of the technology described herein are not limited in this respect.

In some embodiments, the one or more features 654 indicative of the presence of one or more mutations f encompasses one or more DNA features that relate to genetic mutations, including, but not limited to, one or more features indicative of the presence of one or more pathogenic gene mutations 654*a*, one or more features indicative of the presence of one or more mutational hotspots 654*b*, and a feature indicative of the tumor mutational burden (TMB) 654*c*. A feature indicative of the presence of a pathogenic gene mutation or a mutational hotspot may be a binary feature taking on one of two values, with one of the values (e.g., the numerical value "1" or the categorical value "True") indicating the presence of that type of mutation and the other one of the values (e.g., the numerical value "0" or the categorical value "False") indicating the absence of that type of mutation.

In some embodiments, the gene mutations feature(s) 654*a* may be indicative of the presence of one or more alterations in the DNA expression data relative to a reference genome. For example, a gene mutation may be a nonsense mutation, a frame shift insertion, a frame shift deletion, an in-frame insertion, an in-frame deletion, a non-stop mutation, or a missense mutation. In some embodiments, to obtain data indicative of the gene mutations 654*a*, the mutations 654*a* may be encoded in the form of a binary vector, where 1 indicates the presence of a mutation in a gene, and 0 indicates the absence of a mutation in a gene.

In some embodiments, the gene mutations 654 may be pre-filtered. In some embodiments, gene mutations 654*a* may be pre-filtered by classification-type variant allele frequency (VAF), such that only those mutations with a VAF that exceeds a threshold may be considered for further analysis. For example, the VAF threshold may be at least 0.2, at least 0.3, at least 0.4, at least 0.5, at least 0.6, at least 0.7, or any other suitable threshold VAF, as aspects of the technology are not limited in this respect. Additionally or alternatively, the gene mutations 654*a* may be pre-filtered by pathogenicity such that only pathogenic mutations remain. For example, the genetic mutations may be pre-filtered by pathogenicity using the techniques described in Sarachakov et. al. (MutAnt: Mutation annotation machine learning algorithm for pathogenicity evaluation of single nonsynonymous nucleotide substitutions in cancer cells, in Proc. of the AACR Annual Meeting 2021, *Cancer Res.,* 81(13 Suppl.), 192), which is incorporated herein by reference in its entirety. It should be appreciated that any other suitable techniques may be used to filter the gene mutations 654*a*, as aspects of the technology are not limited in this respect.

Mutational hotspots 654*b* are nucleotide positions with an exceptionally high mutation frequency. In some embodiments, two different features may reflect mutational hotspots. The first feature may indicate the presence of a mutation in a certain position in a certain protein (e.g., where the position is a known hotspot site). For example, the feature may be a binary feature, where 1 represents the presence of the mutation at the position and 0 represents the absence of the mutation at the position. The second feature may indicate the presence of any known hotspot(s) in the gene. For example, this may also be a binary feature, where 1 represents the presence of the hotspot(s) and 0 represents the absence of the hotspot(s). In some embodiments, hotspot features are generated from mutations in any suitable file format, such as mutation annotation format (MAF) or variant call format (VCF), as aspects of the technology are not limited in this respect.

Tumor mutational burden (TMB) 654*c* is a feature that is indicative of an amount of gene mutation that occurs in the genome. In some embodiments, determining TMB 654*c* includes determining the number of nonsynonymous somatic mutations per coding region of a tumor genome. For example, the techniques may include determining the total number of nonsynonymous somatic mutations per 1 MB of used whole-exome sequencing (WES) data. In some embodiments, all nonsynonymous somatic coding mutations having a coverage greater than a threshold may be included in the total number. For example, nonsynonymous somatic coding mutations having a coverage greater than 15×, 25×, 35×, or 45× may be included in the total number. Additionally or alternatively, all nonsynonymous somatic coding mutations having an allelic fraction greater than a threshold may be included in the total number. For example, nonsynonymous somatic coding mutations having an allelic fraction greater than 2%, 4%, 5%, 6%, 8%, or 10% may be included in the total number.

In some embodiments, copy number alterations (CNA) feature category 655 encompasses features related to CNA, including, but not limited to, CNA genes 655*a*, CNA and loss of heterozygosity (LOH) values 655*b*, and ploidy 655*c*. In some embodiments, CNA genes 655*a* include deletions or amplifications of portions of the genome. In some embodiments, features, such as the normalized gene copy number, are derived from the CNA genes. For example, Bagaev et. al. (Integrated whole exome and transcriptome analyses of the tumor and microenvironment provide new opportunities for rational design of cancer therapy, in Proc. of the AACR Annual Meeting 2020, *Cancer Res.*, 80(16 Suppl.), 4418), which is incorporated herein by reference in its entirety, describes determining normalized gene copy numbers.

In some embodiments, the techniques include determining CNA and/or LOH values 655. In some embodiments, this may first include splitting a chromosome into bins. In some embodiments, this may include splitting the chromosome into bins of equal length, where the length is any suitable length, as aspects of the technology are not limited in this respect. For example, the bin length may be 106 base pairs (bp), 107 bp, or 108 bp. Additionally or alternatively, the chromosome may be split into arms (e.g., the "p arm" and "q arm"). Additionally or alternatively, the chromosome may not be split.

In some embodiments, the techniques include determining values for each of the bins based on average copy number and/or loss of heterozygosity (LOH). For example, determining the average copy number value for a bin (or arm or chromosome) may include determining the weighted average of the normalized copy number of all segments that intersect with the bin (or arm or chromosome), where the weight of the segment is the length of the intersection, as shown in Equation 1.

$$CNA\ \text{Value} = \frac{\sum\left(\begin{matrix}\text{Normalized Copy Number}\times\\ \text{Intersection Length}\end{matrix}\right)}{\begin{matrix}\text{Bin, Arm, Chromosome Length}\times\\ \text{Number of Intersections}\end{matrix}} \quad \text{(Equation 1)}$$

Similarly, determining the LOH value for a bin (or arm or chromosome) may include determining the weighted average of the LOH values of all segments that intersect with the bin (or arm or chromosome), where the weight of the segment is the length of the intersection, as shown in Equation 2.

$$LOH\ \text{Value} = \frac{\sum\left(\begin{matrix}LOH\ \text{Value}\times\\ \text{Intersection Length}\end{matrix}\right)}{\begin{matrix}\text{Bin, Arm, Chromosome Length}\times\\ \text{Number of Intersections}\end{matrix}} \quad \text{(Equation 2)}$$

Ploidy 655*c* refers to the number of complete sets of chromosomes in a cell. For example, except for gametes, healthy human cells have two sets of homologous chromosomes (e.g., diploid). By contrast, some cancer cells may contain more than two sets of homologous chromosomes (e.g., polyploid). In some embodiments, any suitable technique may be used to calculate ploidy, as aspects of the technology described herein are not limited in this respect. Example algorithms for determining ploidy are described by Favero et. al. (Sequenza: allele-specific copy number and mutation profiles from tumor sequencing data, *Ann. Oncol.*, 26(1): 64-70) and Shen, R. & Seshan, V. E. (FACETS: allele-specific copy number and clonal heterogeneity analysis tool for high throughput DNA sequencing, *Nucleic Acids Res.*, 44(16): e131), each of which is incorporated by reference herein in its entirety.

Gene fusions 656 are hybrid genes that form as a result of chromosomal rearrangements (e.g., translocations, deletions, etc.). In some embodiments, there may be several types of fusion features. A first example includes the fusion of a first gene (e.g., gene A) with a second gene (e.g., gene B). A second example includes the fusion of the first type of gene (e.g., gene A) with any gene. A third example includes the fusion of any gene with the first type of gene (e.g., gene A). It should be appreciated that, due to the nature of fusion, the order is important, and thus the second example differs from the third example. In some embodiments each type of feature may be represented in binary format, where 1 represents the presence of a fusion and 0 represents the absence of the fusion.

Microsatellite instability (MSI) status 657 is a condition in which the number of repeated DNA based in a short, repeated sequence of DNA (a microsatellite) differs from what it was when the microsatellite was inherited. In some embodiments, MSI status 657 may be represented by a binary feature, where 1 represents instability and 0 represents stability. In some embodiments, MSI status may be procured by laboratory analysis, sequencing analysis, or any other suitable technique, as aspects of the technology described herein are not limited to any particular procurement technique.

In some embodiments, genes 658 include protein-coding and non-protein coding genes. In some embodiments, features, such as the normalized gene copy number, are derived from the genes. For example, Bagaev et. al. (Integrated whole exome and transcriptome analyses of the tumor and microenvironment provide new opportunities for rational design of cancer therapy, in Proc. of the AACR Annual Meeting 2020, *Cancer Res.*, 80(16 Suppl.), 4418), which is incorporated herein by reference in its entirety, describes determining normalized gene copy numbers.

While examples of features that can be derived from DNA expression data have been described above, it should be appreciated that this is a non-exhaustive list and any suitable feature may be used in addition to or instead of the features described above.

Example Hierarchies of Molecular Categories

FIGS. 7A-1-7A-3 and FIGS. 7B-1-7B-5 show example hierarchies of molecular categories that could be used in conjunction with the techniques described herein. Table 2 lists the molecular categories shown in FIGS. 7A-1-7A-3 and FIGS. 7B-1-7B-5 However, it should be appreciated that other suitable hierarchies of molecular categories may be used, as the techniques described herein are not limited to any particular labelling of molecular categories or relationships between molecular categories.

In these examples, a molecular category is a category of biological samples that share features from Hoadley et. al. (Cell-Of-Origin Patterns Dominate the Molecular Classification of 10,000 Tumors from 33 Types of Cancer, *Cell,* 173(2), 291-304), Robinson et. al. (Integrative clinical genomics of metastatic cancer, *Nature,* 548, 297-303), and Hoadley et. al. (Multiplatform Analysis of 12 Cancer Types Reveals Molecular Classification within and across Tissues of Origin, *Cell,* 158(4), 929-944), each of which is incorporated herein by reference in its entirety.

FIGS. 7A-1-7A-3 show an example hierarchy 700 of molecular categories, according to some embodiments of the technology described herein. As shown, molecular categories are represented by nodes, and relationships between the molecular categories are represented by edges that connect the nodes. For example, the molecular category "Neoplasm" shown in FIG. 7A-2 is represented by a parent node that has child nodes representing molecular categories "Hematologic Neoplasm" and "Solid Neoplasm." As another example, the node representing "Renal Cell Carcinoma" shown in FIG.

7A-2 is a parent node to child nodes that represent the molecular categories "Non-Clear Cell Carcinoma" and "Clear Cell Carcinoma," also shown in FIG. 7A-2.

As described above, molecular categories at different levels of the hierarchy have differing degrees of specificity—molecular categories at higher levels of the hierarchy are broader categories and have lower specificity, while molecular categories at lower levels of the hierarchy are narrower categories having higher specificity. For example, the molecular category "Adenocarcinoma" has a lower specificity than molecular category "Prostate Adenocarcinoma," since it is at a higher level of the molecular category.

Figures 1, 7B:
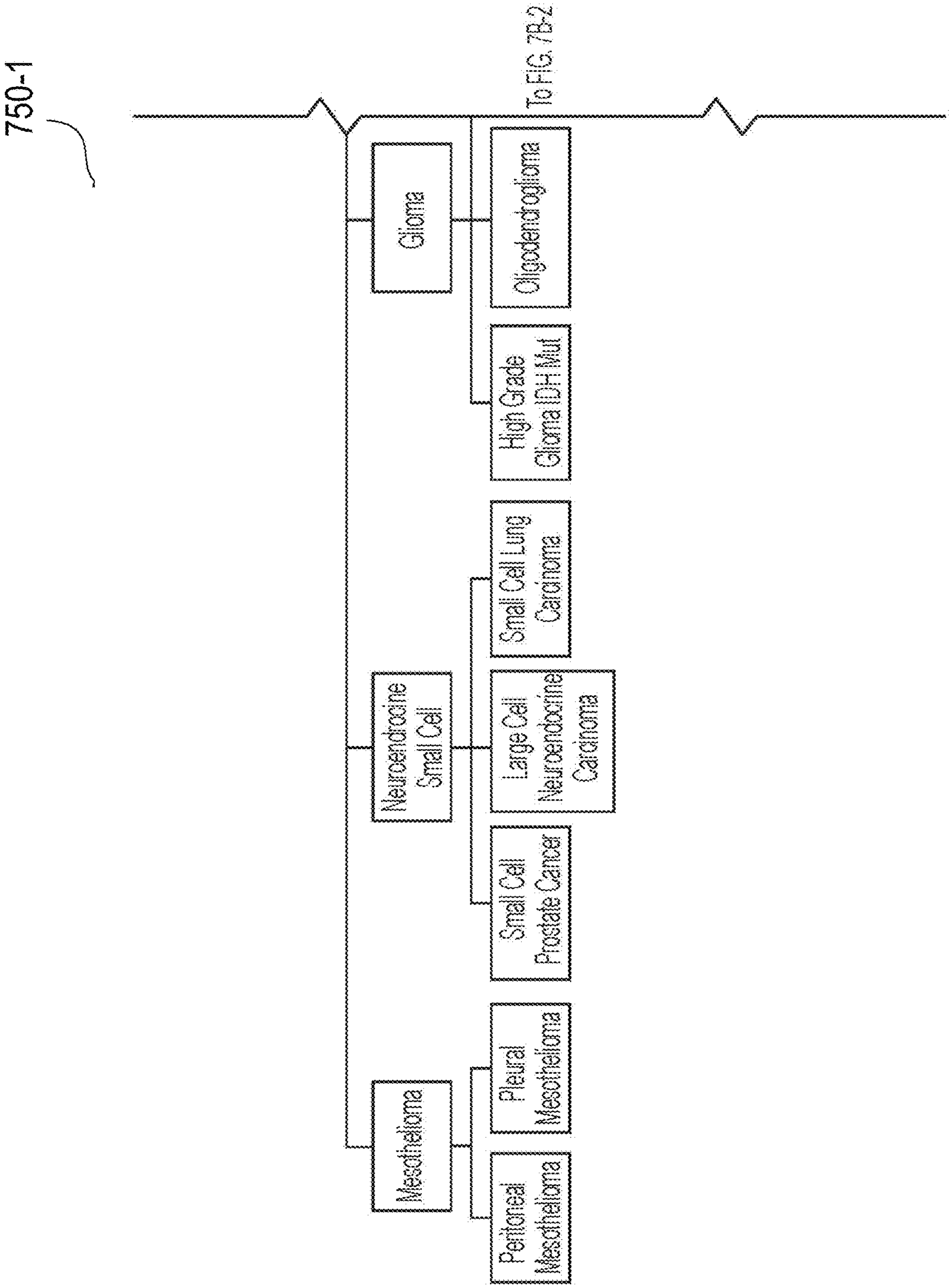
Figures 2, 7B:
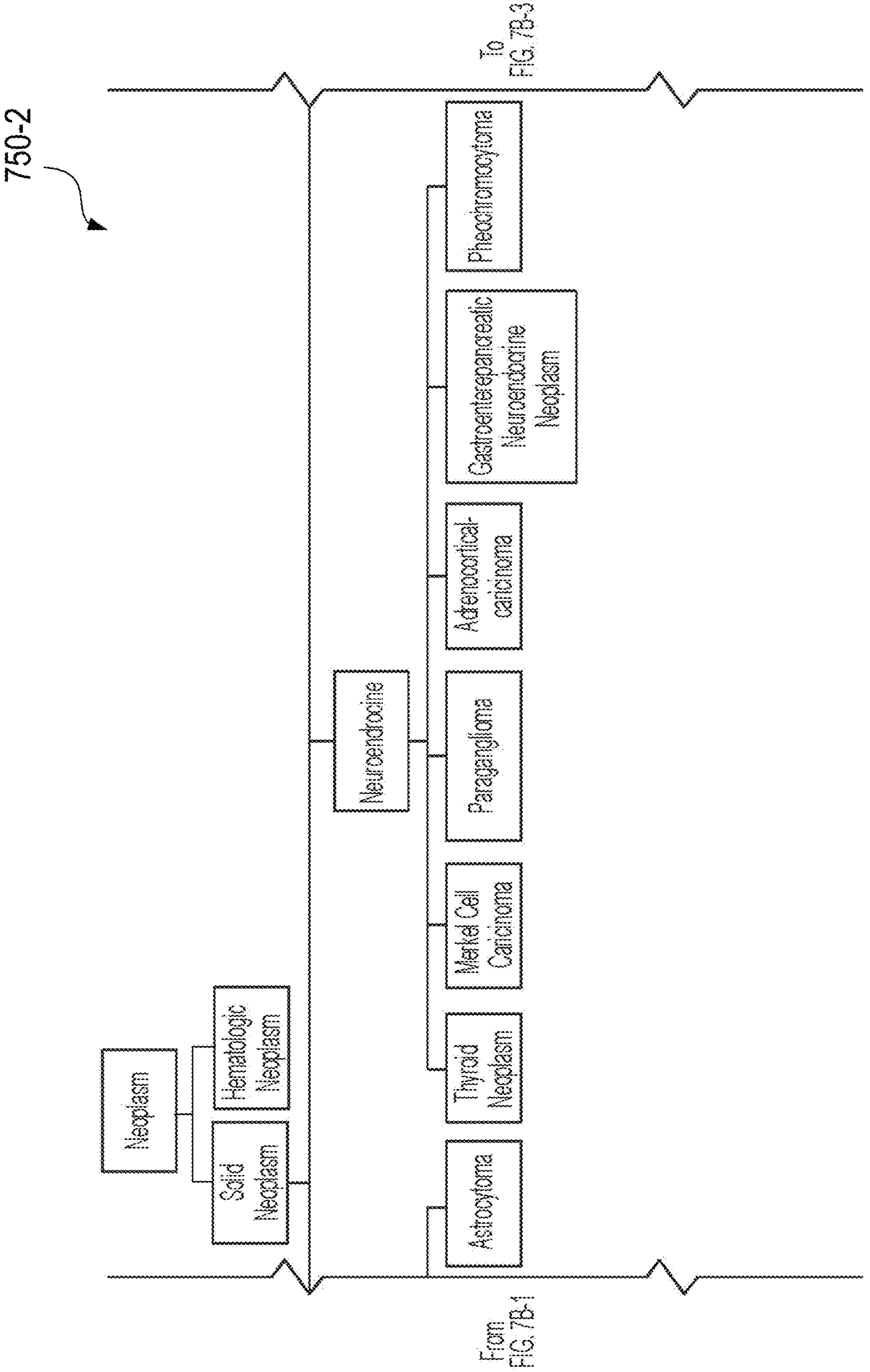
Figures 3, 7B:
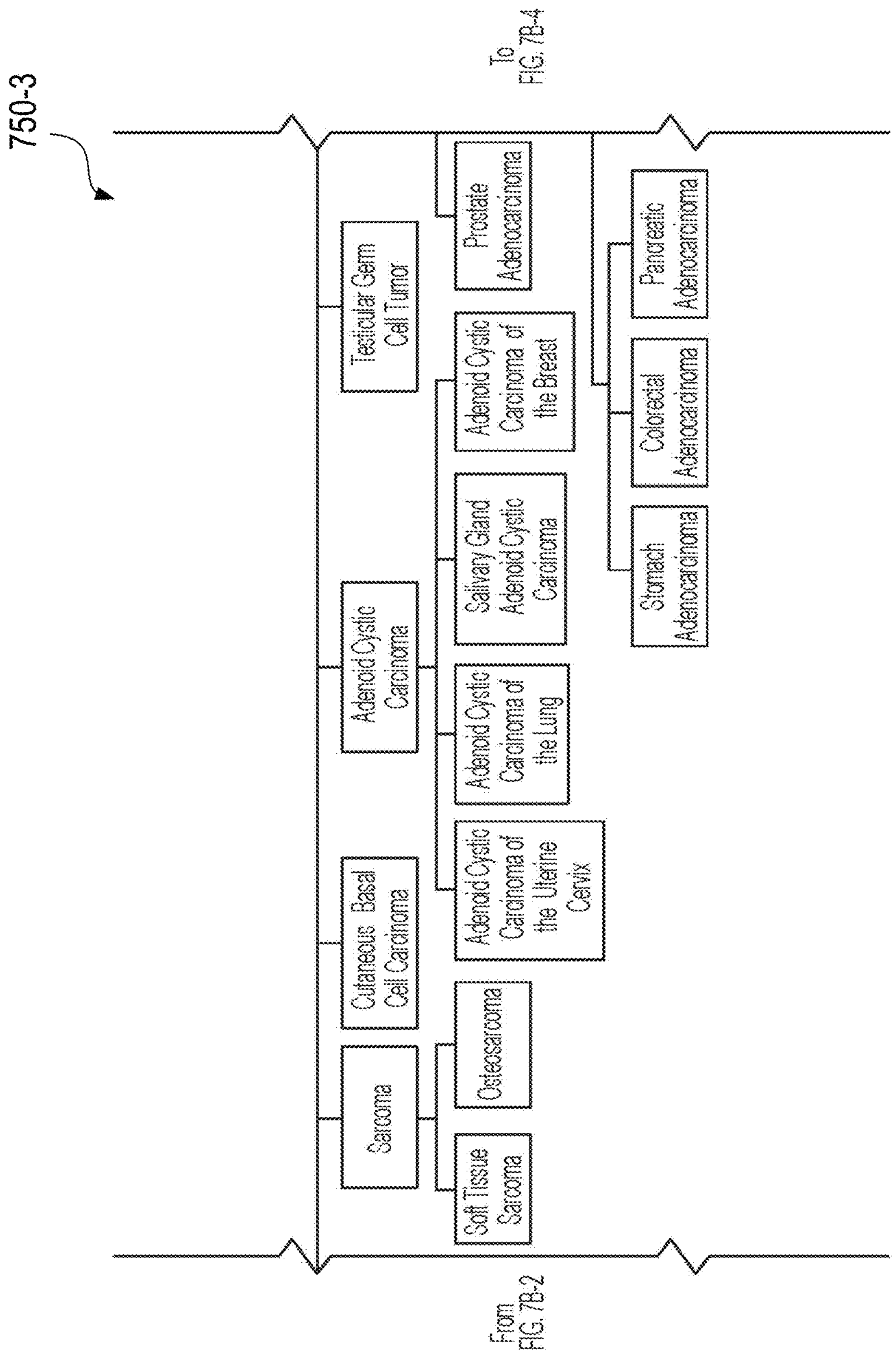
Figures 4, 7B:
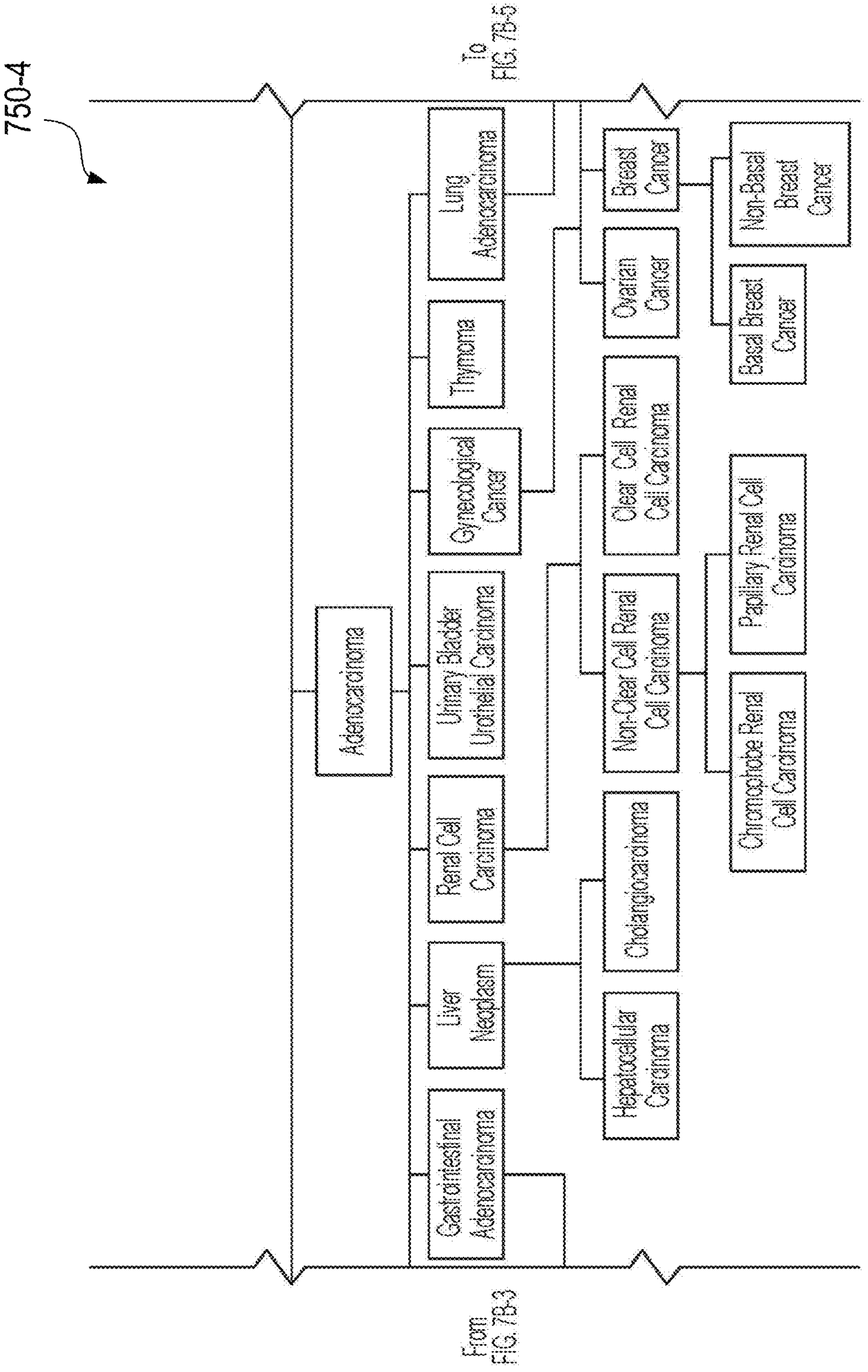
Figures 5, 7B:
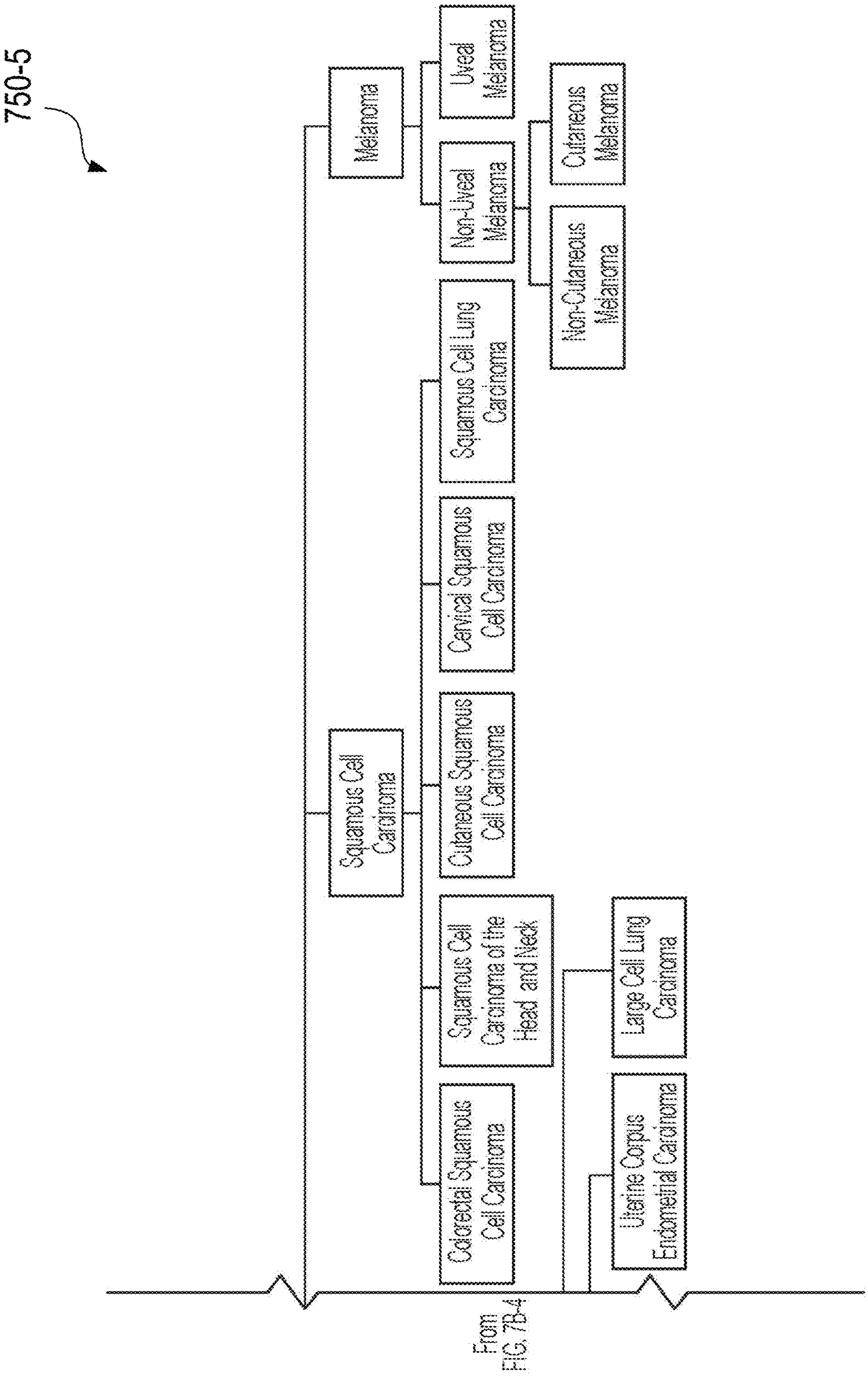

FIG. 7B-1-7B-5 show an example hierarchy 750 of molecular categories, according to some embodiments of the technology described herein. The example hierarchy 750 includes some molecular categories that are also included in 700 and some molecular categories that are not included in example hierarchy 700. For example, at least molecular categories "Hepatocellular Carcinoma" and "Cholangiocarcinoma" as shown in FIG. 7B-4.

As explained above, it should be appreciated that any suitable hierarchy of molecular categories, including either example hierarchy 700 and/or example hierarchy 750, can be used in conjunction with the techniques described herein to identify a candidate molecular category, as aspects the technique are not limited in this respect.

TABLE 2

| Example Molecular Categories<br>Molecular category |
|---|
| Neoplasm |
| Solid Neoplasm |
| Hematologic Neoplasm |
| Melanoma |
| Non-Uveal Melanoma |
| Uveal Melanoma |
| Non-Cutaneous Melanoma |
| Cutaneous Melanoma |
| Sarcoma |
| Soft Tissue Sarcoma |
| Osteosarcoma |
| Mesothelioma |
| Peritoneal Mesothelioma |
| Pleural Mesothelioma |
| Neuroendocrine |
| Neuroendocrine Small Cell |
| Small Cell Prostate Cancer |
| Large Cell Neuroendocrine Carcinoma |
| Small Cell Lung Carcinoma |
| Squamous Cell Carcinoma |
| Colorectal Squamous Cell Carcinoma |
| Cutaneous Squamous Cell Carcinoma |
| Adenocarcinoma |
| Adrenocortical Carcinoma |
| Glioma |
| Adenoid Cystic Carcinoma |
| Adenoid Cystic Carcinoma of the Uterine Cervix |
| Adenoid Cystic Carcinoma of the Breast |
| Salivary Gland Adenoid Cystic Carcinoma |
| Testicular Germ Cell Tumor |
| Pheochromocytoma |
| Cervical Squamous Cell Carcinoma |
| Liver Neoplasm |
| Hepatocellular Carcinoma |
| Cholangiocarcinoma |
| Lung Adenocarcinoma |
| High Grade Glioma IDH Mut |
| Thyroid Neoplasm |
| Merkel Cell Carcinoma |
| Paraganglioma |
| Gastrointestinal Neuroendocrine Neoplasm |
| Squamous Cell Lung Carcinoma |
| Thymoma |

TABLE 2-continued

| Example Molecular Categories<br>Molecular category |
|---|
| Prostate Adenocarcinoma |
| Urinary Bladder Urothelial Carcinoma |
| Oligodendroglioma |
| Squamous Cell Carcinoma of the Head and Neck |
| Gastrointestinal Adenocarcinoma |
| Gynecological |
| Renal Cell Carcinoma |
| Astrocytoma |
| Pancreatic Adenocarcinoma |
| Stomach Adenocarcinoma |
| Pancreatic Adenocarcinoma |
| Colorectal Adenocarcinoma of the Breast |
| Breast Cancer |
| Ovarian Cancer |
| Uterine Corpus Endometrial Carcinoma |
| Non-Clear Cell Carcinoma |
| Clear Cell Carcinoma |
| Basal Breast Cancer |
| Non-Basal Breast Cancer |

Training an RNA-Based Machine Learning Classifier

As described above, the machine learning techniques developed by the inventors include processing RNA expression data for a particular set of genes using a particular machine learning classifier to determine whether to identify a particular molecular category as a candidate molecular category for the biological sample. Illustrative process 800 shows a flowchart for identifying the particular set of genes and for training a machine learning classifier, according to some embodiments of the technology described herein. Process 800 may be performed by a laptop computer, a desktop computer, one or more servers, in a cloud computing environment, computing device 104 as described herein with respect to FIG. 1A, computing device 1000 as described herein with respect to FIG. 10, or in any other suitable way.

Process 800 begins at act 802, where expression level values are obtained for a plurality of genes. In some embodiments, expression level values may be obtained using any suitable technique or combination of techniques, such as the techniques described herein including at least with respect to FIGS. 1A-B and in the "Expression Data" and "Obtaining RNA expression data" sections.

At act 804, the techniques include identifying an initial set of genes of the plurality of genes for which expression data was obtained at act 802. In some embodiments, identifying an initial set of genes includes identifying genes that distinguish the candidate molecular category from all other molecular categories. Additionally or alternatively, this may include identifying genes that distinguish the candidate molecular category from the normal tissue corresponding to the molecular category (e.g., normal tissue from the site of origin). In some embodiments, identifying such genes includes performing a differential expression analysis. In some embodiments, this included performing running a pairwise differential expression analysis between the candidate molecular category and all other molecular categories. Additionally or alternatively, this may include performing a pairwise differential expression analysis between the candidate molecular category and the normal tissue.

After performing the differential expression analysis, in some embodiments, genes that appear greater than a threshold number of times in the differential expression analysis are selected for the initial set of genes. For example, genes appearing greater than a threshold number of times may be selected for initial set of genes. In some embodiments, the initial set of genes includes at least 400 genes, at least 600 genes, at least 700 genes, at least 800 genes, at least 1,000 genes, at least 1,200, at least 1,400 genes, at least 1,500 genes, between 400 genes and 1,500 genes, or between 700 and 1,200 genes. In some embodiments, narrowing down the number of genes to an initial set of genes reduces the computational load required for further processing.

At act 806, the techniques include ranking the expression level values of the genes included in the initial set of genes. In some embodiments, ranking the genes according to their expression level values includes assigning a rank to each gene in the set based on the expression level value associated with that gene. In some embodiments, a rank is an integer that is different from the expression level value to which it has been assigned. Example techniques for ranking genes are described herein including at least with respect to FIG. 6A.

At act 808, the techniques include choosing hyperparameters and fitting a statistical model. In some embodiments, this includes performing cross-validation using any suitable techniques, such as, stratified k-fold cross validation. For example, a 5-fold stratified cross-validation may be used. In some embodiments, any suitable train to test ratio may be used, such as, for example, 80 to 20 percent. Pedregosa et. al. (Scikit-learn: Machine Learning in Python, *Journal of Machine Learning Research,* 12(85): 2825-2830) describes an algorithm for realizing a stratified k-fold cross validation.

In some embodiments, the hyperparameters are selected according to a weighted F1 score of a cross-validation. In some embodiments, the hyperparameters are selected according to a weighted F1 score of a cross-validation. Example hyperparameters include, but are not limited to number of estimators, number of leaver, learning rate, and share of features per one tree.

Equation 3 is an example formula for calculating an average weighted F1 score:

$$\text{Avg. Weighted } F1 = \sum_{classes} \frac{\text{class size}}{\text{total samples}} * \frac{2 * \text{precision}_{class} * \text{recall}_{class}}{\text{precision}_{class} + \text{recall}_{class}} \quad \text{(Equation 3)}$$

where class represents the target molecular category and class size represents the number of samples of the molecular category in the test dataset. In some embodiments, precision and recall for the molecular category are estimated on a full test data set, separated on two classes—the target molecular category and all other molecular categories (and, in some embodiments, normal tissue).

In some embodiments, two different weighted F1 scores are calculated. First, a weighted F1 score may be calculated considering cases where the machine learning classifier is unable to predict any molecular category (e.g., failed). Second, a weighted F1 score may be calculated that excludes failed predictions.

At act 810, process 800 includes calculating the importance each of genes in the initial set. This includes assigning a score to the gene based on how valuable it is in predicting the target variable. Gene importance can be calculated using any suitable method, as aspects of the technology described herein are not limited to any particular gene importance calculation technique. In some embodiments, regression coefficients may be used to determine gene importance (e.g., when using a linear regression classifier). In some embodiments, Gini importance may be used to determine gene importance (e.g., when using a gradient boosting classifier). In some embodiments. SHAP values may be used to determine gene importance (e.g., when using a gradient boosting tree classifier). For example, Lundberg et. al. ("From local explanations to global understanding with explainable AI for trees," *Nat Mach Intell* 2, 56-57), which is incorporate herein by reference in its entirety, describes techniques for determining gene importance using SHAP values for gradient boosting tree classifiers, At act 812, process 800 includes generating an updated set of the genes by discarding at least a threshold number of the least important genes, based on the calculated gene importances. For example, this may include discarding at least 1 gene, at least 2 genes, at least 5 genes, at least 8 genes, at least 10 genes, at least 15 genes, at least 20 genes, at least 25 genes, between 1 and 30 genes, between 2 and 15 genes, between 2 and 5 genes, or between 5 and 10 genes. In some embodiments, the number of genes discarded depends on the number of genes included in the gene set. For example, more genes with be discarded when the gene set is relatively large compared to the number of genes discarded with the initial gene set is relatively small.

At act 814, process 800 includes determining whether there are more genes remaining in the gene set, which was updated at act 812. If there are genes remaining in the gene set, process 800 returns to act 808, where ranks are assigned to genes in the updated gene set. If there are no genes remaining in the set, process 800 proceeds to act 816.

At act 816, process 800 includes identifying a final set of genes. In some embodiments, the final set is identified according to the weighted F1 scores determined at each iteration of act 808 of process 800. For example, the set of genes that resulted in the highest weighted F1 score at act 808 may be selected.

At act 818, process 800 includes applying a rank transform to the expression values corresponding to the final set of genes identified at act 816. Techniques for ranking expression values are described above including at least with respect to act 806 of process 800 and with respect to FIG. 6A.

At act 820, the techniques include choosing the hyperparameters and fitting the statistical model. In some embodiments, this includes selecting the hyperparameters chosen at act 808 of process 800 that correspond to the final set of genes identified at act 816 of process 800.

In some embodiments, the final set of genes may correspond to the particular set of RNA genes for which RNA expression data should be obtained and processed using the trained machine learning classifier to determine whether to identify the molecular category as the candidate molecular category for the biological sample. Example RNA features corresponding to example molecular categories are provided in Table 3.

Training a DNA-Based Machine Learning Classifier

As described above, the machine learning techniques developed by the inventors include processing particular DNA features derived from DNA expression data using a particular machine learning classifier to determine whether to identify a particular molecular category as a candidate molecular category for the biological sample. Illustrative process 850 shows a flowchart for identifying the particular set of DNA features used for training a machine learning classifier, according to some embodiments of the technology described herein. Process 800 may be performed by a laptop computer, a desktop computer, one or more servers, in a cloud computing environment, computing device 104 as described herein with respect to FIG. 1A, computing device 1000 as described herein with respect to FIG. 10, or in any other suitable way.

Process 850 begins with act 852 for obtaining genomic data. In some embodiments, the genomic data may be obtained using any suitable technique or combination of techniques, such as the techniques described herein including at least with respect to FIGS. 1A-B.

At act 854, process 850 includes deriving features from the genomic data. In some embodiments, the features include any feature or combination of features described above with respect to FIG. 1B, including, but not limited to, genes, mutations, mutational hotspots, tumor mutational burden, CNA genes, CNA values, LOH values ploidy, gene fusions, and MSI status.

At act 856, the techniques include choosing hyperparameters and fitting a statistical model. In some embodiments, this includes performing cross-validation using any suitable techniques, such as, stratified k-fold cross validation. For example, a 5-fold stratified cross-validation may be used. In some embodiments, any suitable train to test ratio may be used, such as, for example, 80 to 20 percent. Pedregosa et. al. (Scikit-learn: Machine Learning in Python, *Journal of Machine Learning Research,* 12(85): 2825-2830) describes an algorithm for realizing a stratified k-fold cross validation.

In some embodiments, the hyperparameters are selected according to a weighted F1 score of a cross-validation. Techniques for determining a weighted F1 score are described above including at least with respect to act 808 of process 800. Example hyperparameters include, but are not limited to number of estimators, number of leaver, learning rate, and share of features per one tree.

At act 858, process 850 includes calculating the importance each of features in the current set of features. This includes assigning a score to the feature based on how valuable it is in predicting the target variable. Gene importance can be calculated using any suitable method, as aspects of the technology described herein are not limited to any particular gene importance calculation technique. In some embodiments, regression coefficients may be used to determine gene importance (e.g., when using a linear regression classifier). In some embodiments, Gini importance may be used to determine gene importance (e.g., when using a gradient boosting classifier). In some embodiments. SHAP values may be used to determine gene importance (e.g., when using a gradient boosting tree classifier). For example, Lundberg et. al. ("From local explanations to global understanding with explainable AI for trees," *Nat Mach Intell* 2, 56-57), which is incorporate herein by reference in its entirety, describes techniques for determining gene importance using SHAP values for gradient boosting tree classifiers, At act 860, process 850 includes generating an updated set of the features by discarding at least a threshold number of the least important features, based on the calculated feature importances. For example, this may include discarding at least 1 feature, at least 2 features, at least 5 features, at least 8 features, at least 10 features, at least 15 features, at least 20 features, at least 25 features, between 1 and 30 features, between 2 and 15 features, between 2 and 5 features, or between 5 and 10 features. In some embodiments, the number of features discarded depends on the number of features included in the feature set. For example, more features with be discarded when the feature set is relatively large compared to the number of features discarded with the initial feature set is relatively small.

At act 862, process 850 includes determining whether the updated includes a minimum number of features. For example, the minimum number of features may include 0 features, at least 10 features, at least 20 features, at least 40 features, at least 60 features, at least 80 features, between 10 and 60 features, or between 20 and 40 features. In some embodiments, if the number of features in the updated set of features exceeds the minimum number of features, process 850 returns to act 856, where hyperparameters are chosen and a statistical model is fit. If there are no features remaining in the set, process 800 proceeds to act 864.

At act 864, process 850 includes identifying a final set of features. In some embodiments, the final set is identified according to the weighted F1 scores determined at each iteration of act 856 of process 850. For example, the set of features that resulted in the highest weighted F1 score at act 856 may be selected.

At act 866, the techniques include choosing the hyperparameters and fitting the statistical model. In some embodiments, this includes selecting the hyperparameters chosen at act 856 of process 850 that correspond to the final set of features identified at act 564 of process 500.

In some embodiments, the final set of features may correspond to the particular set of DNA features to be obtained from DNA expression data and processed using the trained machine learning classifier to determine whether to identify the molecular category as the candidate molecular category for the biological sample. Example DNA features corresponding to example molecular categories are provided in Table 5.

Molecular Category Identification Performance

Figure 9A:
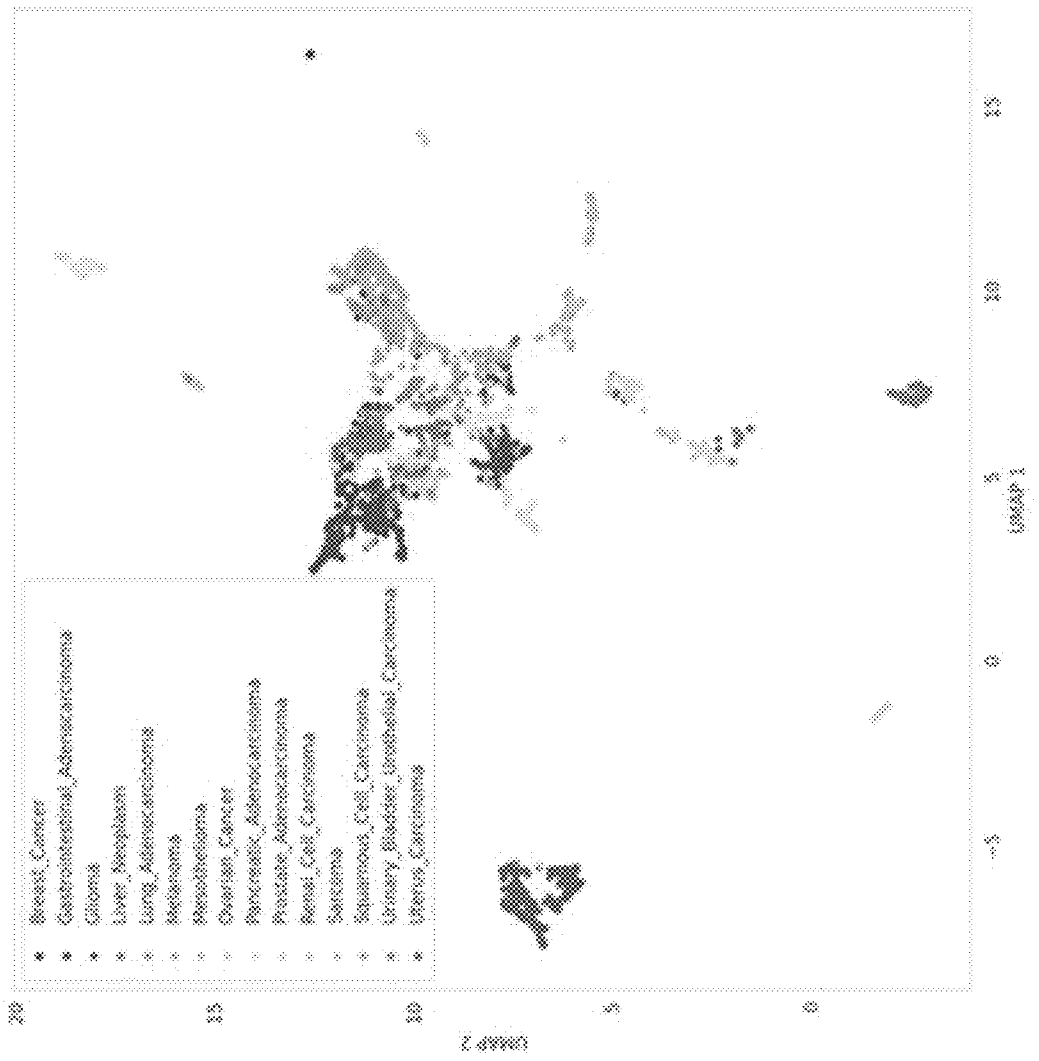
FIG. 9A is a plot showing that tumor samples belonging to a same molecular category share similar gene expression profiles, according to some embodiments of the technology described herein.

FIG. 9A shows an example clustering of tumor samples in the space of gene expression. Each sample corresponds to a molecular category shown in the legend. Points corresponding to the same molecular category are shown to cluster together, indicating gene expression is a feature that may be useful for distinguishing between biological samples belonging to different molecular categories. Accordingly, the techniques described herein utilize gene expression data (e.g., RNA expression data) in identifying molecular categories for the biological samples.

Figure 9B:
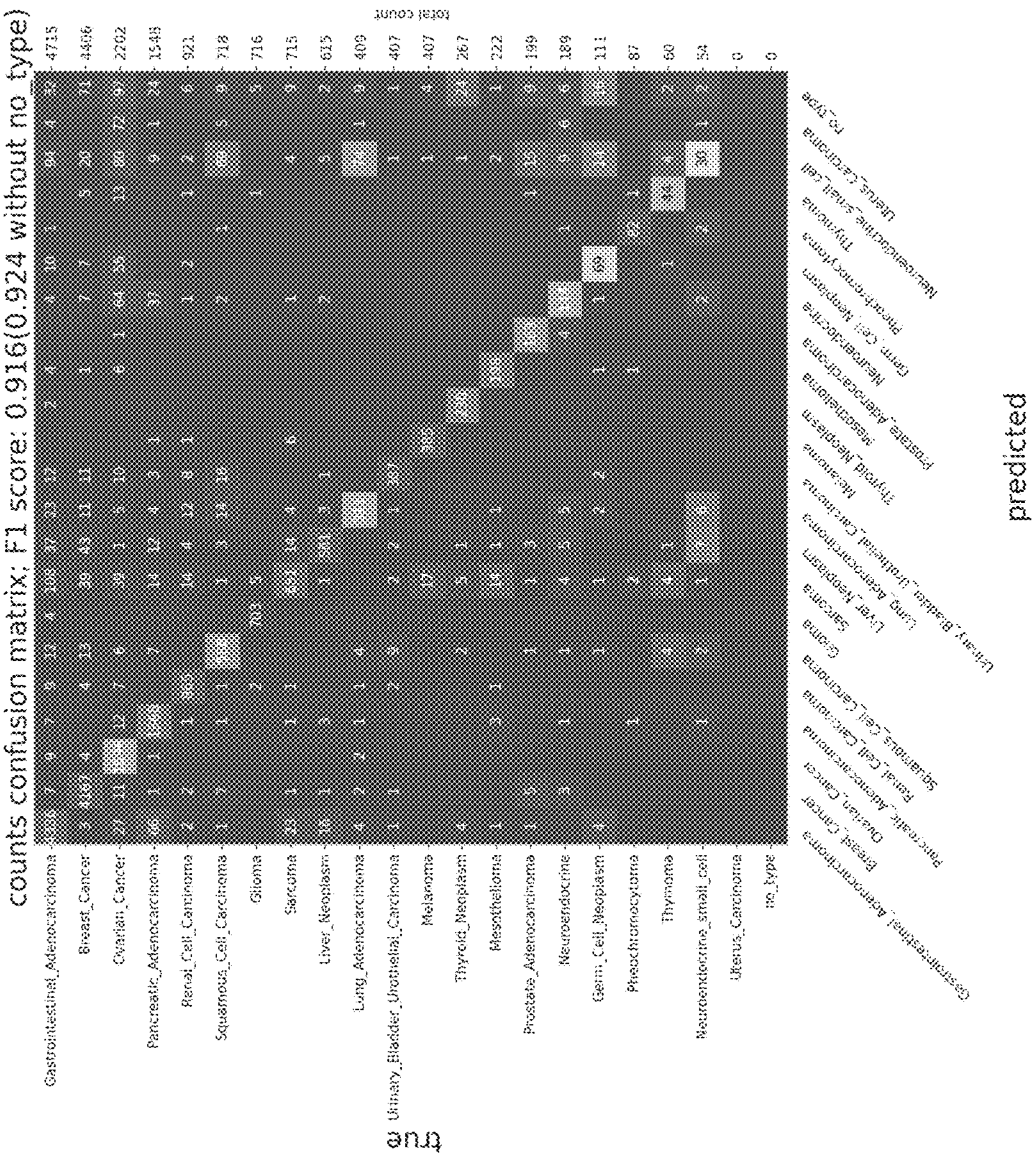
FIG. 9B is a diagram illustrating the performance of the machine learning techniques developed by the inventors, according to some embodiments of the technology described herein.

FIG. 9B is a diagram illustrating the performance of the machine learning techniques developed by the inventors, according to some embodiments of the technology described herein. In particular, the diagram compares the molecular categories predicted according to the techniques developed by the inventors with the corresponding true molecular categories for the biological sample. As shown, the techniques perform with a 92.4% accuracy indicating that the techniques can be used to accurately and reliably identify a candidate molecular category for a biological sample, such as a tumor.

Figure 9C:
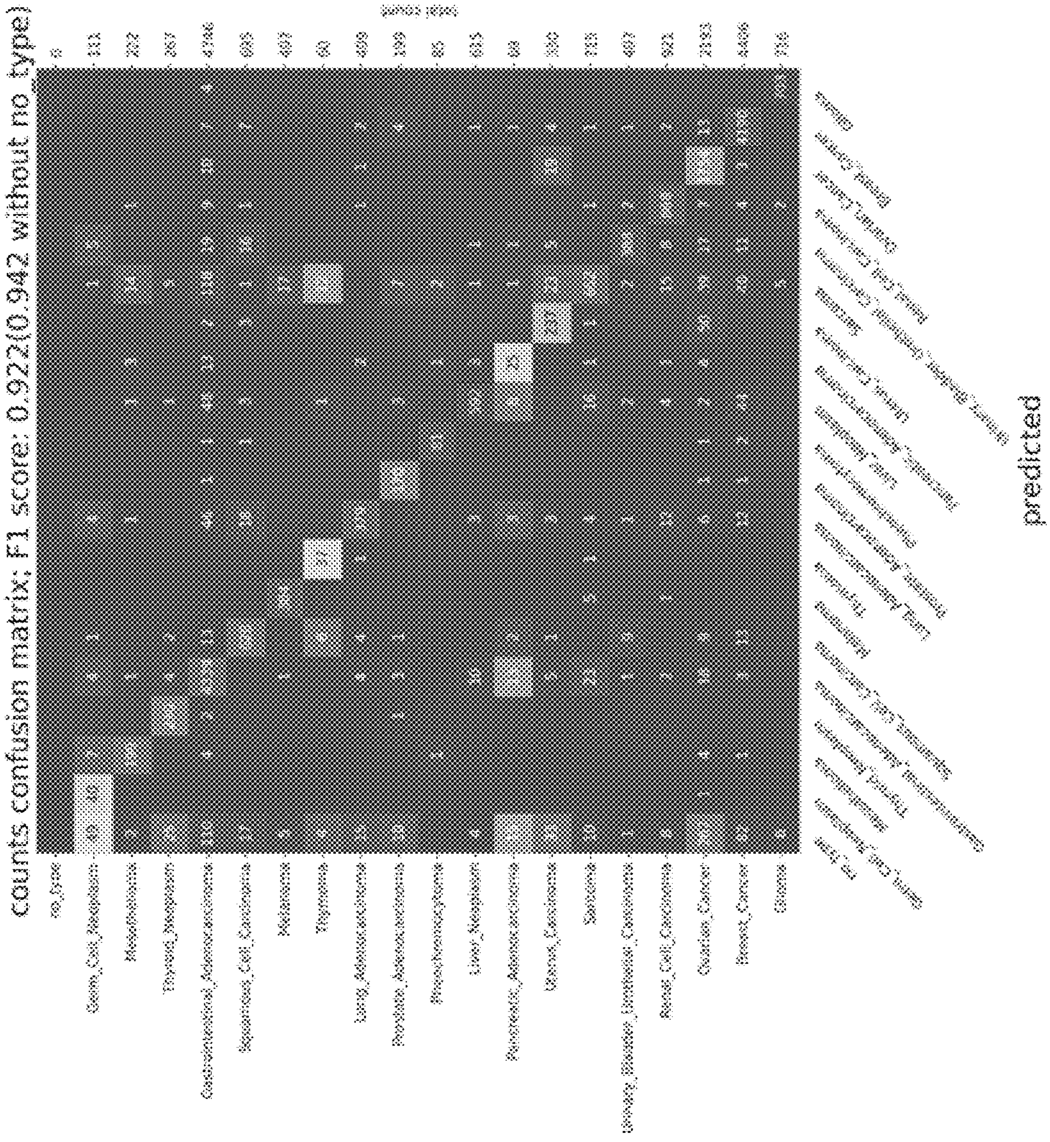
FIG. 9C is a diagram illustrating the performance of an RNA-based machine learning classifier developed by the inventors, according to some embodiments of the technology described herein.

FIG. 9C is a diagram illustrating the performance of an RNA-based machine learning classifier developed by the inventors, according to some embodiments of the technology described herein.

Figure 9D:
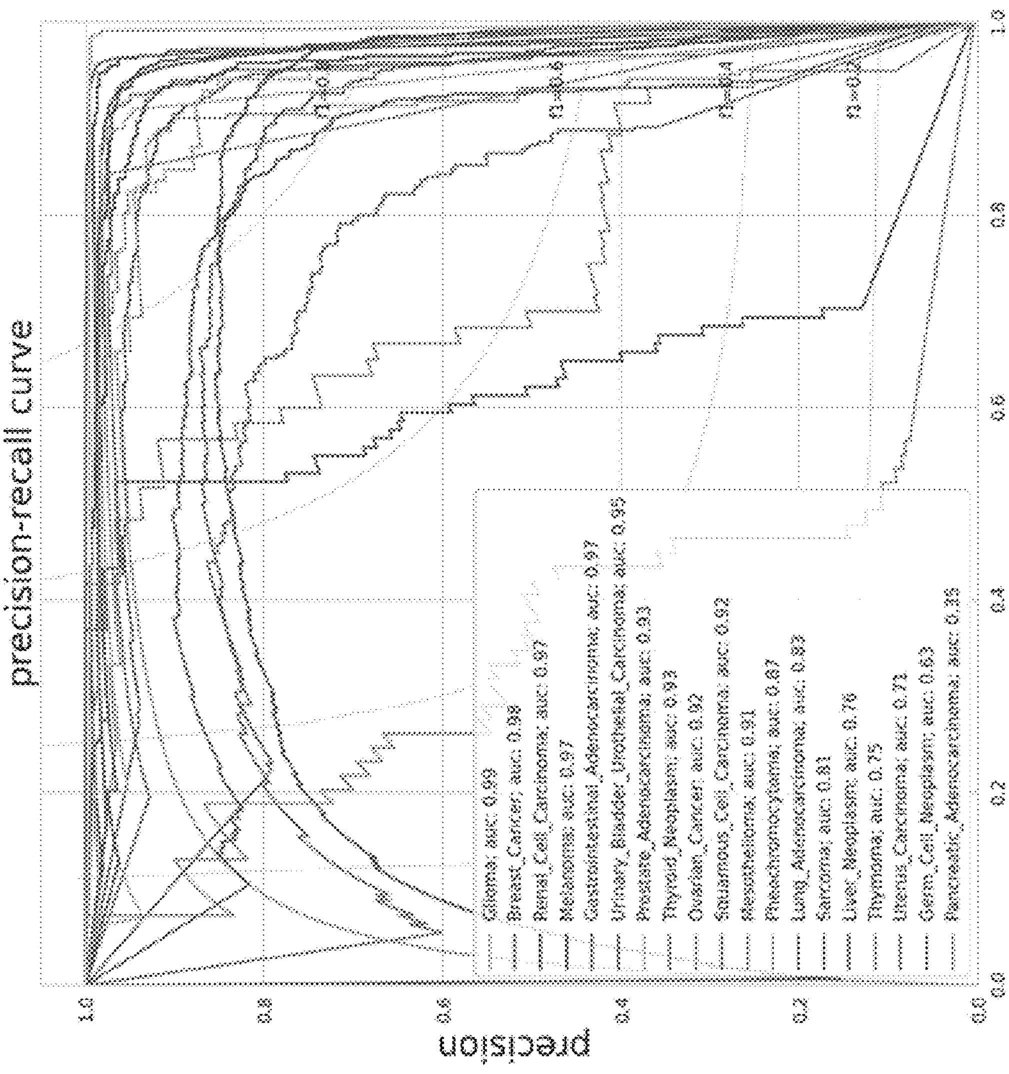
FIG. 9D shows precision-recall curves illustrating the performance of the RNA-based machine learning classifier, according to some embodiments of the technology described herein.

FIG. 9D shows precision-recall curves illustrating the performance of the RNA-based machine learning classifier, according to some embodiments of the technology described herein.

Figure 9E:
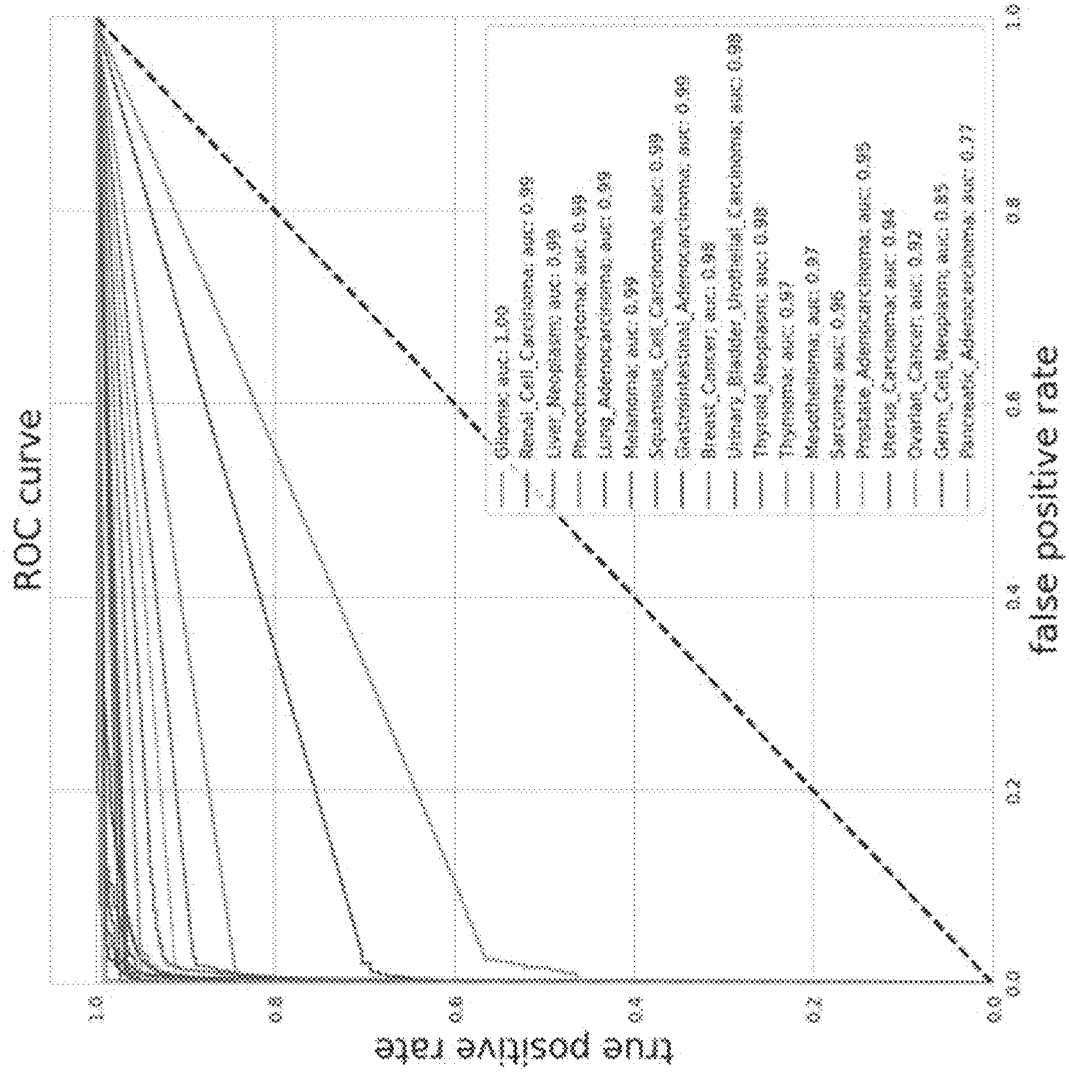
FIG. 9E shows receiver operating characteristic (ROC) curves illustrating performance of the RNA-based machine learning classifier, according to some embodiments of the technology described herein.

FIG. 9E shows receiver operating characteristic (ROC) curves illustrating performance of the RNA-based machine learning classifier, according to some embodiments of the technology described herein.

Figure 9F:
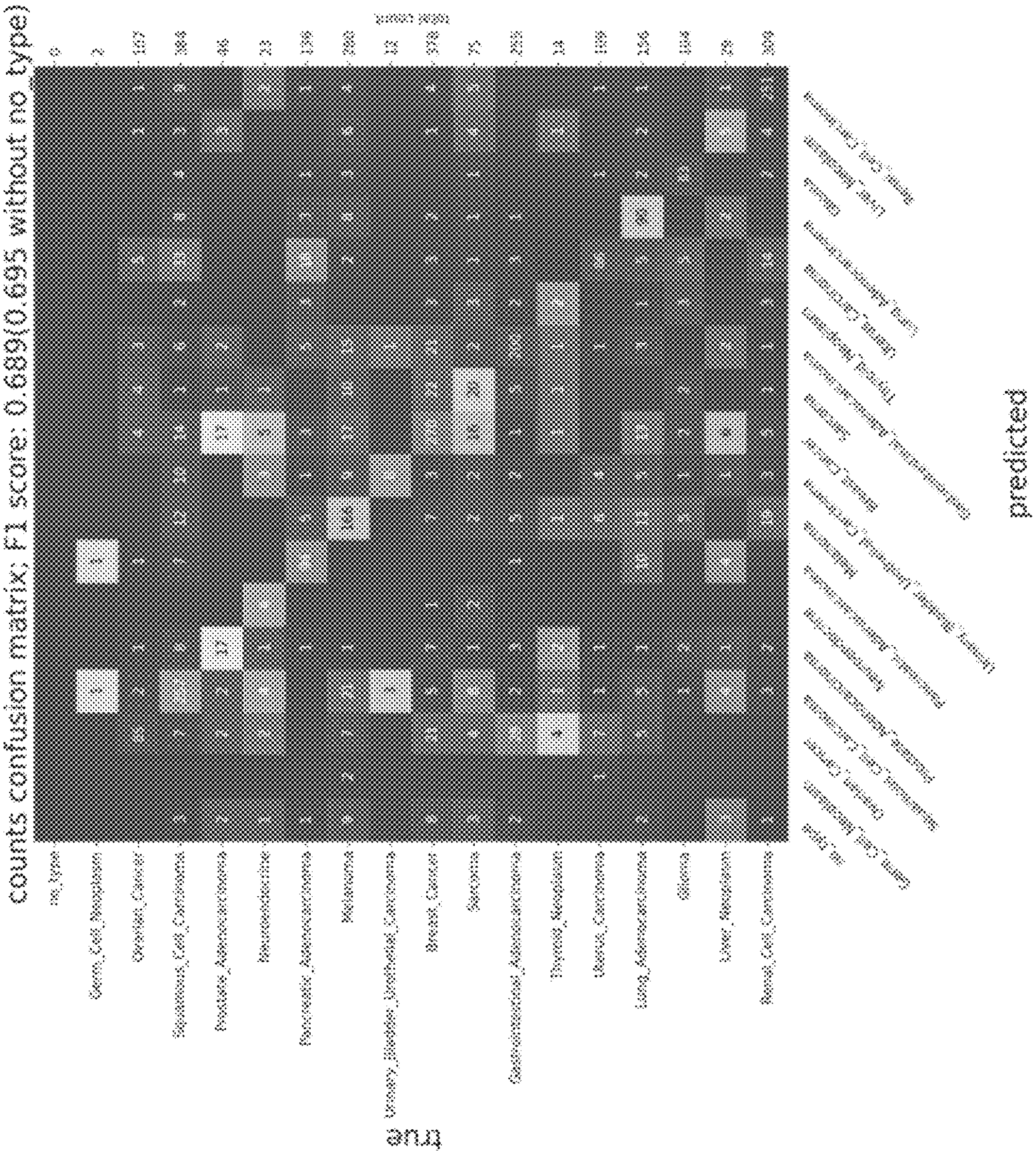
FIG. 9F is a diagram illustrating the performance of a DNA-based machine learning classifier developed by the inventors, according to some embodiments of the technology described herein.

FIG. 9F is a diagram illustrating the performance of a DNA-based machine learning classifier developed by the inventors, according to some embodiments of the technology described herein.

Figure 9G:
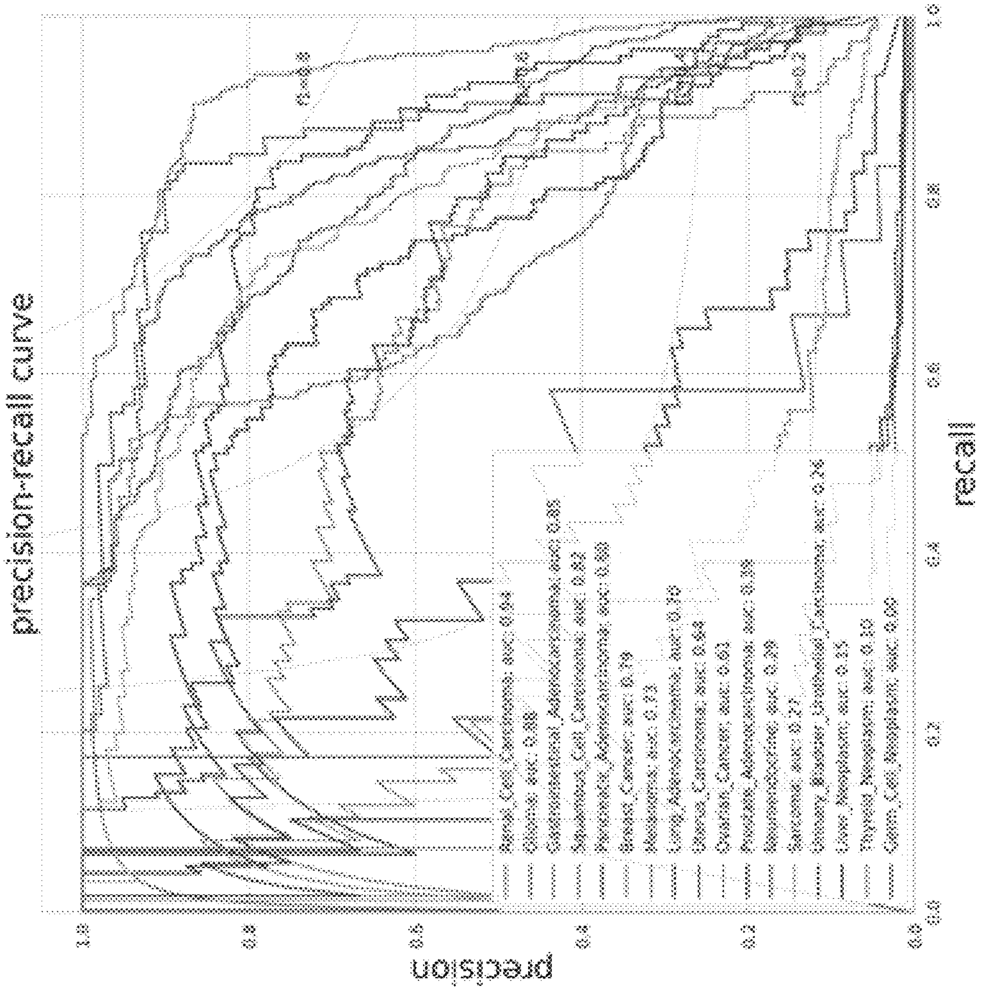
FIG. 9G shows precision-recall curves illustrating the performance of the DNA-based machine learning classifier, according to some embodiments of the technology described herein.

FIG. 9G shows precision-recall curves illustrating the performance of the DNA-based machine learning classifier, according to some embodiments of the technology described herein.

Figure 9H:
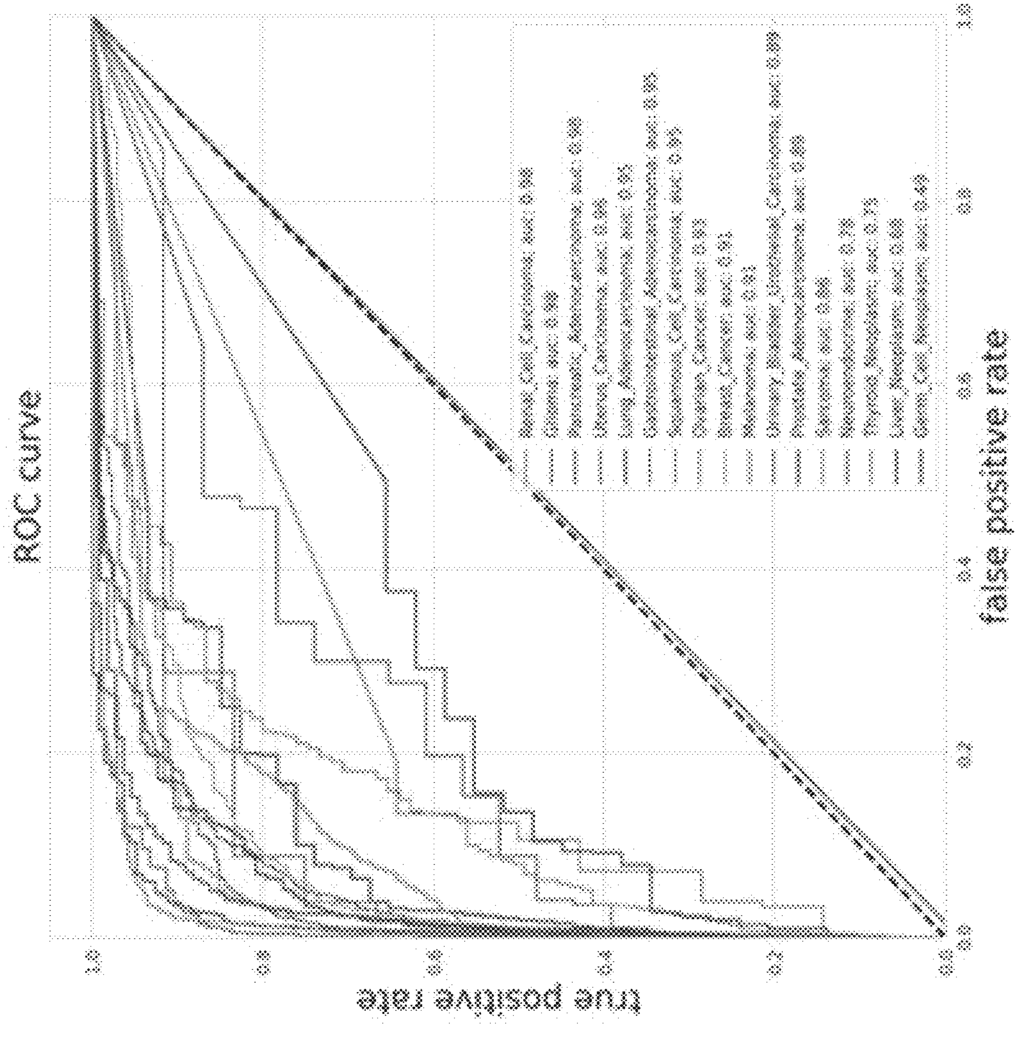
FIG. 9H shows receiver operating characteristic (ROC) curves illustrating performance of the DNA-based machine learning classifier, according to some embodiments of the technology described herein.

FIG. 9H shows receiver operating characteristic (ROC) curves illustrating performance of the DNA-based machine learning classifier, according to some embodiments of the technology described herein.

RNA and DNA Features

As described herein, in some embodiments, a machine learning classifier corresponding to a respective molecular category may be used to determine whether the molecular category is to be identified for a biological sample.

In some embodiments, the machine learning classifier for a particular molecular category may be an RNA-based machine learning classifier and may process, as input, features obtained from RNA expression data for a specific set of genes identified a priori for the particular molecular category.

Table 3 lists, for each of multiple different molecular categories, genes that are associated with the molecular category. In some embodiments, the techniques described herein include obtaining RNA expression data for at least some (e.g., at least ten, at least 15, at least 20, at least 25, at least 30, at least 45, at least 50, between 10 and 50, between 10 and 100) of the genes listed in Table 3 for a particular molecular category (e.g., the molecular categories listed in Table 2), obtaining RNA features from the expression data (e.g., gene rankings, expression levels, and/or any other suitable features) and processing the RNA features using an RNA-based machine learning classifier to determine whether to identify the particular molecular category as a candidate molecular for the biological sample.

Table 3 is divided into portions, where each portion includes genes that are listed for a molecular category. For example, the first portion includes genes listed for the molecular category "Gastrointestinal Adenocarcinoma." For example, another portion includes genes listed for the molecular category "Pancreatic Adenocarcinoma." For example, a third portion includes genes listed for the molecular category "Breast Cancer."

In some embodiments, the machine learning classifier for a particular molecular category may be an DNA-based machine learning classifier and may process, as input, features obtained from DNA expression data for a specific set of features identified a priori for the particular molecular category.

Table 5 lists, for each of multiple different molecular categories, DNA features that are associated with the molecular category. In some embodiments, the techniques described herein include processing DNA expression data to obtain at least some (e.g., at least 10, at least 15, at least 20, at least 25, at least 30, at least 45, at least 50, between 10 and 50, between 10 and 100) of the DNA features listed in Table 5 for a particular molecular category (e.g., the molecular categories listed in Table 2) and processing the DNA features (e.g., mutational burden, normalized copy numbers etc.) using a DNA-based machine learning classifier to determine whether to identify the particular molecular category as a candidate molecular for the biological sample.

Table 5 is divided into portions, where each portion includes DNA features that are associated with a molecular category. For example, the first portion includes DNA features listed for the molecular category "Ovarian Cancer." For example, another portion includes DNA features listed for the molecular category "Breast Cancer." For example, another portion includes DNA features listed for the molecular category "Squamous Cell Carcinoma." Table 4 lists descriptions of the DNA feature notation in Table 5 listed under column "DNA Feature."

TABLE 3

Genes associated with molecular categories.

| Gene | NCBI Gene ID | NCBI Accession Number(s) |
|---|---|---|
| Gastrointestinal_Adenocarcinoma | | |
| TUSC3 | 7991 | XM_011544651; XM_017013861; NM_178234; NM_006765; NM_001356429 |
| ZG16 | 653808 | NM_152338; XM_011545921 |
| COLEC11 | 78989 | XM_006711897; NM_001255986; NM_001255989; NM_001255985; NM_001255982; NM_001255983; NM_001255984; NM_024027; NR_045659; XM_005263853; NM_001255987; NM_001255988; NM_199235 |
| KLF4 | 9314 | NM_004235; NM_001314052 |
| COBL | 23242 | XM_011515239; NM_015198; XM_011515236; XM_005271751; XM_011515237; NM_001287436; NM_001287438; NM_001346441; XM_011515235; XM_011515240; XM_017011898; NM_001346443; NM_001346444; XM_011515234; XM_011515241; NM_001346442; XM_005271750; XM_011515238 |
| SIX1 | 6495 | XM_017021602; NM_005982 |
| COL10A1 | 1300 | XM_011535432; NM_000493; XM_011535433; XM_017010248; XM_006715333 |
| EPHB2 | 2048 | XM_006710441; NM_001309192; NM_004442; NM_001309193; NM_017449; XM_024453895; XM_006710442 |
| CDH19 | 28513 | XM_011525931.3; XM_017025711.2; XM_011525932.1 |
| CDX1 | 1044 | NM_001804 |
| EN1 | 2019 | NM_001426 |
| CDH17 | 1015 | NM_004063; XM_011516790; NM_001144663 |
| WNT7A | 7476 | XM_011534091; NM_004625 |
| SRD5A2 | 6716 | XM_011533069; NM_000348; XM_011533072 |
| ESM1 | 11082 | NM_001135604; NM_007036 |
| PRSS50 | 29122 | NM_013270 |
| PDX1 | 3651 | NM_000209; XR_941580; XR_941578; |
| BMP8A | 353500 | XM_017001198; XM_006710616; XM_011541381; XM_011541382; XR_946642; XR_946640; XR_946641; NM_181809 |

TABLE 3-continued

Genes associated with molecular categories.

| Gene | NCBI Gene ID | NCBI Accession Number(s) |
|---|---|---|
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SYT12 | 91683 | XM_011545346; XM_011545347; NM_177963; XM_017018547; NM_001177880; NM_001318775; XM_017018548; XM_006718737; XM_024448766; NM_001318773 |
| CFD | 1675 | NM_001317335; NM_001928 |
| GAMT | 2593 | NM_138924; NM_000156 |
| VTCN1 | 79679 | NM_001253849; NM_024626; NR_045604; XM_017002335; NM_001253850; NR_045603; XM_011542143 |
| TMSB15A | 11013 | NM_021992 |
| SLC15A2 | 6565 | XM_006713736; XM_017007074; NM_021082; XM_005247722; NM_001145998 |
| CP | 1356 | XM_006713500; XM_006713501; XM_017005735; XM_017005734; XM_006713499; XM_011512435; XR_427361; NM_000096; NR_046371 |
| MAL | 4118 | NM_022438; NM_002371; NM_022440; NM_022439 |
| KRT2 | 3849 | NM_000423 |
| IQCA1 | 79781 | XM_017004960; NM_024726; NM_001270585; XM_011511865; XM_011511866; XM_011511864; NM_001270584; NR_073043 |
| PVRL1 | 5818 | NM_203285; NM_032767; NM_002855; NM_203286 |
| PLA2G7 | 7941 | NM_001168357; XR_001743639; XM_005249408; NM_005084; XR_002956305 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| TREM2 | 54209 | NM_001271821; NM_018965 |
| ADAP1 | 11033 | NM_001284308; NM_006869; NM_001284311; NM_001284310; NM_001284309 |
| MUC13 | 56667 | NM_033049 |
| CLDN18 | 51208 | NM_001002026; NM_016369 |
| DPT | 1805 | NM_001937 |
| PLP1 | 5354 | NM_001128834; NM_000533; NM_001305004; NM_199478 |
| CCNB1 | 891 | NM_031966 |
| GPR162 | 27239 | NM_014449; NM_019858 |
| ONECUT2 | 9480 | NM_004852 |
| SFTPD | 6441 | XM_011540087; NM_003019; XM_011540088 |
| CLDN10 | 9071 | XM_024449432; XM_017020844; NM_006984; XM_011521134; XM_017020843; NM_182848; NM_001160100 |
| NXPH4 | 11247 | XM_017018747; NM_007224 |
| MAB21L2 | 10586 | NM_006439 |
| REG3A | 5068 | NM_138938; NM_002580; NM_138937 |
| LGALS4 | 3960 | NM_006149; XM_011526974; XM_011526973 |
| GPR35 | 2859 | NM_001195382; NM_001195381; NM_001394730; NM_005301 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| SIM2 | 6493 | XM_017028442; XR_001754891; XM_011529694; NM_005069; NM_009586 |
| TCF21 | 6943 | NM_003206; NM_198392 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| CCL11 | 6356 | NM_002986 |
| SLC34A2 | 10568 | NM_001177999; NM_006424; NM_001177998 |
| GIF | 2694 | XM_011544939; NM_005142 |
| SALL1 | 6299 | NM_001127892; NM_002968 |
| HGH1 | 51236 | NM_016458; XR_001745537 |
| KCNC3 | 3748 | NM_004977; NR_110912; NM_001372305 |
| GPA33 | 10223 | XM_017000005; NM_005814 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| FXYD2 | 486 | NM_021603; NM_001127489; NM_001680 |
| HNF4A | 3172 | XM_005260407; NM_001287182; NM_001030003; NM_178850; NM_175914; NM_001030004; NM_178849; NM_001258355; NM_001287183; NM_000457; NM_001287184 |
| GABRQ | 55879 | NM_018558; XM_011531184 |
| ABCA4 | 24 | NM_000350 |
| MMP11 | 4320 | NM_005940; NR_133013 |
| ZWINT | 11130 | XR_428692; NM_007057; NM_001005413; XM_017015605; XM_024447784; NM_032997; NM_001005414 |
| INHBA | 3624 | XM_017012175; NM_002192; XM_017012176; XM_017012174 |
| REG1A | 5967 | NM_002909 |
| TSPYL2 | 64061 | XM_006724592; XM_017029727; NM_022117; XR_001755719; XM_017029726 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| LRRC15 | 131578 | NM_130830; NM_001135057 |

TABLE 3-continued

Genes associated with molecular categories.

| Gene | NCBI Gene ID | NCBI Accession Number(s) |
|---|---|---|
| DES | 1674 | NM_001927; NM_001382708; NM_001382710; NM_001382713; NM_001382709; NM_001382711; NM_001382712 |
| INS | 3630 | NM_001185098; NM_001185097; NM_000207; NM_001291897 |
| FABP4 | 2167 | NM_001442 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| CST1 | 1469 | NM_001898 |
| TM4SF5 | 9032 | NM_003963 |
| PODXL | 5420 | NM_005397; NM_001018111 |
| CRNN | 49860 | NM_016190 |
| WISP2 | 8839 | NM_001323369; XM_017028116; NM_003881; XM_017028117; NM_001323370 |
| SST | 6750 | NM_001048 |
| LIN37 | 55957 | NR_163146; NM_019104; NM_001369780 |
| GREM1 | 26585 | NM_001368719; NM_013372; NM_001191323; NM_001191322 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| GRIN2D | 2906 | XM_011526872; NM_000836 |
| APOC1 | 341 | NM_001645; NM_001321066; NM_001379687; NM_001321065 |
| GDPD3 | 79153 | NM_024307 |
| FOXF1 | 2294 | NM_001451 |
| TGFB3 | 7043 | NM_001329938; NM_003239; NM_001329939 |
| ST3GAL5 | 8869 | NM_001354248; XM_017005208; XM_017005214; NM_001354226; XM_017005204; NM_001354233; NM_001354234; XM_017005205; XM_017005213; XR_001739019; NM_003896; NM_001354223; NM_001354227; NM_001354247; XM_017005206; XR_001739021; NM_001042437; NM_001354229; XM_017005202; XM_017005203; XM_017005212; XR_001739020; XM_017005209; NM_001354224; NM_001363847; NM_001354238 |
| DIRAS2 | 54769 | NM_017594 |
| GABRG3 | 2567 | XM_017022058; XM_017022060; XM_024449889; NM_033223; XM_011521430; NM_001270873; XM_011521431; XM_017022059 |
| HOXC11 | 3227 | NM_014212 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| SLCO4A1 | 28231 | XR_002958473; XR_001754251; XR_001754254; XR_001754255; XR_001754258; NM_016354; XR_001754250; XR_244116; XM_017027827; XR_001754253; XR_001754252; XR_244115; XR_936524; XM_017027826; XR_002958474; XR_001754256; XR_001754257; XM_005260203; XM_011528792; XR_001754249 |
| FABP1 | 2168 | NM_001443 |
| NFE2L3 | 9603 | NM_004289 |
| GLRB | 2743 | XR_001741207; XM_017008035; NM_000824; NM_001166060; XR_002959723; XM_017008034; NM_001166061 |
| PTH1R | 5745 | NM_001184744; XM_017006933; XM_011533968; NM_000316; XM_017006934; XM_011533967; XM_005265344; XM_017006932 |
| C2orf72 | 257407 | NM_001144994 |
| CAPN3 | 825 | NM_173087; NM_173089; NM_024344; NM_173088; NM_212465; NR_027912; NM_000070; NM_173090; NR_027911 |
| SLC2A4 | 6517 | NM_001042 |
| MLF1 | 4291 | NM_001369782; NM_001369785; NM_001378847; NM_022443; NM_001378845; NM_001378848; NM_001378851; NM_001369784; NM_001378853; NM_001378855; NM_001130156; NM_001369783; NM_001378852; NM_001130157; NM_001195432; NM_001195433; NM_001378846; NM_001378850; NM_001369781; NM_001195434 |
| FEZF2 | 55079 | NM_018008 |
| APCS | 325 | NM_001639 |
| SOX9 | 6662 | NM_000346 |
| HOXC10 | 3226 | NM_017409 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| DNAI1 | 27019 | NM_012144; NM_001281428 |
| LIPF | 8513 | NM_004190; NM_001198829; NM_001198830; NM_001198828; XM_011540311 |

TABLE 3-continued

| Genes associated with molecular categories. | | |
|---|---|---|
| Gene | NCBI Gene ID | NCBI Accession Number(s) |
| CDX2 | 1045 | XM_011534876; NM_001354700; XM_011534879; XM_011534875; XM_011534878; NM_001265 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ADH1B | 125 | NM_001286650; NM_000668 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| CHST2 | 9435 | NM_004267 |
| FGGY | 55277 | XM_017001645; XM_017001677; XM_024448207; XM_024448220; NM_001350792; NM_001350797; NM_001350798; NM_018291; XM_011541731; XM_017001671; XM_017001673; NM_001244714; NM_001350793; NM_001350794; NR_103473; XM_011541730; XM_017001649; XM_017001670; XM_017001678; XM_024448227; NM_001113411; XM_017001643; XM_011541736; XM_017001659; XM_017001662; XM_017001664; XM_024448185; XR_001737287; NM_001350791; NM_001350796; XM_017001668; XM_017001679; XR_001737285; XM_017001646; XM_017001652; XM_024448176; XR_001737286; NM_001278224; XM_017001657; XM_017001660; XR_001737284; NM_001350790; NM_001350799; XM_017001655; XM_017001656; XM_017001661; XM_017001663; XM_017001669; XM_024448196; XM_024448229; NM_001350795 |
| FERMT1 | 55612 | NM_017671; XM_024451935 |
| PRSS3 | 5646 | NM_007343; NM_001197097; NM_002771; XM_011517965; NM_001197098 |
| CCNA1 | 8900 | XM_011535294; XM_011535296; NM_001111047; XM_011535295; NM_001111046; NM_003914; NM_001111045 |
| ARL4D | 379 | XM_011524782; NM_001661 |
| LZTS1 | 11178 | XM_011544386; XM_011544384; NM_021020; NM_001362884; XM_011544385 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| KRT24 | 192666 | XM_017024299; NM_019016; XM_006721739; XM_011524460 |
| SCNN1D | 6339 | NM_001130413; NR_037668; NM_002978 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| AQP4 | 361 | NM_001317387; NM_001364287; NM_001364286; NM_001317384; XM_011525942; NM_001650; NM_001364289; NM_004028 |
| MUC2 | 4583 | NM_002457 |
| FGF23 | 8074 | NM_020638 |
| CXCL3 | 2921 | NM_002090 |
| IGFBP3 | 3486 | NM_000598; NM_001013398 |
| GABRA2 | 2555 | XM_024453964; NM_001330690; NM_001377144; NM_001377149; XM_024453966; NM_001377150; XM_011513675; NM_001114175; NM_001377155; NM_000807; NM_001377147; XM_024453967; NM_001377146; NM_001377152; NM_001286827; NM_001377153; NM_001377145; NM_001377148; NM_001377151; NM_001377154 |
| HR | 55806 | XM_006716367; NM_005144; XM_005273569; NM_018411 |
| AKR1C2 | 1646 | NM_001354; NM_001321027; NM_001135241; NM_205845; NM_001393392 |

TABLE 3-continued

Genes associated with molecular categories.

| Gene | NCBI Gene ID | NCBI Accession Number(s) |
|---|---|---|
| MYOC | 4653 | NM_000261 |
| TACR2 | 6865 | NM_001057 |
| VIP | 7432 | XM_006715562; XM_005267135; NM_003381; NM_194435 |
| PRM2 | 5620 | NM_001286358; NR_104428; NM_002762; NM_001286356; NM_001286359; NM_001286357 |
| ACADL | 33 | NM_001608; XM_005246517; XM_017003955 |
| SLC47A1 | 55244 | NM_018242 |
| CLPB | 81570 | NM_030813; XM_005274320; XM_011545289; NM_001258392; NM_001258393; NM_001258394 |
| SCNN1B | 6338 | XM_017023526; XM_011545913; XM_011545914; XM_017023525; NM_000336 |
| GLP2R | 9340 | XM_011524077; NM_004246; XM_017025340; XM_005256861; XM_017025339; XM_017025341 |
| CASR | 846 | XM_017007325; NM_000388; XM_005247837; XM_017007324; NM_001178065; XM_006713789 |
| IFI6 | 2537 | NM_002038; XM_024446207; NM_022873; NM_022872 |
| | | Pancreatic_Adenocarcinoma |
| PNLIP | 5406 | NM_000936 |
| PPY | 5539 | NM_002722; NM_001319209; XM_011524978 |
| CTRC | 11330 | XM_011540550; NM_007272 |
| CTRB2 | 440387 | NM_001025200 |
| CRP | 1401 | NM_000567; NM_001329058; NM_001382703; NM_001329057 |
| GCG | 2641 | NM_002054 |
| PNLIPRP1 | 5407 | XM_011539869; NM_001303135; NM_006229; XR_945774 |
| INS | 3630 | NM_001185098; NM_001185097; NM_000207; NM_001291897 |
| CPA1 | 1357 | NM_001868 |
| CASR | 846 | XM_017007325; NM_000388; XM_005247837; XM_017007324; NM_001178065; XM_006713789 |
| GCNT3 | 9245 | NM_004751 |
| TFF2 | 7032 | NM_005423 |
| PDX1 | 3651 | NM_000209; XR_941580; XR_941578; |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| ALPPL2 | 251 | NM_031313 |
| PADI1 | 29943 | XM_017001102; XR_946617; XR_946619; NM_013358; XR_001737131; XM_011541307; XR_001737130; XM_017001103; XR_946620; XM_017001101 |
| CTSE | 1510 | XM_011509245; NM_001910; NM_148964; XM_011509244; NM_001317331 |
| FOXL1 | 2300 | NM_005250 |
| LHX2 | 9355 | NM_004789; XM_006717323 |
| POU3F3 | 5455 | NM_006236 |
| MIA | 8190 | NM_006533; NM_001202553 |
| HOXD13 | 3239 | XM_011511068; NM_000523; XM_011511069 |
| NMRK2 | 27231 | NM_001289117; NM_001375468; NM_001375469; NM_170678; NM_001375467; NM_014446; XM_006722725; NR_110316 |
| TMPRSS4 | 56649 | XM_011542901; NM_001290094; XM_005271614; NM_001173552; NM_183247; NR_110734; XM_005271613; XM_011542902; XM_011542904; XM_005271615; NM_001083947; NM_001173551; NM_019894; XM_011542903; NM_001290096 |
| HAND2 | 9464 | NM_021973 |
| IHH | 3549 | NM_002181 |
| MAGEA3 | 4102 | XM_011531161; XM_005274676; XM_006724818; XM_011531160; NM_005362 |
| KLK6 | 5653 | XM_024451611; NM_001319949; NM_001012964; NM_001319948; NM_001012965; NM_002774 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MAGEA6 | 4105 | NM_175868; NM_005363 |
| LRP2 | 4036 | XM_011511183; NM_004525; XM_011511184 |
| MYBPH | 4608 | NM_004997 |
| CR2 | 1380 | NM_001877; NM_001006658; XM_011509206 |
| GABRA3 | 2556 | NM_000808; XM_006724811 |
| MYH7 | 4625 | XM_017021340; NM_000257 |
| ENPP3 | 5169 | XR_001743464; NR_133007; NM_005021; XM_017010932; XM_011535897 |
| GABRQ | 55879 | NM_018558; XM_011531184 |
| NXPH4 | 11247 | XM_017018747; NM_007224 |
| FOXA1 | 3169 | NM_004496; XM_017021246 |
| SFTPB | 6439 | XM_005264487; NM_198843; XM_005264488; NM_000542; NM_001367281; XM_005264490 |
| DLX6 | 1750 | NM_005222 |
| CRNN | 49860 | NM_016190 |
| HOXA7 | 3204 | NM_006896 |
| NEFM | 4741 | NM_001105541; NM_005382 |
| KRT24 | 192666 | XM_017024299; NM_019016; XM_006721739; XM_011524460 |
| FCER2 | 2208 | NM_002002; NM_001220500; XM_005272462; NM_001207019 |
| CLDN3 | 1365 | NM_001306 |
| POU2F2 | 5452 | XM_017026886; XM_017026889; XM_017026895; XR_001753709; XR_001753710; |

TABLE 3-continued

Genes associated with molecular categories.

| Gene | NCBI Gene ID | NCBI Accession Number(s) |
|---|---|---|
| | | NM_001393935; XM_017026885; XM_017026891; XM_017026894; XM_024451547; NM_001207026; NM_001393934; NM_001394376; NM_001394378; XM_017026884; XM_011527043; XM_017026887; XM_017026890; NM_001247994; XM_011527041; XM_024451546; NM_001207025; XM_011527042; XM_017026888; XM_017026892; NM_001393936; NM_002698; XM_017026896; NM_001394377 |
| LIPF | 8513 | NM_004190; NM_001198829; NM_001198830; NM_001198828; XM_011540311 |
| BCL11A | 53335 | NM_001365609; NM_022893; NM_138553; XM_017004335; XM_024452962; XM_024452963; XM_017004333; NM_138559; XM_011532910; XM_017004336; NM_018014; XM_011532909; NM_001363864 |
| CX3CR1 | 1524 | NM_001171174; NM_001337; NM_001171171; NM_001171172 |
| ABCA12 | 26154 | XM_011510951; NR_103740; NM_173076; NM_015657 |
| | | Breast_Cancer |
| AMN | 81693 | XM_024449714; XM_011537203; NM_030943; XM_011537202 |
| NMRK2 | 27231 | NM_001289117; NM_001375468; NM_001375469; NM_170678; NM_001375467; NM_014446; XM_006722725; NR_110316 |
| TLX2 | 3196 | NM_001534; NM_016170 |
| MYH15 | 22989 | XM_011512559; NM_014981; XM_017005922 |
| MROH7 | 374977 | NR_026782; NM_198547; NM_001039464; NM_001291332; NR_111931 |
| ERN2 | 10595 | XM_011545708; XM_011545711; XR_950727; XM_011545709; XM_011545712; NM_001308220; XM_011545713; NM_033266 |
| CSF3 | 1440 | NR_168489; NR_168491; NM_000759; NM_172220; NM_001178147; NM_172219; NR_168490; NR_033662 |
| TMEM246 | 84302 | NM_001303107; NM_001303108; NM_032342; XM_024447701; NM_001371233 |
| GCGR | 2642 | XM_011523539; XM_017024446; NM_000160; XM_006722277; XM_017024447 |
| NEFM | 4741 | NM_001105541; NM_005382 |
| SOX21 | 11166 | NM_007084 |
| PMP2 | 5375 | NM_002677; NM_001348381 |
| RGS20 | 8601 | NM_001286673; NM_001286675; NM_170587; NM_001286674; NM_003702; NR_104578; NR_104579 |
| IL13RA2 | 3598 | NM_000640 |
| GPR17 | 2840 | NM_005291; NM_001161416; NM_001161415; XM_017003833; NM_001161417 |
| B3GALT1 | 8708 | NM_020981; XM_006712819; XM_011512085 |
| MT1H | 4496 | NM_005951 |
| GJA3 | 2700 | NM_021954; XM_011535048 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| DBH | 1621 | NM_000787 |
| OGDHL | 55753 | XM_011539946; NM_001347821; NM_001143997; NM_001347820; NM_001347823; NR_144685; XM_017016402; NM_001347819; NM_001347825; NM_018245; NR_144682; NM_001347824; NR_144683; XM_017016403; NM_001143996; NM_001347822; NM_001347826; NR_144684; NR_144686 |
| WNT7A | 7476 | XM_011534091; NM_004625 |
| RPRM | 56475 | NM_019845 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| FOXA2 | 3170 | NM_021784; NM_153675 |
| ZNF536 | 9745 | XM_011527557; XM_017027530; XM_017027533; XM_017027534; XM_017027540; XM_017027535; XM_017027531; XM_017027532; XM_017027539; XM_017027542; XM_011527555; XM_011527560; XM_017027536; NM_001352260; NM_001376110; NM_014717; XM_011527554; XM_017027527; XM_017027537; XM_017027543; XM_024451807; NM_001376111; XM_011527558; XM_017027528; XM_017027529; XM_017027538 |
| CCL16 | 6360 | NM_004590; XM_005258020 |
| SHH | 6469 | NR_132319; NM_000193; NR_132318; XM_011516480; XM_011516479; NM_001310462 |
| TAC3 | 6866 | NR_135164; NR_135166; NR_135165; NM_001006667; NM_001178054; NM_013251; NR_033654 |
| CXCL3 | 2921 | NM_002090 |
| DUSP26 | 78986 | NM_024025; NM_001305116; NM_001305115 |
| SERPIND1 | 3053 | NM_000185 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| TCF21 | 6943 | NM_003206; NM_198392 |
| TYR | 7299 | XM_011542970; NM_000372 |
| DUOX2 | 50506 | NM_014080; NM_001363711 |
| SLC45A2 | 51151 | NM_001297417; NM_016180; NM_001012509 |
| MAB21L2 | 10586 | NM_006439 |
| GAS2 | 2620 | NM_001143830; NM_001391933; NM_001391935; NM_001391936; NM_011519972; NM_001391937; NM_001391934; XM_011519971; NR_147085; XM_017017532; XR_001747829; NM_001351224; XM_011519975; NM_005256; NM_177553 |

TABLE 3-continued

Genes associated with molecular categories.

| Gene | NCBI Gene ID | NCBI Accession Number(s) |
|---|---|---|
| IL1A | 3552 | NM_001371554; NM_000575 |
| SPRR2B | 6701 | NM_001388198; NM_001017418 |
| CYP2W1 | 54905 | NM_017781; XM_011515440; XM_011515441 |
| SPOCK3 | 50859 | NM_001251967; NM_001204354; NM_001204356; XM_011532018; NM_001204359; XM_017008258; NM_001040159; NM_001204358; XM_017008257; NM_001204352; NM_016950; NM_001204353; NM_001204355 |
| KCNK12 | 56660 | NM_022055 |
| HKDC1 | 80201 | NM_025130; XR_001747209; XM_011540195 |
| HNF1B | 6928 | XM_011525161; NM_001165923; NM_001304286; XM_011525163; NM_000458; XM_011525162; NM_006481; XM_011525164; XM_011525160 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| FOXE1 | 2304 | NM_004473 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| NAALAD2 | 10003 | XM_017017044; XR_001747709; XM_017017043; XR_001747707; XR_001747710; XR_001747711; NM_001300930; XR_001747708; XM_017017045; XM_017017046; NM_005467 |
| HMGA2 | 8091 | NM_001015886; NM_003483; NM_001300918; NM_003484; NM_001330190; NM_001300919 |
| FOXF1 | 2294 | NM_001451 |
| RXRG | 6258 | NM_006917; NM_001256570; NM_001256571; NR_033824 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| STXBP6 | 29091 | XM_017021235; NM_001351941; NM_001394415; XM_024449547; NM_001304476; NM_001351942; NM_001394413; XM_006720121; NM_001304477; NM_001394414; NM_001394417; XM_017021232; NM_014178; NM_001394410; NM_001394411; NM_001394420; XM_017021241; NM_001351943; NM_001394418; NM_001351940; NM_001394412; NM_001394416; NM_001394419 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| RPS4Y1 | 6192 | NM_001008 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |

TABLE 3-continued

Genes associated with molecular categories.

| Gene | NCBI Gene ID | NCBI Accession Number(s) |
|---|---|---|
| GFAP | 2670 | XM_024450691; XM_024450690; NM_001131019; XM_024450692; XM_024450693; NM_001242376; NM_002055; NM_001363846 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| PVRL3 | 25945 | XM_011512663; XM_017006126; NM_001243286; XR_924122; NM_015480; XR_002959508; XM_017006125; XM_017006124; XM_017006127; XM_017006123; NM_001243288 |
| SERPINB13 | 5275 | NM_001348267; XM_011526029; NM_001348268; NM_012397; NM_001348269; NM_001307923; NM_001348270 |
| ADH1C | 126 | NM_000669; NR_133005 |
| EYA4 | 2070 | XM_005266851; NM_004100; NM_172105; NM_001370459; NM_172104; XM_017010371; XR_001743220; NM_001301012; XM_017010369; XM_017010370; XM_017010372; XM_017010373; XR_001743219; NM_172103; NM_001301013; NM_001370458; XM_017010368; XM_017010374 |
| RGS6 | 9628 | XM_017021825; XM_017021832; XM_024449763; XR_001750613; NM_001370274; NM_001370279; NM_001370284; NM_001370291; XM_017021820; XM_024449761; XM_024449770; XM_024449774; NM_001370272; NM_001370277; NM_001370278; NM_001370292; XM_011537397; XM_017021831; XM_024449764; NM_001204421; NM_001204423; NM_001370275; NM_001370290; NM_001370293; NR_135235; XM_024449760; XM_024449776; XR_002957573; NM_001204416; NM_001204417; NM_001370271; NM_001370283; NM_001370270; NM_001370273; NM_001370281; NM_001370286; XM_017021822; XM_017021833; NM_001204422; NM_001204424; NM_001370276; NM_001370280; NM_001370287; NM_001370289; NM_001370294; XM_011537393; XM_011537407; XM_017021827; XM_017021830; XM_017021834; XM_024449759; NM_001370282; XM_017021826; XM_017021828; XM_024449768; NM_001204418; NM_001204419; NM_001204420; NM_001370288; NM_004296 |
| ACTC1 | 70 | NM_005159 |
| PAX3 | 5077 | NM_181457; NM_000438; NM_181459; NM_181460; NM_001127366; NM_013942; NM_181461; NM_181458 |
| GALNT12 | 79695 | XM_006717287; XM_017015133; XM_011519018; NM_024642; XM_011519020; XM_024447673 |
| SOX2 | 6657 | NM_003106 |
| SNCA | 6622 | XM_011532204; NM_001146054; NM_000345; NM_001375287; XM_011532206; NM_007308; NR_164675; XM_011532207; NM_001375288; NM_001375290; NR_164676; XM_011532203; XM_011532205; NR_164674; XM_017008563; NM_001146055; NM_001375286; NM_001375285 |
| MYLPF | 29895 | NM_001324458; NM_013292; NM_001324459 |
| EMX2 | 2018 | NM_004098; NM_001165924 |
| FRMPD1 | 22844 | XM_017014482; XM_024447456; XM_011517806; NM_001371223; NM_001371225; XM_017014481; XM_024447454; XM_011517805; XR_929220; NM_014907; NM_001371224 |
| PHYHIP | 9796 | NR_156475; NM_001099335; NM_001363311; NM_014759; XM_017014102; NM_001363312 |
| GUCY2C | 2984 | NM_004963; XM_011520631 |
| FGFBP1 | 9982 | NM_005130 |
| SGK2 | 10110 | NM_016276; NM_001199264; NM_170693 |
| GDF10 | 2662 | NM_004962 |
| REM1 | 28954 | XM_011528795; XM_017027833; NM_014012; XM_005260404 |
| CPEB1 | 64506 | NM_001288819; NM_001365243; NM_001365242; NM_001365244; NM_001365245; NM_001387068; NM_001387076; NM_001365248; NM_001079534; NM_001365250; NM_001387065; NM_001387075; NM_001079535; NM_001288820; NM_001365249; NM_001387061; NM_001387066; NM_001387070; NM_001387062; NM_001387071; NM_001387078; NM_001365246; NM_001365247; NM_001387069; NM_001387077; NM_001079533; NM_001365240; NM_001365241; NM_001387072; NM_001387074; NM_001387063; NM_001387064; NM_001387067; NM_001387073; NM_030594 |
| CYP3A5 | 1577 | NM_001291830; NM_001190484; NR_033807; NR_033812; NM_001291829; NM_000777; NR_033810; NR_033811 |
| SALL1 | 6299 | NM_001127892; NM_002968 |
| HAND2 | 9464 | NM_021973 |
| HOXA3 | 3200 | NM_001384342; NM_001384335; NM_001384336; NM_001384339; NM_001384345; NM_001384346; NM_001384338; NM_001384337; NM_030661; NM_001384341; NM_001384343; NM_001384340; NM_001384344; NM_153631; NM_153632 |
| TMPRSS5 | 80975 | XM_017018366; XR_001747990; NM_001288749; NM_001288751; NM_001288752; NM_001288750; NR_110047; XR_001747991; XR_001747992; NR_110046; NM_030770; XM_017018367 |
| BMP5 | 653 | XM_011514817; NM_001329756; XM_024446524; NM_001329754; NM_021073 |
| TRDN | 10345 | NM_001251987; NM_001256020; NM_001256021; NM_006073; NM_001256022 |
| TACR2 | 6865 | NM_001057 |

TABLE 3-continued

Genes associated with molecular categories.

| Gene | NCBI Gene ID | NCBI Accession Number(s) |
|---|---|---|
| LYVE1 | 10894 | NM_006691 |
| FHL1 | 2273 | NM_001159703; NM_001167819; NM_001369327; NM_001369330; XM_006724746; XM_024452354; NR_027621; NM_001369328; NM_001159702; NM_001369326; XM_006724743; NM_001330659; NM_001369331; NM_001159700; NM_001159701; NM_001159704; NM_001369329; NM_001159699; NM_001449 |
| CAV1 | 857 | NM_001753; NM_001172895; NM_001172897; NM_001172896 |
| FIGF | 2277 | NM_004469 |
| NPR1 | 4881 | XM_017001374; XM_005245218; NM_000906 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| AOC3 | 8639 | XR_934584; NM_001277732; NM_003734; NR_102422; XM_011525419; XR_001752673; XM_011525420; XM_024451015; NM_001277731 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| CIDEC | 63924 | NM_001321142; NM_001199552; NM_001378491; NM_001199623; NM_001199551; NM_001321144; NM_022094; NM_001321143 |
| NEK2 | 4751 | NM_002497; NM_001204182; NM_001204183 |
| MMP11 | 4320 | NM_005940; NR_133013 |
| ADAMTS5 | 11096 | XM_024452053; XM_024452054; NM_007038 |
| ABCD2 | 225 | XR_001748623; NM_005164; XM_017018992; XR_001748622; XM_017018993; XM_011538027 |
| LPL | 4023 | NM_000237 |
| HBB | 3043 | NM_000518 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| COL10A1 | 1300 | XM_011535432; NM_000493; XM_011535433; XM_017010248; XM_006715333 |
| AQP7 | 364 | XM_006716765; XM_017014706; NM_001318158; NR_134513; NR_134515; XM_017014704; XM_024447538; NM_001318156; XM_011517866; NR_134514; NR_164778; XM_011517867; XM_017014701; XM_024447539; NM_001376192; NM_001376193; XM_017014702; NM_001318157; NM_001376191; NR_164779; XM_017014700; NM_001170 |
| LEP | 3952 | XM_005250340; NM_000230 |
| GSTM5 | 2949 | NM_000851; XM_005270785; XM_005270784 |
| FMO2 | 2327 | NM_001460; NR_160266; XR_921761; NM_001365900; XR_001737072; NM_001301347 |
| PLIN1 | 5346 | NM_002666; XM_005254934; NM_001145311 |
| KIAA0101 | 9768 | NR_109934; NM_001029989; NM_014736 |
| CA3 | 761 | NM_005181 |
| CDO1 | 1036 | NM_001323565; NR_136619; NM_001323567; NM_001801; NR_136618; NR_136620; NM_001323566; NR_136621 |
| CSN1S1 | 1446 | XM_006714091; NM_001025104; XM_006714089; XM_006714090; NM_001890 |
| KIF4A | 24137 | NM_012310 |
| GPD1 | 2819 | NM_005276; NM_001257199 |
| DPT | 1805 | NM_001937 |
| ADH1B | 125 | NM_001286650; NM_000668 |
| FABP4 | 2167 | NM_001442 |
| CENPF | 1063 | XM_017000086; NM_016343; XM_011509082 |
| GABRD | 2563 | XM_011541194; XM_017000936; NM_000815 |
| PFKFB1 | 5207 | NM_001271804; XM_017029578; XM_017029576; NM_002625; NR_073450; XM_024452389; XM_017029577; NM_001271805 |
| ATP1A2 | 477 | NM_000702 |
| CHL1 | 10752 | XM_011533294; XM_017005568; XM_017005573; NM_001253387; NR_045572; XM_017005569; XM_017005572; XM_006712939; XM_011533292; XM_017005566; XM_006712940; XM_011533295; NM_001253388; NM_006614; XM_006712938; XM_011533296; XM_017005567; XM_017005570; XM_017005571 |

TABLE 3-continued

Genes associated with molecular categories.

| Gene | NCBI Gene ID | NCBI Accession Number(s) |
|---|---|---|
| SLC7A10 | 56301 | XM_011527120; XM_006723284; XM_024451609; XR_935841; NM_019849; XM_011527119; XM_024451610 |
| ADIPOQ | 9370 | NM_004797; NM_001177800 |
| EXO1 | 9156 | XM_011544325; XM_011544322; NM_130398; XM_011544323; XM_006711840; NM_003686; NM_006027; XM_011544321; XM_011544324; XM_017002793; NM_001319224 |
| INHBA | 3624 | XM_017012175; NM_002192; XM_017012176; XM_017012174 |
| CES1 | 1066 | NM_001025195; NM_001266; XM_005255774; NM_001025194 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| MMRN1 | 22915 | XM_005262856; NM_001371403; NM_007351 |
| HMMR | 3161 | NM_001142557; NM_001142556; NM_012484; NM_012485 |
| PKMYT1 | 9088 | NM_001258451; NM_182687; NM_001258450; XM_011522735; XM_024450490; NM_004203; XM_011522734; XM_011522736 |
| CIDEA | 1149 | NM_001279; NR_134607; NM_001318383 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| OXTR | 5021 | NM_000916; NM_001354654; NM_001354655; NM_001354653; NM_001354656 |
| DTL | 51514 | XM_011509614; NM_001286229; NM_001286230; NM_016448 |
| IBSP | 3381 | NM_004967 |
| PPP1R1A | 5502 | XM_005268995; XM_006719471; NM_006741 |
| WISP1 | 8840 | XM_024447319; NR_037944; XM_024447320; NM_080838; NM_003882; NM_001204870; XM_024447321; NM_001204869 |
| STAB2 | 55576 | NM_017564; XM_011538541; XM_011538538; XM_011538539; XM_011538542; XM_017019585; XM_011538537; XR_429107 |
| CDKN3 | 1033 | XM_024449458; NM_001330173; NM_005192; NM_001130851 |
| TK1 | 7083 | NM_001346663; NM_003258 |
| KIF20A | 10112 | NM_005733 |
| KCNB1 | 3745 | XM_011528799; XM_006723784; NM_004975 |
| S100B | 6285 | NM_006272; XM_017028424 |
| PBK | 55872 | NM_018492; NM_001278945; NM_001363040 |
| TDO2 | 6999 | NM_005651 |
| PITX1 | 5307 | NM_002653 |
| MCM10 | 55388 | NM_182751; NM_018518; XM_011519538 |
| GRM4 | 2914 | NM_001256809; NM_001256812; NM_001256813; NM_001256811; NM_001256814; NM_001256810; NM_001282847; NM_000841 |
| CST1 | 1469 | NM_001898 |
| AIM1L | 55057 | NM_017977; XM_011541672; XM_011541673; XR_001737260; NM_001039775; XR_946681; XM_005245918 |
| TNMD | 64102 | NM_022144 |
| CLEC5A | 23601 | XM_017011916; XM_017011915; XM_011515995; XM_017011917; NM_001301167; NM_013252 |
| LRRC15 | 131578 | NM_130830; NM_001135057 |
| LAMP5 | 24141 | NM_001199897; NM_012261 |
| EPYC | 1833 | NM_004950; XM_011538008 |
| RAB26 | 25837 | XM_011522448; XM_011522450; NM_014353; NM_001308053 |
| CST2 | 1470 | NM_001322 |
| NKAIN1 | 79570 | NM_024522; XM_017002320 |
| LALBA | 3906 | NM_002289; NM_001384350 |
| CENPA | 1058 | NM_001809; NM_001042426 |
| TUBB3 | 10381 | NM_006086; NM_001197181 |
| ARTN | 9048 | NM_057160; NM_057090; NM_001136215; NM_057091; NM_003976 |
| TCL1B | 9623 | NM_004918; NM_199206 |
| SYT13 | 57586 | NM_001247987; NM_020826 |
| CNTD2 | 79935 | XM_006723395; NM_024877; XR_001753763; XR_935861 |
| NEURL1 | 9148 | XM_005270269; XM_011540333; XM_017016909; XM_011540332; XM_011540335; XR_945866; NM_004210; XM_005270270; XM_011540331 |
| NPY2R | 4887 | NM_001370180; NM_000910; NM_001375470 |
| CXCL10 | 3627 | NM_001565; NR_168520 |
| S100P | 6286 | NM_005980 |
| MYT1 | 4661 | NM_004535 |
| ACTL8 | 81569 | NM_030812; XM_011542212 |
| HAPLN1 | 1404 | XM_017009052; XM_017009051; NM_001884; XM_017009054; XM_017009053; XM_011543168 |
| BTN1A1 | 696 | NM_001732 |
| CXCL9 | 4283 | NM_002416 |
| CEACAM6 | 4680 | NM_002483; XM_011526990 |
| FBN2 | 2201 | NM_001999; XM_017009228 |
| NAT1 | 9 | NM_001160175; NM_001160170; NM_001160173; XM_011544688; XM_006716410; XM_017013947; NM_001160171; NM_001160172; NM_001160174; NM_001291962; XM_011544689; NM_001160176; XM_011544687; NM_000662; NM_001160179 |
| FOXJ1 | 2302 | NM_001454 |

TABLE 3-continued

Genes associated with molecular categories.

| Gene | NCBI Gene ID | NCBI Accession Number(s) |
|---|---|---|
| BMPR1B | 658 | XM_017008558; NM_001203; NM_001256793; XM_011532201; NM_001256794; NM_001256792; XM_017008559; XM_017008560; XM_017008561 |
| CNTNAP2 | 26047 | XM_017011950; NM_014141 |
| CEACAM5 | 1048 | XM_011526322; XM_017026146; NM_001291484; NM_004363; XM_017026145; NM_001308398 |
| KCNF1 | 3754 | NM_002236 |
| HOXC11 | 3227 | NM_014212 |
| KCNJ3 | 3760 | NM_001260510; NM_001260508; NM_001260509; NM_002239 |
| MAGEA12 | 4111 | NM_001166386; NM_001166387; NM_005367 |
| GABRQ | 55879 | NM_018558; XM_011531184 |
| HHIPL2 | 79802 | XM_024449814; XR_001737417; XR_426906; XM_017002350; XR_002957624; NM_024746; XR_001737416; XM_011509986 |
| TLX1 | 3195 | NM_001195517; XM_011539744; XM_011539745; NM_005521 |
| SOX11 | 6664 | NM_003108 |
| MAGEA6 | 4105 | NM_175868; NM_005363 |
| CA9 | 768 | XR_428428; NM_001216; XR_001746374 |
| C2orf54 | 79919 | XM_011511877; NM_001085437; NM_001282921; NM_024861 |
| DIO1 | 1733 | NM_000792; NM_001039715; NM_213593; NM_001039716; NM_001324316; NR_136692; NR_136693 |
| F7 | 2155 | XM_011537476; XM_011537475; NM_001267554; XM_011537474; NR_051961; XM_006719963; NM_019616; NM_000131 |
| CYP2B6 | 1555 | NM_000767 |
| TRH | 7200 | NM_007117 |
| CHGB | 1114 | NM_001819 |
| PROL1 | 58503 | NM_021225; NM_001302807; NR_126503 |
| CD177 | 57126 | XM_017027021; XM_017027022; NM_020406 |
| KIF1A | 547 | NM_001379636; NM_001379637; NM_001379639; NM_001379650; NM_001330290; NM_001379633; NM_001379641; NM_001379651; NM_001379653; NM_004321; NM_001379632; NM_001379638; NM_001379645; NM_001379646; NM_001379649; NM_001379635; NM_001379640; NM_001379634; NM_001244008; NM_001379642; NM_001320705; NM_001330289; NM_001379631; NM_001379648 |
| PSCA | 8000 | NR_033343; NM_005672 |
| CRISP3 | 10321 | NM_001368123; NM_006061; NM_001190986 |
| PVALB | 5816 | NM_001315532; NM_002854 |
| GAD1 | 2571 | NM_013445; XM_017003758; NM_000817; XM_005246444; XM_011510922; XM_017003757; XM_017003756; XM_024452783 |
| MYH7 | 4625 | XM_017021340; NM_000257 |
| SERPINB7 | 8710 | XM_024451278; NM_001261831; NM_003784; NM_001040147; NM_001261830 |
| COL2A1 | 1280 | XM_017018831; XM_017018830; NM_001844; NM_033150; XM_017018828; XM_017018829 |
| MSMB | 4477 | NM_138634; NM_002443 |
| IRS4 | 8471 | XM_006724713; NM_003604; NM_001379150; XM_011531061 |
| BEX1 | 55859 | NM_018476 |
| PADI3 | 51702 | NM_016233; XM_011541571; XM_017001463; XM_011541572 |
| UGT2B4 | 7363 | NM_001297616; NM_021139; NM_001297615 |
| PRSS1 | 5644 | NR_172951; XM_011516411; NR_172947; NM_002769; NR_172948; NR_172949; NR_172950 |
| CYP2A7 | 1549 | XR_935754; NM_000764; NM_030589 |
| MSLN | 10232 | NM_001177355; NM_005823; NM_013404 |
| CPB1 | 1360 | NM_001871 |
| CARTPT | 9607 | NM_004291 |
| TGM4 | 7047 | NM_003241; XM_011534042 |
| NCAN | 1463 | NM_004386 |
| CYP2A6 | 1548 | NM_000762 |
| CALML5 | 51806 | NM_017422 |
| TFF1 | 7031 | NM_003225 |
| | | Ovarian_Cancer |
| QARS | 5859 | NR_073590; NM_005051; XM_017006965; NM_001272073 |
| HSD17B2 | 3294 | NM_002153; XR_001751898 |
| CLDN6 | 9074 | NM_021195 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| IZUMO4 | 113177 | XM_024451343; XR_002958248; NM_001039846; XM_024451342; XM_024451344; NM_052878; NM_001031735; NM_001363588 |
| PAQR4 | 124222 | NM_001284513; NM_001284511; NM_001284512; NM_152341; NM_001324118 |
| NGFR | 4804 | NM_002507 |
| MCC | 4163 | NM_002387; NM_001085377 |
| FAM107A | 11170 | NM_001076778; NM_007177; NM_001282713; NM_001282714 |
| FOXL1 | 2300 | NM_005250 |

TABLE 3-continued

Genes associated with molecular categories.

| Gene | NCBI Gene ID | NCBI Accession Number(s) |
|---|---|---|
| KCNC3 | 3748 | NM_004977; NR_110912; NM_001372305 |
| PTGS2 | 5743 | NM_000963 |
| COL17A1 | 1308 | NM_130778; NM_000494 |
| FZD2 | 2535 | NM_001466 |
| EIF1AY | 9086 | NM_004681; NM_001278612 |
| HOXD13 | 3239 | XM_011511068; NM_000523; XM_011511069 |
| FGF14 | 2259 | NM-001321931; NM_001321943; NM_001321949; NM_175929; NM_001321933; NM_001321941; NM_001321932; NM_001321935; NM_001321937; NM_001321945; NM_001321947; NM_001321939; NM_001321936; NM_001321940; NM_001321944; NM_001321946; NM_001321948; NM_001379342; NM_001321934; NM_001321938; NM_001321942; NM_004115 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| MMP13 | 4322 | NM_002427 |
| LHX1 | 3975 | NM_005568 |
| CSDC2 | 27254 | NM_014460 |
| PAX9 | 5083 | NM_001372076; NM_006194 |
| B2M | 567 | XR_002957658; XM_005254549; NM_004048 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| ZNF492 | 57615 | NM_020855 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PRSS1 | 5644 | NR_172951; XM_011516411; NR_172947; NM_002769; NR_172948; NR_172949; NR_172950 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| IRX5 | 10265 | NM_005853; XM_011522809; NM_001252197 |
| DOK5 | 55816 | XM_011528904; NM_001294161; NM_018431; XM_024451946; NM_177959 |
| ASIP | 434 | NM_001385218; XM_011528820; NM_001672; XM_011528821 |
| EMX2 | 2018 | NM_004098; NM_001165924 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| VGLL1 | 51442 | NM_016267 |
| HSPA4L | 22824 | NM_001317381; NM_001317383; XM_011531745; NM_001317382; NM_014278 |
| PAX8 | 7849 | NM_013992; NM_013953; NM_013952; NM_003466; NM_013951 |
| ALDH1A3 | 220 | NM_001293815; NM_000693; NM_001037224 |
| ANGPT4 | 51378 | NM_001322809; XM_011529239; NM_015985 |
| KIAA0513 | 9764 | NM_001286565; NM_001297766; NM_001286566; XM_017023912; NM_014732; NM_001388359 |
| RPS4Y1 | 6192 | NM_001008 |
| NES | 10763 | NM_024609; NM_006617 |
| COL21A1 | 81578 | XM_011514927; XM_024446561; XR_001743657; NM_030820; NR_134851; NR_134849; XM_011514925; NM_001318753; NR_134850; NM_001318752; NM_001318754; XM_011514926; XM_006715223; NM_001318751; XM_011514924 |
| MNX1 | 3110 | NM_001165255; NM_005515 |
| WT1 | 7490 | NM_000378; NR_160306; NM_001367854; NM_001198551; NM_001198552; NM_024424; NM_024426; NM_024425 |
| SLC6A12 | 6539 | XM_005253747; NM_003044; NM_001122847; XM_005253748; XM_011521010; XM_006719005; NM_001122848; NM_001206931 |

TABLE 3-continued

Genes associated with molecular categories.

| Gene | NCBI Gene ID | NCBI Accession Number(s) |
|---|---|---|
| NPR1 | 4881 | XM_017001374; XM_005245218; NM_000906 |
| WISP3 | 8838 | XM_011536223; XM_011536220; NM_198239; NR_125353; NR_125354; XR_001743705; NM_130396; XM_011536222; NM_003880 |
| ASGR1 | 432 | XM_011523861; NM_001197216; NM_001671 |
| FOXL2 | 668 | NM_023067 |
| PNOC | 5368 | NM_006228; XM_011544559; XM_005273532; XM_017013578; NM_001284244 |
| KLK6 | 5653 | XM_024451611; NM_001319949; NM_001012964; NM_001319948; NM_001012965; NM_002774 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| KLK10 | 5655 | XM_006723289; XM_005259061; NM_002776; NM_145888; NM_001077500; XM_017026993; XM_006723287; XM_005259062 |
| HEY1 | 23462 | NM_001040708; NM_012258; NM_001282851 |
| SCD | 6319 | NM_005063 |
| DIO3 | 1735 | NM_001362 |
| SCGN | 10590 | NM_006998; XM_017010181 |
| LGALS14 | 56891 | NM_020129; NM_203471 |
| SLC27A2 | 11001 | NM_001159629; NM_003645 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| BBC3 | 27113 | XM_006723141; XM_011526722; NM_001127241; NM_001127242; NM_001127240; NM_014417 |
| CETP | 1071 | XM_006721124; NM_000078; NM_001286085 |
| GSTM5 | 2949 | NM_000851; XM_005270785; XM_005270784 |
| WNT7A | 7476 | XM_011534091; NM_004625 |
| CCNE1 | 898 | XM_011527440; NM_001238; NM_001322259; NM_001322261; NM_001322262; NM_057182 |
| DLC1 | 10395 | NM_001316668; NM_182643; XM_005273374; NM_001348081; NM_001348083; NM_001348084; NM_001164271; NM_006094; NM_024767; NM_001348082 |
| RAMP3 | 10268 | XM_017011666; NM_005856; XM_006715631 |
| MEIS1 | 4211 | NM_002398 |
| SGCA | 6442 | XM_011525122; XM_011525120; XM_011525121; XM_024450873; NM_001135697; NR_135553; XR_002958056; XM_011525124; NM_000023; XM_011525123 |
| HGH1 | 51236 | NM_016458; XR_001745537 |
| CHODL | 140578 | XM_017028273; NM_001204174; NM_024944; XM_011529453; NM_001204176; NM_001204175; NM_001204177; XM_011529457; NM_001204178 |
| NLRP1 | 22861 | NM_001033053; NM_033006; NM_033007; NM_014922; NM_033004 |
| CLDN9 | 9080 | NM_020982 |
| RPL4 | 6124 | NM_000968 |
| CDH6 | 1004 | NM_004932; NM_001362435; XM_017008910; XM_011513921; XR_001741972 |
| TNFRSF10C | 8794 | NM_003841 |
| ITGA2 | 3673 | NR_073103; NR_073104; NR_073105; NR_073106; NR_073107; NM_002203 |
| GRK5 | 2869 | XM_005269707; XM_005269708; NM_005308 |
| LIPF | 8513 | NM_004190; NM_001198829; NM_001198830; NM_001198828; XM_011540311 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |

TABLE 3-continued

| Genes associated with molecular categories. | | |
|---|---|---|
| Gene | NCBI Gene ID | NCBI Accession Number(s) |
| TCF21 | 6943 | NM_003206; NM_198392 |
| SST | 6750 | NM_001048 |
| IL20RA | 53832 | NM_001278722; XM_011535904; XM_017010955; NM_001278724; NM_014432; XM_006715506; NM_001278723; XM_017010954 |
| FGF18 | 8817 | NM_003862; NM_033649 |
| NR5A1 | 2516 | NM_004959 |
| ULBP2 | 80328 | NM_025217; XM_017011321 |
| RNF128 | 79589 | NM_024539; NM_194463 |
| PRM2 | 5620 | NM_001286358; NR_104428; NM_002762; NM_001286356; NM_001286359; NM_001286357 |
| C7 | 730 | NM_000587 |
| L1CAM | 3897 | NM_024003; NM_001278116; NM_001143963; NM_000425 |
| BCAM | 4059 | NM_001013257; NM_005581 |
| DTL | 51514 | XM_011509614; NM_001286229; NM_001286230; NM_016448 |
| ADRB3 | 155 | NM_000025 |
| CLDN16 | 10686 | NM_006580; NM_001378492; NM_001378493 |
| FMO5 | 2330 | XM_005272946; XM_005272947; XM_011509351; XM_017000802; NM_001144829; NM_001461; XM_006711244; XM_006711245; XM_005272948; NM_001144830; XM_017000801; XM_011509350 |
| KCNIP1 | 30820 | NM_001034837; NM_014592; NM_001034838; NM_001278340; XM_017009407; XM_017009408; NM_001278339 |
| FGF23 | 8074 | NM_020638 |
| PDE3B | 5140 | XR_001747903; NM_000922; NM_001363570; XM_017017912; XM_006718249; XM_017017911; NM_001363569 |
| SLC4A3 | 6508 | XM_011511667; NM_201574; NR_048551; XM_005246790; XM_011511665; NM_001326559; NM_005070 |
| FOLR1 | 2348 | NM_000802; NM_016729; NM_016730; NM_016725; NM_016724 |
| STAR | 6770 | NM_001007243; NM_000349 |
| Uterus_Carcinoma | | |
| SPDEF | 25803 | NM_001252294; XM_005248988; NM_012391; XM_011514457 |
| HLA-G | 3135 | XM_017010817; NM_001384280; XM_017010818; NM_002127; XM_024446420; NM_001363567; NM_001384290 |
| MARCO | 8685 | NM_006770; XM_011512082; XM_011512083; XM_017005171 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| ZNF208 | 7757 | NM_001329971; NM_001329973; NM_001329974; NM_001329972; NR_138252; NM_007153 |
| CHRND | 1144 | NM_001311196; XM_011510524; NM_001256657; NM_001311195; NM_000751 |
| SLC31A2 | 1318 | NM_001860 |
| C1S | 716 | XM_005253760; NM_001734; NM_001346850; NM_201442 |
| GREB1 | 9687 | XM_024453255; NM_014668; NM_033090; XM_024453254; XM_024453256; NM_148903; XM_005246196; XM_024453251; XR_922686; XM_024453250; XM_024453252; XM_011510418; XM_011510423; XM_011510422; XM_024453253; XM_011510419; XM_005246192; XR_001739081 |
| VIP | 7432 | XM_006715562; XM_005267135; NM_003381; NM_194435 |
| ZWINT | 11130 | XR_428692; NM_007057; NM_001005413; XM_017015605; XM_024447784; NM_032997; NM_001005414 |
| CREB5 | 9586 | XM_017012807; XM_017012808; NM_001011666; XM_024447005; XM_017012806; XM_017012809; NM_182898; XM_017012810; XM_005249906; NM_004904; XR_001744893; XM_011515618; NM_182899 |
| EIF1AY | 9086 | NM_004681; NM_001278612 |
| E2F1 | 1869 | NM_005225 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| HOXD13 | 3239 | XM_011511068; NM_000523; XM_011511069 |
| CTSV | 1515 | NM_001201575; NM_001333 |
| HOXD10 | 3236 | NM_002148 |
| DGKG | 1608 | NM_001346; NM_001080745; NM_001080744 |
| SFRP1 | 6422 | NM_003012 |
| PAX9 | 5083 | NM_001372076; NM_006194 |
| SCGB2A1 | 4246 | NM_002407 |
| FOXJ1 | 2302 | NM_001454 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |

TABLE 3-continued

Genes associated with molecular categories.

| Gene | NCBI Gene ID | NCBI Accession Number(s) |
|---|---|---|
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| BEGAIN | 57596 | NM_001385092; NM_001385093; NR_169571; XM_024449671; NM_001385104; XM_024449670; NM_001159531; NM_001385088; NM_001385094; NM_001385095; NM_001385096; NM_001385097; NM_001385098; NM_001385099; NM_001385100; NM_020836; NM_001385089; NM_001385102; NM_001385083; NM_001385084; NM_001385091; NR_169570; NM_001385085; NM_001385086; NM_001385087; NM_001385103; NM_001385082; NM_001385090; NM_001385101 |
| EMX2 | 2018 | NM_004098; NM_001165924 |
| VGLL1 | 51442 | NM_016267 |
| ALDH1A2 | 8854 | NM_001206897; NM_170697; NM_170696; NM_003888 |
| SLCO5A1 | 81796 | XM_017013885; XR_928814; NM_001146008; NM_001146009; XM_017013886; XR_428341; XM_017013884; NM_030958; XM_017013883; XM_005251313 |
| HOχA10 | 3206 | NR_037939; NM_153715; NM_018951 |
| GADD45G | 10912 | XM_011518163; NM_006705 |
| RPS4Y1 | 6192 | NM_001008 |
| TPM2 | 7169 | XM_017015091; NM_213674; XM_017015093; XM_017015088; NM_001301226; NM_001301227; NM_001145822; XM_017015087; XM_017015092; XM_017015090; NM_003289 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| WT1 | 7490 | NM_000378; NR_160306; NM_001367854; NM_001198551; NM_001198552; NM_024424; NM_024426; NM_024425 |
| MNX1 | 3110 | NM_001165255; NM_005515 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| ANKRD2 | 26287 | NM_001291218; NM_001129981; NM_020349; NM_001291219; NM_001346793 |
| EHHADH | 1962 | XM_006713525; NM_001166415; NM_001966 |
| FXYD1 | 5348 | NM_001278718; NM_001278717; NM_021902; XM_017026875; NM_005031; XM_017026874; XM_017026876 |
| FOXL2 | 668 | NM_023067 |
| GLDC | 2731 | NM_000170 |
| TNNC1 | 7134 | NM_003280 |
| EDNRB | 1910 | NM_001122659; NM_003991; NM_001201397; NM_000115; NR_047024 |
| APOD | 347 | NM_001647 |
| SLC27A2 | 11001 | NM_001159629; NM_003645 |
| SLC12A2 | 6558 | XM_011543588; NM_001256461; XR_001742214; NR_046207; NM_001046; XM_017009771 |
| FMO2 | 2327 | NM_001460; NR_160266; XR_921761; NM_001365900; XR_001737072; NM_001301347 |
| GSTM5 | 2949 | NM_000851; XM_005270785; XM_005270784 |
| SOX1 | 6656 | NM_005986 |
| APBA1 | 320 | NM_001163; XM_011518617; XM_017014670; XM_005251968 |
| HOXB13 | 10481 | NM_006361 |
| NPY4R | 5540 | XR_001747124; NM_001278794; NM_005972; XM_011539936; XM_017016387; XM_011539937; XM_017016386; XR_001747123 |
| CIDEB | 27141 | NM_001393334; NM_001393340; NM_001318807; NM_001393339; NM_001393336; NM_001393338; NM_001393335; NM_001393337; NM_014430 |
| MEIS1 | 4211 | NM_002398 |
| TNNC2 | 7125 | NM_003279; XM_011529031 |
| RIMBP2 | 23504 | XM_017019105; XM_011538103; XM_011538105; NM_001351227; NM_001393620; NM_001393627; NM_001393616; NM_001351232; NM_001393615; NM_001393621; NM_001393623; NM_001393628; XM_011538106; XM_011538102; XM_011538108; NM_001351231; NM_001393614; NM_001393617; NM_001393622; NM_001393625; NM_001393629; NM_001351230; NM_001393619; NM_001393626; NM_001351228; NM_001393624; XM_011538107; XM_017019106; NM_001351226; NM_001351229; NM_001351233; NM_001393618; NM_015347 |
| HGH1 | 51236 | NM_016458; XR_001745537 |
| SOX15 | 6665 | NM_006942 |
| PDLIM3 | 27295 | NM_001114107; XR_938723; NM_001257963; XR_938724; NM_001257962; NR_047562; NM_014476; XR_001741206 |
| CX3CR1 | 1524 | NM_001171174; NM_001337; NM_001171171; NM_001171172 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |

TABLE 3-continued

Genes associated with molecular categories.

| Gene | NCBI Gene ID | NCBI Accession Number(s) |
| --- | --- | --- |
| ZBTB16 | 7704 | XR_001747955; NM_001354751; XM_017018259; NM_006006; NM_001354752; XM_005271658; XM_024448681; NM_001018011; NM_001354750 |
| CLCA2 | 9635 | NM_006536; XM_011542448 |
| DLX5 | 1749 | XM_017011803; NM_005221; XM_005250185 |
| GABRQ | 55879 | NM_018558; XM_011531184 |
| FOXA2 | 3170 | NM_021784; NM_153675 |
| TNFSF10 | 8743 | NR_033994; NM_001190943; NM_003810; NM_001190942 |
| IQCA1 | 79781 | XM_017004960; NM_024726; NM_001270585; XM_011511865; XM_011511866; XM_011511864; NM_001270584; NR_073043 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| TUBA1C | 84790 | NM_001303114; NM_032704; NM_001303116; NM_001303117; NM_001303115 |
| GYPC | 2995 | NM_002101; XM_006712460; NM_001256584; NM_016815 |
| CA2 | 760 | NM_001293675; NM_000067 |
| IL20RA | 53832 | NM_001278722; XM_011535904; XM_017010955; NM_001278724; NM_014432; XM_006715506; NM_001278723; XM_017010954 |
| RGN | 9104 | XM_024452477; XM_006724568; XM_017029954; NM_004683; NM_001282848; NM_152869; NM_001282849; XM_006724567 |
| AOC3 | 8639 | XR_934584; NM_001277732; NM_003734; NR_102422; XM_011525419; XR_001752673; XM_011525420; XM_024451015; NM_001277731 |
| FGF18 | 8817 | NM_003862; NM_033649 |
| MYO5A | 4644 | XM_011521607; NM_001142495; NM_001382348; XM_011521610; NM_000259; NM_001382347; XM_011521611; XM_011521609; XM_011521612; XM_017022227; NM_001382349 |
| CCDC33 | 80125 | XR_001751400; XM_011522090; XM_017022624; XM_017022626; NM_001287181; XM_011522088; XM_017022630; XR_001751401; NM_025055; XM_017022625; XM_017022628; XM_017022631; NR_108023; NM_182791; XM_011522087; XM_005254692; XM_017022627; XM_017022633; XM_017022623; XM_011522086; XM_017022632; XM_011522085; XM_011522089 |
| REN | 5972 | NM_000537 |
| NCAPG | 64151 | NM_022346; XM_017008543; NR_073124; XM_017008544; XM_011513876 |
| CT62 | 196993 | NR_168259; NM_001102658; NR_168260 |
| CACNA1G | 8913 | NM_001256326; NM_001256328; NM_018896; NM_198378; NM_198388; NM_198396; NM_001256359; NM_001256361; NM_198383; NM_198385; NM_001256327; NM_001256330; NR_046056; NM_198380; NM_198382; NR_046054; XM_006722160; NM_198379; NM_001256329; NM_001256332; NM_001256333; NM_001256360; NM_198384; NM_198386; NR_046058; NM_001256325; NM_001256334; NM_198387; XM_006722161; NM_001256324; NM_001256331; NM_198376; NM_198377; NR_046055; NR_046057; NM_198397 |
| PIGR | 5284 | XM_011509629; NM_002644 |
| CSTA | 1475 | NM_005213 |
| OSR2 | 116039 | XM_017013018; NM_053001; XM_011516825; XM_005250778; NM_001286841; NM_001142462; XM_011516826; NM_001394683; XM_011516827 |
| FOXF2 | 2295 | NM_001452 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| GAD1 | 2571 | NM_013445; XM_017003758; NM_000817; XM_005246444; XM_011510922; XM_017003757; XM_017003756; XM_024452783 |
| NXPH4 | 11247 | XM_017018747; NM_007224 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EGFR | 1956 | NM_001346899; NM_201282; NM_201284; NM_001346898; NM_001346900; NM_001346897; NM_201283; NM_001346941; NM_005228 |
| FMO3 | 2328 | XM_011509345; XM_024454365; NM_001002294; NM_006894; NM_001319173; NM_001319174 |
| TSPAN7 | 7102 | NM_004615 |
| ASRGL1 | 80150 | XM_005274305; XM_005274306; XM_011545265; NM_001083926; XM_011545266; NM_025080; XR_002957199; XM_017018354; XR_002957198; XR_001747982 |
| ALOX15B | 247 | NM_001141; NM_001039130; NM_001039131 |
| PRPH | 5630 | XM_005269025; XR_944623; NM_006262; |
| EFEMP1 | 2202 | XM_024452757; NM_004105; NM_018894; XM_005264205; NM_001039349; XM_017003586; XM_024452755; XM_024452756; NM_001039348 |
| SALL1 | 6299 | NM_001127892; NM_002968 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |

TABLE 3-continued

| Genes associated with molecular categories. | | |
|---|---|---|
| Gene | NCBI Gene ID | NCBI Accession Number(s) |
| PHOX2A | 401 | NM_005169 |
| AQP5 | 362 | NM_001651; XM_005268838 |
| TTC22 | 55001 | XM_017001582; XM_011541671; NM_001114108; NM_017904 |
| | | Renal_Cell_Carcinoma |
| SLC17A3 | 10786 | NM_006632; NM_001098486 |
| SLC4A1 | 6521 | XM_011525129; XM_005257593; XM_011525130; NM_000342 |
| CDH16 | 1014 | NM_001204746; XM_011522807; NM_004062; XM_005255770; NM_001204744; NM_001204745 |
| SLC22A2 | 6582 | NM_153191; NM_003058 |
| NAT8 | 9027 | NM_003960 |
| SLC3A1 | 6519 | XM_011533047; NM_000341 |
| ENPP3 | 5169 | XR_001743464; NR_133007; NM_005021; XM_017010932; XM_011535897 |
| FXYD2 | 486 | NM_021603; NM_001127489; NM_001680 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| SIM1 | 6492 | XM_011536072; NM_001374769; NM_005068 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| PAX2 | 5076 | NM_001304569; NM_003987; NM_001374303; NM_003989; NM_000278; NM_003990; NM_003988 |
| PVALB | 5816 | NM_001315532; NM_002854 |
| RHBG | 57127 | XR_001737323; NR_146765; XR_001737328; XR_001737329; NR_046115; XM_011509799; XM_017001859; NR_146764; XM_011509800; XM_017001858; XR_001737324; XR_001737325; NM_001256395; NR_146763; XM_017001857; NM_020407; XR_001737330; XR_001737332; NM_001256396 |
| AQP2 | 359 | NM_000486 |
| POU3F3 | 5455 | NM_006236 |
| PAX8 | 7849 | NM_013992; NM_013953; NM_013952; NM_003466; NM_013951 |
| GFRA3 | 2676 | NM_001496 |
| CA12 | 771 | NM_001218; NR_135511; NM_206925; NM_001293642 |
| FOXD3 | 27022 | NM_012183 |
| CACNG4 | 27092 | NM_014405 |
| HAND2 | 9464 | NM_021973 |
| NLGN1 | 22871 | NM_001365923; NM_001365928; NM_001365932; NM_014932; XM_011512551; XM_011512553; XM_017005897; XM_017005902; NM_001365929; NM_001365926; XM_017005895; XM_017005893; NM_001365925; NM_001365931; XM_017005896; XM_017005900; NM_001365933; XM_005247237; NM_001365930; NM_001365936; XM_011512554; XM_017005888; XM_017005894; NM_001365924; NM_001365927; NM_001365934; NM_001365935 |
| TRPM3 | 80036 | NM_001366147; XM_011519045; NM_001366145; NM_206944; XM_011519042; XM_024447681; NM_001007470; NM_001366152; NM_001366153; NM_206946; XM_011519037; NM_001366151; NM_206947; XM_011519040; NM_001007471; NM_001366141; NM_001366150; NM_001366154; XM_011519039; XM_017015156; XM_024447687; NM_001366144; NM_001366146; NM_020952; XM_024447683; NM_001366149; XM_011519038; XM_011519046; XM_024447682; XM_024447684; XM_024447685; XM_024447686; NM_001366142; NM_001366143; NM_001366148; NM_024971; NM_206945; NM_206948 |
| ARHGEF4 | 50649 | XM_011511276; XM_005263689; XR_001738756; NM_001375900; NM_001375902; XM_011511274; XR_001738757; NM_001375901; NM_001375904; NM_001367493; NM_001375903; NM_015320; NM_001395416; NM_032995; XM_005263688; XM_011511277; XM_017004231; XM_024452938 |
| INSM1 | 3642 | NM_002196 |
| S100A14 | 57402 | XM_017001875; NM_020672; XM_005245362 |
| LGR5 | 8549 | NR_110596; NM_001277227; NM_001277226; NM_003667 |
| CFTR | 1080 | NM_000492 |
| TRHDE | 29953 | XM_017019244; XM_017019243; NM_013381; XM_005268819; XM_011538248 |
| ESRP1 | 54845 | XM_005250991; NM_001122827; NM_017697; XM_005250992; NM_001122826; NM_001034915; NM_001122825 |
| LAD1 | 3898 | NM_005558 |
| GRHL2 | 79977 | XM_011517306; XM_024447286; NM_001330593; NM_024915; XM_011517307 |
| ALPPL2 | 251 | NM_031313 |
| HOXC10 | 3226 | NM_017409 |
| EPHB3 | 2049 | NM_004443 |
| SLC6A11 | 6538 | NM_001317406; XM_017007073; XM_011534033; NM_014229 |
| NKX3-2 | 579 | NM_001189 |
| CNKSR1 | 10256 | NM_006314; NR_023345; NM_001297647; NM_001297648 |
| RAMP1 | 10267 | XM_017003153; XM_017003154; XM_017003155; NM_001308353; NM_005855; XM_017003152; XM_017003156 |
| KIF2C | 11004 | NM_001297656; XM_011540541; NM_001297657; XM_011540540; NM_006845; NM_001297655 |

TABLE 3-continued

| Gene | NCBI Gene ID | NCBI Accession Number(s) |
|---|---|---|
| Genes associated with molecular categories. | | |
| ST8SIA2 | 8128 | NM_006011; NM_001330416; XM_017022642 |
| SFRP1 | 6422 | NM_003012 |
| SPAG4 | 6676 | XM_011529009; NM_003116; XM_005260520; NM_001317931 |
| CDKN2A | 1029 | XR_929159; XM_011517676; XM_011517675; NM_001363763; NM_001195132; NM_058195; NM_000077; NM_058196; NM_058197; XM_005251343 |
| SIGLEC8 | 27181 | XM_011526734; NM_014442; NM_001363548 |
| SLC14A2 | 8170 | XM_017026016; NM_007163; NM_001242692; XM_024451271; NM_001371319; XM_024451270 |
| PLA2G7 | 7941 | NM_001168357; XR_001743639; XM_005249408; NM_005084; XR_002956305 |
| KCNN1 | 3780 | NM_001386974; NM_001386976; NR_170373; NM_001386975; NM_001386977; NM_002248; XM_011528004; NR_170374 |
| CA8 | 767 | NM_001321837; NM_001321838; XM_011517587; XM_011517588; NM_001321839; NM_004056; NR_135821; XM_017013818 |
| KLK6 | 5653 | XM_024451611; NM_001319949; NM_001012964; NM_001319948; NM_001012965; NM_002774 |
| CA9 | 768 | XR_428428; NM_001216; XR_001746374 |
| Squamous_Cell_Carcinoma | | |
| TMPRSS11D | 9407 | XM_005265710; XM_017008851; NM_004262 |
| SPRR1B | 6699 | NM_003125 |
| SERPINB3 | 6317 | NM_006919 |
| DSG3 | 1830 | XM_011525850; NM_001944 |
| ADH7 | 131 | NM_001166504; NM_000673 |
| S100A12 | 6283 | NM_005621 |
| SPRR1A | 6698 | NM_005987; NM_001199828 |
| KRT1 | 3848 | NM_006121 |
| SERPINB13 | 5275 | NM_001348267; XM_011526029; NM_001348268; NM_012397; NM_001348269; NM_001307923; NM_001348270 |
| KRT6A | 3853 | NM_005554 |
| CRNN | 49860 | NM_016190 |
| FOXE1 | 2304 | NM_004473 |
| SFTPB | 6439 | XM_005264487; NM_198843; XM_005264488; NM_000542; NM_001367281; XM_005264490 |
| CALML3 | 810 | NM_005185 |
| CRCT1 | 54544 | NM_019060; XM_011509656 |
| SFN | 2810 | NM_006142 |
| TP63 | 8626 | NM_001114978; NM_001329144; NM_001329146; NM_001329964; NM_001329145; NM_003722; NM_001114979; NM_001114982; NM_001329149; NM_001114980; NM_001114981; NM_001329150; NM_001329148 |
| SFTPA2 | 729238 | XM_011540124; XM_005270132; NM_001320813; NM_001320814; XM_017016608; XM_011540125; NM_001098668; XM_005270128 |
| FABP5 | 2171 | NM_001444 |
| KRT5 | 3852 | NM_000424 |
| GPR87 | 53836 | NM_023915 |
| CKM | 1158 | NM_001824 |
| MYL2 | 4633 | NM_000432 |
| SOX2 | 6657 | NM_003106 |
| MYL1 | 4632 | NM_079422; NM_079420 |
| IRX4 | 50805 | NM_016358; NM_001278633; NM_001278632; NM_001278635; NM_001278634 |
| NKX2-1 | 7080 | NM_001079668; NM_003317 |
| KRT20 | 54474 | NM_019010 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| PLA2G3 | 50487 | XM_011530205; XR_937865; XM_011530204; NM_015715 |
| FLG | 2312 | NM_002016 |
| SFTPD | 6441 | XM_011540087; NM_003019; XM_011540088 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SPINK1 | 6690 | NM_003122; NM_001379610; NM_001354966 |
| NTS | 4922 | NM_006183 |
| MMP12 | 4321 | NM_002426 |
| ALDH3B2 | 222 | NM_001354345; NM_001393400; NM_001393402; ; NM_001393401; NM_000695; NM_001031615 |
| HNF1B | 6928 | XM_011525161; NM_001165923; NM_001304286; XM_011525163; NM_000458; XM_011525162; NM_006481; XM_011525164; XM_011525160 |
| UPK1B | 7348 | NM_006952 |
| GJB1 | 2705 | NM_000166; XM_011530907; NM_001097642 |

TABLE 3-continued

Genes associated with molecular categories.

| Gene | NCBI Gene ID | NCBI Accession Number(s) |
|---|---|---|
| FABP4 | 2167 | NM_001442 |
| CTSV | 1515 | NM_001201575; NM_001333 |
| HOXD11 | 3237 | NM_021192 |
| CLDN18 | 51208 | NM_001002026; NM_016369 |
| PITX1 | 5307 | NM_002653 |
| LIPF | 8513 | NM_004190; NM_001198829; NM_001198830; NM_001198828; XM_011540311 |
| FZD10 | 11211 | NM_007197 |
| CYP4B1 | 1580 | XM_011540833; NR_135003; XM_011540832; NM_000779; NM_001319161; NM_001319163; NM_001099772; XM_017000466; NM_001319162; XR_946559 |
| TCN1 | 6947 | NM_001062 |
| CLDN3 | 1365 | NM_001306 |
| MYOT | 9499 | XM_017010060; XM_017010061; NM_001300911; NM_001135940; XM_017010062; NM_006790 |
| LAMC2 | 3918 | NM_005562; NM_018891; XM_017001273 |
| SCNN1B | 6338 | XM_017023526; XM_011545913; XM_011545914; XM_017023525; NM_000336 |
| DES | 1674 | NM_001927; NM_001382708; NM_001382710; NM_001382713; NM_001382709; NM_001382711; NM_001382712 |
| CSF3 | 1440 | NR_168489; NR_168491; NM_000759; NM_172220; NM_001178147; NM_172219; NR_168490; NR_033662 |
| HMGCS2 | 3158 | NM_001166107; XM_011541313; NM_005518 |
| AQP4 | 361 | NM_001317387; NM_001364287; NM_001364286; NM_001317384; XM_011525942; NM_001650; NM_001364289; NM_004028 |
| TMC5 | 79838 | NM_001261841; NM_024780; NM_001308161; NM_001105248; NM_001105249 |
| SLC52A1 | 55065 | XM_011523951; NM_001104577; NM_017986 |
| DMBT1 | 1755 | XM_011539390; XM_011539391; XM_011539407; XM_011539408; NM_007329; XM_006717660; XM_006717665; XM_011539402; XM_024447854; XM_011539392; XM_011539393; XM_011539400; XM_011539403; XM_011539405; XM_011539413; XM_017015798; NM_001320644; NM_004406; XM_011539394; XM_011539409; XM_011539415; NM_017579; XM_011539389; XM_011539395; XM_011539396; XM_011539399; XM_011539401; XM_011539410; XM_011539414; NM_001377530; XM_011539398; XM_011539411 |
| SLC34A2 | 10568 | NM_001177999; NM_006424; NM_001177998 |
| GABRQ | 55879 | NM_018558; XM_011531184 |
| PRSS3 | 5646 | NM_007343; NM_001197097; NM_002771; XM_011517965; NM_001197098 |
| SLC4A4 | 8671 | XM_024454267; XM_024454271; XM_024454272; NM_001098484; XM_024454270; NM_003759; XM_017008793; XM_024454268; NM_001134742; XM_024454269; XM_011532390; XM_017008792 |
| COX6A2 | 1339 | NM_005205 |
| SERPINA5 | 5104 | NM_000624 |
| SDC1 | 6382 | NM_001006946; XM_005262620; XM_005262621; NM_002997; XM_005262622 |
| ENDOU | 8909 | NM_001172439; NM_006025; NM_001172440 |
| UPK1A | 11045 | NM_007000; NM_001281443 |
| NME5 | 8382 | XM_024446227; NM_003551; XM_005272099; XM_024446228; XM_017009945 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| HAND1 | 9421 | NM_004821; XM_005268531 |
| CRH | 1392 | NM_000756 |
| TFAP2A | 7020 | NM_001032280; XM_006715175; NM_001042425; XM_017011232; XM_011514833; NM_001372066; NM_003220 |
| COL9A1 | 1297 | NM_001851; NR_165185; NM_078485; XM_017010246; XM_011535429; XM_017010247; NM_001377289; NM_001377290; NM_001377291 |
| ATP10B | 23120 | XM_011534472; XM_017009253; NM_001366652; NM_001366658; XM_011534468; NM_001366653; NM_001366654; NM_001366655; NM_001366656; NM_025153; NM_001366657; XM_017009252; XM_011534469 |

TABLE 3-continued

Genes associated with molecular categories.

| Gene | NCBI Gene ID | NCBI Accession Number(s) |
|---|---|---|
| ALDOB | 229 | NM_000035 |
| AHNAK2 | 113146 | NM_138420; XM_024449463; NM_001350929 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| EVX1 | 2128 | NM_001304519; NM_001304520; NM_001989 |
| CLDN4 | 1364 | NM_001305 |
| NEB | 4703 | XM_005246590; XM_005246594; XM_005246602; XM_005246611; XM_017004178; XM_017004179; XM_017004180; NM_001164508; XM_005246603; XM_005246617; XM_006712542; XM_017004185; NM_001164507; NM_001271208; XM_005246593; XM_005246598; XM_005246606; XM_005246610; XM_017004177; XM_017004184; NM_004543; XM_005246592; XM_005246599; XM_005246601; XM_005246616; XM_017004181; XM_005246604; XM_005246608; XM_017004182; XM_017004183; XM_005246591; XM_005246596; XM_005246597; XM_006712541; XM_011511225; XM_011511226; XM_005246613; XM_005246612; XM_005246615; XM_011511227 |
| LRP2 | 4036 | XM_011511183; NM_004525; XM_011511184 |
| DLX2 | 1746 | NM_004405 |
| GRIK3 | 2899 | NM_000831 |
| TBX1 | 6899 | NM_005992; NM_080646; XM_017028928; XM_006724312; XM_017028926; NM_001379200; XM_017028925; XM_017028927; NM_080647 |
| XDH | 7498 | NM_000379; XM_011533096; XM_011533095 |
| DLX6 | 1750 | NM_005222 |
| ADH1C | 126 | NM_000669; NR_133005 |
| HKDC1 | 80201 | NM_025130; XR_001747209; XM_011540195 |
| MFAP5 | 8076 | NM_001297709; NR_123733; NR_123734; NM_001297711; NM_003480; NM_001297710; NM_001297712 |
| DNAJC22 | 79962 | NM_001304944; NM_024902; XM_005269157; XM_005269155; XM_005269156 |
| HNF4G | 3174 | NM_001330561; XM_017013373; XM_017013375; XM_017013374; XM_017013376; NM_004133 |
| KCNB1 | 3745 | XM_011528799; XM_006723784; NM_004975 |
| ACTG2 | 72 | NM_001199893; NM_001615 |
| SSX1 | 6756 | NM_001278691; NM_005635 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| FAM107A | 11170 | NM_001076778; NM_007177; NM_001282713; NM_001282714 |
| SEMA3G | 56920 | XM_024453642; NM_020163 |
| FIGF | 2277 | NM_004469 |
| TCF21 | 6943 | NM_003206; NM_198392 |
| FMO2 | 2327 | NM_001460; NR_160266; XR_921761; NM_001365900; XR_001737072; NM_001301347 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| AOC3 | 8639 | XR_934584; NM_001277732; NM_003734; NR_102422; XM_011525419; XR_001752673; XM_011525420; XM_024451015; NM_001277731 |
| ADH1B | 125 | NM_001286650; NM_000668 |
| GDF10 | 2662 | NM_004962 |
| MYOC | 4653 | NM_000261 |
| SOX17 | 64321 | NM_022454 |
| FHL5 | 9457 | NM_001170807; NM_001322466; NM_001322467; NM_020482 |
| PDK4 | 5166 | NM_002612 |
| CCL23 | 6368 | NM_005064; XR_429910; NM_145898 |
| MMP11 | 4320 | NM_005940; NR_133013 |
| HBB | 3043 | NM_000518 |
| HOXA10 | 3206 | NR_037939; NM_153715; NM_018951 |
| MYBL2 | 4605 | NM_002466; NM_001278610 |
| UBE2C | 11065 | NM_001281742; NM_001281741; NM_181802; NM_181803; NR_104036; NR_104037; NM_007019; NM_181800; NM_181801; NM_181799 |
| NPY1R | 4886 | NM_000909; XM_005263031; XM_011532010 |
| TUBB3 | 10381 | NM_006086; NM_001197181 |
| ORC6 | 23594 | NR_037620; NM_014321; XM_011522978 |
| GRIN2D | 2906 | XM_011526872; NM_000836 |
| PRR4 | 11272 | NM_001098538; NM_007244 |
| COL10A1 | 1300 | XM_011535432; NM_000493; XM_011535433; XM_017010248; XM_006715333 |
| CDKN2A | 1029 | XR_929159; XM_011517676; XM_011517675; NM_001363763; NM_001195132; NM_058195; NM_000077; NM_058196; NM_058197; XM_005251343 |
| FOLR1 | 2348 | NM_000802; NM_016729; NM_016730; NM_016725; NM_016724 |
| ONECUT2 | 9480 | NM_004852 |
| MMP9 | 4318 | NM_004994 |

TABLE 3-continued

| Genes associated with molecular categories. | | |
|---|---|---|
| Gene | NCBI Gene ID | NCBI Accession Number(s) |
| HOXA11 | 3207 | NM_005523 |
| HOXB13 | 10481 | NM_006361 |
| CST1 | 1469 | NM_001898 |
| SYT12 | 91683 | XM_011545346; XM_011545347; NM_177963; XM_017018547; NM_001177880; NM_001318775; XM_017018548; XM_006718737; XM_024448766; NM_001318773 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| NXPH4 | 11247 | XM_017018747; NM_007224 |
| CXCL13 | 10563 | NM_001371558; NM_006419 |
| CDX2 | 1045 | XM_011534876; NM_001354700; XM_011534879; XM_011534875; XM_011534878; NM_001265 |
| COL11A1 | 1301 | XM_017000337; XM_017000335; XM_017000336; NR_134980; NM_080629; XM_017000334; NM_001190709; NM_001854; NM_080630 |
| RAB3B | 5865 | XM_017001958; NM_002867 |
| JPH3 | 57338 | NM_001271604; NR_073379; NM_001271605; NM_020655 |
| Lung_Adenocarcinoma | | |
| SFTPA2 | 729238 | XM_011540124; XM_005270132; NM_001320813; NM_001320814; XM_017016608; XM_011540125; NM_001098668; XM_005270128 |
| BPIFA1 | 51297 | NM_130852; NM_001243193; NM_016583 |
| LGSN | 51557 | XM_017010931; XM_017010929; XM_011535889; XM_011535892; NM_016571; XM_017010930; NM_001143940 |
| SCGB1A1 | 7356 | NM_003357 |
| NKX2-1 | 7080 | NM_001079668; NM_003317 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SFTPB | 6439 | XM_005264487; NM_198843; XM_005264488; NM_000542; NM_001367281; XM_005264490 |
| C4BPA | 722 | XM_005273252; NM_000715; XM_005273251 |
| CEACAM6 | 4680 | NM_002483; XM_011526990 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SERPINB13 | 5275 | NM_001348267; XM_011526029; NM_001348268; NM_012397; NM_001348269; NM_001307923; NM_001348270 |
| SPRR1A | 6698 | NM_005987; NM_001199828 |
| HAND2 | 9464 | NM_021973 |
| TMC5 | 79838 | NM_001261841; NM_024780; NM_001308161; NM_001105248; NM_001105249 |
| TSPAN8 | 7103 | NM_001369760; NM_004616; XM_006719583 |
| SPDEF | 25803 | NM_001252294; XM_005248988; NM_012391; XM_011514457 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| CP | 1356 | XM_006713500; XM_006713501; XM_017005735; XM_017005734; XM_006713499; XM_011512435; XR_427361; NM_000096; NR_046371 |
| GCNT3 | 9245 | NM_004751 |
| CLDN8 | 9073 | NM_199328; NM_012132 |
| CARTPT | 9607 | NM_004291 |
| FOXA1 | 3169 | NM_004496; XM_017021246 |
| EDN3 | 1908 | NM_207034; XM_024451847; NM_207032; XR_002958461; XR_002958462; XR_936513; NM_001302455; NM_207033; XM_006723734; XM_011528655; XM_024451848; NM_000114; XM_005260312; XM_005260313; NM_001302456 |
| CCL13 | 6357 | NM_005408 |
| DNAH2 | 146754 | XM_017024219; XM_024450606; XM_024450608; XM_024450609; XM_011523663; XM_024450604; XM_024450605; XM_024450607; NM_001303270; NM_020877; XM_011523667; XM_024450610; XM_011523670 |
| EMX2 | 2018 | NM_004098; NM_001165924 |
| CDHR1 | 92211 | XM_011540338; NM_033100; NM_001171971; XM_011540340; XM_011540337; XM_011540339 |
| RNF186 | 54546 | NM_019062 |
| TBX4 | 9496 | XM_011525490; XM_011525491; NM_001321120; XM_011525495; NM_018488 |
| LAMB3 | 3914 | XM_005273124; NM_001127641; XM_017001272; NM_000228; NM_001017402 |
| S100A7 | 6278 | NM_002963 |
| PLA2G2A | 5320 | NM_001161728; NM_000300; NM_001161729; NM_001161727; NM_001395463 |
| KCNG1 | 3755 | XM_011528800; XM_011528802; XM_011528803; XM_011528805; NM_172318; NM_002237; XM_011528801; XM_011528804; XM_011528806; XM_006723785 |
| KRT5 | 3852 | NM_000424 |
| BARX1 | 56033 | NM_021570 |

TABLE 3-continued

Genes associated with molecular categories.

| Gene | NCBI Gene ID | NCBI Accession Number(s) |
|---|---|---|
| SLC44A4 | 80736 | NM_001178045; NM_001178044; NM_025257 |
| MPPED2 | 744 | NM_001377952; NM_001145399; NR_165347; XM_005253111; NR_165336; NR_165343; NR_165339; NR_165340; NR_165345; XM_024448676; NM_001377954; XM_005253114; NM_001377953; NR_165337; NR_165344; NR_165348; XM_017018231; NR_165346; NM_001377955; NM_001377956; NM_001584; NR_165338; NR_165341; NR_165342 |
| XDH | 7498 | NM_000379; XM_011533096; XM_011533095 |
| CCL25 | 6370 | NM_001394634; NM_001394635; NM_001394638; NM_005624; NM_148888; NM_001394636; NM_001201359; NM_001394637 |
| S100A1 | 6271 | NM_006271 |
| ACTA1 | 58 | NM_001100 |
| HR | 55806 | XM_006716367; NM_005144; XM_005273569; NM_018411 |
| DLL3 | 10683 | NM_016941; NM_203486 |
| KRT13 | 3860 | NM_153490; NM_002274 |
| CBLC | 23624 | XM_011526690; XM_011526688; XR_935783; XM_005258696; XR_243917; XM_011526689; NM_001130852; NM_012116 |
| FAM107A | 11170 | NM_001076778; NM_007177; NM_001282713; NM_001282714 |
| TCF21 | 6943 | NM_003206; NM_198392 |
| FCN3 | 8547 | NM_173452; NM_003665 |
| FABP4 | 2167 | NM_001442 |
| GRIA1 | 2890 | NM_001114183; NM_001258022; NM_001258023; NM_001364166; XM_017009392; NR_157093; NM_000827; NM_001258019; NM_001258020; NM_001364165; NM_001258021; NR_047578; NM_001364167 |
| ALAS2 | 212 | NM_001037968; NM_001037967; NM_000032; NM_001037969 |
| TFAP2A | 7020 | NM_001032280; XM_006715175; NM_001042425; XM_017011232; XM_011514833; NM_001372066; NM_003220 |
| PITX1 | 5307 | NM_002653 |
| IGF2BP3 | 10643 | XM_011515092; NM_006547; XM_011515089; XM_006715639; XM_011515090; XM_011515091; XM_011515093 |
| RASAL1 | 8437 | XR_002957386; NM_001193521; NM_001394081; NM_001394082; XM_005253950; NM_001394084; NM_001394087; NM_004658; XM_017020030; XM_017020031; XM_006719642; XR_001748903; XM_006719641; NM_001301202; NM_001394083; XM_011538854; XM_017020029; NM_001394089; XR_001748902; NM_001193520; NM_001394085; NM_001394086; NM_001394088 |
| MMP11 | 4320 | NM_005940; NR_133013 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| NXPH4 | 11247 | XM_017018747; NM_007224 |
| CXCL14 | 9547 | NM_004887 |
| | | Prostate_Adenocarcinoma |
| RNF128 | 79589 | NM_024539; NM_194463 |
| PRM2 | 5620 | NM_001286358; NR_104428; NM_002762; NM_001286356; NM_001286359; NM_001286357 |
| CENPF | 1063 | XM_017000086; NM_016343; XM_011509082 |
| DES | 1674 | NM_001927; NM_001382708; NM_001382710; NM_001382713; NM_001382709; NM_001382711; NM_001382712 |
| NKX3-1 | 4824 | NM_001256339; NR_046072; NM_006167 |
| CGREF1 | 10669 | NM_001166239; NM_006569; NM_001301324; NM_001166241; NM_001166240 |
| KLK2 | 3817 | NM_005551; NR_045762; NM_001002231; NM_001002232; NM_001256080; NR_045763 |
| SEMG1 | 6406 | NM_198139; NM_003007 |
| ASPN | 54829 | NM_001193335; NM_017680 |
| DEPDC1 | 55635 | NM_001114120; NM_017779 |
| AMACR | 23600 | NM_203382; NM_001167597; NM_001167598; NM_014324; NM_001167596; NM_001167595 |
| COL6A1 | 1291 | NM_001848 |
| ONECUT2 | 9480 | NM_004852 |
| COL10A1 | 1300 | XM_011535432; NM_000493; XM_011535433; XM_017010248; XM_006715333 |
| TRPM8 | 79054 | XM_017004891; NM_024080; XM_011511810; XM_024453132; XM_024453134; XM_024453133 |
| ATP8A2 | 51761 | XM_011535103; XM_011535113; XM_005266419; XM_024449369; XM_011535109; NM_016529; XM_011535104; XM_017020626; NM_001313741; XM_017020625; XM_011535106; XM_011535107 |
| PGC | 5225 | NM_002630; NM_001166424 |
| GDPD3 | 79153 | NM_024307 |
| MKI67 | 4288 | NM_002417; NM_001145966; XM_006717864; XM_011539818 |
| ZIC1 | 7545 | NM_003412 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| APOC1 | 341 | NM_001645; NM_001321066; NM_001379687; NM_001321065 |
| PLP2 | 5355 | NM_002668 |

TABLE 3-continued

| Gene | NCBI Gene ID | NCBI Accession Number(s) |
|---|---|---|
| | | Genes associated with molecular categories. |
| HOXB13 | 10481 | NM_006361 |
| DLX2 | 1746 | NM_004405 |
| TDRD1 | 56165 | XM_024448081; NM_001385365; NM_001365891; NM_001385366; NM_001385372; NM_001395205; XM_011539959; XM_017016415; NM_001385363; NM_001385368; XM_011539960; NM_001385364; XM_011539964; XM_011539962; XM_011539961; NM_001385367; NM_001385369; NM_001385371; NM_198795; NM_031278; XM_017016414; NM_001385370 |
| SCN1A | 6323 | NM_001353960; NM_001202435; NM_001353951; NM_001353952; NM_001353958; NM_001353950; NM_001353957; NR_148667; NM_001353949; NM_001353954; XR_001738884; NM_001353955; NM_001353961; NM_001165963; NM_001165964; NM_001353948; NM_006920; XR_001738883 |
| TRPC4 | 7223 | NM_001354806; XM_011535206; NM_016179; NM_003306; NM_001135958; NM_001135957; NM_001372055; XM_017020723; NM_001135956; NM_001354799; NM_001135955 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| ZWINT | 11130 | XR_428692; NM_007057; NM_001005413; XM_017015605; XM_024447784; NM_032997; NM_001005414 |
| KIF4A | 24137 | NM_012310 |
| CCNJL | 79616 | NM_001308173; NM_024565; NR_131769; XM_011534646; XM_017009847; XM_006714917; XR_427810; XM_011534647; XM_017009848; XR_427811 |
| PAGE4 | 9506 | NM_001318877; NM_007003 |
| TSPYL2 | 64061 | XM_006724592; XM_017029727; NM_022117; XR_001755719; XM_017029726 |
| MMP9 | 4318 | NM_004994 |
| HOXD13 | 3239 | XM_011511068; NM_000523; XM_011511069 |
| TPX2 | 22974 | XM_011528697; XM_011528699; NM_012112; XM_011528700 |
| FHL5 | 9457 | NM_001170807; NM_001322466; NM_001322467; NM_020482 |
| GRIA3 | 2892 | NM_007325; NM_181894; NM_000828; NM_001256743 |
| IFI6 | 2537 | NM_002038; XM_024446207; NM_022873; NM_022872 |
| RPL4 | 6124 | NM_000968 |
| ISL1 | 3670 | XM_011543380; NM_002202 |
| HPN | 3249 | NM_002151; NM_182983; XM_017026732; NM_001384133; XM_017026731; NM_001375441 |
| SRD5A2 | 6716 | XM_011533069; NM_000348; XM_011533072 |
| ACPP | 55 | NM_001099; XM_011512946; NM_001134194; XM_011512947; NM_001292037 |
| GUCY2C | 2984 | NM_004963; XM_011520631 |
| HOXC6 | 3223 | NM_153693; NM_004503 |
| LILRB4 | 11006 | NM_001278429; NM_001394939; XM_017026215; NM_001394934; NM_006847; NM_001278428; XM_017026216; NM_001394935; NM_001081438; NM_001394938; XR_002958246; NM_001278426; NM_001394933; NM_001394937; NM_001278427; NM_001278430; NM_001394936 |
| MSMB | 4477 | NM_138634; NM_002443 |
| STAR | 6770 | NM_001007243; NM_000349 |
| KLK3 | 354 | NM_001030050; NM_001030047; NM_145864; NM_001030049; NM_001030048; NM_001648 |
| FOXF1 | 2294 | NM_001451 |
| | | Urinary_Bladder_Urothelial_Carcinoma |
| UPK2 | 7379 | NM_006760 |
| PLA2G2F | 64600 | NM_022819; NM_001360869; XM_011541955; XM_011541956 |
| CYP1A1 | 1543 | NM_001319216; NM_001319217; NM_000499 |
| S100A2 | 6273 | NM_001366407; NM_001366406; NM_005978 |
| IVL | 3713 | NM_005547 |
| VGLL1 | 51442 | NM_016267 |
| UPK3A | 7380 | NM_006953; NM_001167574 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SERPINB4 | 6318 | NM_175041; NM_002974; XM_011526138 |
| UPK1B | 7348 | NM_006952 |
| KRT20 | 54474 | NM_019010 |
| TMEM40 | 55287 | NM_001284408; NM_018306; XM_011533937; NM_001284406; NM_001284407 |
| BHMT | 635 | NM_001713 |
| GATA3 | 2625 | XM_005252443; NM_002051; XM_005252442; NM_001002295 |
| KRT6A | 3853 | NM_005554 |
| MSMB | 4477 | NM_138634; NM_002443 |
| SLC14A1 | 6563 | XM_005258333; XM_024451238; XR_001753266; NM_001146037; XM_005258329; NM_001146036; NM_001308278; NM_015865; XM_011526144; NM_001308279; XM_006722526; XM_011526142; NM_001128588 |
| SFTPA2 | 729238 | XM_011540124; XM_005270132; NM_001320813; NM_001320814; XM_017016608; XM_011540125; NM_001098668; XM_005270128 |

TABLE 3-continued

Genes associated with molecular categories.

| Gene | NCBI Gene ID | NCBI Accession Number(s) |
|---|---|---|
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| OLFM4 | 10562 | NM_006418 |
| ACTC1 | 70 | NM_005159 |
| GJB1 | 2705 | NM_000166; XM_011530907; NM_001097642 |
| AIM1L | 55057 | NM_017977; XM_011541672; XM_011541673; XR_001737260; NM_001039775; XR_946681; XM_005245918 |
| IL9R | 3581 | XM_011545650; XM_017029496; XM_017029499; XM_017030050; XM_017030051; XM_011531155; XM_017029498; XM_017029502; XM_017029505; XM_017030053; XM_017030055; NM_176786; XM_011531156; XM_011545645; XM_011545651; XM_017029495; XM_017029501; XM_017030054; XM_011531152; XM_011545649; XM_017030045; XM_017030046; XM_017030052; XM_017029497; XM_017030049; XM_011531157; XM_011531154; XM_017029500; XM_017029503; XM_017030044; XM_017030047; NM_002186; XM_011531151; XM_011545646; XM_011545652; XM_017029504; XM_017029506; XM_017030048 |
| NRAP | 4892 | XM_005269867; NM_006175; NM_001322945; NM_198060; XM_005269865; XM_011539832; XM_024448029; NM_001261463; XM_006717870; XM_005269864 |
| SLC5A1 | 6523 | NM_000343; XM_011530331; NM_001256314 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| CASQ1 | 844 | NM_001231 |
| ACTG2 | 72 | NM_001199893; NM_001615 |
| POU3F3 | 5455 | NM_006236 |
| UNC93A | 54346 | XM_011535908; NM_001143947; XM_011535905; XM_011535907; NM_018974; XM_017010958; XM_011535906 |
| TRPA1 | 8989 | XM_011517624; NM_007332; XM_011517625; XM_017013946 |
| KCNIP1 | 30820 | NM_001034837; NM_014592; NM_001034838; NM_001278340; XM_017009407; XM_017009408; NM_001278339 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MSLN | 10232 | NM_001177355; NM_005823; NM_013404 |
| COX6A2 | 1339 | NM_005205 |
| CCL11 | 6356 | NM_002986 |
| IRX4 | 50805 | NM_016358; NM_001278633; NM_001278632; NM_001278635; NM_001278634 |
| REG1A | 5967 | NM_002909 |
| MAGEA11 | 4110 | XM_017029522; NM_001011544; NM_005366; XM_011531164 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| HLF | 3131 | NM_002126; XM_011524705; XR_002957996; NM_001330375; XM_005257269 |
| HAND1 | 9421 | NM_004821; XM_005268531 |
| HPN | 3249 | NM_002151; NM_182983; XM_017026732; NM_001384133; XM_017026731; NM_001375441 |
| SLC34A2 | 10568 | NM_001177999; NM_006424; NM_001177998 |
| TFF3 | 7033 | NM_003226 |
| PNMAL1 | 55228 | NM_001103149; NM_018215; XM_011527067 |
| PITX2 | 5308 | NM_001204397; NM_153427; XM_024454090; NM_000325; NM_001204398; NM_001204399; NM_153426 |
| REG3A | 5068 | NM_138938; NM_002580; NM_138937 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| PENK | 5179 | NM_006211; NM_001135690 |
| CDHR2 | 54825 | NM_001171976; NM_017675 |
| MMP11 | 4320 | NM_005940; NR_133013 |
| CDH4 | 1002 | NM_001252339; NM_001794; NM_001252338 |
| FOXA2 | 3170 | NM_021784; NM_153675 |

TABLE 3-continued

| Genes associated with molecular categories. | | |
|---|---|---|
| Gene | NCBI Gene ID | NCBI Accession Number(s) |
| HOXB8 | 3218 | NM_024016; XM_005257286; XM_017024564 |
| GABRA3 | 2556 | NM_000808; XM_006724811 |
| SLC47A1 | 55244 | NM_018242 |
| F7 | 2155 | XM_011537476; XM_011537475; NM_001267554; XM_011537474; NR_051961; XM_006719963; NM_019616; NM_000131 |
| S100A1 | 6271 | NM_006271 |
| DNAJC22 | 79962 | NM_001304944; NM_024902; XM_005269157; XM_005269155; XM_005269156 |
| NPR3 | 4883 | NM_001363652; NM_001364460; NM_000908; XM_011514047; XM_011514049; XM_017009492; NM_001204375; NM_001364458; NM_024563; XM_011514050; NM_001204376 |
| FOXE1 | 2304 | NM_004473 |
| ALS2CL | 259173 | XR_427263; XR_940409; XR_940410; NR_033815; XR_001740091; XR_001740094; XR_001740095; XM_011533572; XR_001740090; XR_940406; XR_940407; XR_940408; XR_940412; NM_182774; NM_182775; NR_135622; XR_001740092; XR_001740097; XR_002959507; NM_001190707; XM_005265025; XM_006713093; XR_001740093; NM_147129; XM_006713094; XM_006713091; XR_001740096; XR_940405 |
| ACADL | 33 | NM_001608; XM_005246517; XM_017003955 |
| ARSE | 415 | XM_017029526; NM_001369079; NM_001369080; XM_005274521; XM_011545521; NM_000047; XM_005274519; NM_001282628; NM_001282631 |
| AQP5 | 362 | NM_001651; XM_005268838 |
| HOXA11 | 3207 | NM_005523 |
| CYP2W1 | 54905 | NM_017781; XM_011515440; XM_011515441 |
| KBTBD11 | 9920 | XM_017014115; XM_011534772; XM_017014117; XM_017014114; XM_017014116; XM_011534771; NM_014867 |
| TCF21 | 6943 | NM_003206; NM_198392 |
| ADAMTSL3 | 57188 | NM_207517; XM_024450000; XR_931873; XM_017022435; XM_011521822; XM_011521823; XM_017022434; NM_001301110; XM_011521825; XM_011521824 |
| GLP2R | 9340 | XM_011524077; NM_004246; XM_017025340; XM_005256861; XM_017025339; XM_017025341 |
| CFD | 1675 | NM_001317335; NM_001928 |
| FAM107A | 11170 | NM_001076778; NM_007177; NM_001282713; NM_001282714 |
| TPPP | 11076 | XM_024454346; XM_005248237; XM_017008993; NM_007030 |
| FOXF1 | 2294 | NM_001451 |
| HSPB6 | 126393 | NM_144617 |
| P2RX1 | 5023 | XM_006721529; XM_011523898; XR_934029; NM_002558; XM_011523896; XM_011523897; XM_011523899; XM_011523900; XR_934030 |
| TBX5 | 6910 | NM_181486; NM_080717; NM_000192; XM_017019912; NM_080718 |
| SGCD | 6444 | NM_000337; NM_172244; XM_005265967; XM_011534621; XM_017009723; XM_005265966; XM_017009724; NM_001128209 |
| ESM1 | 11082 | NM_001135604; NM_007036 |
| DPT | 1805 | NM_001937 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| SPP1 | 6696 | NM_001251829; NM_001040060; NM_001251830; NM_000582; NM_001040058 |
| CMA1 | 1215 | NM_001836; NM_001308083 |
| FBN2 | 2201 | NM_001999; XM_017009228 |
| MSI1 | 4440 | XM_011538362; XM_011538361; XM_011538366; XM_011538365; XM_011538370; NM_002442; XM_011538364; XM_011538371; XM_006719403; XM_006719404; XM_011538363; XM_011538368 |
| TERT | 7015 | NR_149162; NM_198255; NM_198253; NR_149163; NM_001193376; NM_198254 |
| VGF | 7425 | NM_003378; XM_011516549; XM_005250561 |
| CEDN9 | 9080 | NM_020982 |
| FOER1 | 2348 | NM_000802; NM_016729; NM_016730; NM_016725; NM_016724 |
| Melanoma | | |
| PAX3 | 5077 | NM_181457; NM_000438; NM_181459; NM_181460; NM_001127366; NM_013942; NM_181461; NM_181458 |
| IRF4 | 3662 | NM_001195286; NR_046000; NR_036585; XM_006715090; NM_002460 |
| TYR | 7299 | XM_011542970; NM_000372 |
| GAPDHS | 26330 | NM_014364 |
| PMEL | 6490 | NM_001200054; NM_001200053; NM_001320121; NM_001384361; NM_001320122; NM_006928 |
| TYRP1 | 7306 | NM_000550; XR_001746372 |
| ALX1 | 8092 | XM_011538782; NM_006982 |
| MLANA | 2315 | NM_005511 |
| CDH19 | 28513 | XM_011525931.3; XM_017025711.2; XM_011525932.1 |
| SOX10 | 6663 | NM_006941 |
| MIA | 8190 | NM_006533; NM_001202553 |
| PLP1 | 5354 | NM_001128834; NM_000533; NM_001305004; NM_199478 |
| SLC6A15 | 55117 | XM_011538525; NM_018057; NM_001146335; NM_182767 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |

TABLE 3-continued

Genes associated with molecular categories.

| Gene | NCBI Gene ID | NCBI Accession Number(s) |
|---|---|---|
| KRT2 | 3849 | NM_000423 |
| MFSD12 | 126321 | XM_017026288; XM_011527684; NM_021731; NM_174983; NM_001287529; XM_005259490; NM_001042680; XM_006722647 |
| APOD | 347 | NM_001647 |
| KCNK1 | 3775 | NM_002245; XM_011544184 |
| EFHD1 | 80303 | NM_001243252; NM_001308395; NM_025202 |
| CRCT1 | 54544 | NM_019060; XM_011509656 |
| KRT8 | 390601, 149501, 3856 | NM_001256293; NM_002273 |
| GPM6B | 2824 | NM_001001996; XM_017029432; NM_001318729; NM_005278; NM_001001995; XM_005274489; XM_011545497; NM_001001994 |
| CNTNAP2 | 26047 | XM_017011950; NM_014141 |
| STEAP1B | 256227 | NM_207342; NM_001382447; NM_001164460 |
| RGN | 9104 | XM_024452477; XM_006724568; XM_017029954; NM_004683; NM_001282848; NM_152869; NM_001282849; XM_006724567 |
| FA2H | 79152 | XM_011523319; XM_011523317; NM_024306 |
| TRPV2 | 51393 | XM_011523922; XM_017024730; XM_011523925; XM_017024732; XM_005256677; XM_017024731; XM_006721541; XM_005256678; XM_011523923; NM_016113; XM_005256676; XM_006721543 |
| CLDN7 | 1366 | NM_001307; NM_001185022; NM_001185023 |
| SPINT2 | 10653 | NM_001166103; NM_021102 |
| CD24 | 100133941 | NM_001291739; NR_117090; NR_117089; NM_001291738; NM_001291737; NM_013230; XM_024446293; NM_001359084 |
| HNF1B | 6928 | XM_011525161; NM_001165923; NM_001304286; XM_011525163; NM_000458; XM_011525162; NM_006481; XM_011525164; XM_011525160 |
| SUSD4 | 55061 | XM_011509687; XM_017001584; XM_017001586; XM_017001587; XM_024447937; XM_024447940; XM_005273169; XM_017001588; XM_017001585; XM_024447936; NM_017982; XM_005273172; XM_006711408; XM_011509685; XM_017001583; XM_017001589; NM_001037175 |
| ST8SIA3 | 51046 | NM_015879 |
| GABRE | 2564 | XM_024452360; NM_021990; NM_021984; XM_011531140; XM_017029388; XM_017029389; NM_004961; NM_021987; XM_017029387 |
| PHACTR1 | 221692 | XM_017010452; XM_017010454; XM_017010458; XM_017010465; NM_001322311; NM_001374582; NM_001374583; NM_001374584; NM_001322309; XM_005248934; XM_017010460; NM_001322308; NM_001374581; XM_017010459; XM_017010464; NM_001242648; NM_001322314; XM_017010462; NM_001322312; XM_017010456; XM_017010457; XM_017010466; NM_030948; XM_017010455; NM_001322310; XM_017010469; NM_001322313 |
| ASS1 | 445 | XM_017014729; XM_005272200; XM_011518705; NM_000050; NM_054012 |
| CDS1 | 1040 | XM_017007649; NM_001263; XM_017007650; XM_017007651; XM_005262687; XM_017007648 |
| PLEKHG6 | 55200 | NM_018173; XM_017019555; NM_001384602; NM_001384603; XM_006718985; NM_001384604; NR_169277; XM_011520967; NM_001144857; NM_001384599; NR_169278; NM_001144856; NM_001384598; NM_001384600; NM_001384601 |
| CACNG4 | 27092 | NM_014405 |
| CYTL1 | 54360 | NM_018659; XM_017008299 |
| PITX1 | 5307 | NM_002653 |
| HOXD13 | 3239 | XM_011511068; NM_000523; XM_011511069 |
| CNIH3 | 149111 | NR_136288; NR_136294; NR_136297; NM_152495; NR_136292; NM_001322305; NM_001322303; NR_136293; NR_136296; NR_136295; NR_136287; NM_001322304; NR_136290; NR_136291; NM_001322302; NR_136289 |
| CFB | 629 | NM_001710 |
| MYH7 | 4625 | XM_017021340; NM_000257 |
| CLU | 1191 | NM_001831; NR_045494; NR_038335 |
| SCG5 | 6447 | NM_001144757; NM_001394278; NM_001394279; NM_003020 |
| SH3GL3 | 6457 | XR_001751374; NM_001324184; NM_001324186; XM_017022486; XR_931878; XR_001751372; NR_136712; XR_931880; XR_931882; NM_001301109; NM_001324185; NR_125370; NR_136714; XM_011521892; XR_001751375; XR_931879; NM_001301108; NM_001324183; NM_003027; NR_136713; XM_011521889; XM_011521891; XM_024450017; XR_001751373; XR_002957669; NM_001324182; NM_001324187; NR_136711 |
| RBM47 | 54502 | XM_005248108; XM_017008307; XM_024454098; NM_001371113; XM_005248103; XM_017008306; XM_017008309; XM_017008310; NM_001098634; NM_019027; XM_011513707; XM_005248109; XM_017008304; XM_017008308; NM_001371114; XM_011513708 |
| FUT6 | 2528 | XM_011527875; NM_000150; NM_001381956; NM_001369504; NM_001381957; NM_001381958; NM_001369502; NM_001381959; NM_001369505; NM_001381955; XM_011527872; NM_001040701 |

TABLE 3-continued

| Gene | NCBI Gene ID | NCBI Accession Number(s) |
|---|---|---|
| | | Genes associated with molecular categories. |
| FGFR2 | 2263 | XM_017015924; NM_001144919; XM_006717708; XM_017015925; NM_001144915; NM_001144917; NM_022975; NM_023028; XM_024447890; NM_000141; NM_001144913; NM_001320654; NM_022970; NR_073009; NM_022971; NM_022973; NM_023030; XM_006717710; XM_024447887; XM_024447888; NM_001320658; NM_022976; XM_017015920; NM_001144918; NM_022974; NM_023031; XM_024447889; XM_024447891; XM_024447892; NM_023029; XM_017015921; NM_001144914; NM_001144916; NM_022972 |
| DLX2 | 1746 | NM_004405 |
| LAD1 | 3898 | NM_005558 |
| SPP1 | 6696 | NM_001251829; NM_001040060; NM_001251830; NM_000582; NM_001040058 |
| ADH1B | 125 | NM_001286650; NM_000668 |
| MYL2 | 4633 | NM_000432 |
| ZBTB16 | 7704 | XR_001747955; NM_001354751; XM_017018259; NM_006006; NM_001354752; XM_005271658; XM_024448681; NM_001018011; NM_001354750 |
| CKM | 1158 | NM_001824 |
| FCGR1A | 2209 | NM_001378804; NM_001378805; NM_001378807; NM_001378810; NR_166122; NR_166123; NM_001378809; NM_001378811; NM_001378808; NR_166121; NM_000566; NM_001378806 |
| CCL5 | 6352 | NM_001278736; NM_002985 |
| DBNDD1 | 79007 | NM_001288709; NM_001288708; NM_001371581; NM_001042610; NM_024043 |
| SDS | 10993 | NM_006843 |
| CXCR3 | 2833 | XM_017029435; XM_017029436; NM_001504; NM_001142797; XM_005262256; XM_005262257 |
| MMP27 | 64066 | XM_011542950; XM_017018120; XM_011542948; NM_022122; XM_011542949 |
| TREM2 | 54209 | NM_001271821; NM_018965 |
| CCR5 | 1234 | NM_001100168; NM_001394783; NM_000579 |
| C1QA | 712 | NM_015991; NM_001347465; NM_001347466 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ONECUT2 | 9480 | NM_004852 |
| FAM155B | 27112 | XM_011530908; XM_011530909; NM_015686 |
| DKK1 | 22943 | NM_012242 |
| LOR | 4014 | NM_000427; XM_024447049 |
| | | Liver_Neoplasm |
| APCS | 325 | NM_001639 |
| ITIH2 | 3698 | NM_002216 |
| CRP | 1401 | NM_000567; NM_001329058; NM_001382703; NM_001329057 |
| CPB2 | 1361 | XM_017020393; NM_016413; NM_001872; NM_001278541 |
| ITIH1 | 3697 | NM_001166436; NM_002215; NM_001166434; NM_001166435 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| APOC3 | 345 | NM_000040 |
| GC | 2638 | XM_006714177; NM_001204306; NM_001204307; NM_000583 |
| CYP2C8 | 1558 | NM_001198854; NM_001198855; NM_030878; NM_000770; NM_001198853 |
| C8G | 733 | NM_000606; XR_245338 |
| APOA2 | 336 | NM_001643 |
| ALB | 213 | NM_000477 |
| ART4 | 420 | NM_021071; NM_001354646 |
| AGT | 183 | NM_000029; NM_001384479; NM_001382817 |
| PROZ | 8858 | NM_003891; XR_001749709; XR_001749708; XM_017020812; XR_001749707; NM_001256134; XM_017020813 |
| GRIK3 | 2899 | NM_000831 |
| CRABP1 | 1381 | NM_004378 |
| DRD2 | 1813 | XM_017017296; NM_016574; NM_000795 |
| CYP21A2 | 1589 | NM_000500; NM_001128590; XM_024452555; NM_001368143; NM_001368144 |
| DBH | 1621 | NM_000787 |
| L1CAM | 3897 | NM_024003; NM_001278116; NM_001143963; NM_000425 |
| KLK8 | 11202 | NM_007196; NM_144505; NR_104008; NM_144507; NM_144506; NM_001281431 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| SFRP5 | 6425 | NM_003015 |
| GATA4 | 2626 | NM_001308093; NM_002052; NM_001308094; NM_001374273; NM_001374274 |
| MAB21L2 | 10586 | NM_006439 |
| GRIK5 | 2901 | XM_011526870; XM_011526868; XM_011526865; XM_011526867; XM_011526869; XM_011526862; XM_011526871; XM_017026713; NM_002088; XR_935810; NM_001301030 |
| HOXA7 | 3204 | NM_006896 |
| GLB1L2 | 89944 | NM_001370460; NM_001370463; NM_001370461; NM_001370462; NM_138342 |
| PCSK2 | 5126 | NM_002594; NM_001201529; NM_001201528 |
| TERT | 7015 | NR_149162; NM_198255; NM_198253; NR_149163; NM_001193376; NM_198254 |
| PLP1 | 5354 | NM_001128834; NM_000533; NM_001305004; NM_199478 |

TABLE 3-continued

| Genes associated with molecular categories. | | |
|---|---|---|
| Gene | NCBI Gene ID | NCBI Accession Number(s) |
| CXCL14 | 9547 | NM_004887 |
| KRT4 | 3851 | NM_002272 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SLC5A1 | 6523 | NM_000343; XM_011530331; NM_001256314 |
| GPRC5A | 9052 | NM_003979 |
| GPM6B | 2824 | NM_001001996; XM_017029432; NM_001318729; NM_005278; NM_001001995; XM_005274489; XM_011545497; NM_001001994 |
| NNAT | 4826 | NM_001322802; NM_181689; NM_005386 |
| BDH1 | 622 | XM_005269355; XM_017007012; XM_017007013; NM_004051; XM_017007015; XM_017007007; XM_011513067; XM_017007008; XM_017007009; XR_001740229; NM_203314; XM_017007010; NM_203315; XM_005269352; XM_017007011 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| COLEC10 | 10584 | XM_005250756; NM_006438; NM_001324095 |
| GABRD | 2563 | XM_011541194; XM_017000936; NM_000815 |
| GDF2 | 2658 | NM_016204 |
| COL15A1 | 1306 | XM_011518214; NM_001855 |
| S100A12 | 6283 | NM_005621 |
| MDK | 4192 | NM_001012334; XM_011520116; XM_017017764; NM_001270550; NM_001270551; NM_001012333; NM_001270552; NM_002391; NR_073039 |
| PTTG1 | 9232 | XM_024446260; NM_001282382; NM_001282383; NM_004219 |
| ESMI | 11082 | NM_001135604; NM_007036 |
| DEPDC1 | 55635 | NM_001114120; NM_017779 |
| THBS4 | 7060 | XR_002956176; XM_017009798; NM_001306214; NM_003248; NM_001306213; XM_017009799; NM_001306212 |
| HOXD9 | 3235 | NM_014213 |
| OLFML2B | 25903 | NM_001297713; XM_017000967; NM_001347700; NM_015441; XM_011509398 |
| MMP11 | 4320 | NM_005940; NR_133013 |
| PRSS1 | 5644 | NR_172951; XM_011516411; NR_172947; NM_002769; NR_172948; NR_172949; NR_172950 |
| C1QTNF3 | 114899 | NR_146599; NM_181435; NM_030945 |
| Thyroid_Neoplasm | | |
| TG | 7038 | XM_006716622; XM_017013800; XM_017013793; XM_017013795; XM_017013798; XM_017013796; XM_017013797; XM_017013794; XM_005251038; XM_005251040; NM_003235; XM_017013799; XM_005251042 |
| DCSTAMP | 81501 | XM_024447289; NM_030788; XM_024447290; NM_001257317; XM_011517324; XM_024447288; XM_011517321 |
| DAPK2 | 23604 | XM_017022049; XM_017022051; NM_001384998; NM_001395289; NM_001395290; NM_001395293; XM_011521413; NM_001384999; NM_001395284; NM_014326; XM_017022043; NM_001395288; NM_001395291; NR_169522; NR_172521; XM_017022046; NM_001384997; NM_001385000; NM_001395286; NM_001395287; XM_011521421; XM_017022044; XM_017022047; XM_017022052; NM_001395285; NM_001395292; XM_017022048; XM_017022050; NM_001395282; NR_169524; XM_011521414; XM_011521415; XM_017022045; NM_001395279; NM_001395283; NR_169523; NM_001363730; NM_001395281 |
| SLC26A4 | 5172 | XM_017012318; XM_005250425; NM_000441; XM_006716025 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| TSHR | 7253 | XM_011537119; XM_005268039; XM_005268037; NM_000369; NM_001142626; XM_006720245; NM_001018036 |
| KCNJ16 | 3773 | XM_006721885; NM_170742; NM_001291625; NM_018658; XM_017024609; NM_001291622; NM_001291623; XM_017024610; NM_001270422; NM_170741; XM_005257337; XM_006721887; XM_011524781; NM_001291624; XM_006721886 |
| NKX2-1 | 7080 | NM_001079668; NM_003317 |
| FOXE1 | 2304 | NM_004473 |
| CLDN16 | 10686 | NM_006580; NM_001378492; NM_001378493 |
| GABRB2 | 2561 | NM_000813; NM_021911; NM_001371727 |
| MATN1 | 4146 | NM_002379 |
| INPP5J | 27124 | NM_001284289; XM_017028772; NM_001284288; NM_001284285; NM_014422; NM_001284286; NM_001284287; XM_011530143; NM_001002837 |
| TOX3 | 27324 | NM_001080430; XM_017023142; NM_001146188; XM_005255892; XM_011523002; XM_024450230 |
| TRPC5 | 7224 | XM_017029774; NM_012471 |
| HHEX | 3087 | NM_002729 |
| PAX8 | 7849 | NM_013992; NM_013953; NM_013952; NM_003466; NM_013951 |
| FOXD3 | 27022 | NM_012183 |

TABLE 3-continued

Genes associated with molecular categories.

| Gene | NCBI Gene ID | NCBI Accession Number(s) |
|---|---|---|
| COL4A3 | 1285 | XM_017003295; XM_005246280; XM_006712245; XM_005246277; XR_241280; XM_011510556; NM_000091; NM_031363; NM_031364; NM_031365; XM_011510555; XR_001738601; NM_031362; NM_031366 |
| S100A5 | 6276 | XM_017002031; NM_001394233; NM_001394234; XM_017002032; NM_001394232; NM_002962; XM_017002029 |
| GFRA3 | 2676 | NM_001496 |
| NELL1 | 4745 | NM_001288713; NM_006157; NM_201551; NM_001288714 |
| DUSP9 | 1852 | XM_011531123; NM_001395; NM_001318503; XM_011531124 |
| AZGP1 | 563 | NM_001185 |
| BMP8A | 353500 | XM_017001198; XM_006710616; XM_011541381; XM_011541382; XR_946642; XR_946640; XR_946641; NM_181809 |
| LECT1 | 11061 | XM_011534898; XM_011534899; NM_001011705; NM_007015; XM_011534900; XM_011534897 |
| DIO2 | 1734 | NM_001366496; NM_000793; NM_001324462; NR_158991; NM_001242503; NM_013989; NR_158990; NM_001007023 |
| LRRC2 | 79442 | XM_011534110; XM_017007177; XR_001740264; NM_024750; NM_024512 |
| HOXA7 | 3204 | NM_006896 |
| HOXA10 | 3206 | NR_037939; NM_153715; NM_018951 |
| SLC5A5 | 6528 | XM_011528194; XM_011528193; NM_000453; XM_017027158; XM_011528192 |
| AADAC | 13 | NM_001086; XM_005247104 |
| KCNJ15 | 3772 | XM_017028344; XM_017028343; XM_011529561; NM_170736; NM_170737; XM_005260975; NM_001276438; NM_001276439; NM_002243; XM_006724002; XM_011529560; XM_017028345; NM_001276435; NM_001276436; NM_001276437 |
| CACNA1I | 8911 | NM_021096; XM_017029035; XM_017029036; XM_017029037; NM_001003406 |
| GPC3 | 2719 | NM_004484; XM_017029413; NM_001164618; NM_001164617; NM_001164619 |
| KLHDC8A | 55220 | NM_001271863; NM_001271865; XM_024448121; NM_018203; NM_001271864 |
| SSX1 | 6756 | NM_001278691; NM_005635 |
| SYT12 | 91683 | XM_011545346; XM_011545347; NM_177963; XM_017018547; NM_001177880; NM_001318775; XM_017018548; XM_006718737; XM_024448766; NM_001318773 |
| BMPR1B | 658 | XM_017008558; NM_001203; NM_001256793; XM_011532201; NM_001256794; NM_001256792; XM_017008559; XM_017008560; XM_017008561 |
| MYL2 | 4633 | NM_000432 |
| CLIC3 | 9022 | XM_017015282; NM_004669; XM_017015281 |
| SPINK1 | 6690 | NM_003122; NM_001379610; NM_001354966 |
| S100A1 | 6271 | NM_006271 |
| BIRC5 | 332 | NM_001168; NM_001012271; NM_001012270 |
| UBE2C | 11065 | NM_001281742; NM_001281741; NM_181802; NM_181803; NR_104036; NR_104037; NM_007019; NM_181800; NM_181801; NM_181799 |
| AMN | 81693 | XM_024449714; XM_011537203; NM_030943; XM_011537202 |
| CBLN1 | 869 | NM_004352 |
| PBK | 55872 | NM_018492; NM_001278945; NM_001363040 |
| ALK | 238 | NM_004304; NM_001353765; XM_024452779; XR_001738688; XM_024452778 |
| CYP2J2 | 1573 | NR_134982; NR_134981; NM_000775 |
| TSPAN8 | 7103 | NM_001369760; NM_004616; XM_006719583 |
| CHGA | 1113 | NM_001301690; NM_001275; XM_011536370 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| SCD | 6319 | NM_005063 |
| SCN4A | 6329 | NM_000334 |
| TF | 7018 | NM_001063; NM_001354703; NM_001354704 |
| TPX2 | 22974 | XM_011528697; XM_011528699; NM_012112; XM_011528700 |
| TFAP2A | 7020 | NM_001032280; XM_006715175; NM_001042425; XM_017011232; XM_011514833; NM_001372066; NM_003220 |
| ACADL | 33 | NM_001608; XM_005246517; XM_017003955 |
| IQCA1 | 79781 | XM_017004960; NM_024726; NM_001270585; XM_011511865; XM_011511866; XM_011511864; NM_001270584; NR_073043 |
| CENPF | 1063 | XM_017000086; NM_016343; XM_011509082 |
| EYA1 | 2138 | XM_017013204; XM_017013211; XM_017013212; NM_001370334; XM_011517484; XM_017013203; NM_001288574; XM_017013202; NM_000503; XM_017013207; XM_017013208; XM_017013213; NM_001370336; NM_172059; NM_172060; XM_017013205; NM_172058; NM_001288575; NM_001370333; NM_001370335; XM_011517483 |
| FSCN2 | 25794 | NM_012418; XM_011524587; XM_011524590; XR_001752466; NM_001077182 |
| SEMA3C | 10512 | NM_006379; NM_001350121; NM_001350120 |
| MYH7 | 4625 | XM_017021340; NM_000257 |
| TRIP13 | 9319 | NM_004237; XM_011514163 |
| FGFR4 | 2264 | NM_213647; NM_022963; NM_002011; NM_001291980; NM_001354984 |
| CEP55 | 55165 | XM_017016373; XM_011539920; NM_001127182; NM_018131; XM_017016372; XM_011539919; XM_011539918 |
| TFF1 | 7031 | NM_003225 |
| DLGAP5 | 9787 | XM_017021840; NM_001146015; NM_014750 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |

TABLE 3-continued

| Gene | NCBI Gene ID | NCBI Accession Number(s) |
|---|---|---|
| Genes associated with molecular categories. | | |
| MSC | 9242 | NM_005098 |
| SMR3B | 10879 | NM_006685 |
| PRDM16 | 63976 | NM_199454; NM_022114 |
| HOXB3 | 3213 | XM_006721854; NM_001384749; XM_024450737; XM_011524719; XM_011524720; XM_011524726; NM_001330323; XM_011524708; XM_011524721; NM_002146; XM_011524710; NM_001384747; XM_017024560; NM_001330322; NM_001384750 |
| NNAT | 4826 | NM_001322802; NM_181689; NM_005386 |
| TGFA | 7039 | NM_001308159; NM_001308158; NM_001099691; NM_003236 |
| PID1 | 55022 | NM_001330156; XM_017004404; NM_001330158; NM_017933; NM_001330157; NM_001100818 |
| KIAA1456 | 57604 | XM_005273591; XM_024447215; XM_005273584; XM_005273586; XM_011544600; XM_024447217; XM_005273588; XM_011544598; XM_024447214; XM_005273590; XM_017013710; NM_001099677; XM_005273585; XM_017013714; XM_011544596; XM_011544597; XM_011544601; XM_017013705; XM_024447216; XM_017013706; XM_024447218; XM_024447219; NM_020844 |
| PAPSS2 | 9060 | NM_001015880; NM_004670 |
| MMRN1 | 22915 | XM_005262856; NM_001371403; NM_007351 |
| LYVE1 | 10894 | NM_006691 |
| GALE | 2582 | NM_000403; NM_001127621; NM_001008216 |
| CFD | 1675 | NM_001317335; NM_001928 |
| CDH3 | 1001 | NM_001793; XM_011522800; NM_001317195; NM_001317196 |
| TNFRSF10C | 8794 | NM_003841 |
| CDKN2B | 1030 | NM_078487; NM_004936 |
| BBC3 | 27113 | XM_006723141; XM_011526722; NM_001127241; NM_001127242; NM_001127240; NM_014417 |
| IPCEF1 | 26034 | NM_001394801; NM_001130700; NM_015553; NM_001130699; NM_001394799; NM_001394800; NM_001394802 |
| CDH6 | 1004 | NM_004932; NM_001362435; XM_017008910; XM_011513921; XR_001741972 |
| KCNJ2 | 3759 | NM_000891 |
| LAMB3 | 3914 | XM_005273124; NM_001127641; XM_017001272; NM_000228; NM_001017402 |
| E2F1 | 1869 | NM_005225 |
| DUSP4 | 1846 | NM_001394; NM_057158; XM_011544428 |
| FMO2 | 2327 | NM_001460; NR_160266; XR_921761; NM_001365900; XR_001737072; NM_001301347 |
| GDF15 | 9518 | XM_024451789; NM_004864 |
| CCL21 | 6366 | NM_002989 |
| PLCH1 | 23007 | XM_011512561; XM_011512565; XM_011512566; NM_001349250; XM_011512567; XM_017005925; XM_005247239; XM_005247238; XM_011512560; XM_017005926; NM_001130960; NM_001349252; NM_014996; XM_017005927; NM_001130961; NM_001349251; XM_011512562; XM_017005923 |
| MYOC | 4653 | NM_000261 |
| GABRD | 2563 | XM_011541194; XM_017000936; NM_000815 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SLC12A5 | 57468 | NM_020708; NM_001134771 |
| VTCN1 | 79679 | NM_001253849; NM_024626; NR_045604; XM_017002335; NM_001253850; NR_045603; XM_011542143 |
| OLAH | 55301 | XM_024448060; XM_017016376; NM_018324; NM_001039702 |
| MMP11 | 4320 | NM_005940; NR_133013 |
| AIM1L | 55057 | NM_017977; XM_011541672; XM_011541673; XR_001737260; NM_001039775; XR_946681; XM_005245918 |
| CDH2 | 1000 | XM_011525788; NM_001308176; XM_017025514; NM_001792 |
| HAPLN1 | 1404 | XM_017009052; XM_017009051; NM_001884; XM_017009054; XM_017009053; XM_011543168 |
| DES | 1674 | NM_001927; NM_001382708; NM_001382710; NM_001382713; NM_001382709; NM_001382711; NM_001382712 |
| ADRA2C | 152 | NM_000683 |
| CD19 | 930 | NM_001178098; NM_001385732; NM_001770; XR_950871; XM_006721103; NR_169755; XM_011545981 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| Glioma | | |
| AQP4 | 361 | NM_001317387; NM_001364287; NM_001364286; NM_001317384; XM_011525942; NM_001650; NM_001364289; NM_004028 |

TABLE 3-continued

| Genes associated with molecular categories. | | |
|---|---|---|
| Gene | NCBI Gene ID | NCBI Accession Number(s) |
| OLIG2 | 10215 | XM_005260908; NM_005806 |
| GFAP | 2670 | XM_024450691; XM_024450690; NM_001131019; XM_024450692; XM_024450693; NM_001242376; NM_002055; NM_001363846 |
| HAPLN2 | 60484 | XM_024448828; XM_005245415; XM_011509853; XM_017002020; XM_017002021; NM_021817 |
| GPR37L1 | 9283 | NM_004767; XM_011510158 |
| PMP2 | 5375 | NM_002677; NM_001348381 |
| GPM6A | 2823 | NM_201592; NM_001261447; NM_001388091; NM_001261448; NM_005277; NR_048571; NM_001388090; NM_201591 |
| TIMP4 | 7079 | NM_003256 |
| SLC1A3 | 6507 | XM_024446182; XM_011514084; NM_004172; NM_001289940; NM_001289939; NM_001166695; XM_005248342; XM_024446181; NM_001166696 |
| MLC1 | 23209 | XR_001755180; NM_001376472; NM_001376478; NR_164811; NR_164812; NM_001376473; NM_001376477; NM_139202; NM_001376476; NM_001376479; NM_001376484; NM_015166; NR_164813; NM_001376474; NM_001376481; XM_011530678; NM_001376480; NM_001376483; NM_001376475; NM_001376482 |
| NCAN | 1463 | NM_004386 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| CDH20 | 28316 | XR_001753187; NM_031891; XR_001753186; XM_024451165 |
| PTPRZ1 | 5803 | NM_002851; NM_001206838; NM_001369396; NM_001369395; NM_001206839 |
| MT3 | 4504 | NM_005954 |
| FOXG1 | 2290 | NM_005249 |
| DLL3 | 10683 | NM_016941; NM_203486 |
| KRT8 | 390601, 149501, 3856 | NM_001256293; NM_002273 |
| PERP | 64065 | XM_024446520; NM_022121 |
| TACSTD2 | 4070 | NM_002353 |
| KRT7 | 3855 | XM_017019294; XR_001748700; NM_005556; XM_011538325; XR_001748699 |
| TES | 26136 | NM_015641; NM_152829; XM_005250258 |
| EVPL | 2125 | NM_001988; NM_001320747 |
| KCNK5 | 8645 | XM_006715235; XM_005249456; NM_003740 |
| EPCAM | 4072 | NM_002354 |
| RIPK4 | 54101 | NM_020639 |
| SOX21 | 11166 | NM_007084 |
| DSP | 1832 | NM_001008844; NM_004415; NM_001319034 |
| C2orf54 | 79919 | XM_011511877; NM_001085437; NM_001282921; NM_024861 |
| NEUROD4 | 58158 | NM_021191 |
| CDH1 | 999 | NM_001317186; NM_004360; NM_001317185; NM_001317184 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| CYP2C18 | 1562 | NM_000772; NM_001128925 |
| EPS8L1 | 54869 | NM_133180; NM_139204; XM_011527052; XM_005259020; NM_017729; XM_011527051; XM_011527050 |
| PDLIM1 | 9124 | XM_011540330; NM_020992 |
| SPINK5 | 11005 | XM_011537551; NM_006846; NM_001127698; NM_001127699 |
| TNNC1 | 7134 | NM_003280 |
| CD55 | 1604 | NM_001300904; NM_001114543; NM_001114544; XM_017000467; NM_001114752; NM_001300902; NM_001300903; NM_000574; NR_125349 |
| LLGL2 | 3993 | XM_017024627; XR_002957999; XR_002958003; XM_017024626; XR_002958004; XM_017024629; XM_017024630; XM_017024631; XR_002958005; XR_002958002; NM_001015002; XM_011524802; XM_017024628; XR_002958000; XM_024450747; XR_001752508; NM_001031803; XM_017024625; XR_002958001; NM_004524 |
| ITPR3 | 3710 | XM_017010832; XM_011514577; NM_002224 |
| SPINT2 | 10653 | NM_001166103; NM_021102 |
| ANXA3 | 306 | XR_001741215; NM_005139 |
| HCN2 | 610 | NM_001194 |
| F2R | 2149 | NM_001311313; NM_001992 |
| MYL2 | 4633 | NM_000432 |
| KIFC1 | 3833 | XM_011514585; XM_017010836; NM_002263; XM_011514587; XM_017010837 |
| BIRC5 | 332 | NM_001168; NM_001012271; NM_001012270 |
| NDC80 | 10403 | NM_006101 |
| PBK | 55872 | NM_018492; NM_001278945; NM_001363040 |
| TACC3 | 10460 | XM_005247930; XM_017007653; NM_006342; XM_005247929; XM_011513386 |
| EGFR | 1956 | NM_001346899; NM_201282; NM_201284; NM_001346898; NM_001346900; NM_001346897; NM_201283; NM_001346941; NM_005228 |
| DTL | 51514 | XM_011509614; NM_001286229; NM_001286230; NM_016448 |
| Sarcoma | | |
| RAB11FIP1 | 80223 | NM_001002814; NM_025151; XM_017013869; NM_001002233 |
| LOXL1 | 4016 | XM_017022179; XM_011521555; NM_005576; XR_931824 |
| ZNF385D | 79750 | XM_017007203; NM_024697; XM_017007200; XM_011534124; XM_017007195; XM_017007202; XM_017007193; XM_017007197; XM_011534122; |

TABLE 3-continued

| Genes associated with molecular categories. | | |
|---|---|---|
| Gene | NCBI Gene ID | NCBI Accession Number(s) |
| | | XM_017007191; XM_017007192; XM_017007199; XM_017007201; XM_024453754; XM_011534123; XM_017007194; XM_017007196; XM_017007198 |
| MYL2 | 4633 | NM_000432 |
| AGRN | 375790 | XM_011541429; NM_001305275; NM_001364727; XR_946650; NM_198576; XM_005244749 |
| KCNG1 | 3755 | XM_011528800; XM_011528802; XM_011528803; XM_011528805; NM_172318; NM_002237; XM_011528801; XM_011528804; XM_011528806; XM_006723785 |
| NKX3-2 | 579 | NM_001189 |
| NXPH3 | 11248 | NM_007225 |
| HMX1 | 3166 | NM_018942; NM_001306142 |
| CLDN7 | 1366 | NM_001307; NM_001185022; NM_001185023 |
| TUBB4A | 10382 | NM_001289129; NM_001289131; NM_006087; NM_001289123; NM_001289127; NM_001289130 |
| RAB17 | 64284 | XM_006712689; XM_017004693; NM_022449; XM_017004694; NR_033308 |
| EPCAM | 4072 | NM_002354 |
| GH1 | 2688 | NM_022559; NM_022561; NM_022560; NM_022562; NM_000515 |
| ERBB3 | 2065 | NM_001005915; NM_001982 |
| ELMO3 | 79767 | XM_024450447; NM_024712 |
| SYNC | 81493 | XM_024450011; NM_001161708; XM_024450013; NM_030786; XM_024450012; XM_024450010; XM_024450014 |
| TPD52 | 7163 | NM_005079; NR_105035; NM_001287143; NM_001387779; NR_105037; NR_170694; NM_001025252; NM_001025253; NR_170693; NM_001287140; NR_105034; NM_001387780; NM_001287142; NM_001287144; NM_001387778; NR_105033; NR_105036 |
| S100B | 6285 | NM_006272; XM_017028424 |
| PALMD | 54873 | NM_017734 |
| CYP46A1 | 10858 | NM_006668; XM_005267274; XM_011536365; XM_011536364; XM_017020933 |
| PNPLA2 | 57104 | NM_020376 |
| SERINC2 | 347735 | NM_178865; NM_001199039; NM_018565; NM_001199038; NM_001199037 |
| PRSS12 | 8492 | XM_011532387; NM_003619; XM_005263318 |
| OLR1 | 4973 | NM_002543; NM_001172632; NM_001172633 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| HOOK1 | 51361 | XR_946665; XM_017001424; XM_006710676; XR_246271; XM_011541563; XM_024447520; XM_011541562; NM_015888 |
| GDPD3 | 79153 | NM_024307 |
| EPM2A | 7957 | NM_001368131; XM_017011301; NM_001360057; NM_001360064; NM_001368129; XM_024446550; XM_011536113; NM_001368130; NM_005670; NR_153398; XM_017011302; XM_011536116; NM_001360071; NM_001018041; XM_024446551; NM_001368132 |
| C1orf116 | 79098 | XM_011509973; NM_001083924; XM_005273259; XM_006711530; NM_023938 |
| CCDC68 | 80323 | XM_011526201; XM_017026011; XM_011526198; XM_006722552; NM_001143829; XM_011526199; XM_011526203; XM_011526204; NM_025214; XM_011526200; XM_011526202 |
| VGF | 7425 | NM_003378; XM_011516549; XM_005250561 |
| PLEK2 | 26499 | NM_016445 |
| FBN2 | 2201 | NM_001999; XM_017009228 |
| FGF7 | 2252 | NM_002009 |
| RCN3 | 57333 | NM_020650; XM_024451620 |
| FBXO2 | 26232 | NM_012168 |
| COX7A1 | 1346 | NM_001864 |
| EBF2 | 64641 | NM_022659 |
| ADAMTS2 | 9509 | NM_021599; NM_014244 |
| TAGEN3 | 29114 | NM_001008272; NM_001008273; NM_013259 |
| HAND2 | 9464 | NM_021973 |
| MT3 | 4504 | NM_005954 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; |

TABLE 3-continued

Genes associated with molecular categories.

| Gene | NCBI Gene ID | NCBI Accession Number(s) |
|---|---|---|
| | | NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| GAS1 | 2619 | NM_002048 |
| CDKL2 | 8999 | XR_001741344; XR_001741345; XM_017008811; XM_017008810; XM_006714406; NM_003948; XM_017008809; NM_001330724 |
| SCN4A | 6329 | NM_000334 |
| COL5A1 | 1289 | NM_000093; XM_017014266; XR_001746183; NM_001278074 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| POPDC2 | 64091 | NM_001369919; NM_022135; NM_001308333 |
| TFAP2A | 7020 | NM_001032280; XM_006715175; NM_001042425; XM_017011232; XM_011514833; NM_001372066; NM_003220 |
| EN1 | 2019 | NM_001426 |
| CHRD | 8646 | XM_017007390; NR_130747; NM_177978; XM_017007388; XM_017007391; XM_024453803; XR_001740336; NM_001304472; XM_017007392; XR_001740334; XM_011513254; XR_002959603; NM_001304473; NM_177979; NM_001304474; NM_003741; XM_017007389; XM_017007393; XM_017007394; XR_001740335; XR_001740337 |
| PLS1 | 5357 | NM_001172312; XM_011512901; NM_001145319; XM_006713660; XM_017006626; XM_011512903; XM_017006627; XM_011512900; NM_002670 |
| ELF3 | 1999 | NM_004433; XM_005244942; NM_001114309 |
| DBNDD1 | 79007 | NM_001288709; NM_001288708; NM_001371581; NM_001042610; NM_024043 |
| RAB23 | 51715 | NM_183227; NM_001278666; NM_001278668; NM_016277; NM_001278667; NR_103822 |
| CD24 | 100133941 | NM_001291739; NR_117090; NR_117089; NM_001291738; NM_001291737; NM_013230; XM_024446293; NM_001359084 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| AMPH | 273 | XM_006715689; XM_017011996; XM_006715690; XM_006715691; XM_011515271; XM_017011995; NM_001635; NM_139316 |
| KRT8 | 390601, 149501, 3856 | NM_001256293; NM_002273 |
| HOXA7 | 3204 | NM_006896 |
| CORO2A | 7464 | NM_003389; NM_052820; XM_011518986 |
| RNF43 | 54894 | XM_011524955; XM_011524956; NM_017763; NM_001305544; XM_017024800; NM_001305545 |
| PER1 | 5187 | XM_005256689; XM_005256690; XM_024450803; NM_002616 |
| SHOX2 | 6474 | XM_006713727; NM_001163678; XM_017007055; NM_006884; XM_006713728; XM_017007053; NM_003030; XM_017007054 |
| MYRF | 745 | NM_013279; XM_005274222; XM_005274224; XM_005274226; XM_005274228; XM_005274223; XM_005274225; XM_005274227; XM_011545234; XM_024448677; NM_001127392 |
| GPR1 | 2825 | NM_001098199; NM_001261452; NM_001261454; NM_005279; XM_005246471; NM_001261455; NM_001389445; NM_001261453 |
| CIDEC | 63924 | NM_001321142; NM_001199552; NM_001378491; NM_001199623; NM_001199551; NM_001321144; NM_022094; NM_001321143 |
| APOD | 347 | NM_001647 |
| KRT2 | 3849 | NM_000423 |
| HOXD9 | 3235 | NM_014213 |
| KCNB2 | 9312 | XM_017013981; XR_001745620; XR_001745621; NM_004770; XM_017013982 |
| FABP6 | 2172 | NM_001130958; NM_001040442; NM_001445 |
| CCNB1 | 891 | NM_031966 |
| DSP | 1832 | NM_001008844; NM_004415; NM_001319034 |
| KRT5 | 3852 | NM_000424 |
| LGI2 | 55203 | XM_011513850; NM_018176; XM_017008356 |
| CKM | 1158 | NM_001824 |
| ITGB4 | 3691 | XM_005257311; XM_006721866; XM_006721870; NM_000213; NM_001005619; NM_001005731; XM_005257309; XM_011524752; XM_006721867; XM_011524751; NM_001321123; XM_006721868 |

TABLE 3-continued

| Gene | NCBI Gene ID | NCBI Accession Number(s) |
|---|---|---|
| Genes associated with molecular categories. | | |
| AP1M2 | 10053 | NM_001300887; XM_024451304; NM_005498; XM_024451303 |
| QPRT | 23475 | XM_005255223; NR_134536; NM_001318250; NM_001318249; NM_014298; XM_017023101 |
| FOXD1 | 2297 | NM_004472 |
| NPPA | 4878 | NM_006172 |
| DDR2 | 4921 | NM_001014796; XM_011509587; XM_011509588; NM_001354982; NM_006182; NM_001354983 |
| PFKFB1 | 5207 | NM_001271804; XM_017029578; XM_017029576; NM_002625; NR_073450; XM_024452389; XM_017029577; NM_001271805 |
| BNC2 | 54796 | NM_001317939; NM_017637; NM_001317940 |
| PCOLCE | 5118 | XM_024446785; NM_002593 |
| GIPC2 | 54810 | NM_017655; NM_001304725 |
| FZD2 | 2535 | NM_001466 |
| COL1A2 | 1278 | NM_000089 |
| FST | 10468 | XM_005248403; XM_011543099; XM_005248400; XM_017008955; NM_013409; XM_005248401; XM_005248402; XM_017008954; XM_024454326; NM_006350 |
| BIK | 638 | NM_001197 |
| C1QL1 | 10882 | NM_006688 |
| ZWINT | 11130 | XR_428692; NM_007057; NM_001005413; XM_017015605; XM_024447784; NM_032997; NM_001005414 |
| MYOC | 4653 | NM_000261 |
| GABRQ | 55879 | NM_018558; XM_011531184 |
| SCN5A | 6331 | NM_001160160; NM_001099405; NM_001354701; XM_011533991; XM_017007017; NM_001160161; NM_198056; NM_000335; NM_001099404 |
| DTL | 51514 | XM_011509614; NM_001286229; NM_001286230; NM_016448 |
| Neuroendocrine | | |
| CA7 | 766 | NM_001365337; XM_011523312; NM_001014435; NM_005182 |
| TGM3 | 7053 | NM_003245 |
| HLA-G | 3135 | XM_017010817; NM_001384280; XM_017010818; NM_002127; XM_024446420; NM_001363567; NM_001384290 |
| MYL2 | 4633 | NM_000432 |
| CCNB1 | 891 | NM_031966 |
| UPK3A | 7380 | NM_006953; NM_001167574 |
| LYVE1 | 10894 | NM_006691 |
| DES | 1674 | NM_001927; NM_001382708; NM_001382710; NM_001382713; NM_001382709; NM_001382711; NM_001382712 |
| PLA2G1B | 5319 | NM_000928 |
| DBNDD1 | 79007 | NM_001288709; NM_001288708; NM_001371581; NM_001042610; NM_024043 |
| MET | 4233 | NM_001324402; NM_001324401; XM_006715990; NM_001127500; XM_011516223; NM_000245; XR_001744772; |
| ESMI | 11082 | NM_001135604; NM_007036 |
| COL10A1 | 1300 | XM_011535432; NM_000493; XM_011535433; XM_017010248; XM_006715333 |
| KRT2 | 3849 | NM_000423 |
| HRASLS2 | 54979 | NM_017878; XM_011545120 |
| DGKI | 9162 | NM_004717; NM_001321708; XM_017012788; NM_001321710; NM_001388092; NM_001321709 |
| SLC18A1 | 6570 | XM_011544626; NM_003053; XM_011544625; NM_001142325; NM_001135691; NM_001142324 |
| MMP11 | 4320 | NM_005940; NR_133013 |
| FIGF | 2277 | NM_004469 |
| SLC16A7 | 9194 | XM_011538990; XM_011538992; NM_004731; NM_001270622; XM_017020225; XM_017020227; NR_073055; XM_011538989; NM_001270623; XM_024449276; XM_011538991; XM_011538993; NR_073056; XM_005269231; XM_011538995; XM_017020226; XM_017020224 |
| VIP | 7432 | XM_006715562; XM_005267135; NM_003381; NM_194435 |
| CD200 | 4345 | NM_001318830; NR_158642; NM_001004197; NM_001365853; NM_001365855; NM_001318826; NM_001365852; NM_001004196; NM_001318828; NM_001365851; NM_005944; NM_001365854 |
| SLITRK3 | 22865 | NM_014926; NM_001318810; NM_001318811 |
| FCN2 | 2220 | XM_011518392; NM_015838; NM_015839; NM_015837; NM_004108; XM_006717015 |
| MT3 | 4504 | NM_005954 |
| ADRB2 | 154 | NM_000024 |
| CACNG4 | 27092 | NM_014405 |
| SYNPO2L | 79933 | NM_024875; NM_001114133; XM_005270159; XM_005270158 |
| VILL | 50853 | NM_001370265; NR_163266; NR_163267; NM_001370264; NM_015873; NM_001385039; NM_001385038 |
| AGRN | 375790 | XM_011541429; NM_001305275; NM_001364727; XR_946650; NM_198576; XM_005244749 |
| CYP11B1 | 1584 | NM_001026213; NM_000497 |
| EPHB3 | 2049 | NM_004443 |
| KCNMB1 | 3779 | NM_004137 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |

TABLE 3-continued

Genes associated with molecular categories.

| Gene | NCBI Gene ID | NCBI Accession Number(s) |
|---|---|---|
| SCGB2A1 | 4246 | NM_002407 |
| ABCC4 | 10257 | XM_017020321; NM_001301829; NM_005845; XM_005254025; XM_017020319; NM_001301830; NM_001105515; XM_017020322; XM_017020320 |
| CRNN | 49860 | NM_016190 |
| CHGB | 1114 | NM_001819 |
| HIGD1B | 51751 | XM_011524891; NM_016438; XM_006721946; XM_006721947; XM_017024742; NR_073504; XM_006721948; XM_017024743; NM_001271880 |
| CELA2A | 63036 | NM_033440 |
| CLPS | 1208 | NM_001832; NM_001252597; NM_001252598 |
| HECW1 | 23072 | XM_006715670; XM_006715671; XM_011515225; XM_017011882; XM_011515220; XM_011515223; XM_017011886; XM_017011888; NM_001287059; NM_015052; XM_017011883; XM_006715673; XM_011515222; XM_011515224; XM_017011884; XM_017011889; XM_017011885; XM_017011887; XM_011515226; XM_017011890; XM_005249665 |
| ERBB3 | 2065 | NM_001005915; NM_001982 |
| PPY | 5539 | NM_002722; NM_001319209; XM_011524978 |
| CKM | 1158 | NM_001824 |
| CXorf36 | 79742 | XM_006724559; NM_176819; NM_024689; XM_005272670 |
| HOXA10 | 3206 | NR_037939; NM_153715; NM_018951 |
| RIBC2 | 26150 | XM_005261524; XM_011530126; NM_015653; XM_017028766 |
| CDH19 | 28513 | XM_011525931.3; XM_017025711.2; XM_011525932.1 |
| SLC24A2 | 25769 | XM_017014592; NM_001193288; NM_001375850; NM_020344; NM_001375851 |
| ADAMDEC1 | 27299 | NM_001145272; NM_014479; NM_001145271; NR_156422 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| KRT17 | 3872 | NM_000422 |
| S100P | 6286 | NM_005980 |
| NOX4 | 50507 | NM_001291926; XM_006718849; NM_016931; NM_001143837; XM_011542857; NM_001143836; NM_001291927; XM_017017842; XM_017017843; XM_017017844; XM_017017841; XM_017017845; NM_001291929; NM_001300995; NR_120406 |
| CELSR1 | 9620 | XM_011530554; XM_011530555; NM_001378328; XM_011530553; NM_014246 |
| CPB1 | 1360 | NM_001871 |
| CCL23 | 6368 | NM_005064; XR_429910; NM_145898 |
| CELA3A | 10136 | NM_005747 |
| WISP2 | 8839 | NM_001323369; XM_017028116; NM_003881; XM_017028117; NM_001323370 |
| GCG | 2641 | NM_002054 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| PDX1 | 3651 | NM_000209; XR_941580; XR_941578; |
| FABP7 | 2173 | NM_001319039; NM_001319041; NM_001319042; NM_001446 |
| NRTN | 4902 | NM_004558 |
| NMB | 4828 | XM_017022239; NM_021077; NM_205858 |
| AMHR2 | 269 | XM_011538179; XM_011538184; XM_017019179; NM_020547; XR_002957309; XR_002957311; XM_011538178; XM_011538176; XM_011538181; XM_011538185; NM_001164691; XM_011538174; XM_011538183; XR_002957310; XM_011538186; XR_002957312; NM_001164690; XM_011538173; XM_011538180; XM_024448938 |
| WNT2 | 7472 | NM_003391; NR_024047 |
| GFAP | 2670 | XM_024450691; XM_024450690; NM_001131019; XM_024450692; XM_024450693; NM_001242376; NM_002055; NM_001363846 |
| CYP11B2 | 1585 | NM_000498 |
| SGCA | 6442 | XM_011525122; XM_011525120; XM_011525121; XM_024450873; NM_001135697; NR_135553; XR_002958056; XM_011525124; NM_000023; XM_011525123 |
| PNMA2 | 10687 | NM_007257; XM_011544365 |
| CEL | 1056 | NM_001807 |
| MT1M | 4499 | NM_176870 |
| CST1 | 1469 | NM_001898 |
| ITPKB | 3707 | NM_002221; NM_001388404; XM_017001211 |
| ALAS2 | 212 | NM_001037968; NM_001037967; NM_000032; NM_001037969 |
| INS | 3630 | NM_001185098; NM_001185097; NM_000207; NM_001291897 |
| LGALS4 | 3960 | NM_006149; XM_011526974; XM_011526973 |
| PLP1 | 5354 | NM_001128834; NM_000533; NM_001305004; NM_199478 |
| GABRQ | 55879 | NM_018558; XM_011531184 |
| PLAG1 | 5324 | XM_017013576; XM_017013577; NM_001114635; XM_011517544; NM_001114634; NM_002655 |
| LIPF | 8513 | NM_004190; NM_001198829; NM_001198830; NM_001198828; XM_011540311 |
| CYP11A1 | 1583 | NM_000781; NM_001099773 |
| FABP1 | 2168 | NM_001443 |
| S100A12 | 6283 | NM_005621 |
| IL20RA | 53832 | NM_001278722; XM_011535904; XM_017010955; NM_001278724; NM_014432; XM_006715506; NM_001278723; XM_017010954 |

TABLE 3-continued

Genes associated with molecular categories.

| Gene | NCBI Gene ID | NCBI Accession Number(s) |
|---|---|---|
| NR5A1 | 2516 | NM_004959 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| ERBB2 | 2064 | XM_024450643; NM_001005862; NM_001382784; NM_001382785; NM_001382788; NM_001382792; NM_001382793; NM_001382803; NM_001289937; NM_001382786; NM_001382800; NM_001382802; NM_001382806; XM_024450641; NM_001382782; NM_001382789; NM_001382795; NM_001289936; NM_001382797; NM_001382805; NM_004448; NR_110535; XM_024450642; NM_001289938; NM_001382791; NM_001382801; NM_001382783; NM_001382790; NM_001382794; NM_001382798; NM_001382799; NM_001382787; NM_001382796; NM_001382804 |
| SLC12A3 | 6559 | NM_000339; NM_001126108; NM_001126107; XM_005256119 |
| GRHL2 | 79977 | XM_011517306; XM_024447286; NM_001330593; NM_024915; XM_011517307 |
| HBB | 3043 | NM_000518 |
| C7 | 730 | NM_000587 |
| MOGAT2 | 80168 | XM_024448696; NM_025098; XM_011545267 |
| MYOC | 4653 | NM_000261 |
| TP73 | 7161 | NM_001126242; NM_001204191; NM_001126240; NM_001204185; NM_001204187; NM_001204184; NM_001204186; NM_001204192; NM_001126241; NM_001204190; NM_001204188; NM_001204189; NM_005427 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| BCAM | 4059 | NM_001013257; NM_005581 |
| KHDC1L | 100129128 | NM_001126063 |
| DTL | 51514 | XM_011509614; NM_001286229; NM_001286230; NM_016448 |
| CXCR2 | 3579 | XM_017003992; XM_017003990; NM_001168298; NM_001557; XM_005246530; XM_017003991 |
| KRT24 | 192666 | XM_017024299; NM_019016; XM_006721739; XM_011524460 |
| SIX1 | 6495 | XM_017021602; NM_005982 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| TNXB | 7148 | NM_001365276; NM_019105; NM_032470 |
| SLC6A7 | 6534 | XR_001742210; XM_024446190; XR_001742212; XM_017009770; XR_001742211; XM_017009767; XM_017009769; XM_017009768; NM_014228 |
| PLAGL1 | 5325 | NM_001289037; NM_001289040; NM_001289046; NM_001289047; NM_001317157; NM_001080956; NM_001080951; NM_001080955; NM_001289044; NM_001289048; NM_001289049; NM_001317159; NM_001317162; NM_001289038; NM_001080953; NM_001080954; NM_001289043; NM_001317156; NM_001317158; NM_001080952; NM_001289041; NM_001289045; NM_001317161; NM_002656; NM_006718; NM_001289039; NM_001289042; NM_001317160 |
| ADH1B | 125 | NM_001286650; NM_000668 |
| FSTL4 | 23105 | XM_011543284; XM_011543286; XM_011543287; XM_011543283; XM_017009251; NM_015082 |
| MFAP2 | 4237 | NM_002403; NM_017459; NM_001135247; NM_001135248 |
| TREM2 | 54209 | NM_001271821; NM_018965 |
| COL1A2 | 1278 | NM_000089 |
| LRP2 | 4036 | XM_011511183; NM_004525; XM_011511184 |
| CDK1 | 983 | NM_001320918; NM_033379; NM_001170406; NM_001786; NM_001130829; XM_005270303; NM_001170407 |
| EBF2 | 64641 | NM_022659 |
| CDH3 | 1001 | NM_001793; XM_011522800; NM_001317195; NM_001317196 |
| SVEP1 | 79987 | NM_024500; NM_153366 |
| CNNM1 | 26507 | NM_001345888; XM_011539631; XR_002956974; NM_020348; NM_001345887; NM_001345889; NR_144311; XR_945667 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| ADAM12 | 8038 | XM_017016705; NM_001288973; NM_001288974; NM_001288975; XM_017016706; NM_003474; NM_021641; XM_024448210 |
| MAGEA1 | 4100 | NM_004988 |
| | | Pheochromocytoma |
| PHOX2A | 401 | NM_005169 |
| DDC | 1644 | XM_011515161; NM_001242890; XM_005271745; NM_001082971; NM_001242886; NM_001242887; NM_001242889; NM_000790; NM_001242888 |
| INSM1 | 3642 | NM_002196 |
| CYP11A1 | 1583 | NM_000781; NM_001099773 |
| SYT5 | 6861 | XM_006723339; NM_001297774; NM_003180; XM_017027175; XM_006723340; XM_006723341; XM_024451668 |

TABLE 3-continued

Genes associated with molecular categories.

| Gene | NCBI Gene ID | NCBI Accession Number(s) |
|---|---|---|
| NGB | 58157 | NM_021257 |
| STAR | 6770 | NM_001007243; NM_000349 |
| SLC18A1 | 6570 | XM_011544626; NM_003053; XM_011544625; NM_001142325; NM_001135691; NM_001142324 |
| CHGB | 1114 | NM_001819 |
| CHRNA3 | 1136 | XM_006720382; NM_000743; NR_046313; NM_001166694 |
| CHGA | 1113 | NM_001301690; NM_001275; XM_011536370 |
| SLC18A2 | 6571 | NM_003054 |
| DBH | 1621 | NM_000787 |
| DRD2 | 1813 | XM_017017296; NM_016574; NM_000795 |
| TH | 7054 | XM_011520335; NM_199292; NM_000360; NM_199293 |
| PPP1R17 | 10842 | XR_926912; NM_001145123; XM_011515094; NM_006658 |
| PHOX2B | 8929 | NM_003924 |
| EGR4 | 1961 | NM_001965 |
| CDH22 | 64405 | XM_024451966; XM_011528994; XM_024451967; NM_021248 |
| SFN | 2810 | NM_006142 |
| C1orf106 | 55765 | XM_011509754; XM_011509755; NM_001367289; NM_001367290; XM_011509756; NM_001142569; NM_018265 |
| CDC20 | 991 | NM_001255 |
| TGFA | 7039 | NM_001308159; NM_001308158; NM_001099691; NM_003236 |
| SMO | 6608 | NM_005631; XM_024446891 |
| SDC1 | 6382 | NM_001006946; XM_005262620; XM_005262621; NM_002997; XM_005262622 |
| VAMP8 | 8673 | NM_003761; XM_017005170 |
| SERPINA1 | 5265 | NM_001002235; NM_001127700; NM_001127701; XM_017021370; NM_001127706; NM_000295; NM_001002236; NM_001127702; NM_001127705; NM_001127703; NM_001127704; NM_001127707 |
| EPHB3 | 2049 | NM_004443 |
| BIRC5 | 332 | NM_001168; NM_001012271; NM_001012270 |
| CILP | 8483 | NM_003613; XM_017022679; XM_017022678 |
| ABAT | 18 | NM_001386601; NM_001386602; NM_001386615; NM_000663; NM_001386606; NM_001127448; NM_020686; NM_001386608; NM_001386612; NM_001386613; NM_001386603; NM_001386605; NM_001386611; NM_001386600; NM_001386609; NM_001386610; NM_001386614; NM_001386616; NM_001386604; NM_001386607 |
| CSTA | 1475 | NM_005213 |
| PRUNE2 | 158471 | XM_011518327; XM_005251746; XM_005251751; XM_006716983; XM_017014347; XM_017014349; XM_017014359; XR_001746209; XR_428517; XM_005251748; XM_006716985; NM_001308047; XM_005251754; XM_006716982; XM_017014346; XM_017014348; XM_017014352; XR_001746210; NM_001308050; NR_131751; NM_138818; XM_011518323; XM_017014345; XM_017014357; XR_001746212; NM_001308048; NM_015225; XM_017014354; XM_017014356; NM_001308049; XM_005251750; XM_005251745; XM_006716986; XM_011518326; XM_011518328; XM_017014350; XM_017014351; XM_017014353; XM_017014358; XM_006716984; XR_001746211; NM_001308051; NM_001330680 |
| WNT2 | 7472 | NM_003391; NR_024047 |
| UGT2A3 | 79799 | XM_011532247; NM_024743; NR_024010 |
| IRS4 | 8471 | XM_006724713; NM_003604; NM_001379150; XM_011531061 |
| SLC6A15 | 55117 | XM_011538525; NM_018057; NM_001146335; NM_182767 |
| ATP2B2 | 491 | XM_017006484; NM_001001331; XM_005265179; XM_011533752; XM_017006487; XM_017006488; XM_017006486; XM_017006481; XM_017006482; XM_017006489; XM_006713175; NM_001330611; NM_001353564; XM_017006485; XM_017006483; NM_001683; XM_017006492; NM_001363862 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| FCN2 | 2220 | XM_011518392; NM_015838; NM_015839; NM_015837; NM_004108; XM_006717015 |
| IVL | 3713 | NM_005547 |
| CFTR | 1080 | NM_000492 |
| F2RL1 | 2150 | NM_005242; XM_017009223 |
| MYB | 4602 | NM_001161660; NR_134958; NM_001130173; NM_001130172; NM_001161656; NR_134959; NM_001161657; NR_134963; NR_134965; XR_942444; NR_134962; NM_001161659; NR_134961; NM_001161658; NM_005375; NR_134960; NR_134964 |
| SCGN | 10590 | NM_006998; XM_017010181 |
| TMEM246 | 84302 | NM_001303107; NM_001303108; NM_032342; XM_024447701; NM_001371233 |
| PRSS22 | 64063 | XM_005255473; NM_022119 |
| IHH | 3549 | NM_002181 |
| MYBPH | 4608 | NM_004997 |
| SPOCK2 | 9806 | XM_017016985; NM_001134434; XM_011540404; NM_001244950; NM_014767 |
| MUC2 | 4583 | NM_002457 |
| MYCL | 4610 | NM_001033082; NM_001033081; NM_005376 |

TABLE 3-continued

| Gene | NCBI Gene ID | NCBI Accession Number(s) |
|---|---|---|
| Genes associated with molecular categories. | | |
| Mesothelioma | | |
| CPA4 | 51200 | NM_001163446; NM_016352 |
| CALB2 | 794 | NM_007088; XR_002957842; NM_001740; NR_027910; NM_007087 |
| HAS1 | 3036 | NM_001523; NM_001297436; XM_011526884 |
| ALDH1A2 | 8854 | NM_001206897; NM_170697; NM_170696; NM_003888 |
| PTGIS | 5740 | NM_000961 |
| UPK1B | 7348 | NM_006952 |
| WT1 | 7490 | NM_000378; NR_160306; NM_001367854; NM_001198551; NM_001198552; NM_024424; NM_024426; NM_024425 |
| MYL2 | 4633 | NM_000432 |
| HP | 3240 | NM_001126102; NM_005143; NM_001318138 |
| MSLN | 10232 | NM_001177355; NM_005823; NM_013404 |
| GJB1 | 2705 | NM_000166; XM_011530907; NM_001097642 |
| CKM | 1158 | NM_001824 |
| TM4SF1 | 4071 | NM_014220; XM_017006385 |
| CST1 | 1469 | NM_001898 |
| CTSE | 1510 | XM_011509245; NM_001910; NM_148964; XM_011509244; NM_001317331 |
| SLC44A4 | 80736 | NM_001178045; NM_001178044; NM_025257 |
| CD24 | 100133941 | NM_001291739; NR_117090; NR_117089; NM_001291738; NM_001291737; NM_013230; XM_024446293; NM_001359084 |
| BMP7 | 655 | NM_001719 |
| TBX5 | 6910 | NM_181486; NM_080717; NM_000192; XM_017019912; NM_080718 |
| GATA4 | 2626 | NM_001308093; NM_002052; NM_001308094; NM_001374273; NM_001374274 |
| IRF6 | 3664 | NM_001206696; NM_006147 |
| KRT5 | 3852 | NM_000424 |
| PRSS22 | 64063 | XM_005255473; NM_022119 |
| CLIC3 | 9022 | XM_017015282; NM_004669; XM_017015281 |
| FLNC | 2318 | NM_001458; NM_001127487 |
| SALL1 | 6299 | NM_001127892; NM_002968 |
| ERBB3 | 2065 | NM_001005915; NM_001982 |
| TF | 7018 | NM_001063; NM_001354703; NM_001354704 |
| GJB3 | 2707 | NM_024009; NM_001005752 |
| BDNF | 627 | NM_001143811; NM_001143812; NM_170734; XM_011520280; NM_001143805; NM_001143816; NM_170731; NM_001143808; NM_001143809; NM_001143814; NM_001143815; NM_001143807; NM_001709; NM_001143810; NM_001143813; NM_170732; NM_001143806; NM_170733; NM_170735 |
| ADRA2B | 151 | NM_000682 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| CENPF | 1063 | XM_017000086; NM_016343; XM_011509082 |
| SCN4A | 6329 | NM_000334 |
| KRT18 | 3875 | NM_000224; NM_199187 |
| SPINT2 | 10653 | NM_001166103; NM_021102 |
| KIF4A | 24137 | NM_012310 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SDC1 | 6382 | NM_001006946; XM_005262620; XM_005262621; NM_002997; XM_005262622 |
| ROBO3 | 64221 | NM_001370358; NM_001370359; NR_163412; NM_001370356; NM_001370361; NR_163411; NR_163415; NM_001370364; NM_022370; NR_163410; NR_163413; NR_163414; XM_017018122; NM_001370366; NM_001370357; NR_163409 |
| FHL5 | 9457 | NM_001170807; NM_001322466; NM_001322467; NM_020482 |
| ZWINT | 11130 | XR_428692; NM_007057; NM_001005413; XM_017015605; XM_024447784; NM_032997; NM_001005414 |
| PKMYT1 | 9088 | NM_001258451; NM_182687; NM_001258450; XM_011522735; XM_024450490; NM_004203; XM_011522734; XM_011522736 |
| NEIL3 | 55247 | NM_018248; XM_017008360 |
| PHKG1 | 5260 | NM_001258460; XM_017012327; XM_017012324; XM_017012325; NR_047689; XM_017012326; NM_001258459; XM_005271772; NM_006213 |
| KRT2 | 3849 | NM_000423 |
| CDKN2A | 1029 | XR_929159; XM_011517676; XM_011517675; NM_001363763; NM_001195132; NM_058195; NM_000077; NM_058196; NM_058197; XM_005251343 |
| SEMA6C | 10500 | NM_030913; XM_017000075; XM_017000079; NM_001178061; NM_001178062; XM_017000077; XM_017000082; XM_017000076; XM_017000081; XM_005244835 |
| CIDEC | 63924 | NM_001321142; NM_001199552; NM_001378491; NM_001199623; NM_001199551; NM_001321144; NM_022094; NM_001321143 |
| SPANXB1 | 728695 | NM_145664; NM_032461 |
| GH1 | 2688 | NM_022559; NM_022561; NM_022560; NM_022562; NM_000515 |
| PLIN1 | 5346 | NM_002666; XM_005254934; NM_001145311 |

TABLE 3-continued

Genes associated with molecular categories.

| Gene | NCBI Gene ID | NCBI Accession Number(s) |
|---|---|---|
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| CACNA1S | 779 | XM_005245478; NM_000069 |
| | | Thymoma |
| MAOB | 4129 | XM_005272608; XM_017029524; XM_017029523; NM_000898 |
| ANKS1B | 56899 | XM_006719507; XM_024449067; NM_001204070; NM_001352193; NM_001352198; NM_001352201; NM_001352207; NM_001352219; NM_001352221; XM_006719508; XM_017019654; XM_024449061; XM_024449062; NM_001204065; NM_001352185; NM_001352191; NM_001352194; NM_001352202; NM_001352203; NM_001352209; NM_001352211; NM_001352213; NM_001352220; XM_017019655; XM_024449069; NM_001204068; NM_001352205; NM_001352214; NM_001352216; NM_001352218; NM_001352223; NM_001352225; NM_020140; XM_024449063; XM_024449066; XM_024449070; NM_001204066; NM_001352186; NM_001352187; NM_001352195; NM_001352200; NM_001352212; NM_152788; XM_005269029; XM_006719505; XM_006719510; XM_006719512; XM_011538571; XM_017019656; XM_024449065; NM_001204079; NM_001352189; NM_001352190; NM_001352197; NM_001352222; XM_006719513; XM_006719514; XM_017019652; XM_024449064; XR_001748815; NM_001204069; NM_001204067; NM_001204081; NM_001352199; NM_001352204; NM_001352206; NM_001352210; NM_001352217; NM_181670; XM_017019653; NM_001352196; XM_006719504; XM_017019657; XM_017019658; XM_024449060; XM_024449068; NM_001204080; NM_001352188; NM_001352192; NM_001352208; NM_001352224 |
| SPINK2 | 6691 | XM_024454191; XM_011534405; NM_001271718; NM_001271720; NM_001271721; NR_073417; NM_001271719; XM_011534406; NM_001271722; NM_021114; NR_073418; NR_073419 |
| KREMEN2 | 79412 | NM_145348; NM_145347; NM_024507; NM_172229; NM_001253726; NM_001253725 |
| ORC1 | 4998 | NM_001190818; XM_017001388; XM_017001389; NM_001190819; XM_011541527; NM_004153 |
| GJB1 | 2705 | NM_000166; XM_011530907; NM_001097642 |
| DPF1 | 8193 | XM_006723408; XR_243964; XM_011527356; XM_024451731; NM_004647; XM_005259292; XM_006723407; NM_001135155; XM_006723409; XM_006723410; XM_011527358; NM_001363579; XM_011527357; XM_005259289; NM_001135156; NM_001289978 |
| PAX1 | 5075 | NM_006192; NM_001257096 |
| FCN2 | 2220 | XM_011518392; NM_015838; NM_015839; NM_015837; NM_004108; XM_006717015 |
| KIFC1 | 3833 | XM_011514585; XM_017010836; NM_002263; XM_011514587; XM_017010837 |
| RAG1 | 5896 | NM_001377278; NM_000448; NM_001377280; NM_001377277; NM_001377279 |
| FOXN1 | 8456 | XM_011525358; XM_011525362; XM_011525359; XM_011525367; XM_011525368; XM_011525370; XM_017025230; XM_017025231; XM_017025229; XM_011525369; XM_017025228; NM_001369369; NM_003593 |
| ZAP70 | 7535 | XM_017004868; XR_001738927; NM_001378594; NM_207519; XM_017004869; NM_001079; XR_001738926; XM_017004870; XM_017004867; XR_001738925 |
| PCDH1 | 5097 | XM_005268455; NM_001278613; XM_005268452; XM_017009517; NM_032420; NM_002587; XM_005268454; XM_017009518; NM_001278615 |
| LCK | 3932 | XM_011541453; XM_024447046; NM_001330468; XM_024447047; NM_005356; NM_001042771 |
| MLANA | 2315 | NM_005511 |
| KRT5 | 3852 | NM_000424 |
| NDRG2 | 57447 | NM_016250; NM_001354567; NM_201538; NM_001282215; NM_001354560; NM_001354561; NM_001354569; NM_201535; NM_001282216; NM_001354564; NM_001354565; NM_001354566; NM_201536; NM_201539; NM_201541; NM_001354558; NM_001354562; NM_001282213; NM_001354570; NM_201540; NM_001282211; NM_001320329; NM_001282214; NM_001282212; NM_001354559; NM_001354568; NM_201537 |
| GFI1B | 8328 | NM_001371908; NM_001377304; XM_006717297; NM_001135031; XM_017015175; NM_001377305; XM_011519069; XM_011519070; NM_004188; XM_011519068; XM_017015176 |
| BEND5 | 79656 | XM_017002331; XM_011542141; XM_017002333; NM_001349795; NR_146232; XM_011542142; XR_001737408; NM_001349794; NM_001302082; NM_001349793; NM_024603 |
| ITGB6 | 3694 | NM_001282354; NM_001282353; NM_000888; NM_001282389; NM_001282390; NM_001282355; NM_001282388 |
| AGL | 178 | NM_000646; XM_005270557; NM_000644; NM_000028; NM_000643; XM_017000501; NM_000642; NM_000645 |
| CAMK2N1 | 55450 | NM_018584 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; |

TABLE 3-continued

Genes associated with molecular categories.

| Gene | NCBI Gene ID | NCBI Accession Number(s) |
|---|---|---|
| | | NM_001318113; NM_001318116; XM_017029098; NM_001318104; NM_001318112; NM_001318115 |
| EEF1A2 | 1917 | NM_001958 |
| REN | 5972 | NM_000537 |
| CALML3 | 810 | NM_005185 |
| DNTT | 1791 | NM_004088; NM_001017520 |
| PHLDA2 | 7262 | NM_003311 |
| CTH | 1491 | XM_005270509; NM_001902; NM_153742; XM_017000416; NM_001190463 |
| PRSS16 | 10279 | XM_017010162; XM_017010164; XM_017010165; XM_017010161; XM_017010163; NM_005865 |
| AADAC | 13 | NM_001086; XM_005247104 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| SDCBP | 6386 | NM_001007067; NM_001007069; XM_024447231; NM_001330537; NM_001348340; XM_024447229; NM_001007068; NM_001348341; XM_024447230; NM_005625; NM_001007070; NM_001348339 |
| PAX9 | 5083 | NM_001372076; NM_006194 |
| CCL25 | 6370 | NM_001394634; NM_001394635; NM_001394638; NM_005624; NM_148888; NM_001394636; NM_001201359; NM_001394637 |
| PKP1 | 5317 | NM_000299; NM_001005337 |
| TNFRSF4 | 7293 | XM_011542074; NM_003327; XM_017002232; XM_011542077; XM_011542075; XM_011542076; XM_017002231 |
| ACADL | 33 | NM_001608; XM_005246517; XM_017003955 |
| ARPP21 | 10777 | NM_001267619; NM_001385487; NM_001385490; NM_001385558; NM_001385573; NM_001385582; NR_169635; NR_169644; NR_170706; NR_170707; XM_017005574; XM_017005584; NM_001385485; NM_001385536; NM_001385581; NM_001385589; NM_001385594; XM_011533301; XM_017005580; XM_017005588; NM_001267616; NM_001385495; NM_001385576; NR_169645; XM_017005596; XM_024453320; NM_001385565; NM_001385566; NM_001385590; NM_016300; NR_169632; XM_011533303; XM_017005590; XM_017005598; XM_024453322; NM_001267617; NM_001385484; NM_001385488; NM_001385517; NM_001385585; NM_001385592; NR_169647; XM_011533299; XM_017005607; XM_024453323; NM_001025069; NM_001385489; NM_001385492; NM_001385496; NM_001385567; NM_001385577; NM_001385584; NM_001385587; NM_001385591; NM_001385593; XM_017005591; NM_001267618; NM_001385486; NM_001385491; NM_001385564; NM_001385578; NM_001385595; NM_198399; NR_169633; XM_011533300; XM_011533302; XM_017005575; XM_017005579; XM_017005612; XM_024453324; NM_001025068; NM_001385497; NM_001385556; NM_001385562; NM_001385563; NM_001385574; NM_001385580; NM_001385588; NR_169646; NR_170705 |
| SLC13A2 | 9058 | NM_001145975; NM_001346683; NM_003984; NM_001145976; XM_006722165; XM_011525450; XM_011525453; XM_011525454; NM_001346684; XM_011525452; XM_011525451 |
| FGFR4 | 2264 | NM_213647; NM_022963; NM_002011; NM_001291980; NM_001354984 |
| CD247 | 919 | NM_001378516; NM_198053; XM_011510144; XM_011510145; NM_000734; NM_001378515 |
| RAB23 | 51715 | NM_183227; NM_001278666; NM_001278668; NM_016277; NM_001278667; NR_103822 |
| FBXL6 | 26233 | NM_024555; NM_012162 |
| EFNA2 | 1943 | NM_001405; XM_017026449; XM_017026450 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| GHRH | 2691 | NM_001184731; NM_021081 |
| | | Germ_Cell_Neoplasm |
| CCNB1 | 891 | NM_031966 |
| POMC | 5443 | NM_001319205; NM_001035256; NM_001319204; NM_000939 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| CLDN6 | 9074 | NM_021195 |
| DBNDD1 | 79007 | NM_001288709; NM_001288708; NM_001371581; NM_001042610; NM_024043 |
| CAP2 | 10486 | NM_001363534; NM_006366; NM_001363533 |
| ESM1 | 11082 | NM_001135604; NM_007036 |
| EPS8L1 | 54869 | NM_133180; NM_139204; XM_011527052; XM_005259020; NM_017729; XM_011527051; XM_011527050 |
| MEP1B | 4225 | XM_011526013; XM_011526014; NM_005925; NM_001308171 |
| PLIN1 | 5346 | NM_002666; XM_005254934; NM_001145311 |
| ZWINT | 11130 | XR_428692; NM_007057; NM_001005413; XM_017015605; XM_024447784; NM_032997; NM_001005414 |

TABLE 3-continued

Genes associated with molecular categories.

| Gene | NCBI Gene ID | NCBI Accession Number(s) |
|---|---|---|
| HAMP | 57817 | NM_021175 |
| EIF1AY | 9086 | NM_004681; NM_001278612 |
| MISP | 126353 | NR_135168; XM_011527686; XM_011527685; NM_173481 |
| MMP9 | 4318 | NM_004994 |
| CLEC1B | 51266 | NM_001099431; XM_017019395; XM_011520685; XM_017019396; XM_011520686; NM_016509; NM_001393342 |
| ALLC | 55821 | XM_017004495; XM_017004498; NM_018436; XM_017004496; XM_011510369; XM_011510370; XM_017004497; NM_199232 |
| PGR | 5241 | XM_011542869; NM_001271161; NR_073142; NM_000926; XM_006718858; NM_001202474; NM_001271162; NR_073141; NR_073143 |
| COL9A1 | 1297 | NM_001851; NR_165185; NM_078485; XM_017010246; XM_011535429; XM_017010247; NM_001377289; NM_001377290; NM_001377291 |
| DNM1 | 1759 | NM_001005336; NM_001374269; NM_004408; NM_001288738; NM_001288739; NM_001288737 |
| KERA | 11081 | NM_007035 |
| PLA2G2A | 5320 | NM_001161728; NM_000300; NM_001161729; NM_001161727; NM_001395463 |
| AURKB | 9212 | NM_001313950; NM_001313953; XM_017025309; XM_017025307; XM_017025308; XM_017025311; NM_001313952; NM_004217; NM_001313954; NR_132730; NR_132731; XM_017025310; NM_001284526; XM_011524072; NM_001256834; NM_001313951; NM_001313955 |
| APOBEC3B | 9582 | NM_004900; NM_001270411 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| PTH1R | 5745 | NM_001184744; XM_017006933; XM_011533968; NM_000316; XM_017006934; XM_011533967; XM_005265344; XM_017006932 |
| PTCH2 | 8643 | NM_001166292; NM_003738 |
| CYP46A1 | 10858 | NM_006668; XM_005267274; XM_011536365; XM_011536364; XM_017020933 |
| VRTN | 55237 | XM_011536911; NM_018228 |
| PLVAP | 83483 | NM_031310 |
| PTHLH | 5744 | NM_198965; NM_198966; XM_011520774; NM_002820; XM_017019675; NM_198964 |
| COL8A1 | 1295 | NM_020351; NM_001850 |
| DAZL | 1618 | NM_001351; NM_001190811 |
| NANOG | 79923 | NM_024865; NM_001297698 |
| CXorf36 | 79742 | XM_006724559; NM_176819; NM_024689; XM_005272670 |
| C9 | 735 | NM_001737 |
| FOXH1 | 8928 | NM_003923 |
| MDFI | 4188 | XM_005249117; XM_011514626; NM_005586; NM_001300805; XM_011514625; NM_001300804; XM_017010867; NM_001300806 |
| KLF9 | 687 | NM_001206 |
| EDIL3 | 10085 | NM_005711; NM_001278642 |
| LRRTM4 | 80059 | NM_001134745; NM_001330370; NM_001282924; NM_024993; NM_001282928; NR_146416 |
| PRND | 23627 | NM_012409 |
| GDF3 | 9573 | NM_020634 |
| CDKN2A | 1029 | XR_929159; XM_011517676; XM_011517675; NM_001363763; NM_001195132; NM_058195; NM_000077; NM_058196; NM_058197; XM_005251343 |
| PRM1 | 5619 | NM_002761 |
| LIN28A | 79727 | XM_011542148; NM_024674 |
| DPP4 | 1803 | NR_166823; NM_001379606; NM_001379605; NR_166824; NM_001935; NM_001379604; NR_166825; NR_166822 |
| IBSP | 3381 | NM_004967 |
| CYP17A1 | 1586 | NM_000102 |
| VENTX | 27287 | XM_017016073; NM_014468 |
| LEFTY2 | 7044 | NM_003240; NM_001172425; XM_011544266 |
| GCKR | 2646 | XM_017003797; XM_011532763; XR_001738699; XM_017003796; NM_001486 |
| AKR1C3 | 8644 | NM_003739; NM_016253; NM_001253909; NM_001253908 |
| GATA4 | 2626 | NM_001308093; NM_002052; NM_001308094; NM_001374273; NM_001374274 |
| PLP1 | 5354 | NM_001128834; NM_000533; NM_001305004; NM_199478 |
| ADAM11 | 4185 | XM_005257373; NM_001318933; NM_002390; XM_024450754 |
| PRM2 | 5620 | NM_001286358; NR_104428; NM_002762; NM_001286356; NM_001286359; NM_001286357 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| HAPLN1 | 1404 | XM_017009052; XM_017009051; NM_001884; XM_017009054; XM_017009053; XM_011543168 |
| DEPDC1 | 55635 | NM_001114120; NM_017779 |
| SLPI | 6590 | NM_003064 |
| C3orf36 | 80111 | NM_025041; NR_161373 |
| PEG3 | 5178 | NM_001369718; NM_001146184; NM_001369719; NM_001369734; NM_001369739; NR_161475; NM_001369731; NM_001369720; NM_001369724; NM_001369732; NM_001369733; NM_001146187; NM_001369722; |

TABLE 3-continued

| Genes associated with molecular categories. | | |
|---|---|---|
| Gene | NCBI Gene ID | NCBI Accession Number(s) |
| | | NM_001369723; NM_001369726; NM_001369728; NM_001369735; NM_001369736; NM_001369737; NM_001369738; NM_001146185; NM_001369717; NM_001369721; NM_001369725; NM_006210; NM_001369729; NM_001369730; NM_001369727; NR_161476; NM_001146186 |
| MLANA | 2315 | NM_005511 |
| TREM2 | 54209 | NM_001271821; NM_018965 |
| GDF2 | 2658 | NM_016204 |
| DPPA4 | 55211 | XM_011512954; XM_024453622; NM_001348929; NM_001348928; NM_018189 |
| CDH15 | 1013 | NM_004933 |
| RRM2 | 6241 | NR_161344; NM_001034; NR_164157; NM_001165931 |
| MYL7 | 58498 | XM_011515464; NM_021223; XM_011515465; XM_011515463; XM_017012478; XM_017012479; XM_024446851; XM_005249817 |
| PRR7 | 80758 | NM_001375594; NM_030567; NM_001174102; NM_001174101; NM_001375593 |
| PHC1 | 1911 | XM_017018958; XM_011520600; XM_017018955; XM_017018957; XM_011520599; XM_017018956; XM_011520603; XM_005253334; NM_004426 |
| Neuroendocrine_small_cell | | |
| CD34 | 947 | NM_001025109; NM_001773 |
| NCAM1 | 4684 | NM_001386289; NM_001386290; NM_001386291; NM_001386292; NM_001076682; NM_000615; NM_001242608; NM_181351; NM_001242607 |
| MOGAT2 | 80168 | XM_024448696; NM_025098; XM_011545267 |
| COL11A1 | 1301 | XM_017000337; XM_017000335; XM_017000336; NR_134980; NM_080629; XM_017000334; NM_001190709; NM_001854; NM_080630 |
| DTL | 51514 | XM_011509614; NM_001286229; NM_001286230; NM_016448 |
| MYOC | 4653 | NM_000261 |
| FOXA1 | 3169 | NM_004496; XM_017021246 |
| IBSP | 3381 | NM_004967 |
| GLP2R | 9340 | XM_011524077; NM_004246; XM_017025340; XM_005256861; XM_017025339; XM_017025341 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| ZNF185 | 7739 | XM_005274744; XM_017029823; XM_017029829; NM_001178107; XM_005274735; XM_005274740; XM_005274741; XM_017029825; XM_017029831; NM_001178106; NM_001178113; XM_005274738; XM_005274731; XM_017029822; XM_017029826; XM_017029827; XM_017029832; XM_005274745; XM_017029824; NM_001178108; NM_001178110; XM_011531195; XM_017029828; NM_001178115; NM_007150; NM_001178114; XM_005274730; XM_017029821; XM_011531194; NM_001178109; NM_001395254; XM_005274746; XM_017029830; XM_017029833; NM_001388432; XM_005274742; XM_017029834; XM_017029835 |
| SYN2 | 6854 | XM_006713312; XR_001740240; XM_006713311; XM_006713313; NM_133625; NM_003178; XM_017007087 |
| KRT2 | 3849 | NM_000423 |
| ANGPTL4 | 51129 | NM_016109; NM_139314; XM_005272484; XM_005272485; NR_104213; NM_001039667 |
| GABRG3 | 2567 | XM_017022058; XM_017022060; XM_024449889; NM_033223; XM_011521430; NM_001270873; XM_011521431; XM_017022059 |
| SPP1 | 6696 | NM_001251829; NM_001040060; NM_001251830; NM_000582; NM_001040058 |
| SYT12 | 91683 | XM_011545346; XM_011545347; NM_177963; XM_017018547; NM_001177880; NM_001318775; XM_017018548; XM_006718737; XM_024448766; NM_001318773 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| DLL3 | 10683 | NM_016941; NM_203486 |
| SFRP5 | 6425 | NM_003015 |
| GABRD | 2563 | XM_011541194; XM_017000936; NM_000815 |
| CCNB1 | 891 | NM_031966 |
| PRL | 5617 | XM_011514753; NM_000948; NM_001163558; XM_011514754 |
| RETN | 56729 | NM_020415; NM_001385725; NM_001385727; NM_001385726; NM_001193374 |
| PPM1H | 57460 | XM_017019676; XM_011538578; NM_020700; XM_011538579 |
| ESM1 | 11082 | NM_001135604; NM_007036 |
| CELA3B | 23436 | NM_007352 |
| CHGA | 1113 | NM_001301690; NM_001275; XM_011536370 |
| GGCT | 79017 | NM_001199816; NM_001199817; NM_001199815; NM_024051; NR_037669 |
| ADH1B | 125 | NM_001286650; NM_000668 |
| AOC3 | 8639 | XR_934584; NM_001277732; NM_003734; NR_102422; XM_011525419; XR_001752673; XM_011525420; XM_024451015; NM_001277731 |
| AGL | 178 | NM_000646; XM_005270557; NM_000644; NM_000028; NM_000643; XM_017000501; NM_000642; NM_000645 |
| CELSR3 | 1951 | NM_001407 |
| CLDN3 | 1365 | NM_001306 |

TABLE 3-continued

Genes associated with molecular categories.

| Gene | NCBI Gene ID | NCBI Accession Number(s) |
|---|---|---|
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| ALAS2 | 212 | NM_001037968; NM_001037967; NM_000032; NM_001037969 |
| CST1 | 1469 | NM_001898 |
| CAI | 759 | NM_001128831; NM_001291967; NM_001164830; NM_001738; NM_001128830; NM_001128829; NM_001291968 |
| AOC1 | 26 | XM_017011946; NM_001091; XM_017011947; NM_001272072; XM_017011944; XM_017011945 |
| LIMS2 | 55679 | XM_006712627; XM_024452983; NM_017980; NM_001256542; XM_017004469; NM_001161403; XM_011511453; XM_024452984; NM_001136037; XM_024452986; XR_922961; NM_001161404; XM_006712628; XM_024452985; XM_005263710 |
| HSF2BP | 11077 | XM_017028269; XM_017028272; XM_011529446; XM_017028270; XM_017028271; XM_017028267; XM_017028268; XR_937435; XM_011529445; XM_011529443; XM_011529447; NM_007031 |
| CDK4 | 1019 | NM_000075; NM_052984 |
| HBB | 3043 | NM_000518 |
| HOXC10 | 3226 | NM_017409 |
| KRT1 | 3848 | NM_006121 |
| TTC22 | 55001 | XM_017001582; XM_011541671; NM_001114108; NM_017904 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| S100A12 | 6283 | NM_005621 |
| KRT24 | 192666 | XM_017024299; NM_019016; XM_006721739; XM_011524460 |
| MET | 4233 | NM_001324402; NM_001324401; XM_006715990; NM_001127500; XM_011516223; NM_000245; XR_001744772; |
| DES | 1674 | NM_001927; NM_001382708; NM_001382710; NM_001382713; NM_001382709; NM_001382711; NM_001382712 |
| HOXC11 | 3227 | NM_014212 |
| GUCA2A | 2980 | NM_033553 |
| PTH1R | 5745 | NM_001184744; XM_017006933; XM_011533968; NM_000316; XM_017006934; XM_011533967; XM_005265344; XM_017006932 |
| ULBP2 | 80328 | NM_025217; XM_017011321 |
| TGM3 | 7053 | NM_003245 |
| CTRB2 | 440387 | NM_001025200 |
| CKM | 1158 | NM_001824 |
| ALDOC | 230 | XM_005257949; NM_005165; XM_011524556 |
| CCL23 | 6368 | NM_005064; XR_429910; NM_145898 |
| MMP11 | 4320 | NM_005940; NR_133013 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| HOXC13 | 3229 | NM_017410 |
| MAGEA3 | 4102 | XM_011531161; XM_005274676; XM_006724818; XM_011531160; NM_005362 |
| INS | 3630 | NM_001185098; NM_001185097; NM_000207; NM_001291897 |
| NKX6-1 | 4825 | NM_006168 |
| HINT1 | 3094 | NR_134495; NM_005340; NR_073488; NR_024610; NR_134494; NR_024611 |
| GRIN2D | 2906 | XM_011526872; NM_000836 |
| FCN3 | 8547 | NM_173452; NM_003665 |
| MGLL | 11343 | XM_017005665; NM_001256585; NM_001388313; NM_001388318; NM_001388317; XM_011512383; NM_001003794; XM_017005663; XM_024453334; NM_001388312; NM_001388315; NM_007283; XM_011512382; NM_001388314; NM_001388316 |
| FMO2 | 2327 | NM_001460; NR_160266; XR_921761; NM_001365900; XR_001737072; NM_001301347 |
| PCSK2 | 5126 | NM_002594; NM_001201529; NM_001201528 |
| MYL2 | 4633 | NM_000432 |
| SIM1 | 6492 | XM_011536072; NM_001374769; NM_005068 |
| EFNA3 | 1944 | NM_004952 |
| MT1M | 4499 | NM_176870 |
| CST4 | 1472 | NM_001899 |
| P2RY14 | 9934 | XM_011513340; NM_001081455; XM_005247922; NM_014879; XM_017007583; XM_005247923 |
| MMP14 | 4323 | NM_004995 |
| CDH19 | 28513 | XM_011525931.3; XM_017025711.2; XM_011525932.1 |
| COL10A1 | 1300 | XM_011535432; NM_000493; XM_011535433; XM_017010248; XM_006715333 |
| ETV4 | 2118 | NM_001261437; NM_001261439; NM_001986; NM_001369368; NM_001079675; NM_001261438; XM_024450644; NM_001369366; NM_001369367 |
| SIX1 | 6495 | XM_017021602; NM_005982 |
| ABCA12 | 26154 | XM_011510951; NR_103740; NM_173076; NM_015657 |

TABLE 3-continued

| Gene | NCBI Gene ID | NCBI Accession Number(s) |
|---|---|---|
| Genes associated with molecular categories. | | |
| BARX2 | 8538 | XM_011543043; NM_003658; XM_011543044 |
| CRISP2 | 7180 | XM_011514841; XM_011514842; XR_002956303; NM_001142417; NM_001261822; NM_003296; XM_011514843; XR_926302; XM_005249350; XM_005249352; XM_005249349; XM_005249353; XR_002956302; XM_005249351; NM_001142435; XM_005249356; XR_002956301; NM_001142407; XR_002956300; XR_926303; NM_001142408 |
| IGFBP3 | 3486 | NM_000598; NM_001013398 |
| CA7 | 766 | NM_001365337; XM_011523312; NM_001014435; NM_005182 |
| PPEF1 | 5475 | NM_001377996; NM_001377994; NM_001389623; NM_001377986; NM_006240; NM_152224; NM_152226; NM_152225; NM_001378381; NM_001389624; NM_152223; NM_001377993; NM_001378382; XM_017029612; NM_001389621; NM_001377995; NM_001389620 |
| Clear_Cell_Renal_Cell_Carcinoma | | |
| NKX2-4 | 644524 | NM_033176 |
| LCN2 | 3934 | NM_005564 |
| HGFAC | 3083 | NM_001297439; NM_001528 |
| TNNI3 | 7137 | NM_000363 |
| NMRK2 | 27231 | NM_001289117; NM_001375468; NM_001375469; NM_170678; NM_001375467; NM_014446; XM_006722725; NR_110316 |
| NKAIN3 | 286183 | XM_017013359; XM_011517511; XM_017013360; XM_017013361; NM_001039769; NR_130764; NR_027378; XM_011517512; NM_173688; NM_001304533 |
| ARHGAP40 | 343578 | NM_001164431 |
| KRT7 | 3855 | XM_017019294; XR_001748700; NM_005556; XM_011538325; XR_001748699 |
| CST4 | 1472 | NM_001899 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| DNTT | 1791 | NM_004088; NM_001017520 |
| LRRN4 | 164312 | XM_011529183; NM_152611 |
| NPBWR1 | 2831 | NM_005285 |
| CLDN3 | 1365 | NM_001306 |
| CXCL11 | 6373 | NM_001302123; NM_005409 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| HTR1F | 3355 | NM_001322208; XM_005264751; NM_000866; NM_001322210; NM_001322209; XM_011533664 |
| IFNG | 3458 | NM_000619 |
| GRIN2A | 2903 | XM_017023172; NM_001134407; XM_011522461; NM_001134408; NM_000833; XM_011522458; XM_017023173 |
| REN | 5972 | NM_000537 |
| HILPDA | 29923 | NM_013332; NM_001098786 |
| EGLN3 | 112399 | NM_001308103; NM_022073 |
| C14orf180 | 400258 | XM_005267638; NM_001286399; NM_001286400; XM_011536764; NM_001008404 |
| CIB4 | 130106 | XM_024452692; NM_001029881; XM_017003329; XM_017003331; XM_011532514; XM_017003330 |
| CTAGE9 | 643854 | NM_001145659 |
| IGFBP1 | 3484 | NM_000596; NM_001013029 |
| GDF6 | 392255 | NM_001001557 |
| APOB | 338 | NM_000384 |
| PCSK6 | 5046 | NM_001291309; NM_138322; NM_138325; NM_138320; NM_138324; NM_138319; NM_138321; NM_002570; NM_138323 |
| LOX | 4015 | NM_001317073; NM_001178102; NM_002317 |
| DAZ2 | 57055 | NM_001388495; NM_001389303; NM_001005785; NM_001388494; NM_001005786; NM_001388493; NM_020363 |
| DAZ4 | 57135 | XM_011531509; NM_020420; NM_001388484; NM_001005375; XM_011531510 |
| Papillary_Renal_Cell_Carcinoma | | |
| FABP7 | 2173 | NM_001319039; NM_001319041; NM_001319042; NM_001446 |
| KLK15 | 55554 | XM_011527088; XR_001753713; NM_001277081; NM_017509; NM_138563; XM_011527085; XM_011527087; XM_011527089; NM_023006; XM_006723265; NM_138564; XM_017026943; NM_001277082; NR_102274 |
| NDUFA4L2 | 56901 | NM_001394961; NM_001394960; NM_020142 |
| KISS1R | 84634 | NM_032551; XM_017027382 |
| EBF2 | 64641 | NM_022659 |
| FGG | 2266 | NM_000509; NM_021870 |
| MCHR1 | 2847 | NM_005297 |
| STAP1 | 26228 | NM_001317769; NM_012108; XM_017008018 |

TABLE 3-continued

Genes associated with molecular categories.

| Gene | NCBI Gene ID | NCBI Accession Number(s) |
|---|---|---|
| CP | 1356 | XM_006713500; XM_006713501; XM_017005735; XM_017005734; XM_006713499; XM_011512435; XR_427361; NM_000096; NR_046371 |
| DAZ1 | 1617 | XM_011531482; NM_004081; XM_011531483; NM_001388496 |
| LOX | 4015 | NM_001317073; NM_001178102; NM_002317 |
| IGFBP1 | 3484 | NM_000596; NM_001013029 |
| RGS5 | 8490 | NM_003617; NM_001195303; NM_001254748; NM_001254749 |
| REN | 5972 | NM_000537 |
| FBN3 | 84467 | NM_032447; XM_017027374; XM_017027376; NM_001321431; XM_017027372; XM_017027373; XM_017027378; XM_017027375; XM_017027377; XM_017027379 |
| PTPRN | 5798 | NM_002846; NM_001199764; NM_001199763 |
| APOB | 338 | NM_000384 |
| GRIK3 | 2899 | NM_000831 |
| APLN | 8862 | NM_017413 |
| CA9 | 768 | XR_428428; NM_001216; XR_001746374 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| UBTFL1 | 642623 | NM_001143975 |
| SPARCL1 | 8404 | NM_001291976; NM_004684; NM_001291977; NM_001128310 |
| SLCO1C1 | 53919 | XR_001748769; XR_001748771; NM_001145946; XM_017019486; NM_001145945; XM_011520703; XR_001748768; XR_001748770; XM_005253394; XM_011520711; XM_024449024; XM_017019487; NM_017435; XM_005253396; NM_001145944; XM_024449025; XM_017019489; XM_011520704; XM_017019490 |
| CIB4 | 130106 | XM_024452692; NM_001029881; XM_017003329; XM_017003331; XM_011532514; XM_017003330 |
| TUBA3E | 112714 | NM_207312 |
| COX4I2 | 84701 | XM_005260580; XM_005260581; NM_032609; XM_005260579 |
| ERP27 | 121506 | NM_152321; NM_001300784 |
| CREB3L3 | 84699 | NM_001271997; NM_032607; NM_001271995; NM_001271996 |
| BAALC | 79870 | XR_001745601; NM_001024372; NM_001364874; NM_024812 |
| MEOX2 | 4223 | NM_005924 |
| CSPG4 | 1464 | NM_001897 |
| GRIN2A | 2903 | XM_017023172; NM_001134407; XM_011522461; NM_001134408; NM_000833; XM_011522458; XM_017023173 |
| LHX9 | 56956 | NM_001014434; NM_020204; XM_005245350; XM_011509781; XM_017001849; NM_001370213 |
| GABRQ | 55879 | NM_018558; XM_011531184 |
| AVPR1A | 552 | NM_000706 |
| COL25A1 | 84570 | XM_011532334; NM_001256074; XM_011532358; NM_032518; NM_198721; XM_011532333; XM_011532356; XM_017008736; XM_017008737; NR_045756; XM_011532338; XM_017008735; XM_011532335; XM_011532355 |
| ASB5 | 140458 | XM_005262759; XM_011531617; NM_080874; XM_011531616 |
| ADAMTSL1 | 92949 | XM_017015311; NM_052866; XM_011518063; XM_011518067; XM_017015313; NM_001040272; XM_011518064; XM_011518068; NM_139238; XM_017015310; XM_011518070; XM_017015312; XM_017015314; NM_139264 |
| FHL5 | 9457 | NM_001170807; NM_001322466; NM_001322467; NM_020482 |
| DEFB132 | 400830 | NM_207469 |
| CTAGE9 | 643854 | NM_001145659 |
| OPN4 | 94233 | NM_001030015; XM_017016955; XM_017016956; XM_017016957; NM_033282 |
| CXCL11 | 6373 | NM_001302123; NM_005409 |
| ACAN | 176 | XM_011521313; XM_011521314; NM_001135; NM_001369268; NM_013227 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ADGRL4 | 64123 | NM_022159 |
| SMOC1 | 64093 | NM_001034852; NM_022137; XM_005267996; XM_005267995 |
| SLC38A8 | 146167 | NM_001080442; XM_017022946 |
| DNAAF3 | 352909 | NM_001256716; NM_001256714; NM_001256715; NM_001031802; NM_178837 |
| IGFBP6 | 3489 | NM_002178 |
| SLC47A2 | 146802 | NM_001099646; XM_017024221; XM_017024225; XM_017024222; XM_017024224; XM_017024226; XR_001752432; XM_017024223; NR_135624; NM_001256663; NM_152908; NR_135625; XR_001752433 |
| SFN | 2810 | NM_006142 |
| CPNE4 | 131034 | XM_017005695; NM_130808; XM_017005694; NM_001388327; XM_024453338; XM_011512408; XM_024453339; NM_001388326; NM_153429; XM_017005696; XM_024453340; NM_001289112 |
| CST6 | 10395 | NM_001316668; NM_182643; XM_005273374; NM_001348081; NM_001348083; NM_001348084; NM_001164271; NM_006094; NM_024767; NM_001348082 |
| CLDN3 | 1365 | NM_001306 |
| PIGR | 5284 | XM_011509629; NM_002644 |
| CPLX2 | 10814 | XM_005265798; XM_005265799; XM_017008964; NM_032282; NM_001008220; NM_006650; XM_011534419 |
| LRRN4 | 164312 | XM_011529183; NM_152611 |
| WFDC5 | 149708 | NM_001395506; NM_145652; XM_011528601; XM_011528602 |

TABLE 3-continued

Genes associated with molecular categories.

| Gene | NCBI Gene ID | NCBI Accession Number(s) |
|---|---|---|
| NPBWR1 | 2831 | NM_005285 |
| PRKCG | 5582 | NM_002739; NM_001316329 |
| ARHGAP40 | 343578 | NM_001164431 |
| KRT23 | 25984 | NM_001282433; XM_005257200; XM_011524595; NM_015515; NM_173213 |
| HS3ST4 | 9951 | NM_006040 |
| SPAG6 | 9576 | NM_001253855; XM_005252646; XM_005252645; NM_172242; NM_001253854; NM_012443 |
| HGFAC | 3083 | NM_001297439; NM_001528 |
| CNTN6 | 27255 | NM_001289081; NM_001349352; NM_001349356; XM_017006174; NM_001349361; XM_011533591; NM_001349358; NM_014461; NM_001289080; NM_001349353; NM_001349359; XM_011533590; NM_001349350; NM_001349357; NM_001349354; XR_940415; NM_001349351; NM_001349355; NM_001349360; XM_017006171; XM_017006172; XM_017006177; NM_001349362 |
| LCN2 | 3934 | NM_005564 |
| AKR1B10 | 57016 | XR_927491; XM_011516416; XM_011516417; NM_020299 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| NKX2-4 | 644524 | NM_033176 |
| Chromophobe_Renal_Cell_Carcinoma | | |
| REG1A | 5967 | NM_002909 |
| PADI3 | 51702 | NM_016233; XM_011541571; XM_017001463; XM_011541572 |
| MUC12 | 10071 | NM_001164462 |
| AVPR1B | 553 | NM_000707 |
| CTSE | 1510 | XM_011509245; NM_001910; NM_148964; XM_011509244; NM_001317331 |
| KRT6A | 3853 | NM_005554 |
| KRT6B | 3854 | NM_005555 |
| SLC17A2 | 10246 | XM_006714951; XM_017010160; XM_006714949; XM_006714950; NM_001286123; NM_005835; XM_017010159; NM_001286125 |
| HAVCR1 | 26762 | XM_017009339; XM_024446021; XM_024446023; XM_024446020; XM_024446024; NM_001308156; XM_024446019; XM_011534515; NM_001173393; NM_012206; NM_001099414; XM_024446022 |
| KRT6C | 286887 | NM_173086 |
| TMEM196 | 256130 | NM_001366626; NM_001366628; XM_017011929; NM_001366627; NM_152774; NM_001363562; XM_017011928; NM_001366625 |
| CDH6 | 1004 | NM_004932; NM_001362435; XM_017008910; XM_011513921; XR_001741972 |
| PSORS1C2 | 170680 | NM_014069 |
| LYZL1 | 84569 | XR_428650; XM_017016791; NM_032517; XM_005252627 |
| KRT33B | 3884 | NM_002279 |
| C4orf51 | 646603 | XM_024454188; XR_002959750; XR_002959751; XR_002959755; XR_002959756; XM_024454189; XR_002959749; XR_002959752; NM_001080531; XM_024454190; XR_002959748; XR_002959746; XR_002959747; XR_002959753; XR_002959754 |
| PSG5 | 5673 | NM_001130014; XM_011527132; NM_002781; XM_017027003 |
| UMODL1 | 89766 | XM_017028508; NM_001199527; XM_017028507; NM_001004416; NM_001199528; NM_173568; XM_011529797 |
| DEFB132 | 400830 | NM_207469 |
| PIP | 5304 | NM_002652 |
| DBX1 | 120237 | NM_001029865 |
| SLC6A2 | 6530 | XM_011523295; XM_011523297; XR_933403; XM_011523299; XM_011523300; NM_001172502; NM_001043; NM_001172501; XM_006721263; XM_011523298; NM_001172504; XM_011523296 |
| SPSB4 | 92369 | XM_017007509; XR_924215; XR_924216; NM_080862 |
| ATP6V0D2 | 245972 | NM_152565 |
| RGS8 | 85397 | XM_011510089; XM_017002634; NM_001387848; XM_017002631; NM_001387849; NM_001369564; NM_001387847; XM_017002632; NM_001102450; NM_033345; XM_011510090; XM_011510091 |
| FOXI1 | 2299 | XR_941092; NM_012188; NM_144769 |
| CLEC2L | 154790 | XM_017011770; NM_001353368; NM_001080511 |
| AMTN | 401138 | NM_001286731; NM_212557 |
| Glioblastoma | | |
| TCEAL2 | 140597 | NM_080390 |
| RBP1 | 5947 | NM_002899; NM_001130992; NM_001130993; NM_001365940 |
| CBLN1 | 869 | NM_004352 |
| FBXO17 | 115290 | NR_104026; NM_148169; NM_024907 |
| CLEC2B | 9976 | NM_005127 |
| ATOH8 | 84913 | XM_006712122; XM_011533139; XR_939732; XR_001739003; NM_032827; XR_939733; XR_939731 |
| TSTD1 | 100131187 | NM_001113207; NM_001113205; NM_001113206 |
| SNAP91 | 9892 | XM_017011576; XM_024446600; NM_001376676; NM_001376683; NM_001376689; NM_001376690; NM_001376698; NM_001376700; NM_001376710; NM_001376715; NM_001376739; NR_164846; XM_005248770; XM_006715615; XM_011536276; XM_017011575; XM_017011579; |

TABLE 3-continued

Genes associated with molecular categories.

| Gene | NCBI Gene ID | NCBI Accession Number(s) |
|---|---|---|
| | | XM_017011580; XM_024446599; NR_026669; NM_001256717; NM_001376677; NM_001376687; NM_001376701; NM_001376706; NM_001376713; NM_001376716; NM_001376723; NM_001376736; XM_017011558; XM_017011564; XM_017011566; XM_017011570; NM_001376675; NM_001256718; NM_001376680; NM_001376688; NM_001376694; NM_001376707; NM_001376708; NM_001376711; NM_001376740; XM_017011567; XM_017011590; NM_001376678; NM_001376691; NM_001376705; NM_001376738; NR_164843; XM_011536266; XM_011536269; XM_011536271; XM_011536275; XM_017011562; XM_017011571; XM_017011574; XM_017011582; XM_017011583; XM_017011584; NM_001242792; NM_001363677; NM_001376686; NM_001376712; NM_001376719; NM_001376721; NM_001376731; NM_001376741; XM_011536273; XM_017011559; XM_017011565; XM_017011581; XM_017011585; XM_017011587; XM_017011589; NM_001242794; NM_001376679; NM_001376695; NM_001376696; NM_001376697; NM_001376702; NM_001376709; NM_001376717; NM_001376728; NR_164844; XM_017011569; XM_017011572; XM_017011573; XM_017011577; XM_017011586; NM_001242793; NM_001376681; NM_001376684; NM_001376685; NM_001376692; NM_001376693; NM_001376699; NM_001376703; NM_001376704; NM_001376714; NM_001376720; NM_001376726; NM_001376734; NM_001376737; NM_001376742; NM_014841; NR_164845; XM_011536265; XM_017011557; XM_017011560; NM_001376682; NM_001376718; NM_001376733; NM_001376735 |
| SNX22 | 79856 | NM_024798; XM_005254677; XM_017022581; NR_073534 |
| NDC80 | 10403 | NM_006101 |
| MEOX2 | 4223 | NM_005924 |
| LUZP2 | 338645 | NM_001252008; XM_017017648; XR_930864; NM_001252010; XM_011520056; XM_017017649; NM_001009909 |
| SUSD5 | 26032 | XM_005265034; XM_017006137; NM_015551 |
| ASF1B | 55723 | NM_018154 |
| CARD16 | 114769 | NM_001394580; NM_052889; XM_011542583; NM_001017534 |
| SH3GL2 | 6456 | NM_003026; XR_001746364; XM_011518005 |
| KLRC2 | 3822 | NM_002260 |
| AURKA | 6790 | NM_001323304; NM_001323303; NM_198435; NM_198437; XM_024451974; NM_198433; NM_198434; NM_198436; XM_017028034; XM_017028035; NM_001323305; NM_003600 |
| TNFAIP6 | 7130 | NM_007115 |
| FUT9 | 10690 | XM_011535383; XM_011535385; XM_017010188; NM_006581; XM_017010190 |
| TUBA1C | 84790 | NM_001303114; NM_032704; NM_001303116; NM_001303117; NM_001303115 |
| HDAC4 | 9759 | XM_011512219; XM_011512225; NM_001378415; XM_011512218; XM_017005394; XM_006712879; XM_011512224; XM_017005395; NM_001378416; NM_006037; XM_011512223; XM_011512227; NM_001378414; XM_011512220; XM_011512222; XM_011512230; XM_024453257; XM_011512217; XM_011512226; NM_001378417; XM_006712877; XM_006712880 |
| OPHN1 | 4983 | XM_006724653; XM_011530961; XM_005262270; XM_017029555; NM_002547 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| CRTAC1 | 55118 | NM_018058; XM_017016367; XM_005269938; XM_011539917; NM_001206528; XM_017016366 |
| SLC22A18 | 5002 | NM_002555; NM_183233; XM_011520142; NM_001315501; XM_011520141; NM_001315502 |
| SSTR1 | 6751 | NM_001049 |
| HMX1 | 3166 | NM_018942; NM_001306142 |
| GDF15 | 9518 | XM_024451789; NM_004864 |
| NALCN | 259232 | XM_017020537; XM_011521067; XM_011521069; NM_001350748; NM_052867; NM_001350751; NM_001350749; XM_017020536; XM_024449336; NM_001350750 |
| GABRG1 | 2565 | NM_173536; XM_017007990 |
| PHYHIPL | 84457 | XM_017016783; XM_017016782; XM_011540275; XM_011540276; NM_032439; NM_001143774 |
| TAGEN2 | 8407 | NM_003564; NM_001277223; NM_001277224 |
| PPM1L | 151742 | NM_001317911; NM_001317912; NR_134243; XM_011512440; NM_139245 |
| OCIAD2 | 132299 | NM_001014446; NM_152398; NM_001286773; NR_104589; NM_001286774 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| PDPN | 10630 | NM_001006625; NM_198389; NM_001385053; NM_001006624; XM_006710295; NM_006474; NM_013317; XM_024451404 |
| TOM1L1 | 10040 | XM_017024002; XR_002957936; NM_001321173; NM_001321175; NM_001321174; XR_243612; NM_001321176; NM_005486; XR_001752397 |
| NTNG2 | 84628 | XM_011519105; XM_011519099; XM_011519094; XM_011519097; XM_011519098; NM_032536; XM_011519096; XM_011519100; XM_011519108; |

TABLE 3-continued

| Gene | NCBI Gene ID | NCBI Accession Number(s) |
|---|---|---|
| Genes associated with molecular categories. | | |
| | | XM_011519112; XM_011519104; XM_011519113; XM_017015213; XM_011519102; XM_011519106; XM_011519107; XM_017015216; XM_011519110; XM_017015212; XM_017015215; XM_006717304; XM_011519103; XM_011519109; XM_017015214 |
| PKIB | 5570 | XM_011535937; NM_181795; XM_011535930; XM_011535931; XM_011535935; XM_011535936; NM_001270393; NM_032471; XM_011535932; NM_001270395; XM_011535933; NM_001270394; NM_181794 |
| SHISA7 | 729956 | NM_001145176; NM_175908 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| REPS2 | 9185 | XM_011545605; XM_024452479; XM_011545604; XM_005274625; XM_011545603; XM_005274626; XM_011545607; XM_024452478; XM_017029955; XM_017029956; NM_001080975; NM_004726; XM_017029958; XR_001755742; XM_011545606; XM_011545609; XM_017029957 |
| ATP6V1G2 | 534 | NM_130463; NM_138282; NM_001204078 |
| DIRAS3 | 9077 | NM_004675 |
| SOX8 | 30812 | NM_014587 |
| FCGBP | 8857 | NM_003890 |
| TIMP1 | 7076 | NM_003254; XM_017029766 |
| CSDC2 | 27254 | NM_014460 |
| DDIT4L | 115265 | NM_145244 |
| LGALS3 | 3958 | NM_001357678; NR_003225; NM_002306; NM_001177388 |
| G0S2 | 50486 | NM_015714 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| Astrocytoma | | |
| RBP1 | 5947 | NM_002899; NM_001130992; NM_001130993; NM_001365940 |
| FBXO17 | 115290 | NR_104026; NM_148169; NM_024907 |
| HLF | 3131 | NM_002126; XM_011524705; XR_002957996; NM_001330375; XM_005257269 |
| CNTN3 | 5067 | XM_017006508; NM_020872; NM_001393376; XM_017006509; XM_011533768 |
| TMEM158 | 25907 | NM_015444 |
| CACNG2 | 10369 | XM_017028531; NM_006078; NM_001379051; NR_166440 |
| IRX2 | 153572 | NM_033267; XR_001742016; XM_024454379; NM_001134222; XM_011513979 |
| MEOX2 | 4223 | NM_005924 |
| LSP1 | 4046 | NM_001242932; NM_001013255; NM_001289005; NM_001013254; NM_002339; NM_001013253 |
| LUZP2 | 338645 | NM_001252008; XM_017017648; XR_930864; NM_001252010; XM_011520056; XM_017017649; NM_001009909 |
| ASF1B | 55723 | NM_018154 |
| LYZ | 4069 | NM_000239 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| CTSC | 1075 | NM_001114173; NM_148170; NM_001814 |
| GABBR1 | 2550 | XM_011514455; XM_006715047; XM_024446392; NM_001319053; NM_001470; XM_011514453; XR_001743302; NM_021903; XM_005248982; NM_021904; NM_021905; XR_001743303 |
| PBK | 55872 | NM_018492; NM_001278945; NM_001363040 |
| TUBA1C | 84790 | NM_001303114; NM_032704; NM_001303116; NM_001303117; NM_001303115 |
| PYGL | 5836 | NM_002863; NM_001163940 |
| MARCH4 | 57574 | NM_020814 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| RASL10A | 10633 | XM_011529821; NM_001007279; XM_011529822; XM_011529823; NM_006477 |
| UBE2T | 29089 | NM_001310326; NM_014176 |
| SSTR1 | 6751 | NM_001049 |

TABLE 3-continued

Genes associated with molecular categories.

| Gene | NCBI Gene ID | NCBI Accession Number(s) |
|---|---|---|
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| PHYHIPL | 84457 | XM_017016783; XM_017016782; XM_011540275; XM_011540276; NM_032439; NM_001143774 |
| PPM1L | 151742 | NM_001317911; NM_001317912; NR_134243; XM_011512440; NM_139245 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| STOX1 | 219736 | NM_001130162; NM_001130161; NM_001130160; NM_152709; XM_011539454; NM_001130159 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FKBP11 | 51303 | NM_001143782; NM_016594; NM_001143781 |
| GPX7 | 2882 | NM_015696 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| CLIC1 | 1192 | NM_001288; NM_001287593; NM_001287594 |
| ATP6V1G2 | 534 | NM_130463; NM_138282; NM_001204078 |
| RIMS2 | 9699 | XM_017014008; XM_017014028; XM_024447342; NM_001100117; NM_001348487; NM_001348496; NM_001348503; XM_005251106; XM_017014014; XM_017014019; XM_017014027; XM_024447344; XM_024447345; NM_001348489; NM_001348491; NM_001348505; NM_001348508; NM_001348509; XM_006716698; XM_017014021; NM_014677; XM_017014010; XM_017014022; XM_024447343; NM_001348499; NM_001395653; NM_001395654; XM_011517398; XM_017014009; XM_017014011; XM_017014016; XM_017014024; NM_001282881; NM_001348490; NM_001348497; NM_001348495; NM_001348498; NR_145710; XM_011517395; XM_017014007; NM_001282882; NM_001348484; NM_001348492; NM_001348494; NM_001348500; NM_001348501; NM_001348502; NM_001348504; XM_005251107; XM_017014012; XM_017014015; XM_017014034; XM_024447347; NM_001348488; NM_001348506; NR_145711; XM_017014006; XM_017014017; XM_017014023; XM_017014036; XM_024447346; NM_001348485; NM_001348486; NM_001348493; NM_001348507; NM_001395652 |
| TJP2 | 9414 | XM_011519206; NM_001369871; NM_001369872; XM_011519208; XM_011519209; NM_001369870; NM_004817; XM_011519207; NM_001369874; NM_001170630; NM_001369875; XM_011519204; NM_001170415; NM_001170416; NM_001170414; NM_001369873; NM_201629 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| RGS9 | 8787 | NM_001081955; NM_003835; NM_001165933 |
| FCGBP | 8857 | NM_003890 |
| APOC4-APOC2 | 100533990 | NR_037932 |
| TIMP1 | 7076 | NM_003254; XM_017029766 |
| NTSR2 | 23620 | NM_012344; XM_005246156; XM_006711877; XM_006711876; XM_017003738 |
| CA12 | 771 | NM_001218; NR_135511; NM_206925; NM_001293642 |
| JPH3 | 57338 | NM_001271604; NR_073379; NM_001271605; NM_020655 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| DDIT4L | 115265 | NM_145244 |
| RARRES2 | 5919 | XM_017012491; NM_002889 |
| MDK | 4192 | NM_001012334; XM_011520116; XM_017017764; NM_001270550; NM_001270551; NM_001012333; NM_001270552; NM_002391; NR_073039 |

TABLE 3-continued

| Gene | NCBI Gene ID | NCBI Accession Number(s) |
|---|---|---|
| | | Genes associated with molecular categories. |
| FPR1 | 2357 | NM_002029; NM_001193306 |
| CD58 | 965 | XM_017002869; NM_001779; NM_001144822; NR_026665 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| | | Oligodendroglioma |
| ZNF488 | 118738 | NM_153034; XM_006717617; XM_024447789; XM_017015643; NM_001346932; NM_001346933; NM_001346934; XM_011539244; NM_001346936; NM_001346935 |
| RBP1 | 5947 | NM_002899; NM_001130992; NM_001130993; NM_001365940 |
| WNT7B | 7477 | XM_011530366; NM_058238 |
| SLC7A14 | 57709 | NM_020949; NM_175917 |
| HLF | 3131 | NM_002126; XM_011524705; XR_002957996; NM_001330375; XM_005257269 |
| CACNG2 | 10369 | XM_017028531; NM_006078; NM_001379051; NR_166440 |
| SVOP | 55530 | NM_018711 |
| KCNK3 | 3777 | NM_002246; XM_005264293 |
| SUSD5 | 26032 | XM_005265034; XM_017006137; NM_015551 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| HRH3 | 11255 | NM_007232; XM_005260266; XM_017027623 |
| MYH7 | 4625 | XM_017021340; NM_000257 |
| MYT1 | 4661 | NM_004535 |
| GPR158 | 57512 | NM_020752; XM_017016452; XR_930512 |
| PYGL | 5836 | NM_002863; NM_001163940 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| VSIG4 | 11326 | NM_007268; NM_001184830; NM_001184831; XM_017029251; NM_001100431; NM_001257403 |
| UPP1 | 7378 | XM_011515513; XM_011515512; NM_001287426; NR_109837; XM_005249838; NM_001287428; NM_001287430; XM_011515515; NM_001362774; NM_001287429; NM_181597; XM_011515514; NM_003364 |
| PDZD4 | 57595 | NM_001303513; NM_001303512; NM_001303516; NM_001303515; NM_001303514; NM_032512 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| KCNJ9 | 3765 | NM_004983 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| STOX1 | 219736 | NM_001130162; NM_001130161; NM_001130160; NM_152709; XM_011539454; NM_001130159 |
| BATF3 | 55509 | XR_921869; XR_001737289; XM_017001683; NM_018664 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FAM222A | 84915 | XM_006719654; XM_017020055; NM_032829; XM_024449229 |
| SCRT1 | 83482 | NM_031309; XM_024447291 |
| GPX7 | 2882 | NM_015696 |
| DIRAS3 | 9077 | NM_004675 |
| ATP6V1G2 | 534 | NM_130463; NM_138282; NM_001204078 |
| EIF3CL | 728689 | NM_001317857; NM_001099661; XM_017023620; XM_017023621; NM_001317856 |
| FCGR2A | 2212 | NM_001136219; NM_021642; XM_011509287; XM_024454040; XM_017000664; XM_017000665; XM_017000663; XR_001737042; XM_017000666; XM_011509290; XM_011509291; XM_024454041; NM_001375296; NM_001375297 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |

TABLE 3-continued

| Gene | NCBI Gene ID | NCBI Accession Number(s) |
|---|---|---|
| | | Genes associated with molecular categories. |
| PRLHR | 2834 | NM_004248 |
| FCGBP | 8857 | NM_003890 |
| KLHDC8A | 55220 | NM_001271863; NM_001271865; XM_024448121; NM_018203; NM_001271864 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| BRINP1 | 1620 | NM_014618 |
| CD58 | 965 | XM_017002869; NM_001779; NM_001144822; NR_026665 |
| RDH5 | 5959 | NM_001199771; NM_002905 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| EPN2 | 22905 | NM_001102664; NM_148921; NM_014964 |
| | | Basal_Breast_Cancer |
| CDH6 | 1004 | NM_004932; NM_001362435; XM_017008910; XM_011513921; XR_001741972 |
| ESRI | 2099 | XM_011535545; XM_017010378; XM_017010382; XR_001743223; XR_002956266; NM_001385568; XM_017010381; NM_001122741; NM_001328100; NM_001385570; XM_006715375; XM_017010383; NM_001385572; XM_011535547; XM_011535549; XM_017010377; NM_001385571; XM_017010380; NM_000125; NM_001122740; NM_001122742; NM_001291230; NM_001291241; XM_011535543; XM_017010379; NM_001385569 |
| SULT1C3 | 442038 | NM_001008743; XM_017004155; NM_001320878; XM_017004153; XM_017004154 |
| WNT10A | 80326 | XM_011511930; XM_011511929; NM_025216 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| CTCFL | 140690 | NM_001269041; NM_001269055; NM_001386993; NR_170377; NM_001269054; NM_080618; NR_072975; NM_001269042; NM_001269044; NM_001269047; NM_001269043; NM_001269045; NM_001269051; NM_001386994; NM_001269040; NM_001269048; NM_001269050; NM_001386997; NM_001269052; NM_001386995; NM_001386996; NM_001269046; NM_001269049 |
| UGT2B11 | 10720 | XM_011531550; XM_017007660; NM_001073 |
| KRT16 | 3868 | NM_005557 |
| TFF3 | 7033 | NM_003226 |
| CCL19 | 6363 | NM_006274 |
| DNALI1 | 7802 | NM_003462 |
| EN1 | 2019 | NM_001426 |
| S100B | 6285 | NM_006272; XM_017028424 |
| BPI | 671 | XM_024451972; NM_001725 |
| SERHL2 | 253190 | NM_014509; NR_104301; XR_244363; NR_104300; NM_001284334; XM_024452196; XM_017028739; XM_024452197; XR_001755198 |
| UBXN10 | 127733 | XM_005245742; NM_152376; XM_011540699 |
| SLC44A4 | 80736 | NM_001178045; NM_001178044; NM_025257 |
| ROPN1 | 54763 | NM_001394218; NM_001317775; NR_133919; NR_133916; NR_133917; NM_001394219; NM_001317774; NM_001394217; NM_017578; NR_133918; NR_172091 |
| SPINK8 | 646424 | NM_001080525; XM_017007046; XM_024453712; XR_002959568 |
| CT83 | 203413 | NM_001017978 |
| ACTL8 | 81569 | NM_030812; XM_011542212 |
| MIA | 8190 | NM_006533; NM_001202553 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| GABRP | 2568 | XM_005265872; NM_001291985; NM_014211; XM_024446012 |
| TMEM246 | 84302 | NM_001303107; NM_001303108; NM_032342; XM_024447701; NM_001371233 |
| C1orf64 | 149563 | NM_178840 |
| SPON1 | 10418 | NM_006108 |
| KRT6B | 3854 | NM_005555 |
| KRT79 | 338785 | NM_175834 |
| KCNT1 | 57582 | XM_017014932; XM_017014933; NM_020822; XM_017014931; XM_011518877; XM_011518878; XM_011518879; NM_001272003; XM_011518880; XM_011518881; XM_024447617; XM_024447618 |
| SHC4 | 399694 | NM_203349; XM_005254375 |
| HORMAD1 | 84072 | NM_001199829; NM_032132; XM_011510054 |
| LRRC31 | 79782 | XM_011513158; XM_011513159; XM_011513160; NM_001277127; NM_001277128; NM_024727; XM_017007204 |
| NRTN | 4902 | NM_004558 |
| C1QL4 | 338761 | NM_001008223; XM_011538270 |
| TLX1 | 3195 | NM_001195517; XM_011539744; XM_011539745; NM_005521 |
| CLDN8 | 9073 | NM_199328; NM_012132 |
| MGAM2 | 93432 | NM_001293626; NM_001008748; XM_011516692; XM_011516694; NR_003715; XM_024446997; XM_011516693; XR_927547; NR_003717 |
| ST6GALNAC1 | 55808 | NM_018414; XR_002958047; XM_017024842; XM_017024844; NM_001289107; XM_011524995; XM_011524996; XM_017024843; XR_001752559; NR_110309 |

TABLE 3-continued

Genes associated with molecular categories.

| Gene | NCBI Gene ID | NCBI Accession Number(s) |
|---|---|---|
| GFRA3 | 2676 | NM_001496 |
| MAGEA3 | 4102 | XM_011531161; XM_005274676; XM_006724818; XM_011531160; NM_005362 |
| PRR15 | 222171 | NM_001329997; NM_001329996; NM_175887; XM_011515198; XM_011515199 |
| IGF2 | 3481 | NM_001291862; NM_001291861; NM_000612; NM_001007139; NM_001127598 |
| LY6D | 8581 | NM_003695 |
| TPSG1 | 25823 | NM_012467; XM_011522447; XM_011522446 |
| TAT | 6898 | NM_000353 |
| SMOC1 | 64093 | NM_001034852; NM_022137; XM_005267996; XM_005267995 |
| MT1H | 4496 | NM_005951 |
| REEP6 | 92840 | NM_138393; NM_001329556 |
| FOXA1 | 3169 | NM_004496; XM_017021246 |
| IL12RB2 | 3595 | NR_047584; XM_011541384; XM_005270827; XM_006710617; NM_001374259; XM_011541383; NM_001258215; NM_001258216; XM_017001204; NM_001258214; NM_001319233; XM_005270828; XM_017001203; NM_001559; NR_047583 |
| ART3 | 419 | NM_001377183; XM_017008210; XM_024454058; NM_001377173; NM_001377180; XM_024454052; XM_024454061; XM_024454062; XR_002959732; NM_001130017; NM_001377181; XM_017008208; XR_002959733; NM_001377174; XM_024454051; NM_001377179; XM_024454050; XM_024454053; XM_024454054; XM_024454059; XM_024454063; NM_001377177; NM_001377178; NM_001377182; XM_024454056; NM_001179; NM_001377176; XM_017008206; NM_001130016; NM_001377175; NM_001377184; NM_001377185 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| LOR | 4014 | NM_000427; XM_024447049 |
| GRIK1 | 2897 | NM_001320618; NM_001320616; XM_005260944; NM_001320630; NM_000830; XR_001754829; NM_001320621; NM_001393425; NM_001393426; NM_001330993; NM_001330994; NM_001393424; NM_175611 |
| FDCSP | 260436 | NM_152997 |
| PKP1 | 5317 | NM_000299; NM_001005337 |
| C6orf15 | 29113 | NM_014070 |
| AADAC | 13 | NM_001086; XM_005247104 |
| PGR | 5241 | XM_011542869; NM_001271161; NR_073142; NM_000926; XM_006718858; NM_001202474; NM_001271162; NR_073141; NR_073143 |
| ORM2 | 5005 | NM_000608 |
| ROPN1B | 152015 | XM_006713513; NM_001012337; XM_005247138; NM_001308313 |
| TBC1D9 | 23158 | NM_015130 |
| NPAS3 | 64067 | XM_005267991; NM_001394989; XM_011537069; XM_017021582; XM_017021584; XM_017021585; XM_017021587; NM_022123; XM_011537067; XM_011537071; NM_001165893; NM_001394988; NM_173159; XM_017021583; XM_017021586; XM_017021588; XM_005267992; NM_001164749 |
| HMGCS2 | 3158 | NM_001166107; XM_011541313; NM_005518 |
| NPR1 | 4881 | XM_017001374; XM_005245218; NM_000906 |
| ELOVL2 | 54898 | NM_017770; XM_011514717; XM_011514716; XM_017010985 |
| CA12 | 771 | NM_001218; NR_135511; NM_206925; NM_001293642 |
| CT62 | 196993 | NR_168259; NM_001102658; NR_168260 |
| | | Non_Basal_Breast_Cancer |
| CHODL | 140578 | XM_017028273; NM_001204174; NM_024944; XM_011529453; NM_001204176; NM_001204175; NM_001204177; XM_011529457; NM_001204178 |
| MSLN | 10232 | NM_001177355; NM_005823; NM_013404 |
| CST4 | 1472 | NM_001899 |
| CEACAM6 | 4680 | NM_002483; XM_011526990 |
| OVGP1 | 5016 | NM_002557 |
| FOLR1 | 2348 | NM_000802; NM_016729; NM_016730; NM_016725; NM_016724 |
| LRRTM1 | 347730 | NM_178839; XM_017003987; XM_017003986 |
| TTC6 | 319089 | XM_017021257; XM_011537431; XM_017021254; XM_024449560; XM_011537430; XM_011537432; XR_943762; NM_001310135; XM_017021256; NM_001368142; XM_017021255; XR_001750287; NM_001007795 |
| SPRR2A | 6700 | NM_005988 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| WNT10A | 80326 | XM_011511930; XM_011511929; NM_025216 |
| PKHD1L1 | 93035 | XM_017013970; XM_017013969; XM_011517371; XM_017013971; XM_017013972; XM_017013973; XM_017013974; NM_177531 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| SMYD1 | 150572 | NM_198274; NM_001330364 |
| DACT2 | 168002 | NM_001286350; NM_001286351; XM_011535507; NM_214462; NR_104425 |
| AKR7A3 | 22977 | XM_017000714; NM_012067; XM_011541046; XR_001737055 |
| HPX | 3263 | NM_000613 |

TABLE 3-continued

Genes associated with molecular categories.

| Gene | NCBI Gene ID | NCBI Accession Number(s) |
|---|---|---|
| S100B | 6285 | NM_006272; XM_017028424 |
| MAL | 4118 | NM_022438; NM_002371; NM_022440; NM_022439 |
| D4S234E | 27065 | NM_001287763; NM_001287764; NM_001040101; NR_167932; NM_001382227; NM_001382228; NR_167933; NM_014392 |
| SLC44A4 | 80736 | NM_001178045; NM_001178044; NM_025257 |
| SPINK8 | 646424 | NM_001080525; XM_017007046; XM_024453712; XR_002959568 |
| THSD4 | 79875 | NM_024817; NM_001286429; XM_017022584; NM_001394532; XM_017022586; XM_011522044; XM_017022585; XM_011522043; XM_017022582; XM_017022583 |
| TBX5 | 6910 | NM_181486; NM_080717; NM_000192; XM_017019912; NM_080718 |
| NEK10 | 152110 | XM_006712998; XM_011533415; XM_017005765; XR_001740034; NM_001394966; XM_017005768; NM_001394968; XM_024453374; NM_001031741; NM_001394965; NM_001394967; NM_001394971; XM_006712997; XM_006713002; XM_011533413; XM_011533414; NM_001394970; NM_001394964; NM_001394969; XM_006712999; XM_017005762; XM_017005764; NM_001394963; NM_199347; XM_017005763; XM_017005773; XM_024453373; NM_001304384; XM_006713001; XM_017005774; NM_152534 |
| TFAP2B | 7021 | XM_017011235; XM_017011233; NM_003221; XM_011514837; XM_017011234 |
| MB | 4151 | NM_001382810; NM_001382809; NM_203378; NM_001362846; NM_001382812; NM_203377; NM_001382811; NM_005368; NM_001382813 |
| OCA2 | 4948 | XM_017022264; XM_017022257; XM_017022258; XM_017022262; XM_017022255; XM_017022263; XM_011521640; XM_017022256; XM_017022261; XR_001751294; NM_001300984; XM_017022265; NM_000275; XM_017022259; XM_017022260 |
| CCNA1 | 8900 | XM_011535294; XM_011535296; NM_001111047; XM_011535295; NM_001111046; NM_003914; NM_001111045 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| GABRP | 2568 | XM_005265872; NM_001291985; NM_014211; XM_024446012 |
| C1orf64 | 149563 | NM_178840 |
| MSMB | 4477 | NM_138634; NM_002443 |
| PSAT1 | 29968 | NM_021154; NM_058179 |
| CPA2 | 1358 | NM_001869 |
| SLC3OA8 | 169026 | XM_024447083; NM_001172813; NM_001172814; NM_001172815; NM_001172811; NM_173851 |
| NRTN | 4902 | NM_004558 |
| ZG16B | 124220 | NM_145252 |
| ABCC11 | 85320 | XM_017023802; NM_001370496; NM_032583; XM_017023798; XM_011523397; XM_017023797; XM_017023800; XM_017023803; XM_017023799; XM_017023801; NM_001370497; XM_011523398; NM_145186; XM_024450475; XR_001752012; NM_033151 |
| MGAM2 | 93432 | NM_001293626; NM_001008748; XM_011516692; XM_011516694; NR_003715; XM_024446997; XM_011516693; XR_927547; NR_003717 |
| KCNH1 | 3756 | NM_172362; XM_017001246; NM_002238 |
| CALB2 | 794 | NM_007088; XR_002957842; NM_001740; NR_027910; NM_007087 |
| PGC | 5225 | NM_002630; NM_001166424 |
| FSIP1 | 161835 | XM_011521307; XM_017021972; XM_011521309; NM_152597; XM_011521305; NM_001324338; XM_011521311; XM_011521306 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| HMP19 | 51617 | NM_015980 |
| PRR15 | 222171 | NM_001329997; NM_001329996; NM_175887; XM_011515198; XM_011515199 |
| SERTM1 | 400120 | NM_203451 |
| MMP3 | 4314 | NM_002422 |
| POU3F3 | 5455 | NM_006236 |
| PCK1 | 5105 | NM_002591; XM_024451888 |
| CHAD | 1101 | XM_011524214; NM_001267 |
| SLITRK6 | 84189 | NM_032229 |
| SOX10 | 6663 | NM_006941 |
| TAT | 6898 | NM_000353 |
| PIP | 5304 | NM_002652 |
| F2RL2 | 2151 | NM_001256566; NM_004101 |
| MT1H | 4496 | NM_005951 |
| FOXAl | 3169 | NM_004496; XM_017021246 |
| KRT15 | 3866 | XM_017024614; XM_011524784; NM_002275 |
| TF | 7018 | NM_001063; NM_001354703; NM_001354704 |
| FAM196A | 642938 | XM_017016537; XM_017016538; XM_017016539; XM_005252694; XM_017016540; XM_017016541; XM_017016542; XM_017016543; NM_001039762 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |

TABLE 3-continued

| Gene | NCBI Gene ID | NCBI Accession Number(s) |
|---|---|---|
| | | Genes associated with molecular categories. |
| PRSS33 | 260429 | NM_001385462; NM_001385463; NM_001385464; NM_152891; NR_169625 |
| SCX | 642658 | XM_006716616; NM_001080514; NM_001008271 |
| WNT6 | 7475 | NM_006522 |
| SIAH3 | 283514 | NM_198849 |
| ROPN1B | 152015 | XM_006713513; NM_001012337; XM_005247138; NM_001308313 |
| HOXC13 | 3229 | NM_017410 |
| NPR1 | 4881 | XM_017001374; XM_005245218; NM_000906 |
| RASGEF1C | 255426 | NM_175062; NM_001031799 |
| LEMD1 | 93273 | XM_011510163; XM_011510162; XM_011510165; NM_001199052; XM_011510160; XM_011510161; XM_011510164; NR_037583; NM_001001552; NM_001199050; NM_001199051 |
| PRSS50 | 29122 | NM_013270 |
| | | Squamous_Cell_Carcinoma_of_the_Head_and_Neck |
| IGFBP6 | 3489 | NM_002178 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| SCGB1A1 | 7356 | NM_003357 |
| FGG | 2266 | NM_000509; NM_021870 |
| PLIN1 | 5346 | NM_002666; XM_005254934; NM_001145311 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| MMP13 | 4322 | NM_002427 |
| MYL1 | 4632 | NM_079422; NM_079420 |
| FCN3 | 8547 | NM_173452; NM_003665 |
| IRX4 | 50805 | NM_016358; NM_001278633; NM_001278632; NM_001278635; NM_001278634 |
| BPIFA1 | 51297 | NM_130852; NM_001243193; NM_016583 |
| PAX1 | 5075 | NM_006192; NM_001257096 |
| ADH1B | 125 | NM_001286650; NM_000668 |
| C4BPA | 722 | XM_005273252; NM_000715; XM_005273251 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| F2RL2 | 2151 | NM_001256566; NM_004101 |
| HOXA13 | 3209 | NM_000522 |
| PCSK2 | 5126 | NM_002594; NM_001201529; NM_001201528 |
| BMP8A | 353500 | XM_017001198; XM_006710616; XM_011541381; XM_011541382; XR_946642; XR_946640; XR_946641; NM_181809 |
| TBX4 | 9496 | XM_011525490; XM_011525491; NM_001321120; XM_011525495; NM_018488 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PGC | 5225 | NM_002630; NM_001166424 |
| RPE65 | 6121 | XM_017002027; NM_000329 |
| GSTM5 | 2949 | NM_000851; XM_005270785; XM_005270784 |
| MYH7 | 4625 | XM_017021340; NM_000257 |
| ATP1A2 | 477 | NM_000702 |
| KIF18B | 146909 | XM_011524389; NM_001264573; NM_001265577; XM_011524386; NM_001080443; XM_011524390; XM_011524388; XM_011524385; XM_011524387; XM_011524391 |
| SCARA5 | 286133 | NM_173833 |
| FILIP1 | 27145 | NR_110608; XM_011535756; NM_001289987; NM_001300866; XM_005248713; NM_015687; XM_005248715 |
| DCD | 117159 | NM_001300854; NM_053283 |
| SLURP1 | 57152 | NM_020427 |
| DLX1 | 1745 | NM_178120; NM_001038493 |
| WT1 | 7490 | NM_000378; NR_160306; NM_001367854; NM_001198551; NM_001198552; NM_024424; NM_024426; NM_024425 |
| TCF21 | 6943 | NM_003206; NM_198392 |
| EN1 | 2019 | NM_001426 |
| KRT14 | 3861 | NM_000526 |
| RPS4Y1 | 6192 | NM_001008 |
| TBX5 | 6910 | NM_181486; NM_080717; NM_000192; XM_017019912; NM_080718 |
| CDKN2A | 1029 | XR_929159; XM_011517676; XM_011517675; NM_001363763; NM_001195132; NM_058195; NM_000077; NM_058196; NM_058197; XM_005251343 |
| ALDH1A2 | 8854 | NM_001206897; NM_170697; NM_170696; NM_003888 |
| CFTR | 1080 | NM_000492 |

TABLE 3-continued

| Gene | NCBI Gene ID | NCBI Accession Number(s) |
|---|---|---|
| | | Genes associated with molecular categories. |
| AMY1A | 276 | NM_004038; NM_001008221 |
| NAV3 | 89795 | XM_017020172; NM_001024383; NM_014903; XM_011538944 |
| HPN | 3249 | NM_002151; NM_182983; XM_017026732; NM_001384133; XM_017026731; NM_001375441 |
| MKRN3 | 7681 | NM_005664 |
| SCN7A | 6332 | NM_002976; XM_006712680; XM_006712682; XM_011511615; XM_017004667; NR_045628 |
| ACTC1 | 70 | NM_005159 |
| MYOG | 4656 | NM_002479 |
| HOXB5 | 3215 | NM_002147 |
| PKMYT1 | 9088 | NM_001258451; NM_182687; NM_001258450; XM_011522735; XM_024450490; NM_004203; XM_011522734; XM_011522736 |
| HJURP | 55355 | XM_011511437; NM_001282962; NM_001282963; NM_018410 |
| HP | 3240 | NM_001126102; NM_005143; NM_001318138 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| DLL3 | 10683 | NM_016941; NM_203486 |
| CYP2B6 | 1555 | NM_000767 |
| SNTN | 132203 | NM_001080537; NM_001348756 |
| CRNN | 49860 | NM_016190 |
| HOXB8 | 3218 | NM_024016; XM_005257286; XM_017024564 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| IBSP | 3381 | NM_004967 |
| C7 | 730 | NM_000587 |
| COL10A1 | 1300 | XM_011535432; NM_000493; XM_011535433; XM_017010248; XM_006715333 |
| AJAP1 | 55966 | XM_011541787; NM_001042478; NM_018836; XM_011541786 |
| ADIPOQ | 9370 | NM_004797; NM_001177800 |
| | | Squamous_Cell_Lung_Carcinoma |
| C20orf85 | 128602 | NM_178456 |
| KLK10 | 5655 | XM_006723289; XM_005259061; NM_002776; NM_145888; NM_001077500; XM_017026993; XM_006723287; XM_005259062 |
| ACTC1 | 70 | NM_005159 |
| IGFBP6 | 3489 | NM_002178 |
| ADH1B | 125 | NM_001286650; NM_000668 |
| B4GALNT4 | 338707 | XM_017017654; XR_001747858; NM_178537 |
| C4BPA | 722 | XM_005273252; NM_000715; XM_005273251 |
| CENPM | 79019 | NM_001110215; NM_001304372; NM_024053; XM_011530368; NM_001304371; NM_001002876; NM_001304370; NM_001304373 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MYOG | 4656 | NM_002479 |
| CACNG1 | 786 | NM_000727 |
| HOXB5 | 3215 | NM_002147 |
| FABP4 | 2167 | NM_001442 |
| MMP11 | 4320 | NM_005940; NR_133013 |
| SCGB1A1 | 7356 | NM_003357 |
| RSPO1 | 284654 | XM_006710583; NM_001242909; NM_001242908; NM_001242910; NM_173640; NM_001038633 |
| LRRN4CL | 221091 | NM_203422 |
| ENDOU | 8909 | NM_001172439; NM_006025; NM_001172440 |
| MMP12 | 4321 | NM_002426 |
| GSTA1 | 2938 | XM_005249034; NM_001319059; NM_145740 |
| TNXB | 7148 | NM_001365276; NM_019105; NM_032470 |
| HP | 3240 | NM_001126102; NM_005143; NM_001318138 |
| KLHL41 | 10324 | NM_006063 |
| NEFL | 4747 | NM_006158 |
| TBX5 | 6910 | NM_181486; NM_080717; NM_000192; XM_017019912; NM_080718 |
| NKX2-1 | 7080 | NM_001079668; NM_003317 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| VPREB3 | 29802 | NM_013378 |
| TBX4 | 9496 | XM_011525490; XM_011525491; NM_001321120; XM_011525495; NM_018488 |
| TROAP | 10024 | XM_011537723; NM_005480; XR_944445; XM_011537724; XR_944446; NM_001100620; XM_006719181; NM_001278324 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |

TABLE 3-continued

| Genes associated with molecular categories. | | |
|---|---|---|
| Gene | NCBI Gene ID | NCBI Accession Number(s) |
| PAK7 | 57144 | XM_017027960; XM_017027964; XM_017027962; XM_017027963; XM_017027965; NM_177990; XM_017027961; NM_020341 |
| CASQ2 | 845 | NM_001232 |
| PGC | 5225 | NM_002630; NM_001166424 |
| AMY1C | 278 | NM_001346780; XM_017001058; NM_001008219 |
| COX6A2 | 1339 | NM_005205 |
| MUC7 | 4589 | NM_001145006; NM_152291; NM_001145007 |
| CLEC2L | 154790 | XM_017011770; NM_001353368; NM_001080511 |
| POU6F2 | 11281 | NM_007252; NM_001370959; NM_001166018 |
| ZNF280B | 140883 | XR_002958666; NM_080764; XM_011529897; XR_002958668; XR_002958667; NR_130642; NR_130643 |
| CRNN | 49860 | NM_016190 |
| SNTN | 132203 | NM_001080537; NM_001348756 |
| GREM2 | 64388 | XM_005273226; XM_011544249; NM_022469 |
| OGN | 4969 | NM_033014; NM_014057; NM_024416 |
| MYH7 | 4625 | XM_017021340; NM_000257 |
| KIF18B | 146909 | XM_011524389; NM_001264573; NM_001265577; XM_011524386; NM_001080443; XM_011524390; XM_011524388; XM_011524385; XM_011524387; XM_011524391 |
| PLA2G4F | 255189 | NM_213600; XR_931785; NR_033151; XR_931786 |
| LGSN | 51557 | XM_017010931; XM_017010929; XM_011535889; XM_011535892; NM_016571; XM_017010930; NM_001143940 |
| AHSG | 197 | NM_001354571; NM_001354572; NM_001622; NM_001354573 |
| UBE2C | 11065 | NM_001281742; NM_001281741; NM_181802; NM_181803; NR_104036; NR_104037; NM_007019; NM_181800; NM_181801; NM_181799 |
| DES | 1674 | NM_001927; NM_001382708; NM_001382710; NM_001382713; NM_001382709; NM_001382711; NM_001382712 |
| RNF223 | 401934 | NM_001205252 |
| MYL1 | 4632 | NM_079422; NM_079420 |
| C1orf116 | 79098 | XM_011509973; NM_001083924; XM_005273259; XM_006711530; NM_023938 |
| BMP5 | 653 | XM_011514817; NM_001329756; XM_024446524; NM_001329754; NM_021073 |
| SCARA5 | 286133 | NM_173833 |
| FCN3 | 8547 | NM_173452; NM_003665 |
| HPN | 3249 | NM_002151; NM_182983; XM_017026732; NM_001384133; XM_017026731; NM_001375441 |
| LOR | 4014 | NM_000427; XM_024447049 |
| LDB3 | 11155 | NM_001171610; NM_001368064; NM_007078; NM_001080115; NM_001080114; NM_001368068; NM_001080116; NM_001171611; NM_001368067; NM_001368063; NM_001368065; NM_001368066 |
| DHRS7C | 201140 | NM_001220493; NM_001105571 |
| CRISP3 | 10321 | NM_001368123; NM_006061; NM_001190986 |
| LY6D | 8581 | NM_003695 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| CNTNAP2 | 26047 | XM_017011950; NM_014141 |
| ANLN | 54443 | XM_017012355; NM_018685; NM_001284302; XM_006715746; XM_017012354; XM_017012356; NM_001284301; XM_006715747 |
| DCD | 117159 | NM_001300854; NM_053283 |
| C7 | 730 | NM_000587 |
| THBS4 | 7060 | XR_002956176; XM_017009798; NM_001306214; NM_003248; NM_001306213; XM_017009799; NM_001306212 |
| GPR87 | 53836 | NM_023915 |
| MYOT | 9499 | XM_017010060; XM_017010061; NM_001300911; NM_001135940; XM_017010062; NM_006790 |
| USP43 | 124739 | XM_011523640; XM_011523642; XM_011523641; XM_017024161; XM_017024160; XM_017024159; XM_011523639; NM_001267576; NM_153210; XM_017024162 |
| EMX1 | 2016 | XM_011532697; NM_001040404; NM_004097; XM_005264203 |
| SLURP1 | 57152 | NM_020427 |
| BPIFA1 | 51297 | NM_130852; NM_001243193; NM_016583 |
| KLK5 | 25818 | NM_001077492; XM_011526702; NM_001077491; XM_011526703; NM_012427 |
| GYLTL1B | 120071 | XM_011519891; NM_001300721; NM_001300722; XM_011519888; XM_006718141; XM_011519890; XM_006718140; XM_011519893; NM_152312; XM_005252787; XM_011519886; XM_011519889; XM_011519892; XM_017017173 |
| HAND2 | 9464 | NM_021973 |
| MYOC | 4653 | NM_000261 |
| MCEMP1 | 199675 | NM_174918 |
| DCC | 1630 | XM_011525843; XM_011525844; XM_017025570; NM_005215; XM_017025568; XM_017025569 |
| LRRC26 | 389816 | NM_001013653 |
| KLK13 | 26085 | NM_015596; NR_145464; NM_001348178; NR_145466; NR_145465; XR_935788; NR_145463; NM_001348177; NR_145467 |
| WT1 | 7490 | NM_000378; NR_160306; NM_001367854; NM_001198551; NM_001198552; NM_024424; NM_024426; NM_024425 |

TABLE 3-continued

| Genes associated with molecular categories. | | |
|---|---|---|
| Gene | NCBI Gene ID | NCBI Accession Number(s) |
| KRT4 | 3851 | NM_002272 |
| COL10A1 | 1300 | XM_011535432; NM_000493; XM_011535433; XM_017010248; XM_006715333 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| SGCG | 6445 | NM_000231; NM_001378245; NM_001378244; NM_001378246 |
| SCN7A | 6332 | NM_002976; XM_006712680; XM_006712682; XM_011511615; XM_017004667; NR_045628 |
| FEZF1 | 389549 | NM_001024613; XM_011516202; NM_001160264; XM_005250337 |
| SLCO4C1 | 353189 | XM_011543372; XM_011543370; NM_180991 |
| AJAP1 | 55966 | XM_011541787; NM_001042478; NM_018836; XM_011541786 |
| AMN | 81693 | XM_024449714; XM_011537203; NM_030943; XM_011537202 |
| SDR16C5 | 195814 | NM_001318049; NM_001318050; NM_138969; XM_011517479 |
| AQP4 | 361 | NM_001317387; NM_001364287; NM_001364286; NM_001317384; XM_011525942; NM_001650; NM_001364289; NM_004028 |
| CPNE7 | 27132 | NM_153636; XM_017023139; XM_011523000; XM_017023138; XM_017023140; XM_017023141; XM_011523001; NM_014427 |
| TCF21 | 6943 | NM_003206; NM_198392 |
| PTGER3 | 5733 | XM_011541810; NM_198718; NM_000957; NM_198712; NM_198713; NM_198720; NM_198714; NM_198719; NM_198717; NM_001126044; NM_198715; NR_028292; XR_946714; NM_198716; NR_028293; NR_028294 |
| Cervical_Squamous_Cell_Carcinoma | | |
| SALL1 | 6299 | NM_001127892; NM_002968 |
| MEOX2 | 4223 | NM_005924 |
| BCHE | 590 | NR_137636; NM_000055; NR_137635 |
| SYCP2 | 10388 | XM_011528488; XM_011528487; XM_011528493; XM_017027590; XM_011528490; XM_017027586; XM_017027591; NM_014258; XM_011528489; XM_017027589; XM_017027587; XM_017027588; XM_017027592 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| OLFM4 | 10562 | NM_006418 |
| SYNGR3 | 9143 | NM_004209 |
| SLC6A15 | 55117 | XM_011538525; NM_018057; NM_001146335; NM_182767 |
| ADAMTS20 | 80070 | XM_011538754; XM_017019979; NM_025003; NM_175851 |
| FA2H | 79152 | XM_011523319; XM_011523317; NM_024306 |
| PGR | 5241 | XM_011542869; NM_001271161; NR_073142; NM_000926; XM_006718858; NM_001202474; NM_001271162; NR_073141; NR_073143 |
| FOXL2 | 668 | NM_023067 |
| KRT81 | 3887 | NM_002281 |
| HOXA13 | 3209 | NM_000522 |
| KRT36 | 8689 | NM_003771 |
| KRT83 | 3889 | NM_002282 |
| RPS4Y1 | 6192 | NM_001008 |
| TBX5 | 6910 | NM_181486; NM_080717; NM_000192; XM_017019912; NM_080718 |
| ASF1B | 55723 | NM_018154 |
| E2F8 | 79733 | NM_001256372; XM_011520367; NM_001256371; NM_024680; XR_930907 |
| CASP14 | 23581 | NM_012114; XM_011527861 |
| MYOCD | 93649 | XM_005256863; NM_001378306; NM_001146312; NM_153604; NM_001146313; XM_017025342 |
| KIF4A | 24137 | NM_012310 |
| PDLIM3 | 27295 | NM_001114107; XR_938723; NM_001257963; XR_938724; NM_001257962; NR_047562; NM_014476; XR_001741206 |
| PAGE2B | 389860 | XM_017029513; XM_011530785; XM_011530786; XM_011530787; NM_001015038 |
| RPE65 | 6121 | XM_017002027; NM_000329 |
| POU6F2 | 11281 | NM_007252; NM_001370959; NM_001166018 |
| CDKN2A | 1029 | XR_929159; XM_011517676; XM_011517675; NM_001363763; NM_001195132; NM_058195; NM_000077; NM_058196; NM_058197; XM_005251343 |
| HOXB8 | 3218 | NM_024016; XM_005257286; XM_017024564 |
| ALDH1A2 | 8854 | NM_001206897; NM_170697; NM_170696; NM_003888 |
| HTR2B | 3357 | XM_005246520; NM_000867; XM_006712482; NM_001320758 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| NAV3 | 89795 | XM_017020172; NM_001024383; NM_014903; XM_011538944 |
| BARX1 | 56033 | NM_021570 |
| OR2B6 | 26212 | NM_012367 |
| SEMA3D | 223117 | XM_011515961; NM_152754; NM_001384901; NM_001384902; NM_001384900; NM_001384903 |

TABLE 3-continued

Genes associated with molecular categories.

| Gene | NCBI Gene ID | NCBI Accession Number(s) |
|---|---|---|
| DYNC1I1 | 1780 | NM_001135556; NM_004411; NM_001278422; NM_001278421; NM_001135557 |
| NAP1L2 | 4674 | NM_021963 |
| MYL1 | 4632 | NM_079422; NM_079420 |
| ANO1 | 55107 | XM_006718602; XM_006718605; XM_011545124; XM_011545129; XM_017017956; XM_006718604; NM_001378095; NM_001378096; XM_011545123; XM_011545127; XM_011545131; NM_001378097; NM_018043; NR_030691; NM_001378092; XM_011545126; NM_001378093; NM_001378094 |
| HOXA11 | 3207 | NM_005523 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| EIF1AY | 9086 | NM_004681; NM_001278612 |
| RBFOX3 | 146713 | XM_017024209; XM_017024211; XM_024450595; NM_001385812; NM_001385840; NM_001385844; NM_001385847; XM_011524366; XM_017024208; NM_001385805; NM_001385807; NM_001385843; NM_001385845; NM_001025448; NM_001082575; NM_001385804; NM_001385808; NM_001385813; NM_001385836; NM_001385817; NM_001385819; NM_001385823; NM_001385826; NM_001385827; NM_001385828; NM_001385829; NM_001385831; NM_001385833; NM_001385842; XM_011524360; XM_024450593; XM_024450596; NM_001350453; NM_001385809; NM_001385832; NM_001385834; NM_001385838; NM_001039904; XM_011524367; XM_024450592; NM_001385811; NM_001385824; NM_001385835; NM_001385837; NM_001385846; NM_001350451; NM_001385806; NM_001385810; NM_001385820; NM_001385825; NM_001385830; NM_001385839; NM_001385841; NM_001385814; NM_001385815; NM_001385816; NM_001385818; NM_001385821; NM_001385822 |
| RDM1 | 201299 | NM_001163124; NR_027996; NR_027999; XM_011524509; NM_001163122; NM_001163130; NM_001163121; NM_001163125; NR_027998; NM_001163120; NM_001034836; NM_001330194; NM_145654; NR_027997; NR_028000 |
| SCARA5 | 286133 | NM_173833 |
| KCNS1 | 3787 | XM_017027846; NM_002251; NM_001322799 |
| PIANP | 196500 | NM_001244014; NM_153685; NM_001244015; XM_011520926 |
| C1orf106 | 55765 | XM_011509754; XM_011509755; NM_001367289; NM_001367290; XM_011509756; NM_001142569; NM_018265 |
| HOXA10 | 3206 | NR_037939; NM_153715; NM_018951 |
| AIM1L | 55057 | NM_017977; XM_011541672; XM_011541673; XR_001737260; NM_001039775; XR_946681; XM_005245918 |
| LEFTY2 | 7044 | NM_003240; NM_001172425; XM_011544266 |
| IRX5 | 10265 | NM_005853; XM_011522809; NM_001252197 |
| TRDN | 10345 | NM_001251987; NM_001256020; NM_001256021; NM_006073; NM_001256022 |
| CNTNAP2 | 26047 | XM_017011950; NM_014141 |
| FOXA1 | 3169 | NM_004496; XM_017021246 |
| ADGRD1 | 283383 | NM_198827; XM_005253566; XM_011538204; XM_011538208; XM_011538212; NM_001330497; XM_011538205; XM_011538206; XM_011538207; XM_011538209; XM_011538210; XM_011538211 |
| PENK | 5179 | NM_006211; NM_001135690 |
| AKR1C2 | 1646 | NM_001354; NM_001321027; NM_001135241; NM_205845; NM_001393392 |
| MKRN3 | 7681 | NM_005664 |
| NMU | 10874 | NM_001292046; XM_011534368; XM_011534367; NM_001292045; NM_006681; NR_120489 |
| DIAPH3 | 81624 | XM_011535258; XM_006719876; XM_024449422; NM_001258367; NM_001258370; XR_941672; XM_011535265; XR_002957479; XR_002957480; NM_001258366; XM_017020789; XR_002957478; NM_001042517; NM_001258368; XM_011535263; XR_001749694; XR_002957477; NM_001258369; NM_030932 |
| MUC2 | 4583 | NM_002457 |
| ZIC5 | 85416 | NM_033132; NR_146224; NR_146225 |
| MYLPF | 29895 | NM_001324458; NM_013292; NM_001324459 |
| POLQ | 10721 | NM_199420; NM_006596 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |

TABLE 3-continued

| Gene | NCBI Gene ID | NCBI Accession Number(s) |
|---|---|---|
| | | Genes associated with molecular categories. |
| SMC1B | 27127 | NM_148674; XM_011530145; XR_244368; XM_011530144; NM_001291501 |
| WT1 | 7490 | NM_000378; NR_160306; NM_001367854; NM_001198551; NM_001198552; NM_024424; NM_024426; NM_024425 |
| EPHA7 | 2045 | NM_001288630; NM_001376467; NM_001288629; XM_017010366; NM_001376466; NM_001376471; NM_004440; XR_001743218; NM_001376465; NM_001376470; NR_164810; NM_001376468; NM_001376469 |
| TCF23 | 150921 | NM_175769; XM_005264159 |
| | | Colorectal_Adenocarcinoma |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |

TABLE 3-continued

Genes associated with molecular categories.

| Gene | NCBI Gene ID | NCBI Accession Number(s) |
|---|---|---|
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CEP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; |

TABLE 3-continued

Genes associated with molecular categories.

| Gene | NCBI Gene ID | NCBI Accession Number(s) |
|---|---|---|
| | | NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |

TABLE 3-continued

Genes associated with molecular categories.

| Gene | NCBI Gene ID | NCBI Accession Number(s) |
|---|---|---|
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |

TABLE 3-continued

| Genes associated with molecular categories. | | |
|---|---|---|
| Gene | NCBI Gene ID | NCBI Accession Number(s) |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456 |

TABLE 3-continued

| Genes associated with molecular categories. | | |
|---|---|---|
| Gene | NCBI Gene ID | NCBI Accession Number(s) |
| Stomach_Adenocarcinoma | | |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |

TABLE 3-continued

Genes associated with molecular categories.

| Gene | NCBI Gene ID | NCBI Accession Number(s) |
|---|---|---|
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |

TABLE 3-continued

Genes associated with molecular categories.

| Gene | NCBI Gene ID | NCBI Accession Number(s) |
|---|---|---|
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_OO 1752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |

TABLE 3-continued

| Genes associated with molecular categories. | | |
|---|---|---|
| Gene | NCBI Gene ID | NCBI Accession Number(s) |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; |

TABLE 3-continued

Genes associated with molecular categories.

| Gene | NCBI Gene ID | NCBI Accession Number(s) |
|---|---|---|
| | | XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456 |

TABLE 4

| DNA feature descriptions. | |
|---|---|
| DNA Feature Notation | DNA Feature Description |
| GENENAME_mut | Mutation in GENENAME. |
| GENENAME_hotspots | Hotspot present in the GENENAME. |
| GENENAME_p.LETTERNUMBER | Hotspot in GENENAME. present in protein LETTER at amino acid position NUMBER |
| CNA_NUMBER1_NUMBER2 | Normalized copy number of bin NUMBER2 on chromosome NUMBER1. |
| LOH_NUMBER1_NUMBER2 | LOH status of bin NUMBER2 on chromosome NUMBER1 |
| CNA_LETTER_NUMBER1 | LOH status of bin NUMBER2 on chromosome NUMBER1 |
| LOH_LETTER_NUMBER1 | LOH of bin NUMBER2 on chromosome NUMBER1 |
| GENENAME | Normalized copy numbers of GENENAME |
| fusion_GENENAME1_GENENAME2 | fusion of GENENAME1 with GENENAME2 |
| fusion_GENENAME1_anygene | fusion of GENENAME1 with GENENAME2 |
| fusion_GENENAME1_anygene | fusion of GENENAME1 with GENENAME2 |
| tmb | tumor mutation burden |
| ploidy | ploidy of sample |
| msi | MicroSatellite Instability status |

TABLE 5

| DNA | | |
|---|---|---|
| DNA Feature | NCBI Gene ID | NCBI Accession Number(s) |
| Ovarian_Cancer | | |
| TP53_mut | 7157 | NG_017013; NC_000017 |
| CNA_3_19 | — | — |
| LOH_17_0 | — | — |
| LOH_5_14 | — | — |
| LOH_6_15 | — | — |
| LOH_22_4 | — | — |
| CNA_3_5 | — | — |
| CNA_13_3 | — | — |
| LOH_2_8 | — | — |
| LOH_17_3 | — | — |
| LOH_q_22 | — | — |
| CNA_19_3 | — | — |
| CNA_16_0 | — | — |
| CNA_19_0 | — | — |
| CSMD2_mut | 114784 | NC_000001; NG_053181 |
| CNA_1_0 | — | — |
| CNA_10_7 | — | — |
| CNA_1_9 | — | — |
| CNA_8_9 | — | — |
| CNA_18_0 | — | — |
| LOH_5_15 | — | — |
| LOH_p_3 | — | — |
| CNA_7_14 | — | — |
| LOH_18_6 | — | — |
| CNA_8_10 | — | — |
| CNA_16_7 | — | — |
| LOH_17_7 | — | — |
| LINC00229 | 414351 | NC_000022 |
| CNA_9_9 | — | — |
| FBXW7_hotspots | 55294 | NC_000004; NG_029466 |
| CNA_1_20 | — | — |
| CNA_6_16 | — | — |
| CNA_3_16 | — | — |
| CNA_11_7 | — | — |
| CNA_p_7 | — | — |
| CNA_15_3 | — | — |
| CNA_p_3 | — | — |
| CNA_8_8 | — | — |
| LOH_19_1 | — | — |
| CNA_1_24 | — | — |
| CNA_7_5 | — | — |
| CNA_17_3 | — | — |
| CNA_3_4 | — | — |
| LOH_p_17 | — | — |
| LOH_17_4 | — | — |

TABLE 5-continued

| DNA | | |
|---|---|---|
| DNA Feature | NCBI Gene ID | NCBI Accession Number(s) |
| LOH_18_0 | — | — |
| CNA_q_7 | — | — |
| CNA_12_2 | — | — |
| CNA_8_5 | — | — |
| LOH_1_2 | — | — |
| CNA_3_17 | — | — |
| RPL22P1 | 125371 | NC_000003; NG_009515; NG_028279 |
| CNA_7_4 | — | — |
| CNA_16_8 | — | — |
| LOH_5_3 | — | — |
| LOH_9_2 | — | — |
| LOH_3_6 | — | — |
| DNAH5_mut | 1767 | NC_000005; NG_013081 |
| LOH_17_5 | — | — |
| CNA_11_11 | — | — |
| LOH_17_6 | — | — |
| LOH_9_3 | — | — |
| CNA_5_14 | — | — |
| CNA_1_19 | — | — |
| TP53_hotspots | 7157 | NG_017013; NC_000017 |
| LOH_3_5 | — | — |
| CNA_7_13 | — | — |
| CNA_5_15 | — | — |
| CNA_2_23 | — | — |
| CNA_7_0 | — | — |
| LOH_10_6 | — | — |
| CNA_5_13 | — | — |
| LOH_2_19 | — | — |
| CNA_2_19 | — | — |
| CNA_6_15 | — | — |
| LOH_18_2 | — | — |
| CNA_1_4 | — | — |
| tmb | — | — |
| CNA_3_11 | — | — |
| CNA_11_8 | — | — |
| CNA_4_17 | — | — |
| LOH_1_13 | — | — |
| CNA_10_12 | — | — |
| LOH_11_8 | — | — |
| CNA_2_17 | — | — |
| ARHGAP35_mut | 2909 | NC_000019; NG_047014 |
| LOH_3_4 | — | — |
| SHD | 56961 | NC_000019 |
| FKBP4 | 2288 | NC_000012 |
| PPP2R1A_hotspots | 5518 | NG_047068; NC_000019 |
| CNA_18_2 | — | — |
| CNA_9_12 | — | — |
| CNA_12_1 | — | — |
| CNA_16_5 | — | — |
| LOH_3_7 | — | — |
| CNA_9_0 | — | — |
| LINC00501 | 100820709 | NC_000003 |
| CNA_1_15 | — | — |
| CNA_16_6 | — | — |
| CNA_1_3 | — | — |
| LOH_4_17 | — | — |
| CNA_9_13 | — | — |
| LOH_8_0 | — | — |
| LOH_6_16 | — | — |
| LOH_1_1 | — | — |
| LOH_10_7 | — | — |
| RPSAP33 | 647158 | NC_000003; NG_011277 |
| CNA_p_10 | — | — |
| CNA_2_18 | — | — |
| CNA_2_20 | — | — |
| TMIGD2 | 126259 | NC_000019 |
| Breast_Cancer | | |
| CNA_1_17 | — | — |
| CNA_20_5 | — | — |
| CNA_12_5 | — | — |
| CNA_3_1 | — | — |
| CSMD3_mut | 114788 | NC_000008 |
| CNA_11_9 | — | — |
| LOH_11_10 | — | — |
| CNA_16_4 | — | — |

TABLE 5-continued

| DNA | | |
|---|---|---|
| DNA Feature | NCBI Gene ID | NCBI Accession Number(s) |
| CNA_q_13 | — | — |
| CNA_12_12 | — | — |
| CNA_3_7 | — | — |
| LOH_9_11 | — | — |
| CNA_8_0 | — | — |
| CNA_3_19 | — | — |
| CNA_8_12 | — | — |
| CNA_4_14 | — | — |
| LOH_17_0 | — | — |
| LOH_11_9 | — | — |
| LOH_5_6 | — | — |
| CNA_5_7 | — | — |
| CNA_21_3 | — | — |
| LOH_11_2 | — | — |
| MTCO1P28 | 107075169 | NC_000016; NG_046427 |
| LOH_5_8 | — | — |
| LOH_16_5 | — | — |
| CNA_5_2 | — | — |
| CNA_22_4 | — | — |
| LOH_6_13 | — | — |
| CNA_p_18 | — | — |
| LOH_p_10 | — | — |
| APC_mut | 324 | NG_008481; NC_000005 |
| CNA_3_5 | — | — |
| LOH_17_3 | — | — |
| CNA_17_6 | — | — |
| LOH_17_1 | — | — |
| CNA_9_2 | — | — |
| CNA_4_18 | — | — |
| LOH_22_2 | — | — |
| LOH_11_12 | — | — |
| COG7 | 91949 | NC_000016; NG_021287 |
| LOH_9_0 | — | — |
| LOH_q_22 | — | — |
| CNA_p_16 | — | — |
| CNA_3_13 | — | — |
| LOH_16_7 | — | — |
| CNA_16_0 | — | — |
| CNA_20_3 | — | — |
| SNTB2 | 6645 | NW_003315946; NC_000016 |
| PIK3CA_hotspots | 5290 | NC_000003; NG_012113 |
| CNA_1_0 | — | — |
| LRP1B_mut | 53353 | NC_000002; NG_051023 |
| CNA_10_11 | — | — |
| CNA_10_8 | — | — |
| CNA_8_9 | — | — |
| CNA_4_2 | — | — |
| CNA_1_16 | — | — |
| LOH_18_5 | — | — |
| CDH1_mut | 999 | NC_000016; NG_008021 |
| MRTFB | 57496 | NC_000016 |
| CNA_18_0 | — | — |
| CNA_18_5 | — | — |
| LOH_p_3 | — | — |
| LOH_1_20 | — | — |
| CNA_7_14 | — | — |
| LOH_18_6 | — | — |
| LOH_8_1 | — | — |
| PIK3CA_p.H1047 | 5290 | NC_000003; NG_012113 |
| LOH_19_4 | — | — |
| CNA_8_10 | — | — |
| CNA_3_18 | — | — |
| CNA_16_7 | — | — |
| CNA_16_1 | — | — |
| MUC16_mut | 94025 | NC_000019; NG_055257 |
| CNA_3_10 | — | — |
| CNA_10_9 | — | — |
| RBFOX1 | 54715 | NC_000016; NG_011881 |
| LINC02182 | 101928880 | NC_000016 |
| LOH_1_11 | — | — |
| FBXW7_hotspots | 55294 | NC_000004; NG_029466 |
| CNA_1_20 | — | — |
| CNA_9_9 | — | — |
| CNA_4_9 | — | — |
| CNA_q_18 | — | — |
| CNA_1_14 | — | — |

TABLE 5-continued

| DNA | | |
|---|---|---|
| DNA Feature | NCBI Gene ID | NCBI Accession Number(s) |
| CDKN2A_mut | 1029 | NC_000009; NG_007485 |
| TNR_mut | 7143 | NC_000001; NG_050931 |
| CNA_3_16 | — | — |
| CNA_11_7 | — | — |
| CNA_21_2 | — | — |
| CNA_p_7 | — | — |
| ZSCAN32 | 54925 | NC_000016 |
| LINC00254 | 64735 | NC_000016; NT_187609 |
| CNA_15_3 | — | — |
| LOH_14_8 | — | — |
| IDH1_p.R132 | 3417 | NG_023319; NC_000002 |
| LOH_4_9 | — | — |
| CNA_8_11 | — | — |
| CNA_p_3 | — | — |
| KMT2D_mut | 8085 | NG_027827; NC_000012 |
| CNA_7_8 | — | — |
| LOH_3_8 | — | — |
| DNAJA3 | 9093 | NG_029866; NC_000016; NT_187608 |
| CNA_6_4 | — | — |
| CNA_1_1 | — | — |
| LOH_1_0 | — | — |
| LOH_11_3 | — | — |
| CNA_8_6 | — | — |
| CNA_8_8 | — | — |
| CNA_13_5 | — | — |
| CNA_1_18 | — | — |
| LOH_6_1 | — | — |
| LOH_6_8 | — | — |
| CNA_7_15 | — | — |
| CNA_7_11 | — | — |
| CNA_q_1 | — | — |
| CNA_13_7 | — | — |
| CNA_13_9 | — | — |
| CNA_1_24 | — | — |
| ADCY9 | 115 | NG_011434; NC_000016 |
| CNA_5_11 | — | — |
| CNA_7_5 | — | — |
| LOH_11_11 | — | — |
| CNA_17_3 | — | — |
| CNA_6_12 | — | — |
| CNA_3_6 | — | — |
| CNA_3_4 | — | — |
| CNA_7_9 | — | — |
| LOH_p_17 | — | — |
| CNA_8_1 | — | — |
| LOH_11_7 | — | — |
| LOH_15_6 | — | — |
| LOH_17_4 | — | — |
| CNA_7_10 | — | — |
| CNA_12_2 | — | — |
| CNA_q_7 | — | — |
| CNA_3_17 | — | — |
| CNA_10_0 | — | — |
| CNA_16_8 | — | — |
| LOH_13_7 | — | — |
| LOH_5_3 | — | — |
| GLIS2 | 84662 | NG_016391; NC_000016; NT_187608 |
| CNA_q_16 | — | — |
| CNA_7_1 | — | — |
| LOH_9_1 | — | — |
| LOH_9_2 | — | — |
| CNA_5_1 | — | — |
| LOH_3_6 | — | — |
| CNA_12_11 | — | — |
| CNA_8_2 | — | — |
| TBL3 | 10607 | NC_000016 |
| LOH_22_3 | — | — |
| LOH_10_1 | — | — |
| CNA_8_13 | — | — |
| LOH_3_0 | — | — |
| LOH_12_8 | — | — |
| LOH_17_5 | — | — |
| CNA_9_1 | — | — |
| CNA_11_11 | — | — |
| CNA_1_22 | — | — |

TABLE 5-continued

| DNA | | |
|---|---|---|
| DNA Feature | NCBI Gene ID | NCBI Accession Number(s) |
| LOH_17_6 | — | — |
| LOH_9_12 | — | — |
| DNAH5_mut | 1767 | NC_000005; NG_013081 |
| CNA_11_12 | — | — |
| CNA_6_8 | — | — |
| LOH_9_3 | — | — |
| CNA_3_2 | — | — |
| CNA_1_19 | — | — |
| KMT2C_mut | 58508 | NC_000007; NG_033948 |
| CNA_2_2 | — | — |
| CNA_p_17 | — | — |
| TP53_hotspots | 7157 | NG_017013; NC_000017 |
| LOH_3_5 | — | — |
| LOH_q_9 | — | — |
| CNA_2_23 | — | — |
| CNA_1_2 | — | — |
| CNA_3_0 | — | — |
| CNA_19_0 | — | — |
| TVP23CP2 | 261735 | NC_000016; NG_002361 |
| LOH_3_1 | — | — |
| RB1_mut | 5925 | NG_009009; NC_000013 |
| CNA_13_10 | — | — |
| CNA_1_4 | — | — |
| tmb | — | — |
| KRAS_hotspots | 3845 | NC_000012; NG_007524 |
| LOH_19_5 | — | — |
| CACNA1C_mut | 775 | NW_018654718; NC_000012; NG_008801 |
| CNA_7_3 | — | — |
| SRL | 6345 | NC_000016 |
| MAP3K1_mut | 4214 | NG_031884; NC_000005 |
| CNA_11_8 | — | — |
| CNA_4_17 | — | — |
| LOH_1_8 | — | — |
| CNA_10_1 | — | — |
| LOH_18_7 | — | — |
| CNA_1_23 | — | — |
| CNA_6_10 | — | — |
| LOH_q_16 | — | — |
| CNA_17_1 | — | — |
| CNA_15_4 | — | — |
| CNA_10_12 | — | — |
| CNA_17_5 | — | — |
| CNA_6_13 | — | — |
| CNA_2_17 | — | — |
| CYB5B | 80777 | NC_000016 |
| LOH_3_4 | — | — |
| LOH_14_7 | — | — |
| CNA_p_5 | — | — |
| ST3GAL2 | 6483 | NG_046942; NC_000016 |
| CNA_9_7 | — | — |
| CNA_22_2 | — | — |
| CNA_16_2 | — | — |
| CNA_5_3 | — | — |
| CNA_12_7 | — | — |
| CNA_3_12 | — | — |
| LOH_10_12 | — | — |
| CNA_q_20 | — | — |
| CNA_6_1 | — | — |
| CNA_9_12 | — | — |
| CNA_12_1 | — | — |
| CNA_18_7 | — | — |
| CNA_16_5 | — | — |
| LOH_19_0 | — | — |
| MSRB1 | 51734 | NC_000016 |
| CNA_9_0 | — | — |
| CNA_18_6 | — | — |
| LOH_10_8 | — | — |
| CNA_20_4 | — | — |
| CNA_1_15 | — | — |
| CNA_11_6 | — | — |
| CNA_16_6 | — | — |
| CNA_4_1 | — | — |
| LOH_13_10 | — | — |
| LOH_10_0 | — | — |
| CNA_6_0 | — | — |

TABLE 5-continued

| DNA | | |
|---|---|---|
| DNA Feature | NCBI Gene ID | NCBI Accession Number(s) |
| LOH_9_13 | — | — |
| CNA_17_7 | — | — |
| CNA_1_3 | — | — |
| LOH_4_17 | — | — |
| CNA_3_15 | — | — |
| CNA_11_10 | — | — |
| CNA_9_13 | — | — |
| CNA_22_3 | — | — |
| CNA_2_1 | — | — |
| NTHL1 | 4913 | NC_000016; NG_008412 |
| CNA_5_0 | — | — |
| BRAF_hotspots | 673 | NC_000007; NG_007873 |
| LOH_16_8 | — | — |
| CNA_1_21 | — | — |
| LOH_8_0 | — | — |
| CNA_11_3 | — | — |
| LOH_6_16 | — | — |
| LOH_13_9 | — | — |
| CNA_19_5 | — | — |
| CNA_3_14 | — | — |
| CNA_4_3 | — | — |
| CTNNB1_hotspots | 1499 | NC_000003; NG_013302 |
| CNA_2_11 | — | — |
| CNA_2_13 | — | — |
| LOH_16_6 | — | — |
| CNA_2_20 | — | — |
| CNA_6_2 | — | — |
| CNA_17_0 | — | — |
| CNA_p_10 | — | — |
| CNA_q_22 | — | — |
| Squamous_Cell_Carcinoma | | |
| CNA_8_0 | — | — |
| CNA_19_1 | — | — |
| CNA_22_4 | — | — |
| GM2AP1 | 2761 | NG_001130; NC_000003 |
| LOH_17_3 | — | — |
| CNA_6_9 | — | — |
| CNA_10_7 | — | — |
| CNA_7_14 | — | — |
| CNA_3_18 | — | — |
| CNA_p_7 | — | — |
| IDH1_p.R132 | 3417 | NG_023319; NC_000002 |
| KMT2D_mut | 8085 | NG_027827; NC_000012 |
| LOH_13_3 | — | — |
| LOH_6_1 | — | — |
| TRA2B | 6434 | NG_029862; NC_000003 |
| LOH_11_11 | — | — |
| CNA_17_3 | — | — |
| CNA_3_4 | — | — |
| LOH_18_0 | — | — |
| LOH_3_12 | — | — |
| CNA_2_22 | — | — |
| CNA_q_16 | — | — |
| msi | — | — |
| LOH_9_12 | — | — |
| CNA_1_2 | — | — |
| CNA_19_0 | — | — |
| HMCN1_mut | 83872 | NC_000001; NG_011841 |
| CNA_1_4 | — | — |
| LOH_19_5 | — | — |
| CNA_3_11 | — | — |
| NOTCH1_mut | 4851 | NG_007458; NC_000009 |
| CNA_15_4 | — | — |
| CNA_2_6 | — | — |
| CNA_12_1 | — | — |
| LOH_3_2 | — | — |
| CNA_14_9 | — | — |
| LOH_3_7 | — | — |
| LOH_4_17 | — | — |
| CNA_9_13 | — | — |
| CNA_5_6 | — | — |
| LOH_8_0 | — | — |
| CNA_q_22 | — | — |
| CNA_20_5 | — | — |
| CNA_3_19 | — | — |

TABLE 5-continued

| DNA | | |
|---|---|---|
| DNA Feature | NCBI Gene ID | NCBI Accession Number(s) |
| CNA_8_12 | — | — |
| LOH_17_0 | — | — |
| CNA_5_2 | — | — |
| LOH_6_15 | — | — |
| LOH_22_4 | — | — |
| LOH_22_2 | — | — |
| LOH_18_5 | — | — |
| LOH_13_2 | — | — |
| CNA_16_7 | — | — |
| CNA_1_6 | — | — |
| CNA_3_16 | — | — |
| CNA_11_7 | — | — |
| CNA_13_2 | — | — |
| CNA_p_3 | — | — |
| CNA_q_1 | — | — |
| CNA_6_12 | — | — |
| LOH_p_17 | — | — |
| PBRM1_mut | 55193 | NG_032108; NC_000003 |
| CNA_3_17 | — | — |
| LINC01994 | 401103 | NC_000003 |
| LOH_1_5 | — | — |
| CNA_5_1 | — | — |
| CNA_11_12 | — | — |
| CNA_2_2 | — | — |
| CNA_5_15 | — | — |
| LOH_3_1 | — | — |
| NRAS_mut | 4893 | NG_007572; NC_000001 |
| tmb | — | — |
| KRAS_hotspots | 3845 | NC_000012; NG_007524 |
| CNA_10_1 | — | — |
| LOH_q_16 | — | — |
| CNA_17_1 | — | — |
| CNA_17_5 | — | — |
| CNA_p_5 | — | — |
| CNA_9_7 | — | — |
| LOH_19_0 | — | — |
| CNA_11_6 | — | — |
| CNA_4_1 | — | — |
| LINC00971 | 440970 | NC_000003; NW_018654711 |
| CNA_2_20 | — | — |
| CNA_6_2 | — | — |
| CNA_3_1 | — | — |
| CNA_12_12 | — | — |
| BRAF_p.V600 | 673 | NC_000007; NG_007873 |
| TRIM42 | 287015 | NC_000003 |
| CNA_7_7 | — | — |
| CNA_21_3 | — | — |
| APC_mut | 324 | NG_008481; NC_000005 |
| CNA_13_3 | — | — |
| LOH_17_1 | — | — |
| LOH_3_18 | — | — |
| LOH_9_0 | — | — |
| CNA_1_0 | — | — |
| CNA_10_11 | — | — |
| CNA_18_0 | — | — |
| MGA_mut | 23269 | NC_000015 |
| LOH_5_13 | — | — |
| CDKN2A_mut | 1029 | NC_000009; NG_007485 |
| CNA_8_11 | — | — |
| LOH_3_8 | — | — |
| LOH_2_22 | — | — |
| LOH_9_1 | — | — |
| LOH_10_1 | — | — |
| CNA_9_1 | — | — |
| CNA_11_11 | — | — |
| CNA_3_8 | — | — |
| CNA_7_13 | — | — |
| CNA_5_13 | — | — |
| CNA_11_8 | — | — |
| CNA_13_4 | — | — |
| CNA_16_2 | — | — |
| CNA_5_3 | — | — |
| CNA_9_0 | — | — |
| CNA_1_15 | — | — |
| CNA_17_7 | — | — |
| CNA_3_15 | — | — |

TABLE 5-continued

| DNA Feature | NCBI Gene ID | NCBI Accession Number(s) |
| --- | --- | --- |
| | DNA | |
| CNA_22_3 | — | — |
| CNA_1_8 | — | — |
| CNA_5_0 | — | — |
| ARID1A_mut | 8289 | NC_000001; NG_029965 |
| CNA_12_5 | — | — |
| CNA_3_7 | — | — |
| LOH_3_11 | — | — |
| LOH_3_3 | — | — |
| FAT1_mut | 2195 | NG_046994; NC_000004 |
| SYNE1_mut | 23345 | NG_012855; NC_000006 |
| CNA_p_16 | — | — |
| LOH_16_7 | — | — |
| CNA_19_3 | — | — |
| CNA_14_8 | — | — |
| SRRM1P2 | 100420834 | NC_000003; NG_022252 |
| CNA_18_5 | — | — |
| CNA_5_16 | — | — |
| CNA_5_17 | — | — |
| KBTBD8 | 84541 | NC_000003 |
| CNA_7_15 | — | — |
| VHL_mut | 7428 | NC_000003; NG_008212 |
| LOH_17_4 | — | — |
| CNA_q_7 | — | — |
| LOH_15_6 | — | — |
| LOH_5_16 | — | — |
| CNA_8_13 | — | — |
| LOH_17_5 | — | — |
| CNA_6_8 | — | — |
| SPTA1_mut | 6708 | NC_000001; NG_011474 |
| CNA_1_19 | — | — |
| CNA_p_17 | — | — |
| CNA_6_10 | — | — |
| HRAS_hotspots | 3265 | NT_187586; NG_007666; NC_000011 |
| LOH_5_17 | — | — |
| MAGEF1 | 64110 | NC_000003 |
| RYR2_mut | 6262 | NG_008799; NC_000001 |
| CNA_9_10 | — | — |
| CNA_9_12 | — | — |
| CNA_20_4 | — | — |
| BRAF_hotspots | 673 | NC_000007; NG_007873 |
| CNA_19_5 | — | — |
| CNA_3_14 | — | — |
| CNA_p_10 | — | — |
| | Lung_Adenocarcinoma | |
| DPPA3P2 | 400206 | NC_000014; NG_023379 |
| CNA_20_5 | — | — |
| CSMD3_mut | 114788 | NC_000008 |
| CNA_11_9 | — | — |
| CNA_16_4 | — | — |
| CNA_12_12 | — | — |
| CNA_q_13 | — | — |
| CNA_19_1 | — | — |
| CNA_3_19 | — | — |
| PIK3CA_mut | 5290 | NC_000003; NG_012113 |
| CNA_8_12 | — | — |
| LOH_17_0 | — | — |
| CNA_20_0 | — | — |
| CNA_7_7 | — | — |
| ZFHX4_mut | 79776 | NC_000008 |
| CNA_5_2 | — | — |
| LOH_6_13 | — | — |
| CNA_22_4 | — | — |
| CNA_p_18 | — | — |
| NKX2-1 | 7080 | NC_000014; NG_013365 |
| LINC01511 | 100506791 | NC_000005; NT_187547 |
| LOH_1_9 | — | — |
| LOH_2_23 | — | — |
| APC_mut | 324 | NG_008481; NC_000005 |
| LOH_17_3 | — | — |
| CNA_17_6 | — | — |
| LOH_17_1 | — | — |
| DNAH2_mut | 146754 | NC_000017 |
| LOH_3_18 | — | — |
| LOH_22_2 | — | — |
| SYNE1_mut | 23345 | NG_012855; NC_000006 |

TABLE 5-continued

| DNA | | |
|---|---|---|
| DNA Feature | NCBI Gene ID | NCBI Accession Number(s) |
| EP300_mut | 2033 | NG_009817; NC_000022 |
| LOH_9_0 | — | — |
| LOH_q_22 | — | — |
| CNA_p_16 | — | — |
| SFTA3 | 253970 | NC_000014 |
| ADAMTS12_mut | 81792 | NT_187551; NC_000005 |
| CNA_16_0 | — | — |
| CNA_20_3 | — | — |
| CNA_19_3 | — | — |
| LOH_3_14 | — | — |
| PIK3CA_hotspots | 5290 | NC_000003; NG_012113 |
| EGFR_hotspots | 1956 | NG_007726; NC_000007 |
| CNA_1_0 | — | — |
| CNA_4_2 | — | — |
| LOH_p_3 | — | — |
| STK11_mut | 6794 | NG_007460; NC_000019 |
| LOH_13_2 | — | — |
| LOH_8_1 | — | — |
| MGA_mut | 23269 | NC_000015 |
| TMTC1_mut | 83857 | NC_000012 |
| CNA_3_18 | — | — |
| TTN_mut | 7273 | NC_000002; NG_011618 |
| CNA_16_7 | — | — |
| LOH_17_7 | — | — |
| CNA_3_10 | — | — |
| CNA_10_9 | — | — |
| CDK8 | 1024 | NC_000013 |
| PTEN_mut | 5728 | NC_000010; NW_013171807; NG_007466 |
| CNA_9_9 | — | — |
| CNA_1_20 | — | — |
| CNA_4_9 | — | — |
| CNA_5_16 | — | — |
| CNA_3_16 | — | — |
| CNA_21_2 | — | — |
| CNA_p_7 | — | — |
| RBM10_mut | 8241 | NG_012548; NC_000023 |
| CNA_15_3 | — | — |
| ZMYM2 | 7750 | NG_023348; NC_000013 |
| CNA_13_2 | — | — |
| CNA_8_11 | — | — |
| LOH_4_9 | — | — |
| KMT2D_mut | 8085 | NG_027827; NC_000012 |
| CNA_1_1 | — | — |
| LOH_1_0 | — | — |
| LOH_6_8 | — | — |
| CNA_7_15 | — | — |
| LOH_19_1 | — | — |
| CNA_q_1 | — | — |
| PTPRD_mut | 5789 | NC_000009; NG_033963 |
| LOH_11_11 | — | — |
| CNA_17_3 | — | — |
| CNA_3_6 | — | — |
| LOH_10_9 | — | — |
| LOH_17_4 | — | — |
| CNA_7_4 | — | — |
| GABRB3 | 2562 | NC_000015; NG_012836 |
| LOH_2_22 | — | — |
| KRAS_mut | 3845 | NC_000012; NG_007524 |
| CNA_2_22 | — | — |
| CNA_8_13 | — | — |
| CNA_15_5 | — | — |
| CNA_p_20 | — | — |
| LOH_3_0 | — | — |
| DNAH5_mut | 1767 | NC_000005; NG_013081 |
| LOH_17_5 | — | — |
| msi | — | — |
| CNA_11_11 | — | — |
| LOH_17_6 | — | — |
| NKX2-8 | 26257 | NC_000014 |
| CNA_11_12 | — | — |
| ZNF804A_mut | 91752 | NC_000002; NG_046950 |
| CNA_3_8 | — | — |
| CNA_11_1 | — | — |
| CNA_1_19 | — | — |

TABLE 5-continued

| DNA | | |
|---|---|---|
| DNA Feature | NCBI Gene ID | NCBI Accession Number(s) |
| RPL29P3 | 729042 | NG_009496; NC_000014 |
| CNA_2_23 | — | — |
| CNA_7_0 | — | — |
| LINC02248 | 107984780 | NC_000015 |
| CNA_1_2 | — | — |
| CNA_19_0 | — | — |
| LOH_4_15 | — | — |
| CNA_6_15 | — | — |
| LOH_18_2 | — | — |
| CNA_q_8 | — | — |
| USH2A_mut | 7399 | NC_000001; NG_009497 |
| tmb | — | — |
| CNA_11_8 | — | — |
| LOH_1_3 | — | — |
| LOH_1_8 | — | — |
| CNA_6_10 | — | — |
| LOH_q_16 | — | — |
| CNA_15_4 | — | — |
| LOH_p_18 | — | — |
| CNA_6_13 | — | — |
| LOH_11_8 | — | — |
| CNA_p_5 | — | — |
| CNA_9_7 | — | — |
| RYR2_mut | 6262 | NG_008799; NC_000001 |
| CNA_5_3 | — | — |
| CNA_9_3 | — | — |
| LOH_6_12 | — | — |
| CNA_q_20 | — | — |
| KEAP1_mut | 9817 | NC_000019 |
| CNA_9_10 | — | — |
| CNA_12_1 | — | — |
| LOH_19_0 | — | — |
| CNA_19_4 | — | — |
| LOH_15_4 | — | — |
| CNA_20_4 | — | — |
| KRAS_p.G12 | 3845 | NC_000012; NG_007524 |
| CNA_1_15 | — | — |
| CNA_11_6 | — | — |
| LOH_10_2 | — | — |
| CNA_6_0 | — | — |
| CNA_1_3 | — | — |
| CDH18-AS1 | 102725105 | NC_000005 |
| CNA_11_10 | — | — |
| CNA_9_13 | — | — |
| CNA_22_3 | — | — |
| CNA_5_0 | — | — |
| LOH_1_1 | — | — |
| SETD2_mut | 29072 | NC_000003; NG_032091 |
| CNA_3_14 | — | — |
| CNA_4_3 | — | — |
| CNA_p_10 | — | — |
| CNA_2_13 | — | — |
| CNA_17_0 | — | — |
| CNA_q_22 | — | — |
| LOH_11_1 | — | — |
| CNA_2_20 | — | — |
| Prostate_Adenocarcinoma | | |
| CNA_1_17 | — | — |
| CNA_20_5 | — | — |
| LOH_4_16 | — | — |
| CNA_11_9 | — | — |
| CNA_16_4 | — | — |
| CNA_q_13 | — | — |
| CNA_3_7 | — | — |
| BRAF_p.V600 | 673 | NC_000007; NG_007873 |
| CNA_8_0 | — | — |
| CNA_20_0 | — | — |
| LOH_13_5 | — | — |
| LOH_5_7 | — | — |
| CNA_5_7 | — | — |
| LOH_17_0 | — | — |
| CNA_7_7 | — | — |
| CNA_21_3 | — | — |
| LOH_11_2 | — | — |
| LOH_3_3 | — | — |

TABLE 5-continued

| DNA | | |
|---|---|---|
| DNA Feature | NCBI Gene ID | NCBI Accession Number(s) |
| LOH_6_13 | — | — |
| LOH_16_5 | — | — |
| CNA_22_4 | — | — |
| LOH_6_15 | — | — |
| LOH_p_10 | — | — |
| LOH_22_4 | — | — |
| CNA_3_5 | — | — |
| CNA_13_3 | — | — |
| CNA_17_6 | — | — |
| LOH_17_1 | — | — |
| CNA_9_2 | — | — |
| CNA_4_18 | — | — |
| LOH_11_12 | — | — |
| CNA_p_16 | — | — |
| CNA_19_3 | — | — |
| CNA_20_3 | — | — |
| CNA_6_14 | — | — |
| PIK3CA_hotspots | 5290 | NC_000003; NG_012113 |
| CNA_6_9 | — | — |
| CNA_1_0 | — | — |
| CNA_10_11 | — | — |
| CNA_10_8 | — | — |
| CNA_1_16 | — | — |
| LOH_18_5 | — | — |
| LOH_p_3 | — | — |
| LOH_18_6 | — | — |
| LOH_13_2 | — | — |
| LOH_8_1 | — | — |
| CNA_7_14 | — | — |
| CNA_8_10 | — | — |
| CNA_16_7 | — | — |
| CNA_16_1 | — | — |
| LOH_17_7 | — | — |
| LOH_13_4 | — | — |
| CNA_5_10 | — | — |
| LOH_1_11 | — | — |
| LOH_5_13 | — | — |
| CNA_q_18 | — | — |
| CNA_6_16 | — | — |
| LOH_8_2 | — | — |
| CNA_p_7 | — | — |
| CNA_21_2 | — | — |
| LOH_14_8 | — | — |
| IDH1_p.R132 | 3417 | NG_023319; NC_000002 |
| CNA_13_2 | — | — |
| LOH_16_4 | — | — |
| CNA_p_3 | — | — |
| CNA_1_1 | — | — |
| LOH_1_0 | — | — |
| LOH_6_14 | — | — |
| CNA_8_6 | — | — |
| CNA_8_8 | — | — |
| CNA_1_18 | — | — |
| LOH_6_1 | — | — |
| LOH_6_8 | — | — |
| CNA_7_15 | — | — |
| CNA_q_1 | — | — |
| CNA_13_7 | — | — |
| CNA_1_24 | — | — |
| CNA_5_11 | — | — |
| IDH1_hotspots | 3417 | NG_023319; NC_000002 |
| CNA_17_3 | — | — |
| CNA_3_4 | — | — |
| LOH_10_9 | — | — |
| LOH_p_17 | — | — |
| CNA_3_6 | — | — |
| CNA_8_1 | — | — |
| LOH_17_4 | — | — |
| CNA_q_7 | — | — |
| CNA_8_7 | — | — |
| CNA_7_10 | — | — |
| CNA_12_2 | — | — |
| CNA_8_5 | — | — |
| LOH_1_2 | — | — |
| LOH_13_8 | — | — |
| CNA_10_0 | — | — |

TABLE 5-continued

| DNA | | |
|---|---|---|
| DNA Feature | NCBI Gene ID | NCBI Accession Number(s) |
| SPOP_hotspots | 8405 | NC_000017; NG_041815 |
| CNA_16_8 | — | — |
| CNA_q_16 | — | — |
| LOH_9_1 | — | — |
| LOH_14_3 | — | — |
| LOH_9_2 | — | — |
| CNA_8_2 | — | — |
| LOH_22_3 | — | — |
| CNA_8_13 | — | — |
| CNA_p_20 | — | — |
| CNA_9_1 | — | — |
| LOH_17_5 | — | — |
| CNA_10_4 | — | — |
| CNA_11_11 | — | — |
| CNA_1_22 | — | — |
| LOH_17_6 | — | — |
| LOH_9_7 | — | — |
| CNA_11_1 | — | — |
| CNA_6_8 | — | — |
| CNA_11_12 | — | — |
| ATM_mut | 472 | NC_000011; NG_009830 |
| CNA_5_14 | — | — |
| CNA_1_19 | — | — |
| LOH_9_9 | — | — |
| TP53_hotspots | 7157 | NG_017013; NC_000017 |
| LOH_3_5 | — | — |
| LOH_10_6 | — | — |
| CNA_2_23 | — | — |
| CNA_19_0 | — | — |
| LOH_4_15 | — | — |
| CNA_6_15 | — | — |
| CNA_q_8 | — | — |
| tmb | — | — |
| CNA_7_3 | — | — |
| LOH_19_5 | — | — |
| CNA_11_8 | — | — |
| CNA_4_17 | — | — |
| LOH_18_7 | — | — |
| LOH_q_16 | — | — |
| CNA_20_1 | — | — |
| CNA_10_12 | — | — |
| CNA_17_5 | — | — |
| LOH_2_2 | — | — |
| LOH_10_11 | — | — |
| LOH_3_4 | — | — |
| LOH_14_7 | — | — |
| CNA_p_5 | — | — |
| CNA_9_7 | — | — |
| CNA_16_2 | — | — |
| LOH_10_12 | — | — |
| CNA_q_20 | — | — |
| CNA_18_7 | — | — |
| CNA_9_11 | — | — |
| LOH_10_8 | — | — |
| CNA_12_1 | — | — |
| CNA_16_5 | — | — |
| LOH_19_0 | — | — |
| LOH_3_7 | — | — |
| CNA_6_1 | — | — |
| CNA_19_4 | — | — |
| CNA_1_15 | — | — |
| CNA_11_6 | — | — |
| GTF2I_p.L424 | 2969 | NC_000007; NG_008179 |
| LOH_10_0 | — | — |
| CNA_6_0 | — | — |
| CNA_17_7 | — | — |
| LOH_14_9 | — | — |
| CNA_11_10 | — | — |
| CNA_4_16 | — | — |
| CNA_5_0 | — | — |
| BRAF_hotspots | 673 | NC_000007; NG_007873 |
| LOH_16_8 | — | — |
| LOH_8_0 | — | — |
| LOH_6_16 | — | — |
| LOH_1_1 | — | — |
| CNA_19_5 | — | — |

TABLE 5-continued

| DNA Feature | NCBI Gene ID | NCBI Accession Number(s) |
|---|---|---|
| DNA | | |
| LOH_10_7 | — | — |
| CNA_1_11 | — | — |
| ARID1A_mut | 8289 | NC_000001; NG_029965 |
| CNA_2_13 | — | — |
| LOH_11_1 | — | — |
| CNA_6_2 | — | — |
| LOH_6_9 | — | — |
| CNA_17_0 | — | — |
| COX4I1P2 | 652170 | NG_011339; NC_000013 |
| CNA_10_6 | — | — |
| CNA_3_3 | — | — |
| CNA_11_2 | — | — |
| Neuroendocrine | | |
| CNA_1_17 | — | — |
| CNA_2_5 | — | — |
| CNA_q_13 | — | — |
| CNA_12_12 | — | — |
| CNA_4_11 | — | — |
| MAST4 | 375449 | NC_000005; NG_034036 |
| CNA_5_9 | — | — |
| LOH_1_21 | — | — |
| CNA_8_0 | — | — |
| LOH_3_11 | — | — |
| CNA_3_19 | — | — |
| CNA_20_0 | — | — |
| CNA_1_5 | — | — |
| CNA_8_12 | — | — |
| LOH_17_0 | — | — |
| CNA_5_7 | — | — |
| LOH_11_2 | — | — |
| CNA_5_2 | — | — |
| CNA_22_4 | — | — |
| CNA_p_18 | — | — |
| LOH_22_4 | — | — |
| CNA_13_3 | — | — |
| LOH_2_8 | — | — |
| LOH_17_1 | — | — |
| LOH_22_2 | — | — |
| LOH_9_0 | — | — |
| LOH_q_22 | — | — |
| CNA_p_16 | — | — |
| CNA_19_3 | — | — |
| CNA_20_3 | — | — |
| CNA_1_0 | — | — |
| CNA_1_16 | — | — |
| CNA_18_0 | — | — |
| LOH_p_3 | — | — |
| LOH_1_20 | — | — |
| LOH_1_17 | — | — |
| LOH_8_1 | — | — |
| CNA_10_10 | — | — |
| CNA_3_18 | — | — |
| CNA_16_7 | — | — |
| LOH_1_11 | — | — |
| CNA_9_9 | — | — |
| CNA_1_10 | — | — |
| LOH_5_13 | — | — |
| CNA_4_9 | — | — |
| CNA_1_14 | — | — |
| CNA_6_16 | — | — |
| CNA_5_16 | — | — |
| CNA_p_7 | — | — |
| CNA_11_7 | — | — |
| CNA_3_16 | — | — |
| CNA_13_2 | — | — |
| CNA_8_11 | — | — |
| LOH_1_0 | — | — |
| LOH_11_3 | — | — |
| CNA_1_18 | — | — |
| CNA_q_1 | — | — |
| LOH_1_23 | — | — |
| CNA_13_7 | — | — |
| LOH_6_10 | — | — |
| CNA_17_3 | — | — |
| CNA_12_10 | — | — |

TABLE 5-continued

| DNA | | |
|---|---|---|
| DNA Feature | NCBI Gene ID | NCBI Accession Number(s) |
| LOH_11_6 | — | — |
| LOH_p_17 | — | — |
| CNA_q_7 | — | — |
| LOH_17_4 | — | — |
| TMEM205 | 374882 | NC_000019 |
| CNA_3_17 | — | — |
| LOH_1_2 | — | — |
| CNA_16_8 | — | — |
| CNA_q_16 | — | — |
| CNA_2_8 | — | — |
| CNA_5_1 | — | — |
| CNA_12_11 | — | — |
| CNA_12_6 | — | — |
| CNA_8_13 | — | — |
| CNA_p_20 | — | — |
| CNA_5_8 | — | — |
| LOH_17_6 | — | — |
| CNA_5_14 | — | — |
| CNA_1_19 | — | — |
| CNA_p_17 | — | — |
| CNA_1_2 | — | — |
| CNA_19_0 | — | — |
| CNA_12_8 | — | — |
| tmb | — | — |
| CNA_7_3 | — | — |
| ADAMTS6 | 11174 | NC_000005 |
| LOH_1_8 | — | — |
| CNA_1_23 | — | — |
| ZBED3 | 84327 | NC_000005 |
| CNA_17_5 | — | — |
| CNA_6_13 | — | — |
| CNA_5_12 | — | — |
| CNA_22_2 | — | — |
| CNA_12_7 | — | — |
| CNA_3_12 | — | — |
| CNA_9_10 | — | — |
| CNA_19_4 | — | — |
| CNA_9_11 | — | — |
| CNA_1_15 | — | — |
| CNA_6_0 | — | — |
| CNA_17_7 | — | — |
| CNA_9_13 | — | — |
| CNA_22_3 | — | — |
| CNA_5_0 | — | — |
| CNA_1_8 | — | — |
| CNA_5_6 | — | — |
| CNA_1_21 | — | — |
| CNA_19_5 | — | — |
| CNA_q_22 | — | — |
| CNA_2_11 | — | — |
| LOH_5_8 | — | — |
| LOH_11_1 | — | — |
| CNA_17_0 | — | — |
| CNA_10_6 | — | — |
| Pancreatic_Adenocarcinoma | | |
| LOH_11_10 | — | — |
| CNA_q_13 | — | — |
| CNA_20_0 | — | — |
| LOH_17_0 | — | — |
| LOH_2_18 | — | — |
| CNA_18_4 | — | — |
| APC_mut | 324 | NG_008481; NC_000005 |
| CNA_3_5 | — | — |
| CNA_13_3 | — | — |
| LOH_17_3 | — | — |
| LOH_17_1 | — | — |
| CNA_10_2 | — | — |
| LOH_9_0 | — | — |
| CNA_p_16 | — | — |
| LOH_16_7 | — | — |
| CNA_20_3 | — | — |
| KRAS_p.Q61 | 3845 | NC_000012; NG_007524 |
| CNA_6_14 | — | — |
| CNA_1_0 | — | — |
| CNA_14_8 | — | — |

TABLE 5-continued

| DNA | | |
|---|---|---|
| DNA Feature | NCBI Gene ID | NCBI Accession Number(s) |
| CNA_8_9 | — | — |
| CNA_18_5 | — | — |
| LOH_p_3 | — | — |
| CNA_7_14 | — | — |
| LOH_18_6 | — | — |
| CNA_16_7 | — | — |
| CNA_16_1 | — | — |
| LOH_18_4 | — | — |
| CNA_6_16 | — | — |
| CNA_6_3 | — | — |
| CDKN2A_mut | 1029 | NC_000009; NG_007485 |
| CNA_3_16 | — | — |
| CNA_p_7 | — | — |
| CNA_p_3 | — | — |
| CNA_8_6 | — | — |
| CNA_13_5 | — | — |
| LOH_19_1 | — | — |
| CNA_q_1 | — | — |
| CNA_1_24 | — | — |
| CNA_17_3 | — | — |
| CDKN2A_hotspots | 1029 | NC_000009; NG_007485 |
| LOH_p_17 | — | — |
| CNA_q_7 | — | — |
| CNA_8_5 | — | — |
| KRAS_mut | 3845 | NC_000012; NG_007524 |
| CNA_q_16 | — | — |
| LOH_9_1 | — | — |
| CNA_12_6 | — | — |
| CNA_p_20 | — | — |
| CNA_9_1 | — | — |
| LOH_17_5 | — | — |
| CNA_6_8 | — | — |
| LOH_9_3 | — | — |
| CNA_p_17 | — | — |
| TP53_hotspots | 7157 | NG_017013; NC_000017 |
| CNA_7_0 | — | — |
| CNA_3_0 | — | — |
| CNA_18_3 | — | — |
| CNA_6_15 | — | — |
| CNA_q_8 | — | — |
| LOH_18_2 | — | — |
| tmb | — | — |
| KRAS_hotspots | 3845 | NC_000012; NG_007524 |
| CNA_7_3 | — | — |
| SMAD4_mut | 4089 | NC_000018; NG_013013 |
| LOH_1_8 | — | — |
| LOH_18_7 | — | — |
| LOH_q_16 | — | — |
| CNA_20_1 | — | — |
| CNA_17_1 | — | — |
| CNA_17_5 | — | — |
| CNA_4_8 | — | — |
| CNA_6_11 | — | — |
| CNA_22_2 | — | — |
| CNA_18_2 | — | — |
| LOH_10_12 | — | — |
| CNA_q_20 | — | — |
| CNA_6_1 | — | — |
| CNA_18_7 | — | — |
| CNA_12_1 | — | — |
| CNA_14_9 | — | — |
| CNA_9_0 | — | — |
| CNA_20_4 | — | — |
| CNA_18_6 | — | — |
| CNA_1_15 | — | — |
| KRAS_p.G12 | 3845 | NC_000012; NG_007524 |
| CNA_6_0 | — | — |
| CNA_17_7 | — | — |
| CNA_11_10 | — | — |
| CNA_q_22 | — | — |
| CNA_17_0 | — | — |
| CNA_6_2 | — | — |
| LOH_6_9 | — | — |
| CNA_11_2 | — | — |

TABLE 5-continued

| DNA | | |
|---|---|---|
| DNA Feature | NCBI Gene ID | NCBI Accession Number(s) |
| Gastrointestinal_Adenocarcinoma | | |
| ACVR2A_mut | 92 | NC_000002 |
| APC_mut | 324 | NG_008481; NC_000005 |
| ARID1A_mut | 8289 | NC_000001; NG_029965 |
| CDH1_mut | 999 | NC_000016; NG_008021 |
| FAT1_mut | 2195 | NG_046994; NC_000004 |
| FAT4_mut | 79633 | NG_033865; NC_000004 |
| MED12_mut | 9968 | NG_012808; NC_000023 |
| MED13L_mut | 23389 | NC_000012; NG_023366 |
| MGAM_mut | 8972 | NT_187562; NC_000007; NG_033954 |
| NSD1_mut | 64324 | NC_000005; NG_009821 |
| PCDH17_mut | 27253 | NC_000013 |
| PHKA1_mut | 5255 | NG_016599; NC_000023 |
| PREX2_mut | 80243 | NG_047022; NC_000008 |
| PTEN_mut | 5728 | NC_000010; NW_013171807; NG_007466 |
| SPTA1_mut | 6708 | NC_000001; NG_011474 |
| STAG2_mut | 10735 | NC_000023; NG_033796 |
| SYNE1_mut | 23345 | NG_012855; NC_000006 |
| ZFHX3_mut | 463 | NG_013211; NC_000016 |
| IDH1_p.R132 | 3417 | NG_023319; NC_000002 |
| SMAD4_hotspots | 4089 | NC_000018; NG_013013 |
| NFE2L2_hotspots | 4780 | NC_000002 |
| KRAS_hotspots | 3845 | NC_000012; NG_007524 |
| PTEN_hotspots | 5728 | NC_000010; NW_013171807; NG_007466 |
| HRAS_hotspots | 3265 | NT_187586; NG_007666; NC_000011 |
| CNA_1_4 | — | — |
| LOH_1_4 | — | — |
| CNA_1_9 | — | — |
| CNA_1_15 | — | — |
| CNA_1_17 | — | — |
| CNA_1_19 | — | — |
| CNA_1_20 | — | — |
| CNA_1_22 | — | — |
| CNA_1_23 | — | — |
| CNA_1_24 | — | — |
| CNA_2_5 | — | — |
| LOH_2_16 | — | — |
| CNA_2_17 | — | — |
| LOH_2_18 | — | — |
| CNA_2_22 | — | — |
| CNA_2_23 | — | — |
| CNA_3_0 | — | — |
| CNA_3_1 | — | — |
| CNA_3_2 | — | — |
| CNA_3_3 | — | — |
| CNA_3_4 | — | — |
| CNA_3_6 | — | — |
| LOH_3_6 | — | — |
| CNA_3_7 | — | — |
| LOH_3_7 | — | — |
| CNA_3_11 | — | — |
| CNA_3_12 | — | — |
| CNA_3_13 | — | — |
| CNA_3_14 | — | — |
| CNA_3_15 | — | — |
| CNA_3_16 | — | — |
| CNA_3_17 | — | — |
| CNA_3_18 | — | — |
| CNA_3_19 | — | — |
| CNA_4_2 | — | — |
| CNA_4_8 | — | — |
| LOH_4_8 | — | — |
| CNA_4_9 | — | — |
| LOH_4_9 | — | — |
| LOH_4_17 | — | — |
| CNA_4_18 | — | — |
| CNA_5_0 | — | — |
| CNA_5_1 | — | — |
| CNA_5_2 | — | — |
| CNA_5_6 | — | — |
| LOH_5_6 | — | — |
| CNA_5_7 | — | — |
| LOH_5_7 | — | — |

TABLE 5-continued

| DNA | | |
|---|---|---|
| DNA Feature | NCBI Gene ID | NCBI Accession Number(s) |
| CNA_5_8 | — | — |
| LOH_5_8 | — | — |
| CNA_5_9 | — | — |
| LOH_5_9 | — | — |
| CNA_5_10 | — | — |
| LOH_5_10 | — | — |
| CNA_5_11 | — | — |
| LOH_5_11 | — | — |
| CNA_5_12 | — | — |
| LOH_5_12 | — | — |
| CNA_5_13 | — | — |
| LOH_5_13 | — | — |
| CNA_5_14 | — | — |
| LOH_5_14 | — | — |
| CNA_5_15 | — | — |
| CNA_5_16 | — | — |
| CNA_5_17 | — | — |
| CNA_6_0 | — | — |
| CNA_6_1 | — | — |
| CNA_6_2 | — | — |
| CNA_6_3 | — | — |
| CNA_6_4 | — | — |
| CNA_6_8 | — | — |
| CNA_6_9 | — | — |
| CNA_6_10 | — | — |
| LOH_6_10 | — | — |
| CNA_6_12 | — | — |
| LOH_6_12 | — | — |
| CNA_6_13 | — | — |
| CNA_6_14 | — | — |
| CNA_6_15 | — | — |
| CNA_6_16 | — | — |
| LOH_6_16 | — | — |
| CNA_7_0 | — | — |
| CNA_7_3 | — | — |
| CNA_7_4 | — | — |
| CNA_7_5 | — | — |
| CNA_7_7 | — | — |
| CNA_7_8 | — | — |
| CNA_7_9 | — | — |
| CNA_7_10 | — | — |
| CNA_7_11 | — | — |
| CNA_7_13 | — | — |
| CNA_7_14 | — | — |
| CNA_7_15 | — | — |
| CNA_8_0 | — | — |
| CNA_8_1 | — | — |
| LOH_8_1 | — | — |
| CNA_8_2 | — | — |
| LOH_8_2 | — | — |
| CNA_9_2 | — | — |
| CNA_9_3 | — | — |
| LOH_9_3 | — | — |
| CNA_9_6 | — | — |
| CNA_9_7 | — | — |
| CNA_9_8 | — | — |
| CNA_9_9 | — | — |
| LOH_9_9 | — | — |
| LOH_9_10 | — | — |
| CNA_9_11 | — | — |
| LOH_9_12 | — | — |
| CNA_9_13 | — | — |
| LOH_9_13 | — | — |
| CNA_10_0 | — | — |
| CNA_10_2 | — | — |
| CNA_10_4 | — | — |
| CNA_10_5 | — | — |
| CNA_10_7 | — | — |
| LOH_10_7 | — | — |
| CNA_10_8 | — | — |
| CNA_10_10 | — | — |
| LOH_10_11 | — | — |
| CNA_10_12 | — | — |
| LOH_10_12 | — | — |
| CNA_11_1 | — | — |
| CNA_11_2 | — | — |

TABLE 5-continued

| DNA | | |
|---|---|---|
| DNA Feature | NCBI Gene ID | NCBI Accession Number(s) |
| CNA_11_3 | — | — |
| CNA_11_6 | — | — |
| CNA_11_11 | — | — |
| CNA_11_12 | — | — |
| CNA_12_1 | — | — |
| CNA_12_2 | — | — |
| LOH_12_8 | — | — |
| LOH_12_10 | — | — |
| CNA_12_12 | — | — |
| CNA_13_2 | — | — |
| CNA_13_3 | — | — |
| CNA_13_4 | — | — |
| LOH_13_4 | — | — |
| CNA_13_5 | — | — |
| CNA_13_7 | — | — |
| CNA_14_9 | — | — |
| CNA_16_0 | — | — |
| CNA_16_2 | — | — |
| LOH_16_4 | — | — |
| CNA_16_7 | — | — |
| LOH_16_7 | — | — |
| CNA_16_8 | — | — |
| CNA_17_0 | — | — |
| CNA_17_1 | — | — |
| LOH_17_1 | — | — |
| CNA_17_3 | — | — |
| LOH_17_3 | — | — |
| CNA_17_5 | — | — |
| CNA_17_6 | — | — |
| CNA_17_7 | — | — |
| LOH_18_2 | — | — |
| LOH_18_3 | — | — |
| CNA_18_4 | — | — |
| LOH_18_4 | — | — |
| CNA_18_5 | — | — |
| LOH_18_5 | — | — |
| CNA_19_1 | — | — |
| LOH_19_1 | — | — |
| LOH_19_3 | — | — |
| CNA_19_5 | — | — |
| CNA_20_1 | — | — |
| CNA_20_3 | — | — |
| CNA_20_4 | — | — |
| CNA_20_5 | — | — |
| CNA_21_2 | — | — |
| CNA_21_3 | — | — |
| CNA_22_3 | — | — |
| CNA_p_10 | — | — |
| CNA_p_16 | — | — |
| CNA_p_17 | — | — |
| CNA_p_3 | — | — |
| CNA_p_5 | — | — |
| CNA_q_1 | — | — |
| CNA_q_13 | — | — |
| CNA_q_16 | — | — |
| CNA_q_18 | — | — |
| CNA_q_20 | — | — |
| LOH_p_3 | — | — |
| LOH_q_9 | — | — |
| VDAC1P12 | 100874289 | NG_032346; NC_000013 |
| RPS28P8 | 100271381 | NG_010096; NC_000013 |
| MAPK6P3 | 317684 | NG_002453; NG_029191; NC_000013 |
| SPRYD7 | 57213 | NC_000013 |
| RPL18P10 | 100271286 | NC_000013; NG_010943 |
| VPS36 | 51028 | NC_000013 |
| LINC00393 | 100874156 | NC_000013 |
| ANKRD29 | 147463 | NC_000018 |
| LINC01543 | 100506787 | NC_000018 |
| KCTD1 | 284252 | NG_054919; NC_000018 |
| CIAPIN1P | 728599 | NG_054919; NC_000018; NG_008808 |
| AQP4 | 361 | NG_029560; NC_000018 |
| CHST9 | 83539 | NG_029856; NC_000018 |
| LINC01908 | 105372037 | NC_000018 |
| UBA52P9 | 100271344 | NC_000018; NG_011241 |
| RBM22P1 | 400645 | NG_023396; NC_000018 |
| PA2G4P3 | 619212 | NG_005881; NC_000018 |

TABLE 5-continued

| DNA | | |
|---|---|---|
| DNA Feature | NCBI Gene ID | NCBI Accession Number(s) |
| CDH2 | 1000 | NG_011959; NC_000018 |
| ARIH2P1 | 390844 | NG_009482; NC_000018 |
| DSC3 | 1825 | NC_000018; NG_016782 |
| DSC2 | 1824 | NC_000018; NG_008208 |
| DSC1 | 1823 | NC_000018; NG_029192 |
| DSG3 | 1830 | NC_000018 |
| DSG2 | 1829 | NC_000018; NG_007072 |
| TTR | 7276 | NC_000018; NG_009490 |
| B4GALT6 | 9331 | NC_000018 |
| LRRC37A7P | 100421589 | NC_000018; NG_026286 |
| SLC25A52 | 147407 | NC_000018 |
| TRAPPC8 | 22878 | NC_000018 |
| PGDP1 | 342705 | NG_022489; NC_000018 |
| RNF125 | 54941 | NG_042056; NC_000018 |
| RNF138 | 51444 | NC_000018; NG_029944 |
| GAREM1 | 64762 | NC_000018; NG_030329 |
| MEP1B | 4225 | NC_000018 |
| CLUHP6 | 100418754 | NC_000018; NG_026287 |
| HNRNPA1P7 | 388275 | NG_005529; NG_030329; NC_000018 |
| WBP11P1 | 441818 | NC_000018 |
| KLHL14 | 57565 | NC_000018 |
| CCDC178 | 374864 | NC_000018 |
| ASXL3 | 80816 | NG_055244; NC_000018 |
| NOL4 | 8715 | NC_000018 |
| DTNA | 1837 | NG_009201; NC_000018 |
| MAPRE2 | 10982 | NC_000018; NG_047123 |
| ZNF271P | 10778 | NC_000018 |
| ZNF24 | 7572 | NC_000018 |
| ZNF396 | 252884 | NC_000018 |
| INO80C | 125476 | NC_000018 |
| fusion_FRS2_anygene | 10818 | NC_000012 |
| fusion_SLC45A3_anygene | 85414 | NC_000001 |
| fusion_TMPRSS2_anygene | 7113 | NC_000021; NG_047085 |
| fusion_anygene_C12orf28 | 196446 | NC_000012 |
| fusion_anygene_CPM | 1368 | NC_000012 |
| fusion_anygene_ERG | 2078 | NC_000021; NG_029732 |
| fusion_anygene_RET | 5979 | NG_007489; NC_000010 |
| fusion_TMPRSS2_ERG | 7113; 2078 | NC_000021; NG_047085 NC_000021; NG_029732 |
| tmb | — | — |
| ploidy | — | — |
| msi | — | — |
| Liver_Neoplasm | | |
| BAP1_mut | 8314 | NG_031859; NC_000003 |
| PTEN_mut | 5728 | NC_000010; NW_013171807; NG_007466 |
| SYNE1_mut | 23345 | NG_012855; NC_000006 |
| TTN_mut | 7273 | NC_000002; NG_011618 |
| ZFHX4_mut | 79776 | NC_000008 |
| KRAS_p.G12 | 3845 | NC_000012; NG_007524 |
| PIK3CA_hotspots | 5290 | NC_000003; NG_012113 |
| CTNNB1_hotspots | 1499 | NC_000003; NG_013302 |
| BRAF_hotspots | 673 | NC_000007; NG_007873 |
| KRAS_hotspots | 3845 | NC_000012; NG_007524 |
| CNA_1_0 | — | — |
| LOH_1_0 | — | — |
| CNA_1_3 | — | — |
| CNA_1_9 | — | — |
| CNA_1_10 | — | — |
| CNA_1_11 | — | — |
| CNA_1_14 | — | — |
| CNA_1_15 | — | — |
| CNA_2_20 | — | — |
| LOH_2_22 | — | — |
| CNA_2_23 | — | — |
| LOH_2_23 | — | — |
| LOH_3_0 | — | — |
| LOH_3_1 | — | — |
| LOH_3_8 | — | — |
| LOH_3_11 | — | — |
| LOH_3_12 | — | — |
| CNA_3_14 | — | — |
| CNA_3_16 | — | — |
| CNA_3_19 | — | — |
| CNA_4_1 | — | — |

TABLE 5-continued

| DNA | | |
|---|---|---|
| DNA Feature | NCBI Gene ID | NCBI Accession Number(s) |
| LOH_4_8 | — | — |
| CNA_4_9 | — | — |
| CNA_4_10 | — | — |
| LOH_4_10 | — | — |
| LOH_4_17 | — | — |
| CNA_4_18 | — | — |
| CNA_5_0 | — | — |
| CNA_5_7 | — | — |
| LOH_5_7 | — | — |
| CNA_5_9 | — | — |
| LOH_5_9 | — | — |
| CNA_5_13 | — | — |
| CNA_5_16 | — | — |
| LOH_5_16 | — | — |
| CNA_6_0 | — | — |
| LOH_6_1 | — | — |
| CNA_6_2 | — | — |
| CNA_6_4 | — | — |
| CNA_6_10 | — | — |
| LOH_6_14 | — | — |
| LOH_6_16 | — | — |
| CNA_7_3 | — | — |
| CNA_8_0 | — | — |
| CNA_8_1 | — | — |
| LOH_8_1 | — | — |
| LOH_8_2 | — | — |
| CNA_8_10 | — | — |
| CNA_8_13 | — | — |
| LOH_9_0 | — | — |
| LOH_9_1 | — | — |
| LOH_9_3 | — | — |
| CNA_9_11 | — | — |
| CNA_9_12 | — | — |
| CNA_10_1 | — | — |
| LOH_10_2 | — | — |
| LOH_10_4 | — | — |
| LOH_10_12 | — | — |
| LOH_11_1 | — | — |
| CNA_11_7 | — | — |
| LOH_11_11 | — | — |
| CNA_12_1 | — | — |
| CNA_13_3 | — | — |
| CNA_13_4 | — | — |
| CNA_13_6 | — | — |
| CNA_15_4 | — | — |
| LOH_15_4 | — | — |
| CNA_16_0 | — | — |
| CNA_16_1 | — | — |
| CNA_16_2 | — | — |
| CNA_16_7 | — | — |
| LOH_16_8 | — | — |
| CNA_17_0 | — | — |
| LOH_17_4 | — | — |
| LOH_17_5 | — | — |
| LOH_17_7 | — | — |
| LOH_18_3 | — | — |
| CNA_18_6 | — | — |
| LOH_19_4 | — | — |
| CNA_19_5 | — | — |
| CNA_20_4 | — | — |
| CNA_21_2 | — | — |
| CNA_22_3 | — | — |
| LOH_22_3 | — | — |
| LOH_22_4 | — | — |
| CNA_p_16 | — | — |
| CNA_p_17 | — | — |
| CNA_p_3 | — | — |
| CNA_q_1 | — | — |
| CNA_q_16 | — | — |
| CNA_q_18 | — | — |
| LOH_p_10 | — | — |
| LOH_p_17 | — | — |
| LOH_p_3 | — | — |
| CAMTA1 | 23261 | NG_053148; NC_000001 |
| UCK2 | 7371 | NC_000001 |
| RCSD1 | 92241 | NC_000001 |

TABLE 5-continued

| DNA | | |
|---|---|---|
| DNA Feature | NCBI Gene ID | NCBI Accession Number(s) |
| LINC01724 | 105371673 | NC_000001 |
| KCNU1 | 157855 | NC_000008 |
| ERLIN2 | 11160 | NC_000008; NG_032059 |
| ASH2L | 9070 | NC_000008 |
| C8orf86 | 389649 | NC_000008 |
| tmb | — | — |
| Urinary_Bladder_Urothelial_Carcinoma | | |
| ARID1A_mut | 8289 | NC_000001; NG_029965 |
| ASXL2_mut | 55252 | NG_052995; NC_000002 |
| CSMD1_mut | 64478 | NC_000008 |
| ELF3_mut | 1999 | NC_000001 |
| EP300_mut | 2033 | NG_009817; NC_000022 |
| FAM135B_mut | 51059 | NC_000008 |
| HMCN1_mut | 83872 | NC_000001; NG_011841 |
| HUWE1_mut | 10075 | NC_000023; NG_016261 |
| HYDIN_mut | 54768 | NC_000016; NG_033116; NW_013171813 |
| IGSF10_mut | 285313 | NC_000003 |
| KDM6A_mut | 7403 | NG_016260; NC_000023 |
| KIAA1109_mut | 84162 | NG_015813; NC_000004 |
| KMT2C_mut | 58508 | NC_000007; NG_033948 |
| KMT2D_mut | 8085 | NG_027827; NC_000012 |
| LRP1B_mut | 53353 | NC_000002; NG_051023 |
| LRRTM4_mut | 80059 | NC_000002; NG_053082 |
| MACF1_mut | 23499 | NC_000001; NG_050926 |
| PCLO_mut | 27445 | NG_047145; NC_000007 |
| RB1_mut | 5925 | NG_009009; NC_000013 |
| SLC8A1_mut | 6546 | NC_000002 |
| SPTAN1_mut | 6709 | NC_000009; NG_027748 |
| STAG2_mut | 10735 | NC_000023; NG_033796 |
| THSD7A_mut | 221981 | NC_000007; NG_027670 |
| USH2A_mut | 7399 | NC_000001; NG_009497 |
| BRAF_p.V600 | 673 | NC_000007; NG_007873 |
| TP53_p.R248 | 7157 | NG_017013; NC_000017 |
| ERBB2_hotspots | 2064 | NG_007503; NC_000017 |
| NFE2L2_hotspots | 4780 | NC_000002 |
| FGFR3_hotspots | 2261 | NC_000004; NG_012632 |
| HRAS_hotspots | 3265 | NT_187586; NG_007666; NC_000011 |
| ERCC2_hotspots | 2068 | NC_000019; NG_007067 |
| CNA_1_1 | — | — |
| CNA_1_4 | — | — |
| LOH_1_6 | — | — |
| CNA_1_11 | — | — |
| CNA_1_15 | — | — |
| CNA_1_19 | — | — |
| CNA_1_20 | — | — |
| CNA_2_6 | — | — |
| CNA_2_19 | — | — |
| CNA_2_20 | — | — |
| LOH_2_22 | — | — |
| CNA_3_0 | — | — |
| LOH_3_0 | — | — |
| CNA_3_1 | — | — |
| LOH_3_1 | — | — |
| CNA_3_2 | — | — |
| LOH_3_2 | — | — |
| CNA_3_19 | — | — |
| CNA_4_14 | — | — |
| CNA_5_1 | — | — |
| CNA_5_2 | — | — |
| CNA_5_15 | — | — |
| CNA_5_16 | — | — |
| CNA_5_17 | — | — |
| CNA_6_3 | — | — |
| CNA_6_4 | — | — |
| LOH_6_7 | — | — |
| CNA_6_8 | — | — |
| CNA_6_9 | — | — |
| CNA_6_10 | — | — |
| CNA_6_11 | — | — |
| CNA_6_12 | — | — |
| CNA_6_13 | — | — |
| CNA_6_14 | — | — |
| CNA_6_16 | — | — |
| CNA_7_0 | — | — |

TABLE 5-continued

| DNA | | |
|---|---|---|
| DNA Feature | NCBI Gene ID | NCBI Accession Number(s) |
| CNA_7_2 | — | — |
| CNA_7_4 | — | — |
| CNA_7_7 | — | — |
| CNA_7_9 | — | — |
| CNA_7_10 | — | — |
| CNA_7_11 | — | — |
| CNA_7_12 | — | — |
| CNA_7_13 | — | — |
| CNA_7_14 | — | — |
| CNA_7_15 | — | — |
| CNA_8_0 | — | — |
| CNA_8_1 | — | — |
| LOH_8_1 | — | — |
| CNA_8_2 | — | — |
| CNA_8_6 | — | — |
| CNA_9_2 | — | — |
| LOH_9_2 | — | — |
| LOH_9_3 | — | — |
| CNA_9_7 | — | — |
| LOH_9_7 | — | — |
| LOH_9_11 | — | — |
| LOH_9_13 | — | — |
| CNA_10_0 | — | — |
| LOH_10_0 | — | — |
| CNA_10_1 | — | — |
| CNA_10_4 | — | — |
| LOH_10_4 | — | — |
| CNA_10_5 | — | — |
| CNA_10_11 | — | — |
| CNA_10_12 | — | — |
| CNA_11_1 | — | — |
| LOH_11_1 | — | — |
| CNA_11_2 | — | — |
| LOH_11_2 | — | — |
| CNA_11_3 | — | — |
| LOH_11_3 | — | — |
| CNA_11_6 | — | — |
| CNA_11_7 | — | — |
| LOH_11_7 | — | — |
| CNA_11_10 | — | — |
| CNA_11_11 | — | — |
| LOH_11_11 | — | — |
| CNA_11_12 | — | — |
| CNA_12_7 | — | — |
| CNA_12_8 | — | — |
| CNA_12_11 | — | — |
| LOH_12_11 | — | — |
| CNA_13_2 | — | — |
| LOH_13_2 | — | — |
| CNA_13_3 | — | — |
| LOH_13_3 | — | — |
| LOH_13_4 | — | — |
| CNA_13_5 | — | — |
| CNA_13_6 | — | — |
| LOH_13_7 | — | — |
| CNA_13_8 | — | — |
| LOH_13_8 | — | — |
| CNA_13_9 | — | — |
| LOH_13_10 | — | — |
| CNA_15_3 | — | — |
| CNA_15_4 | — | — |
| LOH_15_6 | — | — |
| CNA_16_0 | — | — |
| CNA_16_1 | — | — |
| LOH_16_4 | — | — |
| CNA_16_5 | — | — |
| LOH_16_5 | — | — |
| CNA_16_6 | — | — |
| LOH_16_6 | — | — |
| CNA_16_7 | — | — |
| LOH_16_7 | — | — |
| CNA_16_8 | — | — |
| LOH_16_8 | — | — |
| CNA_17_0 | — | — |
| LOH_17_0 | — | — |
| CNA_17_1 | — | — |

TABLE 5-continued

| DNA | | |
|---|---|---|
| DNA Feature | NCBI Gene ID | NCBI Accession Number(s) |
| LOH_17_1 | — | — |
| CNA_17_3 | — | — |
| LOH_17_3 | — | — |
| LOH_17_4 | — | — |
| CNA_17_5 | — | — |
| LOH_17_5 | — | — |
| CNA_17_6 | — | — |
| LOH_17_6 | — | — |
| CNA_17_7 | — | — |
| LOH_17_7 | — | — |
| CNA_18_0 | — | — |
| LOH_18_0 | — | — |
| CNA_18_2 | — | — |
| LOH_18_2 | — | — |
| CNA_18_3 | — | — |
| LOH_18_7 | — | — |
| LOH_19_0 | — | — |
| CNA_19_1 | — | — |
| CNA_19_4 | — | — |
| LOH_19_4 | — | — |
| CNA_19_5 | — | — |
| CNA_20_3 | — | — |
| CNA_21_3 | — | — |
| CNA_22_4 | — | — |
| LOH_22_4 | — | — |
| CNA_p_3 | — | — |
| CNA_q_1 | — | — |
| CNA_q_13 | — | — |
| CNA_q_16 | — | — |
| LOH_p_17 | — | — |
| LOH_p_3 | — | — |
| LOH_q_16 | — | — |
| NYAP2 | 57624 | NC_000002 |
| ASB1 | 51665 | NC_000002 |
| LINC01107 | 151171 | NC_000002 |
| OR6B3 | 150681 | NC_000002 |
| OR5S1P | 391496 | NG_004369; NC_000002 |
| DUSP28 | 285193 | NC_000002 |
| RNPEPL1 | 57140 | NC_000002 |
| CAPN10 | 11132 | NC_000002; NG_011558 |
| GPR35 | 2859 | NC_000002 |
| ATG4B | 23192 | NC_000002 |
| DTYMK | 1841 | NC_000002 |
| D2HGDH | 728294 | NC_000002; NG_012012 |
| GAL3ST2 | 64090 | NG_046977; NC_000002; NT_187527 |
| LRRIQ4 | 344657 | NC_000003 |
| LRRC31 | 79782 | NC_000003 |
| KRT18P43 | 151825 | NC_000003; NG_009654 |
| SAMD7 | 344658 | NC_000003 |
| SEC62 | 7095 | NC_000003 |
| GPR160 | 26996 | NC_000003 |
| PRKCI | 5584 | NC_000003 |
| SKIL | 6498 | NC_000003; NG_030357 |
| SLC7A14 | 57709 | NC_000003; NG_034121 |
| KRT8P13 | 730023 | NG_005969; NG_034121; NC_000003 |
| SLC2A2 | 6514 | NG_008108; NC_000003 |
| TNIK | 23043 | NG_054934; NC_000003 |
| PLD1 | 5337 | NG_029851; NC_000003 |
| TMEM212-AS1 | 100874219 | NC_000003 |
| TMEM212 | 389177 | NC_000003 |
| RPS27AP8 | 100271375 | NG_010054; NC_000003 |
| TBL1XR1 | 79718 | NC_000003; NG_047195 |
| LINC00501 | 100820709 | NC_000003 |
| ASS1P7 | 339845 | NC_000003; NG_001079 |
| LINC00578 | 100505566 | NC_000003 |
| LINC02015 | 102724550 | NC_000003 |
| KCNMB2 | 10242 | NC_000003 |
| PPIAP75 | 111082968 | NG_065980; NC_000003 |
| ZMAT3 | 64393 | NG_050678; NC_000003 |
| PIK3CA | 5290 | NC_000003; NG_012113 |
| KCNMB3 | 27094 | NC_000003 |
| LRRFIP1P1 | 101290506 | NC_000003; NG_033175 |
| ACTL6A | 86 | NC_000003 |
| MRPL47 | 57129 | NC_000003 |
| NDUFB5 | 4711 | NC_000003 |
| USP13 | 8975 | NC_000003 |

TABLE 5-continued

| DNA | | |
|---|---|---|
| DNA Feature | NCBI Gene ID | NCBI Accession Number(s) |
| MCCC1 | 56922 | NG_008100; NC_000003 |
| OPA1 | 4976 | NC_000003; NG_011605 |
| LINC02038 | 105374285 | NC_000003 |
| LINC02026 | 647323 | NC_000003 |
| TNK2 | 10188 | NG_029779; NC_000003 |
| fusion_FGFR3_anygene | 2261 | NC_000004; NG_012632 |
| fusion_FRS2_anygene | 10818 | NC_000012 |
| fusion_SLC45A3_anygene | 85414 | NC_000001 |
| fusion_TMPRSS2_anygene | 7113 | NC_000021; NG_047085 |
| fusion_anygene_C12orf28 | 196446 | NC_000012 |
| fusion_anygene_CPM | 1368 | NC_000012 |
| fusion_anygene_ERG | 2078 | NC_000021; NG_029732 |
| fusion_anygene_RET | 5979 | NG_007489; NC_000010 |
| fusion_anygene_TACC3 | 10460 | NG_064424; NC_000004 |
| fusion_FGFR3_TACC3 | 2261; 10460 | NC_000004; NG_012632 NG_064424; NC_000004 |
| fusion_TMPRSS2_ERG | 7113; 2078 | NC_000021; NG_047085 NC_000021; NG_029732 |
| tmb | — | — |
| ploidy | — | — |
| msi | — | — |
| Melanoma | | |
| CNA_12_5 | — | — |
| LOH_11_10 | — | — |
| CNA_q_13 | — | — |
| CNA_3_7 | — | — |
| BRAF_p.V600 | 673 | NC_000007; NG_007873 |
| CNA_8_0 | — | — |
| CNA_3_19 | — | — |
| LOH_17_0 | — | — |
| LOH_11_9 | — | — |
| NF1_mut | 4763 | NC_000017; NG_009018 |
| LOH_3_3 | — | — |
| CNA_5_2 | — | — |
| LOH_6_13 | — | — |
| CNA_22_4 | — | — |
| LOH_p_10 | — | — |
| COL4A4_mut | 1286 | NG_011592; NC_000002 |
| MYH4_mut | 4622 | NC_000017; NG_052846 |
| CNA_7_12 | — | — |
| CNA_13_3 | — | — |
| DESI1 | 27351 | NC_000022 |
| LOH_17_1 | — | — |
| CNA_9_2 | — | — |
| CNA_10_2 | — | — |
| LOH_11_12 | — | — |
| LOH_9_0 | — | — |
| CNA_p_16 | — | — |
| CNA_3_13 | — | — |
| PIK3CA_hotspots | 5290 | NC_000003; NG_012113 |
| CSMD2_mut | 114784 | NC_000001; NG_053181 |
| CNA_10_11 | — | — |
| CNA_10_7 | — | — |
| CNA_10_8 | — | — |
| LOH_18_5 | — | — |
| POLR3H | 171568 | NC_000022 |
| LOH_p_3 | — | — |
| GNAQ_hotspots | 2776 | NG_027904; NC_000009 |
| CNA_7_14 | — | — |
| LOH_18_6 | — | — |
| LOH_3_13 | — | — |
| TTN_mut | 7273 | NC_000002; NG_011618 |
| LOH_3_17 | — | — |
| CNA_3_18 | — | — |
| MUC16_mut | 94025 | NC_000019; NG_055257 |
| CNA_10_9 | — | — |
| KIT_mut | 3815 | NC_000004; NG_007456 |
| CNA_9_9 | — | — |
| PTEN_mut | 5728 | NC_000010; NW_013171807; NG_007466 |
| CNA_6_3 | — | — |
| CNA_3_16 | — | — |
| THSD7B_mut | 80731 | NC_000002 |
| CNA_21_2 | — | — |
| CNA_p_3 | — | — |

TABLE 5-continued

| DNA | | |
|---|---|---|
| DNA Feature | NCBI Gene ID | NCBI Accession Number(s) |
| CNA_6_4 | — | — |
| CNA_8_6 | — | — |
| NRAS_hotspots | 4893 | NG_007572; NC_000001 |
| GNA11_p.Q209 | 2767 | NC_000019; NG_033852 |
| KCNH5_mut | 27133 | NG_034062; NC_000014 |
| CNA_13_5 | — | — |
| PKHD1L1_mut | 93035 | NC_000008 |
| CNA_7_11 | — | — |
| CNA_q_1 | — | — |
| CNA_13_7 | — | — |
| LOH_11_11 | — | — |
| WDFY4_mut | 57705 | NC_000010 |
| CNA_3_6 | — | — |
| LOH_11_6 | — | — |
| LOH_p_17 | — | — |
| CNA_8_1 | — | — |
| LOH_6_7 | — | — |
| CNA_q_7 | — | — |
| CNA_8_5 | — | — |
| CNA_3_17 | — | — |
| CSDC2 | 27254 | NC_000022 |
| LOH_10_5 | — | — |
| LOH_9_1 | — | — |
| LOH_9_2 | — | — |
| NRAS_p.Q61 | 4893 | NG_007572; NC_000001 |
| CNA_5_1 | — | — |
| LOH_3_6 | — | — |
| COL5A3_mut | 50509 | NC_000019; NG_046943 |
| CNA_8_2 | — | — |
| FAM8A1 | 51439 | NC_000006 |
| SHISA8 | 440829 | NC_000022 |
| CNA_8_13 | — | — |
| msi | — | — |
| DNAH8_mut | 1769 | NG_041805; NC_000006 |
| DNAH5_mut | 1767 | NC_000005; NG_013081 |
| CNA_9_1 | — | — |
| CNA_11_11 | — | — |
| LOH_9_6 | — | — |
| CNA_11_12 | — | — |
| LOH_9_3 | — | — |
| CNA_5_14 | — | — |
| PCDH18_mut | 54510 | NC_000004 |
| DSCAM_mut | 1826 | NC_000021 |
| TP53_hotspots | 7157 | NG_017013; NC_000017 |
| CNA_7_13 | — | — |
| COL21A1_mut | 81578 | NC_000006 |
| MGAM_mut | 8972 | NT_187562; NC_000007; NG_033954 |
| C6_mut | 729 | NC_000005; NG_011582 |
| LOH_q_9 | — | — |
| LOH_10_6 | — | — |
| CNA_10_5 | — | — |
| CNA_12_8 | — | — |
| HNRNPA1P37 | 100421379 | NC_000006; NG_033003; NG_025781 |
| NRAS_mut | 4893 | NG_007572; NC_000001 |
| tmb | — | — |
| ANK3_mut | 288 | NG_029917; NC_000010 |
| CNA_7_3 | — | — |
| DNAH7_mut | 56171 | NC_000002 |
| CNA_3_11 | — | — |
| TLL1_mut | 7092 | NC_000004; NG_016278 |
| CNA_10_12 | — | — |
| CNA_6_13 | — | — |
| LOH_11_8 | — | — |
| GNA11_hotspots | 2767 | NC_000019; NG_033852 |
| CNA_p_5 | — | — |
| CNA_13_4 | — | — |
| CNA_9_3 | — | — |
| CNA_5_3 | — | — |
| COL4A3_mut | 1285 | NC_000002; NG_011591 |
| CNA_3_12 | — | — |
| LOH_6_12 | — | — |
| CNA_6_1 | — | — |
| LOH_15_4 | — | — |
| CNA_12_1 | — | — |
| LOH_19_0 | — | — |

TABLE 5-continued

| DNA | | |
|---|---|---|
| DNA Feature | NCBI Gene ID | NCBI Accession Number(s) |
| GNAQ__p.Q209 | 2776 | NG__027904; NC__000009 |
| LOH__3__7 | — | — |
| CNA__9__0 | — | — |
| CNA__18__6 | — | — |
| CNA__1__15 | — | — |
| LOH__10__2 | — | — |
| CNA__6__0 | — | — |
| PCLO__mut | 27445 | NG__047145; NC__000007 |
| BRAF__hotspots | 673 | NC__000007; NG__007873 |
| LOH__8__0 | — | — |
| CNTN5__mut | 53942 | NC__000011; NG__047156 |
| CNA__p__10 | — | — |
| CNA__q__22 | — | — |
| ARID1A__mut | 8289 | NC__000001; NG__029965 |
| CNA__6__2 | — | — |
| CNA__10__6 | — | — |
| Thyroid__Neoplasm | | |
| CNA__2__5 | — | — |
| CNA__20__5 | — | — |
| CNA__q__13 | — | — |
| BRAF__p.V600 | 673 | NC__000007; NG__007873 |
| CNA__8__12 | — | — |
| LOH__17__0 | — | — |
| HRAS__p.Q61 | 3265 | NT__187586; NG__007666; NC__000011 |
| LOH__11__2 | — | — |
| ZFHX4__mut | 79776 | NC__000008 |
| CNA__22__4 | — | — |
| LOH__1__9 | — | — |
| LOH__22__2 | — | — |
| CNA__10__2 | — | — |
| LOH__9__0 | — | — |
| LOH__q__22 | — | — |
| CNA__p__16 | — | — |
| PIK3CA__hotspots | 5290 | NC__000003; NG__012113 |
| CNA__1__0 | — | — |
| CNA__10__11 | — | — |
| CNA__14__8 | — | — |
| LOH__5__11 | — | — |
| LOH__p__3 | — | — |
| CNA__7__14 | — | — |
| LOH__8__1 | — | — |
| TTN__mut | 7273 | NC__000002; NG__011618 |
| CNA__16__7 | — | — |
| MUC16__mut | 94025 | NC__000019; NG__055257 |
| CNA__q__18 | — | — |
| CNA__6__16 | — | — |
| CNA__1__14 | — | — |
| CNA__6__3 | — | — |
| CNA__p__7 | — | — |
| IDH1__p.R132 | 3417 | NG__023319; NC__000002 |
| CNA__p__3 | — | — |
| LOH__1__0 | — | — |
| NRAS__hotspots | 4893 | NG__007572; NC__000001 |
| LOH__19__1 | — | — |
| CNA__q__1 | — | — |
| CNA__5__11 | — | — |
| IDH1__hotspots | 3417 | NG__023319; NC__000002 |
| CNA__17__3 | — | — |
| LOH__p__17 | — | — |
| CNA__q__7 | — | — |
| CNA__8__1 | — | — |
| LOH__17__4 | — | — |
| LOH__6__7 | — | — |
| LOH__1__2 | — | — |
| CNA__3__17 | — | — |
| CNA__16__8 | — | — |
| CNA__q__16 | — | — |
| CNA__2__8 | — | — |
| NRAS__p.Q61 | 4893 | NG__007572; NC__000001 |
| LOH__22__3 | — | — |
| CNA__8__13 | — | — |
| msi | — | — |
| CNA__2__2 | — | — |

TABLE 5-continued

| DNA Feature | NCBI Gene ID | NCBI Accession Number(s) |
|---|---|---|
| DNA | | |
| TRGV3 | 6976 | NC_000007; NG_001336 |
| TP53_hotspots | 7157 | NG_017013; NC_000017 |
| CNA_7_0 | — | — |
| CNA_q_8 | — | — |
| NRAS_mut | 4893 | NG_007572; NC_000001 |
| tmb | — | — |
| CNA_7_3 | — | — |
| RYR3_mut | 6263 | NC_000015; NG_047076 |
| LOH_1_8 | — | — |
| LOH_q_16 | — | — |
| CNA_10_12 | — | — |
| HRAS_hotspots | 3265 | NT_187586; NG_007666; NC_000011 |
| FAT4_mut | 79633 | NG_033865; NC_000004 |
| CNA_p_5 | — | — |
| CNA_22_2 | — | — |
| CNA_q_20 | — | — |
| LOH_3_2 | — | — |
| LOH_19_0 | — | — |
| GTF2I_p.L424 | 2969 | NC_000007; NG_008179 |
| CNA_6_0 | — | — |
| LOH_14_9 | — | — |
| CNA_22_3 | — | — |
| BRAF_hotspots | 673 | NC_000007; NG_007873 |
| LOH_8_0 | — | — |
| LOH_6_16 | — | — |
| CNA_q_22 | — | — |
| ARID1A_mut | 8289 | NC_000001; NG_029965 |
| TRGV8 | 6982 | NC_000007; NG_001336 |
| CNA_2_18 | — | — |
| CNA_6_2 | — | — |
| LOH_6_9 | — | — |
| Sarcoma | | |
| CDH9_mut | 1007 | NC_000005; NG_046968 |
| CDKN2A_mut | 1029 | NC_000009; NG_007485 |
| CHD8_mut | 57680 | NC_000014; NG_021249 |
| CHD9_mut | 80205 | NC_000016 |
| CHL1_mut | 1663 | NC_000012; NG_023352 |
| CHRM2_mut | 1129 | NC_000007; NG_011846 |
| CHRM3_mut | 1131 | NC_000001; NG_032046 |
| CIC_mut | 23152 | NC_000019; NG_042060 |
| CMYA5_mut | 202333 | NC_000005 |
| CNOT1_mut | 23019 | NC_000016 |
| CNTN3_mut | 5067 | NC_000003 |
| CNTNAP5_mut | 129684 | NC_000002 |
| CNTRL_mut | 11064 | NC_000009 |
| COL11A1_mut | 1301 | NC_000001; NG_008033 |
| COL11A2_mut | 1302 | NG_011589; NT_167249; NT_167246; NC_000006; NT_167247; NT_113891; NT_167248; NT_167245 |
| COL21A1_mut | 81578 | NC_000006 |
| COL22A1_mut | 169044 | NG_054761; NC_000008 |
| COL24A1_mut | 255631 | NC_000001; NG_053093 |
| COL28A1_mut | 340267 | NC_000007 |
| COL2A1_mut | 1280 | NG_008072; NC_000012 |
| COL3A1_mut | 1281 | NG_007404; NC_000002 |
| COL4A1_mut | 1282 | NC_000013; NG_011544 |
| COL4A2_mut | 1284 | NG_032137; NC_000013 |
| COL4A3_mut | 1285 | NC_000002; NG_011591 |
| COL4A4_mut | 1286 | NG_011592; NC_000002 |
| COL4A5_mut | 1287 | NC_000023; NG_011977 |
| COL4A6_mut | 1288 | NG_012059; NC_000023 |
| COL5A1_mut | 1289 | NG_008030; NC_000009 |
| COL5A2_mut | 1290 | NC_000002; NG_011799 |
| COL5A3_mut | 50509 | NC_000019; NG_046943 |
| COL6A3_mut | 1293 | NG_008676; NC_000002 |
| COL6A6_mut | 131873 | NC_000003; NG_054914 |
| COL7A1_mut | 1294 | NC_000003; NG_007065 |
| COL8A1_mut | 1295 | NC_000003 |
| COL9A1_mut | 1297 | NC_000006; NG_011654 |
| COPA_mut | 1314 | NG_050927; NC_000001 |
| CORIN_mut | 10699 | NG_032679; NC_000004 |
| CPAMD8_mut | 27151 | NG_054892; NC_000019 |
| CPED1_mut | 79974 | NC_000007 |
| CPS1_mut | 1373 | NC_000002; NG_008285 |
| CRB1_mut | 23418 | NG_008483; NC_000001 |

TABLE 5-continued

| DNA | | |
|---|---|---|
| DNA Feature | NCBI Gene ID | NCBI Accession Number(s) |
| CREBBP__mut | 1387 | NG__009873; NC__000016 |
| CSMD1__mut | 64478 | NC__000008 |
| CSMD2__mut | 114784 | NC__000001; NG__053181 |
| CSMD3__mut | 114788 | NC__000008 |
| CTCF__mut | 10664 | NC__000016; NG__033892 |
| CTNNA2__mut | 1496 | NC__000002 |
| CTNNA3__mut | 29119 | NG__034072; NC__000010 |
| CTNNB1__mut | 1499 | NC__000003; NG__013302 |
| CTNND2__mut | 1501 | NC__000005; NG__023544 |
| CUBN__mut | 8029 | NC__000010; NG__008967 |
| CUL9__mut | 23113 | NC__000006 |
| DCAF4L2__mut | 138009 | NC__000008 |
| DCC__mut | 1630 | NC__000018; NG__013341 |
| DCDC1__mut | 341019 | NC__000011 |
| DCHS1__mut | 8642 | NC__000011; NG__033858 |
| DDX60__mut | 55601 | NG__054636; NC__000004 |
| DDX60L__mut | 91351 | NC__000004; NG__051576 |
| DENND5B__mut | 160518 | NC__000012 |
| DMD__mut | 1756 | NC__000023; NG__012232 |
| DNAH3__mut | 55567 | NC__000016; NG__052617 |
| DNAH7__mut | 56171 | NC__000002 |
| DNAH9__mut | 1770 | NG__047047; NC__000017 |
| IDH1__p.R132 | 3417 | NG__023319; NC__000002 |
| BRAF__hotspots | 673 | NC__000007; NG__007873 |
| IDH1__hotspots | 3417 | NG__023319; NC__000002 |
| CNA__1__1 | — | — |
| CNA__1__2 | — | — |
| CNA__1__5 | — | — |
| CNA__1__6 | — | — |
| CNA__1__18 | — | — |
| CNA__1__19 | — | — |
| CNA__1__20 | — | — |
| LOH__1__20 | — | — |
| CNA__1__21 | — | — |
| CNA__1__22 | — | — |
| CNA__1__23 | — | — |
| CNA__1__24 | — | — |
| CNA__2__1 | — | — |
| LOH__2__1 | — | — |
| CNA__2__2 | — | — |
| CNA__2__4 | — | — |
| CNA__2__5 | — | — |
| LOH__2__6 | — | — |
| CNA__2__8 | — | — |
| CNA__3__0 | — | — |
| LOH__3__0 | — | — |
| CNA__3__1 | — | — |
| CNA__3__2 | — | — |
| CNA__3__3 | — | — |
| LOH__3__7 | — | — |
| CNA__3__8 | — | — |
| CNA__3__15 | — | — |
| CNA__3__16 | — | — |
| CNA__3__17 | — | — |
| LOH__3__17 | — | — |
| CNA__3__19 | — | — |
| CNA__4__2 | — | — |
| CNA__4__3 | — | — |
| CNA__4__10 | — | — |
| CNA__4__11 | — | — |
| LOH__4__11 | — | — |
| CNA__4__14 | — | — |
| CNA__4__16 | — | — |
| LOH__4__17 | — | — |
| CNA__5__0 | — | — |
| CNA__5__1 | — | — |
| CNA__5__2 | — | — |
| CNA__5__3 | — | — |
| LOH__5__3 | — | — |
| CNA__5__6 | — | — |
| LOH__5__6 | — | — |
| LOH__5__7 | — | — |
| LOH__5__9 | — | — |
| LOH__5__10 | — | — |
| LOH__5__12 | — | — |
| CNA__6__0 | — | — |

TABLE 5-continued

| DNA | | |
|---|---|---|
| DNA Feature | NCBI Gene ID | NCBI Accession Number(s) |
| CNA_6_1 | — | — |
| CNA_6_2 | — | — |
| CNA_6_3 | — | — |
| LOH_6_4 | — | — |
| CNA_6_10 | — | — |
| LOH_6_10 | — | — |
| CNA_6_11 | — | — |
| LOH_6_13 | — | — |
| CNA_6_15 | — | — |
| LOH_6_15 | — | — |
| CNA_6_16 | — | — |
| CNA_7_0 | — | — |
| CNA_7_5 | — | — |
| CNA_7_12 | — | — |
| CNA_7_14 | — | — |
| CNA_7_15 | — | — |
| CNA_8_0 | — | — |
| CNA_8_1 | — | — |
| CNA_8_2 | — | — |
| CNA_8_9 | — | — |
| CNA_8_11 | — | — |
| CNA_8_12 | — | — |
| CNA_8_13 | — | — |
| CNA_9_2 | — | — |
| CNA_9_3 | — | — |
| LOH_9_3 | — | — |
| CNA_9_7 | — | — |
| LOH_10_0 | — | — |
| LOH_10_5 | — | — |
| CNA_10_6 | — | — |
| LOH_10_6 | — | — |
| LOH_10_7 | — | — |
| CNA_11_6 | — | — |
| CNA_12_1 | — | — |
| CNA_12_5 | — | — |
| CNA_12_6 | — | — |
| CNA_12_7 | — | — |
| CNA_12_8 | — | — |
| CNA_13_2 | — | — |
| LOH_13_2 | — | — |
| CNA_13_4 | — | — |
| LOH_13_4 | — | — |
| CNA_13_5 | — | — |
| CNA_15_5 | — | — |
| LOH_16_4 | — | — |
| LOH_16_7 | — | — |
| LOH_16_8 | — | — |
| CNA_17_0 | — | — |
| LOH_17_0 | — | — |
| CNA_17_1 | — | — |
| LOH_17_1 | — | — |
| CNA_17_3 | — | — |
| CNA_18_3 | — | — |
| CNA_18_5 | — | — |
| CNA_18_6 | — | — |
| LOH_18_6 | — | — |
| CNA_18_7 | — | — |
| CNA_19_0 | — | — |
| LOH_19_0 | — | — |
| CNA_19_3 | — | — |
| CNA_19_4 | — | — |
| CNA_19_5 | — | — |
| CNA_20_0 | — | — |
| CNA_20_1 | — | — |
| CNA_20_5 | — | — |
| CNA_22_4 | — | — |
| CNA_p_10 | — | — |
| CNA_p_16 | — | — |
| CNA_p_17 | — | — |
| CNA_p_18 | — | — |
| CNA_p_20 | — | — |
| CNA_p_3 | — | — |
| CNA_p_5 | — | — |
| CNA_q_1 | — | — |
| CNA_q_13 | — | — |
| CNA_q_18 | — | — |

TABLE 5-continued

| DNA | | |
|---|---|---|
| DNA Feature | NCBI Gene ID | NCBI Accession Number(s) |
| CNA_q_20 | — | — |
| CNA_q_7 | — | — |
| LOH_p_17 | — | — |
| LOH_p_3 | — | — |
| CEP57L1P1 | 221017 | NG_005976; NC_000010 |
| PRF1 | 5551 | NC_000010; NG_009615 |
| CFAP70 | 118491 | NC_000010 |
| TIMM9P1 | 100862726 | NG_032133; NC_000010; NG_030484 |
| COMTD1 | 118881 | NC_000010 |
| RPL39P25 | 100271517 | NC_000010; NG_010826 |
| HMGA1P5 | 387063 | NC_000010; NG_008009 |
| SPA17P1 | 171424 | NG_001328; NC_000010 |
| ZNF503 | 84858 | NC_000010 |
| LRMDA | 83938 | NC_000010; NG_042180 |
| ATP5MC1P8 | 100288222 | NC_000010; NG_028756 |
| KCNMA1 | 3778 | NC_000010; NG_012270 |
| COX6CP15 | 106480268 | NC_000010; NG_045680; NG_012270 |
| IMPDH1P5 | 340780 | NG_005147; NT_187580; NC_000010 |
| DLG5 | 9231 | NC_000010; NG_011484; NT_187580 |
| POLR3A | 11128 | NG_029648; NC_000010 |
| RPS24 | 6229 | NC_000010; NG_012633 |
| GNAI2P2 | 401646 | NC_000010; NG_030117 |
| ZMIZ1 | 57178 | NC_000010; NG_028289 |
| RPS12P18 | 100271354 | NC_000010; NG_011294 |
| SFTPA2 | 729238 | NG_013046; NC_000010 |
| MBL3P | 50639 | NC_000010; NG_029674 |
| SFTPA3P | 100288405 | NG_016155; NC_000010 |
| SFTPA1 | 653509 | NG_021189; NC_000010 |
| BEND3P3 | 650623 | NG_011922; NC_000010 |
| NUTM2B | 729262 | NG_012780; NC_000010 |
| RPL22P18 | 100271290 | NG_010959; NC_000010 |
| PLAC9 | 219348 | NC_000010 |
| ANXA11 | 311 | NC_000010 |
| LINC00857 | 439990 | NC_000010 |
| RPS12P2 | 619448 | NG_009566; NC_000010 |
| EIF5AP4 | 642592 | NC_000010; NG_006529 |
| DYDC2 | 84332 | NC_000010 |
| PRXL2A | 84293 | NC_000010 |
| TSPAN14 | 81619 | NC_000010 |
| SH2D4B | 387694 | NC_000010 |
| RPS7P9 | 100128756 | NC_000010; NG_011267 |
| FARSBP1 | 647532 | NC_000010; NG_005861 |
| WARS2P1 | 100421633 | NG_025451; NC_000010 |
| RPA2P2 | 389990 | NC_000010; NG_022150 |
| NRG3 | 10718 | NG_013373; NC_000010 |
| MARK2P15 | 100533794 | NC_000010; NG_028751 |
| CACYBPP1 | 100420043 | NG_025452; NC_000010 |
| TUBGCP2 | 10844 | NC_000010 |
| ZNF511 | 118472 | NC_000010 |
| ZNF511-PRAP1 | 104326056 | NC_000010 |
| CALY | 50632 | NC_000010 |
| BANF1P2 | 414169 | NG_029687; NC_000010 |
| ANKRD26P1 | 124149 | NC_000016 |
| SHCBP1 | 79801 | NC_000016 |
| RAB43P1 | 440375 | NC_000016; NG_005358 |
| VPS35 | 55737 | NC_000016; NG_029970 |
| ORC6 | 23594 | NG_028241; NC_000016 |
| NETO2 | 81831 | NC_000016; NG_047201 |
| LINC02133 | 101927132 | NC_000016 |
| LINC01571 | 101927364 | NC_000016 |
| LINC00919 | 100505619 | NC_000016 |
| LINC02180 | 102467079 | NC_000016 |
| CASC22 | 283854 | NC_000016 |
| TOX3 | 27324 | NC_000016; NG_012623 |
| CASC16 | 643714 | NC_000016 |
| PHBP21 | 390730 | NG_022521; NC_000016 |
| CHD9 | 80205 | NC_000016 |
| RBL2 | 5934 | NC_000016 |
| AKTIP | 64400 | NC_000016 |
| RPL13P12 | 388344 | NC_000017; NG_007541 |
| TSEN15P1 | 100288179 | NG_030099; NC_000017 |
| MED9 | 55090 | NC_000017 |
| RASD1 | 51655 | NG_028074; NC_000017 |
| PEMT | 10400 | NC_000017 |
| SMCR2 | 105371564 | NC_000017 |
| RAI1 | 10743 | NC_000017; NG_007101 |

TABLE 5-continued

| DNA | | |
|---|---|---|
| DNA Feature | NCBI Gene ID | NCBI Accession Number(s) |
| SREBF1 | 6720 | NC_000017; NG_029029 |
| TOM1L2 | 146691 | NC_000017; NG_053113 |
| DRC3 | 83450 | NC_000017 |
| ATPAF2 | 91647 | NC_000017; NG_012824 |
| GID4 | 79018 | NC_000017 |
| DRG2 | 1819 | NC_000017 |
| MYO15A | 51168 | NC_000017; NG_011634 |
| ALKBH5 | 54890 | NC_000017 |
| LLGL1 | 3996 | NC_000017; NW_017363819 |
| FLII | 2314 | NC_000017; NW_017363819; NG_023243 |
| MIEF2 | 125170 | NW_017363819; NC_000017 |
| TOP3A | 7156 | NW_017363819; NC_000017 |
| CCDC144B | 284047 | NC_000017 |
| ZNF286B | 729288 | NC_000017 |
| FOXO3B | 2310 | NC_000017; NG_001119 |
| UBE2SP2 | 440406 | NG_031882; NC_000017 |
| TRIM16L | 147166 | NC_000017 |
| B3GNT7 | 93010 | NC_000002 |
| ZBTB8OSP2 | 729898 | NG_028934; NC_000002 |
| NCL | 4691 | NC_000002 |
| LINC00471 | 151477 | NC_000002 |
| NMUR1 | 10316 | NC_000002 |
| RPE23AP26 | 391490 | NG_010355; NC_000002 |
| TEX44 | 165100 | NC_000002 |
| PTMA | 5757 | NC_000002 |
| PDE6D | 5147 | NG_034064; NC_000002 |
| COPS7B | 64708 | NC_000002 |
| NPPC | 4880 | NC_000002 |
| ECEL1P3 | 260332 | NG_002700; NC_000002 |
| ALPP | 250 | NG_012189; NC_000002 |
| ECEL1P2 | 347694 | NG_023671; NC_000002; NG_002701 |
| ALPG | 251 | NC_000002 |
| ALPI | 248 | NC_000002 |
| ECEL1 | 9427 | NG_034065; NC_000002 |
| AGAP1 | 116987 | NG_030314; NC_000002 |
| TMSB10P1 | 100506723 | NG_030314; NC_000002; NG_029007 |
| GBX2 | 2637 | NC_000002 |
| ASB18 | 401036 | NG_053045; NC_000002 |
| IQCA1 | 79781 | NC_000002 |
| RPL3P5 | 100130450 | NC_000002; NG_010767 |
| ACKR3 | 57007 | NC_000002 |
| HDAC4 | 9759 | NC_000002; NG_009235 |
| OR6B3 | 150681 | NC_000002 |
| OR9S24P | 403275 | NC_000002; NG_005821 |
| OR5S1P | 391496 | NG_004369; NC_000002 |
| COPS9 | 150678 | NC_000002 |
| OTOS | 150677 | NC_000002 |
| GPC1 | 2817 | NC_000002 |
| ANKMY1 | 51281 | NC_000002 |
| DUSP28 | 285193 | NC_000002 |
| RNPEPL1 | 57140 | NC_000002 |
| CAPN10 | 11132 | NC_000002; NG_011558 |
| GPR35 | 2859 | NC_000002 |
| AQP12B | 653437 | NC_000002 |
| AQP12A | 375318 | NC_000002 |
| KIF1A | 547 | NG_029724; NC_000002 |
| AGXT | 189 | NC_000002; NG_008005 |
| MAB21L4 | 79919 | NC_000002 |
| CROCC2 | 728763 | NC_000002 |
| SNED1 | 25992 | NC_000002 |
| MTERF4 | 130916 | NC_000002 |
| PASK | 23178 | NG_052850; NC_000002 |
| PPP1R7 | 5510 | NC_000002 |
| ANO7 | 50636 | NC_000002; NG_029845 |
| HDLBP | 3069 | NC_000002 |
| FARP2 | 9855 | NC_000002 |
| STK25 | 10494 | NC_000002 |
| BOK | 666 | NC_000002; NG_029488 |
| THAP4 | 51078 | NC_000002 |
| ATG4B | 23192 | NC_000002 |
| DTYMK | 1841 | NC_000002 |
| ING5 | 84289 | NC_000002 |
| D2HGDH | 728294 | NC_000002; NG_012012 |
| GAL3ST2 | 64090 | NG_046977; NC_000002; NT_187527 |
| NEU4 | 129807 | NT_187527; NC_000002 |

TABLE 5-continued

| DNA | | |
|---|---|---|
| DNA Feature | NCBI Gene ID | NCBI Accession Number(s) |
| PDCD1 | 5133 | NC_000002; NG_012110; NT_187527 |
| RTP5 | 285093 | NT_187527; NC_000002 |
| LINC01880 | 105373979 | NC_000002; NT_187647; NT_187523 |
| RPL23AP88 | 100289034 | NG_030145; NC_000002 |
| fusion_FGFR3_anygene | 2261 | NC_000004; NG_012632 |
| fusion_FRS2_anygene | 10818 | NC_000012 |
| fusion_SLC45A3_anygene | 85414 | NC_000001 |
| fusion_TMPRSS2_anygene | 7113 | NC_000021; NG_047085 |
| fusion_anygene_C12orf28 | 196446 | NC_000012 |
| fusion_anygene_CPM | 1368 | NC_000012 |
| fusion_anygene_ERG | 2078 | NC_000021; NG_029732 |
| fusion_anygene_NUP107 | 57122 | NG_046600; NC_000012 |
| fusion_anygene_RET | 5979 | NG_007489; NC_000010 |
| fusion_anygene_TACC3 | 10460 | NG_064424; NC_000004 |
| fusion_FGFR3_TACC3 | 2261; 10460 | NC_000004; NG_012632<br>NG_064424; NC_000004 |
| fusion_TMPRSS2_ERG | 7113; 2078 | NC_000021; NG_047085<br>NC_000021; NG_029732 |
| tmb | — | — |
| Uterus_Carcinoma | | |
| PTEN_hotspots | 5728 | NC_000010; NW_013171807;<br>NG_007466 |
| LOH_9_11 | — | — |
| PIK3CA_mut | 5290 | NC_000003; NG_012113 |
| CNA_8_12 | — | — |
| CNA_7_7 | — | — |
| LOH_17_0 | — | — |
| CTNNB1_mut | 1499 | NC_000003; NG_013302 |
| LOH_17_1 | — | — |
| CNA_9_2 | — | — |
| CNA_4_18 | — | — |
| LOH_22_2 | — | — |
| LOH_9_0 | — | — |
| CNA_p_16 | — | — |
| CNA_3_13 | — | — |
| LOH_16_7 | — | — |
| CNA_19_3 | — | — |
| PREX2_mut | 80243 | NG_047022; NC_000008 |
| PIK3CA_hotspots | 5290 | NC_000003; NG_012113 |
| CNA_6_9 | — | — |
| CNA_10_7 | — | — |
| CNA_10_8 | — | — |
| LOH_p_3 | — | — |
| LOH_1_4 | — | — |
| LOH_8_1 | — | — |
| CNA_16_7 | — | — |
| PTEN_mut | 5728 | NC_000010; NW_013171807;<br>NG_007466 |
| FBXW7_hotspots | 55294 | NC_000004; NG_029466 |
| LOH_1_11 | — | — |
| CNA_9_9 | — | — |
| LOH_8_2 | — | — |
| CNA_3_16 | — | — |
| CNA_5_17 | — | — |
| LOH_16_4 | — | — |
| CNA_p_3 | — | — |
| CNA_7_8 | — | — |
| LOH_11_3 | — | — |
| CNA_1_18 | — | — |
| CNA_q_1 | — | — |
| CTCF_mut | 10664 | NC_000016; NG_033892 |
| CNA_6_12 | — | — |
| CNA_7_5 | — | — |
| CNA_5_11 | — | — |
| CNA_3_6 | — | — |
| CNA_3_4 | — | — |
| LOH_6_7 | — | — |
| CNA_q_7 | — | — |
| CNA_q_16 | — | — |
| LOH_9_2 | — | — |
| LOH_3_6 | — | — |
| PIK3R1_mut | 5295 | NC_000005; NG_012849 |
| CNA_8_2 | — | — |
| CNA_8_13 | — | — |
| msi | — | — |

TABLE 5-continued

| DNA Feature | NCBI Gene ID | NCBI Accession Number(s) |
|---|---|---|
| DNA | | |
| CNA_10_4 | — | — |
| LOH_9_8 | — | — |
| CNA_1_22 | — | — |
| LOH_11_6 | — | — |
| CNA_2_2 | — | — |
| LOH_9_9 | — | — |
| CNA_5_13 | — | — |
| CNA_19_0 | — | — |
| CNA_6_15 | — | — |
| CNA_q_8 | — | — |
| CNA_1_4 | — | — |
| tmb | — | — |
| KRAS_hotspots | 3845 | NC_000012; NG_007524 |
| CNA_7_3 | — | — |
| CNA_3_11 | — | — |
| CNA_4_17 | — | — |
| CNA_20_1 | — | — |
| CNA_15_4 | — | — |
| CNA_17_1 | — | — |
| LOH_5_17 | — | — |
| LOH_11_8 | — | — |
| TAF1_mut | 6872 | NC_000023; NG_012771 |
| CNA_2_6 | — | — |
| CNA_p_5 | — | — |
| CNA_16_2 | — | — |
| MED12_mut | 9968 | NG_012808; NC_000023 |
| LOH_10_12 | — | — |
| CNA_9_10 | — | — |
| CNA_9_11 | — | — |
| CNA_9_12 | — | — |
| LOH_19_0 | — | — |
| CNA_1_15 | — | — |
| CNA_4_1 | — | — |
| CNA_16_6 | — | — |
| CNA_6_0 | — | — |
| CNA_17_7 | — | — |
| CNA_1_3 | — | — |
| CNA_9_13 | — | — |
| CNA_2_1 | — | — |
| LOH_16_8 | — | — |
| BRAF_hotspots | 673 | NC_000007; NG_007873 |
| CNA_11_3 | — | — |
| CNA_19_5 | — | — |
| CTNNB1_hotspots | 1499 | NC_000003; NG_013302 |
| ARID1A_mut | 8289 | NC_000001; NG_029965 |
| LOH_11_1 | — | — |
| CNA_17_0 | — | — |
| CNA_q_22 | — | — |
| CNA_10_6 | — | — |
| Glioma | | |
| ATRX_mut | 546 | NC_000023; NG_008838 |
| CELSR1_mut | 9620 | NG_030466; NC_000022 |
| PTEN_mut | 5728 | NC_000010; NW_013171807; NG_007466 |
| TTN_mut | 7273 | NC_000002; NG_011618 |
| IDH1_p.R132 | 3417 | NG_023319; NC_000002 |
| TP53_hotspots | 7157 | NG_017013; NC_000017 |
| EGFR_hotspots | 1956 | NG_007726; NC_000007 |
| BRAF_hotspots | 673 | NC_000007; NG_007873 |
| IDH1_hotspots | 3417 | NG_023319; NC_000002 |
| CNA_1_0 | — | — |
| CNA_1_1 | — | — |
| CNA_1_2 | — | — |
| CNA_1_10 | — | — |
| CNA_1_11 | — | — |
| CNA_1_14 | — | — |
| LOH_3_0 | — | — |
| CNA_3_6 | — | — |
| LOH_3_6 | — | — |
| CNA_3_16 | — | — |
| CNA_4_1 | — | — |
| CNA_4_2 | — | — |
| CNA_4_9 | — | — |
| CNA_5_2 | — | — |
| CNA_5_3 | — | — |

TABLE 5-continued

| DNA | | |
|---|---|---|
| DNA Feature | NCBI Gene ID | NCBI Accession Number(s) |
| LOH_5_6 | — | — |
| LOH_5_11 | — | — |
| CNA_6_0 | — | — |
| CNA_6_1 | — | — |
| CNA_6_2 | — | — |
| CNA_6_4 | — | — |
| CNA_7_5 | — | — |
| CNA_7_7 | — | — |
| CNA_7_11 | — | — |
| CNA_7_13 | — | — |
| CNA_7_14 | — | — |
| CNA_7_15 | — | — |
| CNA_8_0 | — | — |
| CNA_8_1 | — | — |
| LOH_8_1 | — | — |
| CNA_8_2 | — | — |
| LOH_8_2 | — | — |
| CNA_8_8 | — | — |
| CNA_8_9 | — | — |
| CNA_8_10 | — | — |
| CNA_8_12 | — | — |
| CNA_9_2 | — | — |
| LOH_9_2 | — | — |
| LOH_9_7 | — | — |
| CNA_9_8 | — | — |
| CNA_10_1 | — | — |
| CNA_10_2 | — | — |
| LOH_10_2 | — | — |
| CNA_10_4 | — | — |
| LOH_10_4 | — | — |
| CNA_10_5 | — | — |
| LOH_10_5 | — | — |
| CNA_10_6 | — | — |
| CNA_10_7 | — | — |
| CNA_10_12 | — | — |
| CNA_11_2 | — | — |
| CNA_11_11 | — | — |
| CNA_11_12 | — | — |
| CNA_12_2 | — | — |
| CNA_12_10 | — | — |
| LOH_14_7 | — | — |
| LOH_14_8 | — | — |
| CNA_16_0 | — | — |
| CNA_16_1 | — | — |
| CNA_16_2 | — | — |
| CNA_16_4 | — | — |
| CNA_17_0 | — | — |
| CNA_17_1 | — | — |
| CNA_17_3 | — | — |
| LOH_18_5 | — | — |
| CNA_18_7 | — | — |
| CNA_19_0 | — | — |
| CNA_19_3 | — | — |
| LOH_19_3 | — | — |
| LOH_19_4 | — | — |
| CNA_19_5 | — | — |
| LOH_19_5 | — | — |
| CNA_20_4 | — | — |
| CNA_21_3 | — | — |
| CNA_p_10 | — | — |
| CNA_p_16 | — | — |
| CNA_p_17 | — | — |
| CNA_p_3 | — | — |
| CNA_p_5 | — | — |
| CNA_p_7 | — | — |
| CNA_q_1 | — | — |
| CNA_q_13 | — | — |
| CNA_q_16 | — | — |
| CNA_q_18 | — | — |
| CNA_q_20 | — | — |
| CNA_q_7 | — | — |
| CNA_q_8 | — | — |
| LOH_p_10 | — | — |
| LOH_p_17 | — | — |
| LOH_p_3 | — | — |
| LOH_q_16 | — | — |

TABLE 5-continued

| DNA Feature | NCBI Gene ID | NCBI Accession Number(s) |
|---|---|---|
| DNA | | |
| NLRP13 | 126204 | NG_053013; NC_000019 |
| LINC01864 | 101928886 | NC_000019 |
| ZNF542P | 147947 | NC_000019 |
| ZNF264 | 9422 | NG_016432; NC_000019 |
| TSGA13 | 114960 | NC_000007 |
| ZC3HAV1L | 92092 | NC_000007 |
| tmb | — | — |
| ploidy | — | — |
| Renal_Cell_Carcinoma | | |
| CNA_12_5 | — | — |
| CNA_16_4 | — | — |
| CNA_q_13 | — | — |
| CNA_12_12 | — | — |
| LOH_5_10 | — | — |
| BRAF_p.V600 | 673 | NC_000007; NG_007873 |
| LOH_1_21 | — | — |
| CNA_5_9 | — | — |
| CNA_8_0 | — | — |
| CNA_19_1 | — | — |
| CNA_3_19 | — | — |
| CNA_20_0 | — | — |
| CNA_8_12 | — | — |
| CNA_7_7 | — | — |
| CNA_5_7 | — | — |
| LOH_17_0 | — | — |
| KCTD16 | 57528 | NC_000005 |
| LOH_2_18 | — | — |
| CNA_21_3 | — | — |
| LOH_3_3 | — | — |
| CNA_5_2 | — | — |
| CNA_22_4 | — | — |
| CNA_18_4 | — | — |
| LOH_p_10 | — | — |
| APC_mut | 324 | NG_008481; NC_000005 |
| CNA_7_12 | — | — |
| CNA_9_2 | — | — |
| LOH_11_12 | — | — |
| LOH_q_22 | — | — |
| LOH_16_7 | — | — |
| CNA_19_3 | — | — |
| CNA_16_0 | — | — |
| PIK3CA_hotspots | 5290 | NC_000003; NG_012113 |
| LOH_2_6 | — | — |
| LOH_14_4 | — | — |
| CNA_1_0 | — | — |
| CNA_10_11 | — | — |
| CNA_10_7 | — | — |
| CNA_10_8 | — | — |
| LOH_5_11 | — | — |
| LOH_p_3 | — | — |
| LOH_1_20 | — | — |
| LOH_1_17 | — | — |
| LOH_1_4 | — | — |
| CNA_7_14 | — | — |
| LOH_13_2 | — | — |
| LOH_8_1 | — | — |
| LOH_19_4 | — | — |
| LOH_3_13 | — | — |
| CNA_16_7 | — | — |
| CNA_3_10 | — | — |
| CNA_10_9 | — | — |
| CNA_5_10 | — | — |
| PTEN_mut | 5728 | NC_000010; NW_013171807; NG_007466 |
| CNA_9_9 | — | — |
| CNA_1_20 | — | — |
| CNA_q_18 | — | — |
| CNA_1_14 | — | — |
| CNA_5_16 | — | — |
| CNA_6_3 | — | — |
| CNA_p_7 | — | — |
| CNA_21_2 | — | — |
| CNA_5_17 | — | — |

TABLE 5-continued

| DNA | | |
|---|---|---|
| DNA Feature | NCBI Gene ID | NCBI Accession Number(s) |
| IDH1_p.R132 | 3417 | NG_023319; NC_000002 |
| CNA_8_11 | — | — |
| CNA_p_3 | — | — |
| LOH_13_3 | — | — |
| CNA_6_4 | — | — |
| LOH_12_12 | — | — |
| CNA_8_8 | — | — |
| CNA_1_18 | — | — |
| LOH_19_1 | — | — |
| CNA_q_1 | — | — |
| CNA_13_7 | — | — |
| CNA_1_24 | — | — |
| LOH_6_10 | — | — |
| IDH1_hotspots | 3417 | NG_023319; NC_000002 |
| CNA_17_3 | — | — |
| CNA_12_10 | — | — |
| VHL_mut | 7428 | NC_000003; NG_008212 |
| LOH_11_6 | — | — |
| LOH_10_9 | — | — |
| LOH_p_17 | — | — |
| LOH_6_7 | — | — |
| LOH_17_4 | — | — |
| CNA_q_7 | — | — |
| CNA_8_1 | — | — |
| CNA_8_7 | — | — |
| ploidy | — | — |
| CNA_8_5 | — | — |
| CNA_12_2 | — | — |
| PBRM1_mut | 55193 | NG_032108; NC_000003 |
| LOH_1_2 | — | — |
| CNA_3_17 | — | — |
| CNA_10_0 | — | — |
| CNA_16_8 | — | — |
| KRAS_mut | 3845 | NC_000012; NG_007524 |
| CNA_q_16 | — | — |
| LOH_9_1 | — | — |
| LOH_14_3 | — | — |
| LOH_9_2 | — | — |
| CNA_5_1 | — | — |
| CNA_12_11 | — | — |
| CNA_12_6 | — | — |
| CNA_8_2 | — | — |
| CNA_15_5 | — | — |
| LOH_3_0 | — | — |
| LOH_12_8 | — | — |
| CNA_10_4 | — | — |
| CNA_5_8 | — | — |
| LOH_9_12 | — | — |
| LOH_1_6 | — | — |
| CNA_11_12 | — | — |
| CNA_3_2 | — | — |
| CNA_5_14 | — | — |
| CNA_1_19 | — | — |
| CNA_p_17 | — | — |
| TP53_hotspots | 7157 | NG_017013; NC_000017 |
| LOH_3_5 | — | — |
| HMGB1P5 | 10354 | NG_000897; NC_000003 |
| CNA_5_15 | — | — |
| LOH_q_9 | — | — |
| CNA_2_23 | — | — |
| CNA_1_2 | — | — |
| CNA_3_0 | — | — |
| LOH_2_19 | — | — |
| CNA_q_8 | — | — |
| LOH_18_2 | — | — |
| LOH_3_1 | — | — |
| CNA_9_8 | — | — |
| tmb | — | — |
| KRAS_hotspots | 3845 | NC_000012; NG_007524 |
| LOH_19_5 | — | — |
| CNA_3_11 | — | — |
| LOH_1_3 | — | — |
| LOH_1_8 | — | — |
| LOH_12_11 | — | — |
| LOH_1_13 | — | — |
| CNA_6_10 | — | — |

TABLE 5-continued

| DNA | | |
|---|---|---|
| DNA Feature | NCBI Gene ID | NCBI Accession Number(s) |
| LOH_q_16 | — | — |
| CNA_17_1 | — | — |
| CNA_17_5 | — | — |
| LOH_10_11 | — | — |
| LOH_5_17 | — | — |
| CNA_2_17 | — | — |
| LOH_3_4 | — | — |
| CNA_5_12 | — | — |
| CNA_p_5 | — | — |
| CNA_2_6 | — | — |
| CNA_9_7 | — | — |
| CNA_22_2 | — | — |
| CNA_9_3 | — | — |
| CNA_12_7 | — | — |
| CNA_3_12 | — | — |
| CNA_q_20 | — | — |
| CNA_6_1 | — | — |
| LOH_3_2 | — | — |
| LOH_10_8 | — | — |
| CNA_12_1 | — | — |
| CNA_16_5 | — | — |
| CNA_19_4 | — | — |
| CNA_9_12 | — | — |
| CNA_1_15 | — | — |
| CNA_11_6 | — | — |
| CNA_16_6 | — | — |
| CNA_6_0 | — | — |
| CNA_17_7 | — | — |
| CNA_1_3 | — | — |
| LOH_4_17 | — | — |
| CNA_9_13 | — | — |
| LOH_1_18 | — | — |
| BRAF_hotspots | 673 | NC_000007; NG_007873 |
| CNA_1_21 | — | — |
| LOH_8_0 | — | — |
| LOH_6_16 | — | — |
| LOH_1_1 | — | — |
| CNA_19_5 | — | — |
| SETD2_mut | 29072 | NC_000003; NG_032091 |
| CNA_p_10 | — | — |
| CNA_q_22 | — | — |
| CTNNB1_hotspots | 1499 | NC_000003; NG_013302 |
| ARID1A_mut | 8289 | NC_000001; NG_029965 |
| CNA_2_13 | — | — |
| CNA_17_0 | — | — |
| CNA_6_2 | — | — |
| CNA_3_14 | — | — |
| Germ_Cell_Neoplasm | | |
| ADAMTS18_mut | 170692 | NG_031879; NC_000016 |
| ADAMTS19_mut | 171019 | NC_000005 |
| ADAMTS2_mut | 9509 | NW_016107298; NC_000005; NG_023212 |
| ADAMTS20_mut | 80070 | NC_000012; NG_028228 |
| ADAMTS3_mut | 9508 | NC_000004; NG_046955 |
| ADAMTS9_mut | 56999 | NC_000003 |
| ADAMTSL3_mut | 57188 | NC_000015 |
| ADCY1_mut | 107 | NG_034198; NC_000007 |
| ADCY10_mut | 55811 | NG_016139; NC_000001 |
| ADCY2_mut | 108 | NG_046913; NC_000005 |
| ADCY5_mut | 111 | NC_000003; NG_033882 |
| ADGRV1_mut | 84059 | NG_007083; NC_000005 |
| AFF2_mut | 2334 | NC_000023; NG_016313 |
| AHCTF1_mut | 25909 | NC_000001 |
| AHNAK_mut | 79026 | NC_000011; NG_051822 |
| AHNAK2_mut | 113146 | NC_000014; NG_054630 |
| AK9_mut | 221264 | NC_000006 |
| AKAP6_mut | 9472 | NC_000014 |
| AKAP9_mut | 10142 | NC_000007; NG_011623 |
| ALPK2_mut | 115701 | NC_000018 |
| KIT_mut | 3815 | NC_000004; NG_007456 |
| TP53_hotspots | 7157 | NG_017013; NC_000017 |
| KIT_hotspots | 3815 | NC_000004; NG_007456 |
| CNA_2_13 | — | — |
| CNA_2_23 | — | — |
| CNA_3_5 | — | — |

TABLE 5-continued

| DNA | | |
|---|---|---|
| DNA Feature | NCBI Gene ID | NCBI Accession Number(s) |
| CNA_3_19 | — | — |
| CNA_5_0 | — | — |
| CNA_5_1 | — | — |
| CNA_5_2 | — | — |
| CNA_5_3 | — | — |
| CNA_7_0 | — | — |
| CNA_7_3 | — | — |
| CNA_7_7 | — | — |
| CNA_7_14 | — | — |
| CNA_8_0 | — | — |
| CNA_8_1 | — | — |
| CNA_8_2 | — | — |
| CNA_8_8 | — | — |
| CNA_11_6 | — | — |
| CNA_11_10 | — | — |
| CNA_12_1 | — | — |
| CNA_13_10 | — | — |
| CNA_14_8 | — | — |
| CNA_14_9 | — | — |
| LOH_16_7 | — | — |
| LOH_17_0 | — | — |
| CNA_18_0 | — | — |
| CNA_18_2 | — | — |
| CNA_20_3 | — | — |
| CNA_21_2 | — | — |
| CNA_21_3 | — | — |
| CNA_22_2 | — | — |
| CNA_p_16 | — | — |
| CNA_p_17 | — | — |
| CNA_p_20 | — | — |
| CNA_p_5 | — | — |
| CNA_p_7 | — | — |
| CNA_q_20 | — | — |
| CNA_q_7 | — | — |
| LOH_p_10 | — | — |
| LOH_p_17 | — | — |
| KDM2A | 22992 | NC_000011 |
| GRK2 | 156 | NC_000011 |
| DEFB109F | 110806268 | NC_000012; NG_065970 |
| AICDA | 57379 | NC_000012; NG_011588 |
| M6PR | 4074 | NC_000012 |
| PRB1 | 5542 | NT_187658; NC_000012 |
| PRB2 | 653247 | NC_000012; NT_187588 |
| HIGD1AP8 | 100874451 | NC_000012; NG_032545 |
| STX8P1 | 100423046 | NG_021191; NC_000012 |
| RPL13AP20 | 387841 | NC_000012 |
| HTR7P1 | 93164 | NC_000012 |
| EGLN3P1 | 100420503 | NG_023986; NC_000012 |
| SLCO1B3 | 28234 | NG_032071; NC_000012 |
| GOLT1B | 51026 | NC_000012 |
| SPX | 80763 | NC_000012 |
| KCNJ8 | 3764 | NG_041794; NC_000012 |
| ABCC9 | 10060 | NC_000012; NG_012819 |
| CMAS | 55907 | NC_000012 |
| ETNK1 | 55500 | NC_000012; NG_065161 |
| SOX5 | 6660 | NC_000012; NG_029612 |
| ITPR2 | 3709 | NG_042142; NC_000012 |
| INTS13 | 55726 | NC_000012 |
| FGFR1OP2 | 26127 | NC_000012 |
| TM7SF3 | 51768 | NC_000012 |
| MED21 | 9412 | NC_000012 |
| STK38L | 23012 | NC_000012 |
| ARNTL2 | 56938 | NG_030359; NC_000012 |
| SMCO2 | 341346 | NC_000012 |
| PPFIBP1 | 8496 | NC_000012 |
| REP15 | 387849 | NC_000012 |
| HMGB1P49 | 100420013 | NC_000012; NG_024073 |
| MRPS35 | 60488 | NC_000012 |
| MANSC4 | 100287284 | NC_000012 |
| KLHL42 | 57542 | NC_000012 |
| PTHLH | 5744 | NC_000012; NG_023197 |
| CCDC91 | 55297 | NC_000012 |
| FAR2 | 55711 | NC_000012 |
| ERGIC2 | 51290 | NC_000012 |
| OVCH1 | 341350 | NC_000012 |
| TMTC1 | 83857 | NC_000012 |

TABLE 5-continued

| DNA Feature | NCBI Gene ID | NCBI Accession Number(s) |
|---|---|---|
| DNA | | |
| RPL21P99 | 100271429 | NC_000012; NG_010366 |
| LINC02386 | 105369717 | NC_000012 |
| IPO8 | 10526 | NC_000012 |
| CAPRIN2 | 65981 | NG_029557; NC_000012 |
| LINC00941 | 100287314 | NC_000012 |
| PPIAP44 | 111082964 | NC_000012; NG_065976 |
| TSPAN11 | 441631 | NC_000012 |
| DDX11 | 1663 | NC_000012; NG_023352 |
| DENND5B | 160518 | NC_000012 |
| fusion_FRS2_anygene | 10818 | NC_000012 |
| fusion_TMPRSS2_anygene | 7113 | NC_000021; NG_047085 |
| fusion_anygene_ERG | 2078 | NC_000021; NG_029732 |
| fusion_TMPRSS2_ERG | 7113; 2078 | NC_000021; NG_047085 NC_000021; NG_029732 |
| tmb | — | — |
| Thymoma | | |
| CNA_12_12 | — | — |
| CNA_4_11 | — | — |
| CNA_3_7 | — | — |
| LOH_6_4 | — | — |
| CNA_5_9 | — | — |
| CNA_8_0 | — | — |
| LOH_13_5 | — | — |
| CNA_22_4 | — | — |
| LOH_p_10 | — | — |
| LOH_17_1 | — | — |
| CNA_4_18 | — | — |
| CNA_p_16 | — | — |
| LOH_14_4 | — | — |
| CNA_14_8 | — | — |
| LOH_p_3 | — | — |
| CNA_7_14 | — | — |
| CNA_16_7 | — | — |
| GTF2I_hotspots | 2969 | NC_000007; NG_008179 |
| CNA_4_9 | — | — |
| CNA_q_18 | — | — |
| CNA_1_14 | — | — |
| EOH_8_2 | — | — |
| CNA_6_3 | — | — |
| CNA_p_7 | — | — |
| CNA_3_16 | — | — |
| LOH_14_8 | — | — |
| EOH_16_4 | — | — |
| CNA_p_3 | — | — |
| CNA_6_4 | — | — |
| CNA_1_1 | — | — |
| CNA_13_5 | — | — |
| LOH_6_1 | — | — |
| CNA_q_1 | — | — |
| CNA_13_9 | — | — |
| CNA_1_24 | — | — |
| CNA_17_3 | — | — |
| LOH_p_17 | — | — |
| CNA_q_7 | — | — |
| CNA_8_1 | — | — |
| CNA_7_4 | — | — |
| CNA_16_8 | — | — |
| CNA_q_16 | — | — |
| LOH_9_1 | — | — |
| LOH_9_2 | — | — |
| CNA_8_2 | — | — |
| LOH_3_0 | — | — |
| CNA_9_1 | — | — |
| CNA_10_4 | — | — |
| CNA_1_19 | — | — |
| CNA_p_17 | — | — |
| TRGV3 | 6976 | NC_000007; NG_001336 |
| CNA_7_0 | — | — |
| CNA_1_2 | — | — |
| CNA_q_8 | — | — |
| tmb | — | — |
| CNA_7_3 | — | — |
| CNA_1_23 | — | — |
| LOH_q_16 | — | — |
| CNA_17_1 | — | — |

TABLE 5-continued

| DNA Feature | NCBI Gene ID | NCBI Accession Number(s) |
|---|---|---|
| DNA | | |
| CNA_15_4 | — | — |
| CNA_22_2 | — | — |
| CNA_9_3 | — | — |
| CNA_12_7 | — | — |
| CNA_6_1 | — | — |
| CNA_9_0 | — | — |
| CNA_1_15 | — | — |
| CNA_4_1 | — | — |
| GTF2I_p.L424 | 2969 | NC_000007; NG_008179 |
| CNA_6_0 | — | — |
| CNA_11_10 | — | — |
| CNA_5_0 | — | — |
| LOH_16_8 | — | — |
| CNA_p_10 | — | — |
| TRGV8 | 6982 | NC_000007; NG_001336 |
| LOH_16_6 | — | — |
| CNA_6_2 | — | — |
| CNA_10_6 | — | — |
| Pheochromocytoma | | |
| CNA_1_17 | — | — |
| CNA_3_1 | — | — |
| CNA_11_9 | — | — |
| CNA_q_13 | — | — |
| CNA_12_12 | — | — |
| CNA_3_7 | — | — |
| CNA_5_9 | — | — |
| CNA_8_0 | — | — |
| CNA_1_5 | — | — |
| CNA_3_19 | — | — |
| CNA_8_12 | — | — |
| CNA_4_14 | — | — |
| LOH_11_2 | — | — |
| LOH_16_5 | — | — |
| CNA_22_4 | — | — |
| CNA_p_18 | — | — |
| LOH_1_9 | — | — |
| LOH_22_4 | — | — |
| CNA_17_6 | — | — |
| CNA_9_2 | — | — |
| LOH_3_18 | — | — |
| CNA_p_16 | — | — |
| CNA_3_13 | — | — |
| CNA_19_3 | — | — |
| LOH_3_14 | — | — |
| LOH_14_4 | — | — |
| CNA_1_0 | — | — |
| CNA_10_8 | — | — |
| CNA_1_9 | — | — |
| CNA_8_9 | — | — |
| LOH_18_5 | — | — |
| CDK4P1 | 359941 | NG_006109; NC_000001 |
| LOH_p_3 | — | — |
| LOH_1_4 | — | — |
| LOH_18_6 | — | — |
| LOH_3_13 | — | — |
| LOH_19_4 | — | — |
| CNA_8_10 | — | — |
| CNA_3_18 | — | — |
| LOH_3_17 | — | — |
| CNA_1_6 | — | — |
| CNA_3_10 | — | — |
| CNA_10_9 | — | — |
| LOH_1_11 | — | — |
| CNA_9_9 | — | — |
| CNA_1_10 | — | — |
| CNA_q_18 | — | — |
| CNA_1_14 | — | — |
| CNA_5_16 | — | — |
| CNA_6_3 | — | — |
| CNA_3_16 | — | — |
| CNA_21_2 | — | — |
| CNA_p_7 | — | — |
| LOH_14_8 | — | — |

TABLE 5-continued

| DNA | | |
| --- | --- | --- |
| DNA Feature | NCBI Gene ID | NCBI Accession Number(s) |
| IDH1__p.R132 | 3417 | NG__023319; NC__000002 |
| CNA__8__11 | — | — |
| CNA__p__3 | — | — |
| CNA__1__1 | — | — |
| LOH__1__0 | — | — |
| LOH__11__3 | — | — |
| CNA__8__6 | — | — |
| LMO4 | 8543 | NC__000001 |
| CNA__13__5 | — | — |
| CNA__8__8 | — | — |
| LOH__14__5 | — | — |
| CNA__q__1 | — | — |
| CNA__1__24 | — | — |
| CNA__17__3 | — | — |
| CNA__3__6 | — | — |
| LOH__11__6 | — | — |
| LOH__11__7 | — | — |
| LOH__17__4 | — | — |
| LOH__3__12 | — | — |
| CNA__8__5 | — | — |
| LOH__1__2 | — | — |
| CNA__3__17 | — | — |
| RPL7P9 | 653702 | NC__000001; NG__007184 |
| LOH__5__16 | — | — |
| CNA__q__16 | — | — |
| LOH__1__5 | — | — |
| LOH__14__3 | — | — |
| LOH__9__2 | — | — |
| LOH__19__3 | — | — |
| CNA__2__8 | — | — |
| LOH__1__10 | — | — |
| LOH__22__3 | — | — |
| GPSM2 | 29899 | NC__000001; NG__028108 |
| LOH__3__0 | — | — |
| CNA__10__4 | — | — |
| LOH__1__6 | — | — |
| CNA__6__8 | — | — |
| CNA__3__2 | — | — |
| CNA__3__8 | — | — |
| CNA__p__17 | — | — |
| CNA__7__13 | — | — |
| LOH__q__9 | — | — |
| CNA__7__0 | — | — |
| CNA__1__2 | — | — |
| CNA__3__0 | — | — |
| CNA__18__3 | — | — |
| NBPF8 | 728841 | NC__000001 |
| CNA__q__8 | — | — |
| CNA__13__6 | — | — |
| CNA__1__4 | — | — |
| tmb | — | — |
| CNA__7__3 | — | — |
| CNA__3__11 | — | — |
| LOH__1__3 | — | — |
| LOH__1__8 | — | — |
| LOH__18__7 | — | — |
| AKNAD1 | 254268 | NC__000001; NG__032762 |
| CNA__1__23 | — | — |
| LOH__q__16 | — | — |
| CNA__17__1 | — | — |
| CNA__17__5 | — | — |
| LOH__10__11 | — | — |
| LOH__11__8 | — | — |
| CNA__5__12 | — | — |
| CNA__2__6 | — | — |
| CNA__13__4 | — | — |
| CNA__3__12 | — | — |
| CNA__q__20 | — | — |
| CNA__18__7 | — | — |
| CNA__19__4 | — | — |
| CNA__1__15 | — | — |
| CNA__11__6 | — | — |
| LOH__10__2 | — | — |
| CNA__6__0 | — | — |
| CNA__17__7 | — | — |
| CNA__1__3 | — | — |

TABLE 5-continued

| DNA Feature | NCBI Gene ID | NCBI Accession Number(s) |
| --- | --- | --- |
| DNA | | |
| NBPF5P | 100507044 | NG_028895; NW_017852928; NC_000001 |
| CNA_3_15 | — | — |
| CNA_11_10 | — | — |
| CNA_22_3 | — | — |
| LOH_3_15 | — | — |
| CNA_1_8 | — | — |
| CNA_11_3 | — | — |
| LOH_8_0 | — | — |
| LOH_1_1 | — | — |
| CNA_1_11 | — | — |
| CNA_19_5 | — | — |
| CNA_3_14 | — | — |
| TRGV8 | 6982 | NC_000007; NG_001336 |
| LOH_11_1 | — | — |
| CNA_6_2 | — | — |
| LOH_16_6 | — | — |
| CNA_17_0 | — | — |
| CNA_11_2 | — | — |
| BRCA_tumor_non_basal | | |
| CDH1_mut | 999 | NC_000016; NG_008021 |
| TP53_mut | 7157 | NG_017013; NC_000017 |
| PIK3CA_mut | 5290 | NC_000003; NG_012113 |
| PIK3CA_hotspots | 5290 | NC_000003; NG_012113 |
| CNA_16_8 | — | — |
| CNA_3_14 | — | — |
| CNA_19_5 | — | — |
| CNA_3_17 | — | — |
| CNA_p_7 | — | — |
| CNA_17_5 | — | — |
| CNA_14_3 | — | — |
| CNA_q_16 | — | — |
| CNA_16_0 | — | — |
| CNA_5_7 | — | — |
| CNA_5_8 | — | — |
| CNA_11_11 | — | — |
| MLST8 | 64223 | NC_000016 |
| SLC22A31 | 146429 | NC_000016 |
| RPA3 | 6119 | NC_000007 |
| MPDZ | 8777 | NC_000009; NG_042810 |
| MIR29C | 407026 | NC_000001 |
| NFIB | 4781 | NC_000009 |
| LASP1 | 3927 | NC_000017 |
| SLC46A1 | 113235 | NG_013306; NC_000017 |
| CORO6 | 84940 | NG_054920; NC_000017 |
| RIMS3 | 9783 | NC_000001 |
| EYS | 346007 | NC_000006; NG_023443 |
| OR6C76 | 390326 | NC_000012 |
| SPAG5-AS1 | 100506436 | NC_000017 |
| ZFP69 | 339559 | NC_000001 |
| SLBP | 7884 | NC_000004 |
| TRAP1 | 10131 | NC_000016; NG_033088 |
| RIMS1 | 22999 | NG_016209; NC_000006 |
| CREBBP | 1387 | NG_009873; NC_000016 |
| MTMR2 | 8898 | NC_000011; NG_008333 |
| RBFOX1 | 54715 | NC_000016; NG_011881 |
| KCNMB2-AS1 | 104797538 | NC_000003 |
| tmb | — | — |
| BRCA_tumor_basal | | |
| TP53_mut | 7157 | NG_017013; NC_000017 |
| PIK3CA_mut | 5290 | NC_000003; NG_012113 |
| BRCA1_mut | 672 | NG_005905; NC_000017 |
| CNA_16_8 | — | — |
| CNA_16_7 | — | — |
| CNA_20_5 | — | — |
| CNA_q_22 | — | — |
| CNA_22_4 | — | — |
| CNA_14_3 | — | — |
| CNA_8_0 | — | — |
| CNA_5_16 | — | — |
| CNA_1_14 | — | — |
| CNA_1_20 | — | — |

TABLE 5-continued

| DNA | | |
|---|---|---|
| DNA Feature | NCBI Gene ID | NCBI Accession Number(s) |
| CNA_22_3 | — | — |
| CNA_3_4 | — | — |
| CNA_15_3 | — | — |
| TTC30A | 92104 | NC_000002 |
| SLC22A31 | 146429 | NC_000016 |
| RCL1 | 10171 | NC_000009 |
| SLC25A51P1 | 442229 | NG_025947; NT_187555; NC_000006 |
| LINC00304 | 283860 | NC_000016 |
| NOP14-AS1 | 317648 | NC_000004 |
| PKN2-AS1 | 101927891 | NC_000001 |
| MPDZ | 8777 | NC_000009; NG_042810 |
| PKIB | 5570 | NC_000006 |
| MMP25-AS1 | 100507419 | NC_000016 |
| NFIB | 4781 | NC_000009 |
| TBC1D30 | 23329 | NC_000012 |
| NELL2 | 4753 | NC_000012 |
| ITGA7 | 3679 | NC_000012; NG_012343 |
| RUNX2 | 860 | NG_008020; NC_000006 |
| SH3GLB1 | 51100 | NG_030018; NC_000001 |
| NCOA7 | 135112 | NC_000006 |
| HIVEP3 | 59269 | NC_000001; NG_030026 |
| CSAD | 51380 | NC_000012; NG_030036 |
| COL2A1 | 1280 | NG_008072; NC_000012 |
| ARL6IP1 | 23204 | NG_042860; NC_000016 |
| KRT76 | 51350 | NC_000012; NG_012420 |
| CREBBP | 1387 | NG_009873; NC_000016 |
| CDCP2 | 200008 | NC_000001 |
| tmb | — | — |
| OV_tumor | — | — |
| TP53_mut | 7157 | NG_017013; NC_000017 |
| PIK3CA_mut | 5290 | NC_000003; NG_012113 |
| MST1R_mut | 4486 | NC_000003; NG_030322 |
| MGA_mut | 23269 | NC_000015 |
| PIK3CA_hotspots | 5290 | NC_000003; NG_012113 |
| CNA_3_14 | — | — |
| CNA_19_5 | — | — |
| CNA_3_17 | — | — |
| CNA_22_4 | — | — |
| CNA_17_7 | — | — |
| CNA_6_15 | — | — |
| CNA_11_12 | — | — |
| CNA_11_10 | — | — |
| CNA_16_0 | — | — |
| CNA_5_7 | — | — |
| CNA_7_0 | — | — |
| CNA_3_4 | — | — |
| CNA_12_5 | — | — |
| CNA_3_19 | — | — |
| TTC30A | 92104 | NC_000002 |
| TTC14 | 151613 | NC_000003 |
| MYO1D | 4642 | NC_000017 |
| SLC22A31 | 146429 | NC_000016 |
| ZFP69B | 65243 | NC_000001 |
| EMP2 | 2013 | NG_042058; NC_000016 |
| SUPT6H | 6830 | NC_000017 |
| NELL2 | 4753 | NC_000012 |
| MIR548AJ1 | 100616191 | NC_000006 |
| LYRM1 | 57149 | NC_000016 |
| PKD1 | 5310 | NC_000016; NG_008617; NT_187607 |
| ESPL1 | 9700 | NC_000012 |
| INSL6 | 11172 | NG_046969; NC_000009 |
| HHAT | 55733 | NW_011332687; NC_000001 |
| CD46 | 4179 | NC_000001; NG_009296 |
| ERBB3 | 2065 | NC_000012; NG_011529 |
| SMARCE1 | 6605 | NG_032163; NC_000017 |
| KCNMB2-AS1 | 104797538 | NC_000003 |
| SSH2 | 85464 | NC_000017 |
| FAM53A | 152877 | NC_000004; NW_021159990 |
| tmb | — | — |
| Squamous_Cell_Lung_Carcinoma | | |
| CNTNAP5_mut | 129684 | NC_000002 |
| CPS1_mut | 1373 | NC_000002; NG_008285 |
| LRRC7_mut | 57554 | NC_000001 |
| PIK3CA_mut | 5290 | NC_000003; NG_012113 |
| RYR2_mut | 6262 | NG_008799; NC_000001 |

TABLE 5-continued

| DNA | | |
|---|---|---|
| DNA Feature | NCBI Gene ID | NCBI Accession Number(s) |
| TP53_mut | 7157 | NG_017013; NC_000017 |
| USH2A_mut | 7399 | NC_000001; NG_009497 |
| CNA_1_15 | — | — |
| CNA_1_17 | — | — |
| CNA_2_6 | — | — |
| LOH_2_21 | — | — |
| LOH_3_3 | — | — |
| LOH_3_5 | — | — |
| LOH_3_6 | — | — |
| CNA_3_8 | — | — |
| CNA_3_18 | — | — |
| CNA_3_19 | — | — |
| CNA_4_3 | — | — |
| CNA_4_8 | — | — |
| CNA_4_11 | — | — |
| CNA_4_13 | — | — |
| CNA_4_18 | — | — |
| CNA_5_0 | — | — |
| CNA_5_10 | — | — |
| LOH_5_10 | — | — |
| CNA_5_11 | — | — |
| CNA_5_12 | — | — |
| CNA_5_13 | — | — |
| CNA_5_17 | — | — |
| CNA_7_0 | — | — |
| CNA_7_4 | — | — |
| CNA_8_1 | — | — |
| CNA_8_2 | — | — |
| CNA_8_6 | — | — |
| CNA_8_7 | — | — |
| CNA_8_13 | — | — |
| CNA_9_1 | — | — |
| LOH_9_1 | — | — |
| LOH_9_11 | — | — |
| LOH_9_12 | — | — |
| LOH_9_13 | — | — |
| CNA_10_10 | — | — |
| CNA_11_11 | — | — |
| LOH_11_11 | — | — |
| CNA_11_12 | — | — |
| CNA_12_2 | — | — |
| LOH_13_3 | — | — |
| CNA_13_5 | — | — |
| CNA_13_7 | — | — |
| LOH_13_7 | — | — |
| CNA_13_10 | — | — |
| CNA_14_5 | — | — |
| CNA_14_9 | — | — |
| LOH_17_0 | — | — |
| CNA_20_5 | — | — |
| CNA_p_5 | — | — |
| CNA_q_8 | — | — |
| PPIAP78 | 202227 | NC_000005; NG_030081 |
| tmb | — | — |
| Squamous_Cell_Carcinoma_of_the_Head_and_Neck | | |
| CDKN2A_mut | 1029 | NC_000009; NG_007485 |
| PTEN_mut | 5728 | NC_000010; NW_013171807; NG_007466 |
| RYR2_mut | 6262 | NG_008799; NC_000001 |
| TP53_mut | 7157 | NG_017013; NC_000017 |
| USH2A_mut | 7399 | NC_000001; NG_009497 |
| TP53_hotspots | 7157 | NG_017013; NC_000017 |
| CNA_1_16 | — | — |
| CNA_1_18 | — | — |
| CNA_1_20 | — | — |
| CNA_2_6 | — | — |
| CNA_2_21 | — | — |
| CNA_2_22 | — | — |
| CNA_3_0 | — | — |
| CNA_3_1 | — | — |
| LOH_3_1 | — | — |
| CNA_3_3 | — | — |
| LOH_3_3 | — | — |
| CNA_3_4 | — | — |
| LOH_3_6 | — | — |

TABLE 5-continued

| DNA | | |
|---|---|---|
| DNA Feature | NCBI Gene ID | NCBI Accession Number(s) |
| LOH_3_7 | — | — |
| CNA_3_8 | — | — |
| LOH_3_8 | — | — |
| CNA_3_13 | — | — |
| CNA_3_19 | — | — |
| CNA_4_2 | — | — |
| CNA_4_8 | — | — |
| CNA_4_13 | — | — |
| CNA_4_17 | — | — |
| CNA_4_18 | — | — |
| CNA_5_0 | — | — |
| CNA_5_1 | — | — |
| CNA_5_3 | — | — |
| CNA_5_6 | — | — |
| LOH_5_6 | — | — |
| LOH_5_10 | — | — |
| CNA_5_11 | — | — |
| CNA_5_12 | — | — |
| CNA_5_13 | — | — |
| CNA_5_17 | — | — |
| CNA_6_14 | — | — |
| CNA_7_0 | — | — |
| CNA_7_3 | — | — |
| CNA_7_4 | — | — |
| CNA_8_2 | — | — |
| CNA_8_5 | — | — |
| CNA_8_6 | — | — |
| CNA_8_7 | — | — |
| CNA_8_9 | — | — |
| CNA_8_11 | — | — |
| CNA_8_12 | — | — |
| CNA_8_13 | — | — |
| CNA_9_1 | — | — |
| LOH_9_1 | — | — |
| LOH_9_11 | — | — |
| LOH_9_12 | — | — |
| CNA_10_10 | — | — |
| CNA_10_11 | — | — |
| CNA_11_12 | — | — |
| CNA_12_2 | — | — |
| LOH_13_2 | — | — |
| CNA_13_3 | — | — |
| LOH_13_3 | — | — |
| CNA_13_5 | — | — |
| LOH_13_5 | — | — |
| LOH_13_6 | — | — |
| CNA_13_7 | — | — |
| LOH_13_7 | — | — |
| CNA_13_9 | — | — |
| CNA_14_5 | — | — |
| LOH_17_0 | — | — |
| CNA_18_4 | — | — |
| CNA_18_5 | — | — |
| CNA_18_6 | — | — |
| CNA_p_5 | — | — |
| CNA_q_20 | — | — |
| CNA_q_8 | — | — |
| GAL | 51083 | NC_000011; NG_052785 |
| CPT1A | 1374 | NC_000011; NG_011801 |
| SHANK2 | 22941 | NG_042866; NC_000011 |
| NADSYN1 | 55191 | NC_000011 |
| TRPS1 | 7227 | NC_000008; NG_012383 |
| PHF20L1 | 51105 | NC_000008 |
| tmb | — | — |
| Cervical_Squamous_Cell_Carcinoma | | |
| CSMD3_mut | 114788 | NC_000008 |
| TP53_mut | 7157 | NG_017013; NC_000017 |
| TP53_hotspots | 7157 | NG_017013; NC_000017 |
| CNA_1_15 | — | — |
| CNA_1_20 | — | — |
| CNA_2_21 | — | — |
| CNA_3_4 | — | — |
| CNA_3_5 | — | — |
| CNA_5_3 | — | — |
| CNA_6_14 | — | — |

TABLE 5-continued

| DNA Feature | NCBI Gene ID | NCBI Accession Number(s) |
|---|---|---|
| | DNA | |
| CNA_7_0 | — | — |
| CNA_8_11 | — | — |
| LOH_9_1 | — | — |
| LOH_9_13 | — | — |
| CNA_11_12 | — | — |
| CNA_12_1 | — | — |
| LOH_13_5 | — | — |
| CNA_13_9 | — | — |
| CNA_18_5 | — | — |
| CDKN2A | 1029 | NC_000009; NG_007485 |
| CDKN2B | 1030 | NC_000009; NG_023297 |
| tmb | — | — |
| | Glioblastoma | |
| CNA_p_10 | — | — |
| AC073324.1 | 102725541 | NC_000007 |
| tmb | — | — |
| CNA_10_0 | — | — |
| LOH_19_5 | — | — |
| LOH_10_5 | — | — |
| IDH1_mut | 3417 | NG_023319; NC_000002 |
| LOH_q_10 | — | — |
| | Astrocytoma | |
| CNA_1_1 | — | — |
| LOH_p_10 | — | — |
| TP53_mut | 7157 | NG_017013; NC_000017 |
| CNA_1_5 | — | — |
| IDH1_mut | 3417 | NG_023319; NC_000002 |
| LOH_1_7 | — | — |
| | Oligodendroglioma | |
| LOH_q_10 | — | — |
| ATG4C | 84938 | NC_000001 |
| LOH_1_0 | — | — |
| LOH_10_4 | — | — |
| TP53_mut | 7157 | NG_017013; NC_000017 |
| CNA_1_5 | — | — |
| LOH_1_6 | — | — |
| LOH_1_7 | — | — |
| | Stomach_Adenocarcinoma | |
| CNA_13_9 | — | — |
| AL627224.2 | — | — |
| KRAS_p.G12 | 3845 | NC_000012; NG_007524 |
| LOH_9_1 | — | — |
| CNA_8_1 | — | — |
| KRAS_mut | 3845 | NC_000012; NG_007524 |
| AL807743.1 | — | — |
| tmb | — | — |
| APC_mut | 324 | NG_008481; NC_000005 |
| BRAF_hotspots | 673 | NC_000007; NG_007873 |
| CNA_p_18 | — | — |
| | Colorectal_Adenocarcinoma | |
| CNA_13_9 | — | — |
| AL627224.2 | — | — |
| KRAS_p.G12 | 3845 | NC_000012; NG_007524 |
| LOH_9_1 | — | — |
| CNA_8_1 | — | — |
| KRAS_mut | 3845 | NC_000012; NG_007524 |
| AL807743.1 | — | — |
| tmb | — | — |
| APC_mut | 324 | NG_008481; NC_000005 |
| BRAF_hotspots | 673 | NC_000007; NG_007873 |
| CNA_p_18 | — | — |
| | Clear_Cell_Renal_Cell_Carcinoma | |
| VHL_mut | 7428 | NC_000003; NG_008212 |
| CNA_1_3 | — | — |
| CNA_3_0 | — | — |
| LOH_3_0 | — | — |
| LOH_3_2 | — | — |
| CNA_3_4 | — | — |
| CNA_5_14 | — | — |
| CNA_5_17 | — | — |

TABLE 5-continued

| DNA | | |
|---|---|---|
| DNA Feature | NCBI Gene ID | NCBI Accession Number(s) |
| CNA_8_2 | — | — |
| CNA_16_4 | — | — |
| CNA_17_4 | — | — |
| CNA_q_14 | — | — |
| CNA_q_17 | — | — |
| LOH_p_1 | — | — |
| PRSS50 | 29122 | NC_000003 |
| tmb | — | — |
| Papillary_Renal_Cell_Carcinoma | | |
| VHL_mut | 7428 | NC_000003; NG_008212 |
| CNA_1_3 | — | — |
| CNA_1_10 | — | — |
| LOH_2_3 | — | — |
| CNA_3_0 | — | — |
| LOH_3_0 | — | — |
| CNA_3_2 | — | — |
| LOH_3_2 | — | — |
| CNA_3_3 | — | — |
| CNA_3_4 | — | — |
| LOH_3_4 | — | — |
| CNA_3_5 | — | — |
| LOH_3_5 | — | — |
| CNA_3_6 | — | — |
| LOH_3_6 | — | — |
| CNA_3_8 | — | — |
| CNA_5_14 | — | — |
| CNA_5_15 | — | — |
| CNA_5_17 | — | — |
| LOH_6_3 | — | — |
| CNA_7_3 | — | — |
| CNA_7_14 | — | — |
| CNA_7_15 | — | — |
| CNA_8_2 | — | — |
| LOH_10_4 | — | — |
| CNA_13_2 | — | — |
| LOH_13_3 | — | — |
| LOH_14_6 | — | — |
| CNA_16_4 | — | — |
| LOH_17_1 | — | — |
| CNA_17_3 | — | — |
| CNA_17_4 | — | — |
| CNA_17_5 | — | — |
| CNA_17_7 | — | — |
| LOH_17_7 | — | — |
| LOH_18_4 | — | — |
| CNA_p_1 | — | — |
| CNA_p_2 | — | — |
| CNA_p_3 | — | — |
| CNA_q_10 | — | — |
| CNA_q_14 | — | — |
| CNA_q_17 | — | — |
| LOH_p_1 | — | — |
| LOH_p_2 | — | — |
| LOH_p_3 | — | — |
| LOH_p_6 | — | — |
| LOH_q_1 | — | — |
| PRSS50 | 29122 | NC_000003 |
| TRGV9 | 6983 | NG_001336; NC_000007 |
| tmb | — | — |
| Chromophobe_Renal_Cell_Carcinoma | | |
| LOH_1_5 | — | — |
| LOH_1_9 | — | — |
| CNA_1_17 | — | — |
| LOH_1_19 | — | — |
| CNA_5_16 | — | — |
| CNA_6_3 | — | — |
| CNA_10_1 | — | — |
| LOH_10_2 | — | — |
| LOH_13_4 | — | — |
| LOH_14_5 | — | — |
| CNA_17_3 | — | — |
| LOH_17_7 | — | — |
| CNA_p_1 | — | — |
| CNA_p_3 | — | — |

TABLE 5-continued

| DNA | | |
|---|---|---|
| DNA Feature | NCBI Gene ID | NCBI Accession Number(s) |
| CNA_q_1 | — | — |
| CNA_q_17 | — | — |
| CNA_q_6 | — | — |
| LOH_p_1 | — | — |
| LOH_p_3 | — | — |
| LOH_q_1 | — | — |
| LOH_q_6 | — | — |
| tmb | — | — |

Biological Samples

Any of the methods, systems, or other claimed elements may use or be used to analyze a biological sample from a subject. In some embodiments, a biological sample is obtained from a subject having, suspected of having cancer, or at risk of having cancer. The biological sample may be any type of biological sample including, for example, a biological sample of a bodily fluid (e.g., blood, urine or cerebrospinal fluid), one or more cells (e.g., from a scraping or brushing such as a cheek swab or tracheal brushing), a piece of tissue (cheek tissue, muscle tissue, lung tissue, heart tissue, brain tissue, or skin tissue), or some or all of an organ (e.g., brain, lung, liver, bladder, kidney, pancreas, intestines, or muscle), or other types of biological samples (e.g., feces or hair).

In some embodiments, the biological sample is a sample of a tumor from a subject. In some embodiments, the biological sample is a sample of blood from a subject. In some embodiments, the biological sample is a sample of tissue from a subject.

A sample of a tumor, in some embodiments, refers to a sample comprising cells from a tumor. In some embodiments, the sample of the tumor comprises cells from a benign tumor, e.g., non-cancerous cells. In some embodiments, the sample of the tumor comprises cells from a premalignant tumor, e.g., precancerous cells. In some embodiments, the sample of the tumor comprises cells from a malignant tumor, e.g., cancerous cells. In some embodiments, the sample of tumor can include a mixture of cancerous, non-cancerous, and/or precancerous cells.

Examples of tumors include, but are not limited to, adenomas, fibromas, hemangiomas, lipomas, cervical dysplasia, metaplasia of the lung, leukoplakia, carcinoma, sarcoma, germ cell tumors, melanomas, mesotheliomas, gliomas, and blastoma.

A sample of blood, in some embodiments, refers to a sample comprising cells, e.g., cells from a blood sample. In some embodiments, the sample of blood comprises non-cancerous cells. In some embodiments, the sample of blood comprises precancerous cells. In some embodiments, the sample of blood comprises cancerous cells. In some embodiments, the sample of blood comprises blood cells. In some embodiments, the sample of blood comprises red blood cells. In some embodiments, the sample of blood comprises white blood cells. In some embodiments, the sample of blood comprises platelets. Examples of cancerous blood cells include, but are not limited to, leukemia, lymphoma, and myeloma. In some embodiments, a sample of blood is collected to obtain the cell-free nucleic acid (e.g., cell-free DNA) in the blood.

A sample of blood may be a sample of whole blood or a sample of fractionated blood. In some embodiments, the sample of blood comprises whole blood. In some embodiments, the sample of blood comprises fractionated blood. In some embodiments, the sample of blood comprises buffy coat. In some embodiments, the sample of blood comprises serum. In some embodiments, the sample of blood comprises plasma. In some embodiments, the sample of blood comprises a blood clot.

A sample of a tissue, in some embodiments, refers to a sample comprising cells from a tissue. In some embodiments, the sample of the tumor comprises non-cancerous cells from a tissue. In some embodiments, the sample of the tumor comprises precancerous cells from a tissue. In some embodiments, the sample of the tumor comprises cancerous tissue. In some embodiments, the sample can comprise cancerous, precancerous, or non-cancerous cells.

Methods of the present disclosure encompass a variety of tissue including organ tissue or non-organ tissue, including but not limited to, muscle tissue, brain tissue, lung tissue, liver tissue, epithelial tissue, connective tissue, and nervous tissue. In some embodiments, the tissue may be normal tissue or it may be diseased tissue or it may be tissue suspected of being diseased. In some embodiments, the tissue may be sectioned tissue or whole intact tissue. In some embodiments, the tissue may be animal tissue or human tissue. Animal tissue includes, but is not limited to, tissues obtained from rodents (e.g., rats or mice), primates (e.g., monkeys), dogs, cats, and farm animals.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

Any of the biological samples described herein may be obtained from the subject using any known technique. See, for example, the following publications on collecting, processing, and storing biological samples, each of which are incorporated herein in its entirety: Biospecimens and biorepositories: from afterthought to science by Vaught et al. (Cancer Epidemiol Biomarkers Prev. 2012 February; 21(2): 253-5), and Biological sample collection, processing, storage and information management by Vaught and Henderson (IARC Sci Publ. 2011; (163):23-42).

In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy).

In some embodiments, one or more than one cell (a cell biological sample) may be obtained from a subject using a scrape or brush method. The cell biological sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) biological samples from one or more tumors or tissues known or suspected of having cancerous cells.

Any of the biological samples from a subject described herein may be stored using any method that preserves stability of the biological sample. In some embodiments, preserving the stability of the biological sample means inhibiting components (e.g., DNA, RNA, protein, or tissue structure or morphology) of the biological sample from degrading until they are measured so that when measured, the measurements represent the state of the sample at the time of obtaining it from the subject. In some embodiments, a biological sample is stored in a composition that is able to penetrate the same and protect components (e.g., DNA, RNA, protein, or tissue structure or morphology) of the biological sample from degrading. As used herein, degradation is the transformation of a component from one from to another such that the first form is no longer detected at the same level as before degradation.

In some embodiments, a biological sample (e.g., tissue sample) is fixed. As used herein, a "fixed" sample relates to a sample that has been treated with one or more agents or processes in order to prevent or reduce decay or degradation, such as autolysis or putrefaction, of the sample. Examples of fixative processes include but are not limited to heat fixation, immersion fixation, and perfusion. In some embodiments a fixed sample is treated with one or more fixative agents. Examples of fixative agents include but are not limited to cross-linking agents (e.g., aldehydes, such as formaldehyde, formalin, glutaraldehyde, etc.), precipitating agents (e.g., alcohols, such as ethanol, methanol, acetone, xylene, etc.), mercurials (e.g., B-5, Zenker's fixative, etc.), picrates, and Hepes-glutamic acid buffer-mediated organic solvent protection effect (HOPE) fixative. In some embodiments, a biological sample (e.g., tissue sample) is treated with a cross-linking agent. In some embodiments, the cross-linking agent comprises formalin. In some embodiments, a formalin-fixed biological sample is embedded in a solid substrate, for example paraffin wax. In some embodiments, the biological sample is a formalin-fixed paraffin-embedded (FFPE) sample. Methods of preparing FFPE samples are known, for example as described by Li et al. JCO Precis Oncol. 2018; 2: PO.17.00091.

In some embodiments, the biological sample is stored using cryopreservation. Non-limiting examples of cryopreservation include, but are not limited to, step-down freezing, blast freezing, direct plunge freezing, snap freezing, slow freezing using a programmable freezer, and vitrification. In some embodiments, the biological sample is stored using lyophilization. In some embodiments, a biological sample is placed into a container that already contains a preservant (e.g., RNALater to preserve RNA) and then frozen (e.g., by snap-freezing), after the collection of the biological sample from the subject. In some embodiments, such storage in frozen state is done immediately after collection of the biological sample. In some embodiments, a biological sample may be kept at either room temperature or 4° C. for some time (e.g., up to an hour, up to 8 h, or up to 1 day, or a few days) in a preservant or in a buffer without a preservant, before being frozen.

Non-limiting examples of preservants include formalin solutions, formaldehyde solutions, RNALater or other equivalent solutions, TriZol or other equivalent solutions, DNA/RNA Shield or equivalent solutions, EDTA (e.g., Buffer AE (10 mM Tris·Cl; 0.5 mM EDTA, pH 9.0)) and other coagulants, and Acids Citrate Dextronse (e.g., for blood specimens).

In some embodiments, special containers may be used for collecting and/or storing a biological sample. For example, a vacutainer may be used to store blood. In some embodiments, a vacutainer may comprise a preservant (e.g., a coagulant, or an anticoagulant). In some embodiments, a container in which a biological sample is preserved may be contained in a secondary container, for the purpose of better preservation, or for the purpose of avoid contamination.

Any of the biological samples from a subject described herein may be stored under any condition that preserves stability of the biological sample. In some embodiments, the biological sample is stored at a temperature that preserves stability of the biological sample. In some embodiments, the sample is stored at room temperature (e.g., 25° C.). In some embodiments, the sample is stored under refrigeration (e.g., 4° C.). In some embodiments, the sample is stored under freezing conditions (e.g., −20° C.). In some embodiments, the sample is stored under ultralow temperature conditions (e.g., −50° C. to −800° C.). In some embodiments, the sample is stored under liquid nitrogen (e.g., −1700° C.). In some embodiments, a biological sample is stored at −60° C. to −80° C. (e.g., −70° C.) for up to 5 years (e.g., up to 1 month, up to 2 months, up to 3 months, up to 4 months, up to 5 months, up to 6 months, up to 7 months, up to 8 months, up to 9 months, up to 10 months, up to 11 months, up to 1 year, up to 2 years, up to 3 years, up to 4 years, or up to 5 years). In some embodiments, a biological sample is stored as described by any of the methods described herein for up to 20 years (e.g., up to 5 years, up to 10 years, up to 15 years, or up to 20 years).

Methods of the present disclosure encompass obtaining one or more biological samples from a subject for analysis. In some embodiments, one biological sample is collected from a subject for analysis. In some embodiments, more than one (e.g., 2, 3, 4, 5, 6, 7, 8, 9, 10, 11, 12, 13, 14, 15, 16, 17, 18, 19, 20, or more) biological samples are collected from a subject for analysis. In some embodiments, one biological sample from a subject will be analyzed. In some embodiments, more than one (e.g., 2, 3, 4, 5, 6, 7, 8, 9, 10, 11, 12, 13, 14, 15, 16, 17, 18, 19, 20, or more) biological samples may be analyzed. If more than one biological sample from a subject is analyzed, the biological samples may be procured at the same time (e.g., more than one biological sample may be taken in the same procedure), or the biological samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure).

A second or subsequent biological sample may be taken or obtained from the same region (e.g., from the same tumor or area of tissue) or a different region (including, e.g., a different tumor). A second or subsequent biological sample may be taken or obtained from the subject after one or more treatments and may be taken from the same region or a different region. As a non-limiting example, the second or subsequent biological sample may be useful in determining whether the cancer in each biological sample has different characteristics (e.g., in the case of biological samples taken from two physically separate tumors in a patient) or whether the cancer has responded to one or more treatments (e.g., in the case of two or more biological samples from the same tumor or different tumors prior to and subsequent to a treatment). In some embodiments, each of the at least one biological sample is a bodily fluid sample, a cell sample, or a tissue biopsy sample.

In some embodiments, one or more biological specimens are combined (e.g., placed in the same container for preservation) before further processing. For example, a first sample of a first tumor obtained from a subject may be combined with a second sample of a second tumor from the subject, wherein the first and second tumors may or may not be the same tumor. In some embodiments, a first tumor and a second tumor are similar but not the same (e.g., two tumors in the brain of a subject). In some embodiments, a first biological sample and a second biological sample from a subject are sample of different types of tumors (e.g., a tumor in muscle tissue and brain tissue).

In some embodiments, a sample from which RNA and/or DNA is extracted (e.g., a sample of tumor, or a blood sample) is sufficiently large such that at least 2 μg (e.g., at least 2 μg, at least 2.5 μg, at least 3 μg, at least 3.5 μg or more) of RNA can be extracted from it. In some embodiments, the sample from which RNA and/or DNA is extracted can be peripheral blood mononuclear cells (PBMCs). In some embodiments, the sample from which RNA and/or DNA is extracted can be any type of cell suspension. In some embodiments, a sample from which RNA and/or DNA is extracted (e.g., a sample of tumor, or a blood sample) is sufficiently large such that at least 1.8 μg RNA can be extracted from it. In some embodiments, at least 50 mg (e.g., at least 1 mg, at least 2 mg, at least 3 mg, at least 4 mg, at least 5 mg, at least 10 mg, at least 12 mg, at least 15 mg, at least 18 mg, at least 20 mg, at least 22 mg, at least 25 mg, at least 30 mg, at least 35 mg, at least 40 mg, at least 45 mg, or at least 50 mg) of tissue sample is collected from which RNA and/or DNA is extracted. In some embodiments, at least 20 mg of tissue sample is collected from which RNA and/or DNA is extracted. In some embodiments, at least 30 mg of tissue sample is collected. In some embodiments, at least 10-50 mg (e.g., 10-50 mg, 10-15 mg, 10-30 mg, 10-40 mg, 20-30 mg, 20-40 mg, 20-50 mg, or 30-50 mg) of tissue sample is collected from which RNA and/or DNA is extracted. In some embodiments, at least 30 mg of tissue sample is collected. In some embodiments, at least 20-30 mg of tissue sample is collected from which RNA and/or DNA is extracted. In some embodiments, a sample from which RNA and/or DNA is extracted (e.g., a sample of tumor, or a blood sample) is sufficiently large such that at least 0.2 μg (e.g., at least 200 ng, at least 300 ng, at least 400 ng, at least 500 ng, at least 600 ng, at least 700 ng, at least 800 ng, at least 900 ng, at least 1 μg, at least 1.1 μg, at least 1.2 μg, at least 1.3 μg, at least 1.4 μg, at least 1.5 μg, at least 1.6 μg, at least 1.7 μg, at least 1.8 μg, at least 1.9 μg, or at least 2 μg) of RNA can be extracted from it. In some embodiments, a sample from which RNA and/or DNA is extracted (e.g., a sample of tumor, or a blood sample) is sufficiently large such that at least 0.1 μg (e.g., at least 100 ng, at least 200 ng, at least 300 ng, at least 400 ng, at least 500 ng, at least 600 ng, at least 700 ng, at least 800 ng, at least 900 ng, at least 1 μg, at least 1.1 μg, at least 1.2 μg, at least 1.3 μg, at least 1.4 μg, at least 1.5 μg, at least 1.6 μg, at least 1.7 μg, at least 1.8 μg, at least 1.9 μg, or at least 2 μg) of RNA can be extracted from it.

Subjects

Aspects of this disclosure relate to a biological sample that has been obtained from a subject. In some embodiments, a subject is a mammal (e.g., a human, a mouse, a cat, a dog, a horse, a hamster, a cow, a pig, or other domesticated animal). In some embodiments, a subject is a human. In some embodiments, a subject is an adult human (e.g., of 18 years of age or older). In some embodiments, a subject is a child (e.g., less than 18 years of age). In some embodiments, a human subject is one who has or has been diagnosed with at least one form of cancer.

In some embodiments, a cancer from which a subject suffers is a carcinoma, a sarcoma, a myeloma, a leukemia, a lymphoma, a melanoma, a mesothelioma, a glioma, or a mixed type of cancer that comprises more than one of a carcinoma, a sarcoma, a myeloma, a leukemia, and a lymphoma. Carcinoma refers to a malignant neoplasm of epithelial origin or cancer of the internal or external lining of the body. Sarcoma refers to cancer that originates in supportive and connective tissues such as bones, tendons, cartilage, muscle, and fat. Myeloma is cancer that originates in the plasma cells of bone marrow. Leukemias ("liquid cancers" or "blood cancers") are cancers of the bone marrow (the site of blood cell production). Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Melanoma is a type of skin cancer that originates in the melanocytes of the skin. Mesothelioma's cancers arise from the mesothelium, which forms the lining of organs and cavities, such as, for example, the lungs and the abdomen. Glioma develops in the brain, and specifically in the glial cells, which provide physical and metabolic support to neurons. Non-limiting examples of a mixed type of cancer include adenosquamous carcinoma, mixed mesodermal tumor, carcinosarcoma, and teratocarcinoma. In some embodiments, a subject has a tumor. A tumor may be benign or malignant.

In some embodiments, a cancer is any one of the following: skin cancer, lung cancer, breast cancer, prostate cancer, colon cancer, pancreatic cancer, rectal cancer, cervical cancer, and cancer of the uterus. In some embodiments, a subject is at risk for developing cancer, e.g., because the subject has one or more genetic risk factors, or has been exposed to or is being exposed to one or more carcinogens (e.g., cigarette smoke, or chewing tobacco).

Expression Data

Expression data (e.g., indicating expression levels) for a plurality of genes may be used for any of the methods or compositions described herein. The number of genes which may be examined may be up to and inclusive of all the genes of the subject. In some embodiments, expression levels may be examined for all of the genes of a subject. As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 35 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of non-limiting examples, the expression data may include, for each molecular category listed in Table 2, expression data for at least 5, at least 10, at least 15, at least 20, at least 25, at least 35, at least 50, at least 75, at least 100 genes selected from the group of genes for that molecular category in Table 2.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA (e.g., copy number of a chromosome, gene, or other genomic region) in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data (e.g., sequencing data) for DNA (e.g., coding or non-coding genomic DNA) present in a sample, for example, sequencing data for a gene that is present in a patient's sample. DNA that is present in a sample may or may not be transcribed, but it may be sequenced using DNA sequencing platforms. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods and compositions described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data is acquired through bulk RNA sequencing. Bulk RNA sequencing may include obtaining expression levels for each gene across RNA extracted from a large population of input cells (e.g., a mixture of different cell types.) In some embodiments, the expression data is acquired through single cell sequencing (e.g., scRNA-seq). Single cell sequencing may include sequencing individual cells In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

Obtaining RNA Expression Data

In some embodiments, a method to process RNA expression data (e.g., data obtained from RNA sequencing (also referred to herein as RNA-seq data)) comprises obtaining RNA expression data for a subject (e.g., a subject who has or has been diagnosed with a cancer). In some embodiments, obtaining RNA expression data comprises obtaining a biological sample and processing it to perform RNA sequencing using any one of the RNA sequencing methods described herein. In some embodiments, RNA expression data is obtained from a lab or center that has performed experiments to obtain RNA expression data (e.g., a lab or center that has performed RNA-seq). In some embodiments, a lab or center is a medical lab or center.

In some embodiments, RNA expression data is obtained by obtaining a computer storage medium (e.g., a data storage drive) on which the data exists. In some embodiments, RNA expression data is obtained via a secured server (e.g., a SFTP server, or Illumina BaseSpace). In some embodiments, data is obtained in the form of a text-based filed (e.g., a FASTQ file). In some embodiments, a file in which sequencing data is stored also contains quality scores of the sequencing data). In some embodiments, a file in which sequencing data is stored also contains sequence identifier information.

Methods of Treatment

In certain methods described herein, an effective amount of anti-cancer therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. At the time of diagnosis the cancer may be cancer of unknown primary. The subject to be treated by the methods described herein may be a mammal (e.g., may be a human). Mammals include, but are not limited to: farm animals (e.g., livestock), sport animals, laboratory animals, pets, primates, horses, dogs, cats, mice, and rats.

A subject having a cancer may be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer may be a subject having one or more of the risk factors for that disorder. For example, risk factors associated with cancer include, but are not limited to, (a) viral infection (e.g., herpes virus infection), (b) age, (c) family history, (d) heavy alcohol consumption, (e) obesity, and (f) tobacco use.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons, or for virtually any other reasons.

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages for an anti-cancer therapeutic agent as described herein may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., tumor formation, tumor growth, molecular category identified for the cancer using the techniques described herein) may be analyzed.

Generally, for administration of any of the anti-cancer antibodies described herein, an initial candidate dosage may be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays. The dosing regimen (including the therapeutic used) may vary over time.

When the anti-cancer therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer.

Alleviating a cancer includes delaying the development or progression of the disease, or reducing disease severity. Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given period and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the anti-cancer therapeutic agent (e.g., an antibody) described herein is administered to a subject in need of the treatment at an amount sufficient to reduce cancer (e.g., tumor) growth by at least 10% (e.g., 20%, 30%, 40%, 50%, 60%, 70%, 80%, 90% or greater). In some embodiments, the anti-cancer therapeutic agent (e.g., an antibody) described herein is administered to a subject in need of the treatment at an amount sufficient to reduce cancer cell number or tumor size by at least 10% (e.g., 20%, 30%, 40%, 50%, 60%, 70%, 80%, 90% or more). In other embodiments, the anti-cancer therapeutic agent is administered in an amount effective in altering cancer type. Alternatively, the anti-cancer therapeutic agent is administered in an amount effective in reducing tumor formation or metastasis.

Conventional methods, known to those of ordinary skill in the art of medicine, may be used to administer the anti-cancer therapeutic agent to the subject, depending upon the type of disease to be treated or the site of the disease. The anti-cancer therapeutic agent can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, an anti-cancer therapeutic agent may be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (e.g., glycerol, propylene glycol, liquid polyethylene glycol, and the like). For intravenous injection, water soluble anti-cancer therapeutic agents can be administered by the drip method, whereby a pharmaceutical formulation containing the antibody and a physiologically acceptable excipients is infused. Physiologically acceptable excipients may include, for example, 5% dextrose, 0.9% saline, Ringer's solution, and/or other suitable excipients. Intramuscular preparations, e.g., a sterile formulation of a suitable soluble salt form of the anti-cancer therapeutic agent, can be dissolved and administered in a pharmaceutical excipient such as Water-for-Injection, 0.9% saline, and/or 5% glucose solution.

In one embodiment, an anti-cancer therapeutic agent is administered via site-specific or targeted local delivery techniques. Examples of site-specific or targeted local delivery techniques include various implantable depot sources of the agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, the contents of each of which are incorporated by reference herein for this purpose.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., *Gene Therapeutics: Methods And Applications Of Direct Gene Transfer* (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. The contents of each of the foregoing are incorporated by reference herein for this purpose.

Therapeutic compositions containing a polynucleotide may be administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

Therapeutic polynucleotides and polypeptides can be delivered using gene delivery vehicles. The gene delivery vehicle can be of viral or non-viral origin (e.g., Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). The contents of each of the foregoing are incorporated by reference herein for this purpose. Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. The contents of each of the foregoing are incorporated by reference herein for this purpose.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581. The contents of each of the foregoing are incorporated by reference herein for this purpose.

It is also apparent that an expression vector can be used to direct expression of any of the protein-based anti-cancer therapeutic agents (e.g., anti-cancer antibody). For example, peptide inhibitors that are capable of blocking (from partial to complete blocking) a cancer-causing biological activity are known in the art.

In some embodiments, more than one anti-cancer therapeutic agent, such as an antibody and a small molecule inhibitory compound, may be administered to a subject in need of the treatment. The agents may be of the same type or different types from each other. At least one, at least two, at least three, at least four, or at least five different agents may be co-administered. Generally anti-cancer agents for administration have complementary activities that do not adversely affect each other. Anti-cancer therapeutic agents may also be used in conjunction with other agents that serve to enhance and/or complement the effectiveness of the agents.

Treatment efficacy can be assessed by methods well-known in the art, e.g., monitoring tumor growth or formation in a patient subjected to the treatment. Alternatively or in addition to, treatment efficacy can be assessed by monitoring tumor type over the course of treatment (e.g., before, during, and after treatment).

A subject having cancer may be treated using any combination of anti-cancer therapeutic agents or one or more anti-cancer therapeutic agents and one or more additional therapies (e.g., surgery and/or radiotherapy). The term combination therapy, as used herein, embraces administration of more than one treatment (e.g., an antibody and a small molecule or an antibody and radiotherapy) in a sequential manner, that is, wherein each therapeutic agent is administered at a different time, as well as administration of these therapeutic agents, or at least two of the agents or therapies, in a substantially simultaneous manner.

Sequential or substantially simultaneous administration of each agent or therapy can be affected by any appropriate route including, but not limited to, oral routes, intravenous routes, intramuscular, subcutaneous routes, and direct absorption through mucous membrane tissues. The agents or therapies can be administered by the same route or by different routes. For example, a first agent (e.g., a small molecule) can be administered orally, and a second agent (e.g., an antibody) can be administered intravenously.

As used herein, the term "sequential" means, unless otherwise specified, characterized by a regular sequence or order, e.g., if a dosage regimen includes the administration of an antibody and a small molecule, a sequential dosage regimen could include administration of the antibody before, simultaneously, substantially simultaneously, or after administration of the small molecule, but both agents will be administered in a regular sequence or order. The term "separate" means, unless otherwise specified, to keep apart one from the other. The term "simultaneously" means, unless otherwise specified, happening or done at the same time, i.e., the agents are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents or therapies described herein.

Combination therapy can also embrace the administration of the anti-cancer therapeutic agent (e.g., an antibody) in further combination with other biologically active ingredients (e.g., a vitamin) and non-drug therapies (e.g., surgery or radiotherapy).

It should be appreciated that any combination of anti-cancer therapeutic agents may be used in any sequence for treating a cancer. The combinations described herein may be selected on the basis of a number of factors, which include but are not limited to reducing tumor formation or tumor growth, and/or alleviating at least one symptom associated with the cancer, or the effectiveness for mitigating the side effects of another agent of the combination. For example, a combined therapy as provided herein may reduce any of the side effects associated with each individual members of the combination, for example, a side effect associated with an administered anti-cancer agent.

In some embodiments, an anti-cancer therapeutic agent is an antibody, an immunotherapy, a radiation therapy, a surgical therapy, and/or a chemotherapy.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, a PD-1 inhibitor or a PD-L1 inhibitor, a CTLA-4 inhibitor, adoptive cell transfer, therapeutic cancer vaccines, oncolytic virus therapy, T-cell therapy, and immune checkpoint inhibitors.

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); *Streptomyces* family antibiotics (e.g., Bleomycin, Mitomycin C, Actinomycin, and Plicamycin); and ultraviolet light.

Computer Implementation

Figure 10:
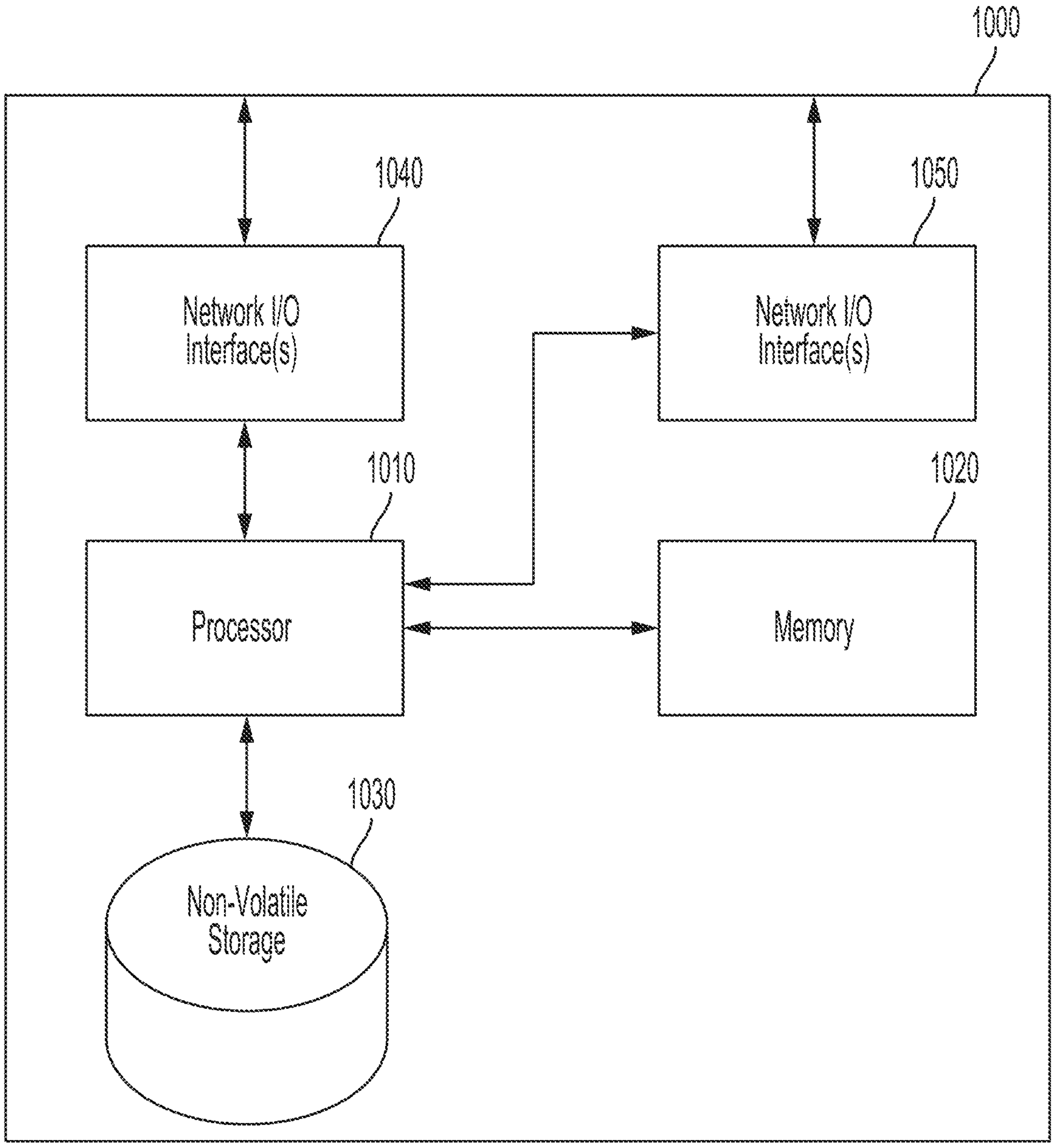
FIG. 10 depicts an illustrative implementation of a computer system that may be used in connection with some embodiments of the technology described herein.

An illustrative implementation of a computer system 1000 that may be used in connection with any of the embodiments of the technology described herein (e.g., such as the methods of FIGS. 4A-C) is shown in FIG. 10. The computer system 1000 includes one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the technology described herein are not limited to any particular techniques for writing or reading data. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

Computing device 1000 may also include a network input/output (I/O) interface 1040 via which the computing device may communicate with other computing devices (e.g., over a network), and may also include one or more user I/O interfaces 1050, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software, or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-described functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-described functions of one or more embodiments. The computer-readable medium may be transportable such that the program stored thereon can be loaded onto any computing device to implement aspects of the techniques described herein. In addition, it should be appreciated that the reference to a computer program which, when executed, performs any of the above-described functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques described herein.

The foregoing description of implementations provides illustration and description but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel.

It will be apparent that example aspects, as described above, may be implemented in many different forms of software, firmware, and hardware in the implementations illustrated in the figures. Further, certain portions of the implementations may be implemented as a "module" that performs one or more functions. This module may include hardware, such as a processor, an application-specific integrated circuit (ASIC), or a field-programmable gate array (FPGA), or a combination of hardware and software.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize or be able to ascertain using no more than routine experimentation many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone, a tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately," "substantially," and "about" may be used to mean within ±20% of a target value in some embodiments, within ±10% of a target value in some embodiments, within ±5% of a target value in some embodiments, within ±2% of a target value in some embodiments. The terms "approximately," "substantially," and "about" may include the target value.

What is claimed is:

1. A method for identifying at least one candidate molecular category for a biological sample obtained from a subject, the method comprising:

using at least one computer hardware processor to perform:

(a) obtaining RNA expression levels previously obtained by processing the biological sample obtained from the subject, wherein the RNA expression levels comprise:

(i) first RNA expression levels for a first set of genes, the first set of genes corresponding to a parent molecular category in a hierarchy of molecular categories and comprising at least ten genes listed for the parent molecular category in Table 3, and (ii) second RNA expression levels for a second set of genes different from the first set of genes, the second set of genes corresponding to a child molecular category, which is a child of the parent molecular category in the hierarchy of molecular categories, and comprising at least ten genes listed for the child molecular category in Table 3;

(b) processing the RNA expression levels to obtain RNA features comprising first ranks for the first set of genes and second ranks for the second set of genes, the processing comprising:

(i) ranking the first set of genes using the first RNA expression levels to obtain the first ranks for the first set of genes; and (ii) ranking the second set of genes using the second RNA expression levels to obtain the second ranks for the second set of genes;

(c) processing the RNA features using a hierarchy of RNA-based gradient-boosted decision tree classifiers corresponding to the hierarchy of molecular categories to obtain probabilities that molecular categories in the hierarchy of molecular categories are candidate molecular categories for the biological sample, the hierarchy of RNA-based gradient-boosted decision tree classifiers comprising a parent RNA-based gradient-boosted decision tree classifier corresponding to the parent molecular category, and a plurality of child RNA-based gradient-boosted decision tree classifiers to a plurality of child molecular categories including the child molecular category, the processing comprising:

(i) providing the first ranks for the first set of genes as input to the parent RNA-based gradient-boosted decision tree classifier to obtain a first probability that the parent molecular category is a first candidate molecular category of the at least one candidate molecular category for the biological sample;

(ii) identifying, based on the first probability, a respective child RNA-based gradient-boosted decision tree classifier from among the plurality of child RNA-based gradient-boosted decision tree classifiers, the identified child RNA-based gradient-boosted decision tree classifier corresponding to the child molecular category of the plurality of child molecular categories; and (iii) after identifying the child RNA-based gradient-boosted decision tree classifier based on the first probability, providing the second ranks for the second set of genes as input to the child RNA-based gradient-boosted decision tree classifier to obtain a second probability that the child molecular category is a second candidate molecular category for the biological sample; and (d) identifying, using the probabilities that the molecular categories in the hierarchy of molecular categories are candidate molecular categories for the biological sample, the at least one candidate molecular category for the biological sample, the identifying comprising:

(i) identifying the parent molecular category as the first candidate molecular category of the at least one candidate molecular category for the biological sample using the first probability that the parent molecular category is the first candidate molecular category; and/or (ii) identifying the child molecular category as the second candidate molecular category of the at least one candidate molecular category for the biological sample using the second probability that the child molecular category is the second candidate molecular category, wherein Table 3 is:

| Gene | NCBI Gene ID | NCBI Accession Number(s) |
|---|---|---|
| | | Gastrointestinal_Adenocarcinoma |
| TUSC3 | 7991 | XM_011544651; XM_017013861; NM_178234; NM_006765; NM_001356429 |
| ZG16 | 653808 | NM_152338; XM_011545921 |
| COLEC11 | 78989 | XM_006711897; NM_001255986; NM_001255989; NM_001255985; NM_001255982; NM_001255983; NM_001255984; NM_024027; NR_045659; XM_005263853; NM_001255987; NM_001255988; NM_199235 |
| KLF4 | 9314 | NM_004235; NM_001314052 |
| COBL | 23242 | XM_011515239; NM_015198; XM_011515236; XM_005271751; XM_011515237; NM_001287436; NM_001287438; NM_001346441; XM_011515235; XM_011515240; XM_017011898; NM_001346443; NM_001346444; XM_011515234; XM_011515241; NM_001346442; XM_005271750; XM_011515238 |
| SIX1 | 6495 | XM_017021602; NM_005982 |
| COL10A1 | 1300 | XM_011535432; NM_000493; XM_011535433; XM_017010248; XM_006715333 |
| EPHB2 | 2048 | XM_006710441; NM_001309192; NM_004442; NM_001309193; NM_017449; XM_024453895; XM_006710442 |
| CDH19 | 28513 | XM_011525931.3; XM_017025711.2; XM_011525932.1 |
| CDX1 | 1044 | NM_001804 |
| EN1 | 2019 | NM_001426 |
| CDH17 | 1015 | NM_004063; XM_011516790; NM_001144663 |
| WNT7A | 7476 | XM_011534091; NM_004625 |
| SRD5A2 | 6716 | XM_011533069; NM_000348; XM_011533072 |

-continued

| Gene | NCBI Gene ID | NCBI Accession Number(s) |
|---|---|---|
| ESM1 | 11082 | NM_001135604; NM_007036 |
| PRSS50 | 29122 | NM_013270 |
| PDX1 | 3651 | NM_000209; XR_941580; XR_941578; |
| BMP8A | 353500 | XM_017001198; XM_006710616; XM_011541381; XM_011541382; XR_946642; XR_946640; XR_946641; NM_181809 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SYT12 | 91683 | XM_011545346; XM_011545347; NM_177963; XM_017018547; NM_001177880; NM_001318775; XM_017018548; XM_006718737; XM_024448766; NM_001318773 |
| CFD | 1675 | NM_001317335; NM_001928 |
| GAMT | 2593 | NM_138924; NM_000156 |
| VTCN1 | 79679 | NM_001253849; NM_024626; NR_045604; XM_017002335; NM_001253850; NR_045603; XM_011542143 |
| TMSB15A | 11013 | NM_021992 |
| SLC15A2 | 6565 | XM_006713736; XM_017007074; NM_021082; XM_005247722; NM_001145998 |
| CP | 1356 | XM_006713500; XM_006713501; XM_017005735; XM_017005734; XM_006713499; XM_011512435; XR_427361; NM_000096; NR_046371 |
| MAL | 4118 | NM_022438; NM_002371; NM_022440; NM_022439 |
| KRT2 | 3849 | NM_000423 |
| IQCA1 | 79781 | XM_017004960; NM_024726; NM_001270585; XM_011511865; XM_011511866; XM_011511864; NM_001270584; NR_073043 |
| PVRL1 | 5818 | NM_203285; NM_032767; NM_002855; NM_203286 |
| PLA2G7 | 7941 | NM_001168357; XR_001743639; XM_005249408; NM_005084; XR_002956305 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| TREM2 | 54209 | NM_001271821; NM_018965 |
| ADAP1 | 11033 | NM_001284308; NM_006869; NM_001284311; NM_001284310; NM_001284309 |
| MUC13 | 56667 | NM_033049 |
| CLDN18 | 51208 | NM_001002026; NM_016369 |
| DPT | 1805 | NM_001937 |
| PLP1 | 5354 | NM_001128834; NM_000533; NM_001305004; NM_199478 |
| CCNB1 | 891 | NM_031966 |
| GPR162 | 27239 | NM_014449; NM_019858 |
| ONECUT2 | 9480 | NM_004852 |
| SFTPD | 6441 | XM_011540087; NM_003019; XM_011540088 |
| CLDN10 | 9071 | XM_024449432; XM_017020844; NM_006984; XM_011521134; XM_017020843; NM_182848; NM_001160100 |
| NXPH4 | 11247 | XM_017018747; NM_007224 |
| MAB21L2 | 10586 | NM_006439 |
| REG3A | 5068 | NM_138938; NM_002580; NM_138937 |

-continued

| Gene | NCBI Gene ID | NCBI Accession Number(s) |
|---|---|---|
| LGALS4 | 3960 | NM_006149; XM_011526974; XM_011526973 |
| GPR35 | 2859 | NM_001195382; NM_001195381; NM_001394730; NM_005301 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| SIM2 | 6493 | XM_017028442; XR_001754891; XM_011529694; NM_005069; NM_009586 |
| TCF21 | 6943 | NM_003206; NM_198392 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| CCL11 | 6356 | NM_002986 |
| SLC34A2 | 10568 | NM_001177999; NM_006424; NM_001177998 |
| GIF | 2694 | XM_011544939; NM_005142 |
| SALL1 | 6299 | NM_001127892; NM_002968 |
| HGH1 | 51236 | NM_016458; XR_001745537 |
| KCNC3 | 3748 | NM_004977; NR_110912; NM_001372305 |
| GPA33 | 10223 | XM_017000005; NM_005814 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| FXYD2 | 486 | NM_021603; NM_001127489; NM_001680 |
| HNF4A | 3172 | XM_005260407; NM_001287182; NM_001030003; NM_178850; NM_175914; NM_001030004; NM_178849; NM_001258355; NM_001287183; NM_000457; NM_001287184 |
| GABRQ | 55879 | NM_018558; XM_011531184 |
| ABCA4 | 24 | NM_000350 |
| MMP11 | 4320 | NM_005940; NR_133013 |
| ZWINT | 11130 | XR_428692; NM_007057; NM_001005413; XM_017015605; XM_024447784; NM_032997; NM_001005414 |
| INHBA | 3624 | XM_017012175; NM_002192; XM_017012176; XM_017012174 |
| REG1A | 5967 | NM_002909 |
| TSPYL2 | 64061 | XM_006724592; XM_017029727; NM_022117; XR_001755719; XM_017029726 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| LRRC15 | 131578 | NM_130830; NM_001135057 |
| DES | 1674 | NM_001927; NM_001382708; NM_001382710; NM_001382713; NM_001382709; NM_001382711; NM_001382712 |
| INS | 3630 | NM_001185098; NM_001185097; NM_000207; NM_001291897 |

-continued

| Gene | NCBI Gene ID | NCBI Accession Number(s) |
|---|---|---|
| FABP4 | 2167 | NM_001442 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| CST1 | 1469 | NM_001898 |
| TM4SF5 | 9032 | NM_003963 |
| PODXL | 5420 | NM_005397; NM_001018111 |
| CRNN | 49860 | NM_016190 |
| WISP2 | 8839 | NM_001323369; XM_017028116; NM_003881; XM_017028117; NM_001323370 |
| SST | 6750 | NM_001048 |
| LIN37 | 55957 | NR_163146; NM_019104; NM_001369780 |
| GREM1 | 26585 | NM_001368719; NM_013372; NM_001191323; NM_001191322 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| GRIN2D | 2906 | XM_011526872; NM_000836 |
| APOC1 | 341 | NM_001645; NM_001321066; NM_001379687; NM_001321065 |
| GDPD3 | 79153 | NM_024307 |
| FOXF1 | 2294 | NM_001451 |
| TGFB3 | 7043 | NM_001329938; NM_003239; NM_001329939 |
| ST3GAL5 | 8869 | NM_001354248; XM_017005208; XM_017005214; NM_001354226; XM_017005204; NM_001354233; NM_001354234; XM_017005205; XM_017005213; XR_001739019; NM_003896; NM_001354223; NM_001354227; NM_001354247; XM_017005206; XR_001739021; NM_001042437; NM_001354229; XM_017005202; XM_017005203; XM_017005212; XR_001739020; XM_017005209; NM_001354224; NM_001363847; NM_001354238 |
| DIRAS2 | 54769 | NM_017594 |
| GABRG3 | 2567 | XM_017022058; XM_017022060; XM_024449889; NM_033223; XM_011521430; NM_001270873; XM_011521431; XM_017022059 |
| HOXC11 | 3227 | NM_014212 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| SLCO4A1 | 28231 | XR_002958473; XR_001754251; XR_001754254; XR_001754255; XR_001754258; NM_016354; XR_001754250; XR_244116; XM_017027827; XR_001754253; XR_001754252; XR_244115; XR_936524; XM_017027826; XR_002958474; XR_001754256; XR_001754257; XM_005260203; XM_011528792; XR_001754249 |
| FABP1 | 2168 | NM_001443 |
| NFE2L3 | 9603 | NM_004289 |
| GLRB | 2743 | XR_001741207; XM_017008035; NM_000824; NM_001166060; XR_002959723; XM_017008034; NM_001166061 |
| PTH1R | 5745 | NM_001184744; XM_017006933; XM_011533968; NM_000316; XM_017006934; XM_011533967; XM_005265344; XM_017006932 |
| C2orf72 | 257407 | NM_001144994 |
| CAPN3 | 825 | NM_173087; NM_173089; NM_024344; NM_173088; NM_212465; NR_027912; NM_000070; NM_173090; NR_027911 |
| SLC2A4 | 6517 | NM_001042 |
| MLF1 | 4291 | NM_001369782; NM_001369785; NM_001378847; NM_022443; NM_001378845; NM_001378848; NM_001378851; NM_001369784; NM_001378853; NM_001378855; NM_001130156; NM_001369783; NM_001378852; NM_001130157; NM_001195432; NM_001195433; NM_001378846; NM_001378850; NM_001369781; NM_001195434 |
| FEZF2 | 55079 | NM_018008 |
| APCS | 325 | NM_001639 |
| SOX9 | 6662 | NM_000346 |
| HOXC10 | 3226 | NM_017409 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| DNAI1 | 27019 | NM_012144; NM_001281428 |
| LIPF | 8513 | NM_004190; NM_001198829; NM_001198830; NM_001198828; XM_011540311 |
| CDX2 | 1045 | XM_011534876; NM_001354700; XM_011534879; XM_011534875; XM_011534878; NM_001265 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ADH1B | 125 | NM_001286650; NM_000668 |
| EPS8L3 | 79574 | XM_017002329; XM_011542135; XM_011542134; NM_139053; NM_001319952; NM_024526; |

| Gene | NCBI Gene ID | NCBI Accession Number(s) |
|---|---|---|
| | | XM_011542133; XM_017002328; XR_001737407; XM_017002327; NM_133181; XM_011542132; XR_001737406 |
| CHST2 | 9435 | NM_004267 |
| FGGY | 55277 | XM_017001645; XM_017001677; XM_024448207; XM_024448220; NM_001350792; NM_001350797; NM_001350798; NM_018291; XM_011541731; XM_017001671; XM_017001673; NM_001244714; NM_001350793; NM_001350794; NR_103473; XM_011541730; XM_017001649; XM_017001670; XM_017001678; XM_024448227; NM_001113411; XM_017001643; XM_011541736; XM_017001659; XM_017001662; XM_017001664; XM_024448185; XR_001737287; NM_001350791; NM_001350796; XM_017001668; XM_017001679; XR_001737285; XM_017001646; XM_017001652; XM_024448176; XR_001737286; NM_001278224; XM_017001657; XM_017001660; XR_001737284; NM_001350790; NM_001350799; XM_017001655; XM_017001656; XM_017001661; XM_017001663; XM_017001669; XM_024448196; XM_024448229; NM_001350795 |
| FERMT1 | 55612 | NM_017671; XM_024451935 |
| PRSS3 | 5646 | NM_007343; NM_001197097; NM_002771; XM_011517965; NM_001197098 |
| CCNA1 | 8900 | XM_011535294; XM_011535296; NM_001111047; XM_011535295; NM_001111046; NM_003914; NM_001111045 |
| ARL4D | 379 | XM_011524782; NM_001661 |
| LZTS1 | 11178 | XM_011544386; XM_011544384; NM_021020; NM_001362884; XM_011544385 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; |

| Gene | NCBI Gene ID | NCBI Accession Number(s) |
|---|---|---|
| | | NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| KRT24 | 192666 | XM_017024299; NM_019016; XM_006721739; XM_011524460 |
| SCNN1D | 6339 | NM_001130413; NR_037668; NM_002978 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| AQP4 | 361 | NM_001317387; NM_001364287; NM_001364286; NM_001317384; XM_011525942; NM_001650; NM_001364289; NM_004028 |
| MUC2 | 4583 | NM_002457 |
| FGF23 | 8074 | NM_020638 |
| CXCL3 | 2921 | NM_002090 |
| IGFBP3 | 3486 | NM_000598; NM_001013398 |
| GABRA2 | 2555 | XM_024453964; NM_001330690; NM_001377144; NM_001377149; XM_024453966; NM_001377150; XM_011513675; NM_001114175; NM_001377155; NM_000807; NM_001377147; XM_024453967; NM_001377146; NM_001377152; NM_001286827; NM_001377153; NM_001377145; NM_001377148; NM_001377151; NM_001377154 |
| HR | 55806 | XM_006716367; NM_005144; XM_005273569; NM_018411 |
| AKR1C2 | 1646 | NM_001354; NM_001321027; NM_001135241; NM_205845; NM_001393392 |
| MYOC | 4653 | NM_000261 |
| TACR2 | 6865 | NM_001057 |
| VIP | 7432 | XM_006715562; XM_005267135; NM_003381; NM_194435 |
| PRM2 | 5620 | NM_001286358; NR_104428; NM_002762; NM_001286356; NM_001286359; NM_001286357 |
| ACADL | 33 | NM_001608; XM_005246517; XM_017003955 |
| SLC47A1 | 55244 | NM_018242 |
| CLPB | 81570 | NM_030813; XM_005274320; |

-continued

| Gene | NCBI Gene ID | NCBI Accession Number(s) |
|---|---|---|
| | | XM_011545289; NM_001258392; NM_001258393; NM_001258394 |
| SCNN1B | 6338 | XM_017023526; XM_011545913; XM_011545914; XM_017023525; NM_000336 |
| GLP2R | 9340 | XM_011524077; NM_004246; XM_017025340; XM_005256861; XM_017025339; XM_017025341 |
| CASR | 846 | XM_017007325; NM_000388; XM_005247837; XM_017007324; NM_001178065; XM_006713789 |
| IFI6 | 2537 | NM_002038; XM_024446207; NM_022873; NM_022872 |
| | Pancreatic_Adenocarcinoma | |
| PNLIP | 5406 | NM_000936 |
| PPY | 5539 | NM_002722; NM_001319209; XM_011524978 |
| CTRC | 11330 | XM_011540550; NM_007272 |
| CTRB2 | 440387 | NM_001025200 |
| CRP | 1401 | NM_000567; NM_001329058; NM_001382703; NM_001329057 |
| GCG | 2641 | NM_002054 |
| PNLIPRP1 | 5407 | XM_011539869; NM_001303135; NM_006229; XR_945774 |
| INS | 3630 | NM_001185098; NM_001185097; NM_000207; NM_001291897 |
| CPA1 | 1357 | NM_001868 |
| CASR | 846 | XM_017007325; NM_000388; XM_005247837; XM_017007324; NM_001178065; XM_006713789 |
| GCNT3 | 9245 | NM_004751 |
| TFF2 | 7032 | NM_005423 |
| PDX1 | 3651 | NM_000209; XR_941580; XR_941578; |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| ALPPL2 | 251 | NM_031313 |
| PADI1 | 29943 | XM_017001102; XR_946617; XR_946619; NM_013358; XR_001737131; XM_011541307; XR_001737130; XM_017001103; XR_946620; XM_017001101 |
| CTSE | 1510 | XM_011509245; NM_001910; NM_148964; XM_011509244; NM_001317331 |
| FOXL1 | 2300 | NM_005250 |
| LHX2 | 9355 | NM_004789; XM_006717323 |
| POU3F3 | 5455 | NM_006236 |
| MIA | 8190 | NM_006533; NM_001202553 |
| HOXD13 | 3239 | XM_011511068; NM_000523; XM_011511069 |
| NMRK2 | 27231 | NM_001289117; NM_001375468; NM_001375469; NM_170678; NM_001375467; NM_014446; XM_006722725; NR_110316 |
| TMPRSS4 | 56649 | XM_011542901; NM_001290094; XM_005271614; NM_001173552; NM_183247; NR_110734; XM_005271613; XM_011542902; XM_011542904; XM_005271615; NM_001083947; NM_001173551; NM_019894; XM_011542903; NM_001290096 |
| HAND2 | 9464 | NM_021973 |
| IHH | 3549 | NM_002181 |
| MAGEA3 | 4102 | XM_011531161; XM_005274676; XM_006724818; XM_011531160; NM_005362 |
| KLK6 | 5653 | XM_024451611; NM_001319949; NM_001012964; NM_001319948; NM_001012965; NM_002774 |

-continued

| Gene | NCBI Gene ID | NCBI Accession Number(s) |
|---|---|---|
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MAGEA6 | 4105 | NM_175868; NM_005363 |
| LRP2 | 4036 | XM_011511183; NM_004525; XM_011511184 |
| MYBPH | 4608 | NM_004997 |
| CR2 | 1380 | NM_001877; NM_001006658; XM_011509206 |
| GABRA3 | 2556 | NM_000808; XM_006724811 |
| MYH7 | 4625 | XM_017021340; NM_000257 |
| ENPP3 | 5169 | XR_001743464; NR_133007; NM_005021; XM_017010932; XM_011535897 |
| GABRQ | 55879 | NM_018558; XM_011531184 |
| NXPH4 | 11247 | XM_017018747; NM_007224 |
| FOXA1 | 3169 | NM_004496; XM_017021246 |
| SFTPB | 6439 | XM_005264487; NM_198843; XM_005264488; NM_000542; NM_001367281; XM_005264490 |
| DLX6 | 1750 | NM_005222 |
| CRNN | 49860 | NM_016190 |
| HOXA7 | 3204 | NM_006896 |
| NEFM | 4741 | NM_001105541; NM_005382 |
| KRT24 | 192666 | XM_017024299; NM_019016; XM_006721739; XM_011524460 |
| FCER2 | 2208 | NM_002002; NM_001220500; XM_005272462; NM_001207019 |
| CLDN3 | 1365 | NM_001306 |
| POU2F2 | 5452 | XM_017026886; XM_017026889; XM_017026895; XR_001753709; XR_001753710; NM_001393935; XM_017026885; XM_017026891; XM_017026894; XM_024451547; NM_001207026; NM_001393934; NM_001394376; NM_001394378; XM_017026884; XM_011527043; XM_017026887; XM_017026890; NM_001247994; XM_011527041; XM_024451546; NM_001207025; XM_011527042; XM_017026888; XM_017026892; NM_001393936; NM_002698; XM_017026896; NM_001394377 |
| LIPF | 8513 | NM_004190; NM_001198829; NM_001198830; NM_001198828; XM_011540311 |
| BCL11A | 53335 | NM_001365609; NM_022893; NM_138553; XM_017004335; XM_024452962; XM_024452963; XM_017004333; NM_138559; XM_011532910; XM_017004336; NM_018014; XM_011532909; NM_001363864 |
| CX3CR1 | 1524 | NM_001171174; NM_001337; NM_001171171; NM_001171172 |
| ABCA12 | 26154 | XM_011510951; NR_103740; NM_173076; NM_015657 |
| | Breast_Cancer | |
| AMN | 81693 | XM_024449714; XM_011537203; NM_030943; XM_011537202 |
| NMRK2 | 27231 | NM_001289117; NM_001375468; NM_001375469; NM_170678; NM_001375467; NM_014446; XM_006722725; NR_110316 |
| TLX2 | 3196 | NM_001534; NM_016170 |
| MYH15 | 22989 | XM_011512559; NM_014981; XM_017005922 |
| MROH7 | 374977 | NR_026782; NM_198547; NM_001039464; NM_001291332; NR_111931 |

-continued

| Gene | NCBI Gene ID | NCBI Accession Number(s) |
|---|---|---|
| ERN2 | 10595 | XM_011545708; XM_011545711; XR_950727; XM_011545709; XM_011545712; NM_001308220; XM_011545713; NM_033266 |
| CSF3 | 1440 | NR_168489; NR_168491; NM_000759; NM_172220; NM_001178147; NM_172219; NR_168490; NR_033662 |
| TMEM246 | 84302 | NM_001303107; NM_001303108; NM_032342; XM_024447701; NM_001371233 |
| GCGR | 2642 | XM_011523539; XM_017024446; NM_000160; XM_006722277; XM_017024447 |
| NEFM | 4741 | NM_001105541; NM_005382 |
| SOX21 | 11166 | NM_007084 |
| PMP2 | 5375 | NM_002677; NM_001348381 |
| RGS20 | 8601 | NM_001286673; NM_001286675; NM_170587; NM_001286674; NM_003702; NR_104578; NR_104579 |
| IL13RA2 | 3598 | NM_000640 |
| GPR17 | 2840 | NM_005291; NM_001161416; NM_001161415; XM_017003833; NM_001161417 |
| B3GALT1 | 8708 | NM_020981; XM_006712819; XM_011512085 |
| MT1H | 4496 | NM_005951 |
| GJA3 | 2700 | NM_021954; XM_011535048 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| DBH | 1621 | NM_000787 |
| OGDHL | 55753 | XM_011539946; NM_001347821; NM_001143997; NM_001347820; NM_001347823; NR_144685; XM_017016402; NM_001347819; NM_001347825; NM_018245; NR_144682; NM_001347824; NR_144683; XM_017016403; NM_001143996; NM_001347822; NM_001347826; NR_144684; NR_144686 |
| WNT7A | 7476 | XM_011534091; NM_004625 |
| RPRM | 56475 | NM_019845 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| FOXA2 | 3170 | NM_021784; NM_153675 |
| ZNF536 | 9745 | XM_011527557; XM_017027530; XM_017027533; XM_017027534; XM_017027540; XM_017027535; XM_017027531; XM_017027532; XM_017027539; XM_017027542; XM_011527555; XM_011527560; XM_017027536; NM_001352260; NM_001376110; NM_014717; XM_011527554; XM_017027527; XM_017027537; XM_017027543; XM_024451807; NM_001376111; XM_011527558; XM_017027528; XM_017027529; XM_017027538 |
| CCL16 | 6360 | NM_004590; XM_005258020 |
| SHH | 6469 | NR_132319; NM_000193; NR_132318; XM_011516480; XM_011516479; NM_001310462 |
| TAC3 | 6866 | NR_135164; NR_135166; NR_135165; NM_001006667; NM_001178054; NM_013251; NR_033654 |

-continued

| Gene | NCBI Gene ID | NCBI Accession Number(s) |
|---|---|---|
| CXCL3 | 2921 | NM_002090 |
| DUSP26 | 78986 | NM_024025; NM_001305116; NM_001305115 |
| SERPIND1 | 3053 | NM_000185 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| TCF21 | 6943 | NM_003206; NM_198392 |
| TYR | 7299 | XM_011542970; NM_000372 |
| DUOX2 | 50506 | NM_014080; NM_001363711 |
| SLC45A2 | 51151 | NM_001297417; NM_016180; NM_001012509 |
| MAB21L2 | 10586 | NM_006439 |
| GAS2 | 2620 | NM_001143830; NM_001391933; NM_001391935; NM_001391936; XM_011519972; NM_001391937; NM_001391934; XM_011519971; NR_147085; XM_017017532; XR_001747829; NM_001351224; XM_011519975; NM_005256; NM_177553 |
| IL1A | 3552 | NM_001371554; NM_000575 |
| SPRR2B | 6701 | NM_001388198; NM_001017418 |
| CYP2W1 | 54905 | NM_017781; XM_011515440; XM_011515441 |
| SPOCK3 | 50859 | NM_001251967; NM_001204354; NM_001204356; XM_011532018; NM_001204359; XM_017008258; NM_001040159; NM_001204358; XM_017008257; NM_001204352; NM_016950; NM_001204353; NM_001204355 |
| KCNK12 | 56660 | NM_022055 |
| HKDC1 | 80201 | NM_025130; XR_001747209; XM_011540195 |
| HNF1B | 6928 | XM_011525161; NM_001165923; NM_001304286; XM_011525163; NM_000458; XM_011525162; NM_006481; XM_011525164; XM_011525160 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| FOXE1 | 2304 | NM_004473 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| NAALAD2 | 10003 | XM_017017044; XR_001747709; XM_017017043; XR_001747707; XR_001747710; XR_001747711; NM_001300930; XR_001747708; XM_017017045; XM_017017046; NM_005467 |
| HMGA2 | 8091 | NM_001015886; NM_003483; NM_001300918; NM_003484; NM_001330190; NM_001300919 |
| FOXF1 | 2294 | NM_001451 |
| RXRG | 6258 | NM_006917; NM_001256570; NM_001256571; NR_033824 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; |

-continued

| Gene | NCBI Gene ID | NCBI Accession Number(s) |
|---|---|---|
| | | XM_011531430; NM_001365588; NM_001365592; NM_001394830; XM_017030040; NM_001365584; NM_001365590; XM_024452490; NM_001365593; NM_001394831 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| STXBP6 | 29091 | XM_017021235; NM_001351941; NM_001394415; XM_024449547; NM_001304476; NM_001351942; NM_001394413; XM_006720121; NM_001304477; NM_001394414; NM_001394417; XM_017021232; NM_014178; NM_001394410; NM_001394411; NM_001394420; XM_017021241; NM_001351943; NM_001394418; NM_001351940; NM_001394412; NM_001394416; NM_001394419 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; |

-continued

| Gene | NCBI Gene ID | NCBI Accession Number(s) |
|---|---|---|
| | | NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| RPS4Y1 | 6192 | NM_001008 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| GFAP | 2670 | XM_024450691; XM_024450690; NM_001131019; XM_024450692; XM_024450693; NM_001242376; NM_002055; NM_001363846 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| PVRL3 | 25945 | XM_011512663; XM_017006126; NM_001243286; XR_924122; NM_015480; XR_002959508; XM_017006125; XM_017006124; XM_017006127; XM_017006123; NM_001243288 |
| SERPINB13 | 5275 | NM_001348267; XM_011526029; NM_001348268; NM_012397; NM_001348269; NM_001307923; NM_001348270 |
| ADH1C | 126 | NM_000669; NR_133005 |
| EYA4 | 2070 | XM_005266851; NM_004100; NM_172105; NM_001370459; NM_172104; XM_017010371; XR_001743220; NM_001301012; XM_017010369; XM_017010370; XM_017010372; XM_017010373; XR_001743219; NM_172103; NM_001301013; NM_001370458; XM_017010368; XM_017010374 |
| RGS6 | 9628 | XM_017021825; XM_017021832; XM_024449763; XR_001750613; NM_001370274; NM_001370279; NM_001370284; NM_001370291; XM_017021820; XM_024449761; XM_024449770; XM_024449774; NM_001370272; NM_001370277; |

-continued

| Gene | NCBI Gene ID | NCBI Accession Number(s) |
|---|---|---|
| | | NM_001370278; NM_001370292; XM_011537397; XM_017021831; XM_024449764; NM_001204421; NM_001204423; NM_001370275; NM_001370290; NM_001370293; NR_135235; XM_024449760; XM_024449776; XR_002957573; NM_001204416; NM_001204417; NM_001370271; NM_001370283; NM_001370270; NM_001370273; NM_001370281; NM_001370286; XM_017021822; XM_017021833; NM_001204422; NM_001204424; NM_001370276; NM_001370280; NM_001370287; NM_001370289; NM_001370294; XM_011537393; XM_011537407; XM_017021827; XM_017021830; XM_017021834; XM_024449759; NM_001370282; XM_017021826; XM_017021828; XM_024449768; NM_001204418; NM_001204419; NM_001204420; NM_001370288; NM_004296 |
| ACTC1 | 70 | NM_005159 |
| PAX3 | 5077 | NM_181457; NM_000438; NM_181459; NM_181460; NM_001127366; NM_013942; NM_181461; NM_181458 |
| GALNT12 | 79695 | XM_006717287; XM_017015133; XM_011519018; NM_024642; XM_011519020; XM_024447673 |
| SOX2 | 6657 | NM_003106 |
| SNCA | 6622 | XM_011532204; NM_001146054; NM_000345; NM_001375287; XM_011532206; NM_007308; NR_164675; XM_011532207; NM_001375288; NM_001375290; NR_164676; XM_011532203; XM_011532205; NR_164674; XM_017008563; NM_001146055; NM_001375286; NM_001375285 |
| MYLPF | 29895 | NM_001324458; NM_013292; NM_001324459 |
| EMX2 | 2018 | NM_004098; NM_001165924 |
| FRMPD1 | 22844 | XM_017014482; XM_024447456; XM_011517806; NM_001371223; NM_001371225; XM_017014481; XM_024447454; XM_011517805; XR_929220; NM_014907; NM_001371224 |
| PHYHIP | 9796 | NR_156475; NM_001099335; NM_001363311; NM_014759; XM_017014102; NM_001363312 |
| GUCY2C | 2984 | NM_004963; XM_011520631 |
| FGFBP1 | 9982 | NM_005130 |
| SGK2 | 10110 | NM_016276; NM_001199264; NM_170693 |
| GDF10 | 2662 | NM_004962 |
| REM1 | 28954 | XM_011528795; XM_017027833; NM_014012; XM_005260404 |
| CPEB1 | 64506 | NM_001288819; NM_001365243; NM_001365242; NM_001365244; NM_001365245; NM_001387068; NM_001387076; NM_001365248; NM_001079534; NM_001365250; NM_001387065; NM_001387075; NM_001079535; NM_001288820; NM_001365249; NM_001387061; NM_001387066; NM_001387070; NM_001387062; NM_001387071; NM_001387078; NM_001365246; NM_001365247; NM_001387069; NM_001387077; NM_001079533; NM_001365240; NM_001365241; NM_001387072; NM_001387074; NM_001387063; NM_001387064; NM_001387067; NM_001387073; NM_030594 |
| CYP3A5 | 1577 | NM_001291830; NM_001190484; NR_033807; NR_033812; NM_001291829; NM_000777; NR_033810; NR_033811 |
| SALL1 | 6299 | NM_001127892; NM_002968 |
| HAND2 | 9464 | NM_021973 |
| HOXA3 | 3200 | NM_001384342; NM_001384335; NM_001384336; NM_001384339; NM_001384345; NM_001384346; NM_001384338; NM_001384337; NM_030661; NM_001384341; NM_001384343; NM_001384340; NM_001384344; NM_153631; NM_153632 |
| TMPRSS5 | 80975 | XM_017018366; XR_001747990; NM_001288749; NM_001288751; NM_001288752; NM_001288750; NR_110047; XR_001747991; XR_001747992; NR_110046; NM_030770; XM_017018367 |
| BMP5 | 653 | XM_011514817; NM_001329756; XM_024446524; NM_001329754; NM_021073 |
| TRDN | 10345 | NM_001251987; NM_001256020; NM_001256021; NM_006073; NM_001256022 |
| TACR2 | 6865 | NM_001057 |
| LYVE1 | 10894 | NM_006691 |
| FHL1 | 2273 | NM_001159703; NM_001167819; NM_001369327; NM_001369330; XM_006724746; XM_024452354; NR_027621; NM_001369328; NM_001159702; NM_001369326; XM_006724743; NM_001330659; NM_001369331; NM_001159700; NM_001159701; NM_001159704; NM_001369329; NM_001159699; NM_001449 |
| CAV1 | 857 | NM_001753; NM_001172895; NM_001172897; NM_001172896 |
| FIGF | 2277 | NM_004469 |
| NPR1 | 4881 | XM_017001374; XM_005245218; NM_000906 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; |

-continued

| Gene | NCBI Gene ID | NCBI Accession Number(s) |
|---|---|---|
| | | NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| AOC3 | 8639 | XR_934584; NM_001277732; NM_003734; NR_102422; XM_011525419; XR_001752673; XM_011525420; XM_024451015; NM_001277731 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| CIDEC | 63924 | NM_001321142; NM_001199552; NM_001378491; NM_001199623; NM_001199551; NM_001321144; NM_022094; NM_001321143 |
| NEK2 | 4751 | NM_002497; NM_001204182; NM_001204183 |
| MMP11 | 4320 | NM_005940; NR_133013 |
| ADAMTS5 | 11096 | XM_024452053; XM_024452054; NM_007038 |
| ABCD2 | 225 | XR_001748623; NM_005164; XM_017018992; XR_001748622; XM_017018993; XM_011538027 |
| LPL | 4023 | NM_000237 |
| HBB | 3043 | NM_000518 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| COL10A1 | 1300 | XM_011535432; NM_000493; XM_011535433; XM_017010248; XM_006715333 |
| AQP7 | 364 | XM_006716765; XM_017014706; NM_001318158; NR_134513; NR_134515; XM_017014704; XM_024447538; NM_001318156; XM_011517866; NR_134514; NR_164778; XM_011517867; XM_017014701; XM_024447539; NM_001376192; NM_001376193; XM_017014702; NM_001318157; NM_001376191; NR_164779; XM_017014700; NM_001170 |
| LEP | 3952 | XM_005250340; NM_000230 |
| GSTM5 | 2949 | NM_000851; XM_005270785; XM_005270784 |
| FMO2 | 2327 | NM_001460; NR_160266; XR_921761; NM_001365900; XR_001737072; NM_001301347 |
| PLIN1 | 5346 | NM_002666; XM_005254934; NM_001145311 |
| KIAA0101 | 9768 | NR_109934; NM_001029989; NM_014736 |
| CA3 | 761 | NM_005181 |
| CDO1 | 1036 | NM_001323565; NR_136619; NM_001323567; NM_001801; NR_136618; NR_136620; NM_001323566; NR_136621 |
| CSN1S1 | 1446 | XM_006714091; NM_001025104; XM_006714089; XM_006714090; NM_001890 |
| KIF4A | 24137 | NM_012310 |
| GPD1 | 2819 | NM_005276; NM_001257199 |

-continued

| Gene | NCBI Gene ID | NCBI Accession Number(s) |
|---|---|---|
| DPT | 1805 | NM_001937 |
| ADH1B | 125 | NM_001286650; NM_000668 |
| FABP4 | 2167 | NM_001442 |
| CENPF | 1063 | XM_017000086; NM_016343; XM_011509082 |
| GABRD | 2563 | XM_011541194; XM_017000936; NM_000815 |
| PFKFB1 | 5207 | NM_001271804; XM_017029578; XM_017029576; NM_002625; NR_073450; XM_024452389; XM_017029577; NM_001271805 |
| ATP1A2 | 477 | NM_000702 |
| CHL1 | 10752 | XM_011533294; XM_017005568; XM_017005573; NM_001253387; NR_045572; XM_017005569; XM_017005572; XM_006712939; XM_011533292; XM_017005566; XM_006712940; XM_011533295; NM_001253388; NM_006614; XM_006712938; XM_011533296; XM_017005567; XM_017005570; XM_017005571 |
| SLC7A10 | 56301 | XM_011527120; XM_006723284; XM_024451609; XR_935841; NM_019849; XM_011527119; XM_024451610 |
| ADIPOQ | 9370 | NM_004797; NM_001177800 |
| EXO1 | 9156 | XM_011544325; XM_011544322; NM_130398; XM_011544323; XM_006711840; NM_003686; NM_006027; XM_011544321; XM_011544324; XM_017002793; NM_001319224 |
| INHBA | 3624 | XM_017012175; NM_002192; XM_017012176; XM_017012174 |
| CES1 | 1066 | NM_001025195; NM_001266; XM_005255774; NM_001025194 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| MMRN1 | 22915 | XM_005262856; NM_001371403; NM_007351 |
| HMMR | 3161 | NM_001142557; NM_001142556; NM_012484; NM_012485 |
| PKMYT1 | 9088 | NM_001258451; NM_182687; NM_001258450; XM_011522735; XM_024450490; NM_004203; XM_011522734; XM_011522736 |
| CIDEA | 1149 | NM_001279; NR_134607; NM_001318383 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| OXTR | 5021 | NM_000916; NM_001354654; NM_001354655; NM_001354653; NM_001354656 |
| DTL | 51514 | XM_011509614; NM_001286229; NM_001286230; NM_016448 |
| IBSP | 3381 | NM_004967 |
| PPP1R1A | 5502 | XM_005268995; XM_006719471; NM_006741 |
| WISP1 | 8840 | XM_024447319; NR_037944; XM_024447320; NM_080838; NM_003882; NM_001204870; XM_024447321; NM_001204869 |

-continued

| Gene | NCBI Gene ID | NCBI Accession Number(s) |
|---|---|---|
| STAB2 | 55576 | NM_017564; XM_011538541; XM_011538538; XM_011538539; XM_011538542; XM_017019585; XM_011538537; XR_429107 |
| CDKN3 | 1033 | XM_024449458; NM_001330173; NM_005192; NM_001130851 |
| TK1 | 7083 | NM_001346663; NM_003258 |
| KIF20A | 10112 | NM_005733 |
| KCNB1 | 3745 | XM_011528799; XM_006723784; NM_004975 |
| S100B | 6285 | NM_006272; XM_017028424 |
| PBK | 55872 | NM_018492; NM_001278945; NM_001363040 |
| TDO2 | 6999 | NM_005651 |
| PITX1 | 5307 | NM_002653 |
| MCM10 | 55388 | NM_182751; NM_018518; XM_011519538 |
| GRM4 | 2914 | NM_001256809; NM_001256812; NM_001256813; NM_001256811; NM_001256814; NM_001256810; NM_001282847; NM_000841 |
| CST1 | 1469 | NM_001898 |
| AIM1L | 55057 | NM_017977; XM_011541672; XM_011541673; XR_001737260; NM_001039775; XR_946681; XM_005245918 |
| TNMD | 64102 | NM_022144 |
| CLEC5A | 23601 | XM_017011916; XM_017011915; XM_011515995; XM_017011917; NM_001301167; NM_013252 |
| LRRC15 | 131578 | NM_130830; NM_001135057 |
| LAMP5 | 24141 | NM_001199897; NM_012261 |
| EPYC | 1833 | NM_004950; XM_011538008 |
| RAB26 | 25837 | XM_011522448; XM_011522450; NM_014353; NM_001308053 |
| CST2 | 1470 | NM_001322 |
| NKAIN1 | 79570 | NM_024522; XM_017002320 |
| LALBA | 3906 | NM_002289; NM_001384350 |
| CENPA | 1058 | NM_001809; NM_001042426 |
| TUBB3 | 10381 | NM_006086; NM_001197181 |
| ARTN | 9048 | NM_057160; NM_057090; NM_001136215; NM_057091; NM_003976 |
| TCL1B | 9623 | NM_004918; NM_199206 |
| SYT13 | 57586 | NM_001247987; NM_020826 |
| CNTD2 | 79935 | XM_006723395; NM_024877; XR_001753763; XR_935861 |
| NEURL1 | 9148 | XM_005270269; XM_011540333; XM_017016909; XM_011540332; XM_011540335; XR_945866; NM_004210; XM_005270270; XM_011540331 |
| NPY2R | 4887 | NM_001370180; NM_000910; NM_001375470 |
| CXCL10 | 3627 | NM_001565; NR_168520 |
| S100P | 6286 | NM_005980 |
| MYT1 | 4661 | NM_004535 |
| ACTL8 | 81569 | NM_030812; XM_011542212 |
| HAPLN1 | 1404 | XM_017009052; XM_017009051; NM_001884; XM_017009054; XM_017009053; XM_011543168 |
| BTN1A1 | 696 | NM_001732 |
| CXCL9 | 4283 | NM_002416 |
| CEACAM6 | 4680 | NM_002483; XM_011526990 |
| FBN2 | 2201 | NM_001999; XM_017009228 |
| NAT1 | 9 | NM_001160175; NM_001160170; NM_001160173; XM_011544688; XM_006716410; XM_017013947; NM_001160171; NM_001160172; NM_001160174; NM_001291962; XM_011544689; NM_001160176; XM_011544687; NM_000662; NM_001160179 |
| FOXJ1 | 2302 | NM_001454 |
| BMPR1B | 658 | XM_017008558; NM_001203; NM_001256793; XM_011532201; NM_001256794; NM_001256792; XM_017008559; XM_017008560; XM_017008561 |
| CNTNAP2 | 26047 | XM_017011950; NM_014141 |
| CEACAM5 | 1048 | XM_011526322; XM_017026146; NM_001291484; NM_004363; XM_017026145; NM_001308398 |
| KCNF1 | 3754 | NM_002236 |
| HOXC11 | 3227 | NM_014212 |
| KCNJ3 | 3760 | NM_001260510; NM_001260508; NM_001260509; NM_002239 |
| MAGEA12 | 4111 | NM_001166386; NM_001166387; NM_005367 |
| GABRQ | 55879 | NM_018558; XM_011531184 |
| HHIPL2 | 79802 | XM_024449814; XR_001737417; XR_426906; XM_017002350; XR_002957624; NM_024746; XR_001737416; XM_011509986 |
| TLX1 | 3195 | NM_001195517; XM_011539744; XM_011539745; NM_005521 |
| SOX11 | 6664 | NM_003108 |
| MAGEA6 | 4105 | NM_175868; NM_005363 |
| CA9 | 768 | XR_428428; NM_001216; XR_001746374 |
| C2orf54 | 79919 | XM_011511877; NM_001085437; NM_001282921; NM_024861 |
| DIO1 | 1733 | NM_000792; NM_001039715; NM_213593; NM_001039716; NM_001324316; NR_136692; NR_136693 |
| F7 | 2155 | XM_011537476; XM_011537475; NM_001267554; XM_011537474; NR_051961; XM_006719963; NM_019616; NM_000131 |
| CYP2B6 | 1555 | NM_000767 |
| TRH | 7200 | NM_007117 |
| CHGB | 1114 | NM_001819 |
| PROL1 | 58503 | NM_021225; NM_001302807; NR_126503 |
| CD177 | 57126 | XM_017027021; XM_017027022; NM_020406 |
| KIF1A | 547 | NM_001379636; NM_001379637; NM_001379639; NM_001379650; NM_001330290; NM_001379633; NM_001379641; NM_001379651; NM_001379653; NM_004321; NM_001379632; NM_001379638; NM_001379645; NM_001379646; NM_001379649; NM_001379635; NM_001379640; NM_001379634; NM_001244008; NM_001379642; NM_001320705; NM_001330289; NM_001379631; NM_001379648 |
| PSCA | 8000 | NR_033343; NM_005672 |
| CRISP3 | 10321 | NM_001368123; NM_006061; NM_001190986 |
| PVALB | 5816 | NM_001315532; NM_002854 |
| GAD1 | 2571 | NM_013445; XM_017003758; NM_000817; XM_005246444; XM_011510922; XM_017003757; XM_017003756; XM_024452783 |
| MYH7 | 4625 | XM_017021340; NM_000257 |
| SERPINB7 | 8710 | XM_024451278; NM_001261831; NM_003784; NM_001040147; NM_001261830 |
| COL2A1 | 1280 | XM_017018831; XM_017018830; NM_001844; NM_033150; XM_017018828; XM_017018829 |
| MSMB | 4477 | NM_138634; NM_002443 |
| IRS4 | 8471 | XM_006724713; NM_003604; NM_001379150; XM_011531061 |
| BEX1 | 55859 | NM_018476 |
| PADI3 | 51702 | NM_016233; XM_011541571; XM_017001463; XM_011541572 |
| UGT2B4 | 7363 | NM_001297616; NM_021139; NM_001297615 |

-continued

| Gene | NCBI Gene ID | NCBI Accession Number(s) |
|---|---|---|
| PRSS1 | 5644 | NR_172951; XM_011516411; NR_172947; NM_002769; NR_172948; NR_172949; NR_172950 |
| CYP2A7 | 1549 | XR_935754; NM_000764; NM_030589 |
| MSLN | 10232 | NM_001177355; NM_005823; NM_013404 |
| CPB1 | 1360 | NM_001871 |
| CARTPT | 9607 | NM_004291 |
| TGM4 | 7047 | NM_003241; XM_011534042 |
| NCAN | 1463 | NM_004386 |
| CYP2A6 | 1548 | NM_000762 |
| CALML5 | 51806 | NM_017422 |
| TFF1 | 7031 | NM_003225 |
| Ovarian_Cancer | | |
| QARS | 5859 | NR_073590; NM_005051; XM_017006965; NM_001272073 |
| HSD17B2 | 3294 | NM_002153; XR_001751898 |
| CLDN6 | 9074 | NM_021195 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| IZUMO4 | 113177 | XM_024451343; XR_002958248; NM_001039846; XM_024451342; XM_024451344; NM_052878; NM_001031735; NM_001363588 |
| PAQR4 | 124222 | NM_001284513; NM_001284511; NM_001284512; NM_152341; NM_001324118 |
| NGFR | 4804 | NM_002507 |
| MCC | 4163 | NM_002387; NM_001085377 |
| FAM107A | 11170 | NM_001076778; NM_007177; NM_001282713; NM_001282714 |
| FOXL1 | 2300 | NM_005250 |
| KCNC3 | 3748 | NM_004977; NR_110912; NM_001372305 |
| PTGS2 | 5743 | NM_000963 |
| COL17A1 | 1308 | NM_130778; NM_000494 |
| FZD2 | 2535 | NM_001466 |
| EIF1AY | 9086 | NM_004681; NM_001278612 |
| HOXD13 | 3239 | XM_011511068; NM_000523; XM_011511069 |
| FGF14 | 2259 | NM_001321931; NM_001321943; NM_001321949; NM_175929; NM_001321933; NM_001321941; NM_001321932; NM_001321935; NM_001321937; NM_001321945; NM_001321947; NM_001321939; NM_001321936; NM_001321940; NM_001321944; NM_001321946; NM_001321948; NM_001379342; NM_001321934; NM_001321938; NM_001321942; NM_004115 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| MMP13 | 4322 | NM_002427 |
| LHX1 | 3975 | NM_005568 |
| CSDC2 | 27254 | NM_014460 |
| PAX9 | 5083 | NM_001372076; NM_006194 |

-continued

| Gene | NCBI Gene ID | NCBI Accession Number(s) |
|---|---|---|
| B2M | 567 | XR_002957658; XM_005254549; NM_004048 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| ZNF492 | 57615 | NM_020855 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PRSS1 | 5644 | NR_172951; XM_011516411; NR_172947; NM_002769; NR_172948; NR_172949; NR_172950 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| IRX5 | 10265 | NM_005853; XM_011522809; NM_001252197 |
| DOK5 | 55816 | XM_011528904; NM_001294161; NM_018431; XM_024451946; NM_177959 |
| ASIP | 434 | NM_001385218; XM_011528820; NM_001672; XM_011528821 |

-continued

| Gene | NCBI Gene ID | NCBI Accession Number(s) |
|---|---|---|
| EMX2 | 2018 | NM_004098; NM_001165924 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| VGLL1 | 51442 | NM_016267 |
| HSPA4L | 22824 | NM_001317381; NM_001317383; XM_011531745; NM_001317382; NM_014278 |
| PAX8 | 7849 | NM_013992; NM_013953; NM_013952; NM_003466; NM_013951 |
| ALDH1A3 | 22 | NM_001293815; NM_000693; NM_001037224 |
| ANGPT4 | 51378 | NM_001322809; XM_011529239; NM_015985 |
| KIAA0513 | 9764 | NM_001286565; NM_001297766; NM_001286566; XM_017023912; NM_014732; NM_001388359 |
| RPS4Y1 | 6192 | NM_001008 |
| NES | 10763 | NM_024609; NM_006617 |
| COL21A1 | 81578 | XM_011514927; XM_024446561; XR_001743657; NM_030820; NR_134851; NR_134849; XM_011514925; NM_001318753; NR_134850; NM_001318752; NM_001318754; XM_011514926; XM_006715223; NM_001318751; XM_011514924 |
| MNX1 | 3110 | NM_001165255; NM_005515 |
| WT1 | 7490 | NM_000378; NR_160306; NM_001367854; NM_001198551; NM_001198552; NM_024424; NM_024426; NM_024425 |
| SLC6A12 | 6539 | XM_005253747; NM_003044; NM_001122847; XM_005253748; XM_011521010; XM_006719005; NM_001122848; NM_001206931 |
| NPR1 | 4881 | XM_017001374; XM_005245218; NM_000906 |
| WISP3 | 8838 | XM_011536223; XM_011536220; NM_198239; NR_125353; NR_125354; XR_001743705; NM_130396; XM_011536222; NM_003880 |
| ASGR1 | 432 | XM_011523861; NM_001197216; NM_001671 |
| FOXL2 | 668 | NM_023067 |
| PNOC | 5368 | NM_006228; XM_011544559; XM_005273532; XM_017013578; NM_001284244 |
| KLK6 | 5653 | XM_024451611; NM_001319949; NM_001012964; NM_001319948; NM_001012965; NM_002774 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| KLK10 | 5655 | XM_006723289; XM_005259061; NM_002776; NM_145888; NM_001077500; XM_017026993; XM_006723287; XM_005259062 |
| HEY1 | 23462 | NM_001040708; NM_012258; NM_001282851 |
| SCD | 6319 | NM_005063 |
| DIO3 | 1735 | NM_001362 |
| SCGN | 10590 | NM_006998; XM_017010181 |
| LGALS14 | 56891 | NM_020129; NM_203471 |

-continued

| Gene | NCBI Gene ID | NCBI Accession Number(s) |
|---|---|---|
| SLC27A2 | 11001 | NM_001159629; NM_003645 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| BBC3 | 27113 | XM_006723141; XM_011526722; NM_001127241; NM_001127242; NM_001127240; NM_014417 |
| CETP | 1071 | XM_006721124; NM_000078; NM_001286085 |
| GSTM5 | 2949 | NM_000851; XM_005270785; XM_005270784 |
| WNT7A | 7476 | XM_011534091; NM_004625 |
| CCNE1 | 898 | XM_011527440; NM_001238; NM_001322259; NM_001322261; NM_001322262; NM_057182 |
| DLC1 | 10395 | NM_001316668; NM_182643; XM_005273374; NM_001348081; NM_001348083; NM_001348084; NM_001164271; NM_006094; NM_024767; NM_001348082 |
| RAMP3 | 10268 | XM_017011666; NM_005856; XM_006715631 |

-continued

| Gene | NCBI Gene ID | NCBI Accession Number(s) |
|---|---|---|
| MEIS1 | 4211 | NM_002398 |
| SGCA | 6442 | XM_011525122; XM_011525120; XM_011525121; XM_024450873; NM_001135697; NR_135553; XR_002958056; XM_011525124; NM_000023; XM_011525123 |
| HGH1 | 51236 | NM_016458; XR_001745537 |
| CHODL | 140578 | XM_017028273; NM_001204174; NM_024944; XM_011529453; NM_001204176; NM_001204175; NM_001204177; XM_011529457; NM_001204178 |
| NLRP1 | 22861 | NM_001033053; NM_033006; NM_033007; NM_014922; NM_033004 |
| CLDN9 | 9080 | NM_020982 |
| RPL4 | 6124 | NM_000968 |
| CDH6 | 1004 | NM_004932; NM_001362435; XM_017008910; XM_011513921; XR_001741972 |
| TNFRSF10C | 8794 | NM_003841 |
| ITGA2 | 3673 | NR_073103; NR_073104; NR_073105; NR_073106; NR_073107; NM_002203 |
| GRK5 | 2869 | XM_005269707; XM_005269708; NM_005308 |
| LIPF | 8513 | NM_004190; NM_001198829; NM_001198830; NM_001198828; XM_011540311 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| SST | 6750 | NM_001048 |
| IL20RA | 53832 | NM_001278722; XM_011535904; XM_017010955; NM_001278724; NM_014432; XM_006715506; NM_001278723; XM_017010954 |
| FGF18 | 8817 | NM_003862; NM_033649 |
| NR5A1 | 2516 | NM_004959 |
| ULBP2 | 80328 | NM_025217; XM_017011321 |
| RNF128 | 79589 | NM_024539; NM_194463 |
| PRM2 | 5620 | NM_001286358; NR_104428; NM_002762; NM_001286356; NM_001286359; NM_001286357 |
| C7 | 730 | NM_000587 |
| L1CAM | 3897 | NM_024003; NM_001278116; NM_001143963; NM_000425 |
| BCAM | 4059 | NM_001013257; NM_005581 |
| DTL | 51514 | XM_011509614; NM_001286229; NM_001286230; NM_016448 |
| ADRB3 | 155 | NM_000025 |
| CLDN16 | 10686 | NM_006580; NM_001378492; NM_001378493 |
| FMO5 | 2330 | XM_005272946; XM_005272947; XM_011509351; XM_017000802; NM_001144829; NM_001461; XM_006711244; XM_006711245; XM_005272948; NM_001144830; XM_017000801; XM_011509350 |
| KCNIP1 | 30820 | NM_001034837; NM_014592; NM_001034838; NM_001278340; XM_017009407; XM_017009408; NM_001278339 |

-continued

| Gene | NCBI Gene ID | NCBI Accession Number(s) |
|---|---|---|
| FGF23 | 8074 | NM_020638 |
| PDE3B | 5140 | XR_001747903; NM_000922; NM_001363570; XM_017017912; XM_006718249; XM_017017911; NM_001363569 |
| SLC4A3 | 6508 | XM_011511667; NM_201574; NR_048551; XM_005246790; XM_011511665; NM_001326559; NM_005070 |
| FOLR1 | 2348 | NM_000802; NM_016729; NM_016730; NM_016725; NM_016724 |
| STAR | 6770 | NM_001007243; NM_000349 |
| Uterus_Carcinoma | | |
| SPDEF | 25803 | NM_001252294; XM_005248988; NM_012391; XM_011514457 |
| HLA-G | 3135 | XM_017010817; NM_001384280; XM_017010818; NM_002127; XM_024446420; NM_001363567; NM_001384290 |
| MARCO | 8685 | NM_006770; XM_011512082; XM_011512083; XM_017005171 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| ZNF208 | 7757 | NM_001329971; NM_001329973; NM_001329974; NM_001329972; NR_138252; NM_007153 |
| CHRND | 1144 | NM_001311196; XM_011510524; NM_001256657; NM_001311195; NM_000751 |
| SLC31A2 | 1318 | NM_001860 |
| C1S | 716 | XM_005253760; NM_001734; NM_001346850; NM_201442 |
| GREB1 | 9687 | XM_024453255; NM_014668; NM_033090; XM_024453254; XM_024453256; NM_148903; XM_005246196; XM_024453251; XR_922686; XM_024453250; XM_024453252; XM_011510418; XM_011510423; XM_011510422; XM_024453253; XM_011510419; XM_005246192; XR_001739081 |
| VIP | 7432 | XM_006715562; XM_005267135; NM_003381; NM_194435 |
| ZWINT | 11130 | XR_428692; NM_007057; NM_001005413; XM_017015605; XM_024447784; NM_032997; NM_001005414 |
| CREB5 | 9586 | XM_017012807; XM_017012808; NM_001011666; XM_024447005; XM_017012806; XM_017012809; NM_182898; XM_017012810; XM_005249906; NM_004904; XR_001744893; XM_011515618; NM_182899 |
| EIF1AY | 9086 | NM_004681; NM_001278612 |
| E2F1 | 1869 | NM_005225 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; |

-continued

| Gene | NCBI Gene ID | NCBI Accession Number(s) |
|---|---|---|
| | | NM_001377328; XM_005252344; NM_001377322; NM_001177483; XR_001746995; XM_005252342; XM_017015468; NM_006393; NM_016365 |
| HOXD13 | 3239 | XM_011511068; NM_000523; XM_011511069 |
| CTSV | 1515 | NM_001201575; NM_001333 |
| HOXD10 | 3236 | NM_002148 |
| DGKG | 1608 | NM_001346; NM_001080745; NM_001080744 |
| SFRP1 | 6422 | NM_003012 |
| PAX9 | 5083 | NM_001372076; NM_006194 |
| SCGB2A1 | 4246 | NM_002407 |
| FOXJ1 | 2302 | NM_001454 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| BEGAIN | 57596 | NM_001385092; NM_001385093; NR_169571; XM_024449671; NM_001385104; XM_024449670; NM_001159531; NM_001385088; NM_001385094; NM_001385095; NM_001385096; NM_001385097; NM_001385098; NM_001385099; NM_001385100; NM_020836; NM_001385089; NM_001385102; NM_001385083; NM_001385084; NM_001385091; NR_169570; NM_001385085; NM_001385086; NM_001385087; NM_001385103; NM_001385082; NM_001385090; NM_001385101 |
| EMX2 | 2018 | NM_004098; NM_001165924 |
| VGLL1 | 51442 | NM_016267 |
| ALDH1A2 | 8854 | NM_001206897; NM_170697; NM_170696; NM_003888 |
| SLCO5A1 | 81796 | XM_017013885; XR_928814; NM_001146008; NM_001146009; XM_017013886; XR_428341; XM_017013884; NM_030958; XM_017013883; XM_005251313 |
| HOXA10 | 3206 | NR_037939; NM_153715; NM_018951 |
| GADD45G | 10912 | XM_011518163; NM_006705 |
| RPS4Y1 | 6192 | NM_001008 |
| TPM2 | 7169 | XM_017015091; NM_213674; XM_017015093; XM_017015088; NM_001301226; NM_001301227; NM_001145822; XM_017015087; XM_017015092; XM_017015090; NM_003289 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |

-continued

| Gene | NCBI Gene ID | NCBI Accession Number(s) |
|---|---|---|
| WT1 | 7490 | NM_000378; NR_160306; NM_001367854; NM_001198551; NM_001198552; NM_024424; NM_024426; NM_024425 |
| MNX1 | 3110 | NM_001165255; NM_005515 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| ANKRD2 | 26287 | NM_001291218; NM_001129981; NM_020349; NM_001291219; NM_001346793 |
| EHHADH | 1962 | XM_006713525; NM_001166415; NM_001966 |
| FXYD1 | 5348 | NM_001278718; NM_001278717; NM_021902; XM_017026875; NM_005031; XM_017026874; XM_017026876 |
| FOXL2 | 668 | NM_023067 |
| GLDC | 2731 | NM_000170 |
| TNNC1 | 7134 | NM_003280 |
| EDNRB | 1910 | NM_001122659; NM_003991; NM_001201397; NM_000115; NR_047024 |
| APOD | 347 | NM_001647 |
| SLC27A2 | 11001 | NM_001159629; NM_003645 |
| SLC12A2 | 6558 | XM_011543588; NM_001256461; XR_001742214; NR_046207; NM_001046; XM_017009771 |
| FMO2 | 2327 | NM_001460; NR_160266; XR_921761; NM_001365900; XR_001737072; NM_001301347 |
| GSTM5 | 2949 | NM_000851; XM_005270785; XM_005270784 |
| SOX1 | 6656 | NM_005986 |
| APBA1 | 320 | NM_001163; XM_011518617; XM_017014670; XM_005251968 |
| HOXB13 | 10481 | NM_006361 |
| NPY4R | 5540 | XR_001747124; NM_001278794; NM_005972; XM_011539936; XM_017016387; XM_011539937; XM_017016386; XR_001747123 |
| CIDEB | 27141 | NM_001393334; NM_001393340; NM_001318807; NM_001393339; NM_001393336; NM_001393338; NM_001393335; NM_001393337; NM_014430 |
| MEIS1 | 4211 | NM_002398 |
| TNNC2 | 7125 | NM_003279; XM_011529031 |
| RIMBP2 | 23504 | XM_017019105; XM_011538103; XM_011538105; NM_001351227; NM_001393620; NM_001393627; NM_001393616; NM_001351232; NM_001393615; NM_001393621; NM_001393623; NM_001393628; XM_011538106; XM_011538102; XM_011538108; NM_001351231; NM_001393614; NM_001393617; NM_001393622; NM_001393625; NM_001393629; NM_001351230; NM_001393619; NM_001393626; NM_001351228; NM_001393624; XM_011538107; XM_017019106; NM_001351226; NM_001351229; NM_001351233; NM_001393618; NM_015347 |

-continued

| Gene | NCBI Gene ID | NCBI Accession Number(s) |
|---|---|---|
| HGH1 | 51236 | NM_016458; XR_001745537 |
| SOX15 | 6665 | NM_006942 |
| PDLIM3 | 27295 | NM_001114107; XR_938723; NM_001257963; XR_938724; NM_001257962; NR_047562; NM_014476; XR_001741206 |
| CX3CR1 | 1524 | NM_001171174; NM_001337; NM_001171171; NM_001171172 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| ZBTB16 | 7704 | XR_001747955; NM_001354751; XM_017018259; NM_006006; NM_001354752; XM_005271658; XM_024448681; NM_001018011; NM_001354750 |
| CLCA2 | 9635 | NM_006536; XM_011542448 |
| DLX5 | 1749 | XM_017011803; NM_005221; XM_005250185 |
| GABRQ | 55879 | NM_018558; XM_011531184 |
| FOXA2 | 3170 | NM_021784; NM_153675 |
| TNFSF10 | 8743 | NR_033994; NM_001190943; NM_003810; NM_001190942 |
| IQCA1 | 79781 | XM_017004960; NM_024726; NM_001270585; XM_011511865; XM_011511866; XM_011511864; NM_001270584; NR_073043 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| TUBA1C | 84790 | NM_001303114; NM_032704; NM_001303116; NM_001303117; NM_001303115 |
| GYPC | 2995 | NM_002101; XM_006712460; NM_001256584; NM_016815 |
| CA2 | 76 | NM_001293675; NM_000067 |
| IL20RA | 53832 | NM_001278722; XM_011535904; XM_017010955; NM_001278724; NM_014432; XM_006715506; NM_001278723; XM_017010954 |
| RGN | 9104 | XM_024452477; XM_006724568; XM_017029954; NM_004683; NM_001282848; NM_152869; NM_001282849; XM_006724567 |
| AOC3 | 8639 | XR_934584; NM_001277732; NM_003734; NR_102422; XM_011525419; XR_001752673; XM_011525420; XM_024451015; NM_001277731 |
| FGF18 | 8817 | NM_003862; NM_033649 |
| MYO5A | 4644 | XM_011521607; NM_001142495; NM_001382348; XM_011521610; NM_000259; NM_001382347; XM_011521611; XM_011521609; XM_011521612; XM_017022227; NM_001382349 |
| CCDC33 | 80125 | XR_001751400; XM_011522090; XM_017022624; XM_017022626; NM_001287181; XM_011522088; XM_017022630; XR_001751401; NM_025055; XM_017022625; XM_017022628; XM_017022631; NR_108023; NM_182791; XM_011522087; XM_005254692; XM_017022627; XM_017022633; XM_017022623; XM_011522086; XM_017022632; XM_011522085; XM_011522089 |
| REN | 5972 | NM_000537 |
| NCAPG | 64151 | NM_022346; XM_017008543; NR_073124; XM_017008544; XM_011513876 |
| CT62 | 196993 | NR_168259; NM_001102658; NR_168260 |
| CACNA1G | 8913 | NM_001256326; NM_001256328; NM_018896; NM_198378; NM_198388; NM_198396; NM_001256359; NM_001256361; NM_198383; NM_198385; NM_001256327; NM_001256330; NR_046056; NM_198380; NM_198382; NR_046054; XM_006722160; NM_198379; NM_001256329; NM_001256332; NM_001256333; NM_001256360; NM_198384; NM_198386; NR_046058; NM_001256325; NM_001256334; NM_198387; XM_006722161; NM_001256324; NM_001256331; NM_198376; NM_198377; NR_046055; NR_046057; NM_198397 |
| PIGR | 5284 | XM_011509629; NM_002644 |
| CSTA | 1475 | NM_005213 |
| OSR2 | 116039 | XM_017013018; NM_053001; XM_011516825; XM_005250778; NM_001286841; NM_001142462; XM_011516826; NM_001394683; XM_011516827 |
| FOXF2 | 2295 | NM_001452 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| GAD1 | 2571 | NM_013445; XM_017003758; NM_000817; XM_005246444; XM_011510922; XM_017003757; XM_017003756; XM_024452783 |
| NXPH4 | 11247 | XM_017018747; NM_007224 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EGFR | 1956 | NM_001346899; NM_201282; NM_201284; NM_001346898; NM_001346900; NM_001346897; NM_201283; NM_001346941; NM_005228 |
| FMO3 | 2328 | XM_011509345; XM_024454365; NM_001002294; NM_006894; NM_001319173; NM_001319174 |
| TSPAN7 | 7102 | NM_004615 |
| ASRGL1 | 80150 | XM_005274305; XM_005274306; XM_011545265; NM_001083926; XM_011545266; NM_025080; XR_002957199; XM_017018354; XR_002957198; XR_001747982 |

-continued

| Gene | NCBI Gene ID | NCBI Accession Number(s) |
|---|---|---|
| ALOX15B | 247 | NM_001141; NM_001039130; NM_001039131 |
| PRPH | 5630 | XM_005269025; XR_944623; NM_006262; |
| EFEMP1 | 2202 | XM_024452757; NM_004105; NM_018894; XM_005264205; NM_001039349; XM_017003586; XM_024452755; XM_024452756; NM_001039348 |
| SALL1 | 6299 | NM_001127892; NM_002968 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| PHOX2A | 401 | NM_005169 |
| AQP5 | 362 | NM_001651; XM_005268838 |
| TTC22 | 55001 | XM_017001582; XM_011541671; NM_001114108; NM_017904 |
| | Renal_Cell_Carcinoma | |
| SLC17A3 | 10786 | NM_006632; NM_001098486 |
| SLC4A1 | 6521 | XM_011525129; XM_005257593; XM_011525130; NM_000342 |
| CDH16 | 1014 | NM_001204746; XM_011522807; NM_004062; XM_005255770; NM_001204744; NM_001204745 |
| SLC22A2 | 6582 | NM_153191; NM_003058 |
| NAT8 | 9027 | NM_003960 |
| SLC3A1 | 6519 | XM_011533047; NM_000341 |
| ENPP3 | 5169 | XR_001743464; NR_133007; NM_005021; XM_017010932; XM_011535897 |
| FXYD2 | 486 | NM_021603; NM_001127489; NM_001680 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| SIM1 | 6492 | XM_011536072; NM_001374769; NM_005068 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| PAX2 | 5076 | NM_001304569; NM_003987; NM_001374303; NM_003989; NM_000278; NM_003990; NM_003988 |
| PVALB | 5816 | NM_001315532; NM_002854 |
| RHBG | 57127 | XR_001737323; NR_146765; XR_001737328; XR_001737329; NR_046115; XM_011509799; XM_017001859; NR_146764; XM_011509800; XM_017001858; XR_001737324; XR_001737325; NM_001256395; NR_146763; XM_017001857; NM_020407; XR_001737330; XR_001737332; NM_001256396 |
| AQP2 | 359 | NM_000486 |
| POU3F3 | 5455 | NM_006236 |
| PAX8 | 7849 | NM_013992; NM_013953; NM_013952; NM_003466; NM_013951 |
| GFRA3 | 2676 | NM_001496 |
| CA12 | 771 | NM_001218; NR_135511; NM_206925; NM_001293642 |

-continued

| Gene | NCBI Gene ID | NCBI Accession Number(s) |
|---|---|---|
| FOXD3 | 27022 | NM_012183 |
| CACNG4 | 27092 | NM_014405 |
| HAND2 | 9464 | NM_021973 |
| NLGN1 | 22871 | NM_001365923; NM_001365928; NM_001365932; NM_014932; XM_011512551; XM_011512553; XM_017005897; XM_017005902; NM_001365929; NM_001365926; XM_017005895; XM_017005893; NM_001365925; NM_001365931; XM_017005896; XM_017005900; NM_001365933; XM_005247237; NM_001365930; NM_001365936; XM_011512554; XM_017005888; XM_017005894; NM_001365924; NM_001365927; NM_001365934; NM_001365935 |
| TRPM3 | 80036 | NM_001366147; XM_011519045; NM_001366145; NM_206944; XM_011519042; XM_024447681; NM_001007470; NM_001366152; NM_001366153; NM_206946; XM_011519037; NM_001366151; NM_206947; XM_011519040; NM_001007471; NM_001366141; NM_001366150; NM_001366154; XM_011519039; XM_017015156; XM_024447687; NM_001366144; NM_001366146; NM_020952; XM_024447683; NM_001366149; XM_011519038; XM_011519046; XM_024447682; XM_024447684; XM_024447685; XM_024447686; NM_001366142; NM_001366143; NM_001366148; NM_024971; NM_206945; NM_206948 |
| ARHGEF4 | 50649 | XM_011511276; XM_005263689; XR_001738756; NM_001375900; NM_001375902; XM_011511274; XR_001738757; NM_001375901; NM_001375904; NM_001367493; NM_001375903; NM_015320; NM_001395416; NM_032995; XM_005263688; XM_011511277; XM_017004231; XM_024452938 |
| INSM1 | 3642 | NM_002196 |
| S100A14 | 57402 | XM_017001875; NM_020672; XM_005245362 |
| LGR5 | 8549 | NR_110596; NM_001277227; NM_001277226; NM_003667 |
| CFTR | 1080 | NM_000492 |
| TRHDE | 29953 | XM_017019244; XM_017019243; NM_013381; XM_005268819; XM_011538248 |
| ESRP1 | 54845 | XM_005250991; NM_001122827; NM_017697; XM_005250992; NM_001122826; NM_001034915; NM_001122825 |
| LAD1 | 3898 | NM_005558 |
| GRHL2 | 79977 | XM_011517306; XM_024447286; NM_001330593; NM_024915; XM_011517307 |
| ALPPL2 | 251 | NM_031313 |
| HOXC10 | 3226 | NM_017409 |
| EPHB3 | 2049 | NM_004443 |
| SLC6A11 | 6538 | NM_001317406; XM_017007073; XM_011534033; NM_014229 |
| NKX3-2 | 579 | NM_001189 |
| CNKSR1 | 10256 | NM_006314; NR_023345; NM_001297647; NM_001297648 |
| RAMP1 | 10267 | XM_017003153; XM_017003154; XM_017003155; NM_001308353; NM_005855; XM_017003152; XM_017003156 |

-continued

| Gene | NCBI Gene ID | NCBI Accession Number(s) |
|---|---|---|
| KIF2C | 11004 | NM_001297656; XM_011540541; NM_001297657; XM_011540540; NM_006845; NM_001297655 |
| ST8SIA2 | 8128 | NM_006011; NM_001330416; XM_017022642 |
| SFRP1 | 6422 | NM_003012 |
| SPAG4 | 6676 | XM_011529009; NM_003116; XM_005260520; NM_001317931 |
| CDKN2A | 1029 | XR_929159; XM_011517676; XM_011517675; NM_001363763; NM_001195132; NM_058195; NM_000077; NM_058196; NM_058197; XM_005251343 |
| SIGLEC8 | 27181 | XM_011526734; NM_014442; NM_001363548 |
| SLC14A2 | 8170 | XM_017026016; NM_007163; NM_001242692; XM_024451271; NM_001371319; XM_024451270 |
| PLA2G7 | 7941 | NM_001168357; XR_001743639; XM_005249408; NM_005084; XR_002956305 |
| KCNN1 | 3780 | NM_001386974; NM_001386976; NR_170373; NM_001386975; NM_001386977; NM_002248; XM_011528004; NR_170374 |
| CA8 | 767 | NM_001321837; NM_001321838; XM_011517587; XM_011517588; NM_001321839; NM_004056; NR_135821; XM_017013818 |
| KLK6 | 5653 | XM_024451611; NM_001319949; NM_001012964; NM_001319948; NM_001012965; NM_002774 |
| CA9 | 768 | XR_428428; NM_001216; XR_001746374 |
| | Squamous_Cell_Carcinoma | |
| TMPRSS11D | 9407 | XM_005265710; XM_017008851; NM_004262 |
| SPRR1B | 6699 | NM_003125 |
| SERPINB3 | 6317 | NM_006919 |
| DSG3 | 1830 | XM_011525850; NM_001944 |
| ADH7 | 131 | NM_001166504; NM_000673 |
| S100A12 | 6283 | NM_005621 |
| SPRR1A | 6698 | NM_005987; NM_001199828 |
| KRT1 | 3848 | NM_006121 |
| SERPINB13 | 5275 | NM_001348267; XM_011526029; NM_001348268; NM_012397; NM_001348269; NM_001307923; NM_001348270 |
| KRT6A | 3853 | NM_005554 |
| CRNN | 49860 | NM_016190 |
| FOXE1 | 2304 | NM_004473 |
| SFTPB | 6439 | XM_005264487; NM_198843; XM_005264488; NM_000542; NM_001367281; XM_005264490 |
| CALML3 | 810 | NM_005185 |
| CRCT1 | 54544 | NM_019060; XM_011509656 |
| SFN | 2810 | NM_006142 |
| TP63 | 8626 | NM_001114978; NM_001329144; NM_001329146; NM_001329964; NM_001329145; NM_003722; NM_001114979; NM_001114982; NM_001329149; NM_001114980; NM_001114981; NM_001329150; NM_001329148 |
| SFTPA2 | 729238 | XM_011540124; XM_005270132; NM_001320813; NM_001320814; XM_017016608; XM_011540125; NM_001098668; XM_005270128 |
| FABP5 | 2171 | NM_001444 |
| KRT5 | 3852 | NM_000424 |
| GPR87 | 53836 | NM_023915 |
| CKM | 1158 | NM_001824 |
| MYL2 | 4633 | NM_000432 |
| SOX2 | 6657 | NM_003106 |
| MYL1 | 4632 | NM_079422; NM_079420 |

-continued

| Gene | NCBI Gene ID | NCBI Accession Number(s) |
|---|---|---|
| IRX4 | 50805 | NM_016358; NM_001278633; NM_001278632; NM_001278635; NM_001278634 |
| NKX2-1 | 7080 | NM_001079668; NM_003317 |
| KRT20 | 54474 | NM_019010 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| PLA2G3 | 50487 | XM_011530205; XR_937865; XM_011530204; NM_015715 |
| FLG | 2312 | NM_002016 |
| SFTPD | 6441 | XM_011540087; NM_003019; XM_011540088 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SPINK1 | 6690 | NM_003122; NM_001379610; NM_001354966 |
| NTS | 4922 | NM_006183 |
| MMP12 | 4321 | NM_002426 |
| ALDH3B2 | 222 | NM_001354345; NM_001393400; NM_001393402; ; NM_001393401; NM_000695; NM_001031615 |
| HNF1B | 6928 | XM_011525161; NM_001165923; NM_001304286; XM_011525163; NM_000458; XM_011525162; NM_006481; XM_011525164; XM_011525160 |
| UPK1B | 7348 | NM_006952 |
| GJB1 | 2705 | NM_000166; XM_011530907; NM_001097642 |
| FABP4 | 2167 | NM_001442 |
| CTSV | 1515 | NM_001201575; NM_001333 |
| HOXD11 | 3237 | NM_021192 |
| CLDN18 | 51208 | NM_001002026; NM_016369 |
| PITX1 | 5307 | NM_002653 |
| LIPF | 8513 | NM_004190; NM_001198829; NM_001198830; NM_001198828; XM_011540311 |
| FZD10 | 11211 | NM_007197 |
| CYP4B1 | 1580 | XM_011540833; NR_135003; XM_011540832; NM_000779; NM_001319161; NM_001319163; NM_001099772; XM_017000466; NM_001319162; XR_946559 |
| TCN1 | 6947 | NM_001062 |
| CLDN3 | 1365 | NM_001306 |
| MYOT | 9499 | XM_017010060; XM_017010061; NM_001300911; NM_001135940; XM_017010062; NM_006790 |
| LAMC2 | 3918 | NM_005562; NM_018891; XM_017001273 |
| SCNN1B | 6338 | XM_017023526; XM_011545913; XM_011545914; XM_017023525; NM_000336 |

-continued

| Gene | NCBI Gene ID | NCBI Accession Number(s) |
|---|---|---|
| DES | 1674 | NM_001927; NM_001382708; NM_001382710; NM_001382713; NM_001382709; NM_001382711; NM_001382712 |
| CSF3 | 1440 | NR_168489; NR_168491; NM_000759; NM_172220; NM_001178147; NM_172219; NR_168490; NR_033662 |
| HMGCS2 | 3158 | NM_001166107; XM_011541313; NM_005518 |
| AQP4 | 361 | NM_001317387; NM_001364287; NM_001364286; NM_001317384; XM_011525942; NM_001650; NM_001364289; NM_004028 |
| TMC5 | 79838 | NM_001261841; NM_024780; NM_001308161; NM_001105248; NM_001105249 |
| SLC52A1 | 55065 | XM_011523951; NM_001104577; NM_017986 |
| DMBT1 | 1755 | XM_011539390; XM_011539391; XM_011539407; XM_011539408; NM_007329; XM_006717660; XM_006717665; XM_011539402; XM_024447854; XM_011539392; XM_011539393; XM_011539400; XM_011539403; XM_011539405; XM_011539413; XM_017015798; NM_001320644; NM_004406; XM_011539394; XM_011539409; XM_011539415; NM_017579; XM_011539389; XM_011539395; XM_011539396; XM_011539399; XM_011539401; XM_011539410; XM_011539414; NM_001377530; XM_011539398; XM_011539411 |
| SLC34A2 | 10568 | NM_001177999; NM_006424; NM_001177998 |
| GABRQ | 55879 | NM_018558; XM_011531184 |
| PRSS3 | 5646 | NM_007343; NM_001197097; NM_002771; XM_011517965; NM_001197098 |
| SLC4A4 | 8671 | XM_024454267; XM_024454271; XM_024454272; NM_001098484; XM_024454270; NM_003759; XM_017008793; XM_024454268; NM_001134742; XM_024454269; XM_011532390; XM_017008792 |
| COX6A2 | 1339 | NM_005205 |
| SERPINA5 | 5104 | NM_000624 |
| SDC1 | 6382 | NM_001006946; XM_005262620; XM_005262621; NM_002997; XM_005262622 |
| ENDOU | 8909 | NM_001172439; NM_006025; NM_001172440 |
| UPKIA | 11045 | NM_007000; NM_001281443 |
| NME5 | 8382 | XM_024446227; NM_003551; XM_005272099; XM_024446228; XM_017009945 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| HAND1 | 9421 | NM_004821; XM_005268531 |
| CRH | 1392 | NM_000756 |
| TFAP2A | 7020 | NM_001032280; XM_006715175; NM_001042425; XM_017011232; XM_011514833; NM_001372066; NM_003220 |
| COL9A1 | 1297 | NM_001851; NR_165185; NM_078485; XM_017010246; XM_011535429; XM_017010247; NM_001377289; NM_001377290; NM_001377291 |
| ATP10B | 23120 | XM_011534472; XM_017009253; NM_001366652; NM_001366658; XM_011534468; NM_001366653; NM_001366654; NM_001366655; NM_001366656; NM_025153; NM_001366657; XM_017009252; XM_011534469 |
| ALDOB | 229 | NM_000035 |
| AHNAK2 | 113146 | NM_138420; XM_024449463; NM_001350929 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| EVX1 | 2128 | NM_001304519; NM_001304520; NM_001989 |
| CLDN4 | 1364 | NM_001305 |
| NEB | 4703 | XM_005246590; XM_005246594; XM_005246602; XM_005246611; XM_017004178; XM_017004179; XM_017004180; NM_001164508; XM_005246603; XM_005246617; XM_006712542; XM_017004185; NM_001164507; NM_001271208; XM_005246593; XM_005246598; XM_005246606; XM_005246610; XM_017004177; XM_017004184; NM_004543; XM_005246592; XM_005246599; XM_005246601; XM_005246616; XM_017004181; XM_005246604; XM_005246608; XM_017004182; XM_017004183; XM_005246591; XM_005246596; XM_005246597; XM_006712541; XM_011511225; XM_011511226; |

-continued

| Gene | NCBI Gene ID | NCBI Accession Number(s) |
|---|---|---|
| | | XM_005246613; XM_005246612; XM_005246615; XM_011511227 |
| LRP2 | 4036 | XM_011511183; NM_004525; XM_011511184 |
| DLX2 | 1746 | NM_004405 |
| GRIK3 | 2899 | NM_000831 |
| TBX1 | 6899 | NM_005992; NM_080646; XM_017028928; XM_006724312; XM_017028926; NM_001379200; XM_017028925; XM_017028927; NM_080647 |
| XDH | 7498 | NM_000379; XM_011533096; XM_011533095 |
| DLX6 | 1750 | NM_005222 |
| ADH1C | 126 | NM_000669; NR_133005 |
| HKDC1 | 80201 | NM_025130; XR_001747209; XM_011540195 |
| MFAP5 | 8076 | NM_001297709; NR_123733; NR_123734; NM_001297711; NM_003480; NM_001297710; NM_001297712 |
| DNAJC22 | 79962 | NM_001304944; NM_024902; XM_005269157; XM_005269155; XM_005269156 |
| HNF4G | 3174 | NM_001330561; XM_017013373; XM_017013375; XM_017013374; XM_017013376; NM_004133 |
| KCNB1 | 3745 | XM_011528799; XM_006723784; NM_004975 |
| ACTG2 | 72 | NM_001199893; NM_001615 |
| SSX1 | 6756 | NM_001278691; NM_005635 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| FAM107A | 11170 | NM_001076778; NM_007177; NM_001282713; NM_001282714 |
| SEMA3G | 56920 | XM_024453642; NM_020163 |
| FIGF | 2277 | NM_004469 |
| TCF21 | 6943 | NM_003206; NM_198392 |
| FMO2 | 2327 | NM_001460; NR_160266; XR_921761; NM_001365900; XR_001737072; NM_001301347 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| AOC3 | 8639 | XR_934584; NM_001277732; NM_003734; NR_102422; XM_011525419; XR_001752673; XM_011525420; XM_024451015; NM_001277731 |
| ADH1B | 125 | NM_001286650; NM_000668 |
| GDF10 | 2662 | NM_004962 |
| MYOC | 4653 | NM_000261 |
| SOX17 | 64321 | NM_022454 |
| FHL5 | 9457 | NM_001170807; NM_001322466; NM_001322467; NM_020482 |
| PDK4 | 5166 | NM_002612 |
| CCL23 | 6368 | NM_005064; XR_429910; NM_145898 |
| MMP11 | 4320 | NM_005940; NR_133013 |
| HBB | 3043 | NM_000518 |
| HOXA10 | 3206 | NR_037939; NM_153715; NM_018951 |

-continued

| Gene | NCBI Gene ID | NCBI Accession Number(s) |
|---|---|---|
| MYBL2 | 4605 | NM_002466; NM_001278610 |
| UBE2C | 11065 | NM_001281742; NM_001281741; NM_181802; NM_181803; NR_104036; NR_104037; NM_007019; NM_181800; NM_181801; NM_181799 |
| NPY1R | 4886 | NM_000909; XM_005263031; XM_011532010 |
| TUBB3 | 10381 | NM_006086; NM_001197181 |
| ORC6 | 23594 | NR_037620; NM_014321; XM_011522978 |
| GRIN2D | 2906 | XM_011526872; NM_000836 |
| PRR4 | 11272 | NM_001098538; NM_007244 |
| COL10A1 | 1300 | XM_011535432; NM_000493; XM_011535433; XM_017010248; XM_006715333 |
| CDKN2A | 1029 | XR_929159; XM_011517676; XM_011517675; NM_001363763; NM_001195132; NM_058195; NM_000077; NM_058196; NM_058197; XM_005251343 |
| FOLR1 | 2348 | NM_000802; NM_016729; NM_016730; NM_016725; NM_016724 |
| ONECUT2 | 9480 | NM_004852 |
| MMP9 | 4318 | NM_004994 |
| HOXA11 | 3207 | NM_005523 |
| HOXB13 | 10481 | NM_006361 |
| CST1 | 1469 | NM_001898 |
| SYT12 | 91683 | XM_011545346; XM_011545347; NM_177963; XM_017018547; NM_001177880; NM_001318775; XM_017018548; XM_006718737; XM_024448766; NM_001318773 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| NXPH4 | 11247 | XM_017018747; NM_007224 |
| CXCL13 | 10563 | NM_001371558; NM_006419 |
| CDX2 | 1045 | XM_011534876; NM_001354700; XM_011534879; XM_011534875; XM_011534878; NM_001265 |
| COL11A1 | 1301 | XM_017000337; XM_017000335; XM_017000336; NR_134980; NM_080629; XM_017000334; NM_001190709; NM_001854; NM_080630 |
| RAB3B | 5865 | XM_017001958; NM_002867 |
| JPH3 | 57338 | NM_001271604; NR_073379; NM_001271605; NM_020655 |
| Lung_Adenocarcinoma | | |
| SFTPA2 | 729238 | XM_011540124; XM_005270132; NM_001320813; NM_001320814; XM_017016608; XM_011540125; NM_001098668; XM_005270128 |
| BPIFA1 | 51297 | NM_130852; NM_001243193; NM_016583 |
| LGSN | 51557 | XM_017010931; XM_017010929; XM_011535889; XM_011535892; NM_016571; XM_017010930; NM_001143940 |
| SCGB1A1 | 7356 | NM_003357 |
| NKX2-1 | 7080 | NM_001079668; NM_003317 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; |

| Gene | NCBI Gene ID | NCBI Accession Number(s) |
|---|---|---|
| | | NM_003018 |
| SFTPB | 6439 | XM_005264487; NM_198843; XM_005264488; NM_000542; NM_001367281; XM_005264490 |
| C4BPA | 722 | XM_005273252; NM_000715; XM_005273251 |
| CEACAM6 | 4680 | NM_002483; XM_011526990 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SERPINB13 | 5275 | NM_001348267; XM_011526029; NM_001348268; NM_012397; NM_001348269; NM_001307923; NM_001348270 |
| SPRR1A | 6698 | NM_005987; NM_001199828 |
| HAND2 | 9464 | NM_021973 |
| TMC5 | 79838 | NM_001261841; NM_024780; NM_001308161; NM_001105248; NM_001105249 |
| TSPAN8 | 7103 | NM_001369760; NM_004616; XM_006719583 |
| SPDEF | 25803 | NM_001252294; XM_005248988; NM_012391; XM_011514457 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| CP | 1356 | XM_006713500; XM_006713501; XM_017005735; XM_017005734; XM_006713499; XM_011512435; XR_427361; NM_000096; NR_046371 |
| GCNT3 | 9245 | NM_004751 |
| CLDN8 | 9073 | NM_199328; NM_012132 |
| CARTPT | 9607 | NM_004291 |
| FOXA1 | 3169 | NM_004496; XM_017021246 |
| EDN3 | 1908 | NM_207034; XM_024451847; NM_207032; XR_002958461; XR_002958462; XR_936513; NM_001302455; NM_207033; XM_006723734; XM_011528655; XM_024451848; NM_000114; XM_005260312; XM_005260313; NM_001302456 |
| CCL13 | 6357 | NM_005408 |
| DNAH2 | 146754 | XM_017024219; XM_024450606; XM_024450608; XM_024450609; XM_011523663; XM_024450604; XM_024450605; XM_024450607; NM_001303270; NM_020877; XM_011523667; XM_024450610; XM_011523670 |
| EMX2 | 2018 | NM_004098; NM_001165924 |
| CDHR1 | 92211 | XM_011540338; NM_033100; NM_001171971; XM_011540340; XM_011540337; XM_011540339 |
| RNF186 | 54546 | NM_019062 |
| TBX4 | 9496 | XM_011525490; XM_011525491; NM_001321120; XM_011525495; NM_018488 |
| LAMB3 | 3914 | XM_005273124; NM_001127641; XM_017001272; NM_000228; NM_001017402 |

| Gene | NCBI Gene ID | NCBI Accession Number(s) |
|---|---|---|
| S100A7 | 6278 | NM_002963 |
| PLA2G2A | 5320 | NM_001161728; NM_000300; NM_001161729; NM_001161727; NM_001395463 |
| KCNG1 | 3755 | XM_011528800; XM_011528802; XM_011528803; XM_011528805; NM_172318; NM_002237; XM_011528801; XM_011528804; XM_011528806; XM_006723785 |
| KRT5 | 3852 | NM_000424 |
| BARX1 | 56033 | NM_021570 |
| SLC44A4 | 80736 | NM_001178045; NM_001178044; NM_025257 |
| MPPED2 | 744 | NM_001377952; NM_001145399; NR_165347; XM_005253111; NR_165336; NR_165343; NR_165339; NR_165340; NR_165345; XM_024448676; NM_001377954; XM_005253114; NM_001377953; NR_165337; NR_165344; NR_165348; XM_017018231; NR_165346; NM_001377955; NM_001377956; NM_001584; NR_165338; NR_165341; NR_165342 |
| XDH | 7498 | NM_000379; XM_011533096; XM_011533095 |
| CCL25 | 6370 | NM_001394634; NM_001394635; NM_001394638; NM_005624; NM_148888; NM_001394636; NM_001201359; NM_001394637 |
| S100A1 | 6271 | NM_006271 |
| ACTA1 | 58 | NM_001100 |
| HR | 55806 | XM_006716367; NM_005144; XM_005273569; NM_018411 |
| DLL3 | 10683 | NM_016941; NM_203486 |
| KRT13 | 3860 | NM_153490; NM_002274 |
| CBLC | 23624 | XM_011526690; XM_011526688; XR_935783; XM_005258696; XR_243917; XM_011526689; NM_001130852; NM_012116 |
| FAM107A | 11170 | NM_001076778; NM_007177; NM_001282713; NM_001282714 |
| TCF21 | 6943 | NM_003206; NM_198392 |
| FCN3 | 8547 | NM_173452; NM_003665 |
| FABP4 | 2167 | NM_001442 |
| GRIA1 | 2890 | NM_001114183; NM_001258022; NM_001258023; NM_001364166; XM_017009392; NR_157093; NM_000827; NM_001258019; NM_001258020; NM_001364165; NM_001258021; NR_047578; NM_001364167 |
| ALAS2 | 212 | NM_001037968; NM_001037967; NM_000032; NM_001037969 |
| TFAP2A | 7020 | NM_001032280; XM_006715175; NM_001042425; XM_017011232; XM_011514833; NM_001372066; NM_003220 |
| PITX1 | 5307 | NM_002653 |
| IGF2BP3 | 10643 | XM_011515092; NM_006547; XM_011515089; XM_006715639; XM_011515090; XM_011515091; XM_011515093 |
| RASAL1 | 8437 | XR_002957386; NM_001193521; NM_001394081; NM_001394082; XM_005253950; NM_001394084; NM_001394087; NM_004658; XM_017020030; XM_017020031; XM_006719642; XR_001748903; XM_006719641; NM_001301202; NM_001394083; XM_011538854; XM_017020029; NM_001394089; XR_001748902; NM_001193520; NM_001394085; NM_001394086; NM_001394088 |

-continued

| Gene | NCBI Gene ID | NCBI Accession Number(s) |
|---|---|---|
| MMP11 | 4320 | NM_005940; NR_133013 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| NXPH4 | 11247 | XM_017018747; NM_007224 |
| CXCL14 | 9547 | NM_004887 |
| | Prostate_Adenocarcinoma | |
| RNF128 | 79589 | NM_024539; NM_194463 |
| PRM2 | 5620 | NM_001286358; NR_104428; NM_002762; NM_001286356; NM_001286359; NM_001286357 |
| CENPF | 1063 | XM_017000086; NM_016343; XM_011509082 |
| DES | 1674 | NM_001927; NM_001382708; NM_001382710; NM_001382713; NM_001382709; NM_001382711; NM_001382712 |
| NKX3-1 | 4824 | NM_001256339; NR_046072; NM_006167 |
| CGREF1 | 10669 | NM_001166239; NM_006569; NM_001301324; NM_001166241; NM_001166240 |
| KLK2 | 3817 | NM_005551; NR_045762; NM_001002231; NM_001002232; NM_001256080; NR_045763 |
| SEMG1 | 6406 | NM_198139; NM_003007 |
| ASPN | 54829 | NM_001193335; NM_017680 |
| DEPDC1 | 55635 | NM_001114120; NM_017779 |
| AMACR | 23600 | NM_203382; NM_001167597; NM_001167598; NM_014324; NM_001167596; NM_001167595 |
| COL6A1 | 1291 | NM_001848 |
| ONECUT2 | 9480 | NM_004852 |
| COL10A1 | 1300 | XM_011535432; NM_000493; XM_011535433; XM_017010248; XM_006715333 |
| TRPM8 | 79054 | XM_017004891; NM_024080; XM_011511810; XM_024453132; XM_024453134; XM_024453133 |
| ATP8A2 | 51761 | XM_011535103; XM_011535113; XM_005266419; XM_024449369; XM_011535109; NM_016529; XM_011535104; XM_017020626; NM_001313741; XM_017020625; XM_011535106; XM_011535107 |
| PGC | 5225 | NM_002630; NM_001166424 |
| GDPD3 | 79153 | NM_024307 |
| MKI67 | 4288 | NM_002417; NM_001145966; XM_006717864; XM_011539818 |
| ZIC1 | 7545 | NM_003412 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| APOC1 | 341 | NM_001645; NM_001321066; NM_001379687; NM_001321065 |
| PLP2 | 5355 | NM_002668 |
| HOXB13 | 10481 | NM_006361 |
| DLX2 | 1746 | NM_004405 |
| TDRD1 | 56165 | XM_024448081; NM_001385365; NM_001365891; NM_001385366; NM_001385372; NM_001395205; XM_011539959; XM_017016415; NM_001385363; NM_001385368; XM_011539960; NM_001385364; XM_011539964; XM_011539962; XM_011539961; NM_001385367; NM_001385369; NM_001385371; NM_198795; NM_031278; XM_017016414; NM_001385370 |
| SCN1A | 6323 | NM_001353960; NM_001202435; NM_001353951; NM_001353952; NM_001353958; NM_001353950; NM_001353957; NR_148667; NM_001353949; NM_001353954; XR_001738884; NM_001353955; NM_001353961; NM_001165963; NM_001165964; NM_001353948; NM_006920; XR_001738883 |
| TRPC4 | 7223 | NM_001354806; XM_011535206; NM_016179; NM_003306; NM_001135958; NM_001135957; NM_001372055; XM_017020723; NM_001135956; NM_001354799; NM_001135955 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| ZWINT | 11130 | XR_428692; NM_007057; NM_001005413; XM_017015605; XM_024447784; NM_032997; NM_001005414 |
| KIF4A | 24137 | NM_012310 |
| CCNJL | 79616 | NM_001308173; NM_024565; NR_131769; XM_011534646; XM_017009847; XM_006714917; XR_427810; XM_011534647; XM_017009848; XR_427811 |
| PAGE4 | 9506 | NM_001318877; NM_007003 |
| TSPYL2 | 64061 | XM_006724592; XM_017029727; NM_022117; XR_001755719; XM_017029726 |
| MMP9 | 4318 | NM_004994 |
| HOXD13 | 3239 | XM_011511068; NM_000523; XM_011511069 |
| TPX2 | 22974 | XM_011528697; XM_011528699; NM_012112; XM_011528700 |
| FHL5 | 9457 | NM_001170807; NM_001322466; NM_001322467; NM_020482 |
| GRIA3 | 2892 | NM_007325; NM_181894; NM_000828; NM_001256743 |
| IFI6 | 2537 | NM_002038; XM_024446207; NM_022873; NM_022872 |
| RPL4 | 6124 | NM_000968 |
| ISL1 | 3670 | XM_011543380; NM_002202 |
| HPN | 3249 | NM_002151; NM_182983; XM_017026732; NM_001384133; XM_017026731; NM_001375441 |
| SRD5A2 | 6716 | XM_011533069; NM_000348; XM_011533072 |
| ACPP | 55 | NM_001099; XM_011512946; NM_001134194; XM_011512947; NM_001292037 |
| GUCY2C | 2984 | NM_004963; XM_011520631 |
| HOXC6 | 3223 | NM_153693; NM_004503 |
| LILRB4 | 11006 | NM_001278429; NM_001394939; XM_017026215; NM_001394934; NM_006847; NM_001278428; XM_017026216; NM_001394935; NM_001081438; NM_001394938; XR_002958246; NM_001278426; NM_001394933; NM_001394937; |

-continued

| Gene | NCBI Gene ID | NCBI Accession Number(s) |
|---|---|---|
| | | NM_001278427; NM_001278430; NM_001394936 |
| MSMB | 4477 | NM_138634; NM_002443 |
| STAR | 6770 | NM_001007243; NM_000349 |
| KLK3 | 354 | NM_001030050; NM_001030047; NM_145864; NM_001030049; NM_001030048; NM_001648 |
| FOXF1 | 2294 | NM_001451 |
| | Urinary_Bladder_Urothelial_Carcinoma | |
| UPK2 | 7379 | NM_006760 |
| PLA2G2F | 64600 | NM_022819; NM_001360869; XM_011541955; XM_011541956 |
| CYP1A1 | 1543 | NM_001319216; NM_001319217; NM_000499 |
| S100A2 | 6273 | NM_001366407; NM_001366406; NM_005978 |
| IVL | 3713 | NM_005547 |
| VGLL1 | 51442 | NM_016267 |
| UPK3A | 7380 | NM_006953; NM_001167574 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SERPINB4 | 6318 | NM_175041; NM_002974; XM_011526138 |
| UPK1B | 7348 | NM_006952 |
| KRT20 | 54474 | NM_019010 |
| TMEM40 | 55287 | NM_001284408; NM_018306; XM_011533937; NM_001284406; NM_001284407 |
| BHMT | 635 | NM_001713 |
| GATA3 | 2625 | XM_005252443; NM_002051; XM_005252442; NM_001002295 |
| KRT6A | 3853 | NM_005554 |
| MSMB | 4477 | NM_138634; NM_002443 |
| SLC14A1 | 6563 | XM_005258333; XM_024451238; XR_001753266; NM_001146037; XM_005258329; NM_001146036; NM_001308278; NM_015865; XM_011526144; NM_001308279; XM_006722526; XM_011526142; NM_001128588 |
| SFTPA2 | 729238 | XM_011540124; XM_005270132; NM_001320813; NM_001320814; XM_017016608; XM_011540125; NM_001098668; XM_005270128 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; |

-continued

| Gene | NCBI Gene ID | NCBI Accession Number(s) |
|---|---|---|
| | | NM_001367842; XM_017018205; NM_006757 |
| OLFM4 | 10562 | NM_006418 |
| ACTC1 | 70 | NM_005159 |
| GJB1 | 2705 | NM_000166; XM_011530907; NM_001097642 |
| AIM1L | 55057 | NM_017977; XM_011541672; XM_011541673; XR_001737260; NM_001039775; XR_946681; XM_005245918 |
| IL9R | 3581 | XM_011545650; XM_017029496; XM_017029499; XM_017030050; XM_017030051; XM_011531155; XM_017029498; XM_017029502; XM_017029505; XM_017030053; XM_017030055; NM_176786; XM_011531156; XM_011545645; XM_011545651; XM_017029495; XM_017029501; XM_017030054; XM_011531152; XM_011545649; XM_017030045; XM_017030046; XM_017030052; XM_017029497; XM_017030049; XM_011531157; XM_011531154; XM_017029500; XM_017029503; XM_017030044; XM_017030047; NM_002186; XM_011531151; XM_011545646; XM_011545652; XM_017029504; XM_017029506; XM_017030048 |
| NRAP | 4892 | XM_005269867; NM_006175; NM_001322945; NM_198060; XM_005269865; XM_011539832; XM_024448029; NM_001261463; XM_006717870; XM_005269864 |
| SLC5A1 | 6523 | NM_000343; XM_011530331; NM_001256314 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| CASQ1 | 844 | NM_001231 |
| ACTG2 | 72 | NM_001199893; NM_001615 |
| POU3F3 | 5455 | NM_006236 |
| UNC93A | 54346 | XM_011535908; NM_001143947; XM_011535905; XM_011535907; NM_018974; XM_017010958; XM_011535906 |
| TRPA1 | 8989 | XM_011517624; NM_007332; XM_011517625; XM_017013946 |
| KCNIP1 | 30820 | NM_001034837; NM_014592; NM_001034838; NM_001278340; XM_017009407; XM_017009408; NM_001278339 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MSLN | 10232 | NM_001177355; NM_005823; NM_013404 |
| COX6A2 | 1339 | NM_005205 |
| CCL11 | 6356 | NM_002986 |
| IRX4 | 50805 | NM_016358; NM_001278633; NM_001278632; NM_001278635; NM_001278634 |
| REG1A | 5967 | NM_002909 |
| MAGEA11 | 4110 | XM_017029522; NM_001011544; NM_005366; XM_011531164 |
| GAL3ST1 | 9514 | XM_017029096; XM_024452304; NM_001318107; NM_001318111; |

-continued

| Gene | NCBI Gene ID | NCBI Accession Number(s) |
|---|---|---|
| | | NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| HLF | 3131 | NM_002126; XM_011524705; XR_002957996; NM_001330375; XM_005257269 |
| HAND1 | 9421 | NM_004821; XM_005268531 |
| HPN | 3249 | NM_002151; NM_182983; XM_017026732; NM_001384133; XM_017026731; NM_001375441 |
| SLC34A2 | 10568 | NM_001177999; NM_006424; NM_001177998 |
| TFF3 | 7033 | NM_003226 |
| PNMAL1 | 55228 | NM_001103149; NM_018215; XM_011527067 |
| PITX2 | 5308 | NM_001204397; NM_153427; XM_024454090; NM_000325; NM_001204398; NM_001204399; NM_153426 |
| REG3A | 5068 | NM_138938; NM_002580; NM_138937 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| PENK | 5179 | NM_006211; NM_001135690 |
| CDHR2 | 54825 | NM_001171976; NM_017675 |
| MMP11 | 4320 | NM_005940; NR_133013 |
| CDH4 | 1002 | NM_001252339; NM_001794; NM_001252338 |
| FOXA2 | 3170 | NM_021784; NM_153675 |
| HOXB8 | 3218 | NM_024016; XM_005257286; XM_017024564 |
| GABRA3 | 2556 | NM_000808; XM_006724811 |
| SLC47A1 | 55244 | NM_018242 |
| F7 | 2155 | XM_011537476; XM_011537475; NM_001267554; XM_011537474; NR_051961; XM_006719963; NM_019616; NM_000131 |
| S100A1 | 6271 | NM_006271 |
| DNAJC22 | 79962 | NM_001304944; NM_024902; XM_005269157; XM_005269155; XM_005269156 |
| NPR3 | 4883 | NM_001363652; NM_001364460; NM_000908; XM_011514047; XM_011514049; XM_017009492; NM_001204375; NM_001364458; NM_024563; XM_011514050; NM_001204376 |
| FOXE1 | 2304 | NM_004473 |
| ALS2CL | 259173 | XR_427263; XR_940409; XR_940410; NR_033815; XR_001740091; XR_001740094; XR_001740095; XM_011533572; XR_001740090; XR_940406; XR_940407; XR_940408; XR_940412; NM_182774; NM_182775; NR_135622; XR_001740092; XR_001740097; XR_002959507; NM_001190707; XM_005265025; XM_006713093; XR_001740093; NM_147129; XM_006713094; XM_006713091; XR_001740096; XR_940405 |
| ACADL | 33 | NM_001608; XM_005246517; XM_017003955 |

-continued

| Gene | NCBI Gene ID | NCBI Accession Number(s) |
|---|---|---|
| ARSE | 415 | XM_017029526; NM_001369079; NM_001369080; XM_005274521; XM_011545521; NM_000047; XM_005274519; NM_001282628; NM_001282631 |
| AQP5 | 362 | NM_001651; XM_005268838 |
| HOXA11 | 3207 | NM_005523 |
| CYP2W1 | 54905 | NM_017781; XM_011515440; XM_011515441 |
| KBTBD11 | 9920 | XM_017014115; XM_011534772; XM_017014117; XM_017014114; XM_017014116; XM_011534771; NM_014867 |
| TCF21 | 6943 | NM_003206; NM_198392 |
| ADAMTSL3 | 57188 | NM_207517; XM_024450000; XR_931873; XM_017022435; XM_011521822; XM_011521823; XM_017022434; NM_001301110; XM_011521825; XM_011521824 |
| GLP2R | 9340 | XM_011524077; NM_004246; XM_017025340; XM_005256861; XM_017025339; XM_017025341 |
| CFD | 1675 | NM_001317335; NM_001928 |
| FAM107A | 11170 | NM_001076778; NM_007177; NM_001282713; NM_001282714 |
| TPPP | 11076 | XM_024454346; XM_005248237; XM_017008993; NM_007030 |
| FOXF1 | 2294 | NM_001451 |
| HSPB6 | 126393 | NM_144617 |
| P2RX1 | 5023 | XM_006721529; XM_011523898; XR_934029; NM_002558; XM_011523896; XM_011523897; XM_011523899; XM_011523900; XR_934030 |
| TBX5 | 6910 | NM_181486; NM_080717; NM_000192; XM_017019912; NM_080718 |
| SGCD | 6444 | NM_000337; NM_172244; XM_005265967; XM_011534621; XM_017009723; XM_005265966; XM_017009724; NM_001128209 |
| ESM1 | 11082 | NM_001135604; NM_007036 |
| DPT | 1805 | NM_001937 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| SPP1 | 6696 | NM_001251829; NM_001040060; NM_001251830; NM_000582; NM_001040058 |
| CMA1 | 1215 | NM_001836; NM_001308083 |
| FBN2 | 2201 | NM_001999; XM_017009228 |
| MSI1 | 4440 | XM_011538362; XM_011538361; XM_011538366; XM_011538365; XM_011538370; NM_002442; XM_011538364; XM_011538371; XM_006719403; XM_006719404; XM_011538363; XM_011538368 |
| TERT | 7015 | NR_149162; NM_198255; NM_198253; NR_149163; NM_001193376; NM_198254 |
| VGF | 7425 | NM_003378; XM_011516549; XM_005250561 |
| CLDN9 | 9080 | NM_020982 |
| FOLR1 | 2348 | NM_000802; NM_016729; NM_016730; NM_016725; NM_016724 |
| | Melanoma | |
| PAX3 | 5077 | NM_181457; NM_000438; NM_181459; NM_181460; NM_001127366; NM_013942; NM_181461; NM_181458 |

-continued

| Gene | NCBI Gene ID | NCBI Accession Number(s) |
|---|---|---|
| IRF4 | 3662 | NM_001195286; NR_046000; NR_036585; XM_006715090; NM_002460 |
| TYR | 7299 | XM_011542970; NM_000372 |
| GAPDHS | 26330 | NM_014364 |
| PMEL | 6490 | NM_001200054; NM_001200053; NM_001320121; NM_001384361; NM_001320122; NM_006928 |
| TYRP1 | 7306 | NM_000550; XR_001746372 |
| ALX1 | 8092 | XM_011538782; NM_006982 |
| MLANA | 2315 | NM_005511 |
| CDH19 | 28513 | XM_011525931.3; XM_017025711.2; XM_011525932.1 |
| SOX10 | 6663 | NM_006941 |
| MIA | 8190 | NM_006533; NM_001202553 |
| PLP1 | 5354 | NM_001128834; NM_000533; NM_001305004; NM_199478 |
| SLC6A15 | 55117 | XM_011538525; NM_018057; NM_001146335; NM_182767 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| KRT2 | 3849 | NM_000423 |
| MFSD12 | 126321 | XM_017026288; XM_011527684; NM_021731; NM_174983; NM_001287529; XM_005259490; NM_001042680; XM_006722647 |
| APOD | 347 | NM_001647 |
| KCNK1 | 3775 | NM_002245; XM_011544184 |
| EFHD1 | 80303 | NM_001243252; NM_001308395; NM_025202 |
| CRCT1 | 54544 | NM_019060; XM_011509656 |
| KRT8 | 390601, 149501, 3856 | NM_001256293; NM_002273 |
| GPM6B | 2824 | NM_001001996; XM_017029432; NM_001318729; NM_005278; NM_001001995; XM_005274489; XM_011545497; NM_001001994 |
| CNTNAP2 | 26047 | XM_017011950; NM_014141 |
| STEAP1B | 256227 | NM_207342; NM_001382447; NM_001164460 |
| RGN | 9104 | XM_024452477; XM_006724568; XM_017029954; NM_004683; NM_001282848; NM_152869; NM_001282849; XM_006724567 |
| FA2H | 79152 | XM_011523319; XM_011523317; NM_024306 |
| TRPV2 | 51393 | XM_011523922; XM_017024730; XM_011523925; XM_017024732; XM_005256677; XM_017024731; XM_006721541; XM_005256678; XM_011523923; NM_016113; XM_005256676; XM_006721543 |
| CLDN7 | 1366 | NM_001307; NM_001185022; NM_001185023 |
| SPINT2 | 10653 | NM_001166103; NM_021102 |
| CD24 | 100133941 | NM_001291739; NR_117090; NR_117089; NM_001291738; NM_001291737; NM_013230; XM_024446293; NM_001359084 |
| HNF1B | 6928 | XM_011525161; NM_001165923; NM_001304286; XM_011525163; NM_000458; XM_011525162; NM_006481; XM_011525164; XM_011525160 |
| SUSD4 | 55061 | XM_011509687; XM_017001584; XM_017001586; XM_017001587; XM_024447937; XM_024447940; XM_005273169; XM_017001588; XM_017001585; XM_024447936; NM_017982; XM_005273172; XM_006711408; XM_011509685; XM_017001583; XM_017001589; NM_001037175 |
| ST8SIA3 | 51046 | NM_015879 |
| GABRE | 2564 | XM_024452360; NM_021990; NM_021984; XM_011531140; XM_017029388; XM_017029389; NM_004961; NM_021987; XM_017029387 |
| PHACTR1 | 221692 | XM_017010452; XM_017010454; XM_017010458; XM_017010465; NM_001322311; NM_001374582; NM_001374583; NM_001374584; NM_001322309; XM_005248934; XM_017010460; NM_001322308; NM_001374581; XM_017010459; XM_017010464; NM_001242648; NM_001322314; XM_017010462; NM_001322312; XM_017010456; XM_017010457; XM_017010466; NM_030948; XM_017010455; NM_001322310; XM_017010469; NM_001322313 |
| ASS1 | 445 | XM_017014729; XM_005272200; XM_011518705; NM_000050; NM_054012 |
| CDS1 | 1040 | XM_017007649; NM_001263; XM_017007650; XM_017007651; XM_005262687; XM_017007648 |
| PLEKHG6 | 55200 | NM_018173; XM_017019555; NM_001384602; NM_001384603; XM_006718985; NM_001384604; NR_169277; XM_011520967; NM_001144857; NM_001384599; NR_169278; NM_001144856; NM_001384598; NM_001384600; NM_001384601 |
| CACNG4 | 27092 | NM_014405 |
| CYTL1 | 54360 | NM_018659; XM_017008299 |
| PITX1 | 5307 | NM_002653 |
| HOXD13 | 3239 | XM_011511068; NM_000523; XM_011511069 |
| CNIH3 | 149111 | NR_136288; NR_136294; NR_136297; NM_152495; NR_136292; NM_001322305; NM_001322303; NR_136293; NR_136296; NR_136295; NR_136287; NM_001322304; NR_136290; NR_136291; NM_001322302; NR_136289 |
| CFB | 629 | NM_001710 |
| MYH7 | 4625 | XM_017021340; NM_000257 |
| CLU | 1191 | NM_001831; NR_045494; NR_038335 |
| SCG5 | 6447 | NM_001144757; NM_001394278; NM_001394279; NM_003020 |
| SH3GL3 | 6457 | XR_001751374; NM_001324184; NM_001324186; XM_017022486; XR_931878; XR_001751372; NR_136712; XR_931880; XR_931882; NM_001301109; NM_001324185; NR_125370; NR_136714; XM_011521892; XR_001751375; XR_931879; NM_001301108; NM_001324183; NM_003027; NR_136713; XM_011521889; XM_011521891; XM_024450017; XR_001751373; XR_002957669; NM_001324182; NM_001324187; NR_136711 |
| RBM47 | 54502 | XM_005248108; XM_017008307; XM_024454098; NM_001371113; XM_005248103; XM_017008306; XM_017008309; XM_017008310; NM_001098634; NM_019027; XM_011513707; XM_005248109; |

-continued

| Gene | NCBI Gene ID | NCBI Accession Number(s) |
|---|---|---|
| | | XM_017008304; XM_017008308; NM_001371114; XM_011513708 |
| FUT6 | 2528 | XM_011527875; NM_000150; NM_001381956; NM_001369504; NM_001381957; NM_001381958; NM_001369502; NM_001381959; NM_001369505; NM_001381955; XM_011527872; NM_001040701 |
| FGFR2 | 2263 | XM_017015924; NM_001144919; XM_006717708; XM_017015925; NM_001144915; NM_001144917; NM_022975; NM_023028; XM_024447890; NM_000141; NM_001144913; NM_001320654; NM_022970; NR_073009; NM_022971; NM_022973; NM_023030; XM_006717710; XM_024447887; XM_024447888; NM_001320658; NM_022976; XM_017015920; NM_001144918; NM_022974; NM_023031; XM_024447889; XM_024447891; XM_024447892; NM_023029; XM_017015921; NM_001144914; NM_001144916; NM_022972 |
| DLX2 | 1746 | NM_004405 |
| LAD1 | 3898 | NM_005558 |
| SPP1 | 6696 | NM_001251829; NM_001040060; NM_001251830; NM_000582; NM_001040058 |
| ADH1B | 125 | NM_001286650; NM_000668 |
| MYL2 | 4633 | NM_000432 |
| ZBTB16 | 7704 | XR_001747955; NM_001354751; XM_017018259; NM_006006; NM_001354752; XM_005271658; XM_024448681; NM_001018011; NM_001354750 |
| CKM | 1158 | NM_001824 |
| FCGR1A | 2209 | NM_001378804; NM_001378805; NM_001378807; NM_001378810; NR_166122; NR_166123; NM_001378809; NM_001378811; NM_001378808; NR_166121; NM_000566; NM_001378806 |
| CCL5 | 6352 | NM_001278736; NM_002985 |
| DBNDD1 | 79007 | NM_001288709; NM_001288708; NM_001371581; NM_001042610; NM_024043 |
| SDS | 10993 | NM_006843 |
| CXCR3 | 2833 | XM_017029435; XM_017029436; NM_001504; NM_001142797; XM_005262256; XM_005262257 |
| MMP27 | 64066 | XM_011542950; XM_017018120; XM_011542948; NM_022122; XM_011542949 |
| TREM2 | 54209 | NM_001271821; NM_018965 |
| CCR5 | 1234 | NM_001100168; NM_001394783; NM_000579 |
| C1QA | 712 | NM_015991; NM_001347465; NM_001347466 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ONECUT2 | 9480 | NM_004852 |
| FAM155B | 27112 | XM_011530908; XM_011530909; NM_015686 |
| DKK1 | 22943 | NM_012242 |
| LOR | 4014 | NM_000427; XM_024447049 |

-continued

| Gene | NCBI Gene ID | NCBI Accession Number(s) |
|---|---|---|
| Liver_Neoplasm | | |
| APCS | 325 | NM_001639 |
| ITIH2 | 3698 | NM_002216 |
| CRP | 1401 | NM_000567; NM_001329058; NM_001382703; NM_001329057 |
| CPB2 | 1361 | XM_017020393; NM_016413; NM_001872; NM_001278541 |
| ITIH1 | 3697 | NM_001166436; NM_002215; NM_001166434; NM_001166435 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| APOC3 | 345 | NM_000040 |
| GC | 2638 | XM_006714177; NM_001204306; NM_001204307; NM_000583 |
| CYP2C8 | 1558 | NM_001198854; NM_001198855; NM_030878; NM_000770; NM_001198853 |
| C8G | 733 | NM_000606; XR_245338 |
| APOA2 | 336 | NM_001643 |
| ALB | 213 | NM_000477 |
| ART4 | 420 | NM_021071; NM_001354646 |
| AGT | 183 | NM_000029; NM_001384479; NM_001382817 |
| PROZ | 8858 | NM_003891; XR_001749709; XR_001749708; XM_017020812; XR_001749707; NM_001256134; XM_017020813 |
| GRIK3 | 2899 | NM_000831 |
| CRABP1 | 1381 | NM_004378 |
| DRD2 | 1813 | XM_017017296; NM_016574; NM_000795 |
| CYP21A2 | 1589 | NM_000500; NM_001128590; XM_024452555; NM_001368143; NM_001368144 |
| DBH | 1621 | NM_000787 |
| L1CAM | 3897 | NM_024003; NM_001278116; NM_001143963; NM_000425 |
| KLK8 | 11202 | NM_007196; NM_144505; NR_104008; NM_144507; NM_144506; NM_001281431 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| SFRP5 | 6425 | NM_003015 |
| GATA4 | 2626 | NM_001308093; NM_002052; NM_001308094; NM_001374273; NM_001374274 |
| MAB21L2 | 10586 | NM_006439 |
| GRIK5 | 2901 | XM_011526870; XM_011526868; XM_011526865; XM_011526867; XM_011526869; XM_011526862; XM_011526871; XM_017026713; NM_002088; XR_935810; NM_001301030 |
| HOXA7 | 3204 | NM_006896 |
| GLB1L2 | 89944 | NM_001370460; NM_001370463; NM_001370461; NM_001370462; NM_138342 |
| PCSK2 | 5126 | NM_002594; NM_001201529; NM_001201528 |
| TERT | 7015 | NR_149162; NM_198255; NM_198253; NR_149163; NM_001193376; NM_198254 |

| Gene | NCBI Gene ID | NCBI Accession Number(s) |
| --- | --- | --- |
| PLP1 | 5354 | NM_001128834; NM_000533; NM_001305004; NM_199478 |
| CXCL14 | 9547 | NM_004887 |
| KRT4 | 3851 | NM_002272 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SLC5A1 | 6523 | NM_000343; XM_011530331; NM_001256314 |
| GPRC5A | 9052 | NM_003979 |
| GPM6B | 2824 | NM_001001996; XM_017029432; NM_001318729; NM_005278; NM_001001995; XM_005274489; XM_011545497; NM_001001994 |
| NNAT | 4826 | NM_001322802; NM_181689; NM_005386 |
| BDH1 | 622 | XM_005269355; XM_017007012; XM_017007013; NM_004051; XM_017007015; XM_017007007; XM_011513067; XM_017007008; XM_017007009; XR_001740229; NM_203314; XM_017007010; NM_203315; XM_005269352; XM_017007011 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| COLEC10 | 10584 | XM_005250756; NM_006438; NM_001324095 |
| GABRD | 2563 | XM_011541194; XM_017000936; NM_000815 |
| GDF2 | 2658 | NM_016204 |
| COL15A1 | 1306 | XM_011518214; NM_001855 |
| S100A12 | 6283 | NM_005621 |
| MDK | 4192 | NM_001012334; XM_011520116; XM_017017764; NM_001270550; NM_001270551; NM_001012333; NM_001270552; NM_002391; NR_073039 |
| PTTG1 | 9232 | XM_024446260; NM_001282382; NM_001282383; NM_004219 |
| ESM1 | 11082 | NM_001135604; NM_007036 |
| DEPDC1 | 55635 | NM_001114120; NM_017779 |
| THBS4 | 7060 | XR_002956176; XM_017009798; NM_001306214; NM_003248; NM_001306213; XM_017009799; NM_001306212 |
| HOXD9 | 3235 | NM_014213 |
| OLFML2B | 25903 | NM_001297713; XM_017000967; NM_001347700; NM_015441; XM_011509398 |
| MMP11 | 4320 | NM_005940; NR_133013 |
| PRSS1 | 5644 | NR_172951; XM_011516411; NR_172947; NM_002769; NR_172948; NR_172949; NR_172950 |
| C1QTNF3 | 114899 | NR_146599; NM_181435; NM_030945 |
| Thyroid_Neoplasm | | |
| TG | 7038 | XM_006716622; XM_017013800; XM_017013793; XM_017013795; XM_017013798; XM_017013796; XM_017013797; XM_017013794; XM_005251038; XM_005251040; NM_003235; XM_017013799; XM_005251042 |

| Gene | NCBI Gene ID | NCBI Accession Number(s) |
| --- | --- | --- |
| DCSTAMP | 81501 | XM_024447289; NM_030788; XM_024447290; NM_001257317; XM_011517324; XM_024447288; XM_011517321 |
| DAPK2 | 23604 | XM_017022049; XM_017022051; NM_001384998; NM_001395289; NM_001395290; NM_001395293; XM_011521413; NM_001384999; NM_001395284; NM_014326; XM_017022043; NM_001395288; NM_001395291; NR_169522; NR_172521; XM_017022046; NM_001384997; NM_001385000; NM_001395286; NM_001395287; XM_011521421; XM_017022044; XM_017022047; XM_017022052; NM_001395285; NM_001395292; XM_017022048; XM_017022050; NM_001395282; NR_169524; XM_011521414; XM_011521415; XM_017022045; NM_001395279; NM_001395283; NR_169523; NM_001363730; NM_001395281 |
| SLC26A4 | 5172 | XM_017012318; XM_005250425; NM_000441; XM_006716025 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| TSHR | 7253 | XM_011537119; XM_005268039; XM_005268037; NM_000369; NM_001142626; XM_006720245; NM_001018036 |
| KCNJ16 | 3773 | XM_006721885; NM_170742; NM_001291625; NM_018658; XM_017024609; NM_001291622; NM_001291623; XM_017024610; NM_001270422; NM_170741; XM_005257337; XM_006721887; XM_011524781; NM_001291624; XM_006721886 |
| NKX2-1 | 7080 | NM_001079668; NM_003317 |
| FOXE1 | 2304 | NM_004473 |
| CLDN16 | 10686 | NM_006580; NM_001378492; NM_001378493 |
| GABRB2 | 2561 | NM_000813; NM_021911; NM_001371727 |
| MATN1 | 4146 | NM_002379 |
| INPP5J | 27124 | NM_001284289; XM_017028772; NM_001284288; NM_001284285; NM_014422; NM_001284286; NM_001284287; XM_011530143; NM_001002837 |
| TOX3 | 27324 | NM_001080430; XM_017023142; NM_001146188; XM_005255892; XM_011523002; XM_024450230 |
| TRPC5 | 7224 | XM_017029774; NM_012471 |
| HHEX | 3087 | NM_002729 |
| PAX8 | 7849 | NM_013992; NM_013953; NM_013952; NM_003466; NM_013951 |
| FOXD3 | 27022 | NM_012183 |
| COL4A3 | 1285 | XM_017003295; XM_005246280; XM_006712245; XM_005246277; XR_241280; XM_011510556; NM_000091; NM_031363; NM_031364; NM_031365; XM_011510555; XR_001738601; NM_031362; NM_031366 |
| S100A5 | 6276 | XM_017002031; NM_001394233; NM_001394234; XM_017002032; |

-continued

| Gene | NCBI Gene ID | NCBI Accession Number(s) |
|---|---|---|
| | | NM_001394232; NM_002962; XM_017002029 |
| GFRA3 | 2676 | NM_001496 |
| NELL1 | 4745 | NM_001288713; NM_006157; NM_201551; NM_001288714 |
| DUSP9 | 1852 | XM_011531123; NM_001395; NM_001318503; XM_011531124 |
| AZGP1 | 563 | NM_001185 |
| BMP8A | 353500 | XM_017001198; XM_006710616; XM_011541381; XM_011541382; XR_946642; XR_946640; XR_946641; NM_181809 |
| LECT1 | 11061 | XM_011534898; XM_011534899; NM_001011705; NM_007015; XM_011534900; XM_011534897 |
| DIO2 | 1734 | NM_001366496; NM_000793; NM_001324462; NR_158991; NM_001242503; NM_013989; NR_158990; NM_001007023 |
| LRRC2 | 79442 | XM_011534110; XM_017007177; XR_001740264; NM_024750; NM_024512 |
| HOXA7 | 3204 | NM_006896 |
| HOXA10 | 3206 | NR_037939; NM_153715; NM_018951 |
| SLC5A5 | 6528 | XM_011528194; XM_011528193; NM_000453; XM_017027158; XM_011528192 |
| AADAC | 13 | NM_001086; XM_005247104 |
| KCNJ15 | 3772 | XM_017028344; XM_017028343; XM_011529561; NM_170736; NM_170737; XM_005260975; NM_001276438; NM_001276439; NM_002243; XM_006724002; XM_011529560; XM_017028345; NM_001276435; NM_001276436; NM_001276437 |
| CACNA1I | 8911 | NM_021096; XM_017029035; XM_017029036; XM_017029037; NM_001003406 |
| GPC3 | 2719 | NM_004484; XM_017029413; NM_001164618; NM_001164617; NM_001164619 |
| KLHDC8A | 55220 | NM_001271863; NM_001271865; XM_024448121; NM_018203; NM_001271864 |
| SSX1 | 6756 | NM_001278691; NM_005635 |
| SYT12 | 91683 | XM_011545346; XM_011545347; NM_177963; XM_017018547; NM_001177880; NM_001318775; XM_017018548; XM_006718737; XM_024448766; NM_001318773 |
| BMPR1B | 658 | XM_017008558; NM_001203; NM_001256793; XM_011532201; NM_001256794; NM_001256792; XM_017008559; XM_017008560; XM_017008561 |
| MYL2 | 4633 | NM_000432 |
| CLIC3 | 9022 | XM_017015282; NM_004669; XM_017015281 |
| SPINK1 | 6690 | NM_003122; NM_001379610; NM_001354966 |
| S100A1 | 6271 | NM_006271 |
| BIRC5 | 332 | NM_001168; NM_001012271; NM_001012270 |
| UBE2C | 11065 | NM_001281742; NM_001281741; NM_181802; NM_181803; NR_104036; NR_104037; NM_007019; NM_181800; NM_181801; NM_181799 |
| AMN | 81693 | XM_024449714; XM_011537203; NM_030943; XM_011537202 |
| CBLN1 | 869 | NM_004352 |
| PBK | 55872 | NM_018492; NM_001278945; NM_001363040 |

-continued

| Gene | NCBI Gene ID | NCBI Accession Number(s) |
|---|---|---|
| ALK | 238 | NM_004304; NM_001353765; XM_024452779; XR_001738688; XM_024452778 |
| CYP2J2 | 1573 | NR_134982; NR_134981; NM_000775 |
| TSPAN8 | 7103 | NM_001369760; NM_004616; XM_006719583 |
| CHGA | 1113 | NM_001301690; NM_001275; XM_011536370 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| SCD | 6319 | NM_005063 |
| SCN4A | 6329 | NM_000334 |
| TF | 7018 | NM_001063; NM_001354703; NM_001354704 |
| TPX2 | 22974 | XM_011528697; XM_011528699; NM_012112; XM_011528700 |
| TFAP2A | 7020 | NM_001032280; XM_006715175; NM_001042425; XM_017011232; XM_011514833; NM_001372066; NM_003220 |
| ACADL | 33 | NM_001608; XM_005246517; XM_017003955 |
| IQCA1 | 79781 | XM_017004960; NM_024726; NM_001270585; XM_011511865; XM_011511866; XM_011511864; NM_001270584; NR_073043 |
| CENPF | 1063 | XM_017000086; NM_016343; XM_011509082 |
| EYA1 | 2138 | XM_017013204; XM_017013211; XM_017013212; NM_001370334; XM_011517484; XM_017013203; NM_001288574; XM_017013202; NM_000503; XM_017013207; XM_017013208; XM_017013213; NM_001370336; NM_172059; NM_172060; XM_017013205; NM_172058; NM_001288575; NM_001370333; NM_001370335; XM_011517483 |
| FSCN2 | 25794 | NM_012418; XM_011524587; XM_011524590; XR_001752466; NM_001077182 |
| SEMA3C | 10512 | NM_006379; NM_001350121; NM_001350120 |
| MYH7 | 4625 | XM_017021340; NM_000257 |
| TRIP13 | 9319 | NM_004237; XM_011514163 |
| FGFR4 | 2264 | NM_213647; NM_022963; NM_002011; NM_001291980; NM_001354984 |
| CEP55 | 55165 | XM_017016373; XM_011539920; NM_001127182; NM_018131; XM_017016372; XM_011539919; XM_011539918 |
| TFF1 | 7031 | NM_003225 |
| DLGAP5 | 9787 | XM_017021840; NM_001146015; NM_014750 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| MSC | 9242 | NM_005098 |
| SMR3B | 10879 | NM_006685 |
| PRDM16 | 63976 | NM_199454; NM_022114 |
| HOXB3 | 3213 | XM_006721854; NM_001384749; XM_024450737; XM_011524719; XM_011524720; XM_011524726; |

-continued

| Gene | NCBI Gene ID | NCBI Accession Number(s) |
|---|---|---|
| | | NM_001330323; XM_011524708; XM_011524721; NM_002146; XM_011524710; NM_001384747; XM_017024560; NM_001330322; NM_001384750 |
| NNAT | 4826 | NM_001322802; NM_181689; NM_005386 |
| TGFA | 7039 | NM_001308159; NM_001308158; NM_001099691; NM_003236 |
| PID1 | 55022 | NM_001330156; XM_017004404; NM_001330158; NM_017933; NM_001330157; NM_001100818 |
| KIAA1456 | 57604 | XM_005273591; XM_024447215; XM_005273584; XM_005273586; XM_011544600; XM_024447217; XM_005273588; XM_011544598; XM_024447214; XM_005273590; XM_017013710; NM_001099677; XM_005273585; XM_017013714; XM_011544596; XM_011544597; XM_011544601; XM_017013705; XM_024447216; XM_017013706; XM_024447218; XM_024447219; NM_020844 |
| PAPSS2 | 9060 | NM_001015880; NM_004670 |
| MMRN1 | 22915 | XM_005262856; NM_001371403; NM_007351 |
| LYVE1 | 10894 | NM_006691 |
| GALE | 2582 | NM_000403; NM_001127621; NM_001008216 |
| CFD | 1675 | NM_001317335; NM_001928 |
| CDH3 | 1001 | NM_001793; XM_011522800; NM_001317195; NM_001317196 |
| TNFRSF10C | 8794 | NM_003841 |
| CDKN2B | 1030 | NM_078487; NM_004936 |
| BBC3 | 27113 | XM_006723141; XM_011526722; NM_001127241; NM_001127242; NM_001127240; NM_014417 |
| IPCEF1 | 26034 | NM_001394801; NM_001130700; NM_015553; NM_001130699; NM_001394799; NM_001394800; NM_001394802 |
| CDH6 | 1004 | NM_004932; NM_001362435; XM_017008910; XM_011513921; XR_001741972 |
| KCNJ2 | 3759 | NM_000891 |
| LAMB3 | 3914 | XM_005273124; NM_001127641; XM_017001272; NM_000228; NM_001017402 |
| E2F1 | 1869 | NM_005225 |
| DUSP4 | 1846 | NM_001394; NM_057158; XM_011544428 |
| FMO2 | 2327 | NM_001460; NR_160266; XR_921761; NM_001365900; XR_001737072; NM_001301347 |
| GDF15 | 9518 | XM_024451789; NM_004864 |
| CCL21 | 6366 | NM_002989 |
| PLCH1 | 23007 | XM_011512561; XM_011512565; XM_011512566; NM_001349250; XM_011512567; XM_017005925; XM_005247239; XM_005247238; XM_011512560; XM_017005926; NM_001130960; NM_001349252; NM_014996; XM_017005927; NM_001130961; NM_001349251; XM_011512562; XM_017005923 |
| MYOC | 4653 | NM_000261 |
| GABRD | 2563 | XM_011541194; XM_017000936; NM_000815 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SLC12A5 | 57468 | NM_020708; NM_001134771 |
| VTCN1 | 79679 | NM_001253849; NM_024626; NR_045604; XM_017002335; NM_001253850; NR_045603; XM_011542143 |
| OLAH | 55301 | XM_024448060; XM_017016376; NM_018324; NM_001039702 |
| MMP11 | 4320 | NM_005940; NR_133013 |
| AIM1L | 55057 | NM_017977; XM_011541672; XM_011541673; XR_001737260; NM_001039775; XR_946681; XM_005245918 |
| CDH2 | 1000 | XM_011525788; NM_001308176; XM_017025514; NM_001792 |
| HAPLN1 | 1404 | XM_017009052; XM_017009051; NM_001884; XM_017009054; XM_017009053; XM_011543168 |
| DES | 1674 | NM_001927; NM_001382708; NM_001382710; NM_001382713; NM_001382709; NM_001382711; NM_001382712 |
| ADRA2C | 152 | NM_000683 |
| CD19 | 930 | NM_001178098; NM_001385732; NM_001770; XR_950871; XM_006721103; NR_169755; XM_011545981 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| | | Glioma |
| AQP4 | 361 | NM_001317387; NM_001364287; NM_001364286; NM_001317384; XM_011525942; NM_001650; NM_001364289; NM_004028 |
| OLIG2 | 10215 | XM_005260908; NM_005806 |
| GFAP | 2670 | XM_024450691; XM_024450690; NM_001131019; XM_024450692; XM_024450693; NM_001242376; NM_002055; NM_001363846 |
| HAPLN2 | 60484 | XM_024448828; XM_005245415; XM_011509853; XM_017002020; XM_017002021; NM_021817 |
| GPR37L1 | 9283 | NM_004767; XM_011510158 |
| PMP2 | 5375 | NM_002677; NM_001348381 |
| GPM6A | 2823 | NM_201592; NM_001261447; NM_001388091; NM_001261448; NM_005277; NR_048571; NM_001388090; NM_201591 |
| TIMP4 | 7079 | NM_003256 |
| SLC1A3 | 6507 | XM_024446182; XM_011514084; NM_004172; NM_001289940; NM_001289939; NM_001166695; XM_005248342; XM_024446181; NM_001166696 |
| MLC1 | 23209 | XR_001755180; NM_001376472; NM_001376478; NR_164811; NR_164812; NM_001376473; NM_001376477; NM_139202; |

-continued

| Gene | NCBI Gene ID | NCBI Accession Number(s) |
|---|---|---|
| | | NM_001376476; NM_001376479; NM_001376484; NM_015166; NR_164813; NM_001376474; NM_001376481; XM_011530678; NM_001376480; NM_001376483; NM_001376475; NM_001376482 |
| NCAN | 1463 | NM_004386 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| CDH20 | 28316 | XR_001753187; NM_031891; XR_001753186; XM_024451165 |
| PTPRZ1 | 5803 | NM_002851; NM_001206838; NM_001369396; NM_001369395; NM_001206839 |
| MT3 | 4504 | NM_005954 |
| FOXG1 | 2290 | NM_005249 |
| DLL3 | 10683 | NM_016941; NM_203486 |
| KRT8 | 390601, 149501, 3856 | NM_001256293; NM_002273 |
| PERP | 64065 | XM_024446520; NM_022121 |
| TACSTD2 | 4070 | NM_002353 |
| KRT7 | 3855 | XM_017019294; XR_001748700; NM_005556; XM_011538325; XR_001748699 |
| TES | 26136 | NM_015641; NM_152829; XM_005250258 |
| EVPL | 2125 | NM_001988; NM_001320747 |
| KCNK5 | 8645 | XM_006715235; XM_005249456; NM_003740 |
| EPCAM | 4072 | NM_002354 |
| RIPK4 | 54101 | NM_020639 |
| SOX21 | 11166 | NM_007084 |
| DSP | 1832 | NM_001008844; NM_004415; NM_001319034 |
| C2orf54 | 79919 | XM_011511877; NM_001085437; NM_001282921; NM_024861 |
| NEUROD4 | 58158 | NM_021191 |
| CDH1 | 999 | NM_001317186; NM_004360; NM_001317185; NM_001317184 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| CYP2C18 | 1562 | NM_000772; NM_001128925 |
| EPS8L1 | 54869 | NM_133180; NM_139204; XM_011527052; XM_005259020; NM_017729; XM_011527051; XM_011527050 |
| PDLIM1 | 9124 | XM_011540330; NM_020992 |
| SPINK5 | 11005 | XM_011537551; NM_006846; NM_001127698; NM_001127699 |
| TNNC1 | 7134 | NM_003280 |
| CD55 | 1604 | NM_001300904; NM_001114543; NM_001114544; XM_017000467; NM_001114752; NM_001300902; NM_001300903; NM_000574; NR_125349 |
| LLGL2 | 3993 | XM_017024627; XR_002957999; XR_002958003; XM_017024626; XR_002958004; XM_017024629; XM_017024630; XM_017024631; XR_002958005; XR_002958002; NM_001015002; XM_011524802; XM_017024628; XR_002958000; |

-continued

| Gene | NCBI Gene ID | NCBI Accession Number(s) |
|---|---|---|
| | | XM_024450747; XR_001752508; NM_001031803; XM_017024625; XR_002958001; NM_004524 |
| ITPR3 | 3710 | XM_017010832; XM_011514577; NM_002224 |
| SPINT2 | 10653 | NM_001166103; NM_021102 |
| ANXA3 | 306 | XR_001741215; NM_005139 |
| HCN2 | 610 | NM_001194 |
| F2R | 2149 | NM_001311313; NM_001992 |
| MYL2 | 4633 | NM_000432 |
| KIFC1 | 3833 | XM_011514585; XM_017010836; NM_002263; XM_011514587; XM_017010837 |
| BIRC5 | 332 | NM_001168; NM_001012271; NM_001012270 |
| NDC80 | 10403 | NM_006101 |
| PBK | 55872 | NM_018492; NM_001278945; NM_001363040 |
| TACC3 | 10460 | XM_005247930; XM_017007653; NM_006342; XM_005247929; XM_011513386 |
| EGFR | 1956 | NM_001346899; NM_201282; NM_201284; NM_001346898; NM_001346900; NM_001346897; NM_201283; NM_001346941; NM_005228 |
| DTL | 51514 | XM_011509614; NM_001286229; NM_001286230; NM_016448 |
| | | Sarcoma |
| RAB11FIP1 | 80223 | NM_001002814; NM_025151; XM_017013869; NM_001002233 |
| LOXL1 | 4016 | XM_017022179; XM_011521555; NM_005576; XR_931824 |
| ZNF385D | 79750 | XM_017007203; NM_024697; XM_017007200; XM_011534124; XM_017007195; XM_017007202; XM_017007193; XM_017007197; XM_011534122; XM_017007191; XM_017007192; XM_017007199; XM_017007201; XM_024453754; XM_011534123; XM_017007194; XM_017007196; XM_017007198 |
| MYL2 | 4633 | NM_000432 |
| AGRN | 375790 | XM_011541429; NM_001305275; NM_001364727; XR_946650; NM_198576; XM_005244749 |
| KCNG1 | 3755 | XM_011528800; XM_011528802; XM_011528803; XM_011528805; NM_172318; NM_002237; XM_011528801; XM_011528804; XM_011528806; XM_006723785 |
| NKX3-2 | 579 | NM_001189 |
| NXPH3 | 11248 | NM_007225 |
| HMX1 | 3166 | NM_018942; NM_001306142 |
| CLDN7 | 1366 | NM_001307; NM_001185022; NM_001185023 |
| TUBB4A | 10382 | NM_001289129; NM_001289131; NM_006087; NM_001289123; NM_001289127; NM_001289130 |
| RAB17 | 64284 | XM_006712689; XM_017004693; NM_022449; XM_017004694; NR_033308 |
| EPCAM | 4072 | NM_002354 |
| GH1 | 2688 | NM_022559; NM_022561; NM_022560; NM_022562; NM_000515 |
| ERBB3 | 2065 | NM_001005915; NM_001982 |
| ELMO3 | 79767 | XM_024450447; NM_024712 |
| SYNC | 81493 | XM_024450011; NM_001161708; XM_024450013; NM_030786; XM_024450012; XM_024450010; XM_024450014 |
| TPD52 | 7163 | NM_005079; NR_105035; NM_001287143; NM_001387779; NR_105037; NR_170694; |

-continued

| Gene | NCBI Gene ID | NCBI Accession Number(s) |
|---|---|---|
| | | NM_001025252; NM_001025253; NR_170693; NM_001287140; NR_105034; NM_001387780; NM_001287142; NM_001287144; NM_001387778; NR_105033; NR_105036 |
| S100B | 6285 | NM_006272; XM_017028424 |
| PALMD | 54873 | NM_017734 |
| CYP46A1 | 10858 | NM_006668; XM_005267274; XM_011536365; XM_011536364; XM_017020933 |
| PNPLA2 | 57104 | NM_020376 |
| SERINC2 | 347735 | NM_178865; NM_001199039; NM_018565; NM_001199038; NM_001199037 |
| PRSS12 | 8492 | XM_011532387; NM_003619; XM_005263318 |
| OLR1 | 4973 | NM_002543; NM_001172632; NM_001172633 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| HOOK1 | 51361 | XR_946665; XM_017001424; XM_006710676; XR_246271; XM_011541563; XM_024447520; XM_011541562; NM_015888 |
| GDPD3 | 79153 | NM_024307 |
| EPM2A | 7957 | NM_001368131; XM_017011301; NM_001360057; NM_001360064; NM_001368129; XM_024446550; XM_011536113; NM_001368130; NM_005670; NR_153398; XM_017011302; XM_011536116; NM_001360071; NM_001018041; XM_024446551; NM_001368132 |
| C1orf116 | 79098 | XM_011509973; NM_001083924; XM_005273259; XM_006711530; NM_023938 |
| CCDC68 | 80323 | XM_011526201; XM_017026011; XM_011526198; XM_006722552; NM_001143829; XM_011526199; XM_011526203; XM_011526204; NM_025214; XM_011526200; XM_011526202 |
| VGF | 7425 | NM_003378; XM_011516549; XM_005250561 |
| PLEK2 | 26499 | NM_016445 |
| FBN2 | 2201 | NM_001999; XM_017009228 |
| FGF7 | 2252 | NM_002009 |
| RCN3 | 57333 | NM_020650; XM_024451620 |
| FBXO2 | 26232 | NM_012168 |
| COX7A1 | 1346 | NM_001864 |
| EBF2 | 64641 | NM_022659 |
| ADAMTS2 | 9509 | NM_021599; NM_014244 |
| TAGLN3 | 29114 | NM_001008272; NM_001008273; NM_013259 |
| HAND2 | 9464 | NM_021973 |
| MT3 | 4504 | NM_005954 |

-continued

| Gene | NCBI Gene ID | NCBI Accession Number(s) |
|---|---|---|
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| GAS1 | 2619 | NM_002048 |
| CDKL2 | 8999 | XR_001741344; XR_001741345; XM_017008811; XM_017008810; XM_006714406; NM_003948; XM_017008809; NM_001330724 |
| SCN4A | 6329 | NM_000334 |
| COL5A1 | 1289 | NM_000093; XM_017014266; XR_001746183; NM_001278074 |
| WWC1 | 23286 | XM_011534487; XM_011534489; NM_015238; XM_005265850; XM_011534485; XM_011534486; XM_005265853; XM_011534488; |

-continued

| Gene | NCBI Gene ID | NCBI Accession Number(s) |
|---|---|---|
| | | XM_011534490; XM_011534491; XM_017009276; XM_017009278; NM_001161662; NM_001161661 |
| POPDC2 | 64091 | NM_001369919; NM_022135; NM_001308333 |
| TFAP2A | 7020 | NM_001032280; XM_006715175; NM_001042425; XM_017011232; XM_011514833; NM_001372066; NM_003220 |
| EN1 | 2019 | NM_001426 |
| CHRD | 8646 | XM_017007390; NR_130747; NM_177978; XM_017007388; XM_017007391; XM_024453803; XR_001740336; NM_001304472; XM_017007392; XR_001740334; XM_011513254; XR_002959603; NM_001304473; NM_177979; NM_001304474; NM_003741; XM_017007389; XM_017007393; XM_017007394; XR_001740335; XR_001740337 |
| PLS1 | 5357 | NM_001172312; XM_011512901; NM_001145319; XM_006713660; XM_017006626; XM_011512903; XM_017006627; XM_011512900; NM_002670 |
| ELF3 | 1999 | NM_004433; XM_005244942; NM_001114309 |
| DBNDD1 | 79007 | NM_001288709; NM_001288708; NM_001371581; NM_001042610; NM_024043 |
| RAB23 | 51715 | NM_183227; NM_001278666; NM_001278668; NM_016277; NM_001278667; NR_103822 |
| CD24 | 100133941 | NM_001291739; NR_117090; NR_117089; NM_001291738; NM_001291737; NM_013230; XM_024446293; NM_001359084 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| AMPH | 273 | XM_006715689; XM_017011996; XM_006715690; XM_006715691; XM_011515271; XM_017011995; NM_001635; NM_139316 |
| KRT8 | 390601, 149501, 3856 | NM_001256293; NM_002273 |
| HOXA7 | 3204 | NM_006896 |
| CORO2A | 7464 | NM_003389; NM_052820; XM_011518986 |
| RNF43 | 54894 | XM_011524955; XM_011524956; NM_017763; NM_001305544; XM_017024800; NM_001305545 |
| PER1 | 5187 | XM_005256689; XM_005256690; XM_024450803; NM_002616 |
| SHOX2 | 6474 | XM_006713727; NM_001163678; XM_017007055; NM_006884; XM_006713728; XM_017007053; NM_003030; XM_017007054 |
| MYRF | 745 | NM_013279; XM_005274222; XM_005274224; XM_005274226; XM_005274228; XM_005274223; XM_005274225; XM_005274227; XM_011545234; XM_024448677; NM_001127392 |
| GPR1 | 2825 | NM_001098199; NM_001261452; NM_001261454; NM_005279; XM_005246471; NM_001261455; NM_001389445; NM_001261453 |

-continued

| Gene | NCBI Gene ID | NCBI Accession Number(s) |
|---|---|---|
| CIDEC | 63924 | NM_001321142; NM_001199552; NM_001378491; NM_001199623; NM_001199551; NM_001321144; NM_022094; NM_001321143 |
| APOD | 347 | NM_001647 |
| KRT2 | 3849 | NM_000423 |
| HOXD9 | 3235 | NM_014213 |
| KCNB2 | 9312 | XM_017013981; XR_001745620; XR_001745621; NM_004770; XM_017013982 |
| FABP6 | 2172 | NM_001130958; NM_001040442; NM_001445 |
| CCNB1 | 891 | NM_031966 |
| DSP | 1832 | NM_001008844; NM_004415; NM_001319034 |
| KRT5 | 3852 | NM_000424 |
| LGI2 | 55203 | XM_011513850; NM_018176; XM_017008356 |
| CKM | 1158 | NM_001824 |
| ITGB4 | 3691 | XM_005257311; XM_006721866; XM_006721870; NM_000213; NM_001005619; NM_001005731; XM_005257309; XM_011524752; XM_006721867; XM_011524751; NM_001321123; XM_006721868 |
| AP1M2 | 10053 | NM_001300887; XM_024451304; NM_005498; XM_024451303 |
| QPRT | 23475 | XM_005255223; NR_134536; NM_001318250; NM_001318249; NM_014298; XM_017023101 |
| FOXD1 | 2297 | NM_004472 |
| NPPA | 4878 | NM_006172 |
| DDR2 | 4921 | NM_001014796; XM_011509587; XM_011509588; NM_001354982; NM_006182; NM_001354983 |
| PFKFB1 | 5207 | NM_001271804; XM_017029578; XM_017029576; NM_002625; NR_073450; XM_024452389; XM_017029577; NM_001271805 |
| BNC2 | 54796 | NM_001317939; NM_017637; NM_001317940 |
| PCOLCE | 5118 | XM_024446785; NM_002593 |
| GIPC2 | 54810 | NM_017655; NM_001304725 |
| FZD2 | 2535 | NM_001466 |
| COL1A2 | 1278 | NM_000089 |
| FST | 10468 | XM_005248403; XM_011543099; XM_005248400; XM_017008955; NM_013409; XM_005248401; XM_005248402; XM_017008954; XM_024454326; NM_006350 |
| BIK | 638 | NM_001197 |
| C1QL1 | 10882 | NM_006688 |
| ZWINT | 11130 | XR_428692; NM_007057; NM_001005413; XM_017015605; XM_024447784; NM_032997; NM_001005414 |
| MYOC | 4653 | NM_000261 |
| GABRQ | 55879 | NM_018558; XM_011531184 |
| SCN5A | 6331 | NM_001160160; NM_001099405; NM_001354701; XM_011533991; XM_017007017; NM_001160161; NM_198056; NM_000335; NM_001099404 |
| DTL | 51514 | XM_011509614; NM_001286229; NM_001286230; NM_016448 |
| Neuroendocrine | | |
| CA7 | 766 | NM_001365337; XM_011523312; NM_001014435; NM_005182 |
| TGM3 | 7053 | NM_003245 |
| HLA-G | 3135 | XM_017010817; NM_001384280; XM_017010818; NM_002127; XM_024446420; NM_001363567; NM_001384290 |

-continued

| Gene | NCBI Gene ID | NCBI Accession Number(s) |
|---|---|---|
| MYL2 | 4633 | NM_000432 |
| CCNB1 | 891 | NM_031966 |
| UPK3A | 7380 | NM_006953; NM_001167574 |
| LYVE1 | 10894 | NM_006691 |
| DES | 1674 | NM_001927; NM_001382708; NM_001382710; NM_001382713; NM_001382709; NM_001382711; NM_001382712 |
| PLA2G1B | 5319 | NM_000928 |
| DBNDD1 | 79007 | NM_001288709; NM_001288708; NM_001371581; NM_001042610; NM_024043 |
| MET | 4233 | NM_001324402; NM_001324401; XM_006715990; NM_001127500; XM_011516223; NM_000245; XR_001744772; |
| ESM1 | 11082 | NM_001135604; NM_007036 |
| COL10A1 | 1300 | XM_011535432; NM_000493; XM_011535433; XM_017010248; XM_006715333 |
| KRT2 | 3849 | NM_000423 |
| HRASLS2 | 54979 | NM_017878; XM_011545120 |
| DGKI | 9162 | NM_004717; NM_001321708; XM_017012788; NM_001321710; NM_001388092; NM_001321709 |
| SLC18A1 | 6570 | XM_011544626; NM_003053; XM_011544625; NM_001142325; NM_001135691; NM_001142324 |
| MMP11 | 4320 | NM_005940; NR_133013 |
| FIGF | 2277 | NM_004469 |
| SLC16A7 | 9194 | XM_011538990; XM_011538992; NM_004731; NM_001270622; XM_017020225; XM_017020227; NR_073055; XM_011538989; NM_001270623; XM_024449276; XM_011538991; XM_011538993; NR_073056; XM_005269231; XM_011538995; XM_017020226; XM_017020224 |
| VIP | 7432 | XM_006715562; XM_005267135; NM_003381; NM_194435 |
| CD200 | 4345 | NM_001318830; NR_158642; NM_001004197; NM_001365853; NM_001365855; NM_001318826; NM_001365852; NM_001004196; NM_001318828; NM_001365851; NM_005944; NM_001365854 |
| SLITRK3 | 22865 | NM_014926; NM_001318810; NM_001318811 |
| FCN2 | 2220 | XM_011518392; NM_015838; NM_015839; NM_015837; NM_004108; XM_006717015 |
| MT3 | 4504 | NM_005954 |
| ADRB2 | 154 | NM_000024 |
| CACNG4 | 27092 | NM_014405 |
| SYNPO2L | 79933 | NM_024875; NM_001114133; XM_005270159; XM_005270158 |
| VILL | 50853 | NM_001370265; NR_163266; NR_163267; NM_001370264; NM_015873; NM_001385039; NM_001385038 |
| AGRN | 375790 | XM_011541429; NM_001305275; NM_001364727; XR_946650; NM_198576; XM_005244749 |
| CYP11B1 | 1584 | NM_001026213; NM_000497 |
| EPHB3 | 2049 | NM_004443 |
| KCNMB1 | 3779 | NM_004137 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |

-continued

| Gene | NCBI Gene ID | NCBI Accession Number(s) |
|---|---|---|
| SCGB2A1 | 4246 | NM_002407 |
| ABCC4 | 10257 | XM_017020321; NM_001301829; NM_005845; XM_005254025; XM_017020319; NM_001301830; NM_001105515; XM_017020322; XM_017020320 |
| CRNN | 49860 | NM_016190 |
| CHGB | 1114 | NM_001819 |
| HIGD1B | 51751 | XM_011524891; NM_016438; XM_006721946; XM_006721947; XM_017024742; NR_073504; XM_006721948; XM_017024743; NM_001271880 |
| CELA2A | 63036 | NM_033440 |
| CLPS | 1208 | NM_001832; NM_001252597; NM_001252598 |
| HECW1 | 23072 | XM_006715670; XM_006715671; XM_011515225; XM_017011882; XM_011515220; XM_011515223; XM_017011886; XM_017011888; NM_001287059; NM_015052; XM_017011883; XM_006715673; XM_011515222; XM_011515224; XM_017011884; XM_017011889; XM_017011885; XM_017011887; XM_011515226; XM_017011890; XM_005249665 |
| ERBB3 | 2065 | NM_001005915; NM_001982 |
| PPY | 5539 | NM_002722; NM_001319209; XM_011524978 |
| CKM | 1158 | NM_001824 |
| CXorf36 | 79742 | XM_006724559; NM_176819; NM_024689; XM_005272670 |
| HOXA10 | 3206 | NR_037939; NM_153715; NM_018951 |
| RIBC2 | 26150 | XM_005261524; XM_011530126; NM_015653; XM_017028766 |
| CDH19 | 28513 | XM_011525931.3; XM_017025711.2; XM_011525932.1 |
| SLC24A2 | 25769 | XM_017014592; NM_001193288; NM_001375850; NM_020344; NM_001375851 |
| ADAMDEC1 | 27299 | NM_001145272; NM_014479; NM_001145271; NR_156422 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| KRT17 | 3872 | NM_000422 |
| S100P | 6286 | NM_005980 |
| NOX4 | 50507 | NM_001291926; XM_006718849; NM_016931; NM_001143837; XM_011542857; NM_001143836; NM_001291927; XM_017017842; XM_017017843; XM_017017844; XM_017017841; XM_017017845; NM_001291929; NM_001300995; NR_120406 |
| CELSR1 | 9620 | XM_011530554; XM_011530555; NM_001378328; XM_011530553; NM_014246 |
| CPB1 | 1360 | NM_001871 |
| CCL23 | 6368 | NM_005064; XR_429910; NM_145898 |
| CELA3A | 10136 | NM_005747 |
| WISP2 | 8839 | NM_001323369; XM_017028116; NM_003881; XM_017028117; NM_001323370 |
| GCG | 2641 | NM_002054 |
| CACNA1H | 8912 | XM_006720965; XM_017023820; XM_006720963; XM_006720967; |

-continued

| Gene | NCBI Gene ID | NCBI Accession Number(s) |
|---|---|---|
| | | XM_011522724; XR_002957850; XM_005255652; XM_017023821; XM_011522727; XM_017023819; NM_021098; XM_006720968; XM_006720964; NM_001005407 |
| PDX1 | 3651 | NM_000209; XR_941580; XR_941578; |
| FABP7 | 2173 | NM_001319039; NM_001319041; NM_001319042; NM_001446 |
| NRTN | 4902 | NM_004558 |
| NMB | 4828 | XM_017022239; NM_021077; NM_205858 |
| AMHR2 | 269 | XM_011538179; XM_011538184; XM_017019179; NM_020547; XR_002957309; XR_002957311; XM_011538178; XM_011538176; XM_011538181; XM_011538185; NM_001164691; XM_011538174; XM_011538183; XR_002957310; XM_011538186; XR_002957312; NM_001164690; XM_011538173; XM_011538180; XM_024448938 |
| WNT2 | 7472 | NM_003391; NR_024047 |
| GFAP | 2670 | XM_024450691; XM_024450690; NM_001131019; XM_024450692; XM_024450693; NM_001242376; NM_002055; NM_001363846 |
| CYP11B2 | 1585 | NM_000498 |
| SGCA | 6442 | XM_011525122; XM_011525120; XM_011525121; XM_024450873; NM_001135697; NR_135553; XR_002958056; XM_011525124; NM_000023; XM_011525123 |
| PNMA2 | 10687 | NM_007257; XM_011544365 |
| CEL | 1056 | NM_001807 |
| MT1M | 4499 | NM_176870 |
| CST1 | 1469 | NM_001898 |
| ITPKB | 3707 | NM_002221; NM_001388404; XM_017001211 |
| ALAS2 | 212 | NM_001037968; NM_001037967; NM_000032; NM_001037969 |
| INS | 3630 | NM_001185098; NM_001185097; NM_000207; NM_001291897 |
| LGALS4 | 3960 | NM_006149; XM_011526974; XM_011526973 |
| PLP1 | 5354 | NM_001128834; NM_000533; NM_001305004; NM_199478 |
| GABRQ | 55879 | NM_018558; XM_011531184 |
| PLAG1 | 5324 | XM_017013576; XM_017013577; NM_001114635; XM_011517544; NM_001114634; NM_002655 |
| LIPF | 8513 | NM_004190; NM_001198829; NM_001198830; NM_001198828; XM_011540311 |
| CYP11A1 | 1583 | NM_000781; NM_001099773 |
| FABP1 | 2168 | NM_001443 |
| S100A12 | 6283 | NM_005621 |
| IL20RA | 53832 | NM_001278722; XM_011535904; XM_017010955; NM_001278724; NM_014432; XM_006715506; NM_001278723; XM_017010954 |
| NR5A1 | 2516 | NM_004959 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| ERBB2 | 2064 | XM_024450643; NM_001005862; NM_001382784; NM_001382785; NM_001382788; NM_001382792; NM_001382793; NM_001382803; NM_001289937; NM_001382786; NM_001382800; NM_001382802; NM_001382806; XM_024450641; NM_001382782; NM_001382789; NM_001382795; NM_001289936; NM_001382797; NM_001382805; NM_004448; NR_110535; XM_024450642; NM_001289938; NM_001382791; NM_001382801; NM_001382783; NM_001382790; NM_001382794; NM_001382798; NM_001382799; NM_001382787; NM_001382796; NM_001382804 |
| SLC12A3 | 6559 | NM_000339; NM_001126108; NM_001126107; XM_005256119 |
| GRHL2 | 79977 | XM_011517306; XM_024447286; NM_001330593; NM_024915; XM_011517307 |
| HBB | 3043 | NM_000518 |
| C7 | 730 | NM_000587 |
| MOGAT2 | 80168 | XM_024448696; NM_025098; XM_011545267 |
| MYOC | 4653 | NM_000261 |
| TP73 | 7161 | NM_001126242; NM_001204191; NM_001126240; NM_001204185; NM_001204187; NM_001204184; NM_001204186; NM_001204192; NM_001126241; NM_001204190; NM_001204188; NM_001204189; NM_005427 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| BCAM | 4059 | NM_001013257; NM_005581 |
| KHDC1L | 100129128 | NM_001126063 |
| DTL | 51514 | XM_011509614; NM_001286229; NM_001286230; NM_016448 |
| CXCR2 | 3579 | XM_017003992; XM_017003990; NM_001168298; NM_001557; XM_005246530; XM_017003991 |
| KRT24 | 192666 | XM_017024299; NM_019016; XM_006721739; XM_011524460 |
| SIX1 | 6495 | XM_017021602; NM_005982 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| TNXB | 7148 | NM_001365276; NM_019105; NM_032470 |
| SLC6A7 | 6534 | XR_001742210; XM_024446190; XR_001742212; XM_017009770; XR_001742211; XM_017009767; XM_017009769; XM_017009768; NM_014228 |
| PLAGL1 | 5325 | NM_001289037; NM_001289040; NM_001289046; NM_001289047; NM_001317157; NM_001080956; NM_001080951; NM_001080955; NM_001289044; NM_001289048; NM_001289049; NM_001317159; NM_001317162; NM_001289038; NM_001080953; NM_001080954; NM_001289043; NM_001317156; NM_001317158; NM_001080952; NM_001289041; NM_001289045; NM_001317161; NM_002656; NM_006718; NM_001289039; NM_001289042; NM_001317160 |

-continued

| Gene | NCBI Gene ID | NCBI Accession Number(s) |
|---|---|---|
| ADH1B | 125 | NM_001286650; NM_000668 |
| FSTL4 | 23105 | XM_011543284; XM_011543286; XM_011543287; XM_011543283; XM_017009251; NM_015082 |
| MFAP2 | 4237 | NM_002403; NM_017459; NM_001135247; NM_001135248 |
| TREM2 | 54209 | NM_001271821; NM_018965 |
| COL1A2 | 1278 | NM_000089 |
| LRP2 | 4036 | XM_011511183; NM_004525; XM_011511184 |
| CDK1 | 983 | NM_001320918; NM_033379; NM_001170406; NM_001786; NM_001130829; XM_005270303; NM_001170407 |
| EBF2 | 64641 | NM_022659 |
| CDH3 | 1001 | NM_001793; XM_011522800; NM_001317195; NM_001317196 |
| SVEP1 | 79987 | NM_024500; NM_153366 |
| CNNM1 | 26507 | NM_001345888; XM_011539631; XR_002956974; NM_020348; NM_001345887; NM_001345889; NR_144311; XR_945667 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| ADAM12 | 8038 | XM_017016705; NM_001288973; NM_001288974; NM_001288975; XM_017016706; NM_003474; NM_021641; XM_024448210 |
| MAGEA1 | 4100 | NM_004988 |
| | Pheochromocytoma | |
| PHOX2A | 401 | NM_005169 |
| DDC | 1644 | XM_011515161; NM_001242890; XM_005271745; NM_001082971; NM_001242886; NM_001242887; NM_001242889; NM_000790; NM_001242888 |
| INSM1 | 3642 | NM_002196 |
| CYP11A1 | 1583 | NM_000781; NM_001099773 |
| SYT5 | 6861 | XM_006723339; NM_001297774; NM_003180; XM_017027175; XM_006723340; XM_006723341; XM_024451668 |
| NGB | 58157 | NM_021257 |
| STAR | 6770 | NM_001007243; NM_000349 |
| SLC18A1 | 6570 | XM_011544626; NM_003053; XM_011544625; NM_001142325; NM_001135691; NM_001142324 |
| CHGB | 1114 | NM_001819 |
| CHRNA3 | 1136 | XM_006720382; NM_000743; NR_046313; NM_001166694 |
| CHGA | 1113 | NM_001301690; NM_001275; XM_011536370 |
| SLC18A2 | 6571 | NM_003054 |
| DBH | 1621 | NM_000787 |
| DRD2 | 1813 | XM_017017296; NM_016574; NM_000795 |
| TH | 7054 | XM_011520335; NM_199292; NM_000360; NM_199293 |
| PPP1R17 | 10842 | XR_926912; NM_001145123; XM_011515094; NM_006658 |
| PHOX2B | 8929 | NM_003924 |
| EGR4 | 196 | NM_001965 |
| CDH22 | 64405 | XM_024451966; XM_011528994; XM_024451967; NM_021248 |

-continued

| Gene | NCBI Gene ID | NCBI Accession Number(s) |
|---|---|---|
| SFN | 2810 | NM_006142 |
| C1orf106 | 55765 | XM_011509754; XM_011509755; NM_001367289; NM_001367290; XM_011509756; NM_001142569; NM_018265 |
| CDC20 | 991 | NM_001255 |
| TGFA | 7039 | NM_001308159; NM_001308158; NM_001099691; NM_003236 |
| SMO | 6608 | NM_005631; XM_024446891 |
| SDC1 | 6382 | NM_001006946; XM_005262620; XM_005262621; NM_002997; XM_005262622 |
| VAMP8 | 8673 | NM_003761; XM_017005170 |
| SERPINA1 | 5265 | NM_001002235; NM_001127700; NM_001127701; XM_017021370; NM_001127706; NM_000295; NM_001002236; NM_001127702; NM_001127705; NM_001127703; NM_001127704; NM_001127707 |
| EPHB3 | 2049 | NM_004443 |
| BIRC5 | 332 | NM_001168; NM_001012271; NM_001012270 |
| CILP | 8483 | NM_003613; XM_017022679; XM_017022678 |
| ABAT | 18 | NM_001386601; NM_001386602; NM_001386615; NM_000663; NM_001386606; NM_001127448; NM_020686; NM_001386608; NM_001386612; NM_001386613; NM_001386603; NM_001386605; NM_001386611; NM_001386600; NM_001386609; NM_001386610; NM_001386614; NM_001386616; NM_001386604; NM_001386607 |
| CSTA | 1475 | NM_005213 |
| PRUNE2 | 158471 | XM_011518327; XM_005251746; XM_005251751; XM_006716983; XM_017014347; XM_017014349; XM_017014359; XR_001746209; XR_428517; XM_005251748; XM_006716985; NM_001308047; XM_005251754; XM_006716982; XM_017014346; XM_017014348; XM_017014352; XR_001746210; NM_001308050; NR_131751; NM_138818; XM_011518323; XM_017014345; XM_017014357; XR_001746212; NM_001308048; NM_015225; XM_017014354; XM_017014356; NM_001308049; XM_005251750; XM_005251745; XM_006716986; XM_011518326; XM_011518328; XM_017014350; XM_017014351; XM_017014353; XM_017014358; XM_006716984; XR_001746211; NM_001308051; NM_001330680 |
| WNT2 | 7472 | NM_003391; NR_024047 |
| UGT2A3 | 79799 | XM_011532247; NM_024743; NR_024010 |
| IRS4 | 8471 | XM_006724713; NM_003604; NM_001379150; XM_011531061 |
| SLC6A15 | 55117 | XM_011538525; NM_018057; NM_001146335; NM_182767 |
| ATP2B2 | 491 | XM_017006484; NM_001001331; XM_005265179; XM_011533752; XM_017006487; XM_017006488; XM_017006486; XM_017006481; XM_017006482; XM_017006489; XM_006713175; NM_001330611; NM_001353564; XM_017006485; XM_017006483; NM_001683; XM_017006492; NM_001363862 |
| WWC1 | 23286 | XM_011534487; XM_011534489; NM_015238; XM_005265850; XM_011534485; XM_011534486; |

-continued

| Gene | NCBI Gene ID | NCBI Accession Number(s) |
|---|---|---|
| | | XM_005265853; XM_011534488; XM_011534490; XM_011534491; XM_017009276; XM_017009278; NM_001161662; NM_001161661 |
| FCN2 | 2220 | XM_011518392; NM_015838; NM_015839; NM_015837; NM_004108; XM_006717015 |
| IVL | 3713 | NM_005547 |
| CFTR | 1080 | NM_000492 |
| F2RL1 | 2150 | NM_005242; XM_017009223 |
| MYB | 4602 | NM_001161660; NR_134958; NM_001130173; NM_001130172; NM_001161656; NR_134959; NM_001161657; NR_134963; NR_134965; XR_942444; NR_134962; NM_001161659; NR_134961; NM_001161658; NM_005375; NR_134960; NR_134964 |
| SCGN | 10590 | NM_006998; XM_017010181 |
| TMEM246 | 84302 | NM_001303107; NM_001303108; NM_032342; XM_024447701; NM_001371233 |
| PRSS22 | 64063 | XM_005255473; NM_022119 |
| IHH | 3549 | NM_002181 |
| MYBPH | 4608 | NM_004997 |
| SPOCK2 | 9806 | XM_017016985; NM_001134434; XM_011540404; NM_001244950; NM_014767 |
| MUC2 | 4583 | NM_002457 |
| MYCL | 4610 | NM_001033082; NM_001033081; NM_005376 |
| | Mesothelioma | |
| CPA4 | 51200 | NM_001163446; NM_016352 |
| CALB2 | 794 | NM_007088; XR_002957842; NM_001740; NR_027910; NM_007087 |
| HAS1 | 3036 | NM_001523; NM_001297436; XM_011526884 |
| ALDH1A2 | 8854 | NM_001206897; NM_170697; NM_170696; NM_003888 |
| PTGIS | 5740 | NM_000961 |
| UPK1B | 7348 | NM_006952 |
| WT1 | 7490 | NM_000378; NR_160306; NM_001367854; NM_001198551; NM_001198552; NM_024424; NM_024426; NM_024425 |
| MYL2 | 4633 | NM_000432 |
| HP | 3240 | NM_001126102; NM_005143; NM_001318138 |
| MSLN | 10232 | NM_001177355; NM_005823; NM_013404 |
| GJB1 | 2705 | NM_000166; XM_011530907; NM_001097642 |
| CKM | 1158 | NM_001824 |
| TM4SF1 | 4071 | NM_014220; XM_017006385 |
| CST1 | 1469 | NM_001898 |
| CTSE | 1510 | XM_011509245; NM_001910; NM_148964; XM_011509244; NM_001317331 |
| SLC44A4 | 80736 | NM_001178045; NM_001178044; NM_025257 |
| CD24 | 100133941 | NM_001291739; NR_117090; NR_117089; NM_001291738; NM_001291737; NM_013230; XM_024446293; NM_001359084 |
| BMP7 | 655 | NM_001719 |
| TBX5 | 6910 | NM_181486; NM_080717; NM_000192; XM_017019912; NM_080718 |
| GATA4 | 2626 | NM_001308093; NM_002052; NM_001308094; NM_001374273; NM_001374274 |
| IRF6 | 3664 | NM_001206696; NM_006147 |
| KRT5 | 3852 | NM_000424 |

-continued

| Gene | NCBI Gene ID | NCBI Accession Number(s) |
|---|---|---|
| PRSS22 | 64063 | XM_005255473; NM_022119 |
| CLIC3 | 9022 | XM_017015282; NM_004669; XM_017015281 |
| FLNC | 2318 | NM_001458; NM_001127487 |
| SALL1 | 6299 | NM_001127892; NM_002968 |
| ERBB3 | 2065 | NM_001005915; NM_001982 |
| TF | 7018 | NM_001063; NM_001354703; NM_001354704 |
| GJB3 | 2707 | NM_024009; NM_001005752 |
| BDNF | 627 | NM_001143811; NM_001143812; NM_170734; XM_011520280; NM_001143805; NM_001143816; NM_170731; NM_001143808; NM_001143809; NM_001143814; NM_001143815; NM_001143807; NM_001709; NM_001143810; NM_001143813; NM_170732; NM_001143806; NM_170733; NM_170735 |
| ADRA2B | 151 | NM_000682 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| CENPF | 1063 | XM_017000086; NM_016343; XM_011509082 |
| SCN4A | 6329 | NM_000334 |
| KRT18 | 3875 | NM_000224; NM_199187 |
| SPINT2 | 10653 | NM_001166103; NM_021102 |
| KIF4A | 24137 | NM_012310 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SDC1 | 6382 | NM_001006946; XM_005262620; XM_005262621; NM_002997; XM_005262622 |
| ROBO3 | 64221 | NM_001370358; NM_001370359; NR_163412; NM_001370356; NM_001370361; NR_163411; NR_163415; NM_001370364; NM_022370; NR_163410; NR_163413; NR_163414; XM_017018122; NM_001370366; NM_001370357; NR_163409 |
| FHL5 | 9457 | NM_001170807; NM_001322466; NM_001322467; NM_020482 |
| ZWINT | 11130 | XR_428692; NM_007057; NM_001005413; XM_017015605; XM_024447784; NM_032997; NM_001005414 |
| PKMYT1 | 9088 | NM_001258451; NM_182687; NM_001258450; XM_011522735; XM_024450490; NM_004203; XM_011522734; XM_011522736 |
| NEIL3 | 55247 | NM_018248; XM_017008360 |
| PHKG1 | 5260 | NM_001258460; XM_017012327; XM_017012324; XM_017012325; NR_047689; XM_017012326; NM_001258459; XM_005271772; NM_006213 |
| KRT2 | 3849 | NM_000423 |
| CDKN2A | 1029 | XR_929159; XM_011517676; XM_011517675; NM_001363763; NM_001195132; NM_058195; NM_000077; NM_058196; NM_058197; XM_005251343 |
| SEMA6C | 10500 | NM_030913; XM_017000075; XM_017000079; NM_001178061; |

-continued

| Gene | NCBI Gene ID | NCBI Accession Number(s) |
|---|---|---|
| | | NM_001178062; XM_017000077; XM_017000082; XM_017000076; XM_017000081; XM_005244835 |
| CIDEC | 63924 | NM_001321142; NM_001199552; NM_001378491; NM_001199623; NM_001199551; NM_001321144; NM_022094; NM_001321143 |
| SPANXB1 | 728695 | NM_145664; NM_032461 |
| GH1 | 2688 | NM_022559; NM_022561; NM_022560; NM_022562; NM_000515 |
| PLIN1 | 5346 | NM_002666; XM_005254934; NM_001145311 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| CACNA1S | 779 | XM_005245478; NM_000069 |
| | | Thymoma |
| MAOB | 4129 | XM_005272608; XM_017029524; XM_017029523; NM_000898 |
| ANKS1B | 56899 | XM_006719507; XM_024449067; NM_001204070; NM_001352193; NM_001352198; NM_001352201; NM_001352207; NM_001352219; NM_001352221; XM_006719508; XM_017019654; XM_024449061; XM_024449062; NM_001204065; NM_001352185; NM_001352191; NM_001352194; NM_001352202; NM_001352203; NM_001352209; NM_001352211; NM_001352213; NM_001352220; XM_017019655; XM_024449069; NM_001204068; NM_001352205; NM_001352214; NM_001352216; NM_001352218; NM_001352223; NM_001352225; NM_020140; XM_024449063; XM_024449066; XM_024449070; NM_001204066; NM_001352186; NM_001352187; NM_001352195; NM_001352200; NM_001352212; NM_152788; XM_005269029; XM_006719505; XM_006719510; XM_006719512; XM_011538571; XM_017019656; XM_024449065; NM_001204079; NM_001352189; NM_001352190; NM_001352197; NM_001352222; XM_006719513; XM_006719514; XM_017019652; XM_024449064; XR_001748815; NM_001204069; NM_001204067; NM_001204081; NM_001352199; NM_001352204; NM_001352206; NM_001352210; NM_001352217; NM_181670; XM_017019653; NM_001352196; XM_006719504; XM_017019657; XM_017019658; XM_024449060; XM_024449068; NM_001204080; NM_001352188; NM_001352192; NM_001352208; NM_001352224 |
| SPINK2 | 6691 | XM_024454191; XM_011534405; NM_001271718; NM_001271720; NM_001271721; NR_073417; NM_001271719; XM_011534406; NM_001271722; NM_021114; NR_073418; NR_073419 |
| KREMEN2 | 79412 | NM_145348; NM_145347; NM_024507; NM_172229; NM_001253726; NM_001253725 |

-continued

| Gene | NCBI Gene ID | NCBI Accession Number(s) |
|---|---|---|
| ORC1 | 4998 | NM_001190818; XM_017001388; XM_017001389; NM_001190819; XM_011541527; NM_004153 |
| GJB1 | 2705 | NM_000166; XM_011530907; NM_001097642 |
| DPF1 | 8193 | XM_006723408; XR_243964; XM_011527356; XM_024451731; NM_004647; XM_005259292; XM_006723407; NM_001135155; XM_006723409; XM_006723410; XM_011527358; NM_001363579; XM_011527357; XM_005259289; NM_001135156; NM_001289978 |
| PAX1 | 5075 | NM_006192; NM_001257096 |
| FCN2 | 2220 | XM_011518392; NM_015838; NM_015839; NM_015837; NM_004108; XM_006717015 |
| KIFC1 | 3833 | XM_011514585; XM_017010836; NM_002263; XM_011514587; XM_017010837 |
| RAG1 | 5896 | NM_001377278; NM_000448; NM_001377280; NM_001377277; NM_001377279 |
| FOXN1 | 8456 | XM_011525358; XM_011525362; XM_011525359; XM_011525367; XM_011525368; XM_011525370; XM_017025230; XM_017025231; XM_017025229; XM_011525369; XM_017025228; NM_001369369; NM_003593 |
| ZAP70 | 7535 | XM_017004868; XR_001738927; NM_001378594; NM_207519; XM_017004869; NM_001079; XR_001738926; XM_017004870; XM_017004867; XR_001738925 |
| PCDH1 | 5097 | XM_005268455; NM_001278613; XM_005268452; XM_017009517; NM_032420; NM_002587; XM_005268454; XM_017009518; NM_001278615 |
| LCK | 3932 | XM_011541453; XM_024447046; NM_001330468; XM_024447047; NM_005356; NM_001042771 |
| MLANA | 2315 | NM_005511 |
| KRT5 | 3852 | NM_000424 |
| NDRG2 | 57447 | NM_016250; NM_001354567; NM_201538; NM_001282215; NM_001354560; NM_001354561; NM_001354569; NM_201535; NM_001282216; NM_001354564; NM_001354565; NM_001354566; NM_201536; NM_201539; NM_201541; NM_001354558; NM_001354562; NM_001282213; NM_001354570; NM_201540; NM_001282211; NM_001320329; NM_001282214; NM_001282212; NM_001354559; NM_001354568; NM_201537 |
| GFI1B | 8328 | NM_001371908; NM_001377304; XM_006717297; NM_001135031; XM_017015175; NM_001377305; XM_011519069; XM_011519070; NM_004188; XM_011519068; XM_017015176 |
| BEND5 | 79656 | XM_017002331; XM_011542141; XM_017002333; NM_001349795; NR_146232; XM_011542142; XR_001737408; NM_001349794; NM_001302082; NM_001349793; NM_024603 |
| ITGB6 | 3694 | NM_001282354; NM_001282353; NM_000888; NM_001282389; NM_001282390; NM_001282355; NM_001282388 |

-continued

| Gene | NCBI Gene ID | NCBI Accession Number(s) |
|---|---|---|
| AGL | 178 | NM_000646; XM_005270557; NM_000644; NM_000028; NM_000643; XM_017000501; NM_000642; NM_000645 |
| CAMK2N1 | 55450 | NM_018584 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| EEF1A2 | 1917 | NM_001958 |
| REN | 5972 | NM_000537 |
| CALML3 | 810 | NM_005185 |
| DNTT | 1791 | NM_004088; NM_001017520 |
| PHLDA2 | 7262 | NM_003311 |
| CTH | 1491 | XM_005270509; NM_001902; NM_153742; XM_017000416; NM_001190463 |
| PRSS16 | 10279 | XM_017010162; XM_017010164; XM_017010165; XM_017010161; XM_017010163; NM_005865 |
| AADAC | 13 | NM_001086; XM_005247104 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| SDCBP | 6386 | NM_001007067; NM_001007069; XM_024447231; NM_001330537; NM_001348340; XM_024447229; NM_001007068; NM_001348341; XM_024447230; NM_005625; NM_001007070; NM_001348339 |
| PAX9 | 5083 | NM_001372076; NM_006194 |
| CCL25 | 6370 | NM_001394634; NM_001394635; NM_001394638; NM_005624; NM_148888; NM_001394636; NM_001201359; NM_001394637 |
| PKP1 | 5317 | NM_000299; NM_001005337 |
| TNFRSF4 | 7293 | XM_011542074; NM_003327; XM_017002232; XM_011542077; XM_011542075; XM_011542076; XM_017002231 |
| ACADL | 33 | NM_001608; XM_005246517; XM_017003955 |
| ARPP21 | 10777 | NM_001267619; NM_001385487; NM_001385490; NM_001385558; NM_001385573; NM_001385582; NR_169635; NR_169644; NR_170706; NR_170707; XM_017005574; XM_017005584; NM_001385485; NM_001385536; NM_001385581; NM_001385589; NM_001385594; XM_011533301; XM_017005580; XM_017005588; NM_001267616; NM_001385495; NM_001385576; NR_169645; XM_017005596; XM_024453320; NM_001385565; NM_001385566; NM_001385590; NM_016300; NR_169632; XM_011533303; XM_017005590; XM_017005598; XM_024453322; NM_001267617; NM_001385484; NM_001385488; NM_001385517; NM_001385585; NM_001385592; NR_169647; XM_011533299; XM_017005607; XM_024453323; NM_001025069; NM_001385489; NM_001385492; NM_001385496; NM_001385567; NM_001385577; NM_001385584; NM_001385587; NM_001385591; NM_001385593; XM_017005591; NM_001267618; NM_001385486; NM_001385491; NM_001385564; NM_001385578; NM_001385595; NM_198399; NR_169633; XM_011533300; XM_011533302; XM_017005575; XM_017005579; XM_017005612; XM_024453324; NM_001025068; NM_001385497; NM_001385556; NM_001385562; NM_001385563; NM_001385574; NM_001385580; NM_001385588; NR_169646; NR_170705 |
| SLC13A2 | 9058 | NM_001145975; NM_001346683; NM_003984; NM_001145976; XM_006722165; XM_011525450; XM_011525453; XM_011525454; NM_001346684; XM_011525452; XM_011525451 |
| FGFR4 | 2264 | NM_213647; NM_022963; NM_002011; NM_001291980; NM_001354984 |
| CD247 | 919 | NM_001378516; NM_198053; XM_011510144; XM_011510145; NM_000734; NM_001378515 |
| RAB23 | 51715 | NM_183227; NM_001278666; NM_001278668; NM_016277; NM_001278667; NR_103822 |
| FBXL6 | 26233 | NM_024555; NM_012162 |
| EFNA2 | 1943 | NM_001405; XM_017026449; XM_017026450 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| GHRH | 2691 | NM_001184731; NM_021081 |
| | | Germ_Cell_Neoplasm |
| CCNB1 | 891 | NM_031966 |
| POMC | 5443 | NM_001319205; NM_001035256; NM_001319204; NM_000939 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| CLDN6 | 9074 | NM_021195 |
| DBNDD1 | 79007 | NM_001288709; NM_001288708; NM_001371581; NM_001042610; NM_024043 |
| CAP2 | 10486 | NM_001363534; NM_006366; NM_001363533 |
| ESM1 | 11082 | NM_001135604; NM_007036 |
| EPS8L1 | 54869 | NM_133180; NM_139204; XM_011527052; XM_005259020; NM_017729; XM_011527051; XM_011527050 |
| MEP1B | 4225 | XM_011526013; XM_011526014; NM_005925; NM_001308171 |
| PLIN1 | 5346 | NM_002666; XM_005254934; NM_001145311 |
| ZWINT | 11130 | XR_428692; NM_007057; NM_001005413; XM_017015605; XM_024447784; NM_032997; NM_001005414 |

-continued

| Gene | NCBI Gene ID | NCBI Accession Number(s) |
|---|---|---|
| HAMP | 57817 | NM_021175 |
| EIF1AY | 9086 | NM_004681; NM_001278612 |
| MISP | 126353 | NR_135168; XM_011527686; XM_011527685; NM_173481 |
| MMP9 | 4318 | NM_004994 |
| CLEC1B | 51266 | NM_001099431; XM_017019395; XM_011520685; XM_017019396; XM_011520686; NM_016509; NM_001393342 |
| ALLC | 55821 | XM_017004495; XM_017004498; NM_018436; XM_017004496; XM_011510369; XM_011510370; XM_017004497; NM_199232 |
| PGR | 5241 | XM_011542869; NM_001271161; NR_073142; NM_000926; XM_006718858; NM_001202474; NM_001271162; NR_073141; NR_073143 |
| COL9A1 | 1297 | NM_001851; NR_165185; NM_078485; XM_017010246; XM_011535429; XM_017010247; NM_001377289; NM_001377290; NM_001377291 |
| DNM1 | 1759 | NM_001005336; NM_001374269; NM_004408; NM_001288738; NM_001288739; NM_001288737 |
| KERA | 11081 | NM_007035 |
| PLA2G2A | 5320 | NM_001161728; NM_000300; NM_001161729; NM_001161727; NM_001395463 |
| AURKB | 9212 | NM_001313950; NM_001313953; XM_017025309; XM_017025307; XM_017025308; XM_017025311; NM_001313952; NM_004217; NM_001313954; NR_132730; NR_132731; XM_017025310; NM_001284526; XM_011524072; NM_001256834; NM_001313951; NM_001313955 |
| APOBEC3B | 9582 | NM_004900; NM_001270411 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| PTH1R | 5745 | NM_001184744; XM_017006933; XM_011533968; NM_000316; XM_017006934; XM_011533967; XM_005265344; XM_017006932 |
| PTCH2 | 8643 | NM_001166292; NM_003738 |
| CYP46A1 | 10858 | NM_006668; XM_005267274; XM_011536365; XM_011536364; XM_017020933 |
| VRTN | 55237 | XM_011536911; NM_018228 |
| PLVAP | 83483 | NM_031310 |
| PTHLH | 5744 | NM_198965; NM_198966; XM_011520774; NM_002820; XM_017019675; NM_198964 |
| COL8A1 | 1295 | NM_020351; NM_001850 |
| DAZL | 1618 | NM_001351; NM_001190811 |
| NANOG | 79923 | NM_024865; NM_001297698 |
| CXorf36 | 79742 | XM_006724559; NM_176819; NM_024689; XM_005272670 |
| C9 | 735 | NM_001737 |
| FOXH1 | 8928 | NM_003923 |
| MDFI | 4188 | XM_005249117; XM_011514626; NM_005586; NM_001300805; XM_011514625; NM_001300804; XM_017010867; NM_001300806 |
| KLF9 | 687 | NM_001206 |
| EDIL3 | 10085 | NM_005711; NM_001278642 |
| LRRTM4 | 80059 | NM_001134745; NM_001330370; NM_001282924; NM_024993; NM_001282928; NR_146416 |

-continued

| Gene | NCBI Gene ID | NCBI Accession Number(s) |
|---|---|---|
| PRND | 23627 | NM_012409 |
| GDF3 | 9573 | NM_020634 |
| CDKN2A | 1029 | XR_929159; XM_011517676; XM_011517675; NM_001363763; NM_001195132; NM_058195; NM_000077; NM_058196; NM_058197; XM_005251343 |
| PRM1 | 5619 | NM_002761 |
| LIN28A | 79727 | XM_011542148; NM_024674 |
| DPP4 | 1803 | NR_166823; NM_001379606; NM_001379605; NR_166824; NM_001935; NM_001379604; NR_166825; NR_166822 |
| IBSP | 3381 | NM_004967 |
| CYP17A1 | 1586 | NM_000102 |
| VENTX | 27287 | XM_017016073; NM_014468 |
| LEFTY2 | 7044 | NM_003240; NM_001172425; XM_011544266 |
| GCKR | 2646 | XM_017003797; XM_011532763; XR_001738699; XM_017003796; NM_001486 |
| AKR1C3 | 8644 | NM_003739; NM_016253; NM_001253909; NM_001253908 |
| GATA4 | 2626 | NM_001308093; NM_002052; NM_001308094; NM_001374273; NM_001374274 |
| PLP1 | 5354 | NM_001128834; NM_000533; NM_001305004; NM_199478 |
| ADAM11 | 4185 | XM_005257373; NM_001318933; NM_002390; XM_024450754 |
| PRM2 | 5620 | NM_001286358; NR_104428; NM_002762; NM_001286356; NM_001286359; NM_001286357 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| HAPLN1 | 1404 | XM_017009052; XM_017009051; NM_001884; XM_017009054; XM_017009053; XM_011543168 |
| DEPDC1 | 55635 | NM_001114120; NM_017779 |
| SLPI | 6590 | NM_003064 |
| C3orf36 | 80111 | NM_025041; NR_161373 |
| PEG3 | 5178 | NM_001369718; NM_001146184; NM_001369719; NM_001369734; NM_001369739; NR_161475; NM_001369731; NM_001369720; NM_001369724; NM_001369732; NM_001369733; NM_001146187; NM_001369722; NM_001369723; NM_001369726; NM_001369728; NM_001369735; NM_001369736; NM_001369737; NM_001369738; NM_001146185; NM_001369717; NM_001369721; NM_001369725; NM_006210; NM_001369729; NM_001369730; NM_001369727; NR_161476; NM_001146186 |
| MLANA | 2315 | NM_005511 |
| TREM2 | 54209 | NM_001271821; NM_018965 |
| GDF2 | 2658 | NM_016204 |
| DPPA4 | 55211 | XM_011512954; XM_024453622; NM_001348929; NM_001348928; NM_018189 |
| CDH15 | 1013 | NM_004933 |
| RRM2 | 6241 | NR_161344; NM_001034; NR_164157; NM_001165931 |
| MYL7 | 58498 | XM_011515464; NM_021223; XM_011515465; XM_011515463; XM_017012478; XM_017012479; |

-continued

| Gene | NCBI Gene ID | NCBI Accession Number(s) |
|---|---|---|
| | | XM_024446851; XM_005249817 |
| PRR7 | 80758 | NM_001375594; NM_030567; NM_001174102; NM_001174101; NM_001375593 |
| PHC1 | 1911 | XM_017018958; XM_011520600; XM_017018955; XM_017018957; XM_011520599; XM_017018956; XM_011520603; XM_005253334; NM_004426 |
| | Neuroendocrine_small_cell | |
| CD34 | 947 | NM_001025109; NM_001773 |
| NCAM1 | 4684 | NM_001386289; NM_001386290; NM_001386291; NM_001386292; NM_001076682; NM_000615; NM_001242608; NM_181351; NM_001242607 |
| MOGAT2 | 80168 | XM_024448696; NM_025098; XM_011545267 |
| COL11A1 | 1301 | XM_017000337; XM_017000335; XM_017000336; NR_134980; NM_080629; XM_017000334; NM_001190709; NM_001854; NM_080630 |
| DTL | 51514 | XM_011509614; NM_001286229; NM_001286230; NM_016448 |
| MYOC | 4653 | NM_000261 |
| FOXA1 | 3169 | NM_004496; XM_017021246 |
| IBSP | 3381 | NM_004967 |
| GLP2R | 9340 | XM_011524077; NM_004246; XM_017025340; XM_005256861; XM_017025339; XM_017025341 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| ZNF185 | 7739 | XM_005274744; XM_017029823; XM_017029829; NM_001178107; XM_005274735; XM_005274740; XM_005274741; XM_017029825; XM_017029831; NM_001178106; NM_001178113; XM_005274738; XM_005274731; XM_017029822; XM_017029826; XM_017029827; XM_017029832; XM_005274745; XM_017029824; NM_001178108; NM_001178110; XM_011531195; XM_017029828; NM_001178115; NM_007150; NM_001178114; XM_005274730; XM_017029821; XM_011531194; NM_001178109; NM_001395254; XM_005274746; XM_017029830; XM_017029833; NM_001388432; XM_005274742; XM_017029834; XM_017029835 |
| SYN2 | 6854 | XM_006713312; XR_001740240; XM_006713311; XM_006713313; NM_133625; NM_003178; XM_017007087 |
| KRT2 | 3849 | NM_000423 |
| ANGPTL4 | 51129 | NM_016109; NM_139314; XM_005272484; XM_005272485; NR_104213; NM_001039667 |
| GABRG3 | 2567 | XM_017022058; XM_017022060; XM_024449889; NM_033223; XM_011521430; NM_001270873; XM_011521431; XM_017022059 |
| SPP1 | 6696 | NM_001251829; NM_001040060; NM_001251830; NM_000582; NM_001040058 |
| SYT12 | 91683 | XM_011545346; XM_011545347; NM_177963; XM_017018547; |

-continued

| Gene | NCBI Gene ID | NCBI Accession Number(s) |
|---|---|---|
| | | NM_001177880; NM_001318775; XM_017018548; XM_006718737; XM_024448766; NM_001318773 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| DLL3 | 10683 | NM_016941; NM_203486 |
| SFRP5 | 6425 | NM_003015 |
| GABRD | 2563 | XM_011541194; XM_017000936; NM_000815 |
| CCNB1 | 891 | NM_031966 |
| PRL | 5617 | XM_011514753; NM_000948; NM_001163558; XM_011514754 |
| RETN | 56729 | NM_020415; NM_001385725; NM_001385727; NM_001385726; NM_001193374 |
| PPM1H | 57460 | XM_017019676; XM_011538578; NM_020700; XM_011538579 |
| ESM1 | 11082 | NM_001135604; NM_007036 |
| CELA3B | 23436 | NM_007352 |
| CHGA | 1113 | NM_001301690; NM_001275; XM_011536370 |
| GGCT | 79017 | NM_001199816; NM_001199817; NM_001199815; NM_024051; NR_037669 |
| ADH1B | 125 | NM_001286650; NM_000668 |
| AOC3 | 8639 | XR_934584; NM_001277732; NM_003734; NR_102422; XM_011525419; XR_001752673; XM_011525420; XM_024451015; NM_001277731 |
| AGL | 178 | NM_000646; XM_005270557; NM_000644; NM_000028; NM_000643; XM_017000501; NM_000642; NM_000645 |
| CELSR3 | 1951 | NM_001407 |
| CLDN3 | 1365 | NM_001306 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| ALAS2 | 212 | NM_001037968; NM_001037967; NM_000032; NM_001037969 |
| CST1 | 1469 | NM_001898 |
| CA1 | 759 | NM_001128831; NM_001291967; NM_001164830; NM_001738; NM_001128830; NM_001128829; NM_001291968 |
| AOC1 | 26 | XM_017011946; NM_001091; XM_017011947; NM_001272072; XM_017011944; XM_017011945 |
| LIMS2 | 55679 | XM_006712627; XM_024452983; NM_017980; NM_001256542; XM_017004469; NM_001161403; XM_011511453; XM_024452984; NM_001136037; XM_024452986; XR_922961; NM_001161404; XM_006712628; XM_024452985; XM_005263710 |
| HSF2BP | 11077 | XM_017028269; XM_017028272; XM_011529446; XM_017028270; XM_017028271; XM_017028267; XM_017028268; XR_937435; XM_011529445; XM_011529443; XM_011529447; NM_007031 |
| CDK4 | 1019 | NM_000075; NM_052984 |
| HBB | 3043 | NM_000518 |
| HOXC10 | 3226 | NM_017409 |

-continued

| Gene | NCBI Gene ID | NCBI Accession Number(s) |
|---|---|---|
| KRT1 | 3848 | NM_006121 |
| TTC22 | 55001 | XM_017001582; XM_011541671; NM_001114108; NM_017904 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| S100A12 | 6283 | NM_005621 |
| KRT24 | 192666 | XM_017024299; NM_019016; XM_006721739; XM_011524460 |
| MET | 4233 | NM_001324402; NM_001324401; XM_006715990; NM_001127500; XM_011516223; NM_000245; XR_001744772; |
| DES | 1674 | NM_001927; NM_001382708; NM_001382710; NM_001382713; NM_001382709; NM_001382711; NM_001382712 |
| HOXC11 | 3227 | NM_014212 |
| GUCA2A | 2980 | NM_033553 |
| PTH1R | 5745 | NM_001184744; XM_017006933; XM_011533968; NM_000316; XM_017006934; XM_011533967; XM_005265344; XM_017006932 |
| ULBP2 | 80328 | NM_025217; XM_017011321 |
| TGM3 | 7053 | NM_003245 |
| CTRB2 | 440387 | NM_001025200 |
| CKM | 1158 | NM_001824 |
| ALDOC | 230 | XM_005257949; NM_005165; XM_011524556 |
| CCL23 | 6368 | NM_005064; XR_429910; NM_145898 |
| MMP11 | 4320 | NM_005940; NR_133013 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| HOXC13 | 3229 | NM_017410 |
| MAGEA3 | 4102 | XM_011531161; XM_005274676; XM_006724818; XM_011531160; NM_005362 |
| INS | 3630 | NM_001185098; NM_001185097; NM_000207; NM_001291897 |
| NKX6-1 | 4825 | NM_006168 |
| HINT1 | 3094 | NR_134495; NM_005340; NR_073488; NR_024610; NR_134494; NR_024611 |
| GRIN2D | 2906 | XM_011526872; NM_000836 |
| FCN3 | 8547 | NM_173452; NM_003665 |
| MGLL | 11343 | XM_017005665; NM_001256585; NM_001388313; NM_001388318; NM_001388317; XM_011512383; NM_001003794; XM_017005663; XM_024453334; NM_001388312; NM_001388315; NM_007283; XM_011512382; NM_001388314; NM_001388316 |
| FMO2 | 2327 | NM_001460; NR_160266; XR_921761; NM_001365900; XR_001737072; NM_001301347 |
| PCSK2 | 5126 | NM_002594; NM_001201529; NM_001201528 |

-continued

| Gene | NCBI Gene ID | NCBI Accession Number(s) |
|---|---|---|
| MYL2 | 4633 | NM_000432 |
| SIM1 | 6492 | XM_011536072; NM_001374769; NM_005068 |
| EFNA3 | 1944 | NM_004952 |
| MT1M | 4499 | NM_176870 |
| CST4 | 1472 | NM_001899 |
| P2RY14 | 9934 | XM_011513340; NM_001081455; XM_005247922; NM_014879; XM_017007583; XM_005247923 |
| MMP14 | 4323 | NM_004995 |
| CDH19 | 28513 | XM_011525931.3; XM_017025711.2; XM_011525932.1 |
| COL10A1 | 1300 | XM_011535432; NM_000493; XM_011535433; XM_017010248; XM_006715333 |
| ETV4 | 2118 | NM_001261437; NM_001261439; NM_001986; NM_001369368; NM_001079675; NM_001261438; XM_024450644; NM_001369366; NM_001369367 |
| SIX1 | 6495 | XM_017021602; NM_005982 |
| ABCA12 | 26154 | XM_011510951; NR_103740; NM_173076; NM_015657 |
| BARX2 | 8538 | XM_011543043; NM_003658; XM_011543044 |
| CRISP2 | 7180 | XM_011514841; XM_011514842; XR_002956303; NM_001142417; NM_001261822; NM_003296; XM_011514843; XR_926302; XM_005249350; XM_005249352; XM_005249349; XM_005249353; XR_002956302; XM_005249351; NM_001142435; XM_005249356; XR_002956301; NM_001142407; XR_002956300; XR_926303; NM_001142408 |
| IGFBP3 | 3486 | NM_000598; NM_001013398 |
| CA7 | 766 | NM_001365337; XM_011523312; NM_001014435; NM_005182 |
| PPEF1 | 5475 | NM_001377996; NM_001377994; NM_001389623; NM_001377986; NM_006240; NM_152224; NM_152226; NM_152225; NM_001378381; NM_001389624; NM_152223; NM_001377993; NM_001378382; XM_017029612; NM_001389621; NM_001377995; NM_001389620 |
| | Clear_Cell_Renal_Cell_Carcinoma | |
| NKX2-4 | 644524 | NM_033176 |
| LCN2 | 3934 | NM_005564 |
| HGFAC | 3083 | NM_001297439; NM_001528 |
| TNNI3 | 7137 | NM_000363 |
| NMRK2 | 27231 | NM_001289117; NM_001375468; NM_001375469; NM_170678; NM_001375467; NM_014446; XM_006722725; NR_110316 |
| NKAIN3 | 286183 | XM_017013359; XM_011517511; XM_017013360; XM_017013361; NM_001039769; NR_130764; NR_027378; XM_011517512; NM_173688; NM_001304533 |
| ARHGAP40 | 343578 | NM_001164431 |
| KRT7 | 3855 | XM_017019294; XR_001748700; NM_005556; XM_011538325; XR_001748699 |
| CST4 | 1472 | NM_001899 |
| SFTPC | 6440 | NM_001317779; NM_001385656; NM_001385658; NM_001385659; NM_001172410; NM_001385654; NM_001385655; NM_001317778; NM_001317780; NM_001385657; |

| Gene | NCBI Gene ID | NCBI Accession Number(s) |
|---|---|---|
| | | NM_001385660; NM_001385653; XM_011544613; NM_001172357; NM_003018 |
| DNTT | 1791 | NM_004088; NM_001017520 |
| LRRN4 | 164312 | XM_011529183; NM_152611 |
| NPBWR1 | 2831 | NM_005285 |
| CLDN3 | 1365 | NM_001306 |
| CXCL11 | 6373 | NM_001302123; NM_005409 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| HTR1F | 3355 | NM_001322208; XM_005264751; NM_000866; NM_001322210; NM_001322209; XM_011533664 |
| IFNG | 3458 | NM_000619 |
| GRIN2A | 2903 | XM_017023172; NM_001134407; XM_011522461; NM_001134408; NM_000833; XM_011522458; XM_017023173 |
| REN | 5972 | NM_000537 |
| HILPDA | 29923 | NM_013332; NM_001098786 |
| EGLN3 | 112399 | NM_001308103; NM_022073 |
| C14orf180 | 400258 | XM_005267638; NM_001286399; NM_001286400; XM_011536764; NM_001008404 |
| CIB4 | 130106 | XM_024452692; NM_001029881; XM_017003329; XM_017003331; XM_011532514; XM_017003330 |
| CTAGE9 | 643854 | NM_001145659 |
| IGFBP1 | 3484 | NM_000596; NM_001013029 |
| GDF6 | 392255 | NM_001001557 |
| APOB | 338 | NM_000384 |
| PCSK6 | 5046 | NM_001291309; NM_138322; NM_138325; NM_138320; NM_138324; NM_138319; NM_138321; NM_002570; NM_138323 |
| LOX | 4015 | NM_001317073; NM_001178102; NM_002317 |
| DAZ2 | 57055 | NM_001388495; NM_001389303; NM_001005785; NM_001388494; NM_001005786; NM_001388493; NM_020363 |
| DAZ4 | 57135 | XM_011531509; NM_020420; NM_001388484; NM_001005375; XM_011531510 |
| | Papillary_Renal_Cell_Carcinoma | |
| FABP7 | 2173 | NM_001319039; NM_001319041; NM_001319042; NM_001446 |
| KLK15 | 55554 | XM_011527088; XR_001753713; NM_001277081; NM_017509; NM_138563; XM_011527085; XM_011527087; XM_011527089; NM_023006; XM_006723265; NM_138564; XM_017026943; NM_001277082; NR_102274 |
| NDUFA4L2 | 56901 | NM_001394961; NM_001394960; NM_020142 |
| KISS1R | 84634 | NM_032551; XM_017027382 |
| EBF2 | 64641 | NM_022659 |
| FGG | 2266 | NM_000509; NM_021870 |
| MCHR1 | 2847 | NM_005297 |

| Gene | NCBI Gene ID | NCBI Accession Number(s) |
|---|---|---|
| STAP1 | 26228 | NM_001317769; NM_012108; XM_017008018 |
| CP | 1356 | XM_006713500; XM_006713501; XM_017005735; XM_017005734; XM_006713499; XM_011512435; XR_427361; NM_000096; NR_046371 |
| DAZ1 | 1617 | XM_011531482; NM_004081; XM_011531483; NM_001388496 |
| LOX | 4015 | NM_001317073; NM_001178102; NM_002317 |
| IGFBP1 | 3484 | NM_000596; NM_001013029 |
| RGS5 | 8490 | NM_003617; NM_001195303; NM_001254748; NM_001254749 |
| REN | 5972 | NM_000537 |
| FBN3 | 84467 | NM_032447; XM_017027374; XM_017027376; NM_001321431; XM_017027372; XM_017027373; XM_017027378; XM_017027375; XM_017027377; XM_017027379 |
| PTPRN | 5798 | NM_002846; NM_001199764; NM_001199763 |
| APOB | 338 | NM_000384 |
| GRIK3 | 2899 | NM_000831 |
| APLN | 8862 | NM_017413 |
| CA9 | 768 | XR_428428; NM_001216; XR_001746374 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| UBTFL1 | 642623 | NM_001143975 |
| SPARCL1 | 8404 | NM_001291976; NM_004684; NM_001291977; NM_001128310 |
| SLCO1C1 | 53919 | XR_001748769; XR_001748771; NM_001145946; XM_017019486; NM_001145945; XM_011520703; XR_001748768; XR_001748770; XM_005253394; XM_011520711; XM_024449024; XM_017019487; NM_017435; XM_005253396; NM_001145944; XM_024449025; XM_017019489; XM_011520704; XM_017019490 |
| CIB4 | 130106 | XM_024452692; NM_001029881; XM_017003329; XM_017003331; XM_011532514; XM_017003330 |
| TUBA3E | 112714 | NM_207312 |
| COX4I2 | 84701 | XM_005260580; XM_005260581; NM_032609; XM_005260579 |
| ERP27 | 121506 | NM_152321; NM_001300784 |
| CREB3L3 | 84699 | NM_001271997; NM_032607; NM_001271995; NM_001271996 |
| BAALC | 79870 | XR_001745601; NM_001024372; NM_001364874; NM_024812 |
| MEOX2 | 4223 | NM_005924 |
| CSPG4 | 1464 | NM_001897 |
| GRIN2A | 2903 | XM_017023172; NM_001134407; XM_011522461; NM_001134408; NM_000833; XM_011522458; XM_017023173 |
| LHX9 | 56956 | NM_001014434; NM_020204; XM_005245350; XM_011509781; XM_017001849; NM_001370213 |
| GABRQ | 55879 | NM_018558; XM_011531184 |
| AVPR1A | 552 | NM_000706 |
| COL25A1 | 84570 | XM_011532334; NM_001256074; XM_011532358; NM_032518; NM_198721; XM_011532333; XM_011532356; XM_017008736; |

-continued

| Gene | NCBI Gene ID | NCBI Accession Number(s) |
|---|---|---|
| | | XM_017008737; NR_045756; XM_011532338; XM_017008735; XM_011532335; XM_011532355 |
| ASB5 | 140458 | XM_005262759; XM_011531617; NM_080874; XM_011531616 |
| ADAMTSL1 | 92949 | XM_017015311; NM_052866; XM_011518063; XM_011518067; XM_017015313; NM_001040272; XM_011518064; XM_011518068; NM_139238; XM_017015310; XM_011518070; XM_017015312; XM_017015314; NM_139264 |
| FHL5 | 9457 | NM_001170807; NM_001322466; NM_001322467; NM_020482 |
| DEFB132 | 400830 | NM_207469 |
| CTAGE9 | 643854 | NM_001145659 |
| OPN4 | 94233 | NM_001030015; XM_017016955; XM_017016956; XM_017016957; NM_033282 |
| CXCL11 | 6373 | NM_001302123; NM_005409 |
| ACAN | 176 | XM_011521313; XM_011521314; NM_001135; NM_001369268; NM_013227 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ADGRLA | 64123 | NM_022159 |
| SMOC1 | 64093 | NM_001034852; NM_022137; XM_005267996; XM_005267995 |
| SLC38A8 | 146167 | NM_001080442; XM_017022946 |
| DNAAF3 | 352909 | NM_001256716; NM_001256714; NM_001256715; NM_001031802; NM_178837 |
| IGFBP6 | 3489 | NM_002178 |
| SLC47A2 | 146802 | NM_001099646; XM_017024221; XM_017024225; XM_017024222; XM_017024224; XM_017024226; XR_001752432; XM_017024223; NR_135624; NM_001256663; NM_152908; NR_135625; XR_001752433 |
| SFN | 2810 | NM_006142 |
| CPNE4 | 131034 | XM_017005695; NM_130808; XM_017005694; NM_001388327; XM_024453338; XM_011512408; XM_024453339; NM_001388326; NM_153429; XM_017005696; XM_024453340; NM_001289112 |
| CST6 | 10395 | NM_001316668; NM_182643; XM_005273374; NM_001348081; NM_001348083; NM_001348084; NM_001164271; NM_006094; NM_024767; NM_001348082 |
| CLDN3 | 1365 | NM_001306 |
| PIGR | 5284 | XM_011509629; NM_002644 |
| CPLX2 | 10814 | XM_005265798; XM_005265799; XM_017008964; NM_032282; NM_001008220; NM_006650; XM_011534419 |
| LRRN4 | 164312 | XM_011529183; NM_152611 |
| WFDC5 | 149708 | NM_001395506; NM_145652; XM_011528601; XM_011528602 |
| NPBWR1 | 2831 | NM_005285 |
| PRKCG | 5582 | NM_002739; NM_001316329 |
| ARHGAP40 | 343578 | NM_001164431 |
| KRT23 | 25984 | NM_001282433; XM_005257200; XM_011524595; NM_015515; NM_173213 |
| HS3ST4 | 9951 | NM_006040 |
| SPAG6 | 9576 | NM_001253855; XM_005252646; XM_005252645; NM_172242; NM_001253854; NM_012443 |

-continued

| Gene | NCBI Gene ID | NCBI Accession Number(s) |
|---|---|---|
| HGFAC | 3083 | NM_001297439; NM_001528 |
| CNTN6 | 27255 | NM_001289081; NM_001349352; NM_001349356; XM_017006174; NM_001349361; XM_011533591; NM_001349358; NM_014461; NM_001289080; NM_001349353; NM_001349359; XM_011533590; NM_001349350; NM_001349357; NM_001349354; XR_940415; NM_001349351; NM_001349355; NM_001349360; XM_017006171; XM_017006172; XM_017006177; NM_001349362 |
| LCN2 | 3934 | NM_005564 |
| AKR1B10 | 57016 | XR_927491; XM_011516416; XM_011516417; NM_020299 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| NKX2-4 | 644524 | NM_033176 |
| | Chromophobe_Renal_Cell_Carcinoma | |
| REG1A | 5967 | NM_002909 |
| PADI3 | 51702 | NM_016233; XM_011541571; XM_017001463; XM_011541572 |
| MUC12 | 10071 | NM_001164462 |
| AVPR1B | 553 | NM_000707 |
| CTSE | 1510 | XM_011509245; NM_001910; NM_148964; XM_011509244; NM_001317331 |
| KRT6A | 3853 | NM_005554 |
| KRT6B | 3854 | NM_005555 |
| SLC17A2 | 10246 | XM_006714951; XM_017010160; XM_006714949; XM_006714950; NM_001286123; NM_005835; XM_017010159; NM_001286125 |
| HAVCR1 | 26762 | XM_017009339; XM_024446021; XM_024446023; XM_024446020; XM_024446024; NM_001308156; XM_024446019; XM_011534515; NM_001173393; NM_012206; NM_001099414; XM_024446022 |
| KRT6C | 286887 | NM_173086 |
| TMEM196 | 256130 | NM_001366626; NM_001366628; XM_017011929; NM_001366627; NM_152774; NM_001363562; XM_017011928; NM_001366625 |
| CDH6 | 1004 | NM_004932; NM_001362435; XM_017008910; XM_011513921; XR_001741972 |
| PSORS1C2 | 170680 | NM_014069 |
| LYZL1 | 84569 | XR_428650; XM_017016791; NM_032517; XM_005252627 |
| KRT33B | 3884 | NM_002279 |
| C4orf51 | 646603 | XM_024454188; XR_002959750; XR_002959751; XR_002959755; XR_002959756; XM_024454189; XR_002959749; XR_002959752; NM_001080531; XM_024454190; XR_002959748; XR_002959746; XR_002959747; XR_002959753; XR_002959754 |
| PSG5 | 5673 | NM_001130014; XM_011527132; NM_002781; XM_017027003 |
| UMODL1 | 89766 | XM_017028508; NM_001199527; XM_017028507; NM_001004416; NM_001199528; NM_173568; XM_011529797 |

-continued

| Gene | NCBI Gene ID | NCBI Accession Number(s) |
|---|---|---|
| DEFB132 | 400830 | NM_207469 |
| PIP | 5304 | NM_002652 |
| DBX1 | 120237 | NM_001029865 |
| SLC6A2 | 6530 | XM_011523295; XM_011523297; XR_933403; XM_011523299; XM_011523300; NM_001172502; NM_001043; NM_001172501; XM_006721263; XM_011523298; NM_001172504; XM_011523296 |
| SPSB4 | 92369 | XM_017007509; XR_924215; XR_924216; NM_080862 |
| ATP6V0D2 | 245972 | NM_152565 |
| RGS8 | 85397 | XM_011510089; XM_017002634; NM_001387848; XM_017002631; NM_001387849; NM_001369564; NM_001387847; XM_017002632; NM_001102450; NM_033345; XM_011510090; XM_011510091 |
| FOXI1 | 2299 | XR_941092; NM_012188; NM_144769 |
| CLEC2L | 154790 | XM_017011770; NM_001353368; NM_001080511 |
| AMTN | 401138 | NM_001286731; NM_212557 |
| | Glioblastoma | |
| TCEAL2 | 140597 | NM_080390 |
| RBP1 | 5947 | NM_002899; NM_001130992; NM_001130993; NM_001365940 |
| CBLN1 | 869 | NM_004352 |
| FBXO17 | 115290 | NR_104026; NM_148169; NM_024907 |
| CLEC2B | 9976 | NM_005127 |
| ATOH8 | 84913 | XM_006712122; XM_011533139; XR_939732; XR_001739003; NM_032827; XR_939733; XR_939731 |
| TSTD1 | 100131187 | NM_001113207; NM_001113205; NM_001113206 |
| SNAP91 | 9892 | XM_017011576; XM_024446600; NM_001376676; NM_001376683; NM_001376689; NM_001376690; NM_001376698; NM_001376700; NM_001376710; NM_001376715; NM_001376739; NR_164846; XM_005248770; XM_006715615; XM_011536276; XM_017011575; XM_017011579; XM_017011580; XM_024446599; NR_026669; NM_001256717; NM_001376677; NM_001376687; NM_001376701; NM_001376706; NM_001376713; NM_001376716; NM_001376723; NM_001376736; XM_017011558; XM_017011564; XM_017011566; XM_017011570; NM_001376675; NM_001256718; NM_001376680; NM_001376688; NM_001376694; NM_001376707; NM_001376708; NM_001376711; NM_001376740; XM_017011567; XM_017011590; NM_001376678; NM_001376691; NM_001376705; NM_001376738; NR_164843; XM_011536266; XM_011536269; XM_011536271; XM_011536275; XM_017011562; XM_017011571; XM_017011574; XM_017011582; XM_017011583; XM_017011584; NM_001242792; NM_001363677; NM_001376686; NM_001376712; NM_001376719; NM_001376721; NM_001376731; NM_001376741; XM_011536273; XM_017011559; XM_017011565; XM_017011581; XM_017011585; XM_017011587; XM_017011589; NM_001242794; NM_001376679; NM_001376695; NM_001376696; NM_001376697; NM_001376702; NM_001376709; NM_001376717; NM_001376728; NR_164844; XM_017011569; XM_017011572; XM_017011573; XM_017011577; XM_017011586; NM_001242793; NM_001376681; NM_001376684; NM_001376685; NM_001376692; NM_001376693; NM_001376699; NM_001376703; NM_001376704; NM_001376714; NM_001376720; NM_001376726; NM_001376734; NM_001376737; NM_001376742; NM_014841; NR_164845; XM_011536265; XM_017011557; XM_017011560; NM_001376682; NM_001376718; NM_001376733; NM_001376735 |
| SNX22 | 79856 | NM_024798; XM_005254677; XM_017022581; NR_073534 |
| NDC80 | 10403 | NM_006101 |
| MEOX2 | 4223 | NM_005924 |
| LUZP2 | 338645 | NM_001252008; XM_017017648; XR_930864; NM_001252010; XM_011520056; XM_017017649; NM_001009909 |
| SUSD5 | 26032 | XM_005265034; XM_017006137; NM_015551 |
| ASF1B | 55723 | NM_018154 |
| CARD16 | 114769 | NM_001394580; NM_052889; XM_011542583; NM_001017534 |
| SH3GL2 | 6456 | NM_003026; XR_001746364; XM_011518005 |
| KLRC2 | 3822 | NM_002260 |
| AURKA | 6790 | NM_001323304; NM_001323303; NM_198435; NM_198437; XM_024451974; NM_198433; NM_198434; NM_198436; XM_017028034; XM_017028035; NM_001323305; NM_003600 |
| TNFAIP6 | 7130 | NM_007115 |
| FUT9 | 10690 | XM_011535383; XM_011535385; XM_017010188; NM_006581; XM_017010190 |
| TUBA1C | 84790 | NM_001303114; NM_032704; NM_001303116; NM_001303117; NM_001303115 |
| HDAC4 | 9759 | XM_011512219; XM_011512225; NM_001378415; XM_011512218; XM_017005394; XM_006712879; XM_011512224; XM_017005395; NM_001378416; NM_006037; XM_011512223; XM_011512227; NM_001378414; XM_011512220; XM_011512222; XM_011512230; XM_024453257; XM_011512217; XM_011512226; NM_001378417; XM_006712877; XM_006712880 |
| OPHN1 | 4983 | XM_006724653; XM_011530961; XM_005262270; XM_017029555; NM_002547 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| CRTAC1 | 55118 | NM_018058; XM_017016367; XM_005269938; XM_011539917; NM_001206528; XM_017016366 |
| SLC22A18 | 5002 | NM_002555; NM_183233; XM_011520142; NM_001315501; |

-continued

| Gene | NCBI Gene ID | NCBI Accession Number(s) |
|---|---|---|
| | | XM_011520141; NM_001315502 |
| SSTR1 | 6751 | NM_001049 |
| HMX1 | 3166 | NM_018942; NM_001306142 |
| GDF15 | 9518 | XM_024451789; NM_004864 |
| NALCN | 259232 | XM_017020537; XM_011521067; XM_011521069; NM_001350748; NM_052867; NM_001350751; NM_001350749; XM_017020536; XM_024449336; NM_001350750 |
| GABRG1 | 2565 | NM_173536; XM_017007990 |
| PHYHIPL | 84457 | XM_017016783; XM_017016782; XM_011540275; XM_011540276; NM_032439; NM_001143774 |
| TAGLN2 | 8407 | NM_003564; NM_001277223; NM_001277224 |
| PPM1L | 151742 | NM_001317911; NM_001317912; NR_134243; XM_011512440; NM_139245 |
| OCIAD2 | 132299 | NM_001014446; NM_152398; NM_001286773; NR_104589; NM_001286774 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| PDPN | 10630 | NM_001006625; NM_198389; NM_001385053; NM_001006624; XM_006710295; NM_006474; NM_013317; XM_024451404 |
| TOM1L1 | 10040 | XM_017024002; XR_002957936; NM_001321173; NM_001321175; NM_001321174; XR_243612; NM_001321176; NM_005486; XR_001752397 |
| NTNG2 | 84628 | XM_011519105; XM_011519099; XM_011519094; XM_011519097; XM_011519098; NM_032536; XM_011519096; XM_011519100; XM_011519108; XM_011519112; XM_011519104; XM_011519113; XM_017015213; XM_011519102; XM_011519106; XM_011519107; XM_017015216; XM_011519110; XM_017015212; XM_017015215; XM_006717304; XM_011519103; XM_011519109; XM_017015214 |
| PKIB | 5570 | XM_011535937; NM_181795; XM_011535930; XM_011535931; XM_011535935; XM_011535936; NM_001270393; NM_032471; XM_011535932; NM_001270395; XM_011535933; NM_001270394; NM_181794 |
| SHISA7 | 729956 | NM_001145176; NM_175908 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| REPS2 | 9185 | XM_011545605; XM_024452479; XM_011545604; XM_005274625; XM_011545603; XM_005274626; XM_011545607; XM_024452478; XM_017029955; XM_017029956; NM_001080975; NM_004726; XM_017029958; XR_001755742; XM_011545606; XM_011545609; XM_017029957 |
| ATP6V1G2 | 534 | NM_130463; NM_138282; NM_001204078 |
| DIRAS3 | 9077 | NM_004675 |
| SOX8 | 30812 | NM_014587 |
| FCGBP | 8857 | NM_003890 |
| TIMP1 | 7076 | NM_003254; XM_017029766 |
| CSDC2 | 27254 | NM_014460 |
| DDIT4L | 115265 | NM_145244 |
| LGALS3 | 3958 | NM_001357678; NR_003225; NM_002306; NM_001177388 |
| GOS2 | 50486 | NM_015714 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| Astrocytoma | | |
| RBP1 | 5947 | NM_002899; NM_001130992; NM_001130993; NM_001365940 |
| FBXO17 | 115290 | NR_104026; NM_148169; NM_024907 |
| HLF | 3131 | NM_002126; XM_011524705; XR_002957996; NM_001330375; XM_005257269 |
| CNTN3 | 5067 | XM_017006508; NM_020872; NM_001393376; XM_017006509; XM_011533768 |
| TMEM158 | 25907 | NM_015444 |
| CACNG2 | 10369 | XM_017028531; NM_006078; NM_001379051; NR_166440 |
| IRX2 | 153572 | NM_033267; XR_001742016; XM_024454379; NM_001134222; XM_011513979 |
| MEOX2 | 4223 | NM_005924 |
| LSP1 | 4046 | NM_001242932; NM_001013255; NM_001289005; NM_001013254; NM_002339; NM_001013253 |
| LUZP2 | 338645 | NM_001252008; XM_017017648; XR_930864; NM_001252010; XM_011520056; XM_017017649; NM_001009909 |
| ASF1B | 55723 | NM_018154 |
| LYZ | 4069 | NM_000239 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| CTSC | 1075 | NM_001114173; NM_148170; NM_001814 |
| GABBR1 | 2550 | XM_011514455; XM_006715047; XM_024446392; NM_001319053; NM_001470; XM_011514453; |

-continued

| Gene | NCBI Gene ID | NCBI Accession Number(s) |
|---|---|---|
| | | XR_001743302; NM_021903; XM_005248982; NM_021904; NM_021905; XR_001743303 |
| PBK | 55872 | NM_018492; NM_001278945; NM_001363040 |
| TUBA1C | 84790 | NM_001303114; NM_032704; NM_001303116; NM_001303117; NM_001303115 |
| PYGL | 5836 | NM_002863; NM_001163940 |
| MARCH4 | 57574 | NM_020814 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| RASL10A | 10633 | XM_011529821; NM_001007279; XM_011529822; XM_011529823; NM_006477 |
| UBE2T | 29089 | NM_001310326; NM_014176 |
| SSTR1 | 6751 | NM_001049 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| PHYHIPL | 84457 | XM_017016783; XM_017016782; XM_011540275; XM_011540276; NM_032439; NM_001143774 |
| PPM1L | 151742 | NM_001317911; NM_001317912; NR_134243; XM_011512440; NM_139245 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| STOX1 | 219736 | NM_001130162; NM_001130161; NM_001130160; NM_152709; XM_011539454; NM_001130159 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; |

-continued

| Gene | NCBI Gene ID | NCBI Accession Number(s) |
|---|---|---|
| | | NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FKBP11 | 51303 | NM_001143782; NM_016594; NM_001143781 |
| GPX7 | 2882 | NM_015696 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| CLIC1 | 1192 | NM_001288; NM_001287593; NM_001287594 |
| ATP6V1G2 | 534 | NM_130463; NM_138282; NM_001204078 |
| RIMS2 | 9699 | XM_017014008; XM_017014028; XM_024447342; NM_001100117; NM_001348487; NM_001348496; NM_001348503; XM_005251106; XM_017014014; XM_017014019; XM_017014027; XM_024447344; XM_024447345; NM_001348489; NM_001348491; NM_001348505; NM_001348508; NM_001348509; XM_006716698; XM_017014021; NM_014677; XM_017014010; XM_017014022; XM_024447343; NM_001348499; NM_001395653; NM_001395654; XM_011517398; XM_017014009; XM_017014011; XM_017014016; XM_017014024; NM_001282881; NM_001348490; NM_001348497; NM_001348495; NM_001348498; NR_145710; XM_011517395; XM_017014007; NM_001282882; NM_001348484; NM_001348492; NM_001348494; NM_001348500; NM_001348501; NM_001348502; NM_001348504; XM_005251107; XM_017014012; XM_017014015; XM_017014034; XM_024447347; NM_001348488; NM_001348506; NR_145711; XM_017014006; XM_017014017; XM_017014023; XM_017014036; XM_024447346; NM_001348485; NM_001348486; NM_001348493; NM_001348507; NM_001395652 |
| TJP2 | 9414 | XM_011519206; NM_001369871; NM_001369872; XM_011519208; XM_011519209; NM_001369870; NM_004817; XM_011519207; NM_001369874; NM_001170630; NM_001369875; XM_011519204; NM_001170415; NM_001170416; NM_001170414; NM_001369873; NM_201629 |
| KCNIP2 | 30819 | XM_006717812; NM_173342; XM_005269729; XM_005269730; NM_014591; NM_173197; XM_011539731; NM_173191; |

-continued

| Gene | NCBI Gene ID | NCBI Accession Number(s) |
|---|---|---|
| | | NM_173195; XM_017016161; NM_173192; NM_173194; NM_173193 |
| RGS9 | 8787 | NM_001081955; NM_003835; NM_001165933 |
| FCGBP | 8857 | NM_003890 |
| APOC4-APOC2 | 100533990 | NR_037932 |
| TIMP1 | 7076 | NM_003254; XM_017029766 |
| NTSR2 | 23620 | NM_012344; XM_005246156; XM_006711877; XM_006711876; XM_017003738 |
| CA12 | 771 | NM_001218; NR_135511; NM_206925; NM_001293642 |
| JPH3 | 57338 | NM_001271604; NR_073379; NM_001271605; NM_020655 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| DDIT4L | 115265 | NM_145244 |
| RARRES2 | 5919 | XM_017012491; NM_002889 |
| MDK | 4192 | NM_001012334; XM_011520116; XM_017017764; NM_001270550; NM_001270551; NM_001012333; NM_001270552; NM_002391; NR_073039 |
| FPR1 | 2357 | NM_002029; NM_001193306 |
| CD58 | 965 | XM_017002869; NM_001779; NM_001144822; NR_026665 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| | Oligodendroglioma | |
| ZNF488 | 118738 | NM_153034; XM_006717617; XM_024447789; XM_017015643; NM_001346932; NM_001346933; NM_001346934; XM_011539244; NM_001346936; NM_001346935 |
| RBP1 | 5947 | NM_002899; NM_001130992; NM_001130993; NM_001365940 |
| WNT7B | 7477 | XM_011530366; NM_058238 |
| SLC7A14 | 57709 | NM_020949; NM_175917 |
| HLF | 3131 | NM_002126; XM_011524705; XR_002957996; NM_001330375; XM_005257269 |
| CACNG2 | 10369 | XM_017028531; NM_006078; NM_001379051; NR_166440 |
| SVOP | 55530 | NM_018711 |
| KCNK3 | 3777 | NM_002246; XM_005264293 |
| SUSD5 | 26032 | XM_005265034; XM_017006137; NM_015551 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| VIM | 7431 | XM_006717500; NM_003380 |
| CUX2 | 23316 | XM_011538069; XM_017019081; XM_017019080; XM_011538063; XM_011538070; NM_001370598; NM_015267 |

-continued

| Gene | NCBI Gene ID | NCBI Accession Number(s) |
|---|---|---|
| HRH3 | 11255 | NM_007232; XM_005260266; XM_017027623 |
| MYH7 | 4625 | XM_017021340; NM_000257 |
| MYT1 | 4661 | NM_004535 |
| GPR158 | 57512 | NM_020752; XM_017016452; XR_930512 |
| PYGL | 5836 | NM_002863; NM_001163940 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| VSIG4 | 11326 | NM_007268; NM_001184830; NM_001184831; XM_017029251; NM_001100431; NM_001257403 |
| UPP1 | 7378 | XM_011515513; XM_011515512; NM_001287426; NR_109837; XM_005249838; NM_001287428; NM_001287430; XM_011515515; NM_001362774; NM_001287429; NM_181597; XM_011515514; NM_003364 |
| PDZD4 | 57595 | NM_001303513; NM_001303512; NM_001303516; NM_001303515; NM_001303514; NM_032512 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| KCNJ9 | 3765 | NM_004983 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| STOX1 | 219736 | NM_001130162; NM_001130161; NM_001130160; NM_152709; NXM_011539454; M_001130159 |
| BATF3 | 55509 | XR_921869; XR_001737289; XM_017001683; NM_018664 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FAM222A | 84915 | XM_006719654; XM_017020055; NM_032829; XM_024449229 |
| SCRT1 | 83482 | NM_031309; XM_024447291 |
| GPX7 | 2882 | NM_015696 |
| DIRAS3 | 9077 | NM_004675 |
| ATP6V1G2 | 534 | NM_130463; NM_138282; NM_001204078 |
| EIF3CL | 728689 | NM_001317857; NM_001099661; XM_017023620; XM_017023621; NM_001317856 |

-continued

| Gene | NCBI Gene ID | NCBI Accession Number(s) |
|---|---|---|
| FCGR2A | 2212 | NM_001136219; NM_021642; XM_011509287; XM_024454040; XM_017000664; XM_017000665; XM_017000663; XR_001737042; XM_017000666; XM_011509290; XM_011509291; XM_024454041; NM_001375296; NM_001375297 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| PRLHR | 2834 | NM_004248 |
| FCGBP | 8857 | NM_003890 |
| KLHDC8A | 55220 | NM_001271863; NM_001271865; XM_024448121; NM_018203; NM_001271864 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| BRINP1 | 1620 | NM_014618 |
| CD58 | 965 | XM_017002869; NM_001779; NM_001144822; NR_026665 |
| RDH5 | 5959 | NM_001199771; NM_002905 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| EPN2 | 22905 | NM_001102664; NM_148921; NM_014964 |
| | Basal_Breast_Cancer | |
| CDH6 | 1004 | NM_004932; NM_001362435; XM_017008910; XM_011513921; XR_001741972 |
| ESR1 | 2099 | XM_011535545; XM_017010378; XM_017010382; XR_001743223; XR_002956266; NM_001385568; XM_017010381; NM_001122741; NM_001328100; NM_001385570; XM_006715375; XM_017010383; NM_001385572; XM_011535547; XM_011535549; XM_017010377; NM_001385571; XM_017010380; NM_000125; NM_001122740; NM_001122742; NM_001291230; NM_001291241; XM_011535543; XM_017010379; NM_001385569 |
| SULT1C3 | 442038 | NM_001008743; XM_017004155; NM_001320878; XM_017004153; XM_017004154 |
| WNT10A | 80326 | XM_011511930; XM_011511929; NM_025216 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| CTCFL | 140690 | NM_001269041; NM_001269055; NM_001386993; NR_170377; NM_001269054; NM_080618; NR_072975; NM_001269042; NM_001269044; NM_001269047; |

-continued

| Gene | NCBI Gene ID | NCBI Accession Number(s) |
|---|---|---|
| | | NM_001269043; NM_001269045; NM_001269051; NM_001386994; NM_001269040; NM_001269048; NM_001269050; NM_001386997; NM_001269052; NM_001386995; NM_001386996; NM_001269046; NM_001269049 |
| UGT2B11 | 10720 | XM_011531550; XM_017007660; NM_001073 |
| KRT16 | 3868 | NM_005557 |
| TFF3 | 7033 | NM_003226 |
| CCL19 | 6363 | NM_006274 |
| DNALI1 | 7802 | NM_003462 |
| EN1 | 2019 | NM_001426 |
| S100B | 6285 | NM_006272; XM_017028424 |
| BPI | 671 | XM_024451972; NM_001725 |
| SERHL2 | 253190 | NM_014509; NR_104301; XR_244363; NR_104300; NM_001284334; XM_024452196; XM_017028739; XM_024452197; XR_001755198 |
| UBXN10 | 127733 | XM_005245742; NM_152376; XM_011540699 |
| SLC44A4 | 80736 | NM_001178045; NM_001178044; NM_025257 |
| ROPN1 | 54763 | NM_001394218; NM_001317775; NR_133919; NR_133916; NR_133917; NM_001394219; NM_001317774; NM_001394217; NM_017578; NR_133918; NR_172091 |
| SPINK8 | 646424 | NM_001080525; XM_017007046; XM_024453712; XR_002959568 |
| CT83 | 203413 | NM_001017978 |
| ACTL8 | 81569 | NM_030812; XM_011542212 |
| MIA | 8190 | NM_006533; NM_001202553 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| GABRP | 2568 | XM_005265872; NM_001291985; NM_014211; XM_024446012 |
| TMEM246 | 84302 | NM_001303107; NM_001303108; NM_032342; XM_024447701; NM_001371233 |
| C1orf64 | 149563 | NM_178840 |
| SPON1 | 10418 | NM_006108 |
| KRT6B | 3854 | NM_005555 |
| KRT79 | 338785 | NM_175834 |
| KCNT1 | 57582 | XM_017014932; XM_017014933; NM_020822; XM_017014931; XM_011518877; XM_011518878; XM_011518879; NM_001272003; XM_011518880; XM_011518881; XM_024447617; XM_024447618 |
| SHC4 | 399694 | NM_203349; XM_005254375 |
| HORMAD1 | 84072 | NM_001199829; NM_032132; XM_011510054 |
| LRRC31 | 79782 | XM_011513158; XM_011513159; XM_011513160; NM_001277127; NM_001277128; NM_024727; XM_017007204 |
| NRTN | 4902 | NM_004558 |
| C1QL4 | 338761 | NM_001008223; XM_011538270 |
| TLX1 | 3195 | NM_001195517; XM_011539744; XM_011539745; NM_005521 |
| CLDN8 | 9073 | NM_199328; NM_012132 |
| MGAM2 | 93432 | NM_001293626; NM_001008748; XM_011516692; XM_011516694; NR_003715; XM_024446997; XM_011516693; XR_927547; NR_003717 |
| ST6GALNAC1 | 55808 | NM_018414; XR_002958047; XM_017024842; XM_017024844; |

-continued

| Gene | NCBI Gene ID | NCBI Accession Number(s) |
|---|---|---|
| | | NM_001289107; XM_011524995; XM_011524996; XM_017024843; XR_001752559; NR_110309 |
| GFRA3 | 2676 | NM_001496 |
| MAGEA3 | 4102 | XM_011531161; XM_005274676; XM_006724818; XM_011531160; NM_005362 |
| PRR15 | 222171 | NM_001329997; NM_001329996; NM_175887; XM_011515198; XM_011515199 |
| IGF2 | 3481 | NM_001291862; NM_001291861; NM_000612; NM_001007139; NM_001127598 |
| LY6D | 8581 | NM_003695 |
| TPSG1 | 25823 | NM_012467; XM_011522447; XM_011522446 |
| TAT | 6898 | NM_000353 |
| SMOC1 | 64093 | NM_001034852; NM_022137; XM_005267996; XM_005267995 |
| MT1H | 4496 | NM_005951 |
| REEP6 | 92840 | NM_138393; NM_001329556 |
| FOXA1 | 3169 | NM_004496; XM_017021246 |
| IL12RB2 | 3595 | NR_047584; XM_011541384; XM_005270827; XM_006710617; NM_001374259; XM_011541383; NM_001258215; NM_001258216; XM_017001204; NM_001258214; NM_001319233; XM_005270828; XM_017001203; NM_001559; NR_047583 |
| ART3 | 419 | NM_001377183; XM_017008210; XM_024454058; NM_001377173; NM_001377180; XM_024454052; XM_024454061; XM_024454062; XR_002959732; NM_001130017; NM_001377181; XM_017008208; XR_002959733; NM_001377174; XM_024454051; NM_001377179; XM_024454050; XM_024454053; XM_024454054; XM_024454059; XM_024454063; NM_001377177; NM_001377178; NM_001377182; XM_024454056; NM_001179; NM_001377176; XM_017008206; NM_001130016; NM_001377175; NM_001377184; NM_001377185 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| LOR | 4014 | NM_000427; XM_024447049 |
| GRIK1 | 2897 | NM_001320618; NM_001320616; XM_005260944; NM_001320630; NM_000830; XR_001754829; NM_001320621; NM_001393425; NM_001393426; NM_001330993; NM_001330994; NM_001393424; NM_175611 |
| FDCSP | 260436 | NM_152997 |
| PKP1 | 5317 | NM_000299; NM_001005337 |
| C6orf15 | 29113 | NM_014070 |
| AADAC | 13 | NM_001086; XM_005247104 |
| PGR | 5241 | XM_011542869; NM_001271161; NR_073142; NM_000926; XM_006718858; NM_001202474; NM_001271162; NR_073141; NR_073143 |
| ORM2 | 5005 | NM_000608 |
| ROPN1B | 152015 | XM_006713513; NM_001012337; XM_005247138; NM_001308313 |
| TBC1D9 | 23158 | NM_015130 |
| NPAS3 | 64067 | XM_005267991; NM_001394989; XM_011537069; XM_017021582; XM_017021584; XM_017021585; |

-continued

| Gene | NCBI Gene ID | NCBI Accession Number(s) |
|---|---|---|
| | | XM_017021587; NM_022123; XM_011537067; XM_011537071; NM_001165893; NM_001394988; NM_173159; XM_017021583; XM_017021586; XM_017021588; XM_005267992; NM_001164749 |
| HMGCS2 | 3158 | NM_001166107; XM_011541313; NM_005518 |
| NPR1 | 4881 | XM_017001374; XM_005245218; NM_000906 |
| ELOVL2 | 54898 | NM_017770; XM_011514717; XM_011514716; XM_017010985 |
| CA12 | 771 | NM_001218; NR_135511; NM_206925; NM_001293642 |
| CT62 | 196993 | NR_168259; NM_001102658; NR_168260 |
| | Non_Basal_Breast_Cancer | |
| CHODL | 140578 | XM_017028273; NM_001204174; NM_024944; XM_011529453; NM_001204176; NM_001204175; NM_001204177; XM_011529457; NM_001204178 |
| MSLN | 10232 | NM_001177355; NM_005823; NM_013404 |
| CST4 | 1472 | NM_001899 |
| CEACAM6 | 4680 | NM_002483; XM_011526990 |
| OVGP1 | 5016 | NM_002557 |
| FOLR1 | 2348 | NM_000802; NM_016729; NM_016730; NM_016725; NM_016724 |
| LRRTM1 | 347730 | NM_178839; XM_017003987; XM_017003986 |
| TTC6 | 319089 | XM_017021257; XM_011537431; XM_017021254; XM_024449560; XM_011537430; XM_011537432; XR_943762; NM_001310135; XM_017021256; NM_001368142; XM_017021255; XR_001750287; NM_001007795 |
| SPRR2A | 6700 | NM_005988 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| WNT10A | 80326 | XM_011511930; XM_011511929; NM_025216 |
| PKHD1L1 | 93035 | XM_017013970; XM_017013969; XM_011517371; XM_017013971; XM_017013972; XM_017013973; XM_017013974; NM_177531 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| SMYD1 | 150572 | NM_198274; NM_001330364 |
| DACT2 | 168002 | NM_001286350; NM_001286351; XM_011535507; NM_214462; NR_104425 |
| AKR7A3 | 22977 | XM_017000714; NM_012067; XM_011541046; XR_001737055 |
| HPX | 3263 | NM_000613 |
| S100B | 6285 | NM_006272; XM_017028424 |
| MAL | 4118 | NM_022438; NM_002371; NM_022440; NM_022439 |
| D4S234E | 27065 | NM_001287763; NM_001287764; NM_001040101; NR_167932; |

-continued

| Gene | NCBI Gene ID | NCBI Accession Number(s) |
|---|---|---|
| | | NM_001382227; NM_001382228; NR_167933; NM_014392 |
| SLC44A4 | 80736 | NM_001178045; NM_001178044; NM_025257 |
| SPINK8 | 646424 | NM_001080525; XM_017007046; XM_024453712; XR_002959568 |
| THSD4 | 79875 | NM_024817; NM_001286429; XM_017022584; NM_001394532; XM_017022586; XM_011522044; XM_017022585; XM_011522043; XM_017022582; XM_017022583 |
| TBX5 | 6910 | NM_181486; NM_080717; NM_000192; XM_017019912; NM_080718 |
| NEK10 | 152110 | XM_006712998; XM_011533415; XM_017005765; XR_001740034; NM_001394966; XM_017005768; NM_001394968; XM_024453374; NM_001031741; NM_001394965; NM_001394967; NM_001394971; XM_006712997; XM_006713002; XM_011533413; XM_011533414; NM_001394970; NM_001394964; NM_001394969; XM_006712999; XM_017005762; XM_017005764; NM_001394963; NM_199347; XM_017005763; XM_017005773; XM_024453373; NM_001304384; XM_006713001; XM_017005774; NM_152534 |
| TFAP2B | 7021 | XM_017011235; XM_017011233; NM_003221; XM_011514837; XM_017011234 |
| MB | 4151 | NM_001382810; NM_001382809; NM_203378; NM_001362846; NM_001382812; NM_203377; NM_001382811; NM_005368; NM_001382813 |
| OCA2 | 4948 | XM_017022264; XM_017022257; XM_017022258; XM_017022262; XM_017022255; XM_017022263; XM_011521640; XM_017022256; XM_017022261; XR_001751294; NM_001300984; XM_017022265; NM_000275; XM_017022259; XM_017022260 |
| CCNA1 | 8900 | XM_011535294; XM_011535296; NM_001111047; XM_011535295; NM_001111046; NM_003914; NM_001111045 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| GABRP | 2568 | XM_005265872; NM_001291985; NM_014211; XM_024446012 |
| C1orf64 | 149563 | NM_178840 |
| MSMB | 4477 | NM_138634; NM_002443 |
| PSAT1 | 29968 | NM_021154; NM_058179 |
| CPA2 | 1358 | NM_001869 |
| SLC30A8 | 169026 | XM_024447083; NM_001172813; NM_001172814; NM_001172815; NM_001172811; NM_173851 |
| NRTN | 4902 | NM_004558 |
| ZG16B | 124220 | NM_145252 |
| ABCC11 | 85320 | XM_017023802; NM_001370496; NM_032583; XM_017023798; XM_011523397; XM_017023797; XM_017023800; XM_017023803; XM_017023799; XM_017023801; NM_001370497; XM_011523398; |

-continued

| Gene | NCBI Gene ID | NCBI Accession Number(s) |
|---|---|---|
| | | NM_145186; XM_024450475; XR_001752012; NM_033151 |
| MGAM2 | 93432 | NM_001293626; NM_001008748; XM_011516692; XM_011516694; NR_003715; XM_024446997; XM_011516693; XR_927547; NR_003717 |
| KCNH1 | 3756 | NM_172362; XM_017001246; NM_002238 |
| CALB2 | 794 | NM_007088; XR_002957842; NM_001740; NR_027910; NM_007087 |
| PGC | 5225 | NM_002630; NM_001166424 |
| FSIP1 | 161835 | XM_011521307; XM_017021972; XM_011521309; NM_152597; XM_011521305; NM_001324338; XM_011521311; XM_011521306 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| HMP19 | 51617 | NM_015980 |
| PRR15 | 222171 | NM_001329997; NM_001329996; NM_175887; XM_011515198; XM_011515199 |
| SERTM1 | 400120 | NM_203451 |
| MMP3 | 4314 | NM_002422 |
| POU3F3 | 5455 | NM_006236 |
| PCK1 | 5105 | NM_002591; XM_024451888 |
| CHAD | 1101 | XM_011524214; NM_001267 |
| SLITRK6 | 84189 | NM_032229 |
| SOX10 | 6663 | NM_006941 |
| TAT | 6898 | NM_000353 |
| PIP | 5304 | NM_002652 |
| F2RL2 | 2151 | NM_001256566; NM_004101 |
| MT1H | 4496 | NM_005951 |
| FOXA1 | 3169 | NM_004496; XM_017021246 |
| KRT15 | 3866 | XM_017024614; XM_011524784; NM_002275 |
| TF | 7018 | NM_001063; NM_001354703; NM_001354704 |
| FAM196A | 642938 | XM_017016537; XM_017016538; XM_017016539; XM_005252694; XM_017016540; XM_017016541; XM_017016542; XM_017016543; NM_001039762 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| PRSS33 | 260429 | NM_001385462; NM_001385463; NM_001385464; NM_152891; NR_169625 |
| SCX | 642658 | XM_006716616; NM_001080514; NM_001008271 |
| WNT6 | 7475 | NM_006522 |
| SIAH3 | 283514 | NM_198849 |
| ROPN1B | 152015 | XM_006713513; NM_001012337; XM_005247138; NM_001308313 |
| HOXC13 | 3229 | NM_017410 |
| NPR1 | 4881 | XM_017001374; XM_005245218; NM_000906 |
| RASGEF1C | 255426 | NM_175062; NM_001031799 |
| LEMD1 | 93273 | XM_011510163; XM_011510162; XM_011510165; NM_001199052; XM_011510160; XM_011510161; |

-continued

| Gene | NCBI Gene ID | NCBI Accession Number(s) |
|---|---|---|
| | | XM_011510164; NR_037583; NM_001001552; NM_001199050; NM_001199051 |
| PRSS50 | 29122 | NM_013270 |
| Squamous_Cell_Carcinoma_of_the_Head_and_Neck | | |
| IGFBP6 | 3489 | NM_002178 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| SCGB1A1 | 7356 | NM_003357 |
| FGG | 2266 | NM_000509; NM_021870 |
| PLIN1 | 5346 | NM_002666; XM_005254934; NM_001145311 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| MMP13 | 4322 | NM_002427 |
| MYL1 | 4632 | NM_079422; NM_079420 |
| FCN3 | 8547 | NM_173452; NM_003665 |
| IRX4 | 50805 | NM_016358; NM_001278633; NM_001278632; NM_001278635; NM_001278634 |
| BPIFA1 | 51297 | NM_130852; NM_001243193; NM_016583 |
| PAX1 | 5075 | NM_006192; NM_001257096 |
| ADH1B | 125 | NM_001286650; NM_000668 |
| C4BPA | 722 | XM_005273252; NM_000715; XM_005273251 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| F2RL2 | 2151 | NM_001256566; NM_004101 |
| HOXA13 | 3209 | NM_000522 |
| PCSK2 | 5126 | NM_002594; NM_001201529; NM_001201528 |
| BMP8A | 353500 | XM_017001198; XM_006710616; XM_011541381; XM_011541382; XR_946642; XR_946640; XR_946641; NM_181809 |
| TBX4 | 9496 | XM_011525490; XM_011525491; NM_001321120; XM_011525495; NM_018488 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |

-continued

| Gene | NCBI Gene ID | NCBI Accession Number(s) |
|---|---|---|
| PGC | 5225 | NM_002630; NM_001166424 |
| RPE65 | 6121 | XM_017002027; NM_000329 |
| GSTM5 | 2949 | NM_000851; XM_005270785; XM_005270784 |
| MYH7 | 4625 | XM_017021340; NM_000257 |
| ATP1A2 | 477 | NM_000702 |
| KIF18B | 146909 | XM_011524389; NM_001264573; NM_001265577; XM_011524386; NM_001080443; XM_011524390; XM_011524388; XM_011524385; XM_011524387; XM_011524391 |
| SCARA5 | 286133 | NM_173833 |
| FILIP1 | 27145 | NR_110608; XM_011535756; NM_001289987; NM_001300866; XM_005248713; NM_015687; XM_005248715 |
| DCD | 117159 | NM_001300854; NM_053283 |
| SLURP1 | 57152 | NM_020427 |
| DLX1 | 1745 | NM_178120; NM_001038493 |
| WT1 | 7490 | NM_000378; NR_160306; NM_001367854; NM_001198551; NM_001198552; NM_024424; NM_024426; NM_024425 |
| TCF21 | 6943 | NM_003206; NM_198392 |
| EN1 | 2019 | NM_001426 |
| KRT14 | 3861 | NM_000526 |
| RPS4Y1 | 6192 | NM_001008 |
| TBX5 | 6910 | NM_181486; NM_080717; NM_000192; XM_017019912; NM_080718 |
| CDKN2A | 1029 | XR_929159; XM_011517676; XM_011517675; NM_001363763; NM_001195132; NM_058195; NM_000077; NM_058196; NM_058197; XM_005251343 |
| ALDH1A2 | 8854 | NM_001206897; NM_170697; NM_170696; NM_003888 |
| CFTR | 1080 | NM_000492 |
| AMY1A | 276 | NM_004038; NM_001008221 |
| NAV3 | 89795 | XM_017020172; NM_001024383; NM_014903; XM_011538944 |
| HPN | 3249 | NM_002151; NM_182983; XM_017026732; NM_001384133; XM_017026731; NM_001375441 |
| MKRN3 | 7681 | NM_005664 |
| SCN7A | 6332 | NM_002976; XM_006712680; XM_006712682; XM_011511615; XM_017004667; NR_045628 |
| ACTC1 | 70 | NM_005159 |
| MYOG | 4656 | NM_002479 |
| HOXB5 | 3215 | NM_002147 |
| PKMYT1 | 9088 | NM_001258451; NM_182687; NM_001258450; XM_011522735; XM_024450490; NM_004203; XM_011522734; XM_011522736 |
| HJURP | 55355 | XM_011511437; NM_001282962; NM_001282963; NM_018410 |
| HP | 3240 | NM_001126102; NM_005143; NM_001318138 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| DLL3 | 10683 | NM_016941; NM_203486 |
| CYP2B6 | 1555 | NM_000767 |
| SNTN | 132203 | NM_001080537; NM_001348756 |
| CRNN | 49860 | NM_016190 |
| HOXB8 | 3218 | NM_024016; XM_005257286; XM_017024564 |
| DDX3Y | 8653 | NR_136716; NR_136718; NR_136719; NR_136721; NM_001122665; NR_136720; NR_136723; NM_004660; NM_001324195; XR_001756014; |

-continued

| Gene | NCBI Gene ID | NCBI Accession Number(s) |
|---|---|---|
| | | NM_001302552; NR_136717; NR_136724; NR_136722 |
| EIF1AY | 9086 | NM_004681; NM_001278612 |
| BSP | 3381 | NM_004967 |
| C7 | 730 | NM_000587 |
| COL10A1 | 1300 | XM_011535432; NM_000493; XM_011535433; XM_017010248; XM_006715333 |
| AJAP1 | 55966 | XM_011541787; NM_001042478; NM_018836; XM_011541786 |
| ADIPOQ | 9370 | NM_004797; NM_001177800 |
| Squamous_Cell_Lung_Carcinoma | | |
| C20orf85 | 128602 | NM_178456 |
| KLK10 | 5655 | XM_006723289; XM_005259061; NM_002776; NM_145888; NM_001077500; XM_017026993; XM_006723287; XM_005259062 |
| ACTC1 | 70 | NM_005159 |
| IGFBP6 | 3489 | NM_002178 |
| ADH1B | 125 | NM_001286650; NM_000668 |
| B4GALNT4 | 338707 | XM_017017654; XR_001747858; NM_178537 |
| C4BPA | 722 | XM_005273252; NM_000715; XM_005273251 |
| CENPM | 79019 | NM_001110215; NM_001304372; NM_024053; XM_011530368; NM_001304371; NM_001002876; NM_001304370; NM_001304373 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MYOG | 4656 | NM_002479 |
| CACNG1 | 786 | NM_000727 |
| HOXB5 | 3215 | NM_002147 |
| FABP4 | 2167 | NM_001442 |
| MMP11 | 4320 | NM_005940; NR_133013 |
| SCGB1A1 | 7356 | NM_003357 |
| RSPO1 | 284654 | XM_006710583; NM_001242909; NM_001242908; NM_001242910; NM_173640; NM_001038633 |
| LRRN4CL | 221091 | NM_203422 |
| ENDOU | 8909 | NM_001172439; NM_006025; NM_001172440 |
| MMP12 | 4321 | NM_002426 |
| GSTA1 | 2938 | XM_005249034; NM_001319059; NM_145740 |
| TNXB | 7148 | NM_001365276; NM_019105; NM_032470 |
| HP | 3240 | NM_001126102; NM_005143; NM_001318138 |
| KLHL41 | 10324 | NM_006063 |
| NEFL | 4747 | NM_006158 |
| TBX5 | 6910 | NM_181486; NM_080717; NM_000192; XM_017019912; NM_080718 |
| NKX2-1 | 7080 | NM_001079668; NM_003317 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| VPREB3 | 29802 | NM_013378 |
| TBX4 | 9496 | XM_011525490; XM_011525491; NM_001321120; XM_011525495; NM_018488 |
| TROAP | 10024 | XM_011537723; NM_005480; XR_944445; XM_011537724; XR_944446; NM_001100620; XM_006719181; NM_001278324 |

-continued

| Gene | NCBI Gene ID | NCBI Accession Number(s) |
|---|---|---|
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PAK7 | 57144 | XM_017027960; XM_017027964; XM_017027962; XM_017027963; XM_017027965; NM_177990; XM_017027961; NM_020341 |
| CASQ2 | 845 | NM_001232 |
| PGC | 5225 | NM_002630; NM_001166424 |
| AMY1C | 278 | NM_001346780; XM_017001058; NM_001008219 |
| COX6A2 | 1339 | NM_005205 |
| MUC7 | 4589 | NM_001145006; NM_152291; NM_001145007 |
| CLEC2L | 154790 | XM_017011770; NM_001353368; NM_001080511 |
| POU6F2 | 11281 | NM_007252; NM_001370959; NM_001166018 |
| ZNF280B | 140883 | XR_002958666; NM_080764; XM_011529897; XR_002958668; XR_002958667; NR_130642; NR_130643 |
| CRNN | 49860 | NM_016190 |
| SNTN | 132203 | NM_001080537; NM_001348756 |
| GREM2 | 64388 | XM_005273226; XM_011544249; NM_022469 |
| OGN | 4969 | NM_033014; NM_014057; NM_024416 |
| MYH7 | 4625 | XM_017021340; NM_000257 |
| KIF18B | 146909 | XM_011524389; NM_001264573; NM_001265577; XM_011524386; NM_001080443; XM_011524390; XM_011524388; XM_011524385; XM_011524387; XM_011524391 |
| PLA2G4F | 255189 | NM_213600; XR_931785; NR_033151; XR_931786 |
| LGSN | 51557 | XM_017010931; XM_017010929; XM_011535889; XM_011535892; NM_016571; XM_017010930; NM_001143940 |
| AHSG | 197 | NM_001354571; NM_001354572; NM_001622; NM_001354573 |
| UBE2C | 11065 | NM_001281742; NM_001281741; NM_181802; NM_181803; NR_104036; NR_104037; NM_007019; NM_181800; NM_181801; NM_181799 |
| DES | 1674 | NM_001927; NM_001382708; NM_001382710; NM_001382713; NM_001382709; NM_001382711; NM_001382712 |
| RNF223 | 401934 | NM_001205252 |
| MYL1 | 4632 | NM_079422; NM_079420 |
| C1orf116 | 79098 | XM_011509973; NM_001083924; XM_005273259; XM_006711530; NM_023938 |
| BMP5 | 653 | XM_011514817; NM_001329756; XM_024446524; NM_001329754; NM_021073 |
| SCARA5 | 286133 | NM_173833 |
| FCN3 | 8547 | NM_173452; NM_003665 |
| HPN | 3249 | NM_002151; NM_182983; XM_017026732; NM_001384133; XM_017026731; NM_001375441 |

| Gene | NCBI Gene ID | NCBI Accession Number(s) |
|---|---|---|
| LOR | 4014 | NM_000427; XM_024447049 |
| LDB3 | 11155 | NM_001171610; NM_001368064; NM_007078; NM_001080115; NM_001080114; NM_001368068; NM_001080116; NM_001171611; NM_001368067; NM_001368063; NM_001368065; NM_001368066 |
| DHRS7C | 201140 | NM_001220493; NM_001105571 |
| CRISP3 | 10321 | NM_001368123; NM_006061; NM_001190986 |
| LY6D | 8581 | NM_003695 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| CNTNAP2 | 26047 | XM_017011950; NM_014141 |
| ANLN | 54443 | XM_017012355; NM_018685; NM_001284302; XM_006715746; XM_017012354; XM_017012356; NM_001284301; XM_006715747 |
| DCD | 117159 | NM_001300854; NM_053283 |
| C7 | 730 | NM_000587 |
| THBS4 | 7060 | XR_002956176; XM_017009798; NM_001306214; NM_003248; NM_001306213; XM_017009799; NM_001306212 |
| GPR87 | 53836 | NM_023915 |
| MYOT | 9499 | XM_017010060; XM_017010061; NM_001300911; NM_001135940; XM_017010062; NM_006790 |
| USP43 | 124739 | XM_011523640; XM_011523642; XM_011523641; XM_017024161; XM_017024160; XM_017024159; XM_011523639; NM_001267576; NM_153210; XM_017024162 |
| EMX1 | 2016 | XM_011532697; NM_001040404; NM_004097; XM_005264203 |
| SLURP1 | 57152 | NM_020427 |
| BPIFA1 | 51297 | NM_130852; NM_001243193; NM_016583 |
| KLK5 | 25818 | NM_001077492; XM_011526702; NM_001077491; XM_011526703; NM_012427 |
| GYLTL1B | 120071 | XM_011519891; NM_001300721; NM_001300722; XM_011519888; XM_006718141; XM_011519890; XM_006718140; XM_011519893; NM_152312; XM_005252787; XM_011519886; XM_011519889; XM_011519892; XM_017017173 |
| HAND2 | 9464 | NM_021973 |
| MYOC | 4653 | NM_000261 |
| MCEMP1 | 199675 | NM_174918 |
| DCC | 1630 | XM_011525843; XM_011525844; XM_017025570; NM_005215; XM_017025568; XM_017025569 |
| LRRC26 | 389816 | NM_001013653 |
| KLK13 | 26085 | NM_015596; NR_145464; NM_001348178; NR_145466; NR_145465; XR_935788; NR_145463; NM_001348177; NR_145467 |
| WT1 | 7490 | NM_000378; NR_160306; NM_001367854; NM_001198551; NM_001198552; NM_024424; NM_024426; NM_024425 |
| KRT4 | 3851 | NM_002272 |
| COL10A1 | 1300 | XM_011535432; NM_000493; XM_011535433; XM_017010248; XM_006715333 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| SGCG | 6445 | NM_000231; NM_001378245; NM_001378244; NM_001378246 |
| SCN7A | 6332 | NM_002976; XM_006712680; XM_006712682; XM_011511615; XM_017004667; NR_045628 |
| FEZF1 | 389549 | NM_001024613; XM_011516202; NM_001160264; XM_005250337 |
| SLCO4C1 | 353189 | XM_011543372; XM_011543370; NM_180991 |
| AJAP1 | 55966 | XM_011541787; NM_001042478; NM_018836; XM_011541786 |
| AMN | 81693 | XM_024449714; XM_011537203; NM_030943; XM_011537202 |
| SDR16C5 | 195814 | NM_001318049; NM_001318050; NM_138969; XM_011517479 |
| AQP4 | 361 | NM_001317387; NM_001364287; NM_001364286; NM_001317384; XM_011525942; NM_001650; NM_001364289; NM_004028 |
| CPNE7 | 27132 | NM_153636; XM_017023139; XM_011523000; XM_017023138; XM_017023140; XM_017023141; XM_011523001; NM_014427 |
| TCF21 | 6943 | NM_003206; NM_198392 |
| PTGER3 | 5733 | XM_011541810; NM_198718; NM_000957; NM_198712; NM_198713; NM_198720; NM_198714; NM_198719; NM_198717; NM_001126044; NM_198715; NR_028292; XR_946714; NM_198716; NR_028293; NR_028294 |
| Cervical_Squamous_Cell_Carcinoma | | |
| SALL1 | 6299 | NM_001127892; NM_002968 |
| MEOX2 | 4223 | NM_005924 |
| BCHE | 590 | NR_137636; NM_000055; NR_137635 |
| SYCP2 | 10388 | XM_011528488; XM_011528487; XM_011528493; XM_017027590; XM_011528490; XM_017027586; XM_017027591; NM_014258; XM_011528489; XM_017027589; XM_017027587; XM_017027588; XM_017027592 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| OLFM4 | 10562 | NM_006418 |
| SYNGR3 | 9143 | NM_004209 |
| SLC6A15 | 55117 | XM_011538525; NM_018057; NM_001146335; NM_182767 |
| ADAMTS20 | 80070 | XM_011538754; XM_017019979; NM_025003; NM_175851 |
| FA2H | 79152 | XM_011523319; XM_011523317; NM_024306 |
| PGR | 5241 | XM_011542869; NM_001271161; NR_073142; NM_000926; |

-continued

| Gene | NCBI Gene ID | NCBI Accession Number(s) |
|---|---|---|
| | | XM_006718858; NM_001202474; NM_001271162; NR_073141; NR_073143 |
| FOXL2 | 668 | NM_023067 |
| KRT81 | 3887 | NM_002281 |
| HOXA13 | 3209 | NM_000522 |
| KRT36 | 8689 | NM_003771 |
| KRT83 | 3889 | NM_002282 |
| RPS4Y1 | 6192 | NM_001008 |
| TBX5 | 6910 | NM_181486; NM_080717; NM_000192; XM_017019912; NM_080718 |
| ASF1B | 55723 | NM_018154 |
| E2F8 | 79733 | NM_001256372; XM_011520367; NM_001256371; NM_024680; XR_930907 |
| CASP14 | 23581 | NM_012114; XM_011527861 |
| MYOCD | 93649 | XM_005256863; NM_001378306; NM_001146312; NM_153604; NM_001146313; XM_017025342 |
| KIF4A | 24137 | NM_012310 |
| PDLIM3 | 27295 | NM_001114107; XR_938723; NM_001257963; XR_938724; NM_001257962; NR_047562; NM_014476; XR_001741206 |
| PAGE2B | 389860 | XM_017029513; XM_011530785; XM_011530786; XM_011530787; NM_001015038 |
| RPE65 | 6121 | XM_017002027; NM_000329 |
| POU6F2 | 11281 | NM_007252; NM_001370959; NM_001166018 |
| CDKN2A | 1029 | XR_929159; XM_011517676; XM_011517675; NM_001363763; NM_001195132; NM_058195; NM_000077; NM_058196; NM_058197; XM_005251343 |
| HOXB8 | 3218 | NM_024016; XM_005257286; XM_017024564 |
| ALDH1A2 | 8854 | NM_001206897; NM_170697; NM_170696; NM_003888 |
| HTR2B | 3357 | XM_005246520; NM_000867; XM_006712482; NM_001320758 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| NAV3 | 89795 | XM_017020172; NM_001024383; NM_014903; XM_011538944 |
| BARX1 | 56033 | NM_021570 |
| OR2B6 | 26212 | NM_012367 |
| SEMA3D | 223117 | XM_011515961; NM_152754; NM_001384901; NM_001384902; NM_001384900; NM_001384903 |
| DYNC1I1 | 1780 | NM_001135556; NM_004411; NM_001278422; NM_001278421; NM_001135557 |
| NAP1L2 | 4674 | NM_021963 |
| MYL1 | 4632 | NM_079422; NM_079420 |
| ANO1 | 55107 | XM_006718602; XM_006718605; XM_011545124; XM_011545129; XM_017017956; XM_006718604; NM_001378095; NM_001378096; XM_011545123; XM_011545127; XM_011545131; NM_001378097; NM_018043; NR_030691; NM_001378092; XM_011545126; NM_001378093; NM_001378094 |
| HOXA11 | 3207 | NM_005523 |
| CDC25C | 995 | XM_011543764; XM_011543760; XM_011543761; XM_011543763; NM_001364026; NM_001364027; XM_005272145; NM_001287582; NM_001287583; NM_001790; |

-continued

| Gene | NCBI Gene ID | NCBI Accession Number(s) |
|---|---|---|
| | | NM_022809; XM_006714739; XM_011543759; XM_011543762; NM_001318098; NM_001364028 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| EIF1AY | 9086 | NM_004681; NM_001278612 |
| RBFOX3 | 146713 | XM_017024209; XM_017024211; XM_024450595; NM_001385812; NM_001385840; NM_001385844; NM_001385847; XM_011524366; XM_017024208; NM_001385805; NM_001385807; NM_001385843; NM_001385845; NM_001025448; NM_001082575; NM_001385804; NM_001385808; NM_001385813; NM_001385836; NM_001385817; NM_001385819; NM_001385823; NM_001385826; NM_001385827; NM_001385828; NM_001385829; NM_001385831; NM_001385833; NM_001385842; XM_011524360; XM_024450593; XM_024450596; NM_001350453; NM_001385809; NM_001385832; NM_001385834; NM_001385838; NM_001039904; XM_011524367; XM_024450592; NM_001385811; NM_001385824; NM_001385835; NM_001385837; NM_001385846; NM_001350451; NM_001385806; NM_001385810; NM_001385820; NM_001385825; NM_001385830; NM_001385839; NM_001385841; NM_001385814; NM_001385815; NM_001385816; NM_001385818; NM_001385821; NM_001385822 |
| RDM1 | 201299 | NM_001163124; NR_027996; NR_027999; XM_011524509; NM_001163122; NM_001163130; NM_001163121; NM_001163125; NR_027998; NM_001163120; NM_001034836; NM_001330194; NM_145654; NR_027997; NR_028000 |
| SCARA5 | 286133 | NM_173833 |
| KCNS1 | 3787 | XM_017027846; NM_002251; NM_001322799 |
| PIANP | 196500 | NM_001244014; NM_153685; NM_001244015; XM_011520926 |
| C1orf106 | 55765 | XM_011509754; XM_011509755; NM_001367289; NM_001367290; XM_011509756; NM_001142569; NM_018265 |
| HOXA10 | 3206 | NR_037939; NM_153715; NM_018951 |

-continued

| Gene | NCBI Gene ID | NCBI Accession Number(s) |
|---|---|---|
| AIM1L | 55057 | NM_017977; XM_011541672; XM_011541673; XR_001737260; NM_001039775; XR_946681; XM_005245918 |
| LEFTY2 | 7044 | NM_003240; NM_001172425; XM_011544266 |
| IRX5 | 10265 | NM_005853; XM_011522809; NM_001252197 |
| TRDN | 10345 | NM_001251987; NM_001256020; NM_001256021; NM_006073; NM_001256022 |
| CNTNAP2 | 26047 | XM_017011950; NM_014141 |
| FOXA1 | 3169 | NM_004496; XM_017021246 |
| ADGRD1 | 283383 | NM_198827; XM_005253566; XM_011538204; XM_011538208; XM_011538212; NM_001330497; XM_011538205; XM_011538206; XM_011538207; XM_011538209; XM_011538210; XM_011538211 |
| PENK | 5179 | NM_006211; NM_001135690 |
| AKR1C2 | 1646 | NM_001354; NM_001321027; NM_001135241; NM_205845; NM_001393392 |
| MKRN3 | 7681 | NM_005664 |
| NMU | 10874 | NM_001292046; XM_011534368; XM_011534367; NM_001292045; NM_006681; NR_120489 |
| DIAPH3 | 81624 | XM_011535258; XM_006719876; XM_024449422; NM_001258367; NM_001258370; XR_941672; XM_011535265; XR_002957479; XR_002957480; NM_001258366; XM_017020789; XR_002957478; NM_001042517; NM_001258368; XM_011535263; XR_001749694; XR_002957477; NM_001258369; NM_030932 |
| MUC2 | 4583 | NM_002457 |
| ZIC5 | 85416 | NM_033132; NR_146224; NR_146225 |
| MYLPF | 29895 | NM_001324458; NM_013292; NM_001324459 |
| POLQ | 10721 | NM_199420; NM_006596 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| SMC1B | 27127 | NM_148674; XM_011530145; XR_244368; XM_011530144; NM_001291501 |
| WT1 | 7490 | NM_000378; NR_160306; NM_001367854; NM_001198551; NM_001198552; NM_024424; NM_024426; NM_024425 |
| EPHA7 | 2045 | NM_001288630; NM_001376467; NM_001288629; XM_017010366; NM_001376466; NM_001376471; NM_004440; XR_001743218; NM_001376465; NM_001376470; NR_164810; NM_001376468; NM_001376469 |
| TCF23 | 150921 | NM_175769; XM_005264159 |
| | Colorectal_Adenocarcinoma | |
| EFHC1 | 114327 | NR_033327; NM_001172420; NM_018100 |
| KCNN3 | 3782 | NM_001204087; NM_001365837; NM_001365838; NM_170782; NM_002249 |

-continued

| Gene | NCBI Gene ID | NCBI Accession Number(s) |
|---|---|---|
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; |

-continued

| Gene | NCBI Gene ID | NCBI Accession Number(s) |
|---|---|---|
| | | NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; |

-continued

| Gene | NCBI Gene ID | NCBI Accession Number(s) |
|---|---|---|
| | | NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; |

-continued

| Gene | NCBI Gene ID | NCBI Accession Number(s) |
|---|---|---|
| | | XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; |

-continued

| Gene | NCBI Gene ID | NCBI Accession Number(s) |
|---|---|---|
| | | XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRAID | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |

-continued

| Gene | NCBI Gene ID | NCBI Accession Number(s) |
|---|---|---|
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |

-continued

| Gene | NCBI Gene ID | NCBI Accession Number(s) |
|---|---|---|
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; |

-continued

| Gene | NCBI Gene ID | NCBI Accession Number(s) |
|---|---|---|
| | | XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456 |
| Stomach_Adenocarcinoma | | |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |

-continued

| Gene | NCBI Gene ID | NCBI Accession Number(s) |
|---|---|---|
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447 |

-continued

| Gene | NCBI Gene ID | NCBI Accession Number(s) |
|---|---|---|
| | | ; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; |

-continued

| Gene | NCBI Gene ID | NCBI Accession Number(s) |
|---|---|---|
| | | NM_001350569; NM_080604; XM_006715262; XM_006715263; XM_006715266; XM_024446586; NM_001146016; NM_001350563; NM_001350564; NM_001394539; / NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; |

-continued

| Gene | NCBI Gene ID | NCBI Accession Number(s) |
|---|---|---|
| | | NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; |
| XR_001752680 | | |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; |

-continued

| Gene | NCBI Gene ID | NCBI Accession Number(s) |
|---|---|---|
| | | XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRAID | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |

-continued

| Gene | NCBI Gene ID | NCBI Accession Number(s) |
|---|---|---|
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |

-continued

| Gene | NCBI Gene ID | NCBI Accession Number(s) |
|---|---|---|
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |

-continued

| Gene | NCBI Gene ID | NCBI Accession Number(s) |
|---|---|---|
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; |

-continued

| Gene | NCBI Gene ID | NCBI Accession Number(s) |
|---|---|---|
| | | XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456. |

2. The method of claim 1, wherein the RNA expression levels further comprise third RNA expression levels for a third set of genes different from the first and second sets of genes, wherein the identified child RNA-based gradient-boosted decision tree classifier comprises a first child RNA-based gradient-boosted decision tree classifier of the plurality of child RNA-based gradient-boosted decision tree classifiers and the child molecular category comprises a first child molecular category of the plurality of child molecular categories, wherein the plurality of child molecular categories further comprises a second child molecular category and the plurality of child RNA-based gradient-boosted decision tree classifiers further comprises a second child RNA-based gradient-boosted decision tree classifier corresponding to the second child molecular category, wherein the RNA features further comprises third ranks for the third set of genes, wherein processing the RNA features using the hierarchy of RNA-based gradient-boosted decision tree classifiers further comprises providing the third ranks for the third set of genes as input to the second child RNA-based gradient-boosted decision tree classifier to obtain a third probability that the second child molecular category is a third candidate molecular category of the at least one candidate molecular category for the biological sample, and wherein identifying the at least one candidate molecular category for the biological sample further comprises identifying the at least one candidate molecular category using the third probability.

3. The method of claim 1, wherein the hierarchy of molecular categories further comprises a plurality of molecular categories that are children of the child molecular category of the plurality of child molecular categories, wherein the hierarchy of RNA-based gradient-boosted decision tree classifiers further comprises a plurality of RNA-based gradient boosted decision tree classifiers corresponding to the plurality of molecular categories that are children of the plurality of child molecular categories, the plurality of RNA-based gradient-boosted decision tree classifiers including a first RNA-based gradient-boosted decision tree classifier corresponding to a first molecular category of the plurality of molecular categories, wherein processing the RNA features using the hierarchy of RNA-based gradient-boosted decision tree classifiers further comprises providing at least some of the RNA features as input to the first RNA-based gradient-boosted decision tree classifier to obtain a probability that the first molecular category is another candidate molecular category for the biological sample, and wherein identifying the at least one candidate molecular category for the biological sample further comprises identifying the at least one candidate molecular category using the probability that the first molecular category is another candidate molecular category for the biological sample.

4. The method of claim 3, wherein processing the RNA features using the hierarchy of RNA-based gradient-boosted decision tree classifiers further comprises, prior to providing the at least some of the RNA expression features as input to the first RNA-based gradient-boosted decision tree classifier, identifying, based on the second probability that the child molecular category is the second candidate molecular category for the biological sample, the first RNA-based gradient-boosted decision tree classifier from among the plurality of RNA-based gradient-boosted decision tree classifiers.

5. The method of claim 1, wherein identifying the at least one candidate molecular category for the biological sample comprises:

comparing the first probability to a threshold; and identifying the parent molecular category as the first candidate molecular category of the at least one candidate molecular category when the first probability exceeds the threshold.

6. The method of claim 1, wherein identifying the parent molecular category as the first candidate molecular category of the at least one candidate molecular category for the biological sample comprises:

comparing the first probability to the second probability; and identifying the parent molecular category as the first candidate molecular category of the at least one candidate molecular category when the first probability exceeds the second probability.

7. The method of claim 1, wherein the parent molecular category is associated with at least one international classification of diseases (ICD) code.

8. The method of claim 1, further comprising:

obtaining DNA expression data previously obtained by processing the biological sample obtained from the subject; and processing the DNA expression data using a hierarchy of DNA-based gradient-boosted decision tree classifiers corresponding to the hierarchy of molecular categories to obtain DNA-based gradient-boosted decision tree classifier outputs, wherein the hierarchy of DNA-based gradient-boosted decision tree classifiers includes DNA-based gradient-boosted decision tree classifiers trained using training DNA expression data, and wherein the hierarchy of RNA-based gradient-boosted decision tree classifiers includes RNA-based gradient-boosted decision tree classifiers trained using training RNA expression data, wherein the identifying of the at least one candidate molecular category for the biological sample is performed also using at least some of the DNA-based gradient-boosted decision tree classifier outputs.

9. The method of claim 8, wherein processing the DNA expression data comprises:

obtaining one or more DNA features using the DNA expression data; and applying at least one DNA-based gradient-boosted decision tree classifier of the hierarchy of DNA-based gradient-boosted decision tree classifiers to at least some of the one or more DNA features to obtain the DNA-based gradient-boosted decision tree classifier outputs.

10. The method of claim 9, wherein the one or more DNA features comprise:

one or more features indicating, for each gene of a respective first set of one or more genes, whether the DNA expression data indicates presence of a pathogenic mutation for the gene, one or more features indicating, for each gene of a respective second set of one or more genes, whether the DNA expression data indicates presence of a hotspot mutation for the gene, a feature indicating tumor mutational burden for the biological sample, one or more features indicating a normalized copy number for each chromosome segment of a respective set of one or more chromosome segments for which expression data is included in the DNA expression data, one or more features indicating loss of heterozygosity (LOH) for each chromosome segment of a respective set of one or more chromosome segments for which expression data is included in the DNA expression data, one or more features indicating whether the DNA expression data indicates presence of one or more protein coding genes, one or more features indicating, for each gene of a respective third set of one or more genes, whether the DNA expression data indicates presence of a fusion with another gene of the respective third set of one or more genes, a feature indicating ploidy for the biological sample, and/or a feature indicating whether the DNA expression data indicates presence of microsatellite instability (MSI).

11. The method of claim 8, wherein the identifying of the at least one candidate molecular category for the biological sample is performed based on data indicative of a purity of the biological sample and/or data indicative of a site form which the biological sample was obtained.

12. The method of claim 1, further comprising:

generating a graphical user interface (GUI) including a visualization indicating the at least one candidate molecular category identified for the biological sample.

13. The method of claim 1, wherein the hierarchy of RNA-based gradient-boosted decision tree classifiers comprises at least 10 RNA-based gradient-boosted decision tree classifiers.

14. The method of claim 1, wherein the first RNA expression levels comprise expression levels for between 20 and 300 genes.

15. The method of claim 1, wherein the biological sample is a sample of a cancer of unknown primary (CUP) tumor.

16. A system, comprising:

at least one computer hardware processor; and at least one non-transitory computer-readable storage medium storing processor-executable instructions that, when executed by the at least one computer hardware processor, cause the at least one computer hardware processor to perform a method for identifying at least one candidate molecular category for a biological sample obtained from a subject, the method comprising:

(a) obtaining RNA expression levels previously obtained by processing the biological sample obtained from the subject, wherein the RNA expression levels comprise:

(i) first RNA expression levels for a first set of genes, the first set of genes corresponding to a parent molecular category in a hierarchy of molecular categories and comprising at least ten genes listed for the parent molecular category in Table 3, and (ii) second RNA expression levels for a second set of genes different from the first set of genes, the second set of genes corresponding to a child molecular category, which is a child of the parent molecular category in the hierarchy of molecular categories, and comprising at least ten genes listed for the child molecular category in Table 3;

(b) processing the RNA expression levels to obtain RNA features comprising first ranks for the first set of genes and second ranks for the second set of genes, the processing comprising:

(i) ranking the first set of genes using the first RNA expression levels to obtain the first ranks for the first set of genes; and (ii) ranking the second set of genes using the second RNA expression levels to obtain the second ranks for the second set of genes;

(c) processing the RNA features using a hierarchy of RNA-based gradient-boosted decision tree classifiers corresponding to the hierarchy of molecular categories to obtain probabilities that molecular categories in the hierarchy of molecular categories are candidate molecular categories for the biological sample, the hierarchy of RNA-based gradient-boosted decision tree classifiers comprising a parent RNA-based gradient-boosted decision tree classifier corresponding to the parent molecular category, and a plurality of child RNA-based gradient-boosted decision tree classifiers corresponding to a plurality of child molecular categories including the child molecular category, the processing comprising:

(i) providing the first ranks for the first set of genes as input to the parent RNA-based gradient-boosted decision tree classifier to obtain a first probability that the parent molecular category is a first candidate molecular category of the at least one candidate molecular category for the biological sample;

(ii) identifying, based on the first probability, a respective child RNA-based gradient-boosted decision tree classifier from among the plurality of child RNA-based gradient-boosted decision tree classifiers, the identified child RNA-based gradient-boosted decision tree classifier corresponding to the child molecular category of the plurality of child molecular categories; and (iii) after identifying the child RNA-based gradient-boosted decision tree classifier based on the first probability, providing the second ranks for the second set of genes as input to the child RNA-based gradient-boosted decision tree classifier to obtain a second probability that the child molecular category is a second candidate molecular category for the biological sample; and (d) identifying, using the probabilities that the molecular categories in the hierarchy of molecular categories are candidate molecular categories for the biological sample, the at least one candidate molecular category for the biological sample, the identifying comprising:

(i) identifying the parent molecular category as the first candidate molecular category of the at least one candidate molecular category for the biological sample using the first probability that the parent molecular category is the first candidate molecular category; and/or (ii) identifying the child molecular category as the second candidate molecular category of the at least one candidate molecular category for the biological sample using the second probability that the child molecular category is the second candidate molecular category, wherein Table 3 is:

| Gene | NCBI Gene ID | NCBI Accession Number(s) |
|---|---|---|
| | | Gastrointestinal_Adenocarcinoma |
| TUSC3 | 7991 | XM_011544651; XM_017013861; NM_178234; NM_006765; NM_001356429 |
| ZG16 | 653808 | NM_152338; XM_011545921 |
| COLEC11 | 78989 | XM_006711897; NM_001255986; NM_001255989; NM_001255985; NM_001255982; NM_001255983; NM_001255984; NM_024027; NR_045659; XM_005263853; NM_001255987; NM_001255988; NM_199235 |
| KLF4 | 9314 | NM_004235; NM_001314052 |
| COBL | 23242 | XM_011515239; NM_015198; XM_011515236; XM_005271751; XM_011515237; NM_001287436; NM_001287438; NM_001346441; XM_011515235; XM_011515240; XM_017011898; NM_001346443; NM_001346444; XM_011515234; XM_011515241; NM_001346442; XM_005271750; XM_011515238 |
| SIX1 | 6495 | XM_017021602; NM_005982 |
| COL10A1 | 1300 | XM_011535432; NM_000493; XM_011535433; XM_017010248; XM_006715333 |
| EPHB2 | 2048 | XM_006710441; NM_001309192; NM_004442; NM_001309193; NM_017449; XM_024453895; XM_006710442 |
| CDH19 | 28513 | XM_011525931.3; XM_017025711.2; XM_011525932.1 |
| CDX1 | 1044 | NM_001804 |
| EN1 | 2019 | NM_001426 |
| CDH17 | 1015 | NM_004063; XM_011516790; NM_001144663 |
| WNT7A | 7476 | XM_011534091; NM_004625 |
| SRD5A2 | 6716 | XM_011533069; NM_000348; XM_011533072 |
| ESM1 | 11082 | NM_001135604; NM_007036 |
| PRSS50 | 29122 | NM_013270 |
| PDX1 | 3651 | NM_000209; XR_941580; XR_941578; |
| BMP8A | 353500 | XM_017001198; XM_006710616; XM_011541381; XM_011541382; XR_946642; XR_946640; XR_946641; NM_181809 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SYT12 | 91683 | XM_011545346; XM_011545347; NM_177963; XM_017018547; NM_001177880; NM_001318775; XM_017018548; XM_006718737; XM_024448766; NM_001318773 |
| CFD | 1675 | NM_001317335; NM_001928 |
| GAMT | 2593 | NM_138924; NM_000156 |
| VTCN1 | 79679 | NM_001253849; NM_024626; NR_045604; XM_017002335; NM_001253850; NR_045603; XM_011542143 |
| TMSB15A | 11013 | NM_021992 |
| SLC15A2 | 6565 | XM_006713736; XM_017007074; NM_021082; XM_005247722; NM_001145998 |
| CP | 1356 | XM_006713500; XM_006713501; XM_017005735; XM_017005734; XM_006713499; XM_011512435; XR_427361; NM_000096; NR_046371 |
| MAL | 4118 | NM_022438; NM_002371; NM_022440; NM_022439 |
| KRT2 | 3849 | NM_000423 |
| IQCA1 | 79781 | XM_017004960; NM_024726; NM_001270585; XM_011511865; XM_011511866; XM_011511864; NM_001270584; NR_073043 |
| PVRL1 | 5818 | NM_203285; NM_032767; NM_002855; NM_203286 |
| PLA2G7 | 7941 | NM_001168357; XR_001743639; XM_005249408; NM_005084; XR_002956305 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| TREM2 | 54209 | NM_001271821; NM_018965 |
| ADAP1 | 11033 | NM_001284308; NM_006869; NM_001284311; NM_001284310; NM_001284309 |
| MUC13 | 56667 | NM_033049 |
| CLDN18 | 51208 | NM_001002026; NM_016369 |
| DPT | 1805 | NM_001937 |
| PLP1 | 5354 | NM_001128834; NM_000533; NM_001305004; NM_199478 |
| CCNB1 | 891 | NM_031966 |
| GPR162 | 27239 | NM_014449; NM_019858 |
| ONECUT2 | 9480 | NM_004852 |
| SFTPD | 6441 | XM_011540087; NM_003019; XM_011540088 |
| CLDN10 | 9071 | XM_024449432; XM_017020844; NM_006984; XM_011521134; XM_017020843; NM_182848; NM_001160100 |
| NXPH4 | 11247 | XM_017018747; NM_007224 |
| MAB21L2 | 10586 | NM_006439 |
| REG3A | 5068 | NM_138938; NM_002580; NM_138937 |
| LGALS4 | 3960 | NM_006149; XM_011526974; XM_011526973 |
| GPR35 | 2859 | NM_001195382; NM_001195381; NM_001394730; NM_005301 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| SIM2 | 6493 | XM_017028442; XR_001754891; XM_011529694; NM_005069; NM_009586 |
| TCF21 | 6943 | NM_003206; NM_198392 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| CCL11 | 6356 | NM_002986 |
| SLC34A2 | 10568 | NM_001177999; NM_006424; NM_001177998 |

-continued

| Gene | NCBI Gene ID | NCBI Accession Number(s) |
|---|---|---|
| GIF | 2694 | XM_011544939; NM_005142 |
| SALL1 | 6299 | NM_001127892; NM_002968 |
| HGH1 | 51236 | NM_016458; XR_001745537 |
| KCNC3 | 3748 | NM_004977; NR_110912; NM_001372305 |
| GPA33 | 10223 | XM_017000005; NM_005814 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| FXYD2 | 486 | NM_021603; NM_001127489; NM_001680 |
| HNF4A | 3172 | XM_005260407; NM_001287182; NM_001030003; NM_178850; NM_175914; NM_001030004; NM_178849; NM_001258355; NM_001287183; NM_000457; NM_001287184 |
| GABRQ | 55879 | NM_018558; XM_011531184 |
| ABCA4 | 24 | NM_000350 |
| MMP11 | 4320 | NM_005940; NR_133013 |
| ZWINT | 11130 | XR_428692; NM_007057; NM_001005413; XM_017015605; XM_024447784; NM_032997; NM_001005414 |
| INHBA | 3624 | XM_017012175; NM_002192; XM_017012176; XM_017012174 |
| REG1A | 5967 | NM_002909 |
| TSPYL2 | 64061 | XM_006724592; XM_017029727; NM_022117; XR_001755719; XM_017029726 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| LRRC15 | 131578 | NM_130830; NM_001135057 |
| DES | 1674 | NM_001927; NM_001382708; NM_001382710; NM_001382713; NM_001382709; NM_001382711; NM_001382712 |
| INS | 3630 | NM_001185098; NM_001185097; NM_000207; NM_001291897 |
| FABP4 | 2167 | NM_001442 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| CST1 | 1469 | NM_001898 |
| TM4SF5 | 9032 | NM_003963 |
| PODXL | 5420 | NM_005397; NM_001018111 |
| CRNN | 49860 | NM_016190 |
| WISP2 | 8839 | NM_001323369; XM_017028116; NM_003881; XM_017028117; NM_001323370 |
| SST | 6750 | NM_001048 |
| LIN37 | 55957 | NR_163146; NM_019104; NM_001369780 |
| GREM1 | 26585 | NM_001368719; NM_013372; NM_001191323; NM_001191322 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| GRIN2D | 2906 | XM_011526872; NM_000836 |
| APOC1 | 341 | NM_001645; NM_001321066; NM_001379687; NM_001321065 |
| GDPD3 | 79153 | NM_024307 |
| FOXF1 | 2294 | NM_001451 |
| TGFB3 | 7043 | NM_001329938; NM_003239; NM_001329939 |
| ST3GAL5 | 8869 | NM_001354248; XM_017005208; XM_017005214; NM_001354226; XM_017005204; NM_001354233; NM_001354234; XM_017005205; XM_017005213; XR_001739019; NM_003896; NM_001354223; NM_001354227; NM_001354247; XM_017005206; XR_001739021; NM_001042437; NM_001354229; XM_017005202; XM_017005203; XM_017005212; XR_001739020; XM_017005209; NM_001354224; NM_001363847; NM_001354238 |
| DIRAS2 | 54769 | NM_017594 |
| GABRG3 | 2567 | XM_017022058; XM_017022060; XM_024449889; NM_033223; XM_011521430; NM_001270873; XM_011521431; XM_017022059 |
| HOXC11 | 3227 | NM_014212 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| SLCO4A1 | 28231 | XR_002958473; XR_001754251; XR_001754254; XR_001754255; XR_001754258; NM_016354; XR_001754250; XR_244116; XM_017027827; XR_001754253; XR_001754252; XR_244115; XR_936524; XM_017027826; XR_002958474; XR_001754256; XR_001754257; XM_005260203; XM_011528792; XR_001754249 |
| FABP1 | 2168 | NM_001443 |
| NFE2L3 | 9603 | NM_004289 |
| GLRB | 2743 | XR_001741207; XM_017008035; NM_000824; NM_001166060; XR_002959723; XM_017008034; NM_001166061 |

-continued

| Gene | NCBI Gene ID | NCBI Accession Number(s) |
|---|---|---|
| PTH1R | 5745 | NM_001184744; XM_017006933; XM_011533968; NM_000316; XM_017006934; XM_011533967; XM_005265344; XM_017006932 |
| C2orf72 | 257407 | NM_001144994 |
| CAPN3 | 825 | NM_173087; NM_173089; NM_024344; NM_173088; NM_212465; NR_027912; NM_000070; NM_173090; NR_027911 |
| SLC2A4 | 6517 | NM_001042 |
| MLF1 | 4291 | NM_001369782; NM_001369785; NM_001378847; NM_022443; NM_001378845; NM_001378848; NM_001378851; NM_001369784; NM_001378853; NM_001378855; NM_001130156; NM_001369783; NM_001378852; NM_001130157; NM_001195432; NM_001195433; NM_001378846; NM_001378850; NM_001369781; NM_001195434 |
| FEZF2 | 55079 | NM_018008 |
| APCS | 325 | NM_001639 |
| SOX9 | 6662 | NM_000346 |
| HOXC10 | 3226 | NM_017409 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| DNAI1 | 27019 | NM_012144; NM_001281428 |
| LIPF | 8513 | NM_004190; NM_001198829; NM_001198830; NM_001198828; XM_011540311 |
| CDX2 | 1045 | XM_011534876; NM_001354700; XM_011534879; XM_011534875; XM_011534878; NM_001265 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ADH1B | 125 | NM_001286650; NM_000668 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| CHST2 | 9435 | NM_004267 |
| FGGY | 55277 | XM_017001645; XM_017001677; XM_024448207; XM_024448220; NM_001350792; NM_001350797; NM_001350798; NM_018291; XM_011541731; XM_017001671; XM_017001673; NM_001244714; NM_001350793; NM_001350794; NR_103473; XM_011541730; XM_017001649; XM_017001670; XM_017001678; XM_024448227; NM_001113411; XM_017001643; XM_011541736; XM_017001659; XM_017001662; XM_017001664; XM_024448185; XR_001737287; NM_001350791; NM_001350796; XM_017001668; XM_017001679; XR_001737285; XM_017001646; XM_017001652; XM_024448176; XR_001737286; NM_001278224; XM_017001657; XM_017001660; XR_001737284; NM_001350790; NM_001350799; XM_017001655; XM_017001656; XM_017001661; XM_017001663; XM_017001669; XM_024448196; XM_024448229; NM_001350795 |
| FERMT1 | 55612 | NM_017671; XM_024451935 |
| PRSS3 | 5646 | NM_007343; NM_001197097; NM_002771; XM_011517965; NM_001197098 |
| CCNA1 | 8900 | XM_011535294; XM_011535296; NM_001111047; XM_011535295; NM_001111046; NM_003914; NM_001111045 |
| ARL4D | 379 | XM_011524782; NM_001661 |
| LZTS1 | 11178 | XM_011544386; XM_011544384; NM_021020; NM_001362884; XM_011544385 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; |

-continued

| Gene | NCBI Gene ID | NCBI Accession Number(s) |
|---|---|---|
| | | NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| KRT24 | 192666 | XM_017024299; NM_019016; XM_006721739; XM_011524460 |
| SCNN1D | 6339 | NM_001130413; NR_037668; NM_002978 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| AQP4 | 361 | NM_001317387; NM_001364287; NM_001364286; NM_001317384; XM_011525942; NM_001650; NM_001364289; NM_004028 |
| MUC2 | 4583 | NM_002457 |
| FGF23 | 8074 | NM_020638 |
| CXCL3 | 2921 | NM_002090 |
| IGFBP3 | 3486 | NM_000598; NM_001013398 |
| GABRA2 | 2555 | XM_024453964; NM_001330690; NM_001377144; NM_001377149; XM_024453966; NM_001377150; XM_011513675; NM_001114175; NM_001377155; NM_000807; NM_001377147; XM_024453967; NM_001377146; NM_001377152; NM_001286827; NM_001377153; NM_001377145; NM_001377148; NM_001377151; NM_001377154 |
| HR | 55806 | XM_006716367; NM_005144; XM_005273569; NM_018411 |
| AKR1C2 | 1646 | NM_001354; NM_001321027; NM_001135241; NM_205845; NM_001393392 |
| MYOC | 4653 | NM_000261 |
| TACR2 | 6865 | NM_001057 |
| VIP | 7432 | XM_006715562; XM_005267135; NM_003381; NM_194435 |
| PRM2 | 5620 | NM_001286358; NR_104428; NM_002762; NM_001286356; NM_001286359; NM_001286357 |
| ACADL | 33 | NM_001608; XM_005246517; XM_017003955 |
| SLC47A1 | 55244 | NM_018242 |
| CLPB | 81570 | NM_030813; XM_005274320; XM_011545289; NM_001258392; NM_001258393; NM_001258394 |
| SCNN1B | 6338 | XM_017023526; XM_011545913; XM_011545914; XM_017023525; NM_000336 |
| GLP2R | 9340 | XM_011524077; NM_004246; XM_017025340; XM_005256861; XM_017025339; XM_017025341 |
| CASR | 846 | XM_017007325; NM_000388; XM_005247837; XM_017007324; NM_001178065; XM_006713789 |
| IFI6 | 2537 | NM_002038; XM_024446207; NM_022873; NM_022872 |
| | | Pancreatic_Adenocarcinoma |
| PNLIP | 5406 | NM_000936 |
| PPY | 5539 | NM_002722; NM_001319209; XM_011524978 |
| CTRC | 11330 | XM_011540550; NM_007272 |
| CTRB2 | 440387 | NM_001025200 |
| CRP | 1401 | NM_000567; NM_001329058; NM_001382703; NM_001329057 |
| GCG | 2641 | NM_002054 |
| PNLIPRP1 | 5407 | XM_011539869; NM_001303135; NM_006229; XR_945774 |
| INS | 3630 | NM_001185098; NM_001185097; NM_000207; NM_001291897 |
| CPA1 | 1357 | NM_001868 |
| CASR | 846 | XM_017007325; NM_000388; XM_005247837; XM_017007324; NM_001178065; XM_006713789 |
| GCNT3 | 9245 | NM_004751 |
| TFF2 | 7032 | NM_005423 |
| PDX1 | 3651 | NM_000209; XR_941580; XR_941578; |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| ALPPL2 | 251 | NM_031313 |
| PADI1 | 29943 | XM_017001102; XR_946617; XR_946619; NM_013358; XR_001737131; XM_011541307; XR_001737130; XM_017001103; XR_946620; XM_017001101 |
| CTSE | 1510 | XM_011509245; NM_001910; NM_148964; XM_011509244; NM_001317331 |
| FOXL1 | 2300 | NM_005250 |
| LHX2 | 9355 | NM_004789; XM_006717323 |
| POU3F3 | 5455 | NM_006236 |
| MIA | 8190 | NM_006533; NM_001202553 |
| HOXD13 | 3239 | XM_011511068; NM_000523; XM_011511069 |
| NMRK2 | 27231 | NM_001289117; NM_001375468; NM_001375469; NM_170678; NM_001375467; NM_014446; XM_006722725; NR_110316 |
| TMPRSS4 | 56649 | XM_011542901; NM_001290094; XM_005271614; NM_001173552; NM_183247; NR_110734; XM_005271613; XM_011542902; XM_011542904; XM_005271615; NM_001083947; NM_001173551; NM_019894; XM_011542903; NM_001290096 |
| HAND2 | 9464 | NM_021973 |
| IHH | 3549 | NM_002181 |
| MAGEA3 | 4102 | XM_011531161; XM_005274676; XM_006724818; XM_011531160; NM_005362 |
| KLK6 | 5653 | XM_024451611; NM_001319949; NM_001012964; NM_001319948; NM_001012965; NM_002774 |

-continued

| Gene | NCBI Gene ID | NCBI Accession Number(s) |
|---|---|---|
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MAGEA6 | 4105 | NM_175868; NM_005363 |
| LRP2 | 4036 | XM_011511183; NM_004525; XM_011511184 |
| MYBPH | 4608 | NM_004997 |
| CR2 | 1380 | NM_001877; NM_001006658; XM_011509206 |
| GABRA3 | 2556 | NM_000808; XM_006724811 |
| MYH7 | 4625 | XM_017021340; NM_000257 |
| ENPP3 | 5169 | XR_001743464; NR_133007; NM_005021; XM_017010932; XM_011535897 |
| GABRQ | 55879 | NM_018558; XM_011531184 |
| NXPH4 | 11247 | XM_017018747; NM_007224 |
| FOXA1 | 3169 | NM_004496; XM_017021246 |
| SFTPB | 6439 | XM_005264487; NM_198843; XM_005264488; NM_000542; NM_001367281; XM_005264490 |
| DLX6 | 1750 | NM_005222 |
| CRNN | 49860 | NM_016190 |
| HOXA7 | 3204 | NM_006896 |
| NEFM | 4741 | NM_001105541; NM_005382 |
| KRT24 | 192666 | XM_017024299; NM_019016; XM_006721739; XM_011524460 |
| FCER2 | 2208 | NM_002002; NM_001220500; XM_005272462; NM_001207019 |
| CLDN3 | 1365 | NM_001306 |
| POU2F2 | 5452 | XM_017026886; XM_017026889; XM_017026895; XR_001753709; XR_001753710; NM_001393935; XM_017026885; XM_017026891; XM_017026894; XM_024451547; NM_001207026; NM_001393934; NM_001394376; NM_001394378; XM_017026884; XM_011527043; XM_017026887; XM_017026890; NM_001247994; XM_011527041; XM_024451546; NM_001207025; XM_011527042; XM_017026888; XM_017026892; NM_001393936; NM_002698; XM_017026896; NM_001394377 |
| LIPF | 8513 | NM_004190; NM_001198829; NM_001198830; NM_001198828; XM_011540311 |
| BCL11A | 53335 | NM_001365609; NM_022893; NM_138553; XM_017004335; XM_024452962; XM_024452963; XM_017004333; NM_138559; XM_011532910; XM_017004336; NM_018014; XM_011532909; NM_001363864 |
| CX3CR1 | 1524 | NM_001171174; NM_001337; NM_001171171; NM_001171172 |
| ABCA12 | 26154 | XM_011510951; NR_103740; NM_173076; NM_015657 |
| | | Breast_Cancer |
| AMN | 81693 | XM_024449714; XM_011537203; NM_030943; XM_011537202 |
| NMRK2 | 27231 | NM_001289117; NM_001375468; NM_001375469; NM_170678; NM_001375467; NM_014446; XM_006722725; NR_110316 |
| TLX2 | 3196 | NM_001534; NM_016170 |
| MYH15 | 22989 | XM_011512559; NM_014981; XM_017005922 |
| MROH7 | 374977 | NR_026782; NM_198547; NM_001039464; NM_001291332; NR_111931 |
| ERN2 | 10595 | XM_011545708; XM_011545711; XR_950727; XM_011545709; XM_011545712; NM_001308220; XM_011545713; NM_033266 |
| CSF3 | 1440 | NR_168489; NR_168491; NM_000759; NM_172220; NM_001178147; NM_172219; NR_168490; NR_033662 |
| TMEM246 | 84302 | NM_001303107; NM_001303108; NM_032342; XM_024447701; NM_001371233 |
| GCGR | 2642 | XM_011523539; XM_017024446; NM_000160; XM_006722277; XM_017024447 |
| NEFM | 4741 | NM_001105541; NM_005382 |
| SOX21 | 11166 | NM_007084 |
| PMP2 | 5375 | NM_002677; NM_001348381 |
| RGS20 | 8601 | NM_001286673; NM_001286675; NM_170587; NM_001286674; NM_003702; NR_104578; NR_104579 |
| IL13RA2 | 3598 | NM_000640 |
| GPR17 | 2840 | NM_005291; NM_001161416; NM_001161415; XM_017003833; NM_001161417 |
| B3GALT1 | 8708 | NM_020981; XM_006712819; XM_011512085 |
| MT1H | 4496 | NM_005951 |
| GJA3 | 2700 | NM_021954; XM_011535048 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| DBH | 1621 | NM_000787 |
| OGDHL | 55753 | XM_011539946; NM_001347821; NM_001143997; NM_001347820; NM_001347823; NR_144685; XM_017016402; NM_001347819; NM_001347825; NM_018245; NR_144682; NM_001347824; NR_144683; XM_017016403; NM_001143996; NM_001347822; NM_001347826; NR_144684; NR_144686 |
| WNT7A | 7476 | XM_011534091; NM_004625 |
| RPRM | 56475 | NM_019845 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| FOXA2 | 3170 | NM_021784; NM_153675 |
| ZNF536 | 9745 | XM_011527557; XM_017027530; XM_017027533; XM_017027534; XM_017027540; XM_017027535; XM_017027531; XM_017027532; XM_017027539; XM_017027542; XM_011527555; XM_011527560; XM_017027536; NM_001352260; NM_001376110; NM_014717; XM_011527554; |

-continued

| Gene | NCBI Gene ID | NCBI Accession Number(s) |
|---|---|---|
| | | XM_017027527; XM_017027537; XM_017027543; XM_024451807; NM_001376111; XM_011527558; XM_017027528; XM_017027529; XM_017027538 |
| CCL16 | 6360 | NM_004590; XM_005258020 |
| SHH | 6469 | NR_132319; NM_000193; NR_132318; XM_011516480; XM_011516479; NM_001310462 |
| TAC3 | 6866 | NR_135164; NR_135166; NR_135165; NM_001006667; NM_001178054; NM_013251; NR_033654 |
| CXCL3 | 2921 | NM_002090 |
| DUSP26 | 78986 | NM_024025; NM_001305116; NM_001305115 |
| SERPIND1 | 3053 | NM_000185 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| TCF21 | 6943 | NM_003206; NM_198392 |
| TYR | 7299 | XM_011542970; NM_000372 |
| DUOX2 | 50506 | NM_014080; NM_001363711 |
| SLC45A2 | 51151 | NM_001297417; NM_016180; NM_001012509 |
| MAB21L2 | 10586 | NM_006439 |
| GAS2 | 2620 | NM_001143830; NM_001391933; NM_001391935; NM_001391936; XM_011519972; NM_001391937; NM_001391934; XM_011519971; NR_147085; XM_017017532; XR_001747829; NM_001351224; XM_011519975; NM_005256; NM_177553 |
| IL1A | 3552 | NM_001371554; NM_000575 |
| SPRR2B | 6701 | NM_001388198; NM_001017418 |
| CYP2W1 | 54905 | NM_017781; XM_011515440; XM_011515441 |
| SPOCK3 | 50859 | NM_001251967; NM_001204354; NM_001204356; XM_011532018; NM_001204359; XM_017008258; NM_001040159; NM_001204358; XM_017008257; NM_001204352; NM_016950; NM_001204353; NM_001204355 |
| KCNK12 | 56660 | NM_022055 |
| HKDC1 | 80201 | NM_025130; XR_001747209; XM_011540195 |
| HNF1B | 6928 | XM_011525161; NM_001165923; NM_001304286; XM_011525163; NM_000458; XM_011525162; NM_006481; XM_011525164; XM_011525160 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| FOXE1 | 2304 | NM_004473 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| NAALAD2 | 10003 | XM_017017044; XR_001747709; XM_017017043; XR_001747707; XR_001747710; XR_001747711; NM_001300930; XR_001747708; XM_017017045; XM_017017046; NM_005467 |
| HMGA2 | 8091 | NM_001015886; NM_003483; NM_001300918; NM_003484; NM_001330190; NM_001300919 |
| FOXF1 | 2294 | NM_001451 |
| RXRG | 6258 | NM_006917; NM_001256570; NM_001256571; NR_033824 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| STXBP6 | 29091 | XM_017021235; NM_001351941; NM_001394415; XM_024449547; NM_001304476; NM_001351942; NM_001394413; XM_006720121; NM_001304477; NM_001394414; NM_001394417; XM_017021232; NM_014178; NM_001394410; NM_001394411; NM_001394420; XM_017021241; NM_001351943; NM_001394418; NM_001351940; NM_001394412; NM_001394416; NM_001394419 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; |

-continued

| Gene | NCBI Gene ID | NCBI Accession Number(s) |
|---|---|---|
| | | XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| RPS4Y1 | 6192 | NM_001008 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| GFAP | 2670 | XM_024450691; XM_024450690; NM_001131019; XM_024450692; XM_024450693; NM_001242376; NM_002055; NM_001363846 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| PVRL3 | 25945 | XM_011512663; XM_017006126; NM_001243286; XR_924122; NM_015480; XR_002959508; XM_017006125; XM_017006124; XM_017006127; XM_017006123; NM_001243288 |
| SERPINB13 | 5275 | NM_001348267; XM_011526029; NM_001348268; NM_012397; NM_001348269; NM_001307923; NM_001348270 |
| ADH1C | 126 | NM_000669; NR_133005 |
| EYA4 | 2070 | XM_005266851; NM_004100; NM_172105; NM_001370459; NM_172104; XM_017010371; XR_001743220; NM_001301012; XM_017010369; XM_017010370; XM_017010372; XM_017010373; XR_001743219; NM_172103; NM_001301013; NM_001370458; XM_017010368; XM_017010374 |
| RGS6 | 9628 | XM_017021825; XM_017021832; XM_024449763; XR_001750613; NM_001370274; NM_001370279; NM_001370284; NM_001370291; XM_017021820; XM_024449761; XM_024449770; XM_024449774; NM_001370272; NM_001370277; NM_001370278; NM_001370292; XM_011537397; XM_017021831; XM_024449764; NM_001204421; NM_001204423; NM_001370275; NM_001370290; NM_001370293; NR_135235; XM_024449760; XM_024449776; XR_002957573; NM_001204416; NM_001204417; NM_001370271; NM_001370283; NM_001370270; NM_001370273; NM_001370281; NM_001370286; XM_017021822; XM_017021833; NM_001204422; NM_001204424; NM_001370276; NM_001370280; NM_001370287; NM_001370289; NM_001370294; XM_011537393; XM_011537407; XM_017021827; XM_017021830; XM_017021834; XM_024449759; NM_001370282; XM_017021826; XM_017021828; XM_024449768; NM_001204418; NM_001204419; NM_001204420; NM_001370288; NM_004296 |
| ACTC1 | 70 | NM_005159 |
| PAX3 | 5077 | NM_181457; NM_000438; NM_181459; NM_181460; NM_001127366; NM_013942; NM_181461; NM_181458 |
| GALNT12 | 79695 | XM_006717287; XM_017015133; XM_011519018; NM_024642; XM_011519020; XM_024447673 |
| SOX2 | 6657 | NM_003106 |
| SNCA | 6622 | XM_011532204; NM_001146054; NM_000345; NM_001375287; XM_011532206; NM_007308; NR_164675; XM_011532207; NM_001375288; NM_001375290; NR_164676; XM_011532203; XM_011532205; NR_164674; XM_017008563; NM_001146055; NM_001375286; NM_001375285 |
| MYLPF | 29895 | NM_001324458; NM_013292; NM_001324459 |
| EMX2 | 2018 | NM_004098; NM_001165924 |
| FRMPD1 | 22844 | XM_017014482; XM_024447456; XM_011517806; NM_001371223; NM_001371225; XM_017014481; XM_024447454; XM_011517805; XR_929220; NM_014907; NM_001371224 |
| PHYHIP | 9796 | NR_156475; NM_001099335; NM_001363311; NM_014759; XM_017014102; NM_001363312 |
| GUCY2C | 2984 | NM_004963; XM_011520631 |
| FGFBP1 | 9982 | NM_005130 |
| SGK2 | 10110 | NM_016276; NM_001199264; NM_170693 |
| GDF10 | 2662 | NM_004962 |
| REM1 | 28954 | XM_011528795; XM_017027833; NM_014012; XM_005260404 |
| CPEB1 | 64506 | NM_001288819; NM_001365243; NM_001365242; NM_001365244; NM_001365245; NM_001387068; NM_001387076; NM_001365248; NM_001079534; NM_001365250; NM_001387065; NM_001387075; |

-continued

| Gene | NCBI Gene ID | NCBI Accession Number(s) |
|---|---|---|
| | | NM_001079535; NM_001288820; NM_001365249; NM_001387061; NM_001387066; NM_001387070; NM_001387062; NM_001387071; NM_001387078; NM_001365246; NM_001365247; NM_001387069; NM_001387077; NM_001079533; NM_001365240; NM_001365241; NM_001387072; NM_001387074; NM_001387063; NM_001387064; NM_001387067; NM_001387073; NM_030594 |
| CYP3A5 | 1577 | NM_001291830; NM_001190484; NR_033807; NR_033812; NM_001291829; NM_000777; NR_033810; NR_033811 |
| SALL1 | 6299 | NM_001127892; NM_002968 |
| HAND2 | 9464 | NM_021973 |
| HOXA3 | 3200 | NM_001384342; NM_001384335; NM_001384336; NM_001384339; NM_001384345; NM_001384346; NM_001384338; NM_001384337; NM_030661; NM_001384341; NM_001384343; NM_001384340; NM_001384344; NM_153631; NM_153632 |
| TMPRSS5 | 80975 | XM_017018366; XR_001747990; NM_001288749; NM_001288751; NM_001288752; NM_001288750; NR_110047; XR_001747991; XR_001747992; NR_110046; NM_030770; XM_017018367 |
| BMP5 | 653 | XM_011514817; NM_001329756; XM_024446524; NM_001329754; NM_021073 |
| TRDN | 10345 | NM_001251987; NM_001256020; NM_001256021; NM_006073; NM_001256022 |
| TACR2 | 6865 | NM_001057 |
| LYVE1 | 10894 | NM_006691 |
| FHL1 | 2273 | NM_001159703; NM_001167819; NM_001369327; NM_001369330; XM_006724746; XM_024452354; NR_027621; NM_001369328; NM_001159702; NM_001369326; XM_006724743; NM_001330659; NM_001369331; NM_001159700; NM_001159701; NM_001159704; NM_001369329; NM_001159699; NM_001449 |
| CAV1 | 857 | NM_001753; NM_001172895; NM_001172897; NM_001172896 |
| FIGF | 2277 | NM_004469 |
| NPR1 | 4881 | XM_017001374; XM_005245218; NM_000906 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| AOC3 | 8639 | XR_934584; NM_001277732; NM_003734; NR_102422; XM_011525419; XR_001752673; XM_011525420; XM_024451015; NM_001277731 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| CIDEC | 63924 | NM_001321142; NM_001199552; NM_001378491; NM_001199623; NM_001199551; NM_001321144; NM_022094; NM_001321143 |
| NEK2 | 4751 | NM_002497; NM_001204182; NM_001204183 |
| MMP11 | 4320 | NM_005940; NR_133013 |
| ADAMTS5 | 11096 | XM_024452053; XM_024452054; NM_007038 |
| ABCD2 | 225 | XR_001748623; NM_005164; XM_017018992; XR_001748622; XM_017018993; XM_011538027 |
| LPL | 4023 | NM_000237 |
| HBB | 3043 | NM_000518 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| COL10A1 | 1300 | XM_011535432; NM_000493; XM_011535433; XM_017010248; XM_006715333 |
| AQP7 | 364 | XM_006716765; XM_017014706; NM_001318158; NR_134513; NR_134515; XM_017014704; XM_024447538; NM_001318156; XM_011517866; NR_134514; NR_164778; XM_011517867; XM_017014701; XM_024447539; NM_001376192; NM_001376193; XM_017014702; NM_001318157; NM_001376191; NR_164779; XM_017014700; NM_001170 |
| LEP | 3952 | XM_005250340; NM_000230 |
| GSTM5 | 2949 | NM_000851; XM_005270785; XM_005270784 |
| FMO2 | 2327 | NM_001460; NR_160266; XR_921761; NM_001365900; XR_001737072; NM_001301347 |

-continued

| Gene | NCBI Gene ID | NCBI Accession Number(s) |
|---|---|---|
| PLIN1 | 5346 | NM_002666; XM_005254934; NM_001145311 |
| KIAA0101 | 9768 | NR_109934; NM_001029989; NM_014736 |
| CA3 | 761 | NM_005181 |
| CDO1 | 1036 | NM_001323565; NR_136619; NM_001323567; NM_001801; NR_136618; NR_136620; NM_001323566; NR_136621 |
| CSN1S1 | 1446 | XM_006714091; NM_001025104; XM_006714089; XM_006714090; NM_001890 |
| KIF4A | 24137 | NM_012310 |
| GPD1 | 2819 | NM_005276; NM_001257199 |
| DPT | 1805 | NM_001937 |
| ADH1B | 125 | NM_001286650; NM_000668 |
| FABP4 | 2167 | NM_001442 |
| CENPF | 1063 | XM_017000086; NM_016343; XM_011509082 |
| GABRD | 2563 | XM_011541194; XM_017000936; NM_000815 |
| PFKFB1 | 5207 | NM_001271804; XM_017029578; XM_017029576; NM_002625; NR_073450; XM_024452389; XM_017029577; NM_001271805 |
| ATP1A2 | 477 | NM_000702 |
| CHL1 | 10752 | XM_011533294; XM_017005568; XM_017005573; NM_001253387; NR_045572; XM_017005569; XM_017005572; XM_006712939; XM_011533292; XM_017005566; XM_006712940; XM_011533295; NM_001253388; NM_006614; XM_006712938; XM_011533296; XM_017005567; XM_017005570; XM_017005571 |
| SLC7A10 | 56301 | XM_011527120; XM_006723284; XM_024451609; XR_935841; NM_019849; XM_011527119; XM_024451610 |
| ADIPOQ | 9370 | NM_004797; NM_001177800 |
| EXO1 | 9156 | XM_011544325; XM_011544322; NM_130398; XM_011544323; XM_006711840; NM_003686; NM_006027; XM_011544321; XM_011544324; XM_017002793; NM_001319224 |
| INHBA | 3624 | XM_017012175; NM_002192; XM_017012176; XM_017012174 |
| CES1 | 1066 | NM_001025195; NM_001266; XM_005255774; NM_001025194 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| MMRN1 | 22915 | XM_005262856; NM_001371403; NM_007351 |
| HMMR | 3161 | NM_001142557; NM_001142556; NM_012484; NM_012485 |
| PKMYT1 | 9088 | NM_001258451; NM_182687; NM_001258450; XM_011522735; XM_024450490; NM_004203; XM_011522734; XM_011522736 |
| CIDEA | 1149 | NM_001279; NR_134607; NM_001318383 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| OXTR | 5021 | NM_000916; NM_001354654; NM_001354655; NM_001354653; NM_001354656 |
| DTL | 51514 | XM_011509614; NM_001286229; NM_001286230; NM_016448 |
| IBSP | 3381 | NM_004967 |
| PPP1R1A | 5502 | XM_005268995; XM_006719471; NM_006741 |
| WISP1 | 8840 | XM_024447319; NR_037944; XM_024447320; NM_080838; NM_003882; NM_001204870; XM_024447321; NM_001204869 |
| STAB2 | 55576 | NM_017564; XM_011538541; XM_011538538; XM_011538539; XM_011538542; XM_017019585; XM_011538537; XR_429107 |
| CDKN3 | 1033 | XM_024449458; NM_001330173; NM_005192; NM_001130851 |
| TK1 | 7083 | NM_001346663; NM_003258 |
| KIF20A | 10112 | NM_005733 |
| KCNB1 | 3745 | XM_011528799; XM_006723784; NM_004975 |
| S100B | 6285 | NM_006272; XM_017028424 |
| PBK | 55872 | NM_018492; NM_001278945; NM_001363040 |
| TDO2 | 6999 | NM_005651 |
| PITX1 | 5307 | NM_002653 |
| MCM10 | 55388 | NM_182751; NM_018518; XM_011519538 |
| GRM4 | 2914 | NM_001256809; NM_001256812; NM_001256813; NM_001256811; NM_001256814; NM_001256810; NM_001282847; NM_000841 |
| CST1 | 1469 | NM_001898 |
| AIM1L | 55057 | NM_017977; XM_011541672; XM_011541673; XR_001737260; NM_001039775; XR_946681; XM_005245918 |
| TNMD | 64102 | NM_022144 |
| CLEC5A | 23601 | XM_017011916; XM_017011915; XM_011515995; XM_017011917; NM_001301167; NM_013252 |
| LRRC15 | 131578 | NM_130830; NM_001135057 |
| LAMP5 | 24141 | NM_001199897; NM_012261 |
| EPYC | 1833 | NM_004950; XM_011538008 |
| RAB26 | 25837 | XM_011522448; XM_011522450; NM_014353; NM_001308053 |
| CST2 | 1470 | NM_001322 |
| NKAIN1 | 79570 | NM_024522; XM_017002320 |
| LALBA | 3906 | NM_002289; NM_001384350 |
| CENPA | 1058 | NM_001809; NM_001042426 |
| TUBB3 | 10381 | NM_006086; NM_001197181 |
| ARTN | 9048 | NM_057160; NM_057090; NM_001136215; NM_057091; NM_003976 |
| TCL1B | 9623 | NM_004918; NM_199206 |
| SYT13 | 57586 | NM_001247987; NM_020826 |

-continued

| Gene | NCBI Gene ID | NCBI Accession Number(s) |
|---|---|---|
| CNTD2 | 79935 | XM_006723395; NM_024877; XR_001753763; XR_935861 |
| NEURL1 | 9148 | XM_005270269; XM_011540333; XM_017016909; XM_011540332; XM_011540335; XR_945866; NM_004210; XM_005270270; XM_011540331 |
| NPY2R | 4887 | NM_001370180; NM_000910; NM_001375470 |
| CXCL10 | 3627 | NM_001565; NR_168520 |
| S100P | 6286 | NM_005980 |
| MYT1 | 4661 | NM_004535 |
| ACTL8 | 81569 | NM_030812; XM_011542212 |
| HAPLN1 | 1404 | XM_017009052; XM_017009051; NM_001884; XM_017009054; XM_017009053; XM_011543168 |
| BTN1A1 | 696 | NM_001732 |
| CXCL9 | 4283 | NM_002416 |
| CEACAM6 | 4680 | NM_002483; XM_011526990 |
| FBN2 | 2201 | NM_001999; XM_017009228 |
| NAT1 | 9 | NM_001160175; NM_001160170; NM_001160173; XM_011544688; XM_006716410; XM_017013947; NM_001160171; NM_001160172; NM_001160174; NM_001291962; XM_011544689; NM_001160176; XM_011544687; NM_000662; NM_001160179 |
| FOXJ1 | 2302 | NM_001454 |
| BMPR1B | 658 | XM_017008558; NM_001203; NM_001256793; XM_011532201; NM_001256794; NM_001256792; XM_017008559; XM_017008560; XM_017008561 |
| CNTNAP2 | 26047 | XM_017011950; NM_014141 |
| CEACAM5 | 1048 | XM_011526322; XM_017026146; NM_001291484; NM_004363; XM_017026145; NM_001308398 |
| KCNF1 | 3754 | NM_002236 |
| HOXC11 | 3227 | NM_014212 |
| KCNJ3 | 3760 | NM_001260510; NM_001260508; NM_001260509; NM_002239 |
| MAGEA12 | 4111 | NM_001166386; NM_001166387; NM_005367 |
| GABRQ | 55879 | NM_018558; XM_011531184 |
| HHIPL2 | 79802 | XM_024449814; XR_001737417; XR_426906; XM_017002350; XR_002957624; NM_024746; XR_001737416; XM_011509986 |
| TLX1 | 3195 | NM_001195517; XM_011539744; XM_011539745; NM_005521 |
| SOX11 | 6664 | NM_003108 |
| MAGEA6 | 4105 | NM_175868; NM_005363 |
| CA9 | 768 | XR_428428; NM_001216; XR_001746374 |
| C2orf54 | 79919 | XM_011511877; NM_001085437; NM_001282921; NM_024861 |
| DIO1 | 1733 | NM_000792; NM_001039715; NM_213593; NM_001039716; NM_001324316; NR_136692; NR_136693 |
| F7 | 2155 | XM_011537476; XM_011537475; NM_001267554; XM_011537474; NR_051961; XM_006719963; NM_019616; NM_000131 |
| CYP2B6 | 1555 | NM_000767 |
| TRH | 7200 | NM_007117 |
| CHGB | 1114 | NM_001819 |
| PROL1 | 58503 | NM_021225; NM_001302807; NR_126503 |
| CD177 | 57126 | XM_017027021; XM_017027022; NM_020406 |
| KIF1A | 547 | NM_001379636; NM_001379637; NM_001379639; NM_001379650; NM_001330290; NM_001379633; NM_001379641; NM_001379651; NM_001379653; NM_004321; NM_001379632; NM_001379638; NM_001379645; NM_001379646; NM_001379649; NM_001379635; NM_001379640; NM_001379634; NM_001244008; NM_001379642; NM_001320705; NM_001330289; NM_001379631; NM_001379648 |
| PSCA | 8000 | NR_033343; NM_005672 |
| CRISP3 | 10321 | NM_001368123; NM_006061; NM_001190986 |
| PVALB | 5816 | NM_001315532; NM_002854 |
| GAD1 | 2571 | NM_013445; XM_017003758; NM_000817; XM_005246444; XM_011510922; XM_017003757; XM_017003756; XM_024452783 |
| MYH7 | 4625 | XM_017021340; NM_000257 |
| SERPINB7 | 8710 | XM_024451278; NM_001261831; NM_003784; NM_001040147; NM_001261830 |
| COL2A1 | 1280 | XM_017018831; XM_017018830; NM_001844; NM_033150; XM_017018828; XM_017018829 |
| MSMB | 4477 | NM_138634; NM_002443 |
| IRS4 | 8471 | XM_006724713; NM_003604; NM_001379150; XM_011531061 |
| BEX1 | 55859 | NM_018476 |
| PADI3 | 51702 | NM_016233; XM_011541571; XM_017001463; XM_011541572 |
| UGT2B4 | 7363 | NM_001297616; NM_021139; NM_001297615 |
| PRSS1 | 5644 | NR_172951; XM_011516411; NR_172947; NM_002769; NR_172948; NR_172949; NR_172950 |
| CYP2A7 | 1549 | XR_935754; NM_000764; NM_030589 |
| MSLN | 10232 | NM_001177355; NM_005823; NM_013404 |
| CPB1 | 1360 | NM_001871 |
| CARTPT | 9607 | NM_004291 |
| TGM4 | 7047 | NM_003241; XM_011534042 |
| NCAN | 1463 | NM_004386 |
| CYP2A6 | 1548 | NM_000762 |
| CALML5 | 51806 | NM_017422 |
| TFF1 | 7031 | NM_003225 |

-continued

| Gene | NCBI Gene ID | NCBI Accession Number(s) |
| --- | --- | --- |
| | | Ovarian_Cancer |
| QARS | 5859 | NR_073590; NM_005051; XM_017006965; NM_001272073 |
| HSD17B2 | 3294 | NM_002153; XR_001751898 |
| CLDN6 | 9074 | NM_021195 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| IZUMO4 | 113177 | XM_024451343; XR_002958248; NM_001039846; XM_024451342; XM_024451344; NM_052878; NM_001031735; NM_001363588 |
| PAQR4 | 124222 | NM_001284513; NM_001284511; NM_001284512; NM_152341; NM_001324118 |
| NGFR | 4804 | NM_002507 |
| MCC | 4163 | NM_002387; NM_001085377 |
| FAM107A | 11170 | NM_001076778; NM_007177; NM_001282713; NM_001282714 |
| FOXL1 | 2300 | NM_005250 |
| KCNC3 | 3748 | NM_004977; NR_110912; NM_001372305 |
| PTGS2 | 5743 | NM_000963 |
| COL17A1 | 1308 | NM_130778; NM_000494 |
| FZD2 | 2535 | NM_001466 |
| EIF1AY | 9086 | NM_004681; NM_001278612 |
| HOXD13 | 3239 | XM_011511068; NM_000523; XM_011511069 |
| FGF14 | 2259 | NM_001321931; NM_001321943; NM_001321949; NM_175929; NM_001321933; NM_001321941; NM_001321932; NM_001321935; NM_001321937; NM_001321945; NM_001321947; NM_001321939; NM_001321936; NM_001321940; NM_001321944; NM_001321946; NM_001321948; NM_001379342; NM_001321934; NM_001321938; NM_001321942; NM_004115 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| MMP13 | 4322 | NM_002427 |
| LHX1 | 3975 | NM_005568 |
| CSDC2 | 27254 | NM_014460 |
| PAX9 | 5083 | NM_001372076; NM_006194 |
| B2M | 567 | XR_002957658; XM_005254549; NM_004048 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| ZNF492 | 57615 | NM_020855 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PRSS1 | 5644 | NR_172951; XM_011516411; NR_172947; NM_002769; NR_172948; NR_172949; NR_172950 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| IRX5 | 10265 | NM_005853; XM_011522809; NM_001252197 |
| DOK5 | 55816 | XM_011528904; NM_001294161; NM_018431; XM_024451946; NM_177959 |

-continued

| Gene | NCBI Gene ID | NCBI Accession Number(s) |
|---|---|---|
| ASIP | 434 | NM_001385218; XM_011528820; NM_001672; XM_011528821 |
| EMX2 | 2018 | NM_004098; NM_001165924 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| VGLL1 | 51442 | NM_016267 |
| HSPA4L | 22824 | NM_001317381; NM_001317383; XM_011531745; NM_001317382; NM_014278 |
| PAX8 | 7849 | NM_013992; NM_013953; NM_013952; NM_003466; NM_013951 |
| ALDH1A3 | 220 | NM_001293815; NM_000693; NM_001037224 |
| ANGPT4 | 51378 | NM_001322809; XM_011529239; NM_015985 |
| KIAA0513 | 9764 | NM_001286565; NM_001297766; NM_001286566; XM_017023912; NM_014732; NM_001388359 |
| RPS4Y1 | 6192 | NM_001008 |
| NES | 10763 | NM_024609; NM_006617 |
| COL21A1 | 81578 | XM_011514927; XM_024446561; XR_001743657; NM_030820; NR_134851; NR_134849; XM_011514925; NM_001318753; NR_134850; NM_001318752; NM_001318754; XM_011514926; XM_006715223; NM_001318751; XM_011514924 |
| MNX1 | 3110 | NM_001165255; NM_005515 |
| WT1 | 7490 | NM_000378; NR_160306; NM_001367854; NM_001198551; NM_001198552; NM_024424; NM_024426; NM_024425 |
| SLC6A12 | 6539 | XM_005253747; NM_003044; NM_001122847; XM_005253748; XM_011521010; XM_006719005; NM_001122848; NM_001206931 |
| NPR1 | 4881 | XM_017001374; XM_005245218; NM_000906 |
| WISP3 | 8838 | XM_011536223; XM_011536220; NM_198239; NR_125353; NR_125354; XR_001743705; NM_130396; XM_011536222; NM_003880 |
| ASGR1 | 432 | XM_011523861; NM_001197216; NM_001671 |
| FOXL2 | 668 | NM_023067 |
| PNOC | 5368 | NM_006228; XM_011544559; XM_005273532; XM_017013578; NM_001284244 |
| KLK6 | 5653 | XM_024451611; NM_001319949; NM_001012964; NM_001319948; NM_001012965; NM_002774 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| KLK10 | 5655 | XM_006723289; XM_005259061; NM_002776; NM_145888; NM_001077500; XM_017026993; XM_006723287; XM_005259062 |
| HEY1 | 23462 | NM_001040708; NM_012258; NM_001282851 |
| SCD | 6319 | NM_005063 |
| DIO3 | 1735 | NM_001362 |
| SCGN | 10590 | NM_006998; XM_017010181 |
| LGALS14 | 56891 | NM_020129; NM_203471 |
| SLC27A2 | 11001 | NM_001159629; NM_003645 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| BBC3 | 27113 | XM_006723141; XM_011526722; NM_001127241; NM_001127242; NM_001127240; NM_014417 |
| CETP | 1071 | XM_006721124; NM_000078; NM_001286085 |
| GSTM5 | 2949 | NM_000851; XM_005270785; XM_005270784 |
| WNT7A | 7476 | XM_011534091; NM_004625 |
| CCNE1 | 898 | XM_011527440; NM_001238; NM_001322259; NM_001322261; NM_001322262; NM_057182 |
| DLC1 | 10395 | NM_001316668; NM_182643; XM_005273374; NM_001348081; NM_001348083; NM_001348084; NM_001164271; NM_006094; NM_024767; NM_001348082 |

-continued

| Gene | NCBI Gene ID | NCBI Accession Number(s) |
|---|---|---|
| RAMP3 | 10268 | XM_017011666; NM_005856; XM_006715631 |
| MEIS1 | 4211 | NM_002398 |
| SGCA | 6442 | XM_011525122; XM_011525120; XM_011525121; XM_024450873; NM_001135697; NR_135553; XR_002958056; XM_011525124; NM_000023; XM_011525123 |
| HGH1 | 51236 | NM_016458; XR_001745537 |
| CHODL | 140578 | XM_017028273; NM_001204174; NM_024944; XM_011529453; NM_001204176; NM_001204175; NM_001204177; XM_011529457; NM_001204178 |
| NLRP1 | 22861 | NM_001033053; NM_033006; NM_033007; NM_014922; NM_033004 |
| CLDN9 | 9080 | NM_020982 |
| RPL4 | 6124 | NM_000968 |
| CDH6 | 1004 | NM_004932; NM_001362435; XM_017008910; XM_011513921; XR_001741972 |
| TNFRSF10C | 8794 | NM_003841 |
| ITGA2 | 3673 | NR_073103; NR_073104; NR_073105; NR_073106; NR_073107; NM_002203 |
| GRK5 | 2869 | XM_005269707; XM_005269708; NM_005308 |
| LIPF | 8513 | NM_004190; NM_001198829; NM_001198830; NM_001198828; XM_011540311 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| SST | 6750 | NM_001048 |
| IL20RA | 53832 | NM_001278722; XM_011535904; XM_017010955; NM_001278724; NM_014432; XM_006715506; NM_001278723; XM_017010954 |
| FGF18 | 8817 | NM_003862; NM_033649 |
| NR5A1 | 2516 | NM_004959 |
| ULBP2 | 80328 | NM_025217; XM_017011321 |
| RNF128 | 79589 | NM_024539; NM_194463 |
| PRM2 | 5620 | NM_001286358; NR_104428; NM_002762; NM_001286356; NM_001286359; NM_001286357 |
| C7 | 730 | NM_000587 |
| L1CAM | 3897 | NM_024003; NM_001278116; NM_001143963; NM_000425 |
| BCAM | 4059 | NM_001013257; NM_005581 |
| DTL | 51514 | XM_011509614; NM_001286229; NM_001286230; NM_016448 |
| ADRB3 | 155 | NM_000025 |
| CLDN16 | 10686 | NM_006580; NM_001378492; NM_001378493 |
| FMO5 | 2330 | XM_005272946; XM_005272947; XM_011509351; XM_017000802; NM_001144829; NM_001461; XM_006711244; XM_006711245; XM_005272948; NM_001144830; XM_017000801; XM_011509350 |
| KCNIP1 | 30820 | NM_001034837; NM_014592; NM_001034838; NM_001278340; XM_017009407; XM_017009408; NM_001278339 |
| FGF23 | 8074 | NM_020638 |
| PDE3B | 5140 | XR_001747903; NM_000922; NM_001363570; XM_017017912; XM_006718249; XM_017017911; NM_001363569 |
| SLC4A3 | 6508 | XM_011511667; NM_201574; NR_048551; XM_005246790; XM_011511665; NM_001326559; NM_005070 |
| FOLR1 | 2348 | NM_000802; NM_016729; NM_016730; NM_016725; NM_016724 |
| STAR | 6770 | NM_001007243; NM_000349 |
| | | Uterus_Carcinoma |
| SPDEF | 25803 | NM_001252294; XM_005248988; NM_012391; XM_011514457 |
| HLA-G | 3135 | XM_017010817; NM_001384280; XM_017010818; NM_002127; XM_024446420; NM_001363567; NM_001384290 |
| MARCO | 8685 | NM_006770; XM_011512082; XM_011512083; XM_017005171 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| ZNF208 | 7757 | NM_001329971; NM_001329973; NM_001329974; NM_001329972; NR_138252; NM_007153 |
| CHRND | 1144 | NM_001311196; XM_011510524; NM_001256657; NM_001311195; NM_000751 |
| SLC31A2 | 1318 | NM_001860 |
| C1S | 716 | XM_005253760; NM_001734; NM_001346850; NM_201442 |
| GREB1 | 9687 | XM_024453255; NM_014668; NM_033090; XM_024453254; XM_024453256; NM_148903; XM_005246196; XM_024453251; XR_922686; XM_024453250; XM_024453252; XM_011510418; XM_011510423; XM_011510422; XM_024453253; XM_011510419; XM_005246192; XR_001739081 |
| VIP | 7432 | XM_006715562; XM_005267135; NM_003381; NM_194435 |
| ZWINT | 11130 | XR_428692; NM_007057; NM_001005413; XM_017015605; XM_024447784; NM_032997; NM_001005414 |
| CREB5 | 9586 | XM_017012807; XM_017012808; NM_001011666; XM_024447005; XM_017012806; XM_017012809; NM_182898; XM_017012810; XM_005249906; NM_004904; XR_001744893; XM_011515618; NM_182899 |

-continued

| Gene | NCBI Gene ID | NCBI Accession Number(s) |
|---|---|---|
| EIF1AY | 9086 | NM_004681; NM_001278612 |
| E2F1 | 1869 | NM_005225 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| HOXD13 | 3239 | XM_011511068; NM_000523; XM_011511069 |
| CTSV | 1515 | NM_001201575; NM_001333 |
| HOXD10 | 3236 | NM_002148 |
| DGKG | 1608 | NM_001346; NM_001080745; NM_001080744 |
| SFRP1 | 6422 | NM_003012 |
| PAX9 | 5083 | NM_001372076; NM_006194 |
| SCGB2A1 | 4246 | NM_002407 |
| FOXJ1 | 2302 | NM_001454 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| BEGAIN | 57596 | NM_001385092; NM_001385093; NR_169571; XM_024449671; NM_001385104; XM_024449670; NM_001159531; NM_001385088; NM_001385094; NM_001385095; NM_001385096; NM_001385097; NM_001385098; NM_001385099; NM_001385100; NM_020836; NM_001385089; NM_001385102; NM_001385083; NM_001385084; NM_001385091; NR_169570; NM_001385085; NM_001385086; NM_001385087; NM_001385103; NM_001385082; NM_001385090; NM_001385101 |
| EMX2 | 2018 | NM_004098; NM_001165924 |
| VGLL1 | 51442 | NM_016267 |
| ALDH1A2 | 8854 | NM_001206897; NM_170697; NM_170696; NM_003888 |
| SLCO5A1 | 81796 | XM_017013885; XR_928814; NM_001146008; NM_001146009; XM_017013886; XR_428341; XM_017013884; NM_030958; XM_017013883; XM_005251313 |
| HOXA10 | 3206 | NR_037939; NM_153715; NM_018951 |
| GADD45G | 10912 | XM_011518163; NM_006705 |
| RPS4Y1 | 6192 | NM_001008 |
| TPM2 | 7169 | XM_017015091; NM_213674; XM_017015093; XM_017015088; NM_001301226; NM_001301227; NM_001145822; XM_017015087; XM_017015092; XM_017015090; NM_003289 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| WT1 | 7490 | NM_000378; NR_160306; NM_001367854; NM_001198551; NM_001198552; NM_024424; NM_024426; NM_024425 |
| MNX1 | 3110 | NM_001165255; NM_005515 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| ANKRD2 | 26287 | NM_001291218; NM_001129981; NM_020349; NM_001291219; NM_001346793 |
| EHHADH | 1962 | XM_006713525; NM_001166415; NM_001966 |
| FXYD1 | 5348 | NM_001278718; NM_001278717; NM_021902; XM_017026875; NM_005031; XM_017026874; XM_017026876 |
| FOXL2 | 668 | NM_023067 |
| GLDC | 2731 | NM_000170 |
| TNNC1 | 7134 | NM_003280 |
| EDNRB | 1910 | NM_001122659; NM_003991; NM_001201397; NM_000115; NR_047024 |
| APOD | 347 | NM_001647 |
| SLC27A2 | 11001 | NM_001159629; NM_003645 |
| SLC12A2 | 6558 | XM_011543588; NM_001256461; XR_001742214; NR_046207; NM_001046; XM_017009771 |
| FMO2 | 2327 | NM_001460; NR_160266; XR_921761; NM_001365900; XR_001737072; NM_001301347 |
| GSTM5 | 2949 | NM_000851; XM_005270785; XM_005270784 |
| SOX1 | 6656 | NM_005986 |
| APBA1 | 320 | NM_001163; XM_011518617; XM_017014670; XM_005251968 |
| HOXB13 | 10481 | NM_006361 |
| NPY4R | 5540 | XR_001747124; NM_001278794; NM_005972; XM_011539936; XM_017016387; XM_011539937; XM_017016386; XR_001747123 |
| CIDEB | 27141 | NM_001393334; NM_001393340; NM_001318807; NM_001393339; NM_001393336; NM_001393338; NM_001393335; NM_001393337; NM_014430 |

-continued

| Gene | NCBI Gene ID | NCBI Accession Number(s) |
|---|---|---|
| MEIS1 | 4211 | NM_002398 |
| TNNC2 | 7125 | NM_003279; XM_011529031 |
| RIMBP2 | 23504 | XM_017019105; XM_011538103; XM_011538105; NM_001351227; NM_001393620; NM_001393627; NM_001393616; NM_001351232; NM_001393615; NM_001393621; NM_001393623; NM_001393628; XM_011538106; XM_011538102; XM_011538108; NM_001351231; NM_001393614; NM_001393617; NM_001393622; NM_001393625; NM_001393629; NM_001351230; NM_001393619; NM_001393626; NM_001351228; NM_001393624; XM_011538107; XM_017019106; NM_001351226; NM_001351229; NM_001351233; NM_001393618; NM_015347 |
| HGH1 | 51236 | NM_016458; XR_001745537 |
| SOX15 | 6665 | NM_006942 |
| PDLIM3 | 27295 | NM_001114107; XR_938723; NM_001257963; XR_938724; NM_001257962; NR_047562; NM_014476; XR_001741206 |
| CX3CR1 | 1524 | NM_001171174; NM_001337; NM_001171171; NM_001171172 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| ZBTB16 | 7704 | XR_001747955; NM_001354751; XM_017018259; NM_006006; NM_001354752; XM_005271658; XM_024448681; NM_001018011; NM_001354750 |
| CLCA2 | 9635 | NM_006536; XM_011542448 |
| DLX5 | 1749 | XM_017011803; NM_005221; XM_005250185 |
| GABRQ | 55879 | NM_018558; XM_011531184 |
| FOXA2 | 3170 | NM_021784; NM_153675 |
| TNFSF10 | 8743 | NR_033994; NM_001190943; NM_003810; NM_001190942 |
| IQCA1 | 79781 | XM_017004960; NM_024726; NM_001270585; XM_011511865; XM_011511866; XM_011511864; NM_001270584; NR_073043 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| TUBA1C | 84790 | NM_001303114; NM_032704; NM_001303116; NM_001303117; NM_001303115 |
| GYPC | 2995 | NM_002101; XM_006712460; NM_001256584; NM_016815 |
| CA2 | 760 | NM_001293675; NM_000067 |
| IL20RA | 53832 | NM_001278722; XM_011535904; XM_017010955; NM_001278724; NM_014432; XM_006715506; NM_001278723; XM_017010954 |
| RGN | 9104 | XM_024452477; XM_006724568; XM_017029954; NM_004683; NM_001282848; NM_152869; NM_001282849; XM_006724567 |
| AOC3 | 8639 | XR_934584; NM_001277732; NM_003734; NR_102422; XM_011525419; XR_001752673; XM_011525420; XM_024451015; NM_001277731 |
| FGF18 | 8817 | NM_003862; NM_033649 |
| MYO5A | 4644 | XM_011521607; NM_001142495; NM_001382348; XM_011521610; NM_000259; NM_001382347; XM_011521611; XM_011521609; XM_011521612; XM_017022227; NM_001382349 |
| CCDC33 | 80125 | XR_001751400; XM_011522090; XM_017022624; XM_017022626; NM_001287181; XM_011522088; XM_017022630; XR_001751401; NM_025055; XM_017022625; XM_017022628; XM_017022631; NR_108023; NM_182791; XM_011522087; XM_005254692; XM_017022627; XM_017022633; XM_017022623; XM_011522086; XM_017022632; XM_011522085; XM_011522089 |
| REN | 5972 | NM_000537 |
| NCAPG | 64151 | NM_022346; XM_017008543; NR_073124; XM_017008544; XM_011513876 |
| CT62 | 196993 | NR_168259; NM_001102658; NR_168260 |
| CACNA1G | 8913 | NM_001256326; NM_001256328; NM_018896; NM_198378; NM_198388; NM_198396; NM_001256359; NM_001256361; NM_198383; NM_198385; NM_001256327; NM_001256330; NR_046056; NM_198380; NM_198382; NR_046054; XM_006722160; NM_198379; NM_001256329; NM_001256332; NM_001256333; NM_001256360; NM_198384; NM_198386; NR_046058; NM_001256325; NM_001256334; NM_198387; XM_006722161; NM_001256324; NM_001256331; NM_198376; NM_198377; NR_046055; NR_046057; NM_198397 |
| PIGR | 5284 | XM_011509629; NM_002644 |
| CSTA | 1475 | NM_005213 |
| OSR2 | 116039 | XM_017013018; NM_053001; XM_011516825; XM_005250778; NM_001286841; NM_001142462; XM_011516826; NM_001394683; XM_011516827 |
| FOXF2 | 2295 | NM_001452 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |

-continued

| Gene | NCBI Gene ID | NCBI Accession Number(s) |
|---|---|---|
| GAD1 | 2571 | NM_013445; XM_017003758; NM_000817; XM_005246444; XM_011510922; XM_017003757; XM_017003756; XM_024452783 |
| NXPH4 | 11247 | XM_017018747; NM_007224 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EGFR | 1956 | NM_001346899; NM_201282; NM_201284; NM_001346898; NM_001346900; NM_001346897; NM_201283; NM_001346941; NM_005228 |
| FMO3 | 2328 | XM_011509345; XM_024454365; NM_001002294; NM_006894; NM_001319173; NM_001319174 |
| TSPAN7 | 7102 | NM_004615 |
| ASRGL1 | 80150 | XM_005274305; XM_005274306; XM_011545265; NM_001083926; XM_011545266; NM_025080; XR_002957199; XM_017018354; XR_002957198; XR_001747982 |
| ALOX15B | 247 | NM_001141; NM_001039130; NM_001039131 |
| PRPH | 5630 | XM_005269025; XR_944623; NM_006262; |
| EFEMP1 | 2202 | XM_024452757; NM_004105; NM_018894; XM_005264205; NM_001039349; XM_017003586; XM_024452755; XM_024452756; NM_001039348 |
| SALL1 | 6299 | NM_001127892; NM_002968 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| PHOX2A | 401 | NM_005169 |
| AQP5 | 362 | NM_001651; XM_005268838 |
| TTC22 | 55001 | XM_017001582; XM_011541671; NM_001114108; NM_017904 |
| | | Renal_Cell_Carcinoma |
| SLC17A3 | 10786 | NM_006632; NM_001098486 |
| SLC4A1 | 6521 | XM_011525129; XM_005257593; XM_011525130; NM_000342 |
| CDH16 | 1014 | NM_001204746; XM_011522807; NM_004062; XM_005255770; NM_001204744; NM_001204745 |
| SLC22A2 | 6582 | NM_153191; NM_003058 |
| NAT8 | 9027 | NM_003960 |
| SLC3A1 | 6519 | XM_011533047; NM_000341 |
| ENPP3 | 5169 | XR_001743464; NR_133007; NM_005021; XM_017010932; XM_011535897 |
| FXYD2 | 486 | NM_021603; NM_001127489; NM_001680 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| SIM1 | 6492 | XM_011536072; NM_001374769; NM_005068 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| PAX2 | 5076 | NM_001304569; NM_003987; NM_001374303; NM_003989; NM_000278; NM_003990; NM_003988 |
| PVALB | 5816 | NM_001315532; NM_002854 |
| RHBG | 57127 | XR_001737323; NR_146765; XR_001737328; XR_001737329; NR_046115; XM_011509799; XM_017001859; NR_146764; XM_011509800; XM_017001858; XR_001737324; XR_001737325; NM_001256395; NR_146763; XM_017001857; NM_020407; XR_001737330; XR_001737332; NM_001256396 |
| AQP2 | 359 | NM_000486 |
| POU3F3 | 5455 | NM_006236 |
| PAX8 | 7849 | NM_013992; NM_013953; NM_013952; NM_003466; NM_013951 |
| GFRA3 | 2676 | NM_001496 |
| CA12 | 771 | NM_001218; NR_135511; NM_206925; NM_001293642 |
| FOXD3 | 27022 | NM_012183 |
| CACNG4 | 27092 | NM_014405 |
| HAND2 | 9464 | NM_021973 |
| NLGN1 | 22871 | NM_001365923; NM_001365928; NM_001365932; NM_014932; XM_011512551; XM_011512553; XM_017005897; XM_017005902; NM_001365929; NM_001365926; XM_017005895; XM_017005893; NM_001365925; NM_001365931; XM_017005896; XM_017005900; NM_001365933; XM_005247237; NM_001365930; NM_001365936; XM_011512554; XM_017005888; XM_017005894; NM_001365924; NM_001365927; NM_001365934; NM_001365935 |
| TRPM3 | 80036 | NM_001366147; XM_011519045; NM_001366145; NM_206944; XM_011519042; XM_024447681; NM_001007470; NM_001366152; NM_001366153; NM_206946; XM_011519037; NM_001366151; NM_206947; XM_011519040; NM_001007471; NM_001366141; NM_001366150; NM_001366154; XM_011519039; XM_017015156; XM_024447687; NM_001366144; NM_001366146; NM_020952; XM_024447683; NM_001366149; XM_011519038; XM_011519046; XM_024447682; XM_024447684; XM_024447685; XM_024447686; NM_001366142; NM_001366143; NM_001366148; NM_024971; NM_206945; NM_206948 |
| ARHGEF4 | 50649 | XM_011511276; XM_005263689; XR_001738756; NM_001375900; NM_001375902; XM_011511274; XR_001738757; NM_001375901; NM_001375904; NM_001367493; |

-continued

| Gene | NCBI Gene ID | NCBI Accession Number(s) |
|---|---|---|
| | | NM_001375903; NM_015320; NM_001395416; NM_032995; XM_005263688; XM_011511277; XM_017004231; XM_024452938 |
| INSM1 | 3642 | NM_002196 |
| S100A14 | 57402 | XM_017001875; NM_020672; XM_005245362 |
| LGR5 | 8549 | NR_110596; NM_001277227; NM_001277226; NM_003667 |
| CFTR | 1080 | NM_000492 |
| TRHDE | 29953 | XM_017019244; XM_017019243; NM_013381; XM_005268819; XM_011538248 |
| ESRP1 | 54845 | XM_005250991; NM_001122827; NM_017697; XM_005250992; NM_001122826; NM_001034915; NM_001122825 |
| LAD1 | 3898 | NM_005558 |
| GRHL2 | 79977 | XM_011517306; XM_024447286; NM_001330593; NM_024915; XM_011517307 |
| ALPPL2 | 251 | NM_031313 |
| HOXC10 | 3226 | NM_017409 |
| EPHB3 | 2049 | NM_004443 |
| SLC6A11 | 6538 | NM_001317406; XM_017007073; XM_011534033; NM_014229 |
| NKX3-2 | 579 | NM_001189 |
| CNKSR1 | 10256 | NM_006314; NR_023345; NM_001297647; NM_001297648 |
| RAMP1 | 10267 | XM_017003153; XM_017003154; XM_017003155; NM_001308353; NM_005855; XM_017003152; XM_017003156 |
| KIF2C | 11004 | NM_001297656; XM_011540541; NM_001297657; XM_011540540; NM_006845; NM_001297655 |
| ST8SIA2 | 8128 | NM_006011; NM_001330416; XM_017022642 |
| SFRP1 | 6422 | NM_003012 |
| SPAG4 | 6676 | XM_011529009; NM_003116; XM_005260520; NM_001317931 |
| CDKN2A | 1029 | XR_929159; XM_011517676; XM_011517675; NM_001363763; NM_001195132; NM_058195; NM_000077; NM_058196; NM_058197; XM_005251343 |
| SIGLEC8 | 27181 | XM_011526734; NM_014442; NM_001363548 |
| SLC14A2 | 8170 | XM_017026016; NM_007163; NM_001242692; XM_024451271; NM_001371319; XM_024451270 |
| PLA2G7 | 7941 | NM_001168357; XR_001743639; XM_005249408; NM_005084; XR_002956305 |
| KCNN1 | 3780 | NM_001386974; NM_001386976; NR_170373; NM_001386975; NM_001386977; NM_002248; XM_011528004; NR_170374 |
| CA8 | 767 | NM_001321837; NM_001321838; XM_011517587; XM_011517588; NM_001321839; NM_004056; NR_135821; XM_017013818 |
| KLK6 | 5653 | XM_024451611; NM_001319949; NM_001012964; NM_001319948; NM_001012965; NM_002774 |
| CA9 | 768 | XR_428428; NM_001216; XR_001746374 |
| | | Squamous_Cell_Carcinoma |
| TMPRSS11D | 9407 | XM_005265710; XM_017008851; NM_004262 |
| SPRR1B | 6699 | NM_003125 |
| SERPINB3 | 6317 | NM_006919 |
| DSG3 | 1830 | XM_011525850; NM_001944 |
| ADH7 | 131 | NM_001166504; NM_000673 |
| S100A12 | 6283 | NM_005621 |
| SPRR1A | 6698 | NM_005987; NM_001199828 |
| KRT1 | 3848 | NM_006121 |
| SERPINB13 | 5275 | NM_001348267; XM_011526029; NM_001348268; NM_012397; NM_001348269; NM_001307923; NM_001348270 |
| KRT6A | 3853 | NM_005554 |
| CRNN | 49860 | NM_016190 |
| FOXE1 | 2304 | NM_004473 |
| SFTPB | 6439 | XM_005264487; NM_198843; XM_005264488; NM_000542; NM_001367281; XM_005264490 |
| CALML3 | 810 | NM_005185 |
| CRCT1 | 54544 | NM_019060; XM_011509656 |
| SFN | 2810 | NM_006142 |
| TP63 | 8626 | NM_001114978; NM_001329144; NM_001329146; NM_001329964; NM_001329145; NM_003722; NM_001114979; NM_001114982; NM_001329149; NM_001114980; NM_001114981; NM_001329150; NM_001329148 |
| SFTPA2 | 729238 | XM_011540124; XM_005270132; NM_001320813; NM_001320814; XM_017016608; XM_011540125; NM_001098668; XM_005270128 |
| FABP5 | 2171 | NM_001444 |
| KRT5 | 3852 | NM_000424 |
| GPR87 | 53836 | NM_023915 |
| CKM | 1158 | NM_001824 |
| MYL2 | 4633 | NM_000432 |
| SOX2 | 6657 | NM_003106 |
| MYL1 | 4632 | NM_079422; NM_079420 |
| IRX4 | 50805 | NM_016358; NM_001278633; NM_001278632; NM_001278635; NM_001278634 |
| NKX2-1 | 7080 | NM_001079668; NM_003317 |
| KRT20 | 54474 | NM_019010 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| PLA2G3 | 50487 | XM_011530205; XR_937865; XM_011530204; NM_015715 |
| FLG | 2312 | NM_002016 |

-continued

| Gene | NCBI Gene ID | NCBI Accession Number(s) |
|---|---|---|
| SFTPD | 6441 | XM_011540087; NM_003019; XM_011540088 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SPINK1 | 6690 | NM_003122; NM_001379610; NM_001354966 |
| NTS | 4922 | NM_006183 |
| MMP12 | 4321 | NM_002426 |
| ALDH3B2 | 222 | NM_001354345; NM_001393400; NM_001393402; ; NM_001393401; NM_000695; NM_001031615 |
| HNF1B | 6928 | XM_011525161; NM_001165923; NM_001304286; XM_011525163; NM_000458; XM_011525162; NM_006481; XM_011525164; XM_011525160 |
| UPK1B | 7348 | NM_006952 |
| GJB1 | 2705 | NM_000166; XM_011530907; NM_001097642 |
| FABP4 | 2167 | NM_001442 |
| CTSV | 1515 | NM_001201575; NM_001333 |
| HOXD11 | 3237 | NM_021192 |
| CLDN18 | 51208 | NM_001002026; NM_016369 |
| PITX1 | 5307 | NM_002653 |
| LIPF | 8513 | NM_004190; NM_001198829; NM_001198830; NM_001198828; XM_011540311 |
| FZD10 | 11211 | NM_007197 |
| CYP4B1 | 1580 | XM_011540833; NR_135003; XM_011540832; NM_000779; NM_001319161; NM_001319163; NM_001099772; XM_017000466; NM_001319162; XR_946559 |
| TCN1 | 6947 | NM_001062 |
| CLDN3 | 1365 | NM_001306 |
| MYOT | 9499 | XM_017010060; XM_017010061; NM_001300911; NM_001135940; XM_017010062; NM_006790 |
| LAMC2 | 3918 | NM_005562; NM_018891; XM_017001273 |
| SCNN1B | 6338 | XM_017023526; XM_011545913; XM_011545914; XM_017023525; NM_000336 |
| DES | 1674 | NM_001927; NM_001382708; NM_001382710; NM_001382713; NM_001382709; NM_001382711; NM_001382712 |
| CSF3 | 1440 | NR_168489; NR_168491; NM_000759; NM_172220; NM_001178147; NM_172219; NR_168490; NR_033662 |
| HMGCS2 | 3158 | NM_001166107; XM_011541313; NM_005518 |
| AQP4 | 361 | NM_001317387; NM_001364287; NM_001364286; NM_001317384; XM_011525942; NM_001650; NM_001364289; NM_004028 |
| TMC5 | 79838 | NM_001261841; NM_024780; NM_001308161; NM_001105248; NM_001105249 |
| SLC52A1 | 55065 | XM_011523951; NM_001104577; NM_017986 |
| DMBT1 | 1755 | XM_011539390; XM_011539391; XM_011539407; XM_011539408; NM_007329; XM_006717660; XM_006717665; XM_011539402; XM_024447854; XM_011539392; XM_011539393; XM_011539400; XM_011539403; XM_011539405; XM_011539413; XM_017015798; NM_001320644; NM_004406; XM_011539394; XM_011539409; XM_011539415; NM_017579; XM_011539389; XM_011539395; XM_011539396; XM_011539399; XM_011539401; XM_011539410; XM_011539414; NM_001377530; XM_011539398; XM_011539411 |
| SLC34A2 | 10568 | NM_001177999; NM_006424; NM_001177998 |
| GABRQ | 55879 | NM_018558; XM_011531184 |
| PRSS3 | 5646 | NM_007343; NM_001197097; NM_002771; XM_011517965; NM_001197098 |
| SLC4A4 | 8671 | XM_024454267; XM_024454271; XM_024454272; NM_001098484; XM_024454270; NM_003759; XM_017008793; XM_024454268; NM_001134742; XM_024454269; XM_011532390; XM_017008792 |
| COX6A2 | 1339 | NM_005205 |
| SERPINA5 | 5104 | NM_000624 |
| SDC1 | 6382 | NM_001006946; XM_005262620; XM_005262621; NM_002997; XM_005262622 |
| ENDOU | 8909 | NM_001172439; NM_006025; NM_001172440 |
| UPK1A | 11045 | NM_007000; NM_001281443 |
| NME5 | 8382 | XM_024446227; NM_003551; XM_005272099; XM_024446228; XM_017009945 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; |

-continued

| Gene | NCBI Gene ID | NCBI Accession Number(s) |
|---|---|---|
| | | NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| HAND1 | 9421 | NM_004821; XM_005268531 |
| CRH | 1392 | NM_000756 |
| TFAP2A | 7020 | NM_001032280; XM_006715175; NM_001042425; XM_017011232; XM_011514833; NM_001372066; NM_003220 |
| COL9A1 | 1297 | NM_001851; NR_165185; NM_078485; XM_017010246; XM_011535429; XM_017010247; NM_001377289; NM_001377290; NM_001377291 |
| ATP10B | 23120 | XM_011534472; XM_017009253; NM_001366652; NM_001366658; XM_011534468; NM_001366653; NM_001366654; NM_001366655; NM_001366656; NM_025153; NM_001366657; XM_017009252; XM_011534469 |
| ALDOB | 229 | NM_000035 |
| AHNAK2 | 113146 | NM_138420; XM_024449463; NM_001350929 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| EVX1 | 2128 | NM_001304519; NM_001304520; NM_001989 |
| CLDN4 | 1364 | NM_001305 |
| NEB | 4703 | XM_005246590; XM_005246594; XM_005246602; XM_005246611; XM_017004178; XM_017004179; XM_017004180; NM_001164508; XM_005246603; XM_005246617; XM_006712542; XM_017004185; NM_001164507; NM_001271208; XM_005246593; XM_005246598; XM_005246606; XM_005246610; XM_017004177; XM_017004184; NM_004543; XM_005246592; XM_005246599; XM_005246601; XM_005246616; XM_017004181; XM_005246604; XM_005246608; XM_017004182; XM_017004183; XM_005246591; XM_005246596; XM_005246597; XM_006712541; XM_011511225; XM_011511226; XM_005246613; XM_005246612; XM_005246615; XM_011511227 |
| LRP2 | 4036 | XM_011511183; NM_004525; XM_011511184 |
| DLX2 | 1746 | NM_004405 |
| GRIK3 | 2899 | NM_000831 |
| TBX1 | 6899 | NM_005992; NM_080646; XM_017028928; XM_006724312; XM_017028926; NM_001379200; XM_017028925; XM_017028927; NM_080647 |
| XDH | 7498 | NM_000379; XM_011533096; XM_011533095 |
| DLX6 | 1750 | NM_005222 |
| ADH1C | 126 | NM_000669; NR_133005 |
| HKDC1 | 80201 | NM_025130; XR_001747209; XM_011540195 |
| MFAP5 | 8076 | NM_001297709; NR_123733; NR_123734; NM_001297711; NM_003480; NM_001297710; NM_001297712 |
| DNAJC22 | 79962 | NM_001304944; NM_024902; XM_005269157; XM_005269155; XM_005269156 |
| HNF4G | 3174 | NM_001330561; XM_017013373; XM_017013375; XM_017013374; XM_017013376; NM_004133 |
| KCNB1 | 3745 | XM_011528799; XM_006723784; NM_004975 |
| ACTG2 | 72 | NM_001199893; NM_001615 |
| SSX1 | 6756 | NM_001278691; NM_005635 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| FAM107A | 11170 | NM_001076778; NM_007177; NM_001282713; NM_001282714 |
| SEMA3G | 56920 | XM_024453642; NM_020163 |
| FIGF | 2277 | NM_004469 |
| TCF21 | 6943 | NM_003206; NM_198392 |
| FMO2 | 2327 | NM_001460; NR_160266; XR_921761; NM_001365900; XR_001737072; NM_001301347 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| AOC3 | 8639 | XR_934584; NM_001277732; NM_003734; NR_102422; XM_011525419; XR_001752673; XM_011525420; XM_024451015; NM_001277731 |
| ADH1B | 125 | NM_001286650; NM_000668 |
| GDF10 | 2662 | NM_004962 |
| MYOC | 4653 | NM_000261 |
| SOX17 | 64321 | NM_022454 |
| FHL5 | 9457 | NM_001170807; NM_001322466; NM_001322467; NM_020482 |
| PDK4 | 5166 | NM_002612 |
| CCL23 | 6368 | NM_005064; XR_429910; NM_145898 |
| MMP11 | 4320 | NM_005940; NR_133013 |

-continued

| Gene | NCBI Gene ID | NCBI Accession Number(s) |
|---|---|---|
| HBB | 3043 | NM_000518 |
| HOXA10 | 3206 | NR_037939; NM_153715; NM_018951 |
| MYBL2 | 4605 | NM_002466; NM_001278610 |
| UBE2C | 11065 | NM_001281742; NM_001281741; NM_181802; NM_181803; NR_104036; NR_104037; NM_007019; NM_181800; NM_181801; NM_181799 |
| NPY1R | 4886 | NM_000909; XM_005263031; XM_011532010 |
| TUBB3 | 10381 | NM_006086; NM_001197181 |
| ORC6 | 23594 | NR_037620; NM_014321; XM_011522978 |
| GRIN2D | 2906 | XM_011526872; NM_000836 |
| PRR4 | 11272 | NM_001098538; NM_007244 |
| COL10A1 | 1300 | XM_011535432; NM_000493; XM_011535433; XM_017010248; XM_006715333 |
| CDKN2A | 1029 | XR_929159; XM_011517676; XM_011517675; NM_001363763; NM_001195132; NM_058195; NM_000077; NM_058196; NM_058197; XM_005251343 |
| FOLR1 | 2348 | NM_000802; NM_016729; NM_016730; NM_016725; NM_016724 |
| ONECUT2 | 9480 | NM_004852 |
| MMP9 | 4318 | NM_004994 |
| HOXA11 | 3207 | NM_005523 |
| HOXB13 | 10481 | NM_006361 |
| CST1 | 1469 | NM_001898 |
| SYT12 | 91683 | XM_011545346; XM_011545347; NM_177963; XM_017018547; NM_001177880; NM_001318775; XM_017018548; XM_006718737; XM_024448766; NM_001318773 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| NXPH4 | 11247 | XM_017018747; NM_007224 |
| CXCL13 | 10563 | NM_001371558; NM_006419 |
| CDX2 | 1045 | XM_011534876; NM_001354700; XM_011534879; XM_011534875; XM_011534878; NM_001265 |
| COL11A1 | 1301 | XM_017000337; XM_017000335; XM_017000336; NR_134980; NM_080629; XM_017000334; NM_001190709; NM_001854; NM_080630 |
| RAB3B | 5865 | XM_017001958; NM_002867 |
| JPH3 | 57338 | NM_001271604; NR_073379; NM_001271605; NM_020655 |
| | | Lung_Adenocarcinoma |
| SFTPA2 | 729238 | XM_011540124; XM_005270132; NM_001320813; NM_001320814; XM_017016608; XM_011540125; NM_001098668; XM_005270128 |
| BPIFA1 | 51297 | NM_130852; NM_001243193; NM_016583 |
| LGSN | 51557 | XM_017010931; XM_017010929; XM_011535889; XM_011535892; NM_016571; XM_017010930; NM_001143940 |
| SCGB1A1 | 7356 | NM_003357 |
| NKX2-1 | 7080 | NM_001079668; NM_003317 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SFTPB | 6439 | XM_005264487; NM_198843; XM_005264488; NM_000542; NM_001367281; XM_005264490 |
| C4BPA | 722 | XM_005273252; NM_000715; XM_005273251 |
| CEACAM6 | 4680 | NM_002483; XM_011526990 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SERPINB13 | 5275 | NM_001348267; XM_011526029; NM_001348268; NM_012397; NM_001348269; NM_001307923; NM_001348270 |
| SPRR1A | 6698 | NM_005987; NM_001199828 |
| HAND2 | 9464 | NM_021973 |
| TMC5 | 79838 | NM_001261841; NM_024780; NM_001308161; NM_001105248; NM_001105249 |
| TSPAN8 | 7103 | NM_001369760; NM_004616; XM_006719583 |
| SPDEF | 25803 | NM_001252294; XM_005248988; NM_012391; XM_011514457 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| CP | 1356 | XM_006713500; XM_006713501; XM_017005735; XM_017005734; XM_006713499; XM_011512435; XR_427361; NM_000096; NR_046371 |
| GCNT3 | 9245 | NM_004751 |
| CLDN8 | 9073 | NM_199328; NM_012132 |
| CARTPT | 9607 | NM_004291 |
| FOXA1 | 3169 | NM_004496; XM_017021246 |
| EDN3 | 1908 | NM_207034; XM_024451847; NM_207032; XR_002958461; XR_002958462; XR_936513; NM_001302455; NM_207033; XM_006723734; XM_011528655; XM_024451848; NM_000114; XM_005260312; XM_005260313; NM_001302456 |

-continued

| Gene | NCBI Gene ID | NCBI Accession Number(s) |
|---|---|---|
| CCL13 | 6357 | NM_005408 |
| DNAH2 | 146754 | XM_017024219; XM_024450606; XM_024450608; XM_024450609; XM_011523663; XM_024450604; XM_024450605; XM_024450607; NM_001303270; NM_020877; XM_011523667; XM_024450610; XM_011523670 |
| EMX2 | 2018 | NM_004098; NM_001165924 |
| CDHR1 | 92211 | XM_011540338; NM_033100; NM_001171971; XM_011540340; XM_011540337; XM_011540339 |
| RNF186 | 54546 | NM_019062 |
| TBX4 | 9496 | XM_011525490; XM_011525491; NM_001321120; XM_011525495; NM_018488 |
| LAMB3 | 3914 | XM_005273124; NM_001127641; XM_017001272; NM_000228; NM_001017402 |
| S100A7 | 6278 | NM_002963 |
| PLA2G2A | 5320 | NM_001161728; NM_000300; NM_001161729; NM_001161727; NM_001395463 |
| KCNG1 | 3755 | XM_011528800; XM_011528802; XM_011528803; XM_011528805; NM_172318; NM_002237; XM_011528801; XM_011528804; XM_011528806; XM_006723785 |
| KRT5 | 3852 | NM_000424 |
| BARX1 | 56033 | NM_021570 |
| SLC44A4 | 80736 | NM_001178045; NM_001178044; NM_025257 |
| MPPED2 | 744 | NM_001377952; NM_001145399; NR_165347; XM_005253111; NR_165336; NR_165343; NR_165339; NR_165340; NR_165345; XM_024448676; NM_001377954; XM_005253114; NM_001377953; NR_165337; NR_165344; NR_165348; XM_017018231; NR_165346; NM_001377955; NM_001377956; NM_001584; NR_165338; NR_165341; NR_165342 |
| XDH | 7498 | NM_000379; XM_011533096; XM_011533095 |
| CCL25 | 6370 | NM_001394634; NM_001394635; NM_001394638; NM_005624; NM_148888; NM_001394636; NM_001201359; NM_001394637 |
| S100A1 | 6271 | NM_006271 |
| ACTA1 | 58 | NM_001100 |
| HR | 55806 | XM_006716367; NM_005144; XM_005273569; NM_018411 |
| DLL3 | 10683 | NM_016941; NM_203486 |
| KRT13 | 3860 | NM_153490; NM_002274 |
| CBLC | 23624 | XM_011526690; XM_011526688; XR_935783; XM_005258696; XR_243917; XM_011526689; NM_001130852; NM_012116 |
| FAM107A | 11170 | NM_001076778; NM_007177; NM_001282713; NM_001282714 |
| TCF21 | 6943 | NM_003206; NM_198392 |
| FCN3 | 8547 | NM_173452; NM_003665 |
| FABP4 | 2167 | NM_001442 |
| GRIA1 | 2890 | NM_001114183; NM_001258022; NM_001258023; NM_001364166; XM_017009392; NR_157093; NM_000827; NM_001258019; NM_001258020; NM_001364165; NM_001258021; NR_047578; NM_001364167 |
| ALAS2 | 212 | NM_001037968; NM_001037967; NM_000032; NM_001037969 |
| TFAP2A | 7020 | NM_001032280; XM_006715175; NM_001042425; XM_017011232; XM_011514833; NM_001372066; NM_003220 |
| PITX1 | 5307 | NM_002653 |
| IGF2BP3 | 10643 | XM_011515092; NM_006547; XM_011515089; XM_006715639; XM_011515090; XM_011515091; XM_011515093 |
| RASAL1 | 8437 | XR_002957386; NM_001193521; NM_001394081; NM_001394082; XM_005253950; NM_001394084; NM_001394087; NM_004658; XM_017020030; XM_017020031; XM_006719642; XR_001748903; XM_006719641; NM_001301202; NM_001394083; XM_011538854; XM_017020029; NM_001394089; XR_001748902; NM_001193520; NM_001394085; NM_001394086; NM_001394088 |
| MMP11 | 4320 | NM_005940; NR_133013 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| NXPH4 | 11247 | XM_017018747; NM_007224 |
| CXCL14 | 9547 | NM_004887 |
| | | Prostate_Adenocarcinoma |
| RNF128 | 79589 | NM_024539; NM_194463 |
| PRM2 | 5620 | NM_001286358; NR_104428; NM_002762; NM_001286356; NM_001286359; NM_001286357 |
| CENPF | 1063 | XM_017000086; NM_016343; XM_011509082 |
| DES | 1674 | NM_001927; NM_001382708; NM_001382710; NM_001382713; NM_001382709; NM_001382711; NM_001382712 |
| NKX3-1 | 4824 | NM_001256339; NR_046072; NM_006167 |
| CGREF1 | 10669 | NM_001166239; NM_006569; NM_001301324; NM_001166241; NM_001166240 |
| KLK2 | 3817 | NM_005551; NR_045762; NM_001002231; NM_001002232; NM_001256080; NR_045763 |
| SEMG1 | 6406 | NM_198139; NM_003007 |
| ASPN | 54829 | NM_001193335; NM_017680 |
| DEPDC1 | 55635 | NM_001114120; NM_017779 |
| AMACR | 23600 | NM_203382; NM_001167597; NM_001167598; NM_014324; NM_001167596; NM_001167595 |
| COL6A1 | 1291 | NM_001848 |
| ONECUT2 | 9480 | NM_004852 |
| COL10A1 | 1300 | XM_011535432; NM_000493; XM_011535433; XM_017010248; XM_006715333 |

-continued

| Gene | NCBI Gene ID | NCBI Accession Number(s) |
|---|---|---|
| TRPM8 | 79054 | XM_017004891; NM_024080; XM_011511810; XM_024453132; XM_024453134; XM_024453133 |
| ATP8A2 | 51761 | XM_011535103; XM_011535113; XM_005266419; XM_024449369; XM_011535109; NM_016529; XM_011535104; XM_017020626; NM_001313741; XM_017020625; XM_011535106; XM_011535107 |
| PGC | 5225 | NM_002630; NM_001166424 |
| GDPD3 | 79153 | NM_024307 |
| MKI67 | 4288 | NM_002417; NM_001145966; XM_006717864; XM_011539818 |
| ZIC1 | 7545 | NM_003412 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| APOC1 | 341 | NM_001645; NM_001321066; NM_001379687; NM_001321065 |
| PLP2 | 5355 | NM_002668 |
| HOXB13 | 10481 | NM_006361 |
| DLX2 | 1746 | NM_004405 |
| TDRD1 | 56165 | XM_024448081; NM_001385365; NM_001365891; NM_001385366; NM_001385372; NM_001395205; XM_011539959; XM_017016415; NM_001385363; NM_001385368; XM_011539960; NM_001385364; XM_011539964; XM_011539962; XM_011539961; NM_001385367; NM_001385369; NM_001385371; NM_198795; NM_031278; XM_017016414; NM_001385370 |
| SCN1A | 6323 | NM_001353960; NM_001202435; NM_001353951; NM_001353952; NM_001353958; NM_001353950; NM_001353957; NR_148667; NM_001353949; NM_001353954; XR_001738884; NM_001353955; NM_001353961; NM_001165963; NM_001165964; NM_001353948; NM_006920; XR_001738883 |
| TRPC4 | 7223 | NM_001354806; XM_011535206; NM_016179; NM_003306; NM_001135958; NM_001135957; NM_001372055; XM_017020723; NM_001135956; NM_001354799; NM_001135955 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| ZWINT | 11130 | XR_428692; NM_007057; NM_001005413; XM_017015605; XM_024447784; NM_032997; NM_001005414 |
| KIF4A | 24137 | NM_012310 |
| CCNJL | 79616 | NM_001308173; NM_024565; NR_131769; XM_011534646; XM_017009847; XM_006714917; XR_427810; XM_011534647; XM_017009848; XR_427811 |
| PAGE4 | 9506 | NM_001318877; NM_007003 |
| TSPYL2 | 64061 | XM_006724592; XM_017029727; NM_022117; XR_001755719; XM_017029726 |
| MMP9 | 4318 | NM_004994 |
| HOXD13 | 3239 | XM_011511068; NM_000523; XM_011511069 |
| TPX2 | 22974 | XM_011528697; XM_011528699; NM_012112; XM_011528700 |
| FHL5 | 9457 | NM_001170807; NM_001322466; NM_001322467; NM_020482 |
| GRIA3 | 2892 | NM_007325; NM_181894; NM_000828; NM_001256743 |
| IFI6 | 2537 | NM_002038; XM_024446207; NM_022873; NM_022872 |
| RPL4 | 6124 | NM_000968 |
| ISL1 | 3670 | XM_011543380; NM_002202 |
| HPN | 3249 | NM_002151; NM_182983; XM_017026732; NM_001384133; XM_017026731; NM_001375441 |
| SRD5A2 | 6716 | XM_011533069; NM_000348; XM_011533072 |
| ACPP | 55 | NM_001099; XM_011512946; NM_001134194; XM_011512947; NM_001292037 |
| GUCY2C | 2984 | NM_004963; XM_011520631 |
| HOXC6 | 3223 | NM_153693; NM_004503 |
| LILRB4 | 11006 | NM_001278429; NM_001394939; XM_017026215; NM_001394934; NM_006847; NM_001278428; XM_017026216; NM_001394935; NM_001081438; NM_001394938; XR_002958246; NM_001278426; NM_001394933; NM_001394937; NM_001278427; NM_001278430; NM_001394936 |
| MSMB | 4477 | NM_138634; NM_002443 |
| STAR | 6770 | NM_001007243; NM_000349 |
| KLK3 | 354 | NM_001030050; NM_001030047; NM_145864; NM_001030049; NM_001030048; NM_001648 |
| FOXF1 | 2294 | NM_001451 |
| | | Urinary_Bladder_Urothelial_Carcinoma |
| UPK2 | 7379 | NM_006760 |
| PLA2G2F | 64600 | NM_022819; NM_001360869; XM_011541955; XM_011541956 |
| CYP1A1 | 1543 | NM_001319216; NM_001319217; NM_000499 |
| S100A2 | 6273 | NM_001366407; NM_001366406; NM_005978 |
| IVL | 3713 | NM_005547 |
| VGLL1 | 51442 | NM_016267 |

-continued

| Gene | NCBI Gene ID | NCBI Accession Number(s) |
|---|---|---|
| UPK3A | 7380 | NM_006953; NM_001167574 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SERPINB4 | 6318 | NM_175041; NM_002974; XM_011526138 |
| UPK1B | 7348 | NM_006952 |
| KRT20 | 54474 | NM_019010 |
| TMEM40 | 55287 | NM_001284408; NM_018306; XM_011533937; NM_001284406; NM_001284407 |
| BHMT | 635 | NM_001713 |
| GATA3 | 2625 | XM_005252443; NM_002051; XM_005252442; NM_001002295 |
| KRT6A | 3853 | NM_005554 |
| MSMB | 4477 | NM_138634; NM_002443 |
| SLC14A1 | 6563 | XM_005258333; XM_024451238; XR_001753266; NM_001146037; XM_005258329; NM_001146036; NM_001308278; NM_015865; XM_011526144; NM_001308279; XM_006722526; XM_011526142; NM_001128588 |
| SFTPA2 | 729238 | XM_011540124; XM_005270132; NM_001320813; NM_001320814; XM_017016608; XM_011540125; NM_001098668; XM_005270128 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| OLFM4 | 10562 | NM_006418 |
| ACTC1 | 70 | NM_005159 |
| GJB1 | 2705 | NM_000166; XM_011530907; NM_001097642 |
| AIM1L | 55057 | NM_017977; XM_011541672; XM_011541673; XR_001737260; NM_001039775; XR_946681; XM_005245918 |
| IL9R | 3581 | XM_011545650; XM_017029496; XM_017029499; XM_017030050; XM_017030051; XM_011531155; XM_017029498; XM_017029502; XM_017029505; XM_017030053; XM_017030055; NM_176786; XM_011531156; XM_011545645; XM_011545651; XM_017029495; XM_017029501; XM_017030054; XM_011531152; XM_011545649; XM_017030045; XM_017030046; XM_017030052; XM_017029497; XM_017030049; XM_011531157; XM_011531154; XM_017029500; XM_017029503; XM_017030044; XM_017030047; NM_002186; XM_011531151; XM_011545646; XM_011545652; XM_017029504; XM_017029506; XM_017030048 |
| NRAP | 4892 | XM_005269867; NM_006175; NM_001322945; NM_198060; XM_005269865; XM_011539832; XM_024448029; NM_001261463; XM_006717870; XM_005269864 |
| SLC5A1 | 6523 | NM_000343; XM_011530331; NM_001256314 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| CASQ1 | 844 | NM_001231 |
| ACTG2 | 72 | NM_001199893; NM_001615 |
| POU3F3 | 5455 | NM_006236 |
| UNC93A | 54346 | XM_011535908; NM_001143947; XM_011535905; XM_011535907; NM_018974; XM_017010958; XM_011535906 |
| TRPA1 | 8989 | XM_011517624; NM_007332; XM_011517625; XM_017013946 |
| KCNIP1 | 30820 | NM_001034837; NM_014592; NM_001034838; NM_001278340; XM_017009407; XM_017009408; NM_001278339 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MSLN | 10232 | NM_001177355; NM_005823; NM_013404 |
| COX6A2 | 1339 | NM_005205 |
| CCL11 | 6356 | NM_002986 |
| IRX4 | 50805 | NM_016358; NM_001278633; NM_001278632; NM_001278635; NM_001278634 |
| REGIA | 5967 | NM_002909 |
| MAGEA11 | 4110 | XM_017029522; NM_001011544; NM_005366; XM_011531164 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |

-continued

| Gene | NCBI Gene ID | NCBI Accession Number(s) |
|---|---|---|
| HLF | 3131 | NM_002126; XM_011524705; XR_002957996; NM_001330375; XM_005257269 |
| HAND1 | 9421 | NM_004821; XM_005268531 |
| HPN | 3249 | NM_002151; NM_182983; XM_017026732; NM_001384133; XM_017026731; NM_001375441 |
| SLC34A2 | 10568 | NM_001177999; NM_006424; NM_001177998 |
| TFF3 | 7033 | NM_003226 |
| PNMAL1 | 55228 | NM_001103149; NM_018215; XM_011527067 |
| PITX2 | 5308 | NM_001204397; NM_153427; XM_024454090; NM_000325; NM_001204398; NM_001204399; NM_153426 |
| REG3A | 5068 | NM_138938; NM_002580; NM_138937 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| PENK | 5179 | NM_006211; NM_001135690 |
| CDHR2 | 54825 | NM_001171976; NM_017675 |
| MMP11 | 4320 | NM_005940; NR_133013 |
| CDH4 | 1002 | NM_001252339; NM_001794; NM_001252338 |
| FOXA2 | 3170 | NM_021784; NM_153675 |
| HOXB8 | 3218 | NM_024016; XM_005257286; XM_017024564 |
| GABRA3 | 2556 | NM_000808; XM_006724811 |
| SLC47A1 | 55244 | NM_018242 |
| F7 | 2155 | XM_011537476; XM_011537475; NM_001267554; XM_011537474; NR_051961; XM_006719963; NM_019616; NM_000131 |
| S100A1 | 6271 | NM_006271 |
| DNAJC22 | 79962 | NM_001304944; NM_024902; XM_005269157; XM_005269155; XM_005269156 |
| NPR3 | 4883 | NM_001363652; NM_001364460; NM_000908; XM_011514047; XM_011514049; XM_017009492; NM_001204375; NM_001364458; NM_024563; XM_011514050; NM_001204376 |
| FOXE1 | 2304 | NM_004473 |
| ALS2CL | 259173 | XR_427263; XR_940409; XR_940410; NR_033815; XR_001740091; XR_001740094; XR_001740095; XM_011533572; XR_001740090; XR_940406; XR_940407; XR_940408; XR_940412; NM_182774; NM_182775; NR_135622; XR_001740092; XR_001740097; XR_002959507; NM_001190707; XM_005265025; XM_006713093; XR_001740093; NM_147129; XM_006713094; XM_006713091; XR_001740096; XR_940405 |
| ACADL | 33 | NM_001608; XM_005246517; XM_017003955 |
| ARSE | 415 | XM_017029526; NM_001369079; NM_001369080; XM_005274521; XM_011545521; NM_000047; XM_005274519; NM_001282628; NM_001282631 |
| AQP5 | 362 | NM_001651; XM_005268838 |
| HOXA11 | 3207 | NM_005523 |
| CYP2W1 | 54905 | NM_017781; XM_011515440; XM_011515441 |
| KBTBD11 | 9920 | XM_017014115; XM_011534772; XM_017014117; XM_017014114; XM_017014116; XM_011534771; NM_014867 |
| TCF21 | 6943 | NM_003206; NM_198392 |
| ADAMTSL3 | 57188 | NM_207517; XM_024450000; XR_931873; XM_017022435; XM_011521822; XM_011521823; XM_017022434; NM_001301110; XM_011521825; XM_011521824 |
| GLP2R | 9340 | XM_011524077; NM_004246; XM_017025340; XM_005256861; XM_017025339; XM_017025341 |
| CFD | 1675 | NM_001317335; NM_001928 |
| FAM107A | 11170 | NM_001076778; NM_007177; NM_001282713; NM_001282714 |
| TPPP | 11076 | XM_024454346; XM_005248237; XM_017008993; NM_007030 |
| FOXF1 | 2294 | NM_001451 |
| HSPB6 | 126393 | NM_144617 |
| P2RX1 | 5023 | XM_006721529; XM_011523898; XR_934029; NM_002558; XM_011523896; XM_011523897; XM_011523899; XM_011523900; XR_934030 |
| TBX5 | 6910 | NM_181486; NM_080717; NM_000192; XM_017019912; NM_080718 |
| SGCD | 6444 | NM_000337; NM_172244; XM_005265967; XM_011534621; XM_017009723; XM_005265966; XM_017009724; NM_001128209 |
| ESM1 | 11082 | NM_001135604; NM_007036 |
| DPT | 1805 | NM_001937 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| SPP1 | 6696 | NM_001251829; NM_001040060; NM_001251830; NM_000582; NM_001040058 |
| CMA1 | 1215 | NM_001836; NM_001308083 |
| FBN2 | 2201 | NM_001999; XM_017009228 |
| MSI1 | 4440 | XM_011538362; XM_011538361; XM_011538366; XM_011538365; XM_011538370; NM_002442; XM_011538364; XM_011538371; XM_006719403; XM_006719404; XM_011538363; XM_011538368 |
| TERT | 7015 | NR_149162; NM_198255; NM_198253; NR_149163; NM_001193376; NM_198254 |
| VGF | 7425 | NM_003378; XM_011516549; XM_005250561 |
| CLDN9 | 9080 | NM_020982 |
| FOLR1 | 2348 | NM_000802; NM_016729; NM_016730; NM_016725; NM_016724 |

-continued

| Gene | NCBI Gene ID | NCBI Accession Number(s) |
|---|---|---|
| Melanoma | | |
| PAX3 | 5077 | NM_181457; NM_000438; NM_181459; NM_181460; NM_001127366; NM_013942; NM_181461; NM_181458 |
| IRF4 | 3662 | NM_001195286; NR_046000; NR_036585; XM_006715090; NM_002460 |
| TYR | 7299 | XM_011542970; NM_000372 |
| GAPDHS | 26330 | NM_014364 |
| PMEL | 6490 | NM_001200054; NM_001200053; NM_001320121; NM_001384361; NM_001320122; NM_006928 |
| TYRP1 | 7306 | NM_000550; XR_001746372 |
| ALX1 | 8092 | XM_011538782; NM_006982 |
| MLANA | 2315 | NM_005511 |
| CDH19 | 28513 | XM_011525931.3; XM_017025711.2; XM_011525932.1 |
| SOX10 | 6663 | NM_006941 |
| MIA | 8190 | NM_006533; NM_001202553 |
| PLP1 | 5354 | NM_001128834; NM_000533; NM_001305004; NM_199478 |
| SLC6A15 | 55117 | XM_011538525; NM_018057; NM_001146335; NM_182767 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| KRT2 | 3849 | NM_000423 |
| MFSD12 | 126321 | XM_017026288; XM_011527684; NM_021731; NM_174983; NM_001287529; XM_005259490; NM_001042680; XM_006722647 |
| APOD | 347 | NM_001647 |
| KCNK1 | 3775 | NM_002245; XM_011544184 |
| EFHD1 | 80303 | NM_001243252; NM_001308395; NM_025202 |
| CRCT1 | 54544 | NM_019060; XM_011509656 |
| KRT8 | 390601, 149501, 3856 | NM_001256293; NM_002273 |
| GPM6B | 2824 | NM_001001996; XM_017029432; NM_001318729; NM_005278; NM_001001995; XM_005274489; XM_011545497; NM_001001994 |
| CNTNAP2 | 26047 | XM_017011950; NM_014141 |
| STEAP1B | 256227 | NM_207342; NM_001382447; NM_001164460 |
| RGN | 9104 | XM_024452477; XM_006724568; XM_017029954; NM_004683; NM_001282848; NM_152869; NM_001282849; XM_006724567 |
| FA2H | 79152 | XM_011523319; XM_011523317; NM_024306 |
| TRPV2 | 51393 | XM_011523922; XM_017024730; XM_011523925; XM_017024732; XM_005256677; XM_017024731; XM_006721541; XM_005256678; XM_011523923; NM_016113; XM_005256676; XM_006721543 |
| CLDN7 | 1366 | NM_001307; NM_001185022; NM_001185023 |
| SPINT2 | 10653 | NM_001166103; NM_021102 |
| CD24 | 100133941 | NM_001291739; NR_117090; NR_117089; NM_001291738; NM_001291737; NM_013230; XM_024446293; NM_001359084 |
| HNF1B | 6928 | XM_011525161; NM_001165923; NM_001304286; XM_011525163; NM_000458; XM_011525162; NM_006481; XM_011525164; XM_011525160 |
| SUSD4 | 55061 | XM_011509687; XM_017001584; XM_017001586; XM_017001587; XM_024447937; XM_024447940; XM_005273169; XM_017001588; XM_017001585; XM_024447936; NM_017982; XM_005273172; XM_006711408; XM_011509685; XM_017001583; XM_017001589; NM_001037175 |
| ST8SIA3 | 51046 | NM_015879 |
| GABRE | 2564 | XM_024452360; NM_021990; NM_021984; XM_011531140; XM_017029388; XM_017029389; NM_004961; NM_021987; XM_017029387 |
| PHACTR1 | 221692 | XM_017010452; XM_017010454; XM_017010458; XM_017010465; NM_001322311; NM_001374582; NM_001374583; NM_001374584; NM_001322309; XM_005248934; XM_017010460; NM_001322308; NM_001374581; XM_017010459; XM_017010464; NM_001242648; NM_001322314; XM_017010462; NM_001322312; XM_017010456; XM_017010457; XM_017010466; NM_030948; XM_017010455; NM_001322310; XM_017010469; NM_001322313 |
| ASS1 | 445 | XM_017014729; XM_005272200; XM_011518705; NM_000050; NM_054012 |
| CDS1 | 1040 | XM_017007649; NM_001263; XM_017007650; XM_017007651; XM_005262687; XM_017007648 |
| PLEKHG6 | 55200 | NM_018173; XM_017019555; NM_001384602; NM_001384603; XM_006718985; NM_001384604; NR_169277; XM_011520967; NM_001144857; NM_001384599; NR_169278; NM_001144856; NM_001384598; NM_001384600; NM_001384601 |
| CACNG4 | 27092 | NM_014405 |
| CYTL1 | 54360 | NM_018659; XM_017008299 |
| PITX1 | 5307 | NM_002653 |
| HOXD13 | 3239 | XM_011511068; NM_000523; XM_011511069 |
| CNIH3 | 149111 | NR_136288; NR_136294; NR_136297; NM_152495; NR_136292; NM_001322305; NM_001322303; NR_136293; NR_136296; NR_136295; NR_136287; NM_001322304; NR_136290; NR_136291; NM_001322302; NR_136289 |
| CFB | 629 | NM_001710 |
| MYH7 | 4625 | XM_017021340; NM_000257 |
| CLU | 1191 | NM_001831; NR_045494; NR_038335 |
| SCG5 | 6447 | NM_001144757; NM_001394278; NM_001394279; NM_003020 |

-continued

| Gene | NCBI Gene ID | NCBI Accession Number(s) |
|---|---|---|
| SH3GL3 | 6457 | XR_001751374; NM_001324184; NM_001324186; XM_017022486; XR_931878; XR_001751372; NR_136712; XR_931880; XR_931882; NM_001301109; NM_001324185; NR_125370; NR_136714; XM_011521892; XR_001751375; XR_931879; NM_001301108; NM_001324183; NM_003027; NR_136713; XM_011521889; XM_011521891; XM_024450017; XR_001751373; XR_002957669; NM_001324182; NM_001324187; NR_136711 |
| RBM47 | 54502 | XM_005248108; XM_017008307; XM_024454098; NM_001371113; XM_005248103; XM_017008306; XM_017008309; XM_017008310; NM_001098634; NM_019027; XM_011513707; XM_005248109; XM_017008304; XM_017008308; NM_001371114; XM_011513708 |
| FUT6 | 2528 | XM_011527875; NM_000150; NM_001381956; NM_001369504; NM_001381957; NM_001381958; NM_001369502; NM_001381959; NM_001369505; NM_001381955; XM_011527872; NM_001040701 |
| FGFR2 | 2263 | XM_017015924; NM_001144919; XM_006717708; XM_017015925; NM_001144915; NM_001144917; NM_022975; NM_023028; XM_024447890; NM_000141; NM_001144913; NM_001320654; NM_022970; NR_073009; NM_022971; NM_022973; NM_023030; XM_006717710; XM_024447887; XM_024447888; NM_001320658; NM_022976; XM_017015920; NM_001144918; NM_022974; NM_023031; XM_024447889; XM_024447891; XM_024447892; NM_023029; XM_017015921; NM_001144914; NM_001144916; NM_022972 |
| DLX2 | 1746 | NM_004405 |
| LAD1 | 3898 | NM_005558 |
| SPP1 | 6696 | NM_001251829; NM_001040060; NM_001251830; NM_000582; NM_001040058 |
| ADH1B | 125 | NM_001286650; NM_000668 |
| MYL2 | 4633 | NM_000432 |
| ZBTB16 | 7704 | XR_001747955; NM_001354751; XM_017018259; NM_006006; NM_001354752; XM_005271658; XM_024448681; NM_001018011; NM_001354750 |
| CKM | 1158 | NM_001824 |
| FCGR1A | 2209 | NM_001378804; NM_001378805; NM_001378807; NM_001378810; NR_166122; NR_166123; NM_001378809; NM_001378811; NM_001378808; NR_166121; NM_000566; NM_001378806 |
| CCL5 | 6352 | NM_001278736; NM_002985 |
| DBNDD1 | 79007 | NM_001288709; NM_001288708; NM_001371581; NM_001042610; NM_024043 |
| SDS | 10993 | NM_006843 |
| CXCR3 | 2833 | XM_017029435; XM_017029436; NM_001504; NM_001142797; XM_005262256; XM_005262257 |
| MMP27 | 64066 | XM_011542950; XM_017018120; XM_011542948; NM_022122; XM_011542949 |
| TREM2 | 54209 | NM_001271821; NM_018965 |
| CCR5 | 1234 | NM_001100168; NM_001394783; NM_000579 |
| C1QA | 712 | NM_015991; NM_001347465; NM_001347466 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ONECUT2 | 9480 | NM_004852 |
| FAM155B | 27112 | XM_011530908; XM_011530909; NM_015686 |
| DKK1 | 22943 | NM_012242 |
| LOR | 4014 | NM_000427; XM_024447049 |
| | | Liver_Neoplasm |
| APCS | 325 | NM_001639 |
| ITIH2 | 3698 | NM_002216 |
| CRP | 1401 | NM_000567; NM_001329058; NM_001382703; NM_001329057 |
| CPB2 | 1361 | XM_017020393; NM_016413; NM_001872; NM_001278541 |
| ITIH1 | 3697 | NM_001166436; NM_002215; NM_001166434; NM_001166435 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| APOC3 | 345 | NM_000040 |
| GC | 2638 | XM_006714177; NM_001204306; NM_001204307; NM_000583 |
| CYP2C8 | 1558 | NM_001198854; NM_001198855; NM_030878; NM_000770; NM_001198853 |
| C8G | 733 | NM_000606; XR_245338 |
| APOA2 | 336 | NM_001643 |
| ALB | 213 | NM_000477 |
| ART4 | 420 | NM_021071; NM_001354646 |
| AGT | 183 | NM_000029; NM_001384479; NM_001382817 |
| PROZ | 8858 | NM_003891; XR_001749709; XR_001749708; XM_017020812; XR_001749707; NM_001256134; XM_017020813 |
| GRIK3 | 2899 | NM_000831 |
| CRABP1 | 1381 | NM_004378 |
| DRD2 | 1813 | XM_017017296; NM_016574; NM_000795 |
| CYP21A2 | 1589 | NM_000500; NM_001128590; XM_024452555; NM_001368143; NM_001368144 |
| DBH | 1621 | NM_000787 |

-continued

| Gene | NCBI Gene ID | NCBI Accession Number(s) |
|---|---|---|
| L1CAM | 3897 | NM_024003; NM_001278116; NM_001143963; NM_000425 |
| KLK8 | 11202 | NM_007196; NM_144505; NR_104008; NM_144507; NM_144506; NM_001281431 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| SFRP5 | 6425 | NM_003015 |
| GATA4 | 2626 | NM_001308093; NM_002052; NM_001308094; NM_001374273; NM_001374274 |
| MAB21L2 | 10586 | NM_006439 |
| GRIK5 | 2901 | XM_011526870; XM_011526868; XM_011526865; XM_011526867; XM_011526869; XM_011526862; XM_011526871; XM_017026713; NM_002088; XR_935810; NM_001301030 |
| HOXA7 | 3204 | NM_006896 |
| GLB1L2 | 89944 | NM_001370460; NM_001370463; NM_001370461; NM_001370462; NM_138342 |
| PCSK2 | 5126 | NM_002594; NM_001201529; NM_001201528 |
| TERT | 7015 | NR_149162; NM_198255; NM_198253; NR_149163; NM_001193376; NM_198254 |
| PLP1 | 5354 | NM_001128834; NM_000533; NM_001305004; NM_199478 |
| CXCL14 | 9547 | NM_004887 |
| KRT4 | 3851 | NM_002272 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SLC5A1 | 6523 | NM_000343; XM_011530331; NM_001256314 |
| GPRC5A | 9052 | NM_003979 |
| GPM6B | 2824 | NM_001001996; XM_017029432; NM_001318729; NM_005278; NM_001001995; XM_005274489; XM_011545497; NM_001001994 |
| NNAT | 4826 | NM_001322802; NM_181689; NM_005386 |
| BDH1 | 622 | XM_005269355; XM_017007012; XM_017007013; NM_004051; XM_017007015; XM_017007007; XM_011513067; XM_017007008; XM_017007009; XR_001740229; NM_203314; XM_017007010; NM_203315; XM_005269352; XM_017007011 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| COLEC10 | 10584 | XM_005250756; NM_006438; NM_001324095 |
| GABRD | 2563 | XM_011541194; XM_017000936; NM_000815 |
| GDF2 | 2658 | NM_016204 |
| COL15A1 | 1306 | XM_011518214; NM_001855 |
| S100A12 | 6283 | NM_005621 |
| MDK | 4192 | NM_001012334; XM_011520116; XM_017017764; NM_001270550; NM_001270551; NM_001012333; NM_001270552; NM_002391; NR_073039 |
| PTTG1 | 9232 | XM_024446260; NM_001282382; NM_001282383; NM_004219 |
| ESM1 | 11082 | NM_001135604; NM_007036 |
| DEPDC1 | 55635 | NM_001114120; NM_017779 |
| THBS4 | 7060 | XR_002956176; XM_017009798; NM_001306214; NM_003248; NM_001306213; XM_017009799; NM_001306212 |
| HOXD9 | 3235 | NM_014213 |
| OLFML2B | 25903 | NM_001297713; XM_017000967; NM_001347700; NM_015441; XM_011509398 |
| MMP11 | 4320 | NM_005940; NR_133013 |
| PRSS1 | 5644 | NR_172951; XM_011516411; NR_172947; NM_002769; NR_172948; NR_172949; NR_172950 |
| C1QTNF3 | 114899 | NR_146599; NM_181435; NM_030945 |
| | | Thyroid_Neoplasm |
| TG | 7038 | XM_006716622; XM_017013800; XM_017013793; XM_017013795; XM_017013798; XM_017013796; XM_017013797; XM_017013794; XM_005251038; XM_005251040; NM_003235; XM_017013799; XM_005251042 |
| DCSTAMP | 81501 | XM_024447289; NM_030788; XM_024447290; NM_001257317; XM_011517324; XM_024447288; XM_011517321 |
| DAPK2 | 23604 | XM_017022049; XM_017022051; NM_001384998; NM_001395289; NM_001395290; NM_001395293; XM_011521413; NM_001384999; NM_001395284; NM_014326; XM_017022043; NM_001395288; NM_001395291; NR_169522; NR_172521; XM_017022046; NM_001384997; NM_001385000; NM_001395286; NM_001395287; XM_011521421; XM_017022044; XM_017022047; XM_017022052; NM_001395285; NM_001395292; XM_017022048; XM_017022050; NM_001395282; NR_169524; XM_011521414; XM_011521415; XM_017022045; NM_001395279; NM_001395283; NR_169523; NM_001363730; NM_001395281 |
| SLC26A4 | 5172 | XM_017012318; XM_005250425; NM_000441; XM_006716025 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| TSHR | 7253 | XM_011537119; XM_005268039; XM_005268037; NM_000369; NM_001142626; XM_006720245; NM_001018036 |
| KCNJ16 | 3773 | XM_006721885; NM_170742; NM_001291625; NM_018658; XM_017024609; NM_001291622; NM_001291623; XM_017024610; NM_001270422; NM_170741; XM_005257337; XM_006721887; XM_011524781; NM_001291624; XM_006721886 |

-continued

| Gene | NCBI Gene ID | NCBI Accession Number(s) |
|---|---|---|
| NKX2-1 | 7080 | NM_001079668; NM_003317 |
| FOXE1 | 2304 | NM_004473 |
| CLDN16 | 10686 | NM_006580; NM_001378492; NM_001378493 |
| GABRB2 | 2561 | NM_000813; NM_021911; NM_001371727 |
| MATN1 | 4146 | NM_002379 |
| INPP5J | 27124 | NM_001284289; XM_017028772; NM_001284288; NM_001284285; NM_014422; NM_001284286; NM_001284287; XM_011530143; NM_001002837 |
| TOX3 | 27324 | NM_001080430; XM_017023142; NM_001146188; XM_005255892; XM_011523002; XM_024450230 |
| TRPC5 | 7224 | XM_017029774; NM_012471 |
| HHEX | 3087 | NM_002729 |
| PAX8 | 7849 | NM_013992; NM_013953; NM_013952; NM_003466; NM_013951 |
| FOXD3 | 27022 | NM_012183 |
| COL4A3 | 1285 | XM_017003295; XM_005246280; XM_006712245; XM_005246277; XR_241280; XM_011510556; NM_000091; NM_031363; NM_031364; NM_031365; XM_011510555; XR_001738601; NM_031362; NM_031366 |
| S100A5 | 6276 | XM_017002031; NM_001394233; NM_001394234; XM_017002032; NM_001394232; NM_002962; XM_017002029 |
| GFRA3 | 2676 | NM_001496 |
| NELL1 | 4745 | NM_001288713; NM_006157; NM_201551; NM_001288714 |
| DUSP9 | 1852 | XM_011531123; NM_001395; NM_001318503; XM_011531124 |
| AZGP1 | 563 | NM_001185 |
| BMP8A | 353500 | XM_017001198; XM_006710616; XM_011541381; XM_011541382; XR_946642; XR_946640; XR_946641; NM_181809 |
| LECT1 | 11061 | XM_011534898; XM_011534899; NM_001011705; NM_007015; XM_011534900; XM_011534897 |
| DIO2 | 1734 | NM_001366496; NM_000793; NM_001324462; NR_158991; NM_001242503; NM_013989; NR_158990; NM_001007023 |
| LRRC2 | 79442 | XM_011534110; XM_017007177; XR_001740264; NM_024750; NM_024512 |
| HOXA7 | 3204 | NM_006896 |
| HOXA10 | 3206 | NR_037939; NM_153715; NM_018951 |
| SLC5A5 | 6528 | XM_011528194; XM_011528193; NM_000453; XM_017027158; XM_011528192 |
| AADAC | 13 | NM_001086; XM_005247104 |
| KCNJ15 | 3772 | XM_017028344; XM_017028343; XM_011529561; NM_170736; NM_170737; XM_005260975; NM_001276438; NM_001276439; NM_002243; XM_006724002; XM_011529560; XM_017028345; NM_001276435; NM_001276436; NM_001276437 |
| CACNA1I | 8911 | NM_021096; XM_017029035; XM_017029036; XM_017029037; NM_001003406 |
| GPC3 | 2719 | NM_004484; XM_017029413; NM_001164618; NM_001164617; NM_001164619 |
| KLHDC8A | 55220 | NM_001271863; NM_001271865; XM_024448121; NM_018203; NM_001271864 |
| SSX1 | 6756 | NM_001278691; NM_005635 |
| SYT12 | 91683 | XM_011545346; XM_011545347; NM_177963; XM_017018547; NM_001177880; NM_001318775; XM_017018548; XM_006718737; XM_024448766; NM_001318773 |
| BMPR1B | 658 | XM_017008558; NM_001203; NM_001256793; XM_011532201; NM_001256794; NM_001256792; XM_017008559; XM_017008560; XM_017008561 |
| MYL2 | 4633 | NM_000432 |
| CLIC3 | 9022 | XM_017015282; NM_004669; XM_017015281 |
| SPINK1 | 6690 | NM_003122; NM_001379610; NM_001354966 |
| S100A1 | 6271 | NM_006271 |
| BIRC5 | 332 | NM_001168; NM_001012271; NM_001012270 |
| UBE2C | 11065 | NM_001281742; NM_001281741; NM_181802; NM_181803; NR_104036; NR_104037; NM_007019; NM_181800; NM_181801; NM_181799 |
| AMN | 81693 | XM_024449714; XM_011537203; NM_030943; XM_011537202 |
| CBLN1 | 869 | NM_004352 |
| PBK | 55872 | NM_018492; NM_001278945; NM_001363040 |
| ALK | 238 | NM_004304; NM_001353765; XM_024452779; XR_001738688; XM_024452778 |
| CYP2J2 | 1573 | NR_134982; NR_134981; NM_000775 |
| TSPAN8 | 7103 | NM_001369760; NM_004616; XM_006719583 |
| CHGA | 1113 | NM_001301690; NM_001275; XM_011536370 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| SCD | 6319 | NM_005063 |
| SCN4A | 6329 | NM_000334 |
| TF | 7018 | NM_001063; NM_001354703; NM_001354704 |
| TPX2 | 22974 | XM_011528697; XM_011528699; NM_012112; XM_011528700 |
| TFAP2A | 7020 | NM_001032280; XM_006715175; NM_001042425; XM_017011232; XM_011514833; NM_001372066; NM_003220 |
| ACADL | 33 | NM_001608; XM_005246517; XM_017003955 |
| IQCA1 | 79781 | XM_017004960; NM_024726; NM_001270585; XM_011511865; XM_011511866; XM_011511864; NM_001270584; NR_073043 |
| CENPF | 1063 | XM_017000086; NM_016343; XM_011509082 |
| EYA1 | 2138 | XM_017013204; XM_017013211; XM_017013212; NM_001370334; XM_011517484; XM_017013203; NM_001288574; XM_017013202; NM_000503; XM_017013207; XM_017013208; XM_017013213; NM_001370336; NM_172059; NM_172060; XM_017013205; NM_172058; NM_001288575; NM_001370333; NM_001370335; XM_011517483 |

-continued

| Gene | NCBI Gene ID | NCBI Accession Number(s) |
|---|---|---|
| FSCN2 | 25794 | NM_012418; XM_011524587; XM_011524590; XR_001752466; NM_001077182 |
| SEMA3C | 10512 | NM_006379; NM_001350121; NM_001350120 |
| MYH7 | 4625 | XM_017021340; NM_000257 |
| TRIP13 | 9319 | NM_004237; XM_011514163 |
| FGFR4 | 2264 | NM_213647; NM_022963; NM_002011; NM_001291980; NM_001354984 |
| CEP55 | 55165 | XM_017016373; XM_011539920; NM_001127182; NM_018131; XM_017016372; XM_011539919; XM_011539918 |
| TFF1 | 7031 | NM_003225 |
| DLGAP5 | 9787 | XM_017021840; NM_001146015; NM_014750 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| MSC | 9242 | NM_005098 |
| SMR3B | 10879 | NM_006685 |
| PRDM16 | 63976 | NM_199454; NM_022114 |
| HOXB3 | 3213 | XM_006721854; NM_001384749; XM_024450737; XM_011524719; XM_011524720; XM_011524726; NM_001330323; XM_011524708; XM_011524721; NM_002146; XM_011524710; NM_001384747; XM_017024560; NM_001330322; NM_001384750 |
| NNAT | 4826 | NM_001322802; NM_181689; NM_005386 |
| TGFA | 7039 | NM_001308159; NM_001308158; NM_001099691; NM_003236 |
| PID1 | 55022 | NM_001330156; XM_017004404; NM_001330158; NM_017933; NM_001330157; NM_001100818 |
| KIAA1456 | 57604 | XM_005273591; XM_024447215; XM_005273584; XM_005273586; XM_011544600; XM_024447217; XM_005273588; XM_011544598; XM_024447214; XM_005273590; XM_017013710; NM_001099677; XM_005273585; XM_017013714; XM_011544596; XM_011544597; XM_011544601; XM_017013705; XM_024447216; XM_017013706; XM_024447218; XM_024447219; NM_020844 |
| PAPSS2 | 9060 | NM_001015880; NM_004670 |
| MMRN1 | 22915 | XM_005262856; NM_001371403; NM_007351 |
| LYVE1 | 10894 | NM_006691 |
| GALE | 2582 | NM_000403; NM_001127621; NM_001008216 |
| CFD | 1675 | NM_001317335; NM_001928 |
| CDH3 | 1001 | NM_001793; XM_011522800; NM_001317195; NM_001317196 |
| TNFRSF10C | 8794 | NM_003841 |
| CDKN2B | 1030 | NM_078487; NM_004936 |
| BBC3 | 27113 | XM_006723141; XM_011526722; NM_001127241; NM_001127242; NM_001127240; NM_014417 |
| IPCEF1 | 26034 | NM_001394801; NM_001130700; NM_015553; NM_001130699; NM_001394799; NM_001394800; NM_001394802 |
| CDH6 | 1004 | NM_004932; NM_001362435; XM_017008910; XM_011513921; XR_001741972 |
| KCNJ2 | 3759 | NM_000891 |
| LAMB3 | 3914 | XM_005273124; NM_001127641; XM_017001272; NM_000228; NM_001017402 |
| E2F1 | 1869 | NM_005225 |
| DUSP4 | 1846 | NM_001394; NM_057158; XM_011544428 |
| FMO2 | 2327 | NM_001460; NR_160266; XR_921761; NM_001365900; XR_001737072; NM_001301347 |
| GDF15 | 9518 | XM_024451789; NM_004864 |
| CCL21 | 6366 | NM_002989 |
| PLCH1 | 23007 | XM_011512561; XM_011512565; XM_011512566; NM_001349250; XM_011512567; XM_017005925; XM_005247239; XM_005247238; XM_011512560; XM_017005926; NM_001130960; NM_001349252; NM_014996; XM_017005927; NM_001130961; NM_001349251; XM_011512562; XM_017005923 |
| MYOC | 4653 | NM_000261 |
| GABRD | 2563 | XM_011541194; XM_017000936; NM_000815 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SLC12A5 | 57468 | NM_020708; NM_001134771 |
| VTCN1 | 79679 | NM_001253849; NM_024626; NR_045604; XM_017002335; NM_001253850; NR_045603; XM_011542143 |
| OLAH | 55301 | XM_024448060; XM_017016376; NM_018324; NM_001039702 |
| MMP11 | 4320 | NM_005940; NR_133013 |
| AIM1L | 55057 | NM_017977; XM_011541672; XM_011541673; XR_001737260; NM_001039775; XR_946681; XM_005245918 |
| CDH2 | 1000 | XM_011525788; NM_001308176; XM_017025514; NM_001792 |
| HAPLN1 | 1404 | XM_017009052; XM_017009051; NM_001884; XM_017009054; XM_017009053; XM_011543168 |

-continued

| Gene | NCBI Gene ID | NCBI Accession Number(s) |
|---|---|---|
| DES | 1674 | NM_001927; NM_001382708; NM_001382710; NM_001382713; NM_001382709; NM_001382711; NM_001382712 |
| ADRA2C | 152 | NM_000683 |
| CD19 | 930 | NM_001178098; NM_001385732; NM_001770; XR_950871; XM_006721103; NR_169755; XM_011545981 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| | | Glioma |
| AQP4 | 361 | NM_001317387; NM_001364287; NM_001364286; NM_001317384; XM_011525942; NM_001650; NM_001364289; NM_004028 |
| OLIG2 | 10215 | XM_005260908; NM_005806 |
| GFAP | 2670 | XM_024450691; XM_024450690; NM_001131019; XM_024450692; XM_024450693; NM_001242376; NM_002055; NM_001363846 |
| HAPLN2 | 60484 | XM_024448828; XM_005245415; XM_011509853; XM_017002020; XM_017002021; NM_021817 |
| GPR37L1 | 9283 | NM_004767; XM_011510158 |
| PMP2 | 5375 | NM_002677; NM_001348381 |
| GPM6A | 2823 | NM_201592; NM_001261447; NM_001388091; NM_001261448; NM_005277; NR_048571; NM_001388090; NM_201591 |
| TIMP4 | 7079 | NM_003256 |
| SLC1A3 | 6507 | XM_024446182; XM_011514084; NM_004172; NM_001289940; NM_001289939; NM_001166695; XM_005248342; XM_024446181; NM_001166696 |
| MLC1 | 23209 | XR_001755180; NM_001376472; NM_001376478; NR_164811; NR_164812; NM_001376473; NM_001376477; NM_139202; NM_001376476; NM_001376479; NM_001376484; NM_015166; NR_164813; NM_001376474; NM_001376481; XM_011530678; NM_001376480; NM_001376483; NM_001376475; NM_001376482 |
| NCAN | 1463 | NM_004386 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| CDH20 | 28316 | XR_001753187; NM_031891; XR_001753186; XM_024451165 |
| PTPRZ1 | 5803 | NM_002851; NM_001206838; NM_001369396; NM_001369395; NM_001206839 |
| MT3 | 4504 | NM_005954 |
| FOXG1 | 2290 | NM_005249 |
| DLL3 | 10683 | NM_016941; NM_203486 |
| KRT8 | 390601, 149501, 3856 | NM_001256293; NM_002273 |
| PERP | 64065 | XM_024446520; NM_022121 |
| TACSTD2 | 4070 | NM_002353 |
| KRT7 | 3855 | XM_017019294; XR_001748700; NM_005556; XM_011538325; XR_001748699 |
| TES | 26136 | NM_015641; NM_152829; XM_005250258 |
| EVPL | 2125 | NM_001988; NM_001320747 |
| KCNK5 | 8645 | XM_006715235; XM_005249456; NM_003740 |
| EPCAM | 4072 | NM_002354 |
| RIPK4 | 54101 | NM_020639 |
| SOX21 | 11166 | NM_007084 |
| DSP | 1832 | NM_001008844; NM_004415; NM_001319034 |
| C2orf54 | 79919 | XM_011511877; NM_001085437; NM_001282921; NM_024861 |
| NEUROD4 | 58158 | NM_021191 |
| CDH1 | 999 | NM_001317186; NM_004360; NM_001317185; NM_001317184 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| CYP2C18 | 1562 | NM_000772; NM_001128925 |
| EPS8L1 | 54869 | NM_133180; NM_139204; XM_011527052; XM_005259020; NM_017729; XM_011527051; XM_011527050 |
| PDLIM1 | 9124 | XM_011540330; NM_020992 |
| SPINK5 | 11005 | XM_011537551; NM_006846; NM_001127698; NM_001127699 |
| TNNC1 | 7134 | NM_003280 |
| CD55 | 1604 | NM_001300904; NM_001114543; NM_001114544; XM_017000467; NM_001114752; NM_001300902; NM_001300903; NM_000574; NR_125349 |
| LLGL2 | 3993 | XM_017024627; XR_002957999; XR_002958003; XM_017024626; XR_002958004; XM_017024629; XM_017024630; XM_017024631; XR_002958005; XR_002958002; NM_001015002; XM_011524802; XM_017024628; XR_002958000; XM_024450747; XR_001752508; NM_001031803; XM_017024625; XR_002958001; NM_004524 |
| ITPR3 | 3710 | XM_017010832; XM_011514577; NM_002224 |
| SPINT2 | 10653 | NM_001166103; NM_021102 |
| ANXA3 | 306 | XR_001741215; NM_005139 |
| HCN2 | 610 | NM_001194 |
| F2R | 2149 | NM_001311313; NM_001992 |
| MYL2 | 4633 | NM_000432 |
| KIFC1 | 3833 | XM_011514585; XM_017010836; NM_002263; XM_011514587; XM_017010837 |
| BIRC5 | 332 | NM_001168; NM_001012271; NM_001012270 |
| NDC80 | 10403 | NM_006101 |

-continued

| Gene | NCBI Gene ID | NCBI Accession Number(s) |
|---|---|---|
| PBK | 55872 | NM_018492; NM_001278945; NM_001363040 |
| TACC3 | 10460 | XM_005247930; XM_017007653; NM_006342; XM_005247929; XM_011513386 |
| EGFR | 1956 | NM_001346899; NM_201282; NM_201284; NM_001346898; NM_001346900; NM_001346897; NM_201283; NM_001346941; NM_005228 |
| DTL | 51514 | XM_011509614; NM_001286229; NM_001286230; NM_016448 |
| | | Sarcoma |
| RAB11FIP1 | 80223 | NM_001002814; NM_025151; XM_017013869; NM_001002233 |
| LOXL1 | 4016 | XM_017022179; XM_011521555; NM_005576; XR_931824 |
| ZNF385D | 79750 | XM_017007203; NM_024697; XM_017007200; XM_011534124; XM_017007195; XM_017007202; XM_017007193; XM_017007197; XM_011534122; XM_017007191; XM_017007192; XM_017007199; XM_017007201; XM_024453754; XM_011534123; XM_017007194; XM_017007196; XM_017007198 |
| MYL2 | 4633 | NM_000432 |
| AGRN | 375790 | XM_011541429; NM_001305275; NM_001364727; XR_946650; NM_198576; XM_005244749 |
| KCNG1 | 3755 | XM_011528800; XM_011528802; XM_011528803; XM_011528805; NM_172318; NM_002237; XM_011528801; XM_011528804; XM_011528806; XM_006723785 |
| NKX3-2 | 579 | NM_001189 |
| NXPH3 | 11248 | NM_007225 |
| HMX1 | 3166 | NM_018942; NM_001306142 |
| CLDN7 | 1366 | NM_001307; NM_001185022; NM_001185023 |
| TUBB4A | 10382 | NM_001289129; NM_001289131; NM_006087; NM_001289123; NM_001289127; NM_001289130 |
| RAB17 | 64284 | XM_006712689; XM_017004693; NM_022449; XM_017004694; NR_033308 |
| EPCAM | 4072 | NM_002354 |
| GH1 | 2688 | NM_022559; NM_022561; NM_022560; NM_022562; NM_000515 |
| ERBB3 | 2065 | NM_001005915; NM_001982 |
| ELMO3 | 79767 | XM_024450447; NM_024712 |
| SYNC | 81493 | XM_024450011; NM_001161708; XM_024450013; NM_030786; XM_024450012; XM_024450010; XM_024450014 |
| TPD52 | 7163 | NM_005079; NR_105035; NM_001287143; NM_001387779; NR_105037; NR_170694; NM_001025252; NM_001025253; NR_170693; NM_001287140; NR_105034; NM_001387780; NM_001287142; NM_001287144; NM_001387778; NR_105033; NR_105036 |
| S100B | 6285 | NM_006272; XM_017028424 |
| PALMD | 54873 | NM_017734 |
| CYP46A1 | 10858 | NM_006668; XM_005267274; XM_011536365; XM_011536364; XM_017020933 |
| PNPLA2 | 57104 | NM_020376 |
| SERINC2 | 347735 | NM_178865; NM_001199039; NM_018565; NM_001199038; NM_001199037 |
| PRSS12 | 8492 | XM_011532387; NM_003619; XM_005263318 |
| OLR1 | 4973 | NM_002543; NM_001172632; NM_001172633 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| HOOK1 | 51361 | XR_946665; XM_017001424; XM_006710676; XR_246271; XM_011541563; XM_024447520; XM_011541562; NM_015888 |
| GDPD3 | 79153 | NM_024307 |
| EPM2A | 7957 | NM_001368131; XM_017011301; NM_001360057; NM_001360064; NM_001368129; XM_024446550; XM_011536113; NM_001368130; NM_005670; NR_153398; XM_017011302; XM_011536116; NM_001360071; NM_001018041; XM_024446551; NM_001368132 |
| C1orf116 | 79098 | XM_011509973; NM_001083924; XM_005273259; XM_006711530; NM_023938 |
| CCDC68 | 80323 | XM_011526201; XM_017026011; XM_011526198; XM_006722552; NM_001143829; XM_011526199; XM_011526203; XM_011526204; NM_025214; XM_011526200; XM_011526202 |
| VGF | 7425 | NM_003378; XM_011516549; XM_005250561 |
| PLEK2 | 26499 | NM_016445 |
| FBN2 | 2201 | NM_001999; XM_017009228 |
| FGF7 | 2252 | NM_002009 |
| RCN3 | 57333 | NM_020650; XM_024451620 |
| FBXO2 | 26232 | NM_012168 |
| COX7A1 | 1346 | NM_001864 |
| EBF2 | 64641 | NM_022659 |
| ADAMTS2 | 9509 | NM_021599; NM_014244 |
| TAGLN3 | 29114 | NM_001008272; NM_001008273; NM_013259 |
| HAND2 | 9464 | NM_021973 |
| MT3 | 4504 | NM_005954 |
| RAP1GAP | 5909 | XR_001737354; XR_001737351; NM_001145657; NM_001350527; NM_001350528; NM_001388217; NM_001388229; NM_001388241; NM_001388254; |

-continued

| Gene | NCBI Gene ID | NCBI Accession Number(s) |
|---|---|---|
| | | NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| GAS1 | 2619 | NM_002048 |
| CDKL2 | 8999 | XR_001741344; XR_001741345; XM_017008811; XM_017008810; XM_006714406; NM_003948; XM_017008809; NM_001330724 |
| SCN4A | 6329 | NM_000334 |
| COL5A1 | 1289 | NM_000093; XM_017014266; XR_001746183; NM_001278074 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| POPDC2 | 64091 | NM_001369919; NM_022135; NM_001308333 |
| TFAP2A | 7020 | NM_001032280; XM_006715175; NM_001042425; XM_017011232; XM_011514833; NM_001372066; NM_003220 |
| EN1 | 2019 | NM_001426 |
| CHRD | 8646 | XM_017007390; NR_130747; NM_177978; XM_017007388; XM_017007391; XM_024453803; XR_001740336; NM_001304472; XM_017007392; XR_001740334; XM_011513254; XR_002959603; NM_001304473; NM_177979; NM_001304474; NM_003741; XM_017007389; XM_017007393; XM_017007394; XR_001740335; XR_001740337 |
| PLS1 | 5357 | NM_001172312; XM_011512901; NM_001145319; XM_006713660; XM_017006626; XM_011512903; XM_017006627; XM_011512900; NM_002670 |
| ELF3 | 1999 | NM_004433; XM_005244942; NM_001114309 |
| DBNDD1 | 79007 | NM_001288709; NM_001288708; NM_001371581; NM_001042610; NM_024043 |
| RAB23 | 51715 | NM_183227; NM_001278666; NM_001278668; NM_016277; NM_001278667; NR_103822 |
| CD24 | 100133941 | NM_001291739; NR_117090; NR_117089; NM_001291738; NM_001291737; NM_013230; XM_024446293; NM_001359084 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| AMPH | 273 | XM_006715689; XM_017011996; XM_006715690; XM_006715691; XM_011515271; XM_017011995; NM_001635; NM_139316 |
| KRT8 | 390601, 149501, 3856 | NM_001256293; NM_002273 |
| HOXA7 | 3204 | NM_006896 |
| CORO2A | 7464 | NM_003389; NM_052820; XM_011518986 |
| RNF43 | 54894 | XM_011524955; XM_011524956; NM_017763; NM_001305544; XM_017024800; NM_001305545 |
| PER1 | 5187 | XM_005256689; XM_005256690; XM_024450803; NM_002616 |
| SHOX2 | 6474 | XM_006713727; NM_001163678; XM_017007055; NM_006884; XM_006713728; XM_017007053; NM_003030; XM_017007054 |
| MYRF | 745 | NM_013279; XM_005274222; XM_005274224; XM_005274226; XM_005274228; XM_005274223; XM_005274225; XM_005274227; XM_011545234; XM_024448677; NM_001127392 |
| GPR1 | 2825 | NM_001098199; NM_001261452; NM_001261454; NM_005279; XM_005246471; NM_001261455; NM_001389445; NM_001261453 |
| CIDEC | 63924 | NM_001321142; NM_001199552; NM_001378491; NM_001199623; NM_001199551; NM_001321144; NM_022094; NM_001321143 |
| APOD | 347 | NM_001647 |
| KRT2 | 3849 | NM_000423 |
| HOXD9 | 3235 | NM_014213 |
| KCNB2 | 9312 | XM_017013981; XR_001745620; XR_001745621; NM_004770; XM_017013982 |
| FABP6 | 2172 | NM_001130958; NM_001040442; NM_001445 |

-continued

| Gene | NCBI Gene ID | NCBI Accession Number(s) |
|---|---|---|
| CCNB1 | 891 | NM_031966 |
| DSP | 1832 | NM_001008844; NM_004415; NM_001319034 |
| KRT5 | 3852 | NM_000424 |
| LGI2 | 55203 | XM_011513850; NM_018176; XM_017008356 |
| CKM | 1158 | NM_001824 |
| ITGB4 | 3691 | XM_005257311; XM_006721866; XM_006721870; NM_000213; NM_001005619; NM_001005731; XM_005257309; XM_011524752; XM_006721867; XM_011524751; NM_001321123; XM_006721868 |
| AP1M2 | 10053 | NM_001300887; XM_024451304; NM_005498; XM_024451303 |
| QPRT | 23475 | XM_005255223; NR_134536; NM_001318250; NM_001318249; NM_014298; XM_017023101 |
| FOXD1 | 2297 | NM_004472 |
| NPPA | 4878 | NM_006172 |
| DDR2 | 4921 | NM_001014796; XM_011509587; XM_011509588; NM_001354982; NM_006182; NM_001354983 |
| PFKFB1 | 5207 | NM_001271804; XM_017029578; XM_017029576; NM_002625; NR_073450; XM_024452389; XM_017029577; NM_001271805 |
| BNC2 | 54796 | NM_001317939; NM_017637; NM_001317940 |
| PCOLCE | 5118 | XM_024446785; NM_002593 |
| GIPC2 | 54810 | NM_017655; NM_001304725 |
| FZD2 | 2535 | NM_001466 |
| COL1A2 | 1278 | NM_000089 |
| FST | 10468 | XM_005248403; XM_011543099; XM_005248400; XM_017008955; NM_013409; XM_005248401; XM_005248402; XM_017008954; XM_024454326; NM_006350 |
| BIK | 638 | NM_001197 |
| C1QL1 | 10882 | NM_006688 |
| ZWINT | 11130 | XR_428692; NM_007057; NM_001005413; XM_017015605; XM_024447784; NM_032997; NM_001005414 |
| MYOC | 4653 | NM_000261 |
| GABRQ | 55879 | NM_018558; XM_011531184 |
| SCN5A | 6331 | NM_001160160; NM_001099405; NM_001354701; XM_011533991; XM_017007017; NM_001160161; NM_198056; NM_000335; NM_001099404 |
| DTL | 51514 | XM_011509614; NM_001286229; NM_001286230; NM_016448 |
| | | Neuroendocrine |
| CA7 | 766 | NM_001365337; XM_011523312; NM_001014435; NM_005182 |
| TGM3 | 7053 | NM_003245 |
| HLA-G | 3135 | XM_017010817; NM_001384280; XM_017010818; NM_002127; XM_024446420; NM_001363567; NM_001384290 |
| MYL2 | 4633 | NM_000432 |
| CCNB1 | 891 | NM_031966 |
| UPK3A | 7380 | NM_006953; NM_001167574 |
| LYVE1 | 10894 | NM_006691 |
| DES | 1674 | NM_001927; NM_001382708; NM_001382710; NM_001382713; NM_001382709; NM_001382711; NM_001382712 |
| PLA2G1B | 5319 | NM_000928 |
| DBNDD1 | 79007 | NM_001288709; NM_001288708; NM_001371581; NM_001042610; NM_024043 |
| MET | 4233 | NM_001324402; NM_001324401; XM_006715990; NM_001127500; XM_011516223; NM_000245; XR_001744772; |
| ESM1 | 11082 | NM_001135604; NM_007036 |
| COL10A1 | 1300 | XM_011535432; NM_000493; XM_011535433; XM_017010248; XM_006715333 |
| KRT2 | 3849 | NM_000423 |
| HRASLS2 | 54979 | NM_017878; XM_011545120 |
| DGKI | 9162 | NM_004717; NM_001321708; XM_017012788; NM_001321710; NM_001388092; NM_001321709 |
| SLC18A1 | 6570 | XM_011544626; NM_003053; XM_011544625; NM_001142325; NM_001135691; NM_001142324 |
| MMP11 | 4320 | NM_005940; NR_133013 |
| FIGF | 2277 | NM_004469 |
| SLC16A7 | 9194 | XM_011538990; XM_011538992; NM_004731; NM_001270622; XM_017020225; XM_017020227; NR_073055; XM_011538989; NM_001270623; XM_024449276; XM_011538991; XM_011538993; NR_073056; XM_005269231; XM_011538995; XM_017020226; XM_017020224 |
| VIP | 7432 | XM_006715562; XM_005267135; NM_003381; NM_194435 |
| CD200 | 4345 | NM_001318830; NR_158642; NM_001004197; NM_001365853; NM_001365855; NM_001318826; NM_001365852; NM_001004196; NM_001318828; NM_001365851; NM_005944; NM_001365854 |
| SLITRK3 | 22865 | NM_014926; NM_001318810; NM_001318811 |
| FCN2 | 2220 | XM_011518392; NM_015838; NM_015839; NM_015837; NM_004108; XM_006717015 |
| MT3 | 4504 | NM_005954 |
| ADRB2 | 154 | NM_000024 |
| CACNG4 | 27092 | NM_014405 |
| SYNPO2L | 79933 | NM_024875; NM_001114133; XM_005270159; XM_005270158 |
| VILL | 50853 | NM_001370265; NR_163266; NR_163267; NM_001370264; NM_015873; NM_001385039; NM_001385038 |

-continued

| Gene | NCBI Gene ID | NCBI Accession Number(s) |
|---|---|---|
| AGRN | 375790 | XM_011541429; NM_001305275; NM_001364727; XR_946650; NM_198576; XM_005244749 |
| CYP11B1 | 1584 | NM_001026213; NM_000497 |
| EPHB3 | 2049 | NM_004443 |
| KCNMB1 | 3779 | NM_004137 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| SCGB2A1 | 4246 | NM_002407 |
| ABCC4 | 10257 | XM_017020321; NM_001301829; NM_005845; XM_005254025; XM_017020319; NM_001301830; NM_001105515; XM_017020322; XM_017020320 |
| CRNN | 49860 | NM_016190 |
| CHGB | 1114 | NM_001819 |
| HIGD1B | 51751 | XM_011524891; NM_016438; XM_006721946; XM_006721947; XM_017024742; NR_073504; XM_006721948; XM_017024743; NM_001271880 |
| CELA2A | 63036 | NM_033440 |
| CLPS | 1208 | NM_001832; NM_001252597; NM_001252598 |
| HECW1 | 23072 | XM_006715670; XM_006715671; XM_011515225; XM_017011882; XM_011515220; XM_011515223; XM_017011886; XM_017011888; NM_001287059; NM_015052; XM_017011883; XM_006715673; XM_011515222; XM_011515224; XM_017011884; XM_017011889; XM_017011885; XM_017011887; XM_011515226; XM_017011890; XM_005249665 |
| ERBB3 | 2065 | NM_001005915; NM_001982 |
| PPY | 5539 | NM_002722; NM_001319209; XM_011524978 |
| CKM | 1158 | NM_001824 |
| CXorf36 | 79742 | XM_006724559; NM_176819; NM_024689; XM_005272670 |
| HOXA10 | 3206 | NR_037939; NM_153715; NM_018951 |
| RIBC2 | 26150 | XM_005261524; XM_011530126; NM_015653; XM_017028766 |
| CDH19 | 28513 | XM_011525931.3; XM_017025711.2; XM_011525932.1 |
| SLC24A2 | 25769 | XM_017014592; NM_001193288; NM_001375850; NM_020344; NM_001375851 |
| ADAMDEC1 | 27299 | NM_001145272; NM_014479; NM_001145271; NR_156422 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| KRT17 | 3872 | NM_000422 |
| S100P | 6286 | NM_005980 |
| NOX4 | 50507 | NM_001291926; XM_006718849; NM_016931; NM_001143837; XM_011542857; NM_001143836; NM_001291927; XM_017017842; XM_017017843; XM_017017844; XM_017017841; XM_017017845; NM_001291929; NM_001300995; NR_120406 |
| CELSR1 | 9620 | XM_011530554; XM_011530555; NM_001378328; XM_011530553; NM_014246 |
| CPB1 | 1360 | NM_001871 |
| CCL23 | 6368 | NM_005064; XR_429910; NM_145898 |
| CELA3A | 10136 | NM_005747 |
| WISP2 | 8839 | NM_001323369; XM_017028116; NM_003881; XM_017028117; NM_001323370 |
| GCG | 2641 | NM_002054 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| PDX1 | 3651 | NM_000209; XR_941580; XR_941578; |
| FABP7 | 2173 | NM_001319039; NM_001319041; NM_001319042; NM_001446 |
| NRTN | 4902 | NM_004558 |
| NMB | 4828 | XM_017022239; NM_021077; NM_205858 |
| AMHR2 | 269 | XM_011538179; XM_011538184; XM_017019179; NM_020547; XR_002957309; XR_002957311; XM_011538178; XM_011538176; XM_011538181; XM_011538185; NM_001164691; XM_011538174; XM_011538183; XR_002957310; XM_011538186; XR_002957312; NM_001164690; XM_011538173; XM_011538180; XM_024448938 |
| WNT2 | 7472 | NM_003391; NR_024047 |
| GFAP | 2670 | XM_024450691; XM_024450690; NM_001131019; XM_024450692; XM_024450693; NM_001242376; NM_002055; NM_001363846 |
| CYP11B2 | 1585 | NM_000498 |
| SGCA | 6442 | XM_011525122; XM_011525120; XM_011525121; XM_024450873; NM_001135697; NR_135553; XR_002958056; XM_011525124; NM_000023; XM_011525123 |
| PNMA2 | 10687 | NM_007257; XM_011544365 |
| CEL | 1056 | NM_001807 |
| MT1M | 4499 | NM_176870 |
| CST1 | 1469 | NM_001898 |
| ITPKB | 3707 | NM_002221; NM_001388404; XM_017001211 |
| ALAS2 | 212 | NM_001037968; NM_001037967; NM_000032; NM_001037969 |
| INS | 3630 | NM_001185098; NM_001185097; NM_000207; NM_001291897 |
| LGALS4 | 3960 | NM_006149; XM_011526974; XM_011526973 |
| PLP1 | 5354 | NM_001128834; NM_000533; NM_001305004; NM_199478 |
| GABRQ | 55879 | NM_018558; XM_011531184 |
| PLAG1 | 5324 | XM_017013576; XM_017013577; NM_001114635; XM_011517544; NM_001114634; NM_002655 |

-continued

| Gene | NCBI Gene ID | NCBI Accession Number(s) |
|---|---|---|
| LIPF | 8513 | NM_004190; NM_001198829; NM_001198830; NM_001198828; XM_011540311 |
| CYP11A1 | 1583 | NM_000781; NM_001099773 |
| FABP1 | 2168 | NM_001443 |
| S100A12 | 6283 | NM_005621 |
| IL20RA | 53832 | NM_001278722; XM_011535904; XM_017010955; NM_001278724; NM_014432; XM_006715506; NM_001278723; XM_017010954 |
| NR5A1 | 2516 | NM_004959 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| ERBB2 | 2064 | XM_024450643; NM_001005862; NM_001382784; NM_001382785; NM_001382788; NM_001382792; NM_001382793; NM_001382803; NM_001289937; NM_001382786; NM_001382800; NM_001382802; NM_001382806; XM_024450641; NM_001382782; NM_001382789; NM_001382795; NM_001289936; NM_001382797; NM_001382805; NM_004448; NR_110535; XM_024450642; NM_001289938; NM_001382791; NM_001382801; NM_001382783; NM_001382790; NM_001382794; NM_001382798; NM_001382799; NM_001382787; NM_001382796; NM_001382804 |
| SLC12A3 | 6559 | NM_000339; NM_001126108; NM_001126107; XM_005256119 |
| GRHL2 | 79977 | XM_011517306; XM_024447286; NM_001330593; NM_024915; XM_011517307 |
| HBB | 3043 | NM_000518 |
| C7 | 730 | NM_000587 |
| MOGAT2 | 80168 | XM_024448696; NM_025098; XM_011545267 |
| MYOC | 4653 | NM_000261 |
| TP73 | 7161 | NM_001126242; NM_001204191; NM_001126240; NM_001204185; NM_001204187; NM_001204184; NM_001204186; NM_001204192; NM_001126241; NM_001204190; NM_001204188; NM_001204189; NM_005427 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| BCAM | 4059 | NM_001013257; NM_005581 |
| KHDC1L | 100129128 | NM_001126063 |
| DTL | 51514 | XM_011509614; NM_001286229; NM_001286230; NM_016448 |
| CXCR2 | 3579 | XM_017003992; XM_017003990; NM_001168298; NM_001557; XM_005246530; XM_017003991 |
| KRT24 | 192666 | XM_017024299; NM_019016; XM_006721739; XM_011524460 |
| SIX1 | 6495 | XM_017021602; NM_005982 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| TNXB | 7148 | NM_001365276; NM_019105; NM_032470 |
| SLC6A7 | 6534 | XR_001742210; XM_024446190; XR_001742212; XM_017009770; XR_001742211; XM_017009767; XM_017009769; XM_017009768; NM_014228 |
| PLAGL1 | 5325 | NM_001289037; NM_001289040; NM_001289046; NM_001289047; NM_001317157; NM_001080956; NM_001080951; NM_001080955; NM_001289044; NM_001289048; NM_001289049; NM_001317159; NM_001317162; NM_001289038; NM_001080953; NM_001080954; NM_001289043; NM_001317156; NM_001317158; NM_001080952; NM_001289041; NM_001289045; NM_001317161; NM_002656; NM_006718; NM_001289039; NM_001289042; NM_001317160 |
| ADH1B | 125 | NM_001286650; NM_000668 |
| FSTL4 | 23105 | XM_011543284; XM_011543286; XM_011543287; XM_011543283; XM_017009251; NM_015082 |
| MFAP2 | 4237 | NM_002403; NM_017459; NM_001135247; NM_001135248 |
| TREM2 | 54209 | NM_001271821; NM_018965 |
| COL1A2 | 1278 | NM_000089 |
| LRP2 | 4036 | XM_011511183; NM_004525; XM_011511184 |
| CDK1 | 983 | NM_001320918; NM_033379; NM_001170406; NM_001786; NM_001130829; XM_005270303; NM_001170407 |
| EBF2 | 64641 | NM_022659 |
| CDH3 | 1001 | NM_001793; XM_011522800; NM_001317195; NM_001317196 |
| SVEP1 | 79987 | NM_024500; NM_153366 |
| CNNM1 | 26507 | NM_001345888; XM_011539631; XR_002956974; NM_020348; NM_001345887; NM_001345889; NR_144311; XR_945667 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| ADAM12 | 8038 | XM_017016705; NM_001288973; NM_001288974; NM_001288975; XM_017016706; NM_003474; NM_021641; XM_024448210 |
| MAGEA1 | 4100 | NM_004988 |

-continued

| Gene | NCBI Gene ID | NCBI Accession Number(s) |
| --- | --- | --- |
| | | Pheochromocytoma |
| PHOX2A | 401 | NM_005169 |
| DDC | 1644 | XM_011515161; NM_001242890; XM_005271745; NM_001082971; NM_001242886; NM_001242887; NM_001242889; NM_000790; NM_001242888 |
| INSM1 | 3642 | NM_002196 |
| CYP11A1 | 1583 | NM_000781; NM_001099773 |
| SYT5 | 6861 | XM_006723339; NM_001297774; NM_003180; XM_017027175; XM_006723340; XM_006723341; XM_024451668 |
| NGB | 58157 | NM_021257 |
| STAR | 6770 | NM_001007243; NM_000349 |
| SLC18A1 | 6570 | XM_011544626; NM_003053; XM_011544625; NM_001142325; NM_001135691; NM_001142324 |
| CHGB | 1114 | NM_001819 |
| CHRNA3 | 1136 | XM_006720382; NM_000743; NR_046313; NM_001166694 |
| CHGA | 1113 | NM_001301690; NM_001275; XM_011536370 |
| SLC18A2 | 6571 | NM_003054 |
| DBH | 1621 | NM_000787 |
| DRD2 | 1813 | XM_017017296; NM_016574; NM_000795 |
| TH | 7054 | XM_011520335; NM_199292; NM_000360; NM_199293 |
| PPP1R17 | 10842 | XR_926912; NM_001145123; XM_011515094; NM_006658 |
| PHOX2B | 8929 | NM_003924 |
| EGR4 | 1961 | NM_001965 |
| CDH22 | 64405 | XM_024451966; XM_011528994; XM_024451967; NM_021248 |
| SFN | 2810 | NM_006142 |
| C1orf106 | 55765 | XM_011509754; XM_011509755; NM_001367289; NM_001367290; XM_011509756; NM_001142569; NM_018265 |
| CDC20 | 991 | NM_001255 |
| TGFA | 7039 | NM_001308159; NM_001308158; NM_001099691; NM_003236 |
| SMO | 6608 | NM_005631; XM_024446891 |
| SDC1 | 6382 | NM_001006946; XM_005262620; XM_005262621; NM_002997; XM_005262622 |
| VAMP8 | 8673 | NM_003761; XM_017005170 |
| SERPINA1 | 5265 | NM_001002235; NM_001127700; NM_001127701; XM_017021370; NM_001127706; NM_000295; NM_001002236; NM_001127702; NM_001127705; NM_001127703; NM_001127704; NM_001127707 |
| EPHB3 | 2049 | NM_004443 |
| BIRC5 | 332 | NM_001168; NM_001012271; NM_001012270 |
| CILP | 8483 | NM_003613; XM_017022679; XM_017022678 |
| ABAT | 18 | NM_001386601; NM_001386602; NM_001386615; NM_000663; NM_001386606; NM_001127448; NM_020686; NM_001386608; NM_001386612; NM_001386613; NM_001386603; NM_001386605; NM_001386611; NM_001386600; NM_001386609; NM_001386610; NM_001386614; NM_001386616; NM_001386604; NM_001386607 |
| CSTA | 1475 | NM_005213 |
| PRUNE2 | 158471 | XM_011518327; XM_005251746; XM_005251751; XM_006716983; XM_017014347; XM_017014349; XM_017014359; XR_001746209; XR_428517; XM_005251748; XM_006716985; NM_001308047; XM_005251754; XM_006716982; XM_017014346; XM_017014348; XM_017014352; XR_001746210; NM_001308050; NR_131751; NM_138818; XM_011518323; XM_017014345; XM_017014357; XR_001746212; NM_001308048; NM_015225; XM_017014354; XM_017014356; NM_001308049; XM_005251750; XM_005251745; XM_006716986; XM_011518326; XM_011518328; XM_017014350; XM_017014351; XM_017014353; XM_017014358; XM_006716984; XR_001746211; NM_001308051; NM_001330680 |
| WNT2 | 7472 | NM_003391; NR_024047 |
| UGT2A3 | 79799 | XM_011532247; NM_024743; NR_024010 |
| IRS4 | 8471 | XM_006724713; NM_003604; NM_001379150; XM_011531061 |
| SLC6A15 | 55117 | XM_011538525; NM_018057; NM_001146335; NM_182767 |
| ATP2B2 | 491 | XM_017006484; NM_001001331; XM_005265179; XM_011533752; XM_017006487; XM_017006488; XM_017006486; XM_017006481; XM_017006482; XM_017006489; XM_006713175; NM_001330611; NM_001353564; XM_017006485; XM_017006483; NM_001683; XM_017006492; NM_001363862 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| FCN2 | 2220 | XM_011518392; NM_015838; NM_015839; NM_015837; NM_004108; XM_006717015 |
| IVL | 3713 | NM_005547 |
| CFTR | 1080 | NM_000492 |
| F2RL1 | 2150 | NM_005242; XM_017009223 |
| MYB | 4602 | NM_001161660; NR_134958; NM_001130173; NM_001130172; NM_001161656; NR_134959; NM_001161657; NR_134963; NR_134965; XR_942444; NR_134962; NM_001161659; NR_134961; NM_001161658; NM_005375; NR_134960; NR 134964 |
| SCGN | 10590 | NM_006998; XM_017010181 |
| TMEM246 | 84302 | NM_001303107; NM_001303108; NM_032342; XM_024447701; NM_001371233 |

-continued

| Gene | NCBI Gene ID | NCBI Accession Number(s) |
|---|---|---|
| PRSS22 | 64063 | XM_005255473; NM_022119 |
| IHH | 3549 | NM_002181 |
| MYBPH | 4608 | NM_004997 |
| SPOCK2 | 9806 | XM_017016985; NM_001134434; XM_011540404; NM_001244950; NM_014767 |
| MUC2 | 4583 | NM_002457 |
| MYCL | 4610 | NM_001033082; NM_001033081; NM_005376 |
| | | Mesothelioma |
| CPA4 | 51200 | NM_001163446; NM_016352 |
| CALB2 | 794 | NM_007088; XR_002957842; NM_001740; NR_027910; NM_007087 |
| HAS1 | 3036 | NM_001523; NM_001297436; XM_011526884 |
| ALDH1A2 | 8854 | NM_001206897; NM_170697; NM_170696; NM_003888 |
| PTGIS | 5740 | NM_000961 |
| UPK1B | 7348 | NM_006952 |
| WT1 | 7490 | NM_000378; NR_160306; NM_001367854; NM_001198551; NM_001198552; NM_024424; NM_024426; NM_024425 |
| MYL2 | 4633 | NM_000432 |
| HP | 3240 | NM_001126102; NM_005143; NM_001318138 |
| MSLN | 10232 | NM_001177355; NM_005823; NM_013404 |
| GJB1 | 2705 | NM_000166; XM_011530907; NM_001097642 |
| CKM | 1158 | NM_001824 |
| TM4SF1 | 4071 | NM_014220; XM_017006385 |
| CST1 | 1469 | NM_001898 |
| CTSE | 1510 | XM_011509245; NM_001910; NM_148964; XM_011509244; NM_001317331 |
| SLC44A4 | 80736 | NM_001178045; NM_001178044; NM_025257 |
| CD24 | 100133941 | NM_001291739; NR_117090; NR_117089; NM_001291738; NM_001291737; NM_013230; XM_024446293; NM_001359084 |
| BMP7 | 655 | NM_001719 |
| TBX5 | 6910 | NM_181486; NM_080717; NM_000192; XM_017019912; NM_080718 |
| GATA4 | 2626 | NM_001308093; NM_002052; NM_001308094; NM_001374273; NM_001374274 |
| IRF6 | 3664 | NM_001206696; NM_006147 |
| KRT5 | 3852 | NM_000424 |
| PRSS22 | 64063 | XM_005255473; NM_022119 |
| CLIC3 | 9022 | XM_017015282; NM_004669; XM_017015281 |
| FLNC | 2318 | NM_001458; NM_001127487 |
| SALL1 | 6299 | NM_001127892; NM_002968 |
| ERBB3 | 2065 | NM_001005915; NM_001982 |
| TF | 7018 | NM_001063; NM_001354703; NM_001354704 |
| GJB3 | 2707 | NM_024009; NM_001005752 |
| BDNF | 627 | NM_001143811; NM_001143812; NM_170734; XM_011520280; NM_001143805; NM_001143816; NM_170731; NM_001143808; NM_001143809; NM_001143814; NM_001143815; NM_001143807; NM_001709; NM_001143810; NM_001143813; NM_170732; NM_001143806; NM_170733; NM_170735 |
| ADRA2B | 151 | NM_000682 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| CENPF | 1063 | XM_017000086; NM_016343; XM_011509082 |
| SCN4A | 6329 | NM_000334 |
| KRT18 | 3875 | NM_000224; NM_199187 |
| SPINT2 | 10653 | NM_001166103; NM_021102 |
| KIF4A | 24137 | NM_012310 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SDC1 | 6382 | NM_001006946; XM_005262620; XM_005262621; NM_002997; XM_005262622 |
| ROBO3 | 64221 | NM_001370358; NM_001370359; NR_163412; NM_001370356; NM_001370361; NR_163411; NR_163415; NM_001370364; NM_022370; NR_163410; NR_163413; NR_163414; XM_017018122; NM_001370366; NM_001370357; NR_163409 |
| FHL5 | 9457 | NM_001170807; NM_001322466; NM_001322467; NM_020482 |
| ZWINT | 11130 | XR_428692; NM_007057; NM_001005413; XM_017015605; XM_024447784; NM_032997; NM_001005414 |
| PKMYT1 | 9088 | NM_001258451; NM_182687; NM_001258450; XM_011522735; XM_024450490; NM_004203; XM_011522734; XM_011522736 |
| NEIL3 | 55247 | NM_018248; XM_017008360 |
| PHKG1 | 5260 | NM_001258460; XM_017012327; XM_017012324; XM_017012325; NR_047689; XM_017012326; NM_001258459; XM_005271772; NM_006213 |
| KRT2 | 3849 | NM_000423 |
| CDKN2A | 1029 | XR_929159; XM_011517676; XM_011517675; NM_001363763; NM_001195132; NM_058195; NM_000077; NM_058196; NM_058197; XM_005251343 |
| SEMA6C | 10500 | NM_030913; XM_017000075; XM_017000079; NM_001178061; NM_001178062; XM_017000077; XM_017000082; XM_017000076; XM_017000081; XM_005244835 |
| CIDEC | 63924 | NM_001321142; NM_001199552; NM_001378491; NM_001199623; NM_001199551; NM_001321144; NM_022094; NM_001321143 |
| SPANXB1 | 728695 | NM_145664; NM_032461 |
| GH1 | 2688 | NM_022559; NM_022561; NM_022560; NM_022562; NM_000515 |

-continued

| Gene | NCBI Gene ID | NCBI Accession Number(s) |
| --- | --- | --- |
| PLIN1 | 5346 | NM_002666; XM_005254934; NM_001145311 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| CACNA1S | 779 | XM_005245478; NM_000069 |
| | | Thymoma |
| MAOB | 4129 | XM_005272608; XM_017029524; XM_017029523; NM_000898 |
| ANKS1B | 56899 | XM_006719507; XM_024449067; NM_001204070; NM_001352193; NM_001352198; NM_001352201; NM_001352207; NM_001352219; NM_001352221; XM_006719508; XM_017019654; XM_024449061; XM_024449062; NM_001204065; NM_001352185; NM_001352191; NM_001352194; NM_001352202; NM_001352203; NM_001352209; NM_001352211; NM_001352213; NM_001352220; XM_017019655; XM_024449069; NM_001204068; NM_001352205; NM_001352214; NM_001352216; NM_001352218; NM_001352223; NM_001352225; NM_020140; XM_024449063; XM_024449066; XM_024449070; NM_001204066; NM_001352186; NM_001352187; NM_001352195; NM_001352200; NM_001352212; NM_152788; XM_005269029; XM_006719505; XM_006719510; XM_006719512; XM_011538571; XM_017019656; XM_024449065; NM_001204079; NM_001352189; NM_001352190; NM_001352197; NM_001352222; XM_006719513; XM_006719514; XM_017019652; XM_024449064; XR_001748815; NM_001204069; NM_001204067; NM_001204081; NM_001352199; NM_001352204; NM_001352206; NM_001352210; NM_001352217; NM_181670; XM_017019653; NM_001352196; XM_006719504; XM_017019657; XM_017019658; XM_024449060; XM_024449068; NM_001204080; NM_001352188; NM_001352192; NM_001352208; NM_001352224 |
| SPINK2 | 6691 | XM_024454191; XM_011534405; NM_001271718; NM_001271720; NM_001271721; NR_073417; NM_001271719; XM_011534406; NM_001271722; NM_021114; NR_073418; NR_073419 |
| KREMEN2 | 79412 | NM_145348; NM_145347; NM_024507; NM_172229; NM_001253726; NM_001253725 |
| ORC1 | 4998 | NM_001190818; XM_017001388; XM_017001389; NM_001190819; XM_011541527; NM_004153 |
| GJB1 | 2705 | NM_000166; XM_011530907; NM_001097642 |
| DPF1 | 8193 | XM_006723408; XR_243964; XM_011527356; XM_024451731; NM_004647; XM_005259292; XM_006723407; NM_001135155; XM_006723409; XM_006723410; XM_011527358; NM_001363579; XM_011527357; XM_005259289; NM_001135156; NM_001289978 |
| PAX1 | 5075 | NM_006192; NM_001257096 |
| FCN2 | 2220 | XM_011518392; NM_015838; NM_015839; NM_015837; NM_004108; XM_006717015 |
| KIFC1 | 3833 | XM_011514585; XM_017010836; NM_002263; XM_011514587; XM_017010837 |
| RAG1 | 5896 | NM_001377278; NM_000448; NM_001377280; NM_001377277; NM_001377279 |
| FOXN1 | 8456 | XM_011525358; XM_011525362; XM_011525359; XM_011525367; XM_011525368; XM_011525370; XM_017025230; XM_017025231; XM_017025229; XM_011525369; XM_017025228; NM_001369369; NM_003593 |
| ZAP70 | 7535 | XM_017004868; XR_001738927; NM_001378594; NM_207519; XM_017004869; NM_001079; XR_001738926; XM_017004870; XM_017004867; XR_001738925 |
| PCDH1 | 5097 | XM_005268455; NM_001278613; XM_005268452; XM_017009517; NM_032420; NM_002587; XM_005268454; XM_017009518; NM_001278615 |
| LCK | 3932 | XM_011541453; XM_024447046; NM_001330468; XM_024447047; NM_005356; NM_001042771 |
| MLANA | 2315 | NM_005511 |
| KRT5 | 3852 | NM_000424 |
| NDRG2 | 57447 | NM_016250; NM_001354567; NM_201538; NM_001282215; NM_001354560; NM_001354561; NM_001354569; NM_201535; NM_001282216; NM_001354564; NM_001354565; NM_001354566; NM_201536; NM_201539; NM_201541; NM_001354558; NM_001354562; NM_001282213; NM_001354570; NM_201540; NM_001282211; NM_001320329; NM_001282214; NM_001282212; NM_001354559; NM_001354568; NM_201537 |
| GFI1B | 8328 | NM_001371908; NM_001377304; XM_006717297; NM_001135031; XM_017015175; NM_001377305; XM_011519069; XM_011519070; NM_004188; XM_011519068; XM_017015176 |
| BEND5 | 79656 | XM_017002331; XM_011542141; XM_017002333; NM_001349795; NR_146232; XM_011542142; XR_001737408; NM_001349794; NM_001302082; NM_001349793; NM_024603 |
| ITGB6 | 3694 | NM_001282354; NM_001282353; NM_000888; NM_001282389; NM_001282390; NM_001282355; NM_001282388 |
| AGL | 178 | NM_000646; XM_005270557; NM_000644; NM_000028; NM_000643; XM_017000501; NM_000642; NM_000645 |
| CAMK2N1 | 55450 | NM_018584 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; |

-continued

| Gene | NCBI Gene ID | NCBI Accession Number(s) |
|---|---|---|
| | | NM_001318113; NM_001318116; XM_017029098; NM_001318104; NM_001318112; NM_001318115 |
| EEF1A2 | 1917 | NM_001958 |
| REN | 5972 | NM_000537 |
| CALML3 | 810 | NM_005185 |
| DNTT | 1791 | NM_004088; NM_001017520 |
| PHLDA2 | 7262 | NM_003311 |
| CTH | 1491 | XM_005270509; NM_001902; NM_153742; XM_017000416; NM_001190463 |
| PRSS16 | 10279 | XM_017010162; XM_017010164; XM_017010165; XM_017010161; XM_017010163; NM_005865 |
| AADAC | 13 | NM_001086; XM_005247104 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| SDCBP | 6386 | NM_001007067; NM_001007069; XM_024447231; NM_001330537; NM_001348340; XM_024447229; NM_001007068; NM_001348341; XM_024447230; NM_005625; NM_001007070; NM_001348339 |
| PAX9 | 5083 | NM_001372076; NM_006194 |
| CCL25 | 6370 | NM_001394634; NM_001394635; NM_001394638; NM_005624; NM_148888; NM_001394636; NM_001201359; NM_001394637 |
| PKP1 | 5317 | NM_000299; NM_001005337 |
| TNFRSF4 | 7293 | XM_011542074; NM_003327; XM_017002232; XM_011542077; XM_011542075; XM_011542076; XM_017002231 |
| ACADL | 33 | NM_001608; XM_005246517; XM_017003955 |
| ARPP21 | 10777 | NM_001267619; NM_001385487; NM_001385490; NM_001385558; NM_001385573; NM_001385582; NR_169635; NR_169644; NR_170706; NR_170707; XM_017005574; XM_017005584; NM_001385485; NM_001385536; NM_001385581; NM_001385589; NM_001385594; XM_011533301; XM_017005580; XM_017005588; NM_001267616; NM_001385495; NM_001385576; NR_169645; XM_017005596; XM_024453320; NM_001385565; NM_001385566; NM_001385590; NM_016300; NR_169632; XM_011533303; XM_017005590; XM_017005598; XM_024453322; NM_001267617; NM_001385484; NM_001385488; NM_001385517; NM_001385585; NM_001385592; NR_169647; XM_011533299; XM_017005607; XM_024453323; NM_001025069; NM_001385489; NM_001385492; NM_001385496; NM_001385567; NM_001385577; NM_001385584; NM_001385587; NM_001385591; NM_001385593; XM_017005591; NM_001267618; NM_001385486; NM_001385491; NM_001385564; NM_001385578; NM_001385595; NM_198399; NR_169633; XM_011533300; XM_011533302; XM_017005575; XM_017005579; XM_017005612; XM_024453324; NM_001025068; NM_001385497; NM_001385556; NM_001385562; NM_001385563; NM_001385574; NM_001385580; NM_001385588; NR_169646; NR_170705 |
| SLC13A2 | 9058 | NM_001145975; NM_001346683; NM_003984; NM_001145976; XM_006722165; XM_011525450; XM_011525453; XM_011525454; NM_001346684; XM_011525452; XM_011525451 |
| FGFR4 | 2264 | NM_213647; NM_022963; NM_002011; NM_001291980; NM_001354984 |
| CD247 | 919 | NM_001378516; NM_198053; XM_011510144; XM_011510145; NM_000734; NM_001378515 |
| RAB23 | 51715 | NM_183227; NM_001278666; NM_001278668; NM_016277; NM_001278667; NR_103822 |
| FBXL6 | 26233 | NM_024555; NM_012162 |
| EFNA2 | 1943 | NM_001405; XM_017026449; XM_017026450 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| GHRH | 2691 | NM_001184731; NM_021081 |
| | | Germ_Cell_Neoplasm |
| CCNB1 | 891 | NM_031966 |
| POMC | 5443 | NM_001319205; NM_001035256; NM_001319204; NM_000939 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| CLDN6 | 9074 | NM_021195 |
| DBNDD1 | 79007 | NM_001288709; NM_001288708; NM_001371581; NM_001042610; NM_024043 |
| CAP2 | 10486 | NM_001363534; NM_006366; NM_001363533 |
| ESM1 | 11082 | NM_001135604; NM_007036 |
| EPS8L1 | 54869 | NM_133180; NM_139204; XM_011527052; XM_005259020; NM_017729; XM_011527051; XM_011527050 |
| MEP1B | 4225 | XM_011526013; XM_011526014; NM_005925; NM_001308171 |
| PLIN1 | 5346 | NM_002666; XM_005254934; NM_001145311 |
| ZWINT | 11130 | XR_428692; NM_007057; NM_001005413; XM_017015605; XM_024447784; NM_032997; NM_001005414 |
| HAMP | 57817 | NM_021175 |
| EIF1AY | 9086 | NM_004681; NM_001278612 |

-continued

| Gene | NCBI Gene ID | NCBI Accession Number(s) |
|---|---|---|
| MISP | 126353 | NR_135168; XM_011527686; XM_011527685; NM_173481 |
| MMP9 | 4318 | NM_004994 |
| CLEC1B | 51266 | NM_001099431; XM_017019395; XM_011520685; XM_017019396; XM_011520686; NM_016509; NM_001393342 |
| ALLC | 55821 | XM_017004495; XM_017004498; NM_018436; XM_017004496; XM_011510369; XM_011510370; XM_017004497; NM_199232 |
| PGR | 5241 | XM_011542869; NM_001271161; NR_073142; NM_000926; XM_006718858; NM_001202474; NM_001271162; NR_073141; NR_073143 |
| COL9A1 | 1297 | NM_001851; NR_165185; NM_078485; XM_017010246; XM_011535429; XM_017010247; NM_001377289; NM_001377290; NM_001377291 |
| DNM1 | 1759 | NM_001005336; NM_001374269; NM_004408; NM_001288738; NM_001288739; NM_001288737 |
| KERA | 11081 | NM_007035 |
| PLA2G2A | 5320 | NM_001161728; NM_000300; NM_001161729; NM_001161727; NM_001395463 |
| AURKB | 9212 | NM_001313950; NM_001313953; XM_017025309; XM_017025307; XM_017025308; XM_017025311; NM_001313952; NM_004217; NM_001313954; NR_132730; NR_132731; XM_017025310; NM_001284526; XM_011524072; NM_001256834; NM_001313951; NM_001313955 |
| APOBEC3B | 9582 | NM_004900; NM_001270411 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| PTH1R | 5745 | NM_001184744; XM_017006933; XM_011533968; NM_000316; XM_017006934; XM_011533967; XM_005265344; XM_017006932 |
| PTCH2 | 8643 | NM_001166292; NM_003738 |
| CYP46A1 | 10858 | NM_006668; XM_005267274; XM_011536365; XM_011536364; XM_017020933 |
| VRTN | 55237 | XM_011536911; NM_018228 |
| PLVAP | 83483 | NM_031310 |
| PTHLH | 5744 | NM_198965; NM_198966; XM_011520774; NM_002820; XM_017019675; NM_198964 |
| COL8A1 | 1295 | NM_020351; NM_001850 |
| DAZL | 1618 | NM_001351; NM_001190811 |
| NANOG | 79923 | NM_024865; NM_001297698 |
| CXorf36 | 79742 | XM_006724559; NM_176819; NM_024689; XM_005272670 |
| C9 | 735 | NM_001737 |
| FOXH1 | 8928 | NM_003923 |
| MDFI | 4188 | XM_005249117; XM_011514626; NM_005586; NM_001300805; XM_011514625; NM_001300804; XM_017010867; NM_001300806 |
| KLF9 | 687 | NM_001206 |
| EDIL3 | 10085 | NM_005711; NM_001278642 |
| LRRTM4 | 80059 | NM_001134745; NM_001330370; NM_001282924; NM_024993; NM_001282928; NR_146416 |
| PRND | 23627 | NM_012409 |
| GDF3 | 9573 | NM_020634 |
| CDKN2A | 1029 | XR_929159; XM_011517676; XM_011517675; NM_001363763; NM_001195132; NM_058195; NM_000077; NM_058196; NM_058197; XM_005251343 |
| PRM1 | 5619 | NM_002761 |
| LIN28A | 79727 | XM_011542148; NM_024674 |
| DPP4 | 1803 | NR_166823; NM_001379606; NM_001379605; NR_166824; NM_001935; NM_001379604; NR_166825; NR_166822 |
| IBSP | 3381 | NM_004967 |
| CYP17A1 | 1586 | NM_000102 |
| VENTX | 27287 | XM_017016073; NM_014468 |
| LEFTY2 | 7044 | NM_003240; NM_001172425; XM_011544266 |
| GCKR | 2646 | XM_017003797; XM_011532763; XR_001738699; XM_017003796; NM_001486 |
| AKR1C3 | 8644 | NM_003739; NM_016253; NM_001253909; NM_001253908 |
| GATA4 | 2626 | NM_001308093; NM_002052; NM_001308094; NM_001374273; NM_001374274 |
| PLP1 | 5354 | NM_001128834; NM_000533; NM_001305004; NM_199478 |
| ADAM11 | 4185 | XM_005257373; NM_001318933; NM_002390; XM_024450754 |
| PRM2 | 5620 | NM_001286358; NR_104428; NM_002762; NM_001286356; NM_001286359; NM_001286357 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| HAPLN1 | 1404 | XM_017009052; XM_017009051; NM_001884; XM_017009054; XM_017009053; XM_011543168 |
| DEPDC1 | 55635 | NM_001114120; NM_017779 |
| SLPI | 6590 | NM_003064 |
| C3orf36 | 80111 | NM_025041; NR_161373 |
| PEG3 | 5178 | NM_001369718; NM_001146184; NM_001369719; NM_001369734; NM_001369739; NR_161475; NM_001369731; NM_001369720; NM_001369724; NM_001369732; NM_001369733; NM_001146187; NM_001369722; NM_001369723; NM_001369726; NM_001369728; NM_001369735; NM_001369736; NM_001369737; NM_001369738; NM_001146185; NM_001369717; NM_001369721; NM_001369725; NM_006210; NM_001369729; NM_001369730; NM_001369727; NR_161476; NM_001146186 |

-continued

| Gene | NCBI Gene ID | NCBI Accession Number(s) |
|---|---|---|
| MLANA | 2315 | NM_005511 |
| TREM2 | 54209 | NM_001271821; NM_018965 |
| GDF2 | 2658 | NM_016204 |
| DPPA4 | 55211 | XM_011512954; XM_024453622; NM_001348929; NM_001348928; NM_018189 |
| CDH15 | 1013 | NM_004933 |
| RRM2 | 6241 | NR_161344; NM_001034; NR_164157; NM_001165931 |
| MYL7 | 58498 | XM_011515464; NM_021223; XM_011515465; XM_011515463; XM_017012478; XM_017012479; XM_024446851; XM_005249817 |
| PRR7 | 80758 | NM_001375594; NM_030567; NM_001174102; NM_001174101; NM_001375593 |
| PHC1 | 1911 | XM_017018958; XM_011520600; XM_017018955; XM_017018957; XM_011520599; XM_017018956; XM_011520603; XM_005253334; NM_004426 |
| | | Neuroendocrine_small_cell |
| CD34 | 947 | NM_001025109; NM_001773 |
| NCAM1 | 4684 | NM_001386289; NM_001386290; NM_001386291; NM_001386292; NM_001076682; NM_000615; NM_001242608; NM_181351; NM_001242607 |
| MOGAT2 | 80168 | XM_024448696; NM_025098; XM_011545267 |
| COL11A1 | 1301 | XM_017000337; XM_017000335; XM_017000336; NR_134980; NM_080629; XM_017000334; NM_001190709; NM_001854; NM_080630 |
| DTL | 51514 | XM_011509614; NM_001286229; NM_001286230; NM_016448 |
| MYOC | 4653 | NM_000261 |
| FOXA1 | 3169 | NM_004496; XM_017021246 |
| IBSP | 3381 | NM_004967 |
| GLP2R | 9340 | XM_011524077; NM_004246; XM_017025340; XM_005256861; XM_017025339; XM_017025341 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| ZNF185 | 7739 | XM_005274744; XM_017029823; XM_017029829; NM_001178107; XM_005274735; XM_005274740; XM_005274741; XM_017029825; XM_017029831; NM_001178106; NM_001178113; XM_005274738; XM_005274731; XM_017029822; XM_017029826; XM_017029827; XM_017029832; XM_005274745; XM_017029824; NM_001178108; NM_001178110; XM_011531195; XM_017029828; NM_001178115; NM_007150; NM_001178114; XM_005274730; XM_017029821; XM_011531194; NM_001178109; NM_001395254; XM_005274746; XM_017029830; XM_017029833; NM_001388432; XM_005274742; XM_017029834; XM_017029835 |
| SYN2 | 6854 | XM_006713312; XR_001740240; XM_006713311; XM_006713313; NM_133625; NM_003178; XM_017007087 |
| KRT2 | 3849 | NM_000423 |
| ANGPTL4 | 51129 | NM_016109; NM_139314; XM_005272484; XM_005272485; NR_104213; NM_001039667 |
| GABRG3 | 2567 | XM_017022058; XM_017022060; XM_024449889; NM_033223; XM_011521430; NM_001270873; XM_011521431; XM_017022059 |
| SPP1 | 6696 | NM_001251829; NM_001040060; NM_001251830; NM_000582; NM_001040058 |
| SYT12 | 91683 | XM_011545346; XM_011545347; NM_177963; XM_017018547; NM_001177880; NM_001318775; XM_017018548; XM_006718737; XM_024448766; NM_001318773 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| DLL3 | 10683 | NM_016941; NM_203486 |
| SFRP5 | 6425 | NM_003015 |
| GABRD | 2563 | XM_011541194; XM_017000936; NM_000815 |
| CCNB1 | 891 | NM_031966 |
| PRL | 5617 | XM_011514753; NM_000948; NM_001163558; XM_011514754 |
| RETN | 56729 | NM_020415; NM_001385725; NM_001385727; NM_001385726; NM_001193374 |
| PPM1H | 57460 | XM_017019676; XM_011538578; NM_020700; XM_011538579 |
| ESM1 | 11082 | NM_001135604; NM_007036 |
| CELA3B | 23436 | NM_007352 |
| CHGA | 1113 | NM_001301690; NM_001275; XM_011536370 |
| GGCT | 79017 | NM_001199816; NM_001199817; NM_001199815; NM_024051; NR_037669 |
| ADH1B | 125 | NM_001286650; NM_000668 |
| AOC3 | 8639 | XR_934584; NM_001277732; NM_003734; NR_102422; XM_011525419; XR_001752673; XM_011525420; XM_024451015; NM_001277731 |
| AGL | 178 | NM_000646; XM_005270557; NM_000644; NM_000028; NM_000643; XM_017000501; NM_000642; NM_000645 |
| CELSR3 | 1951 | NM_001407 |
| CLDN3 | 1365 | NM_001306 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| ALAS2 | 212 | NM_001037968; NM_001037967; NM_000032; NM_001037969 |
| CST1 | 1469 | NM_001898 |
| CA1 | 759 | NM_001128831; NM_001291967; NM_001164830; NM_001738; NM_001128830; NM_001128829; NM_001291968 |

-continued

| Gene | NCBI Gene ID | NCBI Accession Number(s) |
|---|---|---|
| AOC1 | 26 | XM_017011946; NM_001091; XM_017011947; NM_001272072; XM_017011944; XM_017011945 |
| LIMS2 | 55679 | XM_006712627; XM_024452983; NM_017980; NM_001256542; XM_017004469; NM_001161403; XM_011511453; XM_024452984; NM_001136037; XM_024452986; XR_922961; NM_001161404; XM_006712628; XM_024452985; XM_005263710 |
| HSF2BP | 11077 | XM_017028269; XM_017028272; XM_011529446; XM_017028270; XM_017028271; XM_017028267; XM_017028268; XR_937435; XM_011529445; XM_011529443; XM_011529447; NM_007031 |
| CDK4 | 1019 | NM_000075; NM_052984 |
| HBB | 3043 | NM_000518 |
| HOXC10 | 3226 | NM_017409 |
| KRT1 | 3848 | NM_006121 |
| TTC22 | 55001 | XM_017001582; XM_011541671; NM_001114108; NM_017904 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| S100A12 | 6283 | NM_005621 |
| KRT24 | 192666 | XM_017024299; NM_019016; XM_006721739; XM_011524460 |
| MET | 4233 | NM_001324402; NM_001324401; XM_006715990; NM_001127500; XM_011516223; NM_000245; XR_001744772; |
| DES | 1674 | NM_001927; NM_001382708; NM_001382710; NM_001382713; NM_001382709; NM_001382711; NM_001382712 |
| HOXC11 | 3227 | NM_014212 |
| GUCA2A | 2980 | NM_033553 |
| PTH1R | 5745 | NM_001184744; XM_017006933; XM_011533968; NM_000316; XM_017006934; XM_011533967; XM_005265344; XM_017006932 |
| ULBP2 | 80328 | NM_025217; XM_017011321 |
| TGM3 | 7053 | NM_003245 |
| CTRB2 | 440387 | NM_001025200 |
| CKM | 1158 | NM_001824 |
| ALDOC | 230 | XM_005257949; NM_005165; XM_011524556 |
| CCL23 | 6368 | NM_005064; XR_429910; NM_145898 |
| MMP11 | 4320 | NM_005940; NR_133013 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| HOXC13 | 3229 | NM_017410 |
| MAGEA3 | 4102 | XM_011531161; XM_005274676; XM_006724818; XM_011531160; NM_005362 |
| INS | 3630 | NM_001185098; NM_001185097; NM_000207; NM_001291897 |
| NKX6-1 | 4825 | NM_006168 |
| HINT1 | 3094 | NR_134495; NM_005340; NR_073488; NR_024610; NR_134494; NR_024611 |
| GRIN2D | 2906 | XM_011526872; NM_000836 |
| FCN3 | 8547 | NM_173452; NM_003665 |
| MGLL | 11343 | XM_017005665; NM_001256585; NM_001388313; NM_001388318; NM_001388317; XM_011512383; NM_001003794; XM_017005663; XM_024453334; NM_001388312; NM_001388315; NM_007283; XM_011512382; NM_001388314; NM_001388316 |
| FMO2 | 2327 | NM_001460; NR_160266; XR_921761; NM_001365900; XR_001737072; NM_001301347 |
| PCSK2 | 5126 | NM_002594; NM_001201529; NM_001201528 |
| MYL2 | 4633 | NM_000432 |
| SIM1 | 6492 | XM_011536072; NM_001374769; NM_005068 |
| EFNA3 | 1944 | NM_004952 |
| MT1M | 4499 | NM_176870 |
| CST4 | 1472 | NM_001899 |
| P2RY14 | 9934 | XM_011513340; NM_001081455; XM_005247922; NM_014879; XM_017007583; XM_005247923 |
| MMP14 | 4323 | NM_004995 |
| CDH19 | 28513 | XM_011525931.3; XM_017025711.2; XM_011525932.1 |
| COL10A1 | 1300 | XM_011535432; NM_000493; XM_011535433; XM_017010248; XM_006715333 |
| ETV4 | 2118 | NM_001261437; NM_001261439; NM_001986; NM_001369368; NM_001079675; NM_001261438; XM_024450644; NM_001369366; NM_001369367 |
| SIX1 | 6495 | XM_017021602; NM_005982 |
| ABCA12 | 26154 | XM_011510951; NR_103740; NM_173076; NM_015657 |
| BARX2 | 8538 | XM_011543043; NM_003658; XM_011543044 |
| CRISP2 | 7180 | XM_011514841; XM_011514842; XR_002956303; NM_001142417; NM_001261822; NM_003296; XM_011514843; XR_926302; XM_005249350; XM_005249352; XM_005249349; XM_005249353; XR_002956302; XM_005249351; NM_001142435; XM_005249356; XR_002956301; NM_001142407; XR_002956300; XR_926303; NM_001142408 |

-continued

| Gene | NCBI Gene ID | NCBI Accession Number(s) |
|---|---|---|
| IGFBP3 | 3486 | NM_000598; NM_001013398 |
| CA7 | 766 | NM_001365337; XM_011523312; NM_001014435; NM_005182 |
| PPEF1 | 5475 | NM_001377996; NM_001377994; NM_001389623; NM_001377986; NM_006240; NM_152224; NM_152226; NM_152225; NM_001378381; NM_001389624; NM_152223; NM_001377993; NM_001378382; XM_017029612; NM_001389621; NM_001377995; NM_001389620 |
| | | Clear_Cell_Renal_Cell_Carcinoma |
| NKX2-4 | 644524 | NM_033176 |
| LCN2 | 3934 | NM_005564 |
| HGFAC | 3083 | NM_001297439; NM_001528 |
| TNNI3 | 7137 | NM_000363 |
| NMRK2 | 27231 | NM_001289117; NM_001375468; NM_001375469; NM_170678; NM_001375467; NM_014446; XM_006722725; NR_110316 |
| NKAIN3 | 286183 | XM_017013359; XM_011517511; XM_017013360; XM_017013361; NM_001039769; NR_130764; NR_027378; XM_011517512; NM_173688; NM_001304533 |
| ARHGAP40 | 343578 | NM_001164431 |
| KRT7 | 3855 | XM_017019294; XR_001748700; NM_005556; XM_011538325; XR_001748699 |
| CST4 | 1472 | NM_001899 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| DNTT | 1791 | NM_004088; NM_001017520 |
| LRRN4 | 164312 | XM_011529183; NM_152611 |
| NPBWR1 | 2831 | NM_005285 |
| CLDN3 | 1365 | NM_001306 |
| CXCL11 | 6373 | NM_001302123; NM_005409 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| HTR1F | 3355 | NM_001322208; XM_005264751; NM_000866; NM_001322210; NM_001322209; XM_011533664 |
| IFNG | 3458 | NM_000619 |
| GRIN2A | 2903 | XM_017023172; NM_001134407; XM_011522461; NM_001134408; NM_000833; XM_011522458; XM_017023173 |
| REN | 5972 | NM_000537 |
| HILPDA | 29923 | NM_013332; NM_001098786 |
| EGLN3 | 112399 | NM_001308103; NM_022073 |
| C14orf180 | 400258 | XM_005267638; NM_001286399; NM_001286400; XM_011536764; NM_001008404 |
| CIB4 | 130106 | XM_024452692; NM_001029881; XM_017003329; XM_017003331; XM_011532514; XM_017003330 |
| CTAGE9 | 643854 | NM_001145659 |
| IGFBP1 | 3484 | NM_000596; NM_001013029 |
| GDF6 | 392255 | NM_001001557 |
| APOB | 338 | NM_000384 |
| PCSK6 | 5046 | NM_001291309; NM_138322; NM_138325; NM_138320; NM_138324; NM_138319; NM_138321; NM_002570; NM_138323 |
| LOX | 4015 | NM_001317073; NM_001178102; NM_002317 |
| DAZ2 | 57055 | NM_001388495; NM_001389303; NM_001005785; NM_001388494; NM_001005786; NM_001388493; NM_020363 |
| DAZ4 | 57135 | XM_011531509; NM_020420; NM_001388484; NM_001005375; XM_011531510 |
| | | Papillary_Renal_Cell_Carcinoma |
| FABP7 | 2173 | NM_001319039; NM_001319041; NM_001319042; NM_001446 |
| KLK15 | 55554 | XM_011527088; XR_001753713; NM_001277081; NM_017509; NM_138563; XM_011527085; XM_011527087; XM_011527089; NM_023006; XM_006723265; NM_138564; XM_017026943; NM_001277082; NR_102274 |
| NDUFA4L2 | 56901 | NM_001394961; NM_001394960; NM_020142 |
| KISS1R | 84634 | NM_032551; XM_017027382 |
| EBF2 | 64641 | NM_022659 |
| FGG | 2266 | NM_000509; NM_021870 |
| MCHR1 | 2847 | NM_005297 |
| STAP1 | 26228 | NM_001317769; NM_012108; XM_017008018 |
| CP | 1356 | XM_006713500; XM_006713501; XM_017005735; XM_017005734; XM_006713499; XM_011512435; XR_427361; NM_000096; NR_046371 |
| DAZ1 | 1617 | XM_011531482; NM_004081; XM_011531483; NM_001388496 |
| LOX | 4015 | NM_001317073; NM_001178102; NM_002317 |
| IGFBP1 | 3484 | NM_000596; NM_001013029 |
| RGS5 | 8490 | NM_003617; NM_001195303; NM_001254748; NM_001254749 |
| REN | 5972 | NM_000537 |

-continued

| Gene | NCBI Gene ID | NCBI Accession Number(s) |
|---|---|---|
| FBN3 | 84467 | NM_032447; XM_017027374; XM_017027376; NM_001321431; XM_017027372; XM_017027373; XM_017027378; XM_017027375; XM_017027377; XM_017027379 |
| PTPRN | 5798 | NM_002846; NM_001199764; NM_001199763 |
| APOB | 338 | NM_000384 |
| GRIK3 | 2899 | NM_000831 |
| APLN | 8862 | NM_017413 |
| CA9 | 768 | XR_428428; NM_001216; XR_001746374 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| UBTFL1 | 642623 | NM_001143975 |
| SPARCL1 | 8404 | NM_001291976; NM_004684; NM_001291977; NM_001128310 |
| SLCO1C1 | 53919 | XR_001748769; XR_001748771; NM_001145946; XM_017019486; NM_001145945; XM_011520703; XR_001748768; XR_001748770; XM_005253394; XM_011520711; XM_024449024; XM_017019487; NM_017435; XM_005253396; NM_001145944; XM_024449025; XM_017019489; XM_011520704; XM_017019490 |
| CIB4 | 130106 | XM_024452692; NM_001029881; XM_017003329; XM_017003331; XM_011532514; XM_017003330 |
| TUBA3E | 112714 | NM_207312 |
| COX412 | 84701 | XM_005260580; XM_005260581; NM_032609; XM_005260579 |
| ERP27 | 121506 | NM_152321; NM_001300784 |
| CREB3L3 | 84699 | NM_001271997; NM_032607; NM_001271995; NM_001271996 |
| BAALC | 79870 | XR_001745601; NM_001024372; NM_001364874; NM_024812 |
| MEOX2 | 4223 | NM_005924 |
| CSPG4 | 1464 | NM_001897 |
| GRIN2A | 2903 | XM_017023172; NM_001134407; XM_011522461; NM_001134408; NM_000833; XM_011522458; XM_017023173 |
| LHX9 | 56956 | NM_001014434; NM_020204; XM_005245350; XM_011509781; XM_017001849; NM_001370213 |
| GABRQ | 55879 | NM_018558; XM_011531184 |
| AVPRIA | 552 | NM_000706 |
| COL25A1 | 84570 | XM_011532334; NM_001256074; XM_011532358; NM_032518; NM_198721; XM_011532333; XM_011532356; XM_017008736; XM_017008737; NR_045756; XM_011532338; XM_017008735; XM_011532335; XM_011532355 |
| ASB5 | 140458 | XM_005262759; XM_011531617; NM_080874; XM_011531616 |
| ADAMTSL1 | 92949 | XM_017015311; NM_052866; XM_011518063; XM_011518067; XM_017015313; NM_001040272; XM_011518064; XM_011518068; NM_139238; XM_017015310; XM_011518070; XM_017015312; XM_017015314; NM_139264 |
| FHL5 | 9457 | NM_001170807; NM_001322466; NM_001322467; NM_020482 |
| DEFB132 | 400830 | NM_207469 |
| CTAGE9 | 643854 | NM_001145659 |
| OPN4 | 94233 | NM_001030015; XM_017016955; XM_017016956; XM_017016957; NM_033282 |
| CXCL11 | 6373 | NM_001302123; NM_005409 |
| ACAN | 176 | XM_011521313; XM_011521314; NM_001135; NM_001369268; NM_013227 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ADGRL4 | 64123 | NM_022159 |
| SMOC1 | 64093 | NM_001034852; NM_022137; XM_005267996; XM_005267995 |
| SLC38A8 | 146167 | NM_001080442; XM_017022946 |
| DNAAF3 | 352909 | NM_001256716; NM_001256714; NM_001256715; NM_001031802; NM_178837 |
| IGFBP6 | 3489 | NM_002178 |
| SLC47A2 | 146802 | NM_001099646; XM_017024221; XM_017024225; XM_017024222; XM_017024224; XM_017024226; XR_001752432; XM_017024223; NR_135624; NM_001256663; NM_152908; NR_135625; XR_001752433 |
| SFN | 2810 | NM_006142 |
| CPNE4 | 131034 | XM_017005695; NM_130808; XM_017005694; NM_001388327; XM_024453338; XM_011512408; XM_024453339; NM_001388326; NM_153429; XM_017005696; XM_024453340; NM_001289112 |
| CST6 | 10395 | NM_001316668; NM_182643; XM_005273374; NM_001348081; NM_001348083; NM_001348084; NM_001164271; NM_006094; NM_024767; NM_001348082 |
| CLDN3 | 1365 | NM_001306 |
| PIGR | 5284 | XM_011509629; NM_002644 |
| CPLX2 | 10814 | XM_005265798; XM_005265799; XM_017008964; NM_032282; NM_001008220; NM_006650; XM_011534419 |
| LRRN4 | 164312 | XM_011529183; NM_152611 |
| WFDC5 | 149708 | NM_001395506; NM_145652; XM_011528601; XM_011528602 |
| NPBWR1 | 2831 | NM_005285 |
| PRKCG | 5582 | NM_002739; NM_001316329 |
| ARHGAP40 | 343578 | NM_001164431 |
| KRT23 | 25984 | NM_001282433; XM_005257200; XM_011524595; NM_015515; NM_173213 |
| HS3ST4 | 9951 | NM_006040 |
| SPAG6 | 9576 | NM_001253855; XM_005252646; XM_005252645; NM_172242; NM_001253854; NM_012443 |

-continued

| Gene | NCBI Gene ID | NCBI Accession Number(s) |
|---|---|---|
| HGFAC | 3083 | NM_001297439; NM_001528 |
| CNTN6 | 27255 | NM_001289081; NM_001349352; NM_001349356; XM_017006174; NM_001349361; XM_011533591; NM_001349358; NM_014461; NM_001289080; NM_001349353; NM_001349359; XM_011533590; NM_001349350; NM_001349357; NM_001349354; XR_940415; NM_001349351; NM_001349355; NM_001349360; XM_017006171; XM_017006172; XM_017006177; NM_001349362 |
| LCN2 | 3934 | NM_005564 |
| AKR1B10 | 57016 | XR_927491; XM_011516416; XM_011516417; NM_020299 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| NKX2-4 | 644524 | NM_033176 |
| | | Chromophobe_Renal_Cell_Carcinoma |
| REG1A | 5967 | NM_002909 |
| PADI3 | 51702 | NM_016233; XM_011541571; XM_017001463; XM_011541572 |
| MUC12 | 10071 | NM_001164462 |
| AVPR1B | 553 | NM_000707 |
| CTSE | 1510 | XM_011509245; NM_001910; NM_148964; XM_011509244; NM_001317331 |
| KRT6A | 3853 | NM_005554 |
| KRT6B | 3854 | NM_005555 |
| SLC17A2 | 10246 | XM_006714951; XM_017010160; XM_006714949; XM_006714950; NM_001286123; NM_005835; XM_017010159; NM_001286125 |
| HAVCR1 | 26762 | XM_017009339; XM_024446021; XM_024446023; XM_024446020; XM_024446024; NM_001308156; XM_024446019; XM_011534515; NM_001173393; NM_012206; NM_001099414; XM_024446022 |
| KRT6C | 286887 | NM_173086 |
| TMEM196 | 256130 | NM_001366626; NM_001366628; XM_017011929; NM_001366627; NM_152774; NM_001363562; XM_017011928; NM_001366625 |
| CDH6 | 1004 | NM_004932; NM_001362435; XM_017008910; XM_011513921; XR_001741972 |
| PSORS1C2 | 170680 | NM_014069 |
| LYZL1 | 84569 | XR_428650; XM_017016791; NM_032517; XM_005252627 |
| KRT33B | 3884 | NM_002279 |
| C4orf51 | 646603 | XM_024454188; XR_002959750; XR_002959751; XR_002959755; XR_002959756; XM_024454189; XR_002959749; XR_002959752; NM_001080531; XM_024454190; XR_002959748; XR_002959746; XR_002959747; XR_002959753; XR_002959754 |
| PSG5 | 5673 | NM_001130014; XM_011527132; NM_002781; XM_017027003 |
| UMODL1 | 89766 | XM_017028508; NM_001199527; XM_017028507; NM_001004416; NM_001199528; NM_173568; XM_011529797 |
| DEFB132 | 400830 | NM_207469 |
| PIP | 5304 | NM_002652 |
| DBX1 | 120237 | NM_001029865 |
| SLC6A2 | 6530 | XM_011523295; XM_011523297; XR_933403; XM_011523299; XM_011523300; NM_001172502; NM_001043; NM_001172501; XM_006721263; XM_011523298; NM_001172504; XM_011523296 |
| SPSB4 | 92369 | XM_017007509; XR_924215; XR_924216; NM_080862 |
| ATP6V.D2 | 245972 | NM_152565 |
| RGS8 | 85397 | XM_011510089; XM_017002634; NM_001387848; XM_017002631; NM_001387849; NM_001369564; NM_001387847; XM_017002632; NM_001102450; NM_033345; XM_011510090; XM_011510091 |
| FOXI1 | 2299 | XR_941092; NM_012188; NM_144769 |
| CLEC2L | 154790 | XM_017011770; NM_001353368; NM_001080511 |
| AMTN | 401138 | NM_001286731; NM_212557 |
| | | Glioblastoma |
| TCEAL2 | 140597 | NM_080390 |
| RBP1 | 5947 | NM_002899; NM_001130992; NM_001130993; NM_001365940 |
| CBLN1 | 869 | NM_004352 |
| FBXO17 | 115290 | NR_104026; NM_148169; NM_024907 |
| CLEC2B | 9976 | NM_005127 |
| ATOH8 | 84913 | XM_006712122; XM_011533139; XR_939732; XR_001739003; NM_032827; XR_939733; XR_939731 |
| TSTD1 | 100131187 | NM_001113207; NM_001113205; NM_001113206 |
| SNAP91 | 9892 | XM_017011576; XM_024446600; NM_001376676; NM_001376683; NM_001376689; NM_001376690; NM_001376698; NM_001376700; NM_001376710; NM_001376715; NM_001376739; NR_164846; XM_005248770; XM_006715615; XM_011536276; XM_017011575; XM_017011579; XM_017011580; XM_024446599; NR_026669; NM_001256717; NM_001376677; NM_001376687; NM_001376701; NM_001376706; NM_001376713; NM_001376716; NM_001376723; NM_001376736; XM_017011558; XM_017011564; XM_017011566; XM_017011570; NM_001376675; NM_001256718; NM_001376680; NM_001376688; NM_001376694; NM_001376707; NM_001376708; NM_001376711; NM_001376740; XM_017011567; XM_017011590; NM_001376678; NM_001376691; NM_001376705; NM_001376738; NR_164843; XM_011536266; XM_011536269; |

-continued

| Gene | NCBI Gene ID | NCBI Accession Number(s) |
|---|---|---|
| | | XM_011536271; XM_011536275; XM_017011562; XM_017011571; XM_017011574; XM_017011582; XM_017011583; XM_017011584; NM_001242792; NM_001363677; NM_001376686; NM_001376712; NM_001376719; NM_001376721; NM_001376731; NM_001376741; XM_011536273; XM_017011559; XM_017011565; XM_017011581; XM_017011585; XM_017011587; XM_017011589; NM_001242794; NM_001376679; NM_001376695; NM_001376696; NM_001376697; NM_001376702; NM_001376709; NM_001376717; NM_001376728; NR_164844; XM_017011569; XM_017011572; XM_017011573; XM_017011577; XM_017011586; NM_001242793; NM_001376681; NM_001376684; NM_001376685; NM_001376692; NM_001376693; NM_001376699; NM_001376703; NM_001376704; NM_001376714; NM_001376720; NM_001376726; NM_001376734; NM_001376737; NM_001376742; NM_014841; NR_164845; XM_011536265; XM_017011557; XM_017011560; NM_001376682; NM_001376718; NM_001376733; NM_001376735 |
| SNX22 | 79856 | NM_024798; XM_005254677; XM_017022581; NR_073534 |
| NDC80 | 10403 | NM_006101 |
| MEOX2 | 4223 | NM_005924 |
| LUZP2 | 338645 | NM_001252008; XM_017017648; XR_930864; NM_001252010; XM_011520056; XM_017017649; NM_001009909 |
| SUSD5 | 26032 | XM_005265034; XM_017006137; NM_015551 |
| ASF1B | 55723 | NM_018154 |
| CARD16 | 114769 | NM_001394580; NM_052889; XM_011542583; NM_001017534 |
| SH3GL2 | 6456 | NM_003026; XR_001746364; XM_011518005 |
| KLRC2 | 3822 | NM_002260 |
| AURKA | 6790 | NM_001323304; NM_001323303; NM_198435; NM_198437; XM_024451974; NM_198433; NM_198434; NM_198436; XM_017028034; XM_017028035; NM_001323305; NM_003600 |
| TNFAIP6 | 7130 | NM_007115 |
| FUT9 | 10690 | XM_011535383; XM_011535385; XM_017010188; NM_006581; XM_017010190 |
| TUBA1C | 84790 | NM_001303114; NM_032704; NM_001303116; NM_001303117; NM_001303115 |
| HDAC4 | 9759 | XM_011512219; XM_011512225; NM_001378415; XM_011512218; XM_017005394; XM_006712879; XM_011512224; XM_017005395; NM_001378416; NM_006037; XM_011512223; XM_011512227; NM_001378414; XM_011512220; XM_011512222; XM_011512230; XM_024453257; XM_011512217; XM_011512226; NM_001378417; XM_006712877; XM_006712880 |
| OPHN1 | 4983 | XM_006724653; XM_011530961; XM_005262270; XM_017029555; NM_002547 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| CRTAC1 | 55118 | NM_018058; XM_017016367; XM_005269938; XM_011539917; NM_001206528; XM_017016366 |
| SLC22A18 | 5002 | NM_002555; NM_183233; XM_011520142; NM_001315501; XM_011520141; NM_001315502 |
| SSTR1 | 6751 | NM_001049 |
| HMX1 | 3166 | NM_018942; NM_001306142 |
| GDF15 | 9518 | XM_024451789; NM_004864 |
| NALCN | 259232 | XM_017020537; XM_011521067; XM_011521069; NM_001350748; NM_052867; NM_001350751; NM_001350749; XM_017020536; XM_024449336; NM_001350750 |
| GABRG1 | 2565 | NM_173536; XM_017007990 |
| PHYHIPL | 84457 | XM_017016783; XM_017016782; XM_011540275; XM_011540276; NM_032439; NM_001143774 |
| TAGLN2 | 8407 | NM_003564; NM_001277223; NM_001277224 |
| PPM1L | 151742 | NM_001317911; NM_001317912; NR_134243; XM_011512440; NM_139245 |
| OCIAD2 | 132299 | NM_001014446; NM_152398; NM_001286773; NR_104589; NM_001286774 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| PDPN | 10630 | NM_001006625; NM_198389; NM_001385053; NM_001006624; XM_006710295; NM_006474; NM_013317; XM_024451404 |
| TOM1L1 | 10040 | XM_017024002; XR_002957936; NM_001321173; NM_001321175; NM_001321174; XR_243612; NM_001321176; NM_005486; XR_001752397 |
| NTNG2 | 84628 | XM_011519105; XM_011519099; XM_011519094; XM_011519097; XM_011519098; NM_032536; XM_011519096; XM_011519100; XM_011519108; XM_011519112; XM_011519104; XM_011519113; XM_017015213; XM_011519102; XM_011519106; XM_011519107; XM_017015216; XM_011519110; XM_017015212; XM_017015215; XM_006717304; XM_011519103; XM_011519109; XM_017015214 |
| PKIB | 5570 | XM_011535937; NM_181795; XM_011535930; XM_011535931; XM_011535935; XM_011535936; NM_001270393; NM_032471; XM_011535932; NM_001270395; XM_011535933; NM_001270394; NM_181794 |

-continued

| Gene | NCBI Gene ID | NCBI Accession Number(s) |
|---|---|---|
| SHISA7 | 729956 | NM_001145176; NM_175908 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| REPS2 | 9185 | XM_011545605; XM_024452479; XM_011545604; XM_005274625; XM_011545603; XM_005274626; XM_011545607; XM_024452478; XM_017029955; XM_017029956; NM_001080975; NM_004726; XM_017029958; XR_001755742; XM_011545606; XM_011545609; XM_017029957 |
| ATP6V1G2 | 534 | NM_130463; NM_138282; NM_001204078 |
| DIRAS3 | 9077 | NM_004675 |
| SOX8 | 30812 | NM_014587 |
| FCGBP | 8857 | NM_003890 |
| TIMP1 | 7076 | NM_003254; XM_017029766 |
| CSDC2 | 27254 | NM_014460 |
| DDIT4L | 115265 | NM_145244 |
| LGALS3 | 3958 | NM_001357678; NR_003225; NM_002306; NM_001177388 |
| G0S2 | 50486 | NM_015714 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| | | Astrocytoma |
| RBP1 | 5947 | NM_002899; NM_001130992; NM_001130993; NM_001365940 |
| FBXO17 | 115290 | NR_104026; NM_148169; NM_024907 |
| HLF | 3131 | NM_002126; XM_011524705; XR_002957996; NM_001330375; XM_005257269 |
| CNTN3 | 5067 | XM_017006508; NM_020872; NM_001393376; XM_017006509; XM_011533768 |
| TMEM158 | 25907 | NM_015444 |
| CACNG2 | 10369 | XM_017028531; NM_006078; NM_001379051; NR_166440 |
| IRX2 | 153572 | NM_033267; XR_001742016; XM_024454379; NM_001134222; XM_011513979 |
| MEOX2 | 4223 | NM_005924 |
| LSP1 | 4046 | NM_001242932; NM_001013255; NM_001289005; NM_001013254; NM_002339; NM_001013253 |
| LUZP2 | 338645 | NM_001252008; XM_017017648; XR_930864; NM_001252010; XM_011520056; XM_017017649; NM_001009909 |
| ASF1B | 55723 | NM_018154 |
| LYZ | 4069 | NM_000239 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| CTSC | 1075 | NM_001114173; NM_148170; NM_001814 |
| GABBR1 | 2550 | XM_011514455; XM_006715047; XM_024446392; NM_001319053; NM_001470; XM_011514453; XR_001743302; NM_021903; XM_005248982; NM_021904; NM_021905; XR_001743303 |
| PBK | 55872 | NM_018492; NM_001278945; NM_001363040 |
| TUBA1C | 84790 | NM_001303114; NM_032704; NM_001303116; NM_001303117; NM_001303115 |
| PYGL | 5836 | NM_002863; NM_001163940 |
| MARCH4 | 57574 | NM_020814 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| RASL10A | 10633 | XM_011529821; NM_001007279; XM_011529822; XM_011529823; NM_006477 |
| UBE2T | 29089 | NM_001310326; NM_014176 |
| SSTR1 | 6751 | NM_001049 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| PHYHIPL | 84457 | XM_017016783; XM_017016782; XM_011540275; XM_011540276; NM_032439; NM_001143774 |

-continued

| Gene | NCBI Gene ID | NCBI Accession Number(s) |
|---|---|---|
| PPM1L | 151742 | NM_001317911; NM_001317912; NR_134243; XM_011512440; NM_139245 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| STOX1 | 219736 | NM_001130162; NM_001130161; NM_001130160; NM_152709; XM_011539454; NM_001130159 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FKBP11 | 51303 | NM_001143782; NM_016594; NM_001143781 |
| GPX7 | 2882 | NM_015696 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| CLIC1 | 1192 | NM_001288; NM_001287593; NM_001287594 |
| ATP6V1G2 | 534 | NM_130463; NM_138282; NM_001204078 |
| RIMS2 | 9699 | XM_017014008; XM_017014028; XM_024447342; NM_001100117; NM_001348487; NM_001348496; NM_001348503; XM_005251106; XM_017014014; XM_017014019; XM_017014027; XM_024447344; XM_024447345; NM_001348489; NM_001348491; NM_001348505; NM_001348508; NM_001348509; XM_006716698; XM_017014021; NM_014677; XM_017014010; XM_017014022; XM_024447343; NM_001348499; NM_001395653; NM_001395654; XM_011517398; XM_017014009; XM_017014011; XM_017014016; XM_017014024; NM_001282881; NM_001348490; NM_001348497; NM_001348495; NM_001348498; NR_145710; XM_011517395; XM_017014007; NM_001282882; NM_001348484; NM_001348492; NM_001348494; NM_001348500; NM_001348501; NM_001348502; NM_001348504; XM_005251107; XM_017014012; XM_017014015; XM_017014034; XM_024447347; NM_001348488; NM_001348506; NR_145711; XM_017014006; XM_017014017; XM_017014023; XM_017014036; XM_024447346; NM_001348485; NM_001348486; NM_001348493; NM_001348507; NM_001395652 |
| TJP2 | 9414 | XM_011519206; NM_001369871; NM_001369872; XM_011519208; XM_011519209; NM_001369870; NM_004817; XM_011519207; NM_001369874; NM_001170630; NM_001369875; XM_011519204; NM_001170415; NM_001170416; NM_001170414; NM_001369873; NM_201629 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| RGS9 | 8787 | NM_001081955; NM_003835; NM_001165933 |
| FCGBP | 8857 | NM_003890 |
| APOC4-APOC2 | 100533990 | NR_037932 |
| TIMP1 | 7076 | NM_003254; XM_017029766 |
| NTSR2 | 23620 | NM_012344; XM_005246156; XM_006711877; XM_006711876; XM_017003738 |
| CA12 | 771 | NM_001218; NR_135511; NM_206925; NM_001293642 |
| JPH3 | 57338 | NM_001271604; NR_073379; NM_001271605; NM_020655 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| DDIT4L | 115265 | NM_145244 |
| RARRES2 | 5919 | XM_017012491; NM_002889 |
| MDK | 4192 | NM_001012334; XM_011520116; XM_017017764; NM_001270550; NM_001270551; NM_001012333; NM_001270552; NM_002391; NR_073039 |
| FPR1 | 2357 | NM_002029; NM_001193306 |
| CD58 | 965 | XM_017002869; NM_001779; NM_001144822; NR_026665 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |

-continued

| Gene | NCBI Gene ID | NCBI Accession Number(s) |
|---|---|---|
| | | Oligodendroglioma |
| ZNF488 | 118738 | NM_153034; XM_006717617; XM_024447789; XM_017015643; NM_001346932; NM_001346933; NM_001346934; XM_011539244; NM_001346936; NM_001346935 |
| RBP1 | 5947 | NM_002899; NM_001130992; NM_001130993; NM_001365940 |
| WNT7B | 7477 | XM_011530366; NM_058238 |
| SLC7A14 | 57709 | NM_020949; NM_175917 |
| HLF | 3131 | NM_002126; XM_011524705; XR_002957996; NM_001330375; XM_005257269 |
| CACNG2 | 10369 | XM_017028531; NM_006078; NM_001379051; NR_166440 |
| SVOP | 55530 | NM_018711 |
| KCNK3 | 3777 | NM_002246; XM_005264293 |
| SUSD5 | 26032 | XM_005265034; XM_017006137; NM_015551 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| HRH3 | 11255 | NM_007232; XM_005260266; XM_017027623 |
| MYH7 | 4625 | XM_017021340; NM_000257 |
| MYT1 | 4661 | NM_004535 |
| GPR158 | 57512 | NM_020752; XM_017016452; XR_930512 |
| PYGL | 5836 | NM_002863; NM_001163940 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| VSIG4 | 11326 | NM_007268; NM_001184830; NM_001184831; XM_017029251; NM_001100431; NM_001257403 |
| UPP1 | 7378 | XM_011515513; XM_011515512; NM_001287426; NR_109837; XM_005249838; NM_001287428; NM_001287430; XM_011515515; NM_001362774; NM_001287429; NM_181597; XM_011515514; NM_003364 |
| PDZD4 | 57595 | NM_001303513; NM_001303512; NM_001303516; NM_001303515; NM_001303514; NM_032512 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| KCNJ9 | 3765 | NM_004983 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| STOX1 | 219736 | NM_001130162; NM_001130161; NM_001130160; NM_152709; XM_011539454; NM_001130159 |
| BATF3 | 55509 | XR_921869; XR_001737289; XM_017001683; NM_018664 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FAM222A | 84915 | XM_006719654; XM_017020055; NM_032829; XM_024449229 |
| SCRT1 | 83482 | NM_031309; XM_024447291 |
| GPX7 | 2882 | NM_015696 |
| DIRAS3 | 9077 | NM_004675 |
| ATP6V1G2 | 534 | NM_130463; NM_138282; NM_001204078 |
| EIF3CL | 728689 | NM_001317857; NM_001099661; XM_017023620; XM_017023621; NM_001317856 |
| FCGR2A | 2212 | NM_001136219; NM_021642; XM_011509287; XM_024454040; XM_017000664; XM_017000665; XM_017000663; XR_001737042; XM_017000666; XM_011509290; XM_011509291; XM_024454041; NM_001375296; NM_001375297 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| PRLHR | 2834 | NM_004248 |
| FCGBP | 8857 | NM_003890 |
| KLHDC8A | 55220 | NM_001271863; NM_001271865; XM_024448121; NM_018203; NM_001271864 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| BRINP1 | 1620 | NM_014618 |
| CD58 | 965 | XM_017002869; NM_001779; NM_001144822; NR_026665 |
| RDH5 | 5959 | NM_001199771; NM_002905 |

-continued

| Gene | NCBI Gene ID | NCBI Accession Number(s) |
|---|---|---|
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| EPN2 | 22905 | NM_001102664; NM_148921; NM_014964 |
| | | Basal_Breast_Cancer |
| CDH6 | 1004 | NM_004932; NM_001362435; XM_017008910; XM_011513921; XR_001741972 |
| ESR1 | 2099 | XM_011535545; XM_017010378; XM_017010382; XR_001743223; XR_002956266; NM_001385568; XM_017010381; NM_001122741; NM_001328100; NM_001385570; XM_006715375; XM_017010383; NM_001385572; XM_011535547; XM_011535549; XM_017010377; NM_001385571; XM_017010380; NM_000125; NM_001122740; NM_001122742; NM_001291230; NM_001291241; XM_011535543; XM_017010379; NM_001385569 |
| SULT1C3 | 442038 | NM_001008743; XM_017004155; NM_001320878; XM_017004153; XM_017004154 |
| WNT10A | 80326 | XM_011511930; XM_011511929; NM_025216 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| CTCFL | 140690 | NM_001269041; NM_001269055; NM_001386993; NR_170377; NM_001269054; NM_080618; NR_072975; NM_001269042; NM_001269044; NM_001269047; NM_001269043; NM_001269045; NM_001269051; NM_001386994; NM_001269040; NM_001269048; NM_001269050; NM_001386997; NM_001269052; NM_001386995; NM_001386996; NM_001269046; NM_001269049 |
| UGT2B11 | 10720 | XM_011531550; XM_017007660; NM_001073 |
| KRT16 | 3868 | NM_005557 |
| TFF3 | 7033 | NM_003226 |
| CCL19 | 6363 | NM_006274 |
| DNALI1 | 7802 | NM_003462 |
| EN1 | 2019 | NM_001426 |
| S100B | 6285 | NM_006272; XM_017028424 |
| BPI | 671 | XM_024451972; NM_001725 |
| SERHL2 | 253190 | NM_014509; NR_104301; XR_244363; NR_104300; NM_001284334; XM_024452196; XM_017028739; XM_024452197; XR_001755198 |
| UBXN10 | 127733 | XM_005245742; NM_152376; XM_011540699 |
| SLC44A4 | 80736 | NM_001178045; NM_001178044; NM_025257 |
| ROPN1 | 54763 | NM_001394218; NM_001317775; NR_133919; NR_133916; NR_133917; NM_001394219; NM_001317774; NM_001394217; NM_017578; NR_133918; NR_172091 |
| SPINK8 | 646424 | NM_001080525; XM_017007046; XM_024453712; XR_002959568 |
| CT83 | 203413 | NM_001017978 |
| ACTL8 | 81569 | NM_030812; XM_011542212 |
| MIA | 8190 | NM_006533; NM_001202553 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| GABRP | 2568 | XM_005265872; NM_001291985; NM_014211; XM_024446012 |
| TMEM246 | 84302 | NM_001303107; NM_001303108; NM_032342; XM_024447701; NM_001371233 |
| C1orf64 | 149563 | NM_178840 |
| SPON1 | 10418 | NM_006108 |
| KRT6B | 3854 | NM_005555 |
| KRT79 | 338785 | NM_175834 |
| KCNT1 | 57582 | XM_017014932; XM_017014933; NM_020822; XM_017014931; XM_011518877; XM_011518878; XM_011518879; NM_001272003; XM_011518880; XM_011518881; XM_024447617; XM_024447618 |
| SHC4 | 399694 | NM_203349; XM_005254375 |
| HORMAD1 | 84072 | NM_001199829; NM_032132; XM_011510054 |
| LRRC31 | 79782 | XM_011513158; XM_011513159; XM_011513160; NM_001277127; NM_001277128; NM_024727; XM_017007204 |
| NRTN | 4902 | NM_004558 |
| C1QL4 | 338761 | NM_001008223; XM_011538270 |
| TLX1 | 3195 | NM_001195517; XM_011539744; XM_011539745; NM_005521 |
| CLDN8 | 9073 | NM_199328; NM_012132 |
| MGAM2 | 93432 | NM_001293626; NM_001008748; XM_011516692; XM_011516694; NR_003715; XM_024446997; XM_011516693; XR_927547; NR_003717 |
| ST6GALNAC1 | 55808 | NM_018414; XR_002958047; XM_017024842; XM_017024844; NM_001289107; XM_011524995; XM_011524996; XM_017024843; XR_001752559; NR_110309 |
| GFRA3 | 2676 | NM_001496 |
| MAGEA3 | 4102 | XM_011531161; XM_005274676; XM_006724818; XM_011531160; NM_005362 |
| PRR15 | 222171 | NM_001329997; NM_001329996; NM_175887; XM_011515198; XM_011515199 |
| IGF2 | 3481 | NM_001291862; NM_001291861; NM_000612; NM_001007139; NM_001127598 |
| LY6D | 8581 | NM_003695 |
| TPSG1 | 25823 | NM_012467; XM_011522447; XM_011522446 |
| TAT | 6898 | NM_000353 |
| SMOC1 | 64093 | NM_001034852; NM_022137; XM_005267996; XM_005267995 |
| MT1H | 4496 | NM_005951 |
| REEP6 | 92840 | NM_138393; NM_001329556 |

-continued

| Gene | NCBI Gene ID | NCBI Accession Number(s) |
|---|---|---|
| FOXA1 | 3169 | NM_004496; XM_017021246 |
| IL12RB2 | 3595 | NR_047584; XM_011541384; XM_005270827; XM_006710617; NM_001374259; XM_011541383; NM_001258215; NM_001258216; XM_017001204; NM_001258214; NM_001319233; XM_005270828; XM_017001203; NM_001559; NR_047583 |
| ART3 | 419 | NM_001377183; XM_017008210; XM_024454058; NM_001377173; NM_001377180; XM_024454052; XM_024454061; XM_024454062; XR_002959732; NM_001130017; NM_001377181; XM_017008208; XR_002959733; NM_001377174; XM_024454051; NM_001377179; XM_024454050; XM_024454053; XM_024454054; XM_024454059; XM_024454063; NM_001377177; NM_001377178; NM_001377182; XM_024454056; NM_001179; NM_001377176; XM_017008206; NM_001130016; NM_001377175; NM_001377184; NM_001377185 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| LOR | 4014 | NM_000427; XM_024447049 |
| GRIK1 | 2897 | NM_001320618; NM_001320616; XM_005260944; NM_001320630; NM_000830; XR_001754829; NM_001320621; NM_001393425; NM_001393426; NM_001330993; NM_001330994; NM_001393424; NM_175611 |
| FDCSP | 260436 | NM_152997 |
| PKP1 | 5317 | NM_000299; NM_001005337 |
| C6orf15 | 29113 | NM_014070 |
| AADAC | 13 | NM_001086; XM_005247104 |
| PGR | 5241 | XM_011542869; NM_001271161; NR_073142; NM_000926; XM_006718858; NM_001202474; NM_001271162; NR_073141; NR_073143 |
| ORM2 | 5005 | NM_000608 |
| ROPN1B | 152015 | XM_006713513; NM_001012337; XM_005247138; NM_001308313 |
| TBC1D9 | 23158 | NM_015130 |
| NPAS3 | 64067 | XM_005267991; NM_001394989; XM_011537069; XM_017021582; XM_017021584; XM_017021585; XM_017021587; NM_022123; XM_011537067; XM_011537071; NM_001165893; NM_001394988; NM_173159; XM_017021583; XM_017021586; XM_017021588; XM_005267992; NM_001164749 |
| HMGCS2 | 3158 | NM_001166107; XM_011541313; NM_005518 |
| NPR1 | 4881 | XM_017001374; XM_005245218; NM_000906 |
| ELOVL2 | 54898 | NM_017770; XM_011514717; XM_011514716; XM_017010985 |
| CA12 | 771 | NM_001218; NR_135511; NM_206925; NM_001293642 |
| CT62 | 196993 | NR_168259; NM_001102658; NR_168260 |
| | | Non_Basal_Breast_Cancer |
| CHODL | 140578 | XM_017028273; NM_001204174; NM_024944; XM_011529453; NM_001204176; NM_001204175; NM_001204177; XM_011529457; NM_001204178 |
| MSLN | 10232 | NM_001177355; NM_005823; NM_013404 |
| CST4 | 1472 | NM_001899 |
| CEACAM6 | 4680 | NM_002483; XM_011526990 |
| OVGP1 | 5016 | NM_002557 |
| FOLR1 | 2348 | NM_000802; NM_016729; NM_016730; NM_016725; NM_016724 |
| LRRTM1 | 347730 | NM_178839; XM_017003987; XM_017003986 |
| TTC6 | 319089 | XM_017021257; XM_011537431; XM_017021254; XM_024449560; XM_011537430; XM_011537432; XR_943762; NM_001310135; XM_017021256; NM_001368142; XM_017021255; XR_001750287; NM_001007795 |
| SPRR2A | 6700 | NM_005988 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| WNT10A | 80326 | XM_011511930; XM_011511929; NM_025216 |
| PKHD1L1 | 93035 | XM_017013970; XM_017013969; XM_011517371; XM_017013971; XM_017013972; XM_017013973; XM_017013974; NM_177531 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| SMYD1 | 150572 | NM_198274; NM_001330364 |
| DACT2 | 168002 | NM_001286350; NM_001286351; XM_011535507; NM_214462; NR_104425 |
| AKR7A3 | 22977 | XM_017000714; NM_012067; XM_011541046; XR_001737055 |
| HPX | 3263 | NM_000613 |
| S100B | 6285 | NM_006272; XM_017028424 |
| MAL | 4118 | NM_022438; NM_002371; NM_022440; NM_022439 |
| D4S234E | 27065 | NM_001287763; NM_001287764; NM_001040101; NR_167932; NM_001382227; NM_001382228; NR_167933; NM_014392 |
| SLC44A4 | 80736 | NM_001178045; NM_001178044; NM_025257 |
| SPINK8 | 646424 | NM_001080525; XM_017007046; XM_024453712; XR_002959568 |
| THSD4 | 79875 | NM_024817; NM_001286429; XM_017022584; NM_001394532; XM_017022586; XM_011522044; XM_017022585; XM_011522043; XM_017022582; XM_017022583 |
| TBX5 | 6910 | NM_181486; NM_080717; NM_000192; XM_017019912; NM_080718 |
| NEK10 | 152110 | XM_006712998; XM_011533415; XM_017005765; XR_001740034; NM_001394966; XM_017005768; NM_001394968; XM_024453374; NM_001031741; |

-continued

| Gene | NCBI Gene ID | NCBI Accession Number(s) |
|---|---|---|
| | | NM_001394965; NM_001394967; NM_001394971; XM_006712997; XM_006713002; XM_011533413; XM_011533414; NM_001394970; NM_001394964; NM_001394969; XM_006712999; XM_017005762; XM_017005764; NM_001394963; NM_199347; XM_017005763; XM_017005773; XM_024453373; NM_001304384; XM_006713001; XM_017005774; NM_152534 |
| TFAP2B | 7021 | XM_017011235; XM_017011233; NM_003221; XM_011514837; XM_017011234 |
| MB | 4151 | NM_001382810; NM_001382809; NM_203378; NM_001362846; NM_001382812; NM_203377; NM_001382811; NM_005368; NM_001382813 |
| OCA2 | 4948 | XM_017022264; XM_017022257; XM_017022258; XM_017022262; XM_017022255; XM_017022263; XM_011521640; XM_017022256; XM_017022261; XR_001751294; NM_001300984; XM_017022265; NM_000275; XM_017022259; XM_017022260 |
| CCNA1 | 8900 | XM_011535294; XM_011535296; NM_001111047; XM_011535295; NM_001111046; NM_003914; NM_001111045 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| GABRP | 2568 | XM_005265872; NM_001291985; NM_014211; XM_024446012 |
| C1orf64 | 149563 | NM_178840 |
| MSMB | 4477 | NM_138634; NM_002443 |
| PSAT1 | 29968 | NM_021154; NM_058179 |
| CPA2 | 1358 | NM_001869 |
| SLC30A8 | 169026 | XM_024447083; NM_001172813; NM_001172814; NM_001172815; NM_001172811; NM_173851 |
| NRTN | 4902 | NM_004558 |
| ZG16B | 124220 | NM_145252 |
| ABCC11 | 85320 | XM_017023802; NM_001370496; NM_032583; XM_017023798; XM_011523397; XM_017023797; XM_017023800; XM_017023803; XM_017023799; XM_017023801; NM_001370497; XM_011523398; NM_145186; XM_024450475; XR_001752012; NM_033151 |
| MGAM2 | 93432 | NM_001293626; NM_001008748; XM_011516692; XM_011516694; NR_003715; XM_024446997; XM_011516693; XR_927547; NR_003717 |
| KCNH1 | 3756 | NM_172362; XM_017001246; NM_002238 |
| CALB2 | 794 | NM_007088; XR_002957842; NM_001740; NR_027910; NM_007087 |
| PGC | 5225 | NM_002630; NM_001166424 |
| FSIP1 | 161835 | XM_011521307; XM_017021972; XM_011521309; NM_152597; XM_011521305; NM_001324338; XM_011521311; XM_011521306 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| HMP19 | 51617 | NM_015980 |
| PRR15 | 222171 | NM_001329997; NM_001329996; NM_175887; XM_011515198; XM_011515199 |
| SERTM1 | 400120 | NM_203451 |
| MMP3 | 4314 | NM_002422 |
| POU3F3 | 5455 | NM_006236 |
| PCK1 | 5105 | NM_002591; XM_024451888 |
| CHAD | 1101 | XM_011524214; NM_001267 |
| SLITRK6 | 84189 | NM_032229 |
| SOX10 | 6663 | NM_006941 |
| TAT | 6898 | NM_000353 |
| PIP | 5304 | NM_002652 |
| F2RL2 | 2151 | NM_001256566; NM_004101 |
| MT1H | 4496 | NM_005951 |
| FOXA1 | 3169 | NM_004496; XM_017021246 |
| KRT15 | 3866 | XM_017024614; XM_011524784; NM_002275 |
| TF | 7018 | NM_001063; NM_001354703; NM_001354704 |
| FAM196A | 642938 | XM_017016537; XM_017016538; XM_017016539; XM_005252694; XM_017016540; XM_017016541; XM_017016542; XM_017016543; NM_001039762 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| PRSS33 | 260429 | NM_001385462; NM_001385463; NM_001385464; NM_152891; NR_169625 |
| SCX | 642658 | XM_006716616; NM_001080514; NM_001008271 |
| WNT6 | 7475 | NM_006522 |
| SIAH3 | 283514 | NM_198849 |
| ROPN1B | 152015 | XM_006713513; NM_001012337; XM_005247138; NM_001308313 |
| HOXC13 | 3229 | NM_017410 |
| NPR1 | 4881 | XM_017001374; XM_005245218; NM_000906 |
| RASGEF1C | 255426 | NM_175062; NM_001031799 |
| LEMD1 | 93273 | XM_011510163; XM_011510162; XM_011510165; NM_001199052; XM_011510160; XM_011510161; XM_011510164; NR_037583; NM_001001552; NM_001199050; NM_001199051 |
| PRSS50 | 29122 | NM_013270 |

-continued

| Gene | NCBI Gene ID | NCBI Accession Number(s) |
|---|---|---|
| | | Squamous_Cell_Carcinoma_of_the_Head_and_Neck |
| IGFBP6 | 3489 | NM_002178 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| SCGB1A1 | 7356 | NM_003357 |
| FGG | 2266 | NM_000509; NM_021870 |
| PLIN1 | 5346 | NM_002666; XM_005254934; NM_001145311 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| MMP13 | 4322 | NM_002427 |
| MYL1 | 4632 | NM_079422; NM_079420 |
| FCN3 | 8547 | NM_173452; NM_003665 |
| IRX4 | 50805 | NM_016358; NM_001278633; NM_001278632; NM_001278635; NM_001278634 |
| BPIFA1 | 51297 | NM_130852; NM_001243193; NM_016583 |
| PAX1 | 5075 | NM_006192; NM_001257096 |
| ADH1B | 125 | NM_001286650; NM_000668 |
| C4BPA | 722 | XM_005273252; NM_000715; XM_005273251 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| F2RL2 | 2151 | NM_001256566; NM_004101 |
| HOXA13 | 3209 | NM_000522 |
| PCSK2 | 5126 | NM_002594; NM_001201529; NM_001201528 |
| BMP8A | 353500 | XM_017001198; XM_006710616; XM_011541381; XM_011541382; XR_946642; XR_946640; XR_946641; NM_181809 |
| TBX4 | 9496 | XM_011525490; XM_011525491; NM_001321120; XM_011525495; NM_018488 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PGC | 5225 | NM_002630; NM_001166424 |
| RPE65 | 6121 | XM_017002027; NM_000329 |
| GSTM5 | 2949 | NM_000851; XM_005270785; XM_005270784 |
| MYH7 | 4625 | XM_017021340; NM_000257 |
| ATP1A2 | 477 | NM_000702 |
| KIF18B | 146909 | XM_011524389; NM_001264573; NM_001265577; XM_011524386; NM_001080443; XM_011524390; XM_011524388; XM_011524385; XM_011524387; XM_011524391 |
| SCARA5 | 286133 | NM_173833 |
| FILIP1 | 27145 | NR_110608; XM_011535756; NM_001289987; NM_001300866; XM_005248713; NM_015687; XM_005248715 |
| DCD | 117159 | NM_001300854; NM_053283 |
| SLURP1 | 57152 | NM_020427 |
| DLX1 | 1745 | NM_178120; NM_001038493 |
| WT1 | 7490 | NM_000378; NR_160306; NM_001367854; NM_001198551; NM_001198552; NM_024424; NM_024426; NM_024425 |
| TCF21 | 6943 | NM_003206; NM_198392 |
| EN1 | 2019 | NM_001426 |
| KRT14 | 3861 | NM_000526 |
| RPS4Y1 | 6192 | NM_001008 |
| TBX5 | 6910 | NM_181486; NM_080717; NM_000192; XM_017019912; NM_080718 |
| CDKN2A | 1029 | XR_929159; XM_011517676; XM_011517675; NM_001363763; NM_001195132; NM_058195; NM_000077; NM_058196; NM_058197; XM_005251343 |
| ALDH1A2 | 8854 | NM_001206897; NM_170697; NM_170696; NM_003888 |
| CFTR | 1080 | NM_000492 |
| AMY1A | 276 | NM_004038; NM_001008221 |
| NAV3 | 89795 | XM_017020172; NM_001024383; NM_014903; XM_011538944 |
| HPN | 3249 | NM_002151; NM_182983; XM_017026732; NM_001384133; XM_017026731; NM_001375441 |
| MKRN3 | 7681 | NM_005664 |
| SCN7A | 6332 | NM_002976; XM_006712680; XM_006712682; XM_011511615; XM_017004667; NR_045628 |
| ACTC1 | 70 | NM_005159 |
| MYOG | 4656 | NM_002479 |
| HOXB5 | 3215 | NM_002147 |
| PKMYT1 | 9088 | NM_001258451; NM_182687; NM_001258450; XM_011522735; XM_024450490; NM_004203; XM_011522734; XM_011522736 |

-continued

| Gene | NCBI Gene ID | NCBI Accession Number(s) |
|---|---|---|
| HJURP | 55355 | XM_011511437; NM_001282962; NM_001282963; NM_018410 |
| HP | 3240 | NM_001126102; NM_005143; NM_001318138 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| DLL3 | 10683 | NM_016941; NM_203486 |
| CYP2B6 | 1555 | NM_000767 |
| SNTN | 132203 | NM_001080537; NM_001348756 |
| CRNN | 49860 | NM_016190 |
| HOXB8 | 3218 | NM_024016; XM_005257286; XM_017024564 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| IBSP | 3381 | NM_004967 |
| C7 | 730 | NM_000587 |
| COL10A1 | 1300 | XM_011535432; NM_000493; XM_011535433; XM_017010248; XM_006715333 |
| AJAP1 | 55966 | XM_011541787; NM_001042478; NM_018836; XM_011541786 |
| ADIPOQ | 9370 | NM_004797; NM_001177800 |
| | | Squamous_Cell_Lung_Carcinoma |
| C20orf85 | 128602 | NM_178456 |
| KLK10 | 5655 | XM_006723289; XM_005259061; NM_002776; NM_145888; NM_001077500; XM_017026993; XM_006723287; XM_005259062 |
| ACTC1 | 70 | NM_005159 |
| IGFBP6 | 3489 | NM_002178 |
| ADH1B | 125 | NM_001286650; NM_000668 |
| B4GALNT4 | 338707 | XM_017017654; XR_001747858; NM_178537 |
| C4BPA | 722 | XM_005273252; NM_000715; XM_005273251 |
| CENPM | 79019 | NM_001110215; NM_001304372; NM_024053; XM_011530368; NM_001304371; NM_001002876; NM_001304370; NM_001304373 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MYOG | 4656 | NM_002479 |
| CACNG1 | 786 | NM_000727 |
| HOXB5 | 3215 | NM_002147 |
| FABP4 | 2167 | NM_001442 |
| MMP11 | 4320 | NM_005940; NR_133013 |
| SCGB1A1 | 7356 | NM_003357 |
| RSPO1 | 284654 | XM_006710583; NM_001242909; NM_001242908; NM_001242910; NM_173640; NM_001038633 |
| LRRN4CL | 221091 | NM_203422 |
| ENDOU | 8909 | NM_001172439; NM_006025; NM_001172440 |
| MMP12 | 4321 | NM_002426 |
| GSTA1 | 2938 | XM_005249034; NM_001319059; NM_145740 |
| TNXB | 7148 | NM_001365276; NM_019105; NM_032470 |
| HP | 3240 | NM_001126102; NM_005143; NM_001318138 |
| KLHL41 | 10324 | NM_006063 |
| NEFL | 4747 | NM_006158 |
| TBX5 | 6910 | NM_181486; NM_080717; NM_000192; XM_017019912; NM_080718 |
| NKX2-1 | 7080 | NM_001079668; NM_003317 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| VPREB3 | 29802 | NM_013378 |
| TBX4 | 9496 | XM_011525490; XM_011525491; NM_001321120; XM_011525495; NM_018488 |
| TROAP | 10024 | XM_011537723; NM_005480; XR_944445; XM_011537724; XR_944446; NM_001100620; XM_006719181; NM_001278324 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PAK7 | 57144 | XM_017027960; XM_017027964; XM_017027962; XM_017027963; XM_017027965; NM_177990; XM_017027961; NM_020341 |
| CASQ2 | 845 | NM_001232 |
| PGC | 5225 | NM_002630; NM_001166424 |
| AMY1C | 278 | NM_001346780; XM_017001058; NM_001008219 |
| COX6A2 | 1339 | NM_005205 |
| MUC7 | 4589 | NM_001145006; NM_152291; NM_001145007 |
| CLEC2L | 154790 | XM_017011770; NM_001353368; NM_001080511 |
| POU6F2 | 11281 | NM_007252; NM_001370959; NM_001166018 |
| ZNF280B | 140883 | XR_002958666; NM_080764; XM_011529897; XR_002958668; XR_002958667; NR_130642; NR_130643 |
| CRNN | 49860 | NM_016190 |
| SNTN | 132203 | NM_001080537; NM_001348756 |

-continued

| Gene | NCBI Gene ID | NCBI Accession Number(s) |
|---|---|---|
| GREM2 | 64388 | XM_005273226; XM_011544249; NM_022469 |
| OGN | 4969 | NM_033014; NM_014057; NM_024416 |
| MYH7 | 4625 | XM_017021340; NM_000257 |
| KIF18B | 146909 | XM_011524389; NM_001264573; NM_001265577; XM_011524386; NM_001080443; XM_011524390; XM_011524388; XM_011524385; XM_011524387; XM_011524391 |
| PLA2G4F | 255189 | NM_213600; XR_931785; NR_033151; XR_931786 |
| LGSN | 51557 | XM_017010931; XM_017010929; XM_011535889; XM_011535892; NM_016571; XM_017010930; NM_001143940 |
| AHSG | 197 | NM_001354571; NM_001354572; NM_001622; NM_001354573 |
| UBE2C | 11065 | NM_001281742; NM_001281741; NM_181802; NM_181803; NR_104036; NR_104037; NM_007019; NM_181800; NM_181801; NM_181799 |
| DES | 1674 | NM_001927; NM_001382708; NM_001382710; NM_001382713; NM_001382709; NM_001382711; NM_001382712 |
| RNF223 | 401934 | NM_001205252 |
| MYL1 | 4632 | NM_079422; NM_079420 |
| C1orf116 | 79098 | XM_011509973; NM_001083924; XM_005273259; XM_006711530; NM_023938 |
| BMP5 | 653 | XM_011514817; NM_001329756; XM_024446524; NM_001329754; NM_021073 |
| SCARA5 | 286133 | NM_173833 |
| FCN3 | 8547 | NM_173452; NM_003665 |
| HPN | 3249 | NM_002151; NM_182983; XM_017026732; NM_001384133; XM_017026731; NM_001375441 |
| LOR | 4014 | NM_000427; XM_024447049 |
| LDB3 | 11155 | NM_001171610; NM_001368064; NM_007078; NM_001080115; NM_001080114; NM_001368068; NM_001080116; NM_001171611; NM_001368067; NM_001368063; NM_001368065; NM_001368066 |
| DHRS7C | 201140 | NM_001220493; NM_001105571 |
| CRISP3 | 10321 | NM_001368123; NM_006061; NM_001190986 |
| LY6D | 8581 | NM_003695 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| CNTNAP2 | 26047 | XM_017011950; NM_014141 |
| ANLN | 54443 | XM_017012355; NM_018685; NM_001284302; XM_006715746; XM_017012354; XM_017012356; NM_001284301; XM_006715747 |
| DCD | 117159 | NM_001300854; NM_053283 |
| C7 | 730 | NM_000587 |
| THBS4 | 7060 | XR_002956176; XM_017009798; NM_001306214; NM_003248; NM_001306213; XM_017009799; NM_001306212 |
| GPR87 | 53836 | NM_023915 |
| MYOT | 9499 | XM_017010060; XM_017010061; NM_001300911; NM_001135940; XM_017010062; NM_006790 |
| USP43 | 124739 | XM_011523640; XM_011523642; XM_011523641; XM_017024161; XM_017024160; XM_017024159; XM_011523639; NM_001267576; NM_153210; XM_017024162 |
| EMX1 | 2016 | XM_011532697; NM_001040404; NM_004097; XM_005264203 |
| SLURP1 | 57152 | NM_020427 |
| BPIFA1 | 51297 | NM_130852; NM_001243193; NM_016583 |
| KLK5 | 25818 | NM_001077492; XM_011526702; NM_001077491; XM_011526703; NM_012427 |
| GYLTL1B | 120071 | XM_011519891; NM_001300721; NM_001300722; XM_011519888; XM_006718141; XM_011519890; XM_006718140; XM_011519893; NM_152312; XM_005252787; XM_011519886; XM_011519889; XM_011519892; XM_017017173 |
| HAND2 | 9464 | NM_021973 |
| MYOC | 4653 | NM_000261 |
| MCEMP1 | 199675 | NM_174918 |
| DCC | 1630 | XM_011525843; XM_011525844; XM_017025570; NM_005215; XM_017025568; XM_017025569 |
| LRRC26 | 389816 | NM_001013653 |
| KLK13 | 26085 | NM_015596; NR_145464; NM_001348178; NR_145466; NR_145465; XR_935788; NR_145463; NM_001348177; NR_145467 |
| WT1 | 7490 | NM_000378; NR_160306; NM_001367854; NM_001198551; NM_001198552; NM_024424; NM_024426; NM_024425 |
| KRT4 | 3851 | NM_002272 |
| COL10A1 | 1300 | XM_011535432; NM_000493; XM_011535433; XM_017010248; XM_006715333 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| SGCG | 6445 | NM_000231; NM_001378245; NM_001378244; NM_001378246 |
| SCN7A | 6332 | NM_002976; XM_006712680; XM_006712682; XM_011511615; XM_017004667; NR_045628 |
| FEZF1 | 389549 | NM_001024613; XM_011516202; NM_001160264; XM_005250337 |
| SLCO4C1 | 353189 | XM_011543372; XM_011543370; NM_180991 |
| AJAP1 | 55966 | XM_011541787; NM_001042478; NM_018836; XM_011541786 |
| AMN | 81693 | XM_024449714; XM_011537203; NM_030943; XM_011537202 |

-continued

| Gene | NCBI Gene ID | NCBI Accession Number(s) |
|---|---|---|
| SDR16C5 | 195814 | NM_001318049; NM_001318050; NM_138969; XM_011517479 |
| AQP4 | 361 | NM_001317387; NM_001364287; NM_001364286; NM_001317384; XM_011525942; NM_001650; NM_001364289; NM_004028 |
| CPNE7 | 27132 | NM_153636; XM_017023139; XM_011523000; XM_017023138; XM_017023140; XM_017023141; XM_011523001; NM_014427 |
| TCF21 | 6943 | NM_003206; NM_198392 |
| PTGER3 | 5733 | XM_011541810; NM_198718; NM_000957; NM_198712; NM_198713; NM_198720; NM_198714; NM_198719; NM_198717; NM_001126044; NM_198715; NR_028292; XR_946714; NM_198716; NR_028293; NR_028294 |
| | | Cervical_Squamous_Cell_Carcinoma |
| SALL1 | 6299 | NM_001127892; NM_002968 |
| MEOX2 | 4223 | NM_005924 |
| BCHE | 590 | NR_137636; NM_000055; NR_137635 |
| SYCP2 | 10388 | XM_011528488; XM_011528487; XM_011528493; XM_017027590; XM_011528490; XM_017027586; XM_017027591; NM_014258; XM_011528489; XM_017027589; XM_017027587; XM_017027588; XM_017027592 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| OLFM4 | 10562 | NM_006418 |
| SYNGR3 | 9143 | NM_004209 |
| SLC6A15 | 55117 | XM_011538525; NM_018057; NM_001146335; NM_182767 |
| ADAMTS20 | 80070 | XM_011538754; XM_017019979; NM_025003; NM_175851 |
| FA2H | 79152 | XM_011523319; XM_011523317; NM_024306 |
| PGR | 5241 | XM_011542869; NM_001271161; NR_073142; NM_000926; XM_006718858; NM_001202474; NM_001271162; NR_073141; NR_073143 |
| FOXL2 | 668 | NM_023067 |
| KRT81 | 3887 | NM_002281 |
| HOXA13 | 3209 | NM_000522 |
| KRT36 | 8689 | NM_003771 |
| KRT83 | 3889 | NM_002282 |
| RPS4Y1 | 6192 | NM_001008 |
| TBX5 | 6910 | NM_181486; NM_080717; NM_000192; XM_017019912; NM_080718 |
| ASF1B | 55723 | NM_018154 |
| E2F8 | 79733 | NM_001256372; XM_011520367; NM_001256371; NM_024680; XR_930907 |
| CASP14 | 23581 | NM_012114; XM_011527861 |
| MYOCD | 93649 | XM_005256863; NM_001378306; NM_001146312; NM_153604; NM_001146313; XM_017025342 |
| KIF4A | 24137 | NM_012310 |
| PDLIM3 | 27295 | NM_001114107; XR_938723; NM_001257963; XR_938724; NM_001257962; NR_047562; NM_014476; XR_001741206 |
| PAGE2B | 389860 | XM_017029513; XM_011530785; XM_011530786; XM_011530787; NM_001015038 |
| RPE65 | 6121 | XM_017002027; NM_000329 |
| POU6F2 | 11281 | NM_007252; NM_001370959; NM_001166018 |
| CDKN2A | 1029 | XR_929159; XM_011517676; XM_011517675; NM_001363763; NM_001195132; NM_058195; NM_000077; NM_058196; NM_058197; XM_005251343 |
| HOXB8 | 3218 | NM_024016; XM_005257286; XM_017024564 |
| ALDH1A2 | 8854 | NM_001206897; NM_170697; NM_170696; NM_003888 |
| HTR2B | 3357 | XM_005246520; NM_000867; XM_006712482; NM_001320758 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| NAV3 | 89795 | XM_017020172; NM_001024383; NM_014903; XM_011538944 |
| BARX1 | 56033 | NM_021570 |
| OR2B6 | 26212 | NM_012367 |
| SEMA3D | 223117 | XM_011515961; NM_152754; NM_001384901; NM_001384902; NM_001384900; NM_001384903 |
| DYNC1I1 | 1780 | NM_001135556; NM_004411; NM_001278422; NM_001278421; NM_001135557 |
| NAP1L2 | 4674 | NM_021963 |
| MYL1 | 4632 | NM_079422; NM_079420 |
| ANO1 | 55107 | XM_006718602; XM_006718605; XM_011545124; XM_011545129; XM_017017956; XM_006718604; NM_001378095; NM_001378096; XM_011545123; XM_011545127; XM_011545131; NM_001378097; NM_018043; NR_030691; NM_001378092; XM_011545126; NM_001378093; NM_001378094 |
| HOXA11 | 3207 | NM_005523 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; |

-continued

| Gene | NCBI Gene ID | NCBI Accession Number(s) |
|---|---|---|
| | | NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| EIF1AY | 9086 | NM_004681; NM_001278612 |
| RBFOX3 | 146713 | XM_017024209; XM_017024211; XM_024450595; NM_001385812; NM_001385840; NM_001385844; NM_001385847; XM_011524366; XM_017024208; NM_001385805; NM_001385807; NM_001385843; NM_001385845; NM_001025448; NM_001082575; NM_001385804; NM_001385808; NM_001385813; NM_001385836; NM_001385817; NM_001385819; NM_001385823; NM_001385826; NM_001385827; NM_001385828; NM_001385829; NM_001385831; NM_001385833; NM_001385842; XM_011524360; XM_024450593; XM_024450596; NM_001350453; NM_001385809; NM_001385832; NM_001385834; NM_001385838; NM_001039904; XM_011524367; XM_024450592; NM_001385811; NM_001385824; NM_001385835; NM_001385837; NM_001385846; NM_001350451; NM_001385806; NM_001385810; NM_001385820; NM_001385825; NM_001385830; NM_001385839; NM_001385841; NM_001385814; NM_001385815; NM_001385816; NM_001385818; NM_001385821; NM_001385822 |
| RDM1 | 201299 | NM_001163124; NR_027996; NR_027999; XM_011524509; NM_001163122; NM_001163130; NM_001163121; NM_001163125; NR_027998; NM_001163120; NM_001034836; NM_001330194; NM_145654; NR_027997; NR_028000 |
| SCARA5 | 286133 | NM_173833 |
| KCNS1 | 3787 | XM_017027846; NM_002251; NM_001322799 |
| PIANP | 196500 | NM_001244014; NM_153685; NM_001244015; XM_011520926 |
| C1orf106 | 55765 | XM_011509754; XM_011509755; NM_001367289; NM_001367290; XM_011509756; NM_001142569; NM_018265 |
| HOXA10 | 3206 | NR_037939; NM_153715; NM_018951 |
| AIM1L | 55057 | NM_017977; XM_011541672; XM_011541673; XR_001737260; NM_001039775; XR_946681; XM_005245918 |
| LEFTY2 | 7044 | NM_003240; NM_001172425; XM_011544266 |
| IRX5 | 10265 | NM_005853; XM_011522809; NM_001252197 |
| TRDN | 10345 | NM_001251987; NM_001256020; NM_001256021; NM_006073; NM_001256022 |
| CNTNAP2 | 26047 | XM_017011950; NM_014141 |
| FOXA1 | 3169 | NM_004496; XM_017021246 |
| ADGRD1 | 283383 | NM_198827; XM_005253566; XM_011538204; XM_011538208; XM_011538212; NM_001330497; XM_011538205; XM_011538206; XM_011538207; XM_011538209; XM_011538210; XM_011538211 |
| PENK | 5179 | NM_006211; NM_001135690 |
| AKR1C2 | 1646 | NM_001354; NM_001321027; NM_001135241; NM_205845; NM_001393392 |
| MKRN3 | 7681 | NM_005664 |
| NMU | 10874 | NM_001292046; XM_011534368; XM_011534367; NM_001292045; NM_006681; NR_120489 |
| DIAPH3 | 81624 | XM_011535258; XM_006719876; XM_024449422; NM_001258367; NM_001258370; XR_941672; XM_011535265; XR_002957479; XR_002957480; NM_001258366; XM_017020789; XR_002957478; NM_001042517; NM_001258368; XM_011535263; XR_001749694; XR_002957477; NM_001258369; NM_030932 |
| MUC2 | 4583 | NM_002457 |
| ZIC5 | 85416 | NM_033132; NR_146224; NR_146225 |
| MYLPF | 29895 | NM_001324458; NM_013292; NM_001324459 |
| POLQ | 10721 | NM_199420; NM_006596 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| SMC1B | 27127 | NM_148674; XM_011530145; XR_244368; XM_011530144; NM_001291501 |
| WT1 | 7490 | NM_000378; NR_160306; NM_001367854; NM_001198551; NM_001198552; NM_024424; NM_024426; NM_024425 |
| EPHA7 | 2045 | NM_001288630; NM_001376467; NM_001288629; XM_017010366; NM_001376466; NM_001376471; NM_004440; XR_001743218; NM_001376465; NM_001376470; NR_164810; NM_001376468; NM_001376469 |
| TCF23 | 150921 | NM_175769; XM_005264159 |
| | | Colorectal_Adenocarcinoma |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |

-continued

| Gene | NCBI Gene ID | NCBI Accession Number(s) |
|---|---|---|
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |

-continued

| Gene | NCBI Gene ID | NCBI Accession Number(s) |
|---|---|---|
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |

-continued

| Gene | NCBI Gene ID | NCBI Accession Number(s) |
|---|---|---|
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |

-continued

| Gene | NCBI Gene ID | NCBI Accession Number(s) |
|---|---|---|
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |

-continued

| Gene | NCBI Gene ID | NCBI Accession Number(s) |
|---|---|---|
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456 |
| | | Stomach_Adenocarcinoma |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |

-continued

| Gene | NCBI Gene ID | NCBI Accession Number(s) |
|---|---|---|
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; |

-continued

| Gene | NCBI Gene ID | NCBI Accession Number(s) |
|---|---|---|
| | | NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; |

-continued

| Gene | NCBI Gene ID | NCBI Accession Number(s) |
|---|---|---|
| | | NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; |

-continued

| Gene | NCBI Gene ID | NCBI Accession Number(s) |
|---|---|---|
| | | NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |

-continued

| Gene | NCBI Gene ID | NCBI Accession Number(s) |
|---|---|---|
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456. |

17. At least one non-transitory computer-readable storage medium storing processor-executable instructions that, when executed by at least one computer hardware processor, cause the at least one computer hardware processor to perform a method for identifying at least one candidate molecular category for a biological sample obtained from a subject, the method comprising:

(a) obtaining RNA expression levels previously obtained by processing the biological sample obtained from the subject, wherein the RNA expression levels comprise:
  (i) first RNA expression levels for a first set of genes, the first set of genes corresponding to a parent molecular category in a hierarchy of molecular categories and comprising at least ten genes listed for the parent molecular category in Table 3, and
  (ii) second RNA expression levels for a second set of genes different from the first set of genes, the second set of genes corresponding to a child molecular category, which is a child of the parent molecular category in the hierarchy of molecular categories, and comprising at least ten genes listed for the child molecular category in Table 3;

(b) processing the RNA expression levels to obtain RNA features comprising first ranks for the first set of genes and second ranks for the second set of genes, the processing comprising:
  (i) ranking the first set of genes using the first RNA expression levels to obtain the first ranks for the first set of genes; and
  (ii) ranking the second set of genes using the second RNA expression levels to obtain the second ranks for the second set of genes;

(c) processing the RNA features using a hierarchy of RNA-based gradient-boosted decision tree classifiers corresponding to the hierarchy of molecular categories to obtain probabilities that molecular categories in the hierarchy of molecular categories are candidate molecular categories for the biological sample, the hierarchy of RNA-based gradient-boosted decision tree classifiers comprising a parent RNA-based gradient-boosted decision tree classifier corresponding to the parent molecular category, and a plurality of child RNA-based gradient-boosted decision tree classifiers corresponding to a plurality of child molecular categories including the child molecular category, the processing comprising:
  (i) providing the first ranks for the first set of genes as input to the parent RNA-based gradient-boosted decision tree classifier to obtain a first probability that the parent molecular category is a first candidate molecular category of the at least one candidate molecular category for the biological sample;
  (ii) identifying, based on the first, a respective child RNA-based gradient-boosted decision tree classifier from among the plurality of child RNA-based gradient-boosted decision tree classifiers, the identified child RNA-based gradient-boosted decision tree classifier corresponding to the child molecular category of the plurality of child molecular categories; and
  (iii) after identifying the child RNA-based gradient-boosted decision tree classifier based on the first probability, providing the second ranks for the second set of genes as input to the child RNA-based gradient-boosted decision tree classifier to obtain a second probability that the child molecular category is a second candidate molecular category for the biological sample; and (d) identifying, using the probabilities that the molecular categories in the hierarchy of molecular categories are candidate molecular categories for the biological sample, the at least one candidate molecular category for the biological sample, the identifying comprising:

(i) identifying the parent molecular category as the first candidate molecular category of the at least one candidate molecular category for the biological sample using the first probability that the parent molecular category is the first candidate molecular category; and/or (ii) identifying the child molecular category as the second candidate molecular category of the at least one candidate molecular category for the biological sample using the second probability that the child molecular category is the second candidate molecular category, wherein Table 3 is:

| Gene | NCBI Gene ID | NCBI Accession Number(s) |
|---|---|---|
| | | Gastrointestinal_Adenocarcinoma |
| TUSC3 | 7991 | XM_011544651; XM_017013861; NM_178234; NM_006765; NM_001356429 |
| ZG16 | 653808 | NM_152338; XM_011545921 |
| COLEC11 | 78989 | XM_006711897; NM_001255986; NM_001255989; NM_001255985; NM_001255982; NM_001255983; NM_001255984; NM_024027; NR_045659; XM_005263853; NM_001255987; NM_001255988; NM_199235 |
| KLF4 | 9314 | NM_004235; NM_001314052 |
| COBL | 23242 | XM_011515239; NM_015198; XM_011515236; XM_005271751; XM_011515237; NM_001287436; NM_001287438; NM_001346441; XM_011515235; XM_011515240; XM_017011898; NM_001346443; NM_001346444; XM_011515234; XM_011515241; NM_001346442; XM_005271750; XM_011515238 |
| SIX1 | 6495 | XM_017021602; NM_005982 |
| COL10A1 | 1300 | XM_011535432; NM_000493; XM_011535433; XM_017010248; XM_006715333 |
| EPHB2 | 2048 | XM_006710441; NM_001309192; NM_004442; NM_001309193; NM_017449; XM_024453895; XM_006710442 |
| CDH19 | 28513 | XM_011525931.3; XM_017025711.2; XM_011525932.1 |
| CDX1 | 1044 | NM_001804 |
| EN1 | 2019 | NM_001426 |
| CDH17 | 1015 | NM_004063; XM_011516790; NM_001144663 |
| WNT7A | 7476 | XM_011534091; NM_004625 |
| SRD5A2 | 6716 | XM_011533069; NM_000348; XM_011533072 |
| ESM1 | 11082 | NM_001135604; NM_007036 |
| PRSS50 | 29122 | NM_013270 |
| PDX1 | 3651 | NM_000209; XR_941580; XR_941578; |
| BMP8A | 353500 | XM_017001198; XM_006710616; XM_011541381; XM_011541382; XR_946642; XR_946640; XR_946641; NM_181809 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SYT12 | 91683 | XM_011545346; XM_011545347; NM_177963; XM_017018547; NM_001177880; NM_001318775; XM_017018548; XM_006718737; XM_024448766; NM_001318773 |
| CFD | 1675 | NM_001317335; NM_001928 |
| GAMT | 2593 | NM_138924; NM_000156 |
| VTCN1 | 79679 | NM_001253849; NM_024626; NR_045604; XM_017002335; NM_001253850; NR_045603; XM_011542143 |
| TMSB15A | 11013 | NM_021992 |
| SLC15A2 | 6565 | XM_006713736; XM_017007074; NM_021082; XM_005247722; NM_001145998 |
| CP | 1356 | XM_006713500; XM_006713501; XM_017005735; XM_017005734; XM_006713499; XM_011512435; XR_427361; NM_000096; NR_046371 |
| MAL | 4118 | NM_022438; NM_002371; NM_022440; NM_022439 |
| KRT2 | 3849 | NM_000423 |
| IQCA1 | 79781 | XM_017004960; NM_024726; NM_001270585; XM_011511865; XM_011511866; XM_011511864; NM_001270584; NR_073043 |
| PVRL1 | 5818 | NM_203285; NM_032767; NM_002855; NM_203286 |
| PLA2G7 | 7941 | NM_001168357; XR_001743639; XM_005249408; NM_005084; XR_002956305 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| TREM2 | 54209 | NM_001271821; NM_018965 |
| ADAP1 | 11033 | NM_001284308; NM_006869; NM_001284311; NM_001284310; NM_001284309 |
| MUC13 | 56667 | NM_033049 |
| CLDN18 | 51208 | NM_001002026; NM_016369 |
| DPT | 1805 | NM_001937 |
| PLP1 | 5354 | NM_001128834; NM_000533; NM_001305004; NM_199478 |
| CCNB1 | 891 | NM_031966 |
| GPR162 | 27239 | NM_014449; NM_019858 |
| ONECUT2 | 9480 | NM_004852 |
| SFTPD | 6441 | XM_011540087; NM_003019; XM_011540088 |
| CLDN10 | 9071 | XM_024449432; XM_017020844; NM_006984; XM_011521134; XM_017020843; NM_182848; NM_001160100 |

-continued

| Gene | NCBI Gene ID | NCBI Accession Number(s) |
|---|---|---|
| NXPH4 | 11247 | XM_017018747; NM_007224 |
| MAB21L2 | 10586 | NM_006439 |
| REG3A | 5068 | NM_138938; NM_002580; NM_138937 |
| LGALS4 | 3960 | NM_006149; XM_011526974; XM_011526973 |
| GPR35 | 2859 | NM_001195382; NM_001195381; NM_001394730; NM_005301 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| SIM2 | 6493 | XM_017028442; XR_001754891; XM_011529694; NM_005069; NM_009586 |
| TCF21 | 6943 | NM_003206; NM_198392 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| CCL11 | 6356 | NM_002986 |
| SLC34A2 | 10568 | NM_001177999; NM_006424; NM_001177998 |
| GIF | 2694 | XM_011544939; NM_005142 |
| SALL1 | 6299 | NM_001127892; NM_002968 |
| HGH1 | 51236 | NM_016458; XR_001745537 |
| KCNC3 | 3748 | NM_004977; NR_110912; NM_001372305 |
| GPA33 | 10223 | XM_017000005; NM_005814 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| FXYD2 | 486 | NM_021603; NM_001127489; NM_001680 |
| HNF4A | 3172 | XM_005260407; NM_001287182; NM_001030003; NM_178850; NM_175914; NM_001030004; NM_178849; NM_001258355; NM_001287183; NM_000457; NM_001287184 |
| GABRQ | 55879 | NM_018558; XM_011531184 |
| ABCA4 | 24 | NM_000350 |
| MMP11 | 4320 | NM_005940; NR_133013 |
| ZWINT | 11130 | XR_428692; NM_007057; NM_001005413; XM_017015605; XM_024447784; NM_032997; NM_001005414 |
| INHBA | 3624 | XM_017012175; NM_002192; XM_017012176; XM_017012174 |
| REG1A | 5967 | NM_002909 |
| TSPYL2 | 64061 | XM_006724592; XM_017029727; NM_022117; XR_001755719; XM_017029726 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| LRRC15 | 131578 | NM_130830; NM_001135057 |
| DES | 1674 | NM_001927; NM_001382708; NM_001382710; NM_001382713; NM_001382709; NM_001382711; NM_001382712 |
| INS | 3630 | NM_001185098; NM_001185097; NM_000207; NM_001291897 |
| FABP4 | 2167 | NM_001442 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| CST1 | 1469 | NM_001898 |
| TM4SF5 | 9032 | NM_003963 |
| PODXL | 5420 | NM_005397; NM_001018111 |
| CRNN | 49860 | NM_016190 |
| WISP2 | 8839 | NM_001323369; XM_017028116; NM_003881; XM_017028117; NM_001323370 |
| SST | 6750 | NM_001048 |
| LIN37 | 55957 | NR_163146; NM_019104; NM_001369780 |
| GREM1 | 26585 | NM_001368719; NM_013372; NM_001191323; NM_001191322 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| GRIN2D | 2906 | XM_011526872; NM_000836 |
| APOC1 | 341 | NM_001645; NM_001321066; NM_001379687; NM_001321065 |
| GDPD3 | 79153 | NM_024307 |
| FOXF1 | 2294 | NM_001451 |
| TGFB3 | 7043 | NM_001329938; NM_003239; NM_001329939 |
| ST3GAL5 | 8869 | NM_001354248; XM_017005208; XM_017005214; NM_001354226; XM_017005204; NM_001354233; NM_001354234; XM_017005205; XM_017005213; XR_001739019; NM_003896; NM_001354223; NM_001354227; |

-continued

| Gene | NCBI Gene ID | NCBI Accession Number(s) |
|---|---|---|
| | | NM_001354247; XM_017005206; XR_001739021; NM_001042437; NM_001354229; XM_017005202; XM_017005203; XM_017005212; XR_001739020; XM_017005209; NM_001354224; NM_001363847; NM_001354238 |
| DIRAS2 | 54769 | NM_017594 |
| GABRG3 | 2567 | XM_017022058; XM_017022060; XM_024449889; NM_033223; XM_011521430; NM_001270873; XM_011521431; XM_017022059 |
| HOXC11 | 3227 | NM_014212 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| SLCO4A1 | 28231 | XR_002958473; XR_001754251; XR_001754254; XR_001754255; XR_001754258; NM_016354; XR_001754250; XR_244116; XM_017027827; XR_001754253; XR_001754252; XR_244115; XR_936524; XM_017027826; XR_002958474; XR_001754256; XR_001754257; XM_005260203; XM_011528792; XR_001754249 |
| FABP1 | 2168 | NM_001443 |
| NFE2L3 | 9603 | NM_004289 |
| GLRB | 2743 | XR_001741207; XM_017008035; NM_000824; NM_001166060; XR_002959723; XM_017008034; NM_001166061 |
| PTH1R | 5745 | NM_001184744; XM_017006933; XM_011533968; NM_000316; XM_017006934; XM_011533967; XM_005265344; XM_017006932 |
| C2orf72 | 257407 | NM_001144994 |
| CAPN3 | 825 | NM_173087; NM_173089; NM_024344; NM_173088; NM_212465; NR_027912; NM_000070; NM_173090; NR_027911 |
| SLC2A4 | 6517 | NM_001042 |
| MLF1 | 4291 | NM_001369782; NM_001369785; NM_001378847; NM_022443; NM_001378845; NM_001378848; NM_001378851; NM_001369784; NM_001378853; NM_001378855; NM_001130156; NM_001369783; NM_001378852; NM_001130157; NM_001195432; NM_001195433; NM_001378846; NM_001378850; NM_001369781; NM_001195434 |
| FEZF2 | 55079 | NM_018008 |
| APCS | 325 | NM_001639 |
| SOX9 | 6662 | NM_000346 |
| HOXC10 | 3226 | NM_017409 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| DNAI1 | 27019 | NM_012144; NM_001281428 |
| LIPF | 8513 | NM_004190; NM_001198829; NM_001198830; NM_001198828; XM_011540311 |
| CDX2 | 1045 | XM_011534876; NM_001354700; XM_011534879; XM_011534875; XM_011534878; NM_001265 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ADH1B | 125 | NM_001286650; NM_000668 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| CHST2 | 9435 | NM_004267 |
| FGGY | 55277 | XM_017001645; XM_017001677; XM_024448207; XM_024448220; NM_001350792; NM_001350797; NM_001350798; NM_018291; XM_011541731; XM_017001671; XM_017001673; NM_001244714; NM_001350793; NM_001350794; NR_103473; XM_011541730; XM_017001649; XM_017001670; XM_017001678; XM_024448227; NM_001113411; XM_017001643; XM_011541736; XM_017001659; XM_017001662; XM_017001664; XM_024448185; XR_001737287; NM_001350791; NM_001350796; XM_017001668; XM_017001679; XR_001737285; XM_017001646; XM_017001652; XM_024448176; XR_001737286; NM_001278224; XM_017001657; XM_017001660; XR_001737284; NM_001350790; NM_001350799; XM_017001655; XM_017001656; XM_017001661; XM_017001663; XM_017001669; XM_024448196; XM_024448229; NM_001350795 |
| FERMT1 | 55612 | NM_017671; XM_024451935 |
| PRSS3 | 5646 | NM_007343; NM_001197097; NM_002771; XM_011517965; NM_001197098 |
| CCNA1 | 8900 | XM_011535294; XM_011535296; NM_001111047; XM_011535295; NM_001111046; NM_003914; NM_001111045 |
| ARL4D | 379 | XM_011524782; NM_001661 |
| LZTS1 | 11178 | XM_011544386; XM_011544384; NM_021020; NM_001362884; XM_011544385 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; |

-continued

| Gene | NCBI Gene ID | NCBI Accession Number(s) |
| --- | --- | --- |
| | | NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| KRT24 | 192666 | XM_017024299; NM_019016; XM_006721739; XM_011524460 |
| SCNN1D | 6339 | NM_001130413; NR_037668; NM_002978 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| AQP4 | 361 | NM_001317387; NM_001364287; NM_001364286; NM_001317384; XM_011525942; NM_001650; NM_001364289; NM_004028 |
| MUC2 | 4583 | NM_002457 |
| FGF23 | 8074 | NM_020638 |
| CXCL3 | 2921 | NM_002090 |
| IGFBP3 | 3486 | NM_000598; NM_001013398 |
| GABRA2 | 2555 | XM_024453964; NM_001330690; NM_001377144; NM_001377149; XM_024453966; NM_001377150; XM_011513675; NM_001114175; NM_001377155; NM_000807; NM_001377147; XM_024453967; NM_001377146; NM_001377152; NM_001286827; NM_001377153; NM_001377145; NM_001377148; NM_001377151; NM_001377154 |
| HR | 55806 | XM_006716367; NM_005144; XM_005273569; NM_018411 |
| AKR1C2 | 1646 | NM_001354; NM_001321027; NM_001135241; NM_205845; NM_001393392 |
| MYOC | 4653 | NM_000261 |
| TACR2 | 6865 | NM_001057 |
| VIP | 7432 | XM_006715562; XM_005267135; NM_003381; NM_194435 |
| PRM2 | 5620 | NM_001286358; NR_104428; NM_002762; NM_001286356; NM_001286359; NM_001286357 |
| ACADL | 33 | NM_001608; XM_005246517; XM_017003955 |
| SLC47A1 | 55244 | NM_018242 |
| CLPB | 81570 | NM_030813; XM_005274320; XM_011545289; NM_001258392; NM_001258393; NM_001258394 |
| SCNN1B | 6338 | XM_017023526; XM_011545913; XM_011545914; XM_017023525; NM_000336 |
| GLP2R | 9340 | XM_011524077; NM_004246; XM_017025340; XM_005256861; XM_017025339; XM_017025341 |
| CASR | 846 | XM_017007325; NM_000388; XM_005247837; XM_017007324; NM_001178065; XM_006713789 |
| IFI6 | 2537 | NM_002038; XM_024446207; NM_022873; NM_022872 |
| | | Pancreatic_Adenocarcinoma |
| PNLIP | 5406 | NM_000936 |
| PPY | 5539 | NM_002722; NM_001319209; XM_011524978 |
| CTRC | 11330 | XM_011540550; NM_007272 |
| CTRB2 | 440387 | NM_001025200 |
| CRP | 1401 | NM_000567; NM_001329058; NM_001382703; NM_001329057 |
| GCG | 2641 | NM_002054 |
| PNLIPRP1 | 5407 | XM_011539869; NM_001303135; NM_006229; XR_945774 |
| INS | 3630 | NM_001185098; NM_001185097; NM_000207; NM_001291897 |
| CPA1 | 1357 | NM_001868 |
| CASR | 846 | XM_017007325; NM_000388; XM_005247837; XM_017007324; NM_001178065; XM_006713789 |
| GCNT3 | 9245 | NM_004751 |
| TFF2 | 7032 | NM_005423 |
| PDX1 | 3651 | NM_000209; XR_941580; XR_941578; |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |

-continued

| Gene | NCBI Gene ID | NCBI Accession Number(s) |
|---|---|---|
| ALPPL2 | 251 | NM_031313 |
| PADI1 | 29943 | XM_017001102; XR_946617; XR_946619; NM_013358; XR_001737131; XM_011541307; XR_001737130; XM_017001103; XR_946620; XM_017001101 |
| CTSE | 1510 | XM_011509245; NM_001910; NM_148964; XM_011509244; NM_001317331 |
| FOXL1 | 2300 | NM_005250 |
| LHX2 | 9355 | NM_004789; XM_006717323 |
| POU3F3 | 5455 | NM_006236 |
| MIA | 8190 | NM_006533; NM_001202553 |
| HOXD13 | 3239 | XM_011511068; NM_000523; XM_011511069 |
| NMRK2 | 27231 | NM_001289117; NM_001375468; NM_001375469; NM_170678; NM_001375467; NM_014446; XM_006722725; NR_110316 |
| TMPRSS4 | 56649 | XM_011542901; NM_001290094; XM_005271614; NM_001173552; NM_183247; NR_110734; XM_005271613; XM_011542902; XM_011542904; XM_005271615; NM_001083947; NM_001173551; NM_019894; XM_011542903; NM_001290096 |
| HAND2 | 9464 | NM_021973 |
| IHH | 3549 | NM_002181 |
| MAGEA3 | 4102 | XM_011531161; XM_005274676; XM_006724818; XM_011531160; NM_005362 |
| KLK6 | 5653 | XM_024451611; NM_001319949; NM_001012964; NM_001319948; NM_001012965; NM_002774 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MAGEA6 | 4105 | NM_175868; NM_005363 |
| LRP2 | 4036 | XM_011511183; NM_004525; XM_011511184 |
| MYBPH | 4608 | NM_004997 |
| CR2 | 1380 | NM_001877; NM_001006658; XM_011509206 |
| GABRA3 | 2556 | NM_000808; XM_006724811 |
| MYH7 | 4625 | XM_017021340; NM_000257 |
| ENPP3 | 5169 | XR_001743464; NR_133007; NM_005021; XM_017010932; XM_011535897 |
| GABRQ | 55879 | NM_018558; XM_011531184 |
| NXPH4 | 11247 | XM_017018747; NM_007224 |
| FOXA1 | 3169 | NM_004496; XM_017021246 |
| SFTPB | 6439 | XM_005264487; NM_198843; XM_005264488; NM_000542; NM_001367281; XM_005264490 |
| DLX6 | 1750 | NM_005222 |
| CRNN | 49860 | NM_016190 |
| HOXA7 | 3204 | NM_006896 |
| NEFM | 4741 | NM_001105541; NM_005382 |
| KRT24 | 192666 | XM_017024299; NM_019016; XM_006721739; XM_011524460 |
| FCER2 | 2208 | NM_002002; NM_001220500; XM_005272462; NM_001207019 |
| CLDN3 | 1365 | NM_001306 |
| POU2F2 | 5452 | XM_017026886; XM_017026889; XM_017026895; XR_001753709; XR_001753710; NM_001393935; XM_017026885; XM_017026891; XM_017026894; XM_024451547; NM_001207026; NM_001393934; NM_001394376; NM_001394378; XM_017026884; XM_011527043; XM_017026887; XM_017026890; NM_001247994; XM_011527041; XM_024451546; NM_001207025; XM_011527042; XM_017026888; XM_017026892; NM_001393936; NM_002698; XM_017026896; NM_001394377 |
| LIPF | 8513 | NM_004190; NM_001198829; NM_001198830; NM_001198828; XM_011540311 |
| BCL11A | 53335 | NM_001365609; NM_022893; NM_138553; XM_017004335; XM_024452962; XM_024452963; XM_017004333; NM_138559; XM_011532910; XM_017004336; NM_018014; XM_011532909; NM_001363864 |
| CX3CR1 | 1524 | NM_001171174; NM_001337; NM_001171171; NM_001171172 |
| ABCA12 | 26154 | XM_011510951; NR_103740; NM_173076; NM_015657 |
| | | Breast_Cancer |
| AMN | 81693 | XM_024449714; XM_011537203; NM_030943; XM_011537202 |
| NMRK2 | 27231 | NM_001289117; NM_001375468; NM_001375469; NM_170678; NM_001375467; NM_014446; XM_006722725; NR_110316 |
| TLX2 | 3196 | NM_001534; NM_016170 |
| MYH15 | 22989 | XM_011512559; NM_014981; XM_017005922 |
| MROH7 | 374977 | NR_026782; NM_198547; NM_001039464; NM_001291332; NR_111931 |
| ERN2 | 10595 | XM_011545708; XM_011545711; XR_950727; XM_011545709; XM_011545712; NM_001308220; XM_011545713; NM_033266 |
| CSF3 | 1440 | NR_168489; NR_168491; NM_000759; NM_172220; NM_001178147; NM_172219; NR_168490; NR_033662 |
| TMEM246 | 84302 | NM_001303107; NM_001303108; NM_032342; XM_024447701; NM_001371233 |
| GCGR | 2642 | XM_011523539; XM_017024446; NM_000160; XM_006722277; XM_017024447 |
| NEFM | 4741 | NM_001105541; NM_005382 |
| SOX21 | 11166 | NM_007084 |
| PMP2 | 5375 | NM_002677; NM_001348381 |
| RGS20 | 8601 | NM_001286673; NM_001286675; NM_170587; NM_001286674; NM_003702; NR_104578; NR_104579 |
| IL13RA2 | 3598 | NM_000640 |
| GPR17 | 2840 | NM_005291; NM_001161416; NM_001161415; XM_017003833; NM_001161417 |
| B3GALT1 | 8708 | NM_020981; XM_006712819; XM_011512085 |
| MT1H | 4496 | NM_005951 |

-continued

| Gene | NCBI Gene ID | NCBI Accession Number(s) |
|---|---|---|
| GJA3 | 2700 | NM_021954; XM_011535048 |
| SCTR | 6344 | XM_005263730; XR_001738888; XR_922984; XM_017004672; XM_011511621; XM_017004673; XM_024453038; XM_017004670; XR_001738887; XR_001738889; XM_017004671; NM_002980 |
| DBH | 1621 | NM_000787 |
| OGDHL | 55753 | XM_011539946; NM_001347821; NM_001143997; NM_001347820; NM_001347823; NR_144685; XM_017016402; NM_001347819; NM_001347825; NM_018245; NR_144682; NM_001347824; NR_144683; XM_017016403; NM_001143996; NM_001347822; NM_001347826; NR_144684; NR_144686 |
| WNT7A | 7476 | XM_011534091; NM_004625 |
| RPRM | 56475 | NM_019845 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| FOXA2 | 3170 | NM_021784; NM_153675 |
| ZNF536 | 9745 | XM_011527557; XM_017027530; XM_017027533; XM_017027534; XM_017027540; XM_017027535; XM_017027531; XM_017027532; XM_017027539; XM_017027542; XM_011527555; XM_011527560; XM_017027536; NM_001352260; NM_001376110; NM_014717; XM_011527554; XM_017027527; XM_017027537; XM_017027543; XM_024451807; NM_001376111; XM_011527558; XM_017027528; XM_017027529; XM_017027538 |
| CCL16 | 6360 | NM_004590; XM_005258020 |
| SHH | 6469 | NR_132319; NM_000193; NR_132318; XM_011516480; XM_011516479; NM_001310462 |
| TAC3 | 6866 | NR_135164; NR_135166; NR_135165; NM_001006667; NM_001178054; NM_013251; NR_033654 |
| CXCL3 | 2921 | NM_002090 |
| DUSP26 | 78986 | NM_024025; NM_001305116; NM_001305115 |
| SERPIND1 | 3053 | NM_000185 |
| SLC6A13 | 6540 | XM_006719008; XM_011521012; XM_017019842; XM_017019845; XM_017019846; NM_016615; XM_017019847; NM_001190997; XM_011521013; XM_017019844; XR_001748849; XR_002957372; NM_001243392 |
| TCF21 | 6943 | NM_003206; NM_198392 |
| TYR | 7299 | XM_011542970; NM_000372 |
| DUOX2 | 50506 | NM_014080; NM_001363711 |
| SLC45A2 | 51151 | NM_001297417; NM_016180; NM_001012509 |
| MAB21L2 | 10586 | NM_006439 |
| GAS2 | 2620 | NM_001143830; NM_001391933; NM_001391935; NM_001391936; XM_011519972; NM_001391937; NM_001391934; XM_011519971; NR_147085; XM_017017532; XR_001747829; NM_001351224; XM_011519975; NM_005256; NM_177553 |
| IL1A | 3552 | NM_001371554; NM_000575 |
| SPRR2B | 6701 | NM_001388198; NM_001017418 |
| CYP2W1 | 54905 | NM_017781; XM_011515440; XM_011515441 |
| SPOCK3 | 50859 | NM_001251967; NM_001204354; NM_001204356; XM_011532018; NM_001204359; XM_017008258; NM_001040159; NM_001204358; XM_017008257; NM_001204352; NM_016950; NM_001204353; NM_001204355 |
| KCNK12 | 56660 | NM_022055 |
| HKDC1 | 80201 | NM_025130; XR_001747209; XM_011540195 |
| HNF1B | 6928 | XM_011525161; NM_001165923; NM_001304286; XM_011525163; NM_000458; XM_011525162; NM_006481; XM_011525164; XM_011525160 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| FOXE1 | 2304 | NM_004473 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| NAALAD2 | 10003 | XM_017017044; XR_001747709; XM_017017043; XR_001747707; XR_001747710; XR_001747711; NM_001300930; XR_001747708; XM_017017045; XM_017017046; NM_005467 |
| HMGA2 | 8091 | NM_001015886; NM_003483; NM_001300918; NM_003484; NM_001330190; NM_001300919 |
| FOXF1 | 2294 | NM_001451 |
| RXRG | 6258 | NM_006917; NM_001256570; NM_001256571; NR_033824 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |

-continued

| Gene | NCBI Gene ID | NCBI Accession Number(s) |
|---|---|---|
| EIF1AY | 9086 | NM_004681; NM_001278612 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| STXBP6 | 29091 | XM_017021235; NM_001351941; NM_001394415; XM_024449547; NM_001304476; NM_001351942; NM_001394413; XM_006720121; NM_001304477; NM_001394414; NM_001394417; XM_017021232; NM_014178; NM_001394410; NM_001394411; NM_001394420; XM_017021241; NM_001351943; NM_001394418; NM_001351940; NM_001394412; NM_001394416; NM_001394419 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| RPS4Y1 | 6192 | NM_001008 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| GFAP | 2670 | XM_024450691; XM_024450690; NM_001131019; XM_024450692; XM_024450693; NM_001242376; NM_002055; NM_001363846 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| PVRL3 | 25945 | XM_011512663; XM_017006126; NM_001243286; XR_924122; NM_015480; XR_002959508; XM_017006125; XM_017006124; XM_017006127; XM_017006123; NM_001243288 |
| SERPINB13 | 5275 | NM_001348267; XM_011526029; NM_001348268; NM_012397; NM_001348269; NM_001307923; NM_001348270 |
| ADH1C | 126 | NM_000669; NR_133005 |
| EYA4 | 2070 | XM_005266851; NM_004100; NM_172105; NM_001370459; NM_172104; XM_017010371; XR_001743220; NM_001301012; XM_017010369; XM_017010370; XM_017010372; XM_017010373; XR_001743219; NM_172103; NM_001301013; NM_001370458; XM_017010368; XM_017010374 |
| RGS6 | 9628 | XM_017021825; XM_017021832; XM_024449763; XR_001750613; NM_001370274; NM_001370279; NM_001370284; NM_001370291; XM_017021820; XM_024449761; XM_024449770; XM_024449774; NM_001370272; NM_001370277; NM_001370278; NM_001370292; XM_011537397; XM_017021831; XM_024449764; NM_001204421; NM_001204423; NM_001370275; NM_001370290; NM_001370293; NR_135235; XM_024449760; XM_024449776; XR_002957573; NM_001204416; NM_001204417; NM_001370271; NM_001370283; NM_001370270; NM_001370273; NM_001370281; NM_001370286; XM_017021822; XM_017021833; NM_001204422; NM_001204424; NM_001370276; NM_001370280; NM_001370287; NM_001370289; NM_001370294; XM_011537393; XM_011537407; XM_017021827; XM_017021830; XM_017021834; XM_024449759; NM_001370282; XM_017021826; XM_017021828; XM_024449768; NM_001204418; NM_001204419; NM_001204420; NM_001370288; NM_004296 |

-continued

| Gene | NCBI Gene ID | NCBI Accession Number(s) |
|---|---|---|
| ACTC1 | 70 | NM_005159 |
| PAX3 | 5077 | NM_181457; NM_000438; NM_181459; NM_181460; NM_001127366; NM_013942; NM_181461; NM_181458 |
| GALNT12 | 79695 | XM_006717287; XM_017015133; XM_011519018; NM_024642; XM_011519020; XM_024447673 |
| SOX2 | 6657 | NM_003106 |
| SNCA | 6622 | XM_011532204; NM_001146054; NM_000345; NM_001375287; XM_011532206; NM_007308; NR_164675; XM_011532207; NM_001375288; NM_001375290; NR_164676; XM_011532203; XM_011532205; NR_164674; XM_017008563; NM_001146055; NM_001375286; NM_001375285 |
| MYLPF | 29895 | NM_001324458; NM_013292; NM_001324459 |
| EMX2 | 2018 | NM_004098; NM_001165924 |
| FRMPD1 | 22844 | XM_017014482; XM_024447456; XM_011517806; NM_001371223; NM_001371225; XM_017014481; XM_024447454; XM_011517805; XR_929220; NM_014907; NM_001371224 |
| PHYHIP | 9796 | NR_156475; NM_001099335; NM_001363311; NM_014759; XM_017014102; NM_001363312 |
| GUCY2C | 2984 | NM_004963; XM_011520631 |
| FGFBP1 | 9982 | NM_005130 |
| SGK2 | 10110 | NM_016276; NM_001199264; NM_170693 |
| GDF10 | 2662 | NM_004962 |
| REM1 | 28954 | XM_011528795; XM_017027833; NM_014012; XM_005260404 |
| CPEB1 | 64506 | NM_001288819; NM_001365243; NM_001365242; NM_001365244; NM_001365245; NM_001387068; NM_001387076; NM_001365248; NM_001079534; NM_001365250; NM_001387065; NM_001387075; NM_001079535; NM_001288820; NM_001365249; NM_001387061; NM_001387066; NM_001387070; NM_001387062; NM_001387071; NM_001387078; NM_001365246; NM_001365247; NM_001387069; NM_001387077; NM_001079533; NM_001365240; NM_001365241; NM_001387072; NM_001387074; NM_001387063; NM_001387064; NM_001387067; NM_001387073; NM_030594 |
| CYP3A5 | 1577 | NM_001291830; NM_001190484; NR_033807; NR_033812; NM_001291829; NM_000777; NR_033810; NR_033811 |
| SALL1 | 6299 | NM_001127892; NM_002968 |
| HAND2 | 9464 | NM_021973 |
| HOXA3 | 3200 | NM_001384342; NM_001384335; NM_001384336; NM_001384339; NM_001384345; NM_001384346; NM_001384338; NM_001384337; NM_030661; NM_001384341; NM_001384343; NM_001384340; NM_001384344; NM_153631; NM_153632 |
| TMPRSS5 | 80975 | XM_017018366; XR_001747990; NM_001288749; NM_001288751; NM_001288752; NM_001288750; NR_110047; XR_001747991; XR_001747992; NR_110046; NM_030770; XM_017018367 |
| BMP5 | 653 | XM_011514817; NM_001329756; XM_024446524; NM_001329754; NM_021073 |
| TRDN | 10345 | NM_001251987; NM_001256020; NM_001256021; NM_006073; NM_001256022 |
| TACR2 | 6865 | NM_001057 |
| LYVE1 | 10894 | NM_006691 |
| FHL1 | 2273 | NM_001159703; NM_001167819; NM_001369327; NM_001369330; XM_006724746; XM_024452354; NR_027621; NM_001369328; NM_001159702; NM_001369326; XM_006724743; NM_001330659; NM_001369331; NM_001159700; NM_001159701; NM_001159704; NM_001369329; NM_001159699; NM_001449 |
| CAV1 | 857 | NM_001753; NM_001172895; NM_001172897; NM_001172896 |
| FIGF | 2277 | NM_004469 |
| NPR1 | 4881 | XM_017001374; XM_005245218; NM_000906 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| AOC3 | 8639 | XR_934584; NM_001277732; NM_003734; NR_102422; XM_011525419; XR_001752673; XM_011525420; XM_024451015; NM_001277731 |

-continued

| Gene | NCBI Gene ID | NCBI Accession Number(s) |
|---|---|---|
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| CIDEC | 63924 | NM_001321142; NM_001199552; NM_001378491; NM_001199623; NM_001199551; NM_001321144; NM_022094; NM_001321143 |
| NEK2 | 4751 | NM_002497; NM_001204182; NM_001204183 |
| MMP11 | 4320 | NM_005940; NR_133013 |
| ADAMTS5 | 11096 | XM_024452053; XM_024452054; NM_007038 |
| ABCD2 | 225 | XR_001748623; NM_005164; XM_017018992; XR_001748622; XM_017018993; XM_011538027 |
| LPL | 4023 | NM_000237 |
| HBB | 3043 | NM_000518 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| COL10A1 | 1300 | XM_011535432; NM_000493; XM_011535433; XM_017010248; XM_006715333 |
| AQP7 | 364 | XM_006716765; XM_017014706; NM_001318158; NR_134513; NR_134515; XM_017014704; XM_024447538; NM_001318156; XM_011517866; NR_134514; NR_164778; XM_011517867; XM_017014701; XM_024447539; NM_001376192; NM_001376193; XM_017014702; NM_001318157; NM_001376191; NR_164779; XM_017014700; NM_001170 |
| LEP | 3952 | XM_005250340; NM_000230 |
| GSTM5 | 2949 | NM_000851; XM_005270785; XM_005270784 |
| FMO2 | 2327 | NM_001460; NR_160266; XR_921761; NM_001365900; XR_001737072; NM_001301347 |
| PLIN1 | 5346 | NM_002666; XM_005254934; NM_001145311 |
| KIAA0101 | 9768 | NR_109934; NM_001029989; NM_014736 |
| CA3 | 761 | NM_005181 |
| CDO1 | 1036 | NM_001323565; NR_136619; NM_001323567; NM_001801; NR_136618; NR_136620; NM_001323566; NR_136621 |
| CSN1S1 | 1446 | XM_006714091; NM_001025104; XM_006714089; XM_006714090; NM_001890 |
| KIF4A | 24137 | NM_012310 |
| GPD1 | 2819 | NM_005276; NM_001257199 |
| DPT | 1805 | NM_001937 |
| ADH1B | 125 | NM_001286650; NM_000668 |
| FABP4 | 2167 | NM_001442 |
| CENPF | 1063 | XM_017000086; NM_016343; XM_011509082 |
| GABRD | 2563 | XM_011541194; XM_017000936; NM_000815 |
| PFKFB1 | 5207 | NM_001271804; XM_017029578; XM_017029576; NM_002625; NR_073450; XM_024452389; XM_017029577; NM_001271805 |
| ATP1A2 | 477 | NM_000702 |
| CHL1 | 10752 | XM_011533294; XM_017005568; XM_017005573; NM_001253387; NR_045572; XM_017005569; XM_017005572; XM_006712939; XM_011533292; XM_017005566; XM_006712940; XM_011533295; NM_001253388; NM_006614; XM_006712938; XM_011533296; XM_017005567; XM_017005570; XM_017005571 |
| SLC7A10 | 56301 | XM_011527120; XM_006723284; XM_024451609; XR_935841; NM_019849; XM_011527119; XM_024451610 |
| ADIPOQ | 9370 | NM_004797; NM_001177800 |
| EXO1 | 9156 | XM_011544325; XM_011544322; NM_130398; XM_011544323; XM_006711840; NM_003686; NM_006027; XM_011544321; XM_011544324; XM_017002793; NM_001319224 |
| INHBA | 3624 | XM_017012175; NM_002192; XM_017012176; XM_017012174 |
| CES1 | 1066 | NM_001025195; NM_001266; XM_005255774; NM_001025194 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| MMRN1 | 22915 | XM_005262856; NM_001371403; NM_007351 |
| HMMR | 3161 | NM_001142557; NM_001142556; NM_012484; NM_012485 |
| PKMYT1 | 9088 | NM_001258451; NM_182687; NM_001258450; XM_011522735; XM_024450490; NM_004203; XM_011522734; XM_011522736 |
| CIDEA | 1149 | NM_001279; NR_134607; NM_001318383 |
| CDC25C | 995 | XM_011543764; XM_011543760; XM_011543761; XM_011543763; NM_001364026; NM_001364027; XM_005272145; NM_001287582; NM_001287583; NM_001790; NM_022809; XM_006714739; XM_011543759; XM_011543762; NM_001318098; NM_001364028 |
| OXTR | 5021 | NM_000916; NM_001354654; NM_001354655; NM_001354653; NM_001354656 |
| DTL | 51514 | XM_011509614; NM_001286229; NM_001286230; NM_016448 |
| IBSP | 3381 | NM_004967 |
| PPP1R1A | 5502 | XM_005268995; XM_006719471; NM_006741 |
| WISP1 | 8840 | XM_024447319; NR_037944; XM_024447320; NM_080838; NM_003882; NM_001204870; XM_024447321; NM_001204869 |
| STAB2 | 55576 | NM_017564; XM_011538541; XM_011538538; XM_011538539; XM_011538542; XM_017019585; XM_011538537; XR_429107 |
| CDKN3 | 1033 | XM_024449458; NM_001330173; NM_005192; NM_001130851 |
| TK1 | 7083 | NM_001346663; NM_003258 |
| KIF20A | 10112 | NM_005733 |

-continued

| Gene | NCBI Gene ID | NCBI Accession Number(s) |
|---|---|---|
| KCNB1 | 3745 | XM_011528799; XM_006723784; NM_004975 |
| S100B | 6285 | NM_006272; XM_017028424 |
| PBK | 55872 | NM_018492; NM_001278945; NM_001363040 |
| TDO2 | 6999 | NM_005651 |
| PITX1 | 5307 | NM_002653 |
| MCM10 | 55388 | NM_182751; NM_018518; XM_011519538 |
| GRM4 | 2914 | NM_001256809; NM_001256812; NM_001256813; NM_001256811; NM_001256814; NM_001256810; NM_001282847; NM_000841 |
| CST1 | 1469 | NM_001898 |
| AIM1L | 55057 | NM_017977; XM_011541672; XM_011541673; XR_001737260; NM_001039775; XR_946681; XM_005245918 |
| TNMD | 64102 | NM_022144 |
| CLEC5A | 23601 | XM_017011916; XM_017011915; XM_011515995; XM_017011917; NM_001301167; NM_013252 |
| LRRC15 | 131578 | NM_130830; NM_001135057 |
| LAMP5 | 24141 | NM_001199897; NM_012261 |
| EPYC | 1833 | NM_004950; XM_011538008 |
| RAB26 | 25837 | XM_011522448; XM_011522450; NM_014353; NM_001308053 |
| CST2 | 1470 | NM_001322 |
| NKAIN1 | 79570 | NM_024522; XM_017002320 |
| LALBA | 3906 | NM_002289; NM_001384350 |
| CENPA | 1058 | NM_001809; NM_001042426 |
| TUBB3 | 10381 | NM_006086; NM_001197181 |
| ARTN | 9048 | NM_057160; NM_057090; NM_001136215; NM_057091; NM_003976 |
| TCL1B | 9623 | NM_004918; NM_199206 |
| SYT13 | 57586 | NM_001247987; NM_020826 |
| CNTD2 | 79935 | XM_006723395; NM_024877; XR_001753763; XR_935861 |
| NEURL1 | 9148 | XM_005270269; XM_011540333; XM_017016909; XM_011540332; XM_011540335; XR_945866; NM_004210; XM_005270270; XM_011540331 |
| NPY2R | 4887 | NM_001370180; NM_000910; NM_001375470 |
| CXCL10 | 3627 | NM_001565; NR_168520 |
| S100P | 6286 | NM_005980 |
| MYT1 | 4661 | NM_004535 |
| ACTL8 | 81569 | NM_030812; XM_011542212 |
| HAPLN1 | 1404 | XM_017009052; XM_017009051; NM_001884; XM_017009054; XM_017009053; XM_011543168 |
| BTN1A1 | 696 | NM_001732 |
| CXCL9 | 4283 | NM_002416 |
| CEACAM6 | 4680 | NM_002483; XM_011526990 |
| FBN2 | 2201 | NM_001999; XM_017009228 |
| NAT1 | 9 | NM_001160175; NM_001160170; NM_001160173; XM_011544688; XM_006716410; XM_017013947; NM_001160171; NM_001160172; NM_001160174; NM_001291962; XM_011544689; NM_001160176; XM_011544687; NM_000662; NM_001160179 |
| FOXJ1 | 2302 | NM_001454 |
| BMPR1B | 658 | XM_017008558; NM_001203; NM_001256793; XM_011532201; NM_001256794; NM_001256792; XM_017008559; XM_017008560; XM_017008561 |
| CNTNAP2 | 26047 | XM_017011950; NM_014141 |
| CEACAM5 | 1048 | XM_011526322; XM_017026146; NM_001291484; NM_004363; XM_017026145; NM_001308398 |
| KCNF1 | 3754 | NM_002236 |
| HOXC11 | 3227 | NM_014212 |
| KCNJ3 | 3760 | NM_001260510; NM_001260508; NM_001260509; NM_002239 |
| MAGEA12 | 4111 | NM_001166386; NM_001166387; NM_005367 |
| GABRQ | 55879 | NM_018558; XM_011531184 |
| HHIPL2 | 79802 | XM_024449814; XR_001737417; XR_426906; XM_017002350; XR_002957624; NM_024746; XR_001737416; XM_011509986 |
| TLX1 | 3195 | NM_001195517; XM_011539744; XM_011539745; NM_005521 |
| SOX11 | 6664 | NM_003108 |
| MAGEA6 | 4105 | NM_175868; NM_005363 |
| CA9 | 768 | XR_428428; NM_001216; XR_001746374 |
| C2orf54 | 79919 | XM_011511877; NM_001085437; NM_001282921; NM_024861 |
| DIO1 | 1733 | NM_000792; NM_001039715; NM_213593; NM_001039716; NM_001324316; NR_136692; NR_136693 |
| F7 | 2155 | XM_011537476; XM_011537475; NM_001267554; XM_011537474; NR_051961; XM_006719963; NM_019616; NM_000131 |
| CYP2B6 | 1555 | NM_000767 |
| TRH | 7200 | NM_007117 |
| CHGB | 1114 | NM_001819 |
| PROL1 | 58503 | NM_021225; NM_001302807; NR_126503 |
| CD177 | 57126 | XM_017027021; XM_017027022; NM_020406 |
| KIF1A | 547 | NM_001379636; NM_001379637; NM_001379639; NM_001379650; NM_001330290; NM_001379633; NM_001379641; NM_001379651; NM_001379653; NM_004321; NM_001379632; NM_001379638; NM_001379645; NM_001379646; NM_001379649; NM_001379635; NM_001379640; NM_001379634; NM_001244008; NM_001379642; NM_001320705; NM_001330289; NM_001379631; NM_001379648 |

-continued

| Gene | NCBI Gene ID | NCBI Accession Number(s) |
|---|---|---|
| PSCA | 8000 | NR_033343; NM_005672 |
| CRISP3 | 10321 | NM_001368123; NM_006061; NM_001190986 |
| PVALB | 5816 | NM_001315532; NM_002854 |
| GAD1 | 2571 | NM_013445; XM_017003758; NM_000817; XM_005246444; XM_011510922; XM_017003757; XM_017003756; XM_024452783 |
| MYH7 | 4625 | XM_017021340; NM_000257 |
| SERPINB7 | 8710 | XM_024451278; NM_001261831; NM_003784; NM_001040147; NM_001261830 |
| COL2A1 | 1280 | XM_017018831; XM_017018830; NM_001844; NM_033150; XM_017018828; XM_017018829 |
| MSMB | 4477 | NM_138634; NM_002443 |
| IRS4 | 8471 | XM_006724713; NM_003604; NM_001379150; XM_011531061 |
| BEX1 | 55859 | NM_018476 |
| PADI3 | 51702 | NM_016233; XM_011541571; XM_017001463; XM_011541572 |
| UGT2B4 | 7363 | NM_001297616; NM_021139; NM_001297615 |
| PRSS1 | 5644 | NR_172951; XM_011516411; NR_172947; NM_002769; NR_172948; NR_172949; NR_172950 |
| CYP2A7 | 1549 | XR_935754; NM_000764; NM_030589 |
| MSLN | 10232 | NM_001177355; NM_005823; NM_013404 |
| CPB1 | 1360 | NM_001871 |
| CARTPT | 9607 | NM_004291 |
| TGM4 | 7047 | NM_003241; XM_011534042 |
| NCAN | 1463 | NM_004386 |
| CYP2A6 | 1548 | NM_000762 |
| CALML5 | 51806 | NM_017422 |
| TFF1 | 7031 | NM_003225 |
| | | Ovarian_Cancer |
| QARS | 5859 | NR_073590; NM_005051; XM_017006965; NM_001272073 |
| HSD17B2 | 3294 | NM_002153; XR_001751898 |
| CLDN6 | 9074 | NM_021195 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| IZUMO4 | 113177 | XM_024451343; XR_002958248; NM_001039846; XM_024451342; XM_024451344; NM_052878; NM_001031735; NM_001363588 |
| PAQR4 | 124222 | NM_001284513; NM_001284511; NM_001284512; NM_152341; NM_001324118 |
| NGFR | 4804 | NM_002507 |
| MCC | 4163 | NM_002387; NM_001085377 |
| FAM107A | 11170 | NM_001076778; NM_007177; NM_001282713; NM_001282714 |
| FOXL1 | 2300 | NM_005250 |
| KCNC3 | 3748 | NM_004977; NR_110912; NM_001372305 |
| PTGS2 | 5743 | NM_000963 |
| COL17A1 | 1308 | NM_130778; NM_000494 |
| FZD2 | 2535 | NM_001466 |
| EIF1AY | 9086 | NM_004681; NM_001278612 |
| HOXD13 | 3239 | XM_011511068; NM_000523; XM_011511069 |
| FGF14 | 2259 | NM_001321931; NM_001321943; NM_001321949; NM_175929; NM_001321933; NM_001321941; NM_001321932; NM_001321935; NM_001321937; NM_001321945; NM_001321947; NM_001321939; NM_001321936; NM_001321940; NM_001321944; NM_001321946; NM_001321948; NM_001379342; NM_001321934; NM_001321938; NM_001321942; NM_004115 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| MMP13 | 4322 | NM_002427 |
| LHX1 | 3975 | NM_005568 |
| CSDC2 | 27254 | NM_014460 |
| PAX9 | 5083 | NM_001372076; NM_006194 |
| B2M | 567 | XR_002957658; XM_005254549; NM_004048 |
| SORBS2 | 8470 | XM_005263312; XM_017008740; XM_017008751; XM_017008760; XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; |

-continued

| Gene | NCBI Gene ID | NCBI Accession Number(s) |
|---|---|---|
| | | NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| ZNF492 | 57615 | NM_020855 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PRSS1 | 5644 | NR_172951; XM_011516411; NR_172947; NM_002769; NR_172948; NR_172949; NR_172950 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| IRX5 | 10265 | NM_005853; XM_011522809; NM_001252197 |
| DOK5 | 55816 | XM_011528904; NM_001294161; NM_018431; XM_024451946; NM_177959 |
| ASIP | 434 | NM_001385218; XM_011528820; NM_001672; XM_011528821 |
| EMX2 | 2018 | NM_004098; NM_001165924 |
| RAPGEF3 | 10411 | XM_011537758; XM_024448795; XR_001748551; XR_002957282; NM_001098532; XM_005268571; XM_017018688; NM_001098531; XM_011537752; XR_001748550; NM_006105; XM_011537755 |
| VGLL1 | 51442 | NM_016267 |
| HSPA4L | 22824 | NM_001317381; NM_001317383; XM_011531745; NM_001317382; NM_014278 |
| PAX8 | 7849 | NM_013992; NM_013953; NM_013952; NM_003466; NM_013951 |
| ALDH1A3 | 220 | NM_001293815; NM_000693; NM_001037224 |
| ANGPT4 | 51378 | NM_001322809; XM_011529239; NM_015985 |
| KIAA0513 | 9764 | NM_001286565; NM_001297766; NM_001286566; XM_017023912; NM_014732; NM_001388359 |
| RPS4Y1 | 6192 | NM_001008 |
| NES | 10763 | NM_024609; NM_006617 |
| COL21A1 | 81578 | XM_011514927; XM_024446561; XR_001743657; NM_030820; NR_134851; NR_134849; XM_011514925; NM_001318753; NR_134850; NM_001318752; NM_001318754; XM_011514926; XM_006715223; NM_001318751; XM_011514924 |
| MNX1 | 3110 | NM_001165255; NM_005515 |
| WT1 | 7490 | NM_000378; NR_160306; NM_001367854; NM_001198551; NM_001198552; NM_024424; NM_024426; NM_024425 |
| SLC6A12 | 6539 | XM_005253747; NM_003044; NM_001122847; XM_005253748; XM_011521010; XM_006719005; NM_001122848; NM_001206931 |
| NPR1 | 4881 | XM_017001374; XM_005245218; NM_000906 |
| WISP3 | 8838 | XM_011536223; XM_011536220; NM_198239; NR_125353; NR_125354; XR_001743705; NM_130396; XM_011536222; NM_003880 |
| ASGR1 | 432 | XM_011523861; NM_001197216; NM_001671 |
| FOXL2 | 668 | NM_023067 |
| PNOC | 5368 | NM_006228; XM_011544559; XM_005273532; XM_017013578; NM_001284244 |
| KLK6 | 5653 | XM_024451611; NM_001319949; NM_001012964; NM_001319948; NM_001012965; NM_002774 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| KLK10 | 5655 | XM_006723289; XM_005259061; NM_002776; NM_145888; NM_001077500; XM_017026993; XM_006723287; XM_005259062 |
| HEY1 | 23462 | NM_001040708; NM_012258; NM_001282851 |
| SCD | 6319 | NM_005063 |
| DIO3 | 1735 | NM_001362 |
| SCGN | 10590 | NM_006998; XM_017010181 |
| LGALS14 | 56891 | NM_020129; NM_203471 |
| SLC27A2 | 11001 | NM_001159629; NM_003645 |
| UTY | 7404 | XM_011531453; XM_011531464; XM_017030066; XM_017030067; NM_001258252; NM_001258260; NM_001258261; NM_001258270; NM_182659; NR_047597; NR_047618; NR_047621; XM_011531465; XM_024452493; NM_001258249; NM_001258251; NM_001258268; NR_047598; NR_047600; NR_047615; NR_047640; XM_006724875; XM_011531451; NM_001258269; NM_007125; NM_182660; NR_047606; NR_047616; NR_047620; NR_047631; NR_047639; NR_047641; NR_047647; XM_005262518; XM_011531454; XM_011531458; XM_011531459; XM_011531462; XM_017030073; XR_002958831; NM_001258257; NM_001258263; NM_001258266; NR_047601; NR_047611; NR_047613; NR_047619; NR_047627; NR_047634; NR_047645; NR_047646; XM_011531460; XM_011531461; XM_017030070; NM_001258256; NM_001258262; NM_001258264; NM_001258265; NR_047607; NR_047612; NR_047617; NR_047625; NR_047629; NR_047636; NR_047643; XM_011531442; XM_011531447; XM_011531450; XM_011531452; XM_017030074; XR_001756008; |

-continued

| Gene | NCBI Gene ID | NCBI Accession Number(s) |
|---|---|---|
| | | NM_001258253; NM_001258258; NM_001258259; NM_001258267; NR_047596; NR_047603; NR_047608; NR_047609; NR_047610; NR_047614; NR_047622; NR_047623; NR_047628; NR_047637; NR_047644; XM_011531448; XM_011531449; XM_017030068; XM_017030072; XM_024452494; NM_001258250; NR_047599; NR_047602; NR_047604; NR_047605; NR_047624; NR_047630; NR_047638; XM_011531441; XM_011531443; XM_011531445; XM_011531446; XM_011531455; XM_011531463; XM_017030071; NM_001258254; NM_001258255; NR_047626; NR_047635; NR_047632; NR_047633; NR_047642 |
| BBC3 | 27113 | XM_006723141; XM_011526722; NM_001127241; NM_001127242; NM_001127240; NM_014417 |
| CETP | 1071 | XM_006721124; NM_000078; NM_001286085 |
| GSTM5 | 2949 | NM_000851; XM_005270785; XM_005270784 |
| WNT7A | 7476 | XM_011534091; NM_004625 |
| CCNE1 | 898 | XM_011527440; NM_001238; NM_001322259; NM_001322261; NM_001322262; NM_057182 |
| DLC1 | 10395 | NM_001316668; NM_182643; XM_005273374; NM_001348081; NM_001348083; NM_001348084; NM_001164271; NM_006094; NM_024767; NM_001348082 |
| RAMP3 | 10268 | XM_017011666; NM_005856; XM_006715631 |
| MEIS1 | 4211 | NM_002398 |
| SGCA | 6442 | XM_011525122; XM_011525120; XM_011525121; XM_024450873; NM_001135697; NR_135553; XR_002958056; XM_011525124; NM_000023; XM_011525123 |
| HGH1 | 51236 | NM_016458; XR_001745537 |
| CHODL | 140578 | XM_017028273; NM_001204174; NM_024944; XM_011529453; NM_001204176; NM_001204175; NM_001204177; XM_011529457; NM_001204178 |
| NLRP1 | 22861 | NM_001033053; NM_033006; NM_033007; NM_014922; NM_033004 |
| CLDN9 | 9080 | NM_020982 |
| RPL4 | 6124 | NM_000968 |
| CDH6 | 1004 | NM_004932; NM_001362435; XM_017008910; XM_011513921; XR_001741972 |
| TNFRSF10C | 8794 | NM_003841 |
| ITGA2 | 3673 | NR_073103; NR_073104; NR_073105; NR_073106; NR_073107; NM_002203 |
| GRK5 | 2869 | XM_005269707; XM_005269708; NM_005308 |
| LIPF | 8513 | NM_004190; NM_001198829; NM_001198830; NM_001198828; XM_011540311 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| SST | 6750 | NM_001048 |
| IL20RA | 53832 | NM_001278722; XM_011535904; XM_017010955; NM_001278724; NM_014432; XM_006715506; NM_001278723; XM_017010954 |
| FGF18 | 8817 | NM_003862; NM_033649 |
| NR5A1 | 2516 | NM_004959 |
| ULBP2 | 80328 | NM_025217; XM_017011321 |
| RNF128 | 79589 | NM_024539; NM_194463 |
| PRM2 | 5620 | NM_001286358; NR_104428; NM_002762; NM_001286356; NM_001286359; NM_001286357 |
| C7 | 730 | NM_000587 |
| L1CAM | 3897 | NM_024003; NM_001278116; NM_001143963; NM_000425 |
| BCAM | 4059 | NM_001013257; NM_005581 |
| DTL | 51514 | XM_011509614; NM_001286229; NM_001286230; NM_016448 |
| ADRB3 | 155 | NM_000025 |
| CLDN16 | 10686 | NM_006580; NM_001378492; NM_001378493 |
| FMO5 | 2330 | XM_005272946; XM_005272947; XM_011509351; XM_017000802; NM_001144829; NM_001461; XM_006711244; XM_006711245; XM_005272948; NM_001144830; XM_017000801; XM_011509350 |
| KCNIP1 | 30820 | NM_001034837; NM_014592; NM_001034838; NM_001278340; XM_017009407; XM_017009408; NM_001278339 |
| FGF23 | 8074 | NM_020638 |
| PDE3B | 5140 | XR_001747903; NM_000922; NM_001363570; XM_017017912; XM_006718249; XM_017017911; NM_001363569 |
| SLC4A3 | 6508 | XM_011511667; NM_201574; NR_048551; XM_005246790; XM_011511665; NM_001326559; NM_005070 |
| FOLR1 | 2348 | NM_000802; NM_016729; NM_016730; NM_016725; NM_016724 |
| STAR | 6770 | NM_001007243; NM_000349 |
| | | Uterus_Carcinoma |
| SPDEF | 25803 | NM_001252294; XM_005248988; NM_012391; XM_011514457 |
| HLA-G | 3135 | XM_017010817; NM_001384280; XM_017010818; NM_002127; XM_024446420; NM_001363567; NM_001384290 |
| MARCO | 8685 | NM_006770; XM_011512082; XM_011512083; XM_017005171 |
| FEZF2 | 55079 | NM_018008 |
| SOX17 | 64321 | NM_022454 |
| HIF3A | 64344 | XM_017027133; XM_017027139; XM_024451649; XR_001753736; XR_935849; NM_022462; XM_017027132; XM_017027142; XM_005259152; XM_017027138; |

-continued

| Gene | NCBI Gene ID | NCBI Accession Number(s) |
|---|---|---|
| | | NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| ZNF208 | 7757 | NM_001329971; NM_001329973; NM_001329974; NM_001329972; NR_138252; NM_007153 |
| CHRND | 1144 | NM_001311196; XM_011510524; NM_001256657; NM_001311195; NM_000751 |
| SLC31A2 | 1318 | NM_001860 |
| C1S | 716 | XM_005253760; NM_001734; NM_001346850; NM_201442 |
| GREB1 | 9687 | XM_024453255; NM_014668; NM_033090; XM_024453254; XM_024453256; NM_148903; XM_005246196; XM_024453251; XR_922686; XM_024453250; XM_024453252; XM_011510418; XM_011510423; XM_011510422; XM_024453253; XM_011510419; XM_005246192; XR_001739081 |
| VIP | 7432 | XM_006715562; XM_005267135; NM_003381; NM_194435 |
| ZWINT | 11130 | XR_428692; NM_007057; NM_001005413; XM_017015605; XM_024447784; NM_032997; NM_001005414 |
| CREB5 | 9586 | XM_017012807; XM_017012808; NM_001011666; XM_024447005; XM_017012806; XM_017012809; NM_182898; XM_017012810; XM_005249906; NM_004904; XR_001744893; XM_011515618; NM_182899 |
| EIF1AY | 9086 | NM_004681; NM_001278612 |
| E2F1 | 1869 | NM_005225 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| HOXD13 | 3239 | XM_011511068; NM_000523; XM_011511069 |
| CTSV | 1515 | NM_001201575; NM_001333 |
| HOXD10 | 3236 | NM_002148 |
| DGKG | 1608 | NM_001346; NM_001080745; NM_001080744 |
| SFRP1 | 6422 | NM_003012 |
| PAX9 | 5083 | NM_001372076; NM_006194 |
| SCGB2A1 | 4246 | NM_002407 |
| FOXJ1 | 2302 | NM_001454 |
| ZBTB20 | 26137 | NM_001164345; NR_121662; NM_001164347; NM_001348803; NM_001164343; NM_001393393; NM_001164342; NM_001348800; NM_001348801; NM_001348804; NM_001393395; NM_001393396; NM_001164344; NM_001348802; NM_001348805; NM_001393394; NM_001164346; NM_015642 |
| PTGS1 | 5742 | NM_001271166; XM_011518875; XM_024447615; NM_001271164; XM_005252105; XM_024447614; NM_000962; XM_011518876; NM_001271165; NM_001271367; NM_001271368; NM_080591 |
| NOVA2 | 4858 | XM_017026838; XM_006723230; NM_002516; XM_017026840; XM_017026839 |
| BEGAIN | 57596 | NM_001385092; NM_001385093; NR_169571; XM_024449671; NM_001385104; XM_024449670; NM_001159531; NM_001385088; NM_001385094; NM_001385095; NM_001385096; NM_001385097; NM_001385098; NM_001385099; NM_001385100; NM_020836; NM_001385089; NM_001385102; NM_001385083; NM_001385084; NM_001385091; NR_169570; NM_001385085; NM_001385086; NM_001385087; NM_001385103; NM_001385082; NM_001385090; NM_001385101 |
| EMX2 | 2018 | NM_004098; NM_001165924 |
| VGLL1 | 51442 | NM_016267 |
| ALDH1A2 | 8854 | NM_001206897; NM_170697; NM_170696; NM_003888 |
| SLCO5A1 | 81796 | XM_017013885; XR_928814; NM_001146008; NM_001146009; XM_017013886; XR_428341; XM_017013884; NM_030958; XM_017013883; XM_005251313 |
| HOXA10 | 3206 | NR_037939; NM_153715; NM_018951 |
| GADD45G | 10912 | XM_011518163; NM_006705 |
| RPS4Y1 | 6192 | NM_001008 |
| TPM2 | 7169 | XM_017015091; NM_213674; XM_017015093; XM_017015088; NM_001301226; NM_001301227; NM_001145822; XM_017015087; XM_017015092; XM_017015090; NM_003289 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| WT1 | 7490 | NM_000378; NR_160306; NM_001367854; NM_001198551; NM_001198552; NM_024424; NM_024426; NM_024425 |
| MNX1 | 3110 | NM_001165255; NM_005515 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| ANKRD2 | 26287 | NM_001291218; NM_001129981; NM_020349; NM_001291219; NM_001346793 |
| EHHADH | 1962 | XM_006713525; NM_001166415; NM_001966 |
| FXYD1 | 5348 | NM_001278718; NM_001278717; NM_021902; XM_017026875; NM_005031; XM_017026874; XM_017026876 |

-continued

| Gene | NCBI Gene ID | NCBI Accession Number(s) |
|---|---|---|
| FOXL2 | 668 | NM_023067 |
| GLDC | 2731 | NM_000170 |
| TNNC1 | 7134 | NM_003280 |
| EDNRB | 1910 | NM_001122659; NM_003991; NM_001201397; NM_000115; NR_047024 |
| APOD | 347 | NM_001647 |
| SLC27A2 | 11001 | NM_001159629; NM_003645 |
| SLC12A2 | 6558 | XM_011543588; NM_001256461; XR_001742214; NR_046207; NM_001046; XM_017009771 |
| FMO2 | 2327 | NM_001460; NR_160266; XR_921761; NM_001365900; XR_001737072; NM_001301347 |
| GSTM5 | 2949 | NM_000851; XM_005270785; XM_005270784 |
| SOX1 | 6656 | NM_005986 |
| APBA1 | 320 | NM_001163; XM_011518617; XM_017014670; XM_005251968 |
| HOXB13 | 10481 | NM_006361 |
| NPY4R | 5540 | XR_001747124; NM_001278794; NM_005972; XM_011539936; XM_017016387; XM_011539937; XM_017016386; XR_001747123 |
| CIDEB | 27141 | NM_001393334; NM_001393340; NM_001318807; NM_001393339; NM_001393336; NM_001393338; NM_001393335; NM_001393337; NM_014430 |
| MEIS1 | 4211 | NM_002398 |
| TNNC2 | 7125 | NM_003279; XM_011529031 |
| RIMBP2 | 23504 | XM_017019105; XM_011538103; XM_011538105; NM_001351227; NM_001393620; NM_001393627; NM_001393616; NM_001351232; NM_001393615; NM_001393621; NM_001393623; NM_001393628; XM_011538106; XM_011538102; XM_011538108; NM_001351231; NM_001393614; NM_001393617; NM_001393622; NM_001393625; NM_001393629; NM_001351230; NM_001393619; NM_001393626; NM_001351228; NM_001393624; XM_011538107; XM_017019106; NM_001351226; NM_001351229; NM_001351233; NM_001393618; NM_015347 |
| HGH1 | 51236 | NM_016458; XR_001745537 |
| SOX15 | 6665 | NM_006942 |
| PDLIM3 | 27295 | NM_001114107; XR_938723; NM_001257963; XR_938724; NM_001257962; NR_047562; NM_014476; XR_001741206 |
| CX3CR1 | 1524 | NM_001171174; NM_001337; NM_001171171; NM_001171172 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| ZBTB16 | 7704 | XR_001747955; NM_001354751; XM_017018259; NM_006006; NM_001354752; XM_005271658; XM_024448681; NM_001018011; NM_001354750 |
| CLCA2 | 9635 | NM_006536; XM_011542448 |
| DLX5 | 1749 | XM_017011803; NM_005221; XM_005250185 |
| GABRQ | 55879 | NM_018558; XM_011531184 |
| FOXA2 | 3170 | NM_021784; NM_153675 |
| TNFSF10 | 8743 | NR_033994; NM_001190943; NM_003810; NM_001190942 |
| IQCA1 | 79781 | XM_017004960; NM_024726; NM_001270585; XM_011511865; XM_011511866; XM_011511864; NM_001270584; NR_073043 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| TCF21 | 6943 | NM_003206; NM_198392 |
| TUBA1C | 84790 | NM_001303114; NM_032704; NM_001303116; NM_001303117; NM_001303115 |
| GYPC | 2995 | NM_002101; XM_006712460; NM_001256584; NM_016815 |
| CA2 | 760 | NM_001293675; NM_000067 |
| IL20RA | 53832 | NM_001278722; XM_011535904; XM_017010955; NM_001278724; NM_014432; XM_006715506; NM_001278723; XM_017010954 |
| RGN | 9104 | XM_024452477; XM_006724568; XM_017029954; NM_004683; NM_001282848; NM_152869; NM_001282849; XM_006724567 |
| AOC3 | 8639 | XR_934584; NM_001277732; NM_003734; NR_102422; XM_011525419; XR_001752673; XM_011525420; XM_024451015; NM_001277731 |
| FGF18 | 8817 | NM_003862; NM_033649 |
| MYO5A | 4644 | XM_011521607; NM_001142495; NM_001382348; XM_011521610; NM_000259; NM_001382347; XM_011521611; XM_011521609; XM_011521612; XM_017022227; NM_001382349 |
| CCDC33 | 80125 | XR_001751400; XM_011522090; XM_017022624; XM_017022626; NM_001287181; XM_011522088; XM_017022630; XR_001751401; NM_025055; XM_017022625; XM_017022628; XM_017022631; NR_108023; NM_182791; XM_011522087; XM_005254692; XM_017022627; XM_017022633; XM_017022623; XM_011522086; XM_017022632; XM_011522085; XM_011522089 |
| REN | 5972 | NM_000537 |
| NCAPG | 64151 | NM_022346; XM_017008543; NR_073124; XM_017008544; XM_011513876 |
| CT62 | 196993 | NR_168259; NM_001102658; NR_168260 |
| CACNA1G | 8913 | NM_001256326; NM_001256328; NM_018896; NM_198378; NM_198388; NM_198396; NM_001256359; NM_001256361; NM_198383; NM_198385; NM_001256327; NM_001256330; NR_046056; NM_198380; NM_198382; NR_046054; XM_006722160; NM_198379; NM_001256329; NM_001256332; NM_001256333; NM_001256360; NM_198384; NM_198386; NR_046058; |

-continued

| Gene | NCBI Gene ID | NCBI Accession Number(s) |
|---|---|---|
| | | NM_001256325; NM_001256334; NM_198387; XM_006722161; NM_001256324; NM_001256331; NM_198376; NM_198377; NR_046055; NR_046057; NM_198397 |
| PIGR | 5284 | XM_011509629; NM_002644 |
| CSTA | 1475 | NM_005213 |
| OSR2 | 116039 | XM_017013018; NM_053001; XM_011516825; XM_005250778; NM_001286841; NM_001142462; XM_011516826; NM_001394683; XM_011516827 |
| FOXF2 | 2295 | NM_001452 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| GAD1 | 2571 | NM_013445; XM_017003758; NM_000817; XM_005246444; XM_011510922; XM_017003757; XM_017003756; XM_024452783 |
| NXPH4 | 11247 | XM_017018747; NM_007224 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EGFR | 1956 | NM_001346899; NM_201282; NM_201284; NM_001346898; NM_001346900; NM_001346897; NM_201283; NM_001346941; NM_005228 |
| FMO3 | 2328 | XM_011509345; XM_024454365; NM_001002294; NM_006894; NM_001319173; NM_001319174 |
| TSPAN7 | 7102 | NM_004615 |
| ASRGL1 | 80150 | XM_005274305; XM_005274306; XM_011545265; NM_001083926; XM_011545266; NM_025080; XR_002957199; XM_017018354; XR_002957198; XR_001747982 |
| ALOX15B | 247 | NM_001141; NM_001039130; NM_001039131 |
| PRPH | 5630 | XM_005269025; XR_944623; NM_006262; |
| EFEMP1 | 2202 | XM_024452757; NM_004105; NM_018894; XM_005264205; NM_001039349; XM_017003586; XM_024452755; XM_024452756; NM_001039348 |
| SALL1 | 6299 | NM_001127892; NM_002968 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| PHOX2A | 401 | NM_005169 |
| AQP5 | 362 | NM_001651; XM_005268838 |
| TTC22 | 55001 | XM_017001582; XM_011541671; NM_001114108; NM_017904 |
| | | Renal_Cell_Carcinoma |
| SLC17A3 | 10786 | NM_006632; NM_001098486 |
| SLC4A1 | 6521 | XM_011525129; XM_005257593; XM_011525130; NM_000342 |
| CDH16 | 1014 | NM_001204746; XM_011522807; NM_004062; XM_005255770; NM_001204744; NM_001204745 |
| SLC22A2 | 6582 | NM_153191; NM_003058 |
| NAT8 | 9027 | NM_003960 |
| SLC3A1 | 6519 | XM_011533047; NM_000341 |
| ENPP3 | 5169 | XR_001743464; NR_133007; NM_005021; XM_017010932; XM_011535897 |
| FXYD2 | 486 | NM_021603; NM_001127489; NM_001680 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| SIM1 | 6492 | XM_011536072; NM_001374769; NM_005068 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| PAX2 | 5076 | NM_001304569; NM_003987; NM_001374303; NM_003989; NM_000278; NM_003990; NM_003988 |
| PVALB | 5816 | NM_001315532; NM_002854 |
| RHBG | 57127 | XR_001737323; NR_146765; XR_001737328; XR_001737329; NR_046115; XM_011509799; XM_017001859; NR_146764; XM_011509800; XM_017001858; XR_001737324; XR_001737325; NM_001256395; NR_146763; XM_017001857; NM_020407; XR_001737330; XR_001737332; NM_001256396 |
| AQP2 | 359 | NM_000486 |
| POU3F3 | 5455 | NM_006236 |
| PAX8 | 7849 | NM_013992; NM_013953; NM_013952; NM_003466; NM_013951 |
| GFRA3 | 2676 | NM_001496 |
| CA12 | 771 | NM_001218; NR_135511; NM_206925; NM_001293642 |
| FOXD3 | 27022 | NM_012183 |
| CACNG4 | 27092 | NM_014405 |
| HAND2 | 9464 | NM_021973 |
| NLGN1 | 22871 | NM_001365923; NM_001365928; NM_001365932; NM_014932; XM_011512551; XM_011512553; XM_017005897; XM_017005902; NM_001365929; NM_001365926; XM_017005895; XM_017005893; NM_001365925; NM_001365931; XM_017005896; XM_017005900; NM_001365933; XM_005247237; NM_001365930; NM_001365936; XM_011512554; |

-continued

| Gene | NCBI Gene ID | NCBI Accession Number(s) |
|---|---|---|
| | | XM_017005888; XM_017005894; NM_001365924; NM_001365927; NM_001365934; NM_001365935 |
| TRPM3 | 80036 | NM_001366147; XM_011519045; NM_001366145; NM_206944; XM_011519042; XM_024447681; NM_001007470; NM_001366152; NM_001366153; NM_206946; XM_011519037; NM_001366151; NM_206947; XM_011519040; NM_001007471; NM_001366141; NM_001366150; NM_001366154; XM_011519039; XM_017015156; XM_024447687; NM_001366144; NM_001366146; NM_020952; XM_024447683; NM_001366149; XM_011519038; XM_011519046; XM_024447682; XM_024447684; XM_024447685; XM_024447686; NM_001366142; NM_001366143; NM_001366148; NM_024971; NM_206945; NM_206948 |
| ARHGEF4 | 50649 | XM_011511276; XM_005263689; XR_001738756; NM_001375900; NM_001375902; XM_011511274; XR_001738757; NM_001375901; NM_001375904; NM_001367493; NM_001375903; NM_015320; NM_001395416; NM_032995; XM_005263688; XM_011511277; XM_017004231; XM_024452938 |
| INSM1 | 3642 | NM_002196 |
| S100A14 | 57402 | XM_017001875; NM_020672; XM_005245362 |
| LGR5 | 8549 | NR_110596; NM_001277227; NM_001277226; NM_003667 |
| CFTR | 1080 | NM_000492 |
| TRHDE | 29953 | XM_017019244; XM_017019243; NM_013381; XM_005268819; XM_011538248 |
| ESRP1 | 54845 | XM_005250991; NM_001122827; NM_017697; XM_005250992; NM_001122826; NM_001034915; NM_001122825 |
| LAD1 | 3898 | NM_005558 |
| GRHL2 | 79977 | XM_011517306; XM_024447286; NM_001330593; NM_024915; XM_011517307 |
| ALPPL2 | 251 | NM_031313 |
| HOXC10 | 3226 | NM_017409 |
| EPHB3 | 2049 | NM_004443 |
| SLC6A11 | 6538 | NM_001317406; XM_017007073; XM_011534033; NM_014229 |
| NKX3-2 | 579 | NM_001189 |
| CNKSR1 | 10256 | NM_006314; NR_023345; NM_001297647; NM_001297648 |
| RAMP1 | 10267 | XM_017003153; XM_017003154; XM_017003155; NM_001308353; NM_005855; XM_017003152; XM_017003156 |
| KIF2C | 11004 | NM_001297656; XM_011540541; NM_001297657; XM_011540540; NM_006845; NM_001297655 |
| ST8SIA2 | 8128 | NM_006011; NM_001330416; XM_017022642 |
| SFRP1 | 6422 | NM_003012 |
| SPAG4 | 6676 | XM_011529009; NM_003116; XM_005260520; NM_001317931 |
| CDKN2A | 1029 | XR_929159; XM_011517676; XM_011517675; NM_001363763; NM_001195132; NM_058195; NM_000077; NM_058196; NM_058197; XM_005251343 |
| SIGLEC8 | 27181 | XM_011526734; NM_014442; NM_001363548 |
| SLC14A2 | 8170 | XM_017026016; NM_007163; NM_001242692; XM_024451271; NM_001371319; XM_024451270 |
| PLA2G7 | 7941 | NM_001168357; XR_001743639; XM_005249408; NM_005084; XR_002956305 |
| KCNN1 | 3780 | NM_001386974; NM_001386976; NR_170373; NM_001386975; NM_001386977; NM_002248; XM_011528004; NR_170374 |
| CA8 | 767 | NM_001321837; NM_001321838; XM_011517587; XM_011517588; NM_001321839; NM_004056; NR_135821; XM_017013818 |
| KLK6 | 5653 | XM_024451611; NM_001319949; NM_001012964; NM_001319948; NM_001012965; NM_002774 |
| CA9 | 768 | XR_428428; NM_001216; XR_001746374 |
| | | Squamous_Cell_Carcinoma |
| TMPRSS11D | 9407 | XM_005265710; XM_017008851; NM_004262 |
| SPRR1B | 6699 | NM_003125 |
| SERPINB3 | 6317 | NM_006919 |
| DSG3 | 1830 | XM_011525850; NM_001944 |
| ADH7 | 131 | NM_001166504; NM_000673 |
| S100A12 | 6283 | NM_005621 |
| SPRR1A | 6698 | NM_005987; NM_001199828 |
| KRT1 | 3848 | NM_006121 |
| SERPINB13 | 5275 | NM_001348267; XM_011526029; NM_001348268; NM_012397; NM_001348269; NM_001307923; NM_001348270 |
| KRT6A | 3853 | NM_005554 |
| CRNN | 49860 | NM_016190 |
| FOXE1 | 2304 | NM_004473 |
| SFTPB | 6439 | XM_005264487; NM_198843; XM_005264488; NM_000542; NM_001367281; XM_005264490 |
| CALML3 | 810 | NM_005185 |
| CRCT1 | 54544 | NM_019060; XM_011509656 |
| SFN | 2810 | NM_006142 |
| TP63 | 8626 | NM_001114978; NM_001329144; NM_001329146; NM_001329964; NM_001329145; NM_003722; NM_001114979; NM_001114982; NM_001329149; NM_001114980; NM_001114981; NM_001329150; NM_001329148 |
| SFTPA2 | 729238 | XM_011540124; XM_005270132; NM_001320813; NM_001320814; XM_017016608; XM_011540125; NM_001098668; XM_005270128 |
| FABP5 | 2171 | NM_001444 |
| KRT5 | 3852 | NM_000424 |

-continued

| Gene | NCBI Gene ID | NCBI Accession Number(s) |
|---|---|---|
| GPR87 | 53836 | NM_023915 |
| CKM | 1158 | NM_001824 |
| MYL2 | 4633 | NM_000432 |
| SOX2 | 6657 | NM_003106 |
| MYL1 | 4632 | NM_079422; NM_079420 |
| IRX4 | 50805 | NM_016358; NM_001278633; NM_001278632; NM_001278635; NM_001278634 |
| NKX2-1 | 7080 | NM_001079668; NM_003317 |
| KRT20 | 54474 | NM_019010 |
| NR1H4 | 9971 | NR_135146; XM_006719719; NM_001206978; NM_001206993; NM_001206977; XM_011539040; XM_011539042; NM_001206979; NM_005123; XM_011539041; NM_001206992 |
| PLA2G3 | 50487 | XM_011530205; XR_937865; XM_011530204; NM_015715 |
| FLG | 2312 | NM_002016 |
| SFTPD | 6441 | XM_011540087; NM_003019; XM_011540088 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SPINK1 | 6690 | NM_003122; NM_001379610; NM_001354966 |
| NTS | 4922 | NM_006183 |
| MMP12 | 4321 | NM_002426 |
| ALDH3B2 | 222 | NM_001354345; NM_001393400; NM_001393402; ; NM_001393401; NM_000695; NM_001031615 |
| HNF1B | 6928 | XM_011525161; NM_001165923; NM_001304286; XM_011525163; NM_000458; XM_011525162; NM_006481; XM_011525164; XM_011525160 |
| UPK1B | 7348 | NM_006952 |
| GJB1 | 2705 | NM_000166; XM_011530907; NM_001097642 |
| FABP4 | 2167 | NM_001442 |
| CTSV | 1515 | NM_001201575; NM_001333 |
| HOXD11 | 3237 | NM_021192 |
| CLDN18 | 51208 | NM_001002026; NM_016369 |
| PITX1 | 5307 | NM_002653 |
| LIPF | 8513 | NM_004190; NM_001198829; NM_001198830; NM_001198828; XM_011540311 |
| FZD10 | 11211 | NM_007197 |
| CYP4B1 | 1580 | XM_011540833; NR_135003; XM_011540832; NM_000779; NM_001319161; NM_001319163; NM_001099772; XM_017000466; NM_001319162; XR_946559 |
| TCN1 | 6947 | NM_001062 |
| CLDN3 | 1365 | NM_001306 |
| MYOT | 9499 | XM_017010060; XM_017010061; NM_001300911; NM_001135940; XM_017010062; NM_006790 |
| LAMC2 | 3918 | NM_005562; NM_018891; XM_017001273 |
| SCNN1B | 6338 | XM_017023526; XM_011545913; XM_011545914; XM_017023525; NM_000336 |
| DES | 1674 | NM_001927; NM_001382708; NM_001382710; NM_001382713; NM_001382709; NM_001382711; NM_001382712 |
| CSF3 | 1440 | NR_168489; NR_168491; NM_000759; NM_172220; NM_001178147; NM_172219; NR_168490; NR_033662 |
| HMGCS2 | 3158 | NM_001166107; XM_011541313; NM_005518 |
| AQP4 | 361 | NM_001317387; NM_001364287; NM_001364286; NM_001317384; XM_011525942; NM_001650; NM_001364289; NM_004028 |
| TMC5 | 79838 | NM_001261841; NM_024780; NM_001308161; NM_001105248; NM_001105249 |
| SLC52A1 | 55065 | XM_011523951; NM_001104577; NM_017986 |
| DMBT1 | 1755 | XM_011539390; XM_011539391; XM_011539407; XM_011539408; NM_007329; XM_006717660; XM_006717665; XM_011539402; XM_024447854; XM_011539392; XM_011539393; XM_011539400; XM_011539403; XM_011539405; XM_011539413; XM_017015798; NM_001320644; NM_004406; XM_011539394; XM_011539409; XM_011539415; NM_017579; XM_011539389; XM_011539395; XM_011539396; XM_011539399; XM_011539401; XM_011539410; XM_011539414; NM_001377530; XM_011539398; XM_011539411 |
| SLC34A2 | 10568 | NM_001177999; NM_006424; NM_001177998 |
| GABRQ | 55879 | NM_018558; XM_011531184 |
| PRSS3 | 5646 | NM_007343; NM_001197097; NM_002771; XM_011517965; NM_001197098 |
| SLC4A4 | 8671 | XM_024454267; XM_024454271; XM_024454272; NM_001098484; XM_024454270; NM_003759; XM_017008793; XM_024454268; NM_001134742; XM_024454269; XM_011532390; XM_017008792 |
| COX6A2 | 1339 | NM_005205 |
| SERPINA5 | 5104 | NM_000624 |
| SDC1 | 6382 | NM_001006946; XM_005262620; XM_005262621; NM_002997; XM_005262622 |
| ENDOU | 8909 | NM_001172439; NM_006025; NM_001172440 |
| UPK1A | 11045 | NM_007000; NM_001281443 |
| NME5 | 8382 | XM_024446227; NM_003551; XM_005272099; XM_024446228; XM_017009945 |
| SORBS2 | 8470 | XM_005263312; XM_017008740; XM_017008751; XM_017008760; |

-continued

| Gene | NCBI Gene ID | NCBI Accession Number(s) |
|---|---|---|
| | | XM_017008764; XM_017008770; NM_001145674; NM_001270771; NM_001394266; NM_001395207; NM_021069; XM_017008738; XM_017008741; XM_017008748; XM_017008754; XM_017008762; XM_017008765; XM_017008766; NM_001145671; NM_001394247; NM_001394252; NM_001394258; NM_001394262; NM_001394263; NM_001394274; NM_001394275; NM_001394277; XM_017008743; XM_017008755; XM_017008758; XM_017008768; XM_017008771; XM_024454258; NM_001145672; NM_001394245; NM_001394246; NM_001394257; NM_001394260; NM_001394265; NM_001394267; XM_005263308; XM_005263310; XM_017008753; XM_017008763; XM_017008772; XM_017008774; XM_024454260; NM_001145675; NM_001394264; NM_001394272; XM_005263311; XM_005263313; XM_017008739; XM_017008756; XM_017008767; NM_001145670; NM_001145673; NM_001394256; NM_001394268; NM_001394270; NM_001394271; XM_005263307; XM_017008757; NM_001394248; NM_001394254; NM_001394261; NM_003603; XM_006714390; XM_017008750; XM_017008752; XM_017008769; XM_017008775; NM_001394249; NM_001394250; NM_001394255; NM_001394259; XM_006714388; XM_017008744; XM_017008759; XM_017008761; XM_017008773; XM_024454259; XM_024454257; XR_002959769; NM_001394251; NM_001394253; NM_001394273; NM_001394276 |
| HAND1 | 9421 | NM_004821; XM_005268531 |
| CRH | 1392 | NM_000756 |
| TFAP2A | 7020 | NM_001032280; XM_006715175; NM_001042425; XM_017011232; XM_011514833; NM_001372066; NM_003220 |
| COL9A1 | 1297 | NM_001851; NR_165185; NM_078485; XM_017010246; XM_011535429; XM_017010247; NM_001377289; NM_001377290; NM_001377291 |
| ATP10B | 23120 | XM_011534472; XM_017009253; NM_001366652; NM_001366658; XM_011534468; NM_001366653; NM_001366654; NM_001366655; NM_001366656; NM_025153; NM_001366657; XM_017009252; XM_011534469 |
| ALDOB | 229 | NM_000035 |
| AHNAK2 | 113146 | NM_138420; XM_024449463; NM_001350929 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| EVX1 | 2128 | NM_001304519; NM_001304520; NM_001989 |
| CLDN4 | 1364 | NM_001305 |
| NEB | 4703 | XM_005246590; XM_005246594; XM_005246602; XM_005246611; XM_017004178; XM_017004179; XM_017004180; NM_001164508; XM_005246603; XM_005246617; XM_006712542; XM_017004185; NM_001164507; NM_001271208; XM_005246593; XM_005246598; XM_005246606; XM_005246610; XM_017004177; XM_017004184; NM_004543; XM_005246592; XM_005246599; XM_005246601; XM_005246616; XM_017004181; XM_005246604; XM_005246608; XM_017004182; XM_017004183; XM_005246591; XM_005246596; XM_005246597; XM_006712541; XM_011511225; XM_011511226; XM_005246613; XM_005246612; XM_005246615; XM_011511227 |
| LRP2 | 4036 | XM_011511183; NM_004525; XM_011511184 |
| DLX2 | 1746 | NM_004405 |
| GRIK3 | 2899 | NM_000831 |
| TBX1 | 6899 | NM_005992; NM_080646; XM_017028928; XM_006724312; XM_017028926; NM_001379200; XM_017028925; XM_017028927; NM_080647 |
| XDH | 7498 | NM_000379; XM_011533096; XM_011533095 |
| DLX6 | 1750 | NM_005222 |
| ADH1C | 126 | NM_000669; NR_133005 |
| HKDC1 | 80201 | NM_025130; XR_001747209; XM_011540195 |
| MFAP5 | 8076 | NM_001297709; NR_123733; NR_123734; NM_001297711; NM_003480; NM_001297710; NM_001297712 |
| DNAJC22 | 79962 | NM_001304944; NM_024902; XM_005269157; XM_005269155; XM_005269156 |
| HNF4G | 3174 | NM_001330561; XM_017013373; XM_017013375; XM_017013374; XM_017013376; NM_004133 |
| KCNB1 | 3745 | XM_011528799; XM_006723784; NM_004975 |
| ACTG2 | 72 | NM_001199893; NM_001615 |
| SSX1 | 6756 | NM_001278691; NM_005635 |
| NELL2 | 4753 | XM_017019343; XM_017019344; NM_001145107; XM_011538396; NM_001145109; XM_017019341; NM_001145110; XM_017019342; NM_006159; XM_005268905; NM_001145108 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| FAM107A | 11170 | NM_001076778; NM_007177; NM_001282713; NM_001282714 |
| SEMA3G | 56920 | XM_024453642; NM_020163 |
| FIGF | 2277 | NM_004469 |
| TCF21 | 6943 | NM_003206; NM_198392 |
| FMO2 | 2327 | NM_001460; NR_160266; XR_921761; NM_001365900; XR_001737072; NM_001301347 |

-continued

| Gene | NCBI Gene ID | NCBI Accession Number(s) |
|---|---|---|
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| AOC3 | 8639 | XR_934584; NM_001277732; NM_003734; NR_102422; XM_011525419; XR_001752673; XM_011525420; XM_024451015; NM_001277731 |
| ADH1B | 125 | NM_001286650; NM_000668 |
| GDF10 | 2662 | NM_004962 |
| MYOC | 4653 | NM_000261 |
| SOX17 | 64321 | NM_022454 |
| FHL5 | 9457 | NM_001170807; NM_001322466; NM_001322467; NM_020482 |
| PDK4 | 5166 | NM_002612 |
| CCL23 | 6368 | NM_005064; XR_429910; NM_145898 |
| MMP11 | 4320 | NM_005940; NR_133013 |
| HBB | 3043 | NM_000518 |
| HOXA10 | 3206 | NR_037939; NM_153715; NM_018951 |
| MYBL2 | 4605 | NM_002466; NM_001278610 |
| UBE2C | 11065 | NM_001281742; NM_001281741; NM_181802; NM_181803; NR_104036; NR_104037; NM_007019; NM_181800; NM_181801; NM_181799 |
| NPY1R | 4886 | NM_000909; XM_005263031; XM_011532010 |
| TUBB3 | 10381 | NM_006086; NM_001197181 |
| ORC6 | 23594 | NR_037620; NM_014321; XM_011522978 |
| GRIN2D | 2906 | XM_011526872; NM_000836 |
| PRR4 | 11272 | NM_001098538; NM_007244 |
| COL10A1 | 1300 | XM_011535432; NM_000493; XM_011535433; XM_017010248; XM_006715333 |
| CDKN2A | 1029 | XR_929159; XM_011517676; XM_011517675; NM_001363763; NM_001195132; NM_058195; NM_000077; NM_058196; NM_058197; XM_005251343 |
| FOLR1 | 2348 | NM_000802; NM_016729; NM_016730; NM_016725; NM_016724 |
| ONECUT2 | 9480 | NM_004852 |
| MMP9 | 4318 | NM_004994 |
| HOXA11 | 3207 | NM_005523 |
| HOXB13 | 10481 | NM_006361 |
| CST1 | 1469 | NM_001898 |
| SYT12 | 91683 | XM_011545346; XM_011545347; NM_177963; XM_017018547; NM_001177880; NM_001318775; XM_017018548; XM_006718737; XM_024448766; NM_001318773 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| NXPH4 | 11247 | XM_017018747; NM_007224 |
| CXCL13 | 10563 | NM_001371558; NM_006419 |
| CDX2 | 1045 | XM_011534876; NM_001354700; XM_011534879; XM_011534875; XM_011534878; NM_001265 |
| COL11A1 | 1301 | XM_017000337; XM_017000335; XM_017000336; NR_134980; NM_080629; XM_017000334; NM_001190709; NM_001854; NM_080630 |
| RAB3B | 5865 | XM_017001958; NM_002867 |
| JPH3 | 57338 | NM_001271604; NR_073379; NM_001271605; NM_020655 |
| | | Lung_Adenocarcinoma |
| SFTPA2 | 729238 | XM_011540124; XM_005270132; NM_001320813; NM_001320814; XM_017016608; XM_011540125; NM_001098668; XM_005270128 |
| BPIFA1 | 51297 | NM_130852; NM_001243193; NM_016583 |
| LGSN | 51557 | XM_017010931; XM_017010929; XM_011535889; XM_011535892; NM_016571; XM_017010930; NM_001143940 |
| SCGB1A1 | 7356 | NM_003357 |
| NKX2-1 | 7080 | NM_001079668; NM_003317 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SFTPB | 6439 | XM_005264487; NM_198843; XM_005264488; NM_000542; NM_001367281; XM_005264490 |
| C4BPA | 722 | XM_005273252; NM_000715; XM_005273251 |
| CEACAM6 | 4680 | NM_002483; XM_011526990 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| SERPINB13 | 5275 | NM_001348267; XM_011526029; NM_001348268; NM_012397; NM_001348269; NM_001307923; NM_001348270 |
| SPRR1A | 6698 | NM_005987; NM_001199828 |
| HAND2 | 9464 | NM_021973 |
| TMC5 | 79838 | NM_001261841; NM_024780; NM_001308161; NM_001105248; NM_001105249 |
| TSPAN8 | 7103 | NM_001369760; NM_004616; XM_006719583 |

-continued

| Gene | NCBI Gene ID | NCBI Accession Number(s) |
|---|---|---|
| SPDEF | 25803 | NM_001252294; XM_005248988; NM_012391; XM_011514457 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| CP | 1356 | XM_006713500; XM_006713501; XM_017005735; XM_017005734; XM_006713499; XM_011512435; XR_427361; NM_000096; NR_046371 |
| GCNT3 | 9245 | NM_004751 |
| CLDN8 | 9073 | NM_199328; NM_012132 |
| CARTPT | 9607 | NM_004291 |
| FOXA1 | 3169 | NM_004496; XM_017021246 |
| EDN3 | 1908 | NM_207034; XM_024451847; NM_207032; XR_002958461; XR_002958462; XR_936513; NM_001302455; NM_207033; XM_006723734; XM_011528655; XM_024451848; NM_000114; XM_005260312; XM_005260313; NM_001302456 |
| CCL13 | 6357 | NM_005408 |
| DNAH2 | 146754 | XM_017024219; XM_024450606; XM_024450608; XM_024450609; XM_011523663; XM_024450604; XM_024450605; XM_024450607; NM_001303270; NM_020877; XM_011523667; XM_024450610; XM_011523670 |
| EMX2 | 2018 | NM_004098; NM_001165924 |
| CDHR1 | 92211 | XM_011540338; NM_033100; NM_001171971; XM_011540340; XM_011540337; XM_011540339 |
| RNF186 | 54546 | NM_019062 |
| TBX4 | 9496 | XM_011525490; XM_011525491; NM_001321120; XM_011525495; NM_018488 |
| LAMB3 | 3914 | XM_005273124; NM_001127641; XM_017001272; NM_000228; NM_001017402 |
| S100A7 | 6278 | NM_002963 |
| PLA2G2A | 5320 | NM_001161728; NM_000300; NM_001161729; NM_001161727; NM_001395463 |
| KCNG1 | 3755 | XM_011528800; XM_011528802; XM_011528803; XM_011528805; NM_172318; NM_002237; XM_011528801; XM_011528804; XM_011528806; XM_006723785 |
| KRT5 | 3852 | NM_000424 |
| BARX1 | 56033 | NM_021570 |
| SLC44A4 | 80736 | NM_001178045; NM_001178044; NM_025257 |
| MPPED2 | 744 | NM_001377952; NM_001145399; NR_165347; XM_005253111; NR_165336; NR_165343; NR_165339; NR_165340; NR_165345; XM_024448676; NM_001377954; XM_005253114; NM_001377953; NR_165337; NR_165344; NR_165348; XM_017018231; NR_165346; NM_001377955; NM_001377956; NM_001584; NR_165338; NR_165341; NR_165342 |
| XDH | 7498 | NM_000379; XM_011533096; XM_011533095 |
| CCL25 | 6370 | NM_001394634; NM_001394635; NM_001394638; NM_005624; NM_148888; NM_001394636; NM_001201359; NM_001394637 |
| S100A1 | 6271 | NM_006271 |
| ACTA1 | 58 | NM_001100 |
| HR | 55806 | XM_006716367; NM_005144; XM_005273569; NM_018411 |
| DLL3 | 10683 | NM_016941; NM_203486 |
| KRT13 | 3860 | NM_153490; NM_002274 |
| CBLC | 23624 | XM_011526690; XM_011526688; XR_935783; XM_005258696; XR_243917; XM_011526689; NM_001130852; NM_012116 |
| FAM107A | 11170 | NM_001076778; NM_007177; NM_001282713; NM_001282714 |
| TCF21 | 6943 | NM_003206; NM_198392 |
| FCN3 | 8547 | NM_173452; NM_003665 |
| FABP4 | 2167 | NM_001442 |
| GRIA1 | 2890 | NM_001114183; NM_001258022; NM_001258023; NM_001364166; XM_017009392; NR_157093; NM_000827; NM_001258019; NM_001258020; NM_001364165; NM_001258021; NR_047578; NM_001364167 |
| ALAS2 | 212 | NM_001037968; NM_001037967; NM_000032; NM_001037969 |
| TFAP2A | 7020 | NM_001032280; XM_006715175; NM_001042425; XM_017011232; XM_011514833; NM_001372066; NM_003220 |
| PITX1 | 5307 | NM_002653 |
| IGF2BP3 | 10643 | XM_011515092; NM_006547; XM_011515089; XM_006715639; XM_011515090; XM_011515091; XM_011515093 |
| RASAL1 | 8437 | XR_002957386; NM_001193521; NM_001394081; NM_001394082; XM_005253950; NM_001394084; NM_001394087; NM_004658; XM_017020030; XM_017020031; XM_006719642; XR_001748903; XM_006719641; NM_001301202; NM_001394083; XM_011538854; XM_017020029; NM_001394089; XR_001748902; NM_001193520; NM_001394085; NM_001394086; NM_001394088 |
| MMP11 | 4320 | NM_005940; NR_133013 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| NXPH4 | 11247 | XM_017018747; NM_007224 |
| CXCL14 | 9547 | NM_004887 |
| | | Prostate_Adenocarcinoma |
| RNF128 | 79589 | NM_024539; NM_194463 |
| PRM2 | 5620 | NM_001286358; NR_104428; NM_002762; NM_001286356; NM_001286359; NM_001286357 |

-continued

| Gene | NCBI Gene ID | NCBI Accession Number(s) |
|---|---|---|
| CENPF | 1063 | XM_017000086; NM_016343; XM_011509082 |
| DES | 1674 | NM_001927; NM_001382708; NM_001382710; NM_001382713; NM_001382709; NM_001382711; NM_001382712 |
| NKX3-1 | 4824 | NM_001256339; NR_046072; NM_006167 |
| CGREF1 | 10669 | NM_001166239; NM_006569; NM_001301324; NM_001166241; NM_001166240 |
| KLK2 | 3817 | NM_005551; NR_045762; NM_001002231; NM_001002232; NM_001256080; NR_045763 |
| SEMG1 | 6406 | NM_198139; NM_003007 |
| ASPN | 54829 | NM_001193335; NM_017680 |
| DEPDC1 | 55635 | NM_001114120; NM_017779 |
| AMACR | 23600 | NM_203382; NM_001167597; NM_001167598; NM_014324; NM_001167596; NM_001167595 |
| COL6A1 | 1291 | NM_001848 |
| ONECUT2 | 9480 | NM_004852 |
| COL10A1 | 1300 | XM_011535432; NM_000493; XM_011535433; XM_017010248; XM_006715333 |
| TRPM8 | 79054 | XM_017004891; NM_024080; XM_011511810; XM_024453132; XM_024453134; XM_024453133 |
| ATP8A2 | 51761 | XM_011535103; XM_011535113; XM_005266419; XM_024449369; XM_011535109; NM_016529; XM_011535104; XM_017020626; NM_001313741; XM_017020625; XM_011535106; XM_011535107 |
| PGC | 5225 | NM_002630; NM_001166424 |
| GDPD3 | 79153 | NM_024307 |
| MKI67 | 4288 | NM_002417; NM_001145966; XM_006717864; XM_011539818 |
| ZIC1 | 7545 | NM_003412 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| APOC1 | 341 | NM_001645; NM_001321066; NM_001379687; NM_001321065 |
| PLP2 | 5355 | NM_002668 |
| HOXB13 | 10481 | NM_006361 |
| DLX2 | 1746 | NM_004405 |
| TDRD1 | 56165 | XM_024448081; NM_001385365; NM_001365891; NM_001385366; NM_001385372; NM_001395205; XM_011539959; XM_017016415; NM_001385363; NM_001385368; XM_011539960; NM_001385364; XM_011539964; XM_011539962; XM_011539961; NM_001385367; NM_001385369; NM_001385371; NM_198795; NM_031278; XM_017016414; NM_001385370 |
| SCN1A | 6323 | NM_001353960; NM_001202435; NM_001353951; NM_001353952; NM_001353958; NM_001353950; NM_001353957; NR_148667; NM_001353949; NM_001353954; XR_001738884; NM_001353955; NM_001353961; NM_001165963; NM_001165964; NM_001353948; NM_006920; XR_001738883 |
| TRPC4 | 7223 | NM_001354806; XM_011535206; NM_016179; NM_003306; NM_001135958; NM_001135957; NM_001372055; XM_017020723; NM_001135956; NM_001354799; NM_001135955 |
| TRO | 7216 | XM_011530814; XM_017029770; XM_024452433; NM_177557; XR_001755720; NM_001039705; NM_177556; NR_073149; XM_011530808; XR_001755721; XR_001755722; NM_001271183; NR_073148; XM_006724600; XM_011530809; XM_017029768; XM_017029771; XM_017029772; XM_017029773; XM_011530811; XM_011530812; NM_016157; XM_017029769; XM_011530813; XM_017029767; NM_001271184 |
| ZWINT | 11130 | XR_428692; NM_007057; NM_001005413; XM_017015605; XM_024447784; NM_032997; NM_001005414 |
| KIF4A | 24137 | NM_012310 |
| CCNJL | 79616 | NM_001308173; NM_024565; NR_131769; XM_011534646; XM_017009847; XM_006714917; XR_427810; XM_011534647; XM_017009848; XR_427811 |
| PAGE4 | 9506 | NM_001318877; NM_007003 |
| TSPYL2 | 64061 | XM_006724592; XM_017029727; NM_022117; XR_001755719; XM_017029726 |
| MMP9 | 4318 | NM_004994 |
| HOXD13 | 3239 | XM_011511068; NM_000523; XM_011511069 |
| TPX2 | 22974 | XM_011528697; XM_011528699; NM_012112; XM_011528700 |
| FHL5 | 9457 | NM_001170807; NM_001322466; NM_001322467; NM_020482 |
| GRIA3 | 2892 | NM_007325; NM_181894; NM_000828; NM_001256743 |
| IFI6 | 2537 | NM_002038; XM_024446207; NM_022873; NM_022872 |
| RPL4 | 6124 | NM_000968 |
| ISL1 | 3670 | XM_011543380; NM_002202 |
| HPN | 3249 | NM_002151; NM_182983; XM_017026732; NM_001384133; XM_017026731; NM_001375441 |
| SRD5A2 | 6716 | XM_011533069; NM_000348; XM_011533072 |
| ACPP | 55 | NM_001099; XM_011512946; NM_001134194; XM_011512947; NM_001292037 |
| GUCY2C | 2984 | NM_004963; XM_011520631 |
| HOXC6 | 3223 | NM_153693; NM_004503 |
| LILRB4 | 11006 | NM_001278429; NM_001394939; XM_017026215; NM_001394934; NM_006847; NM_001278428; XM_017026216; NM_001394935; NM_001081438; NM_001394938; XR_002958246; NM_001278426; NM_001394933; NM_001394937; NM_001278427; NM_001278430; NM_001394936 |

-continued

| Gene | NCBI Gene ID | NCBI Accession Number(s) |
|---|---|---|
| MSMB | 4477 | NM_138634; NM_002443 |
| STAR | 6770 | NM_001007243; NM_000349 |
| KLK3 | 354 | NM_001030050; NM_001030047; NM_145864; NM_001030049; NM_001030048; NM_001648 |
| FOXF1 | 2294 | NM_001451 |
| | | Urinary_Bladder_Urothelial_Carcinoma |
| UPK2 | 7379 | NM_006760 |
| PLA2G2F | 64600 | NM_022819; NM_001360869; XM_011541955; XM_011541956 |
| CYP1A1 | 1543 | NM_001319216; NM_001319217; NM_000499 |
| S100A2 | 6273 | NM_001366407; NM_001366406; NM_005978 |
| IVL | 3713 | NM_005547 |
| VGLL1 | 51442 | NM_016267 |
| UPK3A | 7380 | NM_006953; NM_001167574 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SERPINB4 | 6318 | NM_175041; NM_002974; XM_011526138 |
| UPK1B | 7348 | NM_006952 |
| KRT20 | 54474 | NM_019010 |
| TMEM40 | 55287 | NM_001284408; NM_018306; XM_011533937; NM_001284406; NM_001284407 |
| BHMT | 635 | NM_001713 |
| GATA3 | 2625 | XM_005252443; NM_002051; XM_005252442; NM_001002295 |
| KRT6A | 3853 | NM_005554 |
| MSMB | 4477 | NM_138634; NM_002443 |
| SLC14A1 | 6563 | XM_005258333; XM_024451238; XR_001753266; NM_001146037; XM_005258329; NM_001146036; NM_001308278; NM_015865; XM_011526144; NM_001308279; XM_006722526; XM_011526142; NM_001128588 |
| SFTPA2 | 729238 | XM_011540124; XM_005270132; NM_001320813; NM_001320814; XM_017016608; XM_011540125; NM_001098668; XM_005270128 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| OLFM4 | 10562 | NM_006418 |
| ACTC1 | 70 | NM_005159 |
| GJB1 | 2705 | NM_000166; XM_011530907; NM_001097642 |
| AIM1L | 55057 | NM_017977; XM_011541672; XM_011541673; XR_001737260; NM_001039775; XR_946681; XM_005245918 |
| IL9R | 3581 | XM_011545650; XM_017029496; XM_017029499; XM_017030050; XM_017030051; XM_011531155; XM_017029498; XM_017029502; XM_017029505; XM_017030053; XM_017030055; NM_176786; XM_011531156; XM_011545645; XM_011545651; XM_017029495; XM_017029501; XM_017030054; XM_011531152; XM_011545649; XM_017030045; XM_017030046; XM_017030052; XM_017029497; XM_017030049; XM_011531157; XM_011531154; XM_017029500; XM_017029503; XM_017030044; XM_017030047; NM_002186; XM_011531151; XM_011545646; XM_011545652; XM_017029504; XM_017029506; XM_017030048 |
| NRAP | 4892 | XM_005269867; NM_006175; NM_001322945; NM_198060; XM_005269865; XM_011539832; XM_024448029; NM_001261463; XM_006717870; XM_005269864 |
| SLC5A1 | 6523 | NM_000343; XM_011530331; NM_001256314 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| CASQ1 | 844 | NM_001231 |
| ACTG2 | 72 | NM_001199893; NM_001615 |
| POU3F3 | 5455 | NM_006236 |
| UNC93A | 54346 | XM_011535908; NM_001143947; XM_011535905; XM_011535907; NM_018974; XM_017010958; XM_011535906 |
| TRPA1 | 8989 | XM_011517624; NM_007332; XM_011517625; XM_017013946 |
| KCNIP1 | 30820 | NM_001034837; NM_014592; NM_001034838; NM_001278340; XM_017009407; XM_017009408; NM_001278339 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |

-continued

| Gene | NCBI Gene ID | NCBI Accession Number(s) |
|---|---|---|
| MSLN | 10232 | NM_001177355; NM_005823; NM_013404 |
| COX6A2 | 1339 | NM_005205 |
| CCL11 | 6356 | NM_002986 |
| IRX4 | 50805 | NM_016358; NM_001278633; NM_001278632; NM_001278635; NM_001278634 |
| REG1A | 5967 | NM_002909 |
| MAGEA11 | 4110 | XM_017029522; NM_001011544; NM_005366; XM_011531164 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| HLF | 3131 | NM_002126; XM_011524705; XR_002957996; NM_001330375; XM_005257269 |
| HAND1 | 9421 | NM_004821; XM_005268531 |
| HPN | 3249 | NM_002151; NM_182983; XM_017026732; NM_001384133; XM_017026731; NM_001375441 |
| SLC34A2 | 10568 | NM_001177999; NM_006424; NM_001177998 |
| TFF3 | 7033 | NM_003226 |
| PNMAL1 | 55228 | NM_001103149; NM_018215; XM_011527067 |
| PITX2 | 5308 | NM_001204397; NM_153427; XM_024454090; NM_000325; NM_001204398; NM_001204399; NM_153426 |
| REG3A | 5068 | NM_138938; NM_002580; NM_138937 |
| CHRM2 | 1129 | NM_000739; NM_001006631; NM_001006632; NM_001378972; NM_001006630; NM_001006633; NM_001006628; NM_001006626; NM_001006627; NM_001378973; NM_001006629 |
| PENK | 5179 | NM_006211; NM_001135690 |
| CDHR2 | 54825 | NM_001171976; NM_017675 |
| MMP11 | 4320 | NM_005940; NR_133013 |
| CDH4 | 1002 | NM_001252339; NM_001794; NM_001252338 |
| FOXA2 | 3170 | NM_021784; NM_153675 |
| HOXB8 | 3218 | NM_024016; XM_005257286; XM_017024564 |
| GABRA3 | 2556 | NM_000808; XM_006724811 |
| SLC47A1 | 55244 | NM_018242 |
| F7 | 2155 | XM_011537476; XM_011537475; NM_001267554; XM_011537474; NR_051961; XM_006719963; NM_019616; NM_000131 |
| S100A1 | 6271 | NM_006271 |
| DNAJC22 | 79962 | NM_001304944; NM_024902; XM_005269157; XM_005269155; XM_005269156 |
| NPR3 | 4883 | NM_001363652; NM_001364460; NM_000908; XM_011514047; XM_011514049; XM_017009492; NM_001204375; NM_001364458; NM_024563; XM_011514050; NM_001204376 |
| FOXE1 | 2304 | NM_004473 |
| ALS2CL | 259173 | XR_427263; XR_940409; XR_940410; NR_033815; XR_001740091; XR_001740094; XR_001740095; XM_011533572; XR_001740090; XR_940406; XR_940407; XR_940408; XR_940412; NM_182774; NM_182775; NR_135622; XR_001740092; XR_001740097; XR_002959507; NM_001190707; XM_005265025; XM_006713093; XR_001740093; NM_147129; XM_006713094; XM_006713091; XR_001740096; XR_940405 |
| ACADL | 33 | NM_001608; XM_005246517; XM_017003955 |
| ARSE | 415 | XM_017029526; NM_001369079; NM_001369080; XM_005274521; XM_011545521; NM_000047; XM_005274519; NM_001282628; NM_001282631 |
| AQP5 | 362 | NM_001651; XM_005268838 |
| HOXA11 | 3207 | NM_005523 |
| CYP2W1 | 54905 | NM_017781; XM_011515440; XM_011515441 |
| KBTBD11 | 9920 | XM_017014115; XM_011534772; XM_017014117; XM_017014114; XM_017014116; XM_011534771; NM_014867 |
| TCF21 | 6943 | NM_003206; NM_198392 |
| ADAMTSL3 | 57188 | NM_207517; XM_024450000; XR_931873; XM_017022435; XM_011521822; XM_011521823; XM_017022434; NM_001301110; XM_011521825; XM_011521824 |
| GLP2R | 9340 | XM_011524077; NM_004246; XM_017025340; XM_005256861; XM_017025339; XM_017025341 |
| CFD | 1675 | NM_001317335; NM_001928 |
| FAM107A | 11170 | NM_001076778; NM_007177; NM_001282713; NM_001282714 |
| TPPP | 11076 | XM_024454346; XM_005248237; XM_017008993; NM_007030 |
| FOXF1 | 2294 | NM_001451 |
| HSPB6 | 126393 | NM_144617 |
| P2RX1 | 5023 | XM_006721529; XM_011523898; XR_934029; NM_002558; XM_011523896; XM_011523897; XM_011523899; XM_011523900; XR_934030 |
| TBX5 | 6910 | NM_181486; NM_080717; NM_000192; XM_017019912; NM_080718 |
| SGCD | 6444 | NM_000337; NM_172244; XM_005265967; XM_011534621; XM_017009723; XM_005265966; XM_017009724; NM_001128209 |
| ESM1 | 11082 | NM_001135604; NM_007036 |
| DPT | 1805 | NM_001937 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |

-continued

| Gene | NCBI Gene ID | NCBI Accession Number(s) |
|---|---|---|
| SPP1 | 6696 | NM_001251829; NM_001040060; NM_001251830; NM_000582; NM_001040058 |
| CMA1 | 1215 | NM_001836; NM_001308083 |
| FBN2 | 2201 | NM_001999; XM_017009228 |
| MSI1 | 4440 | XM_011538362; XM_011538361; XM_011538366; XM_011538365; XM_011538370; NM_002442; XM_011538364; XM_011538371; XM_006719403; XM_006719404; XM_011538363; XM_011538368 |
| TERT | 7015 | NR_149162; NM_198255; NM_198253; NR_149163; NM_001193376; NM_198254 |
| VGF | 7425 | NM_003378; XM_011516549; XM_005250561 |
| CLDN9 | 9080 | NM_020982 |
| FOLR1 | 2348 | NM_000802; NM_016729; NM_016730; NM_016725; NM_016724 |
| | | Melanoma |
| PAX3 | 5077 | NM_181457; NM_000438; NM_181459; NM_181460; NM_001127366; NM_013942; NM_181461; NM_181458 |
| IRF4 | 3662 | NM_001195286; NR_046000; NR_036585; XM_006715090; NM_002460 |
| TYR | 7299 | XM_011542970; NM_000372 |
| GAPDHS | 26330 | NM_014364 |
| PMEL | 6490 | NM_001200054; NM_001200053; NM_001320121; NM_001384361; NM_001320122; NM_006928 |
| TYRP1 | 7306 | NM_000550; XR_001746372 |
| ALX1 | 8092 | XM_011538782; NM_006982 |
| MLANA | 2315 | NM_005511 |
| CDH19 | 28513 | XM_011525931.3; XM_017025711.2; XM_011525932.1 |
| SOX10 | 6663 | NM_006941 |
| MIA | 8190 | NM_006533; NM_001202553 |
| PLP1 | 5354 | NM_001128834; NM_000533; NM_001305004; NM_199478 |
| SLC6A15 | 55117 | XM_011538525; NM_018057; NM_001146335; NM_182767 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| KRT2 | 3849 | NM_000423 |
| MFSD12 | 126321 | XM_017026288; XM_011527684; NM_021731; NM_174983; NM_001287529; XM_005259490; NM_001042680; XM_006722647 |
| APOD | 347 | NM_001647 |
| KCNK1 | 3775 | NM_002245; XM_011544184 |
| EFHD1 | 80303 | NM_001243252; NM_001308395; NM_025202 |
| CRCT1 | 54544 | NM_019060; XM_011509656 |
| KRT8 | 390601, 149501, 3856 | NM_001256293; NM_002273 |
| GPM6B | 2824 | NM_001001996; XM_017029432; NM_001318729; NM_005278; NM_001001995; XM_005274489; XM_011545497; NM_001001994 |
| CNTNAP2 | 26047 | XM_017011950; NM_014141 |
| STEAP1B | 256227 | NM_207342; NM_001382447; NM_001164460 |
| RGN | 9104 | XM_024452477; XM_006724568; XM_017029954; NM_004683; NM_001282848; NM_152869; NM_001282849; XM_006724567 |
| FA2H | 79152 | XM_011523319; XM_011523317; NM_024306 |
| TRPV2 | 51393 | XM_011523922; XM_017024730; XM_011523925; XM_017024732; XM_005256677; XM_017024731; XM_006721541; XM_005256678; XM_011523923; NM_016113; XM_005256676; XM_006721543 |
| CLDN7 | 1366 | NM_001307; NM_001185022; NM_001185023 |
| SPINT2 | 10653 | NM_001166103; NM_021102 |
| CD24 | 100133941 | NM_001291739; NR_117090; NR_117089; NM_001291738; NM_001291737; NM_013230; XM_024446293; NM_001359084 |
| HNF1B | 6928 | XM_011525161; NM_001165923; NM_001304286; XM_011525163; NM_000458; XM_011525162; NM_006481; XM_011525164; XM_011525160 |
| SUSD4 | 55061 | XM_011509687; XM_017001584; XM_017001586; XM_017001587; XM_024447937; XM_024447940; XM_005273169; XM_017001588; XM_017001585; XM_024447936; NM_017982; XM_005273172; XM_006711408; XM_011509685; XM_017001583; XM_017001589; NM_001037175 |
| ST8SIA3 | 51046 | NM_015879 |
| GABRE | 2564 | XM_024452360; NM_021990; NM_021984; XM_011531140; XM_017029388; XM_017029389; NM_004961; NM_021987; XM_017029387 |
| PHACTR1 | 221692 | XM_017010452; XM_017010454; XM_017010458; XM_017010465; NM_001322311; NM_001374582; NM_001374583; NM_001374584; NM_001322309; XM_005248934; XM_017010460; NM_001322308; NM_001374581; XM_017010459; XM_017010464; NM_001242648; NM_001322314; XM_017010462; NM_001322312; XM_017010456; XM_017010457; XM_017010466; NM_030948; XM_017010455; NM_001322310; XM_017010469; NM_001322313 |
| ASS1 | 445 | XM_017014729; XM_005272200; XM_011518705; NM_000050; NM_054012 |
| CDS1 | 1040 | XM_017007649; NM_001263; XM_017007650; XM_017007651; XM_005262687; XM_017007648 |
| PLEKHG6 | 55200 | NM_018173; XM_017019555; NM_001384602; NM_001384603; XM_006718985; NM_001384604; NR_169277; XM_011520967; NM_001144857; NM_001384599; NR_169278; NM_001144856; NM_001384598; NM_001384600; NM_001384601 |
| CACNG4 | 27092 | NM_014405 |
| CYTL1 | 54360 | NM_018659; XM_017008299 |

-continued

| Gene | NCBI Gene ID | NCBI Accession Number(s) |
|---|---|---|
| PITX1 | 5307 | NM_002653 |
| HOXD13 | 3239 | XM_011511068; NM_000523; XM_011511069 |
| CNIH3 | 149111 | NR_136288; NR_136294; NR_136297; NM_152495; NR_136292; NM_001322305; NM_001322303; NR_136293; NR_136296; NR_136295; NR_136287; NM_001322304; NR_136290; NR_136291; NM_001322302; NR_136289 |
| CFB | 629 | NM_001710 |
| MYH7 | 4625 | XM_017021340; NM_000257 |
| CLU | 1191 | NM_001831; NR_045494; NR_038335 |
| SCG5 | 6447 | NM_001144757; NM_001394278; NM_001394279; NM_003020 |
| SH3GL3 | 6457 | XR_001751374; NM_001324184; NM_001324186; XM_017022486; XR_931878; XR_001751372; NR_136712; XR_931880; XR_931882; NM_001301109; NM_001324185; NR_125370; NR_136714; XM_011521892; XR_001751375; XR_931879; NM_001301108; NM_001324183; NM_003027; NR_136713; XM_011521889; XM_011521891; XM_024450017; XR_001751373; XR_002957669; NM_001324182; NM_001324187; NR_136711 |
| RBM47 | 54502 | XM_005248108; XM_017008307; XM_024454098; NM_001371113; XM_005248103; XM_017008306; XM_017008309; XM_017008310; NM_001098634; NM_019027; XM_011513707; XM_005248109; XM_017008304; XM_017008308; NM_001371114; XM_011513708 |
| FUT6 | 2528 | XM_011527875; NM_000150; NM_001381956; NM_001369504; NM_001381957; NM_001381958; NM_001369502; NM_001381959; NM_001369505; NM_001381955; XM_011527872; NM_001040701 |
| FGFR2 | 2263 | XM_017015924; NM_001144919; XM_006717708; XM_017015925; NM_001144915; NM_001144917; NM_022975; NM_023028; XM_024447890; NM_000141; NM_001144913; NM_001320654; NM_022970; NR_073009; NM_022971; NM_022973; NM_023030; XM_006717710; XM_024447887; XM_024447888; NM_001320658; NM_022976; XM_017015920; NM_001144918; NM_022974; NM_023031; XM_024447889; XM_024447891; XM_024447892; NM_023029; XM_017015921; NM_001144914; NM_001144916; NM_022972 |
| DLX2 | 1746 | NM_004405 |
| LAD1 | 3898 | NM_005558 |
| SPP1 | 6696 | NM_001251829; NM_001040060; NM_001251830; NM_000582; NM_001040058 |
| ADH1B | 125 | NM_001286650; NM_000668 |
| MYL2 | 4633 | NM_000432 |
| ZBTB16 | 7704 | XR_001747955; NM_001354751; XM_017018259; NM_006006; NM_001354752; XM_005271658; XM_024448681; NM_001018011; NM_001354750 |
| CKM | 1158 | NM_001824 |
| FCGR1A | 2209 | NM_001378804; NM_001378805; NM_001378807; NM_001378810; NR_166122; NR_166123; NM_001378809; NM_001378811; NM_001378808; NR_166121; NM_000566; NM_001378806 |
| CCL5 | 6352 | NM_001278736; NM_002985 |
| DBNDD1 | 79007 | NM_001288709; NM_001288708; NM_001371581; NM_001042610; NM_024043 |
| SDS | 10993 | NM_006843 |
| CXCR3 | 2833 | XM_017029435; XM_017029436; NM_001504; NM_001142797; XM_005262256; XM_005262257 |
| MMP27 | 64066 | XM_011542950; XM_017018120; XM_011542948; NM_022122; XM_011542949 |
| TREM2 | 54209 | NM_001271821; NM_018965 |
| CCR5 | 1234 | NM_001100168; NM_001394783; NM_000579 |
| C1QA | 712 | NM_015991; NM_001347465; NM_001347466 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ONECUT2 | 9480 | NM_004852 |
| FAM155B | 27112 | XM_011530908; XM_011530909; NM_015686 |
| DKK1 | 22943 | NM_012242 |
| LOR | 4014 | NM_000427; XM_024447049 |
| | | Liver_Neoplasm |
| APCS | 325 | NM_001639 |
| ITIH2 | 3698 | NM_002216 |
| CRP | 1401 | NM_000567; NM_001329058; NM_001382703; NM_001329057 |
| CPB2 | 1361 | XM_017020393; NM_016413; NM_001872; NM_001278541 |
| ITIH1 | 3697 | NM_001166436; NM_002215; NM_001166434; NM_001166435 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| APOC3 | 345 | NM_000040 |
| GC | 2638 | XM_006714177; NM_001204306; NM_001204307; NM_000583 |
| CYP2C8 | 1558 | NM_001198854; NM_001198855; NM_030878; NM_000770; NM_001198853 |
| C8G | 733 | NM_000606; XR_245338 |
| APOA2 | 336 | NM_001643 |
| ALB | 213 | NM_000477 |
| ART4 | 420 | NM_021071; NM_001354646 |
| AGT | 183 | NM_000029; NM_001384479; NM_001382817 |
| PROZ | 8858 | NM_003891; XR_001749709; XR_001749708; XM_017020812; XR_001749707; NM_001256134; XM_017020813 |

-continued

| Gene | NCBI Gene ID | NCBI Accession Number(s) |
|---|---|---|
| GRIK3 | 2899 | NM_000831 |
| CRABP1 | 1381 | NM_004378 |
| DRD2 | 1813 | XM_017017296; NM_016574; NM_000795 |
| CYP21A2 | 1589 | NM_000500; NM_001128590; XM_024452555; NM_001368143; NM_001368144 |
| DBH | 1621 | NM_000787 |
| L1CAM | 3897 | NM_024003; NM_001278116; NM_001143963; NM_000425 |
| KLK8 | 11202 | NM_007196; NM_144505; NR_104008; NM_144507; NM_144506; NM_001281431 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| SFRP5 | 6425 | NM_003015 |
| GATA4 | 2626 | NM_001308093; NM_002052; NM_001308094; NM_001374273; NM_001374274 |
| MAB21L2 | 10586 | NM_006439 |
| GRIK5 | 2901 | XM_011526870; XM_011526868; XM_011526865; XM_011526867; XM_011526869; XM_011526862; XM_011526871; XM_017026713; NM_002088; XR_935810; NM_001301030 |
| HOXA7 | 3204 | NM_006896 |
| GLB1L2 | 89944 | NM_001370460; NM_001370463; NM_001370461; NM_001370462; NM_138342 |
| PCSK2 | 5126 | NM_002594; NM_001201529; NM_001201528 |
| TERT | 7015 | NR_149162; NM_198255; NM_198253; NR_149163; NM_001193376; NM_198254 |
| PLP1 | 5354 | NM_001128834; NM_000533; NM_001305004; NM_199478 |
| CXCL14 | 9547 | NM_004887 |
| KRT4 | 3851 | NM_002272 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| SLC5A1 | 6523 | NM_000343; XM_011530331; NM_001256314 |
| GPRC5A | 9052 | NM_003979 |
| GPM6B | 2824 | NM_001001996; XM_017029432; NM_001318729; NM_005278; NM_001001995; XM_005274489; XM_011545497; NM_001001994 |
| NNAT | 4826 | NM_001322802; NM_181689; NM_005386 |
| BDH1 | 622 | XM_005269355; XM_017007012; XM_017007013; NM_004051; XM_017007015; XM_017007007; XM_011513067; XM_017007008; XM_017007009; XR_001740229; NM_203314; XM_017007010; NM_203315; XM_005269352; XM_017007011 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| COLEC10 | 10584 | XM_005250756; NM_006438; NM_001324095 |
| GABRD | 2563 | XM_011541194; XM_017000936; NM_000815 |
| GDF2 | 2658 | NM_016204 |
| COL15A1 | 1306 | XM_011518214; NM_001855 |
| S100A12 | 6283 | NM_005621 |
| MDK | 4192 | NM_001012334; XM_011520116; XM_017017764; NM_001270550; NM_001270551; NM_001012333; NM_001270552; NM_002391; NR_073039 |
| PTTG1 | 9232 | XM_024446260; NM_001282382; NM_001282383; NM_004219 |
| ESM1 | 11082 | NM_001135604; NM_007036 |
| DEPDC1 | 55635 | NM_001114120; NM_017779 |
| THBS4 | 7060 | XR_002956176; XM_017009798; NM_001306214; NM_003248; NM_001306213; XM_017009799; NM_001306212 |
| HOXD9 | 3235 | NM_014213 |
| OLFML2B | 25903 | NM_001297713; XM_017000967; NM_001347700; NM_015441; XM_011509398 |
| MMP11 | 4320 | NM_005940; NR_133013 |
| PRSS1 | 5644 | NR_172951; XM_011516411; NR_172947; NM_002769; NR_172948; NR_172949; NR_172950 |
| C1QTNF3 | 114899 | NR_146599; NM_181435; NM_030945 |
| | | Thyroid_Neoplasm |
| TG | 7038 | XM_006716622; XM_017013800; XM_017013793; XM_017013795; XM_017013798; XM_017013796; XM_017013797; XM_017013794; XM_005251038; XM_005251040; NM_003235; XM_017013799; XM_005251042 |
| DCSTAMP | 81501 | XM_024447289; NM_030788; XM_024447290; NM_001257317; XM_011517324; XM_024447288; XM_011517321 |
| DAPK2 | 23604 | XM_017022049; XM_017022051; NM_001384998; NM_001395289; NM_001395290; NM_001395293; XM_011521413; NM_001384999; NM_001395284; NM_014326; XM_017022043; NM_001395288; NM_001395291; NR_169522; NR_172521; XM_017022046; NM_001384997; NM_001385000; NM_001395286; NM_001395287; XM_011521421; XM_017022044; XM_017022047; XM_017022052; NM_001395285; NM_001395292; XM_017022048; XM_017022050; NM_001395282; NR_169524; XM_011521414; XM_011521415; XM_017022045; NM_001395279; NM_001395283; NR_169523; NM_001363730; NM_001395281 |
| SLC26A4 | 5172 | XM_017012318; XM_005250425; NM_000441; XM_006716025 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |

-continued

| Gene | NCBI Gene ID | NCBI Accession Number(s) |
|---|---|---|
| TSHR | 7253 | XM_011537119; XM_005268039; XM_005268037; NM_000369; NM_001142626; XM_006720245; NM_001018036 |
| KCNJ16 | 3773 | XM_006721885; NM_170742; NM_001291625; NM_018658; XM_017024609; NM_001291622; NM_001291623; XM_017024610; NM_001270422; NM_170741; XM_005257337; XM_006721887; XM_011524781; NM_001291624; XM_006721886 |
| NKX2-1 | 7080 | NM_001079668; NM_003317 |
| FOXE1 | 2304 | NM_004473 |
| CLDN16 | 10686 | NM_006580; NM_001378492; NM_001378493 |
| GABRB2 | 2561 | NM_000813; NM_021911; NM_001371727 |
| MATN1 | 4146 | NM_002379 |
| INPP5J | 27124 | NM_001284289; XM_017028772; NM_001284288; NM_001284285; NM_014422; NM_001284286; NM_001284287; XM_011530143; NM_001002837 |
| TOX3 | 27324 | NM_001080430; XM_017023142; NM_001146188; XM_005255892; XM_011523002; XM_024450230 |
| TRPC5 | 7224 | XM_017029774; NM_012471 |
| HHEX | 3087 | NM_002729 |
| PAX8 | 7849 | NM_013992; NM_013953; NM_013952; NM_003466; NM_013951 |
| FOXD3 | 27022 | NM_012183 |
| COL4A3 | 1285 | XM_017003295; XM_005246280; XM_006712245; XM_005246277; XR_241280; XM_011510556; NM_000091; NM_031363; NM_031364; NM_031365; XM_011510555; XR_001738601; NM_031362; NM_031366 |
| S100A5 | 6276 | XM_017002031; NM_001394233; NM_001394234; XM_017002032; NM_001394232; NM_002962; XM_017002029 |
| GFRA3 | 2676 | NM_001496 |
| NELL1 | 4745 | NM_001288713; NM_006157; NM_201551; NM_001288714 |
| DUSP9 | 1852 | XM_011531123; NM_001395; NM_001318503; XM_011531124 |
| AZGP1 | 563 | NM_001185 |
| BMP8A | 353500 | XM_017001198; XM_006710616; XM_011541381; XM_011541382; XR_946642; XR_946640; XR_946641; NM_181809 |
| LECT1 | 11061 | XM_011534898; XM_011534899; NM_001011705; NM_007015; XM_011534900; XM_011534897 |
| DIO2 | 1734 | NM_001366496; NM_000793; NM_001324462; NR_158991; NM_001242503; NM_013989; NR_158990; NM_001007023 |
| LRRC2 | 79442 | XM_011534110; XM_017007177; XR_001740264; NM_024750; NM_024512 |
| HOXA7 | 3204 | NM_006896 |
| HOXA10 | 3206 | NR_037939; NM_153715; NM_018951 |
| SLC5A5 | 6528 | XM_011528194; XM_011528193; NM_000453; XM_017027158; XM_011528192 |
| AADAC | 13 | NM_001086; XM_005247104 |
| KCNJ15 | 3772 | XM_017028344; XM_017028343; XM_011529561; NM_170736; NM_170737; XM_005260975; NM_001276438; NM_001276439; NM_002243; XM_006724002; XM_011529560; XM_017028345; NM_001276435; NM_001276436; NM_001276437 |
| CACNA1I | 8911 | NM_021096; XM_017029035; XM_017029036; XM_017029037; NM_001003406 |
| GPC3 | 2719 | NM_004484; XM_017029413; NM_001164618; NM_001164617; NM_001164619 |
| KLHDC8A | 55220 | NM_001271863; NM_001271865; XM_024448121; NM_018203; NM_001271864 |
| SSX1 | 6756 | NM_001278691; NM_005635 |
| SYT12 | 91683 | XM_011545346; XM_011545347; NM_177963; XM_017018547; NM_001177880; NM_001318775; XM_017018548; XM_006718737; XM_024448766; NM_001318773 |
| BMPR1B | 658 | XM_017008558; NM_001203; NM_001256793; XM_011532201; NM_001256794; NM_001256792; XM_017008559; XM_017008560; XM_017008561 |
| MYL2 | 4633 | NM_000432 |
| CLIC3 | 9022 | XM_017015282; NM_004669; XM_017015281 |
| SPINK1 | 6690 | NM_003122; NM_001379610; NM_001354966 |
| S100A1 | 6271 | NM_006271 |
| BIRC5 | 332 | NM_001168; NM_001012271; NM_001012270 |
| UBE2C | 11065 | NM_001281742; NM_001281741; NM_181802; NM_181803; NR_104036; NR_104037; NM_007019; NM_181800; NM_181801; NM_181799 |
| AMN | 81693 | XM_024449714; XM_011537203; NM_030943; XM_011537202 |
| CBLN1 | 869 | NM_004352 |
| PBK | 55872 | NM_018492; NM_001278945; NM_001363040 |
| ALK | 238 | NM_004304; NM_001353765; XM_024452779; XR_001738688; XM_024452778 |
| CYP2J2 | 1573 | NR_134982; NR_134981; NM_000775 |
| TSPAN8 | 7103 | NM_001369760; NM_004616; XM_006719583 |
| CHGA | 1113 | NM_001301690; NM_001275; XM_011536370 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| SCD | 6319 | NM_005063 |
| SCN4A | 6329 | NM_000334 |
| TF | 7018 | NM_001063; NM_001354703; NM_001354704 |
| TPX2 | 22974 | XM_011528697; XM_011528699; NM_012112; XM_011528700 |
| TFAP2A | 7020 | NM_001032280; XM_006715175; NM_001042425; XM_017011232; XM_011514833; NM_001372066; NM_003220 |
| ACADL | 33 | NM_001608; XM_005246517; XM_017003955 |
| IQCA1 | 79781 | XM_017004960; NM_024726; NM_001270585; XM_011511865; XM_011511866; XM_011511864; NM_001270584; NR_073043 |

-continued

| Gene | NCBI Gene ID | NCBI Accession Number(s) |
|---|---|---|
| CENPF | 1063 | XM_017000086; NM_016343; XM_011509082 |
| EYA1 | 2138 | XM_017013204; XM_017013211; XM_017013212; NM_001370334; XM_011517484; XM_017013203; NM_001288574; XM_017013202; NM_000503; XM_017013207; XM_017013208; XM_017013213; NM_001370336; NM_172059; NM_172060; XM_017013205; NM_172058; NM_001288575; NM_001370333; NM_001370335; XM_011517483 |
| FSCN2 | 25794 | NM_012418; XM_011524587; XM_011524590; XR_001752466; NM_001077182 |
| SEMA3C | 10512 | NM_006379; NM_001350121; NM_001350120 |
| MYH7 | 4625 | XM_017021340; NM_000257 |
| TRIP13 | 9319 | NM_004237; XM_011514163 |
| FGFR4 | 2264 | NM_213647; NM_022963; NM_002011; NM_001291980; NM_001354984 |
| CEP55 | 55165 | XM_017016373; XM_011539920; NM_001127182; NM_018131; XM_017016372; XM_011539919; XM_011539918 |
| TFF1 | 7031 | NM_003225 |
| DLGAP5 | 9787 | XM_017021840; NM_001146015; NM_014750 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| MSC | 9242 | NM_005098 |
| SMR3B | 10879 | NM_006685 |
| PRDM16 | 63976 | NM_199454; NM_022114 |
| HOXB3 | 3213 | XM_006721854; NM_001384749; XM_024450737; XM_011524719; XM_011524720; XM_011524726; NM_001330323; XM_011524708; XM_011524721; NM_002146; XM_011524710; NM_001384747; XM_017024560; NM_001330322; NM_001384750 |
| NNAT | 4826 | NM_001322802; NM_181689; NM_005386 |
| TGFA | 7039 | NM_001308159; NM_001308158; NM_001099691; NM_003236 |
| PID1 | 55022 | NM_001330156; XM_017004404; NM_001330158; NM_017933; NM_001330157; NM_001100818 |
| KIAA1456 | 57604 | XM_005273591; XM_024447215; XM_005273584; XM_005273586; XM_011544600; XM_024447217; XM_005273588; XM_011544598; XM_024447214; XM_005273590; XM_017013710; NM_001099677; XM_005273585; XM_017013714; XM_011544596; XM_011544597; XM_011544601; XM_017013705; XM_024447216; XM_017013706; XM_024447218; XM_024447219; NM_020844 |
| PAPSS2 | 9060 | NM_001015880; NM_004670 |
| MMRN1 | 22915 | XM_005262856; NM_001371403; NM_007351 |
| LYVE1 | 10894 | NM_006691 |
| GALE | 2582 | NM_000403; NM_001127621; NM_001008216 |
| CFD | 1675 | NM_001317335; NM_001928 |
| CDH3 | 1001 | NM_001793; XM_011522800; NM_001317195; NM_001317196 |
| TNFRSF10C | 8794 | NM_003841 |
| CDKN2B | 1030 | NM_078487; NM_004936 |
| BBC3 | 27113 | XM_006723141; XM_011526722; NM_001127241; NM_001127242; NM_001127240; NM_014417 |
| IPCEF1 | 26034 | NM_001394801; NM_001130700; NM_015553; NM_001130699; NM_001394799; NM_001394800; NM_001394802 |
| CDH6 | 1004 | NM_004932; NM_001362435; XM_017008910; XM_011513921; XR_001741972 |
| KCNJ2 | 3759 | NM_000891 |
| LAMB3 | 3914 | XM_005273124; NM_001127641; XM_017001272; NM_000228; NM_001017402 |
| E2F1 | 1869 | NM_005225 |
| DUSP4 | 1846 | NM_001394; NM_057158; XM_011544428 |
| FMO2 | 2327 | NM_001460; NR_160266; XR_921761; NM_001365900; XR_001737072; NM_001301347 |
| GDF15 | 9518 | XM_024451789; NM_004864 |
| CCL21 | 6366 | NM_002989 |
| PLCH1 | 23007 | XM_011512561; XM_011512565; XM_011512566; NM_001349250; XM_011512567; XM_017005925; XM_005247239; XM_005247238; XM_011512560; XM_017005926; NM_001130960; NM_001349252; NM_014996; XM_017005927; NM_001130961; NM_001349251; XM_011512562; XM_017005923 |
| MYOC | 4653 | NM_000261 |
| GABRD | 2563 | XM_011541194; XM_017000936; NM_000815 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| SLC12A5 | 57468 | NM_020708; NM_001134771 |
| VTCN1 | 79679 | NM_001253849; NM_024626; NR_045604; XM_017002335; NM_001253850; NR_045603; XM_011542143 |

-continued

| Gene | NCBI Gene ID | NCBI Accession Number(s) |
|---|---|---|
| OLAH | 55301 | XM_024448060; XM_017016376; NM_018324; NM_001039702 |
| MMP11 | 4320 | NM_005940; NR_133013 |
| AIM1L | 55057 | NM_017977; XM_011541672; XM_011541673; XR_001737260; NM_001039775; XR_946681; XM_005245918 |
| CDH2 | 1000 | XM_011525788; NM_001308176; XM_017025514; NM_001792 |
| HAPLN1 | 1404 | XM_017009052; XM_017009051; NM_001884; XM_017009054; XM_017009053; XM_011543168 |
| DES | 1674 | NM_001927; NM_001382708; NM_001382710; NM_001382713; NM_001382709; NM_001382711; NM_001382712 |
| ADRA2C | 152 | NM_000683 |
| CD19 | 930 | NM_001178098; NM_001385732; NM_001770; XR_950871; XM_006721103; NR_169755; XM_011545981 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| | | Glioma |
| AQP4 | 361 | NM_001317387; NM_001364287; NM_001364286; NM_001317384; XM_011525942; NM_001650; NM_001364289; NM_004028 |
| OLIG2 | 10215 | XM_005260908; NM_005806 |
| GFAP | 2670 | XM_024450691; XM_024450690; NM_001131019; XM_024450692; XM_024450693; NM_001242376; NM_002055; NM_001363846 |
| HAPLN2 | 60484 | XM_024448828; XM_005245415; XM_011509853; XM_017002020; XM_017002021; NM_021817 |
| GPR37L1 | 9283 | NM_004767; XM_011510158 |
| PMP2 | 5375 | NM_002677; NM_001348381 |
| GPM6A | 2823 | NM_201592; NM_001261447; NM_001388091; NM_001261448; NM_005277; NR_048571; NM_001388090; NM_201591 |
| TIMP4 | 7079 | NM_003256 |
| SLC1A3 | 6507 | XM_024446182; XM_011514084; NM_004172; NM_001289940; NM_001289939; NM_001166695; XM_005248342; XM_024446181; NM_001166696 |
| MLC1 | 23209 | XR_001755180; NM_001376472; NM_001376478; NR_164811; NR_164812; NM_001376473; NM_001376477; NM_139202; NM_001376476; NM_001376479; NM_001376484; NM_015166; NR_164813; NM_001376474; NM_001376481; XM_011530678; NM_001376480; NM_001376483; NM_001376475; NM_001376482 |
| NCAN | 1463 | NM_004386 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| CDH20 | 28316 | XR_001753187; NM_031891; XR_001753186; XM_024451165 |
| PTPRZ1 | 5803 | NM_002851; NM_001206838; NM_001369396; NM_001369395; NM_001206839 |
| MT3 | 4504 | NM_005954 |
| FOXG1 | 2290 | NM_005249 |
| DLL3 | 10683 | NM_016941; NM_203486 |
| KRT8 | 390601, 149501, 3856 | NM_001256293; NM_002273 |
| PERP | 64065 | XM_024446520; NM_022121 |
| TACSTD2 | 4070 | NM_002353 |
| KRT7 | 3855 | XM_017019294; XR_001748700; NM_005556; XM_011538325; XR_001748699 |
| TES | 26136 | NM_015641; NM_152829; XM_005250258 |
| EVPL | 2125 | NM_001988; NM_001320747 |
| KCNK5 | 8645 | XM_006715235; XM_005249456; NM_003740 |
| EPCAM | 4072 | NM_002354 |
| RIPK4 | 54101 | NM_020639 |
| SOX21 | 11166 | NM_007084 |
| DSP | 1832 | NM_001008844; NM_004415; NM_001319034 |
| C2orf54 | 79919 | XM_011511877; NM_001085437; NM_001282921; NM_024861 |
| NEUROD4 | 58158 | NM_021191 |
| CDH1 | 999 | NM_001317186; NM_004360; NM_001317185; NM_001317184 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |
| CYP2C18 | 1562 | NM_000772; NM_001128925 |
| EPS8L1 | 54869 | NM_133180; NM_139204; XM_011527052; XM_005259020; NM_017729; XM_011527051; XM_011527050 |
| PDLIM1 | 9124 | XM_011540330; NM_020992 |
| SPINK5 | 11005 | XM_011537551; NM_006846; NM_001127698; NM_001127699 |
| TNNC1 | 7134 | NM_003280 |
| CD55 | 1604 | NM_001300904; NM_001114543; NM_001114544; XM_017000467; NM_001114752; NM_001300902; NM_001300903; NM_000574; NR_125349 |
| LLGL2 | 3993 | XM_017024627; XR_002957999; XR_002958003; XM_017024626; XR_002958004; XM_017024629; XM_017024630; XM_017024631; XR_002958005; XR_002958002; NM_001015002; XM_011524802; XM_017024628; XR_002958000; XM_024450747; XR_001752508; NM_001031803; XM_017024625; XR_002958001; NM_004524 |
| ITPR3 | 3710 | XM_017010832; XM_011514577; NM_002224 |
| SPINT2 | 10653 | NM_001166103; NM_021102 |
| ANXA3 | 306 | XR_001741215; NM_005139 |

-continued

| Gene | NCBI Gene ID | NCBI Accession Number(s) |
|---|---|---|
| HCN2 | 610 | NM_001194 |
| F2R | 2149 | NM_001311313; NM_001992 |
| MYL2 | 4633 | NM_000432 |
| KIFC1 | 3833 | XM_011514585; XM_017010836; NM_002263; XM_011514587; XM_017010837 |
| BIRC5 | 332 | NM_001168; NM_001012271; NM_001012270 |
| NDC80 | 10403 | NM_006101 |
| PBK | 55872 | NM_018492; NM_001278945; NM_001363040 |
| TACC3 | 10460 | XM_005247930; XM_017007653; NM_006342; XM_005247929; XM_011513386 |
| EGFR | 1956 | NM_001346899; NM_201282; NM_201284; NM_001346898; NM_001346900; NM_001346897; NM_201283; NM_001346941; NM_005228 |
| DTL | 51514 | XM_011509614; NM_001286229; NM_001286230; NM_016448 |
| | | Sarcoma |
| RAB11FIP1 | 80223 | NM_001002814; NM_025151; XM_017013869; NM_001002233 |
| LOXL1 | 4016 | XM_017022179; XM_011521555; NM_005576; XR_931824 |
| ZNF385D | 79750 | XM_017007203; NM_024697; XM_017007200; XM_011534124; XM_017007195; XM_017007202; XM_017007193; XM_017007197; XM_011534122; XM_017007191; XM_017007192; XM_017007199; XM_017007201; XM_024453754; XM_011534123; XM_017007194; XM_017007196; XM_017007198 |
| MYL2 | 4633 | NM_000432 |
| AGRN | 375790 | XM_011541429; NM_001305275; NM_001364727; XR_946650; NM_198576; XM_005244749 |
| KCNG1 | 3755 | XM_011528800; XM_011528802; XM_011528803; XM_011528805; NM_172318; NM_002237; XM_011528801; XM_011528804; XM_011528806; XM_006723785 |
| NKX3-2 | 579 | NM_001189 |
| NXPH3 | 11248 | NM_007225 |
| HMX1 | 3166 | NM_018942; NM_001306142 |
| CLDN7 | 1366 | NM_001307; NM_001185022; NM_001185023 |
| TUBB4A | 10382 | NM_001289129; NM_001289131; NM_006087; NM_001289123; NM_001289127; NM_001289130 |
| RAB17 | 64284 | XM_006712689; XM_017004693; NM_022449; XM_017004694; NR_033308 |
| EPCAM | 4072 | NM_002354 |
| GH1 | 2688 | NM_022559; NM_022561; NM_022560; NM_022562; NM_000515 |
| ERBB3 | 2065 | NM_001005915; NM_001982 |
| ELMO3 | 79767 | XM_024450447; NM_024712 |
| SYNC | 81493 | XM_024450011; NM_001161708; XM_024450013; NM_030786; XM_024450012; XM_024450010; XM_024450014 |
| TPD52 | 7163 | NM_005079; NR_105035; NM_001287143; NM_001387779; NR_105037; NR_170694; NM_001025252; NM_001025253; NR_170693; NM_001287140; NR_105034; NM_001387780; NM_001287142; NM_001287144; NM_001387778; NR_105033; NR_105036 |
| S100B | 6285 | NM_006272; XM_017028424 |
| PALMD | 54873 | NM_017734 |
| CYP46A1 | 10858 | NM_006668; XM_005267274; XM_011536365; XM_011536364; XM_017020933 |
| PNPLA2 | 57104 | NM_020376 |
| SERINC2 | 347735 | NM_178865; NM_001199039; NM_018565; NM_001199038; NM_001199037 |
| PRSS12 | 8492 | XM_011532387; NM_003619; XM_005263318 |
| OLR1 | 4973 | NM_002543; NM_001172632; NM_001172633 |
| TNNT3 | 7140 | NM_001042781; NM_001363561; NM_001367847; NM_001367849; XM_006718299; XM_017018207; XM_017018208; XM_017018217; XM_024448669; XM_024448670; XM_024448671; XM_011520343; XM_017018211; XM_017018215; NM_001297646; NM_001367848; NM_001367850; XM_006718294; XM_006718300; XM_017018212; XM_017018219; NM_001042780; NM_001367845; XM_006718288; XM_017018209; XM_017018210; XM_017018218; NM_001367852; XM_017018206; XM_017018213; XM_024448672; NM_001367843; NM_001367844; NM_001367846; NM_001367851; XM_017018214; XM_017018216; NM_001042782; NM_001367842; XM_017018205; NM_006757 |
| HOOK1 | 51361 | XR_946665; XM_017001424; XM_006710676; XR_246271; XM_011541563; XM_024447520; XM_011541562; NM_015888 |
| GDPD3 | 79153 | NM_024307 |
| EPM2A | 7957 | NM_001368131; XM_017011301; NM_001360057; NM_001360064; NM_001368129; XM_024446550; XM_011536113; NM_001368130; NM_005670; NR_153398; XM_017011302; XM_011536116; NM_001360071; NM_001018041; XM_024446551; NM_001368132 |
| C1orf116 | 79098 | XM_011509973; NM_001083924; XM_005273259; XM_006711530; NM_023938 |
| CCDC68 | 80323 | XM_011526201; XM_017026011; XM_011526198; XM_006722552; NM_001143829; XM_011526199; XM_011526203; XM_011526204; NM_025214; XM_011526200; XM_011526202 |
| VGF | 7425 | NM_003378; XM_011516549; XM_005250561 |
| PLEK2 | 26499 | NM_016445 |
| FBN2 | 2201 | NM_001999; XM_017009228 |
| FGF7 | 2252 | NM_002009 |
| RCN3 | 57333 | NM_020650; XM_024451620 |
| FBXO2 | 26232 | NM_012168 |
| COX7A1 | 1346 | NM_001864 |
| EBF2 | 64641 | NM_022659 |

-continued

| Gene | NCBI Gene ID | NCBI Accession Number(s) |
|---|---|---|
| ADAMTS2 | 9509 | NM_021599; NM_014244 |
| TAGLN3 | 29114 | NM_001008272; NM_001008273; NM_013259 |
| HAND2 | 9464 | NM_021973 |
| MT3 | 4504 | NM_005954 |
| RAP1GAP | 5909 | XR_001737354; XR_001737351; NM_001145657; NM_001350527; NM_001350528; NM_001388217; NM_001388229; NM_001388241; NM_001388254; NM_001388259; NM_001388263; NM_001388266; NM_001388267; NM_001388276; NM_001388285; NM_001388287; NM_001388290; NM_001388294; NM_001388295; NR_170904; NR_170911; NR_170915; NR_170920; NR_170928; XR_001737352; XR_946730; NM_001145658; NM_001330383; NM_001388205; NM_001388211; NM_001388216; NM_001388221; NM_001388224; NM_001388227; NM_001388239; NM_001388245; NM_001388280; NM_001388281; NR_170900; NR_170923; NR_170927; NM_001350526; NM_001388222; NM_001388243; NM_001388252; NM_001388256; NM_001388258; NM_001388261; XR_946728; NM_001388203; NM_001388209; NM_001388206; NM_001388230; NM_001388231; NM_001388240; NM_001388242; NM_001388247; NM_001388253; NM_001388255; NM_001388288; NM_001388289; NM_001388296; NR_170907; NR_170909; XR_001737349; NM_001350525; NM_001388204; NM_001388207; NM_001388210; NM_001388219; NM_001388220; NM_001388228; NM_001388233; NM_001388235; NM_001388236; NM_001388238; NM_001388248; NM_001388284; NM_001388286; NR_170910; NR_170924; NM_001388202; NM_001388208; NM_001388214; NM_001388218; NM_001388234; NM_001388249; NM_001388270; NM_001388279; NM_002885; NR_170901; NR_170902; NR_170903; NR_170912; NR_170913; NR_170926; XR_946726; NM_001350524; NM_001388200; NM_001388212; NM_001388213; NM_001388215; NM_001388225; NM_001388226; NM_001388244; NM_001388246; NM_001388251; NM_001388282; NM_001388283; NR_170908; NR_170914; NR_170921; NR_170925; NM_001388201; NM_001388223; NM_001388237; NM_001388250; NM_001388264; NM_001388269; NM_001388273; NM_001388291; NM_001388292; NM_001388293 |
| GAS1 | 2619 | NM_002048 |
| CDKL2 | 8999 | XR_001741344; XR_001741345; XM_017008811; XM_017008810; XM_006714406; NM_003948; XM_017008809; NM_001330724 |
| SCN4A | 6329 | NM_000334 |
| COL5A1 | 1289 | NM_000093; XM_017014266; XR_001746183; NM_001278074 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| POPDC2 | 64091 | NM_001369919; NM_022135; NM_001308333 |
| TFAP2A | 7020 | NM_001032280; XM_006715175; NM_001042425; XM_017011232; XM_011514833; NM_001372066; NM_003220 |
| EN1 | 2019 | NM_001426 |
| CHRD | 8646 | XM_017007390; NR_130747; NM_177978; XM_017007388; XM_017007391; XM_024453803; XR_001740336; NM_001304472; XM_017007392; XR_001740334; XM_011513254; XR_002959603; NM_001304473; NM_177979; NM_001304474; NM_003741; XM_017007389; XM_017007393; XM_017007394; XR_001740335; XR_001740337 |
| PLS1 | 5357 | NM_001172312; XM_011512901; NM_001145319; XM_006713660; XM_017006626; XM_011512903; XM_017006627; XM_011512900; NM_002670 |
| ELF3 | 1999 | NM_004433; XM_005244942; NM_001114309 |
| DBNDD1 | 79007 | NM_001288709; NM_001288708; NM_001371581; NM_001042610; NM_024043 |
| RAB23 | 51715 | NM_183227; NM_001278666; NM_001278668; NM_016277; NM_001278667; NR_103822 |
| CD24 | 100133941 | NM_001291739; NR_117090; NR_117089; NM_001291738; NM_001291737; NM_013230; XM_024446293; NM_001359084 |
| SLC43A1 | 8501 | XM_017018453; XM_024448727; XM_011545322; XM_011545321; XM_017018452; XM_011545320; XM_024448728; NM_001198810; XM_005274358; XM_017018451; NM_003627 |
| AMPH | 273 | XM_006715689; XM_017011996; XM_006715690; XM_006715691; XM_011515271; XM_017011995; NM_001635; NM_139316 |
| KRT8 | 390601, 149501, 3856 | NM_001256293; NM_002273 |
| HOXA7 | 3204 | NM_006896 |
| CORO2A | 7464 | NM_003389; NM_052820; XM_011518986 |
| RNF43 | 54894 | XM_011524955; XM_011524956; NM_017763; NM_001305544; XM_017024800; NM_001305545 |
| PER1 | 5187 | XM_005256689; XM_005256690; XM_024450803; NM_002616 |
| SHOX2 | 6474 | XM_006713727; NM_001163678; XM_017007055; NM_006884; XM_006713728; XM_017007053; NM_003030; XM_017007054 |
| MYRF | 745 | NM_013279; XM_005274222; XM_005274224; XM_005274226; XM_005274228; XM_005274223; XM_005274225; XM_005274227; XM_011545234; XM_024448677; NM_001127392 |
| GPR1 | 2825 | NM_001098199; NM_001261452; NM_001261454; NM_005279; XM_005246471; NM_001261455; NM_001389445; NM_001261453 |
| CIDEC | 63924 | NM_001321142; NM_001199552; NM_001378491; NM_001199623; NM_001199551; NM_001321144; NM_022094; NM_001321143 |

-continued

| Gene | NCBI Gene ID | NCBI Accession Number(s) |
|---|---|---|
| APOD | 347 | NM_001647 |
| KRT2 | 3849 | NM_000423 |
| HOXD9 | 3235 | NM_014213 |
| KCNB2 | 9312 | XM_017013981; XR_001745620; XR_001745621; NM_004770; XM_017013982 |
| FABP6 | 2172 | NM_001130958; NM_001040442; NM_001445 |
| CCNB1 | 891 | NM_031966 |
| DSP | 1832 | NM_001008844; NM_004415; NM_001319034 |
| KRT5 | 3852 | NM_000424 |
| LGI2 | 55203 | XM_011513850; NM_018176; XM_017008356 |
| CKM | 1158 | NM_001824 |
| ITGB4 | 3691 | XM_005257311; XM_006721866; XM_006721870; NM_000213; NM_001005619; NM_001005731; XM_005257309; XM_011524752; XM_006721867; XM_011524751; NM_001321123; XM_006721868 |
| AP1M2 | 10053 | NM_001300887; XM_024451304; NM_005498; XM_024451303 |
| QPRT | 23475 | XM_005255223; NR_134536; NM_001318250; NM_001318249; NM_014298; XM_017023101 |
| FOXD1 | 2297 | NM_004472 |
| NPPA | 4878 | NM_006172 |
| DDR2 | 4921 | NM_001014796; XM_011509587; XM_011509588; NM_001354982; NM_006182; NM_001354983 |
| PFKFB1 | 5207 | NM_001271804; XM_017029578; XM_017029576; NM_002625; NR_073450; XM_024452389; XM_017029577; NM_001271805 |
| BNC2 | 54796 | NM_001317939; NM_017637; NM_001317940 |
| PCOLCE | 5118 | XM_024446785; NM_002593 |
| GIPC2 | 54810 | NM_017655; NM_001304725 |
| FZD2 | 2535 | NM_001466 |
| COL1A2 | 1278 | NM_000089 |
| FST | 10468 | XM_005248403; XM_011543099; XM_005248400; XM_017008955; NM_013409; XM_005248401; XM_005248402; XM_017008954; XM_024454326; NM_006350 |
| BIK | 638 | NM_001197 |
| C1QL1 | 10882 | NM_006688 |
| ZWINT | 11130 | XR_428692; NM_007057; NM_001005413; XM_017015605; XM_024447784; NM_032997; NM_001005414 |
| MYOC | 4653 | NM_000261 |
| GABRQ | 55879 | NM_018558; XM_011531184 |
| SCN5A | 6331 | NM_001160160; NM_001099405; NM_001354701; XM_011533991; XM_017007017; NM_001160161; NM_198056; NM_000335; NM_001099404 |
| DTL | 51514 | XM_011509614; NM_001286229; NM_001286230; NM_016448 |
| | | Neuroendocrine |
| CA7 | 766 | NM_001365337; XM_011523312; NM_001014435; NM_005182 |
| TGM3 | 7053 | NM_003245 |
| HLA-G | 3135 | XM_017010817; NM_001384280; XM_017010818; NM_002127; XM_024446420; NM_001363567; NM_001384290 |
| MYL2 | 4633 | NM_000432 |
| CCNB1 | 891 | NM_031966 |
| UPK3A | 7380 | NM_006953; NM_001167574 |
| LYVE1 | 10894 | NM_006691 |
| DES | 1674 | NM_001927; NM_001382708; NM_001382710; NM_001382713; NM_001382709; NM_001382711; NM_001382712 |
| PLA2G1B | 5319 | NM_000928 |
| DBNDD1 | 79007 | NM_001288709; NM_001288708; NM_001371581; NM_001042610; NM_024043 |
| MET | 4233 | NM_001324402; NM_001324401; XM_006715990; NM_001127500; XM_011516223; NM_000245; XR_001744772; |
| ESM1 | 11082 | NM_001135604; NM_007036 |
| COL10A1 | 1300 | XM_011535432; NM_000493; XM_011535433; XM_017010248; XM_006715333 |
| KRT2 | 3849 | NM_000423 |
| HRASLS2 | 54979 | NM_017878; XM_011545120 |
| DGKI | 9162 | NM_004717; NM_001321708; XM_017012788; NM_001321710; NM_001388092; NM_001321709 |
| SLC18A1 | 6570 | XM_011544626; NM_003053; XM_011544625; NM_001142325; NM_001135691; NM_001142324 |
| MMP11 | 4320 | NM_005940; NR_133013 |
| FIGF | 2277 | NM_004469 |
| SLC16A7 | 9194 | XM_011538990; XM_011538992; NM_004731; NM_001270622; XM_017020225; XM_017020227; NR_073055; XM_011538989; NM_001270623; XM_024449276; XM_011538991; XM_011538993; NR_073056; XM_005269231; XM_011538995; XM_017020226; XM_017020224 |
| VIP | 7432 | XM_006715562; XM_005267135; NM_003381; NM_194435 |
| CD200 | 4345 | NM_001318830; NR_158642; NM_001004197; NM_001365853; NM_001365855; NM_001318826; NM_001365852; NM_001004196; NM_001318828; NM_001365851; NM_005944; NM_001365854 |
| SLITRK3 | 22865 | NM_014926; NM_001318810; NM_001318811 |
| FCN2 | 2220 | XM_011518392; NM_015838; NM_015839; NM_015837; NM_004108; XM_006717015 |
| MT3 | 4504 | NM_005954 |
| ADRB2 | 154 | NM_000024 |

-continued

| Gene | NCBI Gene ID | NCBI Accession Number(s) |
|---|---|---|
| CACNG4 | 27092 | NM_014405 |
| SYNPO2L | 79933 | NM_024875; NM_001114133; XM_005270159; XM_005270158 |
| VILL | 50853 | NM_001370265; NR_163266; NR_163267; NM_001370264; NM_015873; NM_001385039; NM_001385038 |
| AGRN | 375790 | XM_011541429; NM_001305275; NM_001364727; XR_946650; NM_198576; XM_005244749 |
| CYP11B1 | 1584 | NM_001026213; NM_000497 |
| EPHB3 | 2049 | NM_004443 |
| KCNMB1 | 3779 | NM_004137 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| SCGB2A1 | 4246 | NM_002407 |
| ABCC4 | 10257 | XM_017020321; NM_001301829; NM_005845; XM_005254025; XM_017020319; NM_001301830; NM_001105515; XM_017020322; XM_017020320 |
| CRNN | 49860 | NM_016190 |
| CHGB | 1114 | NM_001819 |
| HIGD1B | 51751 | XM_011524891; NM_016438; XM_006721946; XM_006721947; XM_017024742; NR_073504; XM_006721948; XM_017024743; NM_001271880 |
| CELA2A | 63036 | NM_033440 |
| CLPS | 1208 | NM_001832; NM_001252597; NM_001252598 |
| HECW1 | 23072 | XM_006715670; XM_006715671; XM_011515225; XM_017011882; XM_011515220; XM_011515223; XM_017011886; XM_017011888; NM_001287059; NM_015052; XM_017011883; XM_006715673; XM_011515222; XM_011515224; XM_017011884; XM_017011889; XM_017011885; XM_017011887; XM_011515226; XM_017011890; XM_005249665 |
| ERBB3 | 2065 | NM_001005915; NM_001982 |
| PPY | 5539 | NM_002722; NM_001319209; XM_011524978 |
| CKM | 1158 | NM_001824 |
| CXorf36 | 79742 | XM_006724559; NM_176819; NM_024689; XM_005272670 |
| HOXA10 | 3206 | NR_037939; NM_153715; NM_018951 |
| RIBC2 | 26150 | XM_005261524; XM_011530126; NM_015653; XM_017028766 |
| CDH19 | 28513 | XM_011525931.3; XM_017025711.2; XM_011525932.1 |
| SLC24A2 | 25769 | XM_017014592; NM_001193288; NM_001375850; NM_020344; NM_001375851 |
| ADAMDEC1 | 27299 | NM_001145272; NM_014479; NM_001145271; NR_156422 |
| MMP28 | 79148 | XM_017025061; XM_017025062; NM_024302; XM_011525227; NM_001032278; NM_032950; XM_011525228; XM_011525225; XM_011525230; XM_024450943; XM_011525226; NR_111988; XM_011525229; XM_011525231; XM_011525232; XM_017025063; XM_017025064 |
| KRT17 | 3872 | NM_000422 |
| S100P | 6286 | NM_005980 |
| NOX4 | 50507 | NM_001291926; XM_006718849; NM_016931; NM_001143837; XM_011542857; NM_001143836; NM_001291927; XM_017017842; XM_017017843; XM_017017844; XM_017017841; XM_017017845; NM_001291929; NM_001300995; NR_120406 |
| CELSR1 | 9620 | XM_011530554; XM_011530555; NM_001378328; XM_011530553; NM_014246 |
| CPB1 | 1360 | NM_001871 |
| CCL23 | 6368 | NM_005064; XR_429910; NM_145898 |
| CELA3A | 10136 | NM_005747 |
| WISP2 | 8839 | NM_001323369; XM_017028116; NM_003881; XM_017028117; NM_001323370 |
| GCG | 2641 | NM_002054 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| PDX1 | 3651 | NM_000209; XR_941580; XR_941578; |
| FABP7 | 2173 | NM_001319039; NM_001319041; NM_001319042; NM_001446 |
| NRTN | 4902 | NM_004558 |
| NMB | 4828 | XM_017022239; NM_021077; NM_205858 |
| AMHR2 | 269 | XM_011538179; XM_011538184; XM_017019179; NM_020547; XR_002957309; XR_002957311; XM_011538178; XM_011538176; XM_011538181; XM_011538185; NM_001164691; XM_011538174; XM_011538183; XR_002957310; XM_011538186; XR_002957312; NM_001164690; XM_011538173; XM_011538180; XM_024448938 |
| WNT2 | 7472 | NM_003391; NR_024047 |
| GFAP | 2670 | XM_024450691; XM_024450690; NM_001131019; XM_024450692; XM_024450693; NM_001242376; NM_002055; NM_001363846 |
| CYP11B2 | 1585 | NM_000498 |
| SGCA | 6442 | XM_011525122; XM_011525120; XM_011525121; XM_024450873; NM_001135697; NR_135553; XR_002958056; XM_011525124; NM_000023; XM_011525123 |
| PNMA2 | 10687 | NM_007257; XM_011544365 |
| CEL | 1056 | NM_001807 |
| MT1M | 4499 | NM_176870 |
| CST1 | 1469 | NM_001898 |
| ITPKB | 3707 | NM_002221; NM_001388404; XM_017001211 |
| ALAS2 | 212 | NM_001037968; NM_001037967; NM_000032; NM_001037969 |
| INS | 3630 | NM_001185098; NM_001185097; NM_000207; NM_001291897 |
| LGALS4 | 3960 | NM_006149; XM_011526974; XM_011526973 |

-continued

| Gene | NCBI Gene ID | NCBI Accession Number(s) |
|---|---|---|
| PLP1 | 5354 | NM_001128834; NM_000533; NM_001305004; NM_199478 |
| GABRQ | 55879 | NM_018558; XM_011531184 |
| PLAG1 | 5324 | XM_017013576; XM_017013577; NM_001114635; XM_011517544; NM_001114634; NM_002655 |
| LIPF | 8513 | NM_004190; NM_001198829; NM_001198830; NM_001198828; XM_011540311 |
| CYP11A1 | 1583 | NM_000781; NM_001099773 |
| FABP1 | 2168 | NM_001443 |
| S100A12 | 6283 | NM_005621 |
| IL20RA | 53832 | NM_001278722; XM_011535904; XM_017010955; NM_001278724; NM_014432; XM_006715506; NM_001278723; XM_017010954 |
| NR5A1 | 2516 | NM_004959 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| ERBB2 | 2064 | XM_024450643; NM_001005862; NM_001382784; NM_001382785; NM_001382788; NM_001382792; NM_001382793; NM_001382803; NM_001289937; NM_001382786; NM_001382800; NM_001382802; NM_001382806; XM_024450641; NM_001382782; NM_001382789; NM_001382795; NM_001289936; NM_001382797; NM_001382805; NM_004448; NR_110535; XM_024450642; NM_001289938; NM_001382791; NM_001382801; NM_001382783; NM_001382790; NM_001382794; NM_001382798; NM_001382799; NM_001382787; NM_001382796; NM_001382804 |
| SLC12A3 | 6559 | NM_000339; NM_001126108; NM_001126107; XM_005256119 |
| GRHL2 | 79977 | XM_011517306; XM_024447286; NM_001330593; NM_024915; XM_011517307 |
| HBB | 3043 | NM_000518 |
| C7 | 730 | NM_000587 |
| MOGAT2 | 80168 | XM_024448696; NM_025098; XM_011545267 |
| MYOC | 4653 | NM_000261 |
| TP73 | 7161 | NM_001126242; NM_001204191; NM_001126240; NM_001204185; NM_001204187; NM_001204184; NM_001204186; NM_001204192; NM_001126241; NM_001204190; NM_001204188; NM_001204189; NM_005427 |
| EPS8L3 | 79574 | XM_017002329; XM_011542135; XM_011542134; NM_139053; NM_001319952; NM_024526; XM_011542133; XM_017002328; XR_001737407; XM_017002327; NM_133181; XM_011542132; XR_001737406 |
| BCAM | 4059 | NM_001013257; NM_005581 |
| KHDC1L | 100129128 | NM_001126063 |
| DTL | 51514 | XM_011509614; NM_001286229; NM_001286230; NM_016448 |
| CXCR2 | 3579 | XM_017003992; XM_017003990; NM_001168298; NM_001557; XM_005246530; XM_017003991 |
| KRT24 | 192666 | XM_017024299; NM_019016; XM_006721739; XM_011524460 |
| SIX1 | 6495 | XM_017021602; NM_005982 |
| PTPRH | 5794 | XM_011527188; XM_017027061; NM_001161440; XM_017027058; XR_001753731; XM_017027056; XM_017027062; XM_017027059; XM_011527183; XR_001753730; XM_017027063; XM_017027064; XM_011527190; XM_017027057; XM_017027060; NM_002842 |
| TNXB | 7148 | NM_001365276; NM_019105; NM_032470 |
| SLC6A7 | 6534 | XR_001742210; XM_024446190; XR_001742212; XM_017009770; XR_001742211; XM_017009767; XM_017009769; XM_017009768; NM_014228 |
| PLAGL1 | 5325 | NM_001289037; NM_001289040; NM_001289046; NM_001289047; NM_001317157; NM_001080956; NM_001080951; NM_001080955; NM_001289044; NM_001289048; NM_001289049; NM_001317159; NM_001317162; NM_001289038; NM_001080953; NM_001080954; NM_001289043; NM_001317156; NM_001317158; NM_001080952; NM_001289041; NM_001289045; NM_001317161; NM_002656; NM_006718; NM_001289039; NM_001289042; NM_001317160 |
| ADH1B | 125 | NM_001286650; NM_000668 |
| FSTL4 | 23105 | XM_011543284; XM_011543286; XM_011543287; XM_011543283; XM_017009251; NM_015082 |
| MFAP2 | 4237 | NM_002403; NM_017459; NM_001135247; NM_001135248 |
| TREM2 | 54209 | NM_001271821; NM_018965 |
| COL1A2 | 1278 | NM_000089 |
| LRP2 | 4036 | XM_011511183; NM_004525; XM_011511184 |
| CDK1 | 983 | NM_001320918; NM_033379; NM_001170406; NM_001786; NM_001130829; XM_005270303; NM_001170407 |
| EBF2 | 64641 | NM_022659 |
| CDH3 | 1001 | NM_001793; XM_011522800; NM_001317195; NM_001317196 |
| SVEP1 | 79987 | NM_024500; NM_153366 |
| CNNM1 | 26507 | NM_001345888; XM_011539631; XR_002956974; NM_020348; NM_001345887; NM_001345889; NR_144311; XR_945667 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |

-continued

| Gene | NCBI Gene ID | NCBI Accession Number(s) |
|---|---|---|
| ADAM12 | 8038 | XM_017016705; NM_001288973; NM_001288974; NM_001288975; XM_017016706; NM_003474; NM_021641; XM_024448210 |
| MAGEA1 | 4100 | NM_004988 |
| | | Pheochromocytoma |
| PHOX2A | 401 | NM_005169 |
| DDC | 1644 | XM_011515161; NM_001242890; XM_005271745; NM_001082971; NM_001242886; NM_001242887; NM_001242889; NM_000790; NM_001242888 |
| INSM1 | 3642 | NM_002196 |
| CYP11A1 | 1583 | NM_000781; NM_001099773 |
| SYT5 | 6861 | XM_006723339; NM_001297774; NM_003180; XM_017027175; XM_006723340; XM_006723341; XM_024451668 |
| NGB | 58157 | NM_021257 |
| STAR | 6770 | NM_001007243; NM_000349 |
| SLC18A1 | 6570 | XM_011544626; NM_003053; XM_011544625; NM_001142325; NM_001135691; NM_001142324 |
| CHGB | 1114 | NM_001819 |
| CHRNA3 | 1136 | XM_006720382; NM_000743; NR_046313; NM_001166694 |
| CHGA | 1113 | NM_001301690; NM_001275; XM_011536370 |
| SLC18A2 | 6571 | NM_003054 |
| DBH | 1621 | NM_000787 |
| DRD2 | 1813 | XM_017017296; NM_016574; NM_000795 |
| TH | 7054 | XM_011520335; NM_199292; NM_000360; NM_199293 |
| PPP1R17 | 10842 | XR_926912; NM_001145123; XM_011515094; NM_006658 |
| PHOX2B | 8929 | NM_003924 |
| EGR4 | 1961 | NM_001965 |
| CDH22 | 64405 | XM_024451966; XM_011528994; XM_024451967; NM_021248 |
| SFN | 2810 | NM_006142 |
| C1orf106 | 55765 | XM_011509754; XM_011509755; NM_001367289; NM_001367290; XM_011509756; NM_001142569; NM_018265 |
| CDC20 | 991 | NM_001255 |
| TGFA | 7039 | NM_001308159; NM_001308158; NM_001099691; NM_003236 |
| SMO | 6608 | NM_005631; XM_024446891 |
| SDC1 | 6382 | NM_001006946; XM_005262620; XM_005262621; NM_002997; XM_005262622 |
| VAMP8 | 8673 | NM_003761; XM_017005170 |
| SERPINA1 | 5265 | NM_001002235; NM_001127700; NM_001127701; XM_017021370; NM_001127706; NM_000295; NM_001002236; NM_001127702; NM_001127705; NM_001127703; NM_001127704; NM_001127707 |
| EPHB3 | 2049 | NM_004443 |
| BIRC5 | 332 | NM_001168; NM_001012271; NM_001012270 |
| CILP | 8483 | NM_003613; XM_017022679; XM_017022678 |
| ABAT | 18 | NM_001386601; NM_001386602; NM_001386615; NM_000663; NM_001386606; NM_001127448; NM_020686; NM_001386608; NM_001386612; NM_001386613; NM_001386603; NM_001386605; NM_001386611; NM_001386600; NM_001386609; NM_001386610; NM_001386614; NM_001386616; NM_001386604; NM_001386607 |
| CSTA | 1475 | NM_005213 |
| PRUNE2 | 158471 | XM_011518327; XM_005251746; XM_005251751; XM_006716983; XM_017014347; XM_017014349; XM_017014359; XR_001746209; XR_428517; XM_005251748; XM_006716985; NM_001308047; XM_005251754; XM_006716982; XM_017014346; XM_017014348; XM_017014352; XR_001746210; NM_001308050; NR_131751; NM_138818; XM_011518323; XM_017014345; XM_017014357; XR_001746212; NM_001308048; NM_015225; XM_017014354; XM_017014356; NM_001308049; XM_005251750; XM_005251745; XM_006716986; XM_011518326; XM_011518328; XM_017014350; XM_017014351; XM_017014353; XM_017014358; XM_006716984; XR_001746211; NM_001308051; NM_001330680 |
| WNT2 | 7472 | NM_003391; NR_024047 |
| UGT2A3 | 79799 | XM_011532247; NM_024743; NR_024010 |
| IRS4 | 8471 | XM_006724713; NM_003604; NM_001379150; XM_011531061 |
| SLC6A15 | 55117 | XM_011538525; NM_018057; NM_001146335; NM_182767 |
| ATP2B2 | 491 | XM_017006484; NM_001001331; XM_005265179; XM_011533752; XM_017006487; XM_017006488; XM_017006486; XM_017006481; XM_017006482; XM_017006489; XM_006713175; NM_001330611; NM_001353564; XM_017006485; XM_017006483; NM_001683; XM_017006492; NM_001363862 |
| WWC1 | 23286 | XM_011534487; XM_011534489; NM_015238; XM_005265850; XM_011534485; XM_011534486; XM_005265853; XM_011534488; XM_011534490; XM_011534491; XM_017009276; XM_017009278; NM_001161662; NM_001161661 |
| FCN2 | 2220 | XM_011518392; NM_015838; NM_015839; NM_015837; NM_004108; XM_006717015 |

-continued

| Gene | NCBI Gene ID | NCBI Accession Number(s) |
|---|---|---|
| IVL | 3713 | NM_005547 |
| CFTR | 1080 | NM_000492 |
| F2RL1 | 2150 | NM_005242; XM_017009223 |
| MYB | 4602 | NM_001161660; NR_134958; NM_001130173; NM_001130172; NM_001161656; NR_134959; NM_001161657; NR_134963; NR_134965; XR_942444; NR_134962; NM_001161659; NR_134961; NM_001161658; NM_005375; NR_134960; NR_134964 |
| SCGN | 10590 | NM_006998; XM_017010181 |
| TMEM246 | 84302 | NM_001303107; NM_001303108; NM_032342; XM_024447701; NM_001371233 |
| PRSS22 | 64063 | XM_005255473; NM_022119 |
| IHH | 3549 | NM_002181 |
| MYBPH | 4608 | NM_004997 |
| SPOCK2 | 9806 | XM_017016985; NM_001134434; XM_011540404; NM_001244950; NM_014767 |
| MUC2 | 4583 | NM_002457 |
| MYCL | 4610 | NM_001033082; NM_001033081; NM_005376 |
| | | Mesothelioma |
| CPA4 | 51200 | NM_001163446; NM_016352 |
| CALB2 | 794 | NM_007088; XR_002957842; NM_001740; NR_027910; NM_007087 |
| HAS1 | 3036 | NM_001523; NM_001297436; XM_011526884 |
| ALDH1A2 | 8854 | NM_001206897; NM_170697; NM_170696; NM_003888 |
| PTGIS | 5740 | NM_000961 |
| UPK1B | 7348 | NM_006952 |
| WT1 | 7490 | NM_000378; NR_160306; NM_001367854; NM_001198551; NM_001198552; NM_024424; NM_024426; NM_024425 |
| MYL2 | 4633 | NM_000432 |
| HP | 3240 | NM_001126102; NM_005143; NM_001318138 |
| MSLN | 10232 | NM_001177355; NM_005823; NM_013404 |
| GJB1 | 2705 | NM_000166; XM_011530907; NM_001097642 |
| CKM | 1158 | NM_001824 |
| TM4SF1 | 4071 | NM_014220; XM_017006385 |
| CST1 | 1469 | NM_001898 |
| CTSE | 1510 | XM_011509245; NM_001910; NM_148964; XM_011509244; NM_001317331 |
| SLC44A4 | 80736 | NM_001178045; NM_001178044; NM_025257 |
| CD24 | 100133941 | NM_001291739; NR_117090; NR_117089; NM_001291738; NM_001291737; NM_013230; XM_024446293; NM_001359084 |
| BMP7 | 655 | NM_001719 |
| TBX5 | 6910 | NM_181486; NM_080717; NM_000192; XM_017019912; NM_080718 |
| GATA4 | 2626 | NM_001308093; NM_002052; NM_001308094; NM_001374273; NM_001374274 |
| IRF6 | 3664 | NM_001206696; NM_006147 |
| KRT5 | 3852 | NM_000424 |
| PRSS22 | 64063 | XM_005255473; NM_022119 |
| CLIC3 | 9022 | XM_017015282; NM_004669; XM_017015281 |
| FLNC | 2318 | NM_001458; NM_001127487 |
| SALL1 | 6299 | NM_001127892; NM_002968 |
| ERBB3 | 2065 | NM_001005915; NM_001982 |
| TF | 7018 | NM_001063; NM_001354703; NM_001354704 |
| GJB3 | 2707 | NM_024009; NM_001005752 |
| BDNF | 627 | NM_001143811; NM_001143812; NM_170734; XM_011520280; NM_001143805; NM_001143816; NM_170731; NM_001143808; NM_001143809; NM_001143814; NM_001143815; NM_001143807; NM_001709; NM_001143810; NM_001143813; NM_170732; NM_001143806; NM_170733; NM_170735 |
| ADRA2B | 151 | NM_000682 |
| TPO | 7173 | XM_024453088; XM_024453087; NM_175722; XM_024453091; XM_024453085; XM_024453086; NM_001206745; XM_024453090; NM_175719; NM_175721; NM_175720; XM_024453093; XM_011510380; NM_001206744; XM_024453089; XM_024453092; NM_000547 |
| CENPF | 1063 | XM_017000086; NM_016343; XM_011509082 |
| SCN4A | 6329 | NM_000334 |
| KRT18 | 3875 | NM_000224; NM_199187 |
| SPINT2 | 10653 | NM_001166103; NM_021102 |
| KIF4A | 24137 | NM_012310 |
| DHRS2 | 10202 | NM_005794; XM_006720001; XM_005267249; NM_001318835; XR_001750107; XM_011536338; XR_001750106; XR_943366; NM_182908; XR_001750105; XR_943367; XM_011536339 |
| SDC1 | 6382 | NM_001006946; XM_005262620; XM_005262621; NM_002997; XM_005262622 |
| ROBO3 | 64221 | NM_001370358; NM_001370359; NR_163412; NM_001370356; NM_001370361; NR_163411; NR_163415; NM_001370364; NM_022370; NR_163410; NR_163413; NR_163414; XM_017018122; NM_001370366; NM_001370357; NR_163409 |
| FHL5 | 9457 | NM_001170807; NM_001322466; NM_001322467; NM_020482 |
| ZWINT | 11130 | XR_428692; NM_007057; NM_001005413; XM_017015605; XM_024447784; NM_032997; NM_001005414 |
| PKMYT1 | 9088 | NM_001258451; NM_182687; NM_001258450; XM_011522735; XM_024450490; NM_004203; XM_011522734; XM_011522736 |
| NEIL3 | 55247 | NM_018248; XM_017008360 |
| PHKG1 | 5260 | NM_001258460; XM_017012327; XM_017012324; XM_017012325; NR_047689; XM_017012326; NM_001258459; XM_005271772; NM_006213 |

-continued

| Gene | NCBI Gene ID | NCBI Accession Number(s) |
|---|---|---|
| KRT2 | 3849 | NM_000423 |
| CDKN2A | 1029 | XR_929159; XM_011517676; XM_011517675; NM_001363763; NM_001195132; NM_058195; NM_000077; NM_058196; NM_058197; XM_005251343 |
| SEMA6C | 10500 | NM_030913; XM_017000075; XM_017000079; NM_001178061; NM_001178062; XM_017000077; XM_017000082; XM_017000076; XM_017000081; XM_005244835 |
| CIDEC | 63924 | NM_001321142; NM_001199552; NM_001378491; NM_001199623; NM_001199551; NM_001321144; NM_022094; NM_001321143 |
| SPANXB1 | 728695 | NM_145664; NM_032461 |
| GH1 | 2688 | NM_022559; NM_022561; NM_022560; NM_022562; NM_000515 |
| PLIN1 | 5346 | NM_002666; XM_005254934; NM_001145311 |
| PPARG | 5468 | NM_001354669; NM_001354670; NM_001374263; NM_001330615; NM_001374262; NM_005037; NM_001374261; NM_138711; NM_138712; NM_001374264; NM_001374266; NM_001354668; NM_015869; NM_001354667; NM_001354666; NM_001374265 |
| CACNA1S | 779 | XM_005245478; NM_000069 |
| | | Thymoma |
| MAOB | 4129 | XM_005272608; XM_017029524; XM_017029523; NM_000898 |
| ANKS1B | 56899 | XM_006719507; XM_024449067; NM_001204070; NM_001352193; NM_001352198; NM_001352201; NM_001352207; NM_001352219; NM_001352221; XM_006719508; XM_017019654; XM_024449061; XM_024449062; NM_001204065; NM_001352185; NM_001352191; NM_001352194; NM_001352202; NM_001352203; NM_001352209; NM_001352211; NM_001352213; NM_001352220; XM_017019655; XM_024449069; NM_001204068; NM_001352205; NM_001352214; NM_001352216; NM_001352218; NM_001352223; NM_001352225; NM_020140; XM_024449063; XM_024449066; XM_024449070; NM_001204066; NM_001352186; NM_001352187; NM_001352195; NM_001352200; NM_001352212; NM_152788; XM_005269029; XM_006719505; XM_006719510; XM_006719512; XM_011538571; XM_017019656; XM_024449065; NM_001204079; NM_001352189; NM_001352190; NM_001352197; NM_001352222; XM_006719513; XM_006719514; XM_017019652; XM_024449064; XR_001748815; NM_001204069; NM_001204067; NM_001204081; NM_001352199; NM_001352204; NM_001352206; NM_001352210; NM_001352217; NM_181670; XM_017019653; NM_001352196; XM_006719504; XM_017019657; XM_017019658; XM_024449060; XM_024449068; NM_001204080; NM_001352188; NM_001352192; NM_001352208; NM_001352224 |
| SPINK2 | 6691 | XM_024454191; XM_011534405; NM_001271718; NM_001271720; NM_001271721; NR_073417; NM_001271719; XM_011534406; NM_001271722; NM_021114; NR_073418; NR_073419 |
| KREMEN2 | 79412 | NM_145348; NM_145347; NM_024507; NM_172229; NM_001253726; NM_001253725 |
| ORC1 | 4998 | NM_001190818; XM_017001388; XM_017001389; NM_001190819; XM_011541527; NM_004153 |
| GJB1 | 2705 | NM_000166; XM_011530907; NM_001097642 |
| DPF1 | 8193 | XM_006723408; XR_243964; XM_011527356; XM_024451731; NM_004647; XM_005259292; XM_006723407; NM_001135155; XM_006723409; XM_006723410; XM_011527358; NM_001363579; XM_011527357; XM_005259289; NM_001135156; NM_001289978 |
| PAX1 | 5075 | NM_006192; NM_001257096 |
| FCN2 | 2220 | XM_011518392; NM_015838; NM_015839; NM_015837; NM_004108; XM_006717015 |
| KIFC1 | 3833 | XM_011514585; XM_017010836; NM_002263; XM_011514587; XM_017010837 |
| RAG1 | 5896 | NM_001377278; NM_000448; NM_001377280; NM_001377277; NM_001377279 |
| FOXN1 | 8456 | XM_011525358; XM_011525362; XM_011525359; XM_011525367; XM_011525368; XM_011525370; XM_017025230; XM_017025231; XM_017025229; XM_011525369; XM_017025228; NM_001369369; NM_003593 |
| ZAP70 | 7535 | XM_017004868; XR_001738927; NM_001378594; NM_207519; XM_017004869; NM_001079; XR_001738926; XM_017004870; XM_017004867; XR_001738925 |
| PCDH1 | 5097 | XM_005268455; NM_001278613; XM_005268452; XM_017009517; NM_032420; NM_002587; XM_005268454; XM_017009518; NM_001278615 |
| LCK | 3932 | XM_011541453; XM_024447046; NM_001330468; XM_024447047; NM_005356; NM_001042771 |
| MLANA | 2315 | NM_005511 |
| KRT5 | 3852 | NM_000424 |
| NDRG2 | 57447 | NM_016250; NM_001354567; NM_201538; NM_001282215; NM_001354560; NM_001354561; NM_001354569; NM_201535; NM_001282216; NM_001354564; NM_001354565; NM_001354566; NM_201536; NM_201539; NM_201541; NM_001354558; NM_001354562; NM_001282213; NM_001354570; NM_201540; NM_001282211; NM_001320329; NM_001282214; NM_001282212; NM_001354559; NM_001354568; NM_201537 |
| GFI1B | 8328 | NM_001371908; NM_001377304; XM_006717297; NM_001135031; XM_017015175; NM_001377305; XM_011519069; XM_011519070; NM_004188; XM_011519068; XM_017015176 |
| BEND5 | 79656 | XM_017002331; XM_011542141; XM_017002333; NM_001349795; NR_146232; XM_011542142; XR_001737408; NM_001349794; NM_001302082; NM_001349793; NM_024603 |

-continued

| Gene | NCBI Gene ID | NCBI Accession Number(s) |
|---|---|---|
| ITGB6 | 3694 | NM_001282354; NM_001282353; NM_000888; NM_001282389; NM_001282390; NM_001282355; NM_001282388 |
| AGL | 178 | NM_000646; XM_005270557; NM_000644; NM_000028; NM_000643; XM_017000501; NM_000642; NM_000645 |
| CAMK2N1 | 55450 | NM_018584 |
| GAL3ST1 | 9514 | XM_017029096; XM_024452304; NM_001318107; NM_001318111; NM_001318109; NM_001318114; XM_011530528; NM_001318105; NM_004861; XM_011530518; XM_011530524; NM_001318106; XM_011530522; XM_017029097; NM_001318108; NM_001318110; NM_001318103; NM_001318113; NM_001318116; XM_017029098; NM_001318104; NM_001318112; NM_001318115 |
| EEF1A2 | 1917 | NM_001958 |
| REN | 5972 | NM_000537 |
| CALML3 | 810 | NM_005185 |
| DNTT | 1791 | NM_004088; NM_001017520 |
| PHLDA2 | 7262 | NM_003311 |
| CTH | 1491 | XM_005270509; NM_001902; NM_153742; XM_017000416; NM_001190463 |
| PRSS16 | 10279 | XM_017010162; XM_017010164; XM_017010165; XM_017010161; XM_017010163; NM_005865 |
| AADAC | 13 | NM_001086; XM_005247104 |
| ASGR2 | 433 | XM_006721524; XM_011523866; XM_017024651; XM_024450755; NM_080913; XM_024450757; NM_001201352; XM_005256648; XM_011523865; NM_080912; XM_011523863; NM_080914; XM_006721526; XM_011523862; XM_011523864; XM_017024653; NM_001181; XM_017024652; XM_024450756 |
| SDCBP | 6386 | NM_001007067; NM_001007069; XM_024447231; NM_001330537; NM_001348340; XM_024447229; NM_001007068; NM_001348341; XM_024447230; NM_005625; NM_001007070; NM_001348339 |
| PAX9 | 5083 | NM_001372076; NM_006194 |
| CCL25 | 6370 | NM_001394634; NM_001394635; NM_001394638; NM_005624; NM_148888; NM_001394636; NM_001201359; NM_001394637 |
| PKP1 | 5317 | NM_000299; NM_001005337 |
| TNFRSF4 | 7293 | XM_011542074; NM_003327; XM_017002232; XM_011542077; XM_011542075; XM_011542076; XM_017002231 |
| ACADL | 33 | NM_001608; XM_005246517; XM_017003955 |
| ARPP21 | 10777 | NM_001267619; NM_001385487; NM_001385490; NM_001385558; NM_001385573; NM_001385582; NR_169635; NR_169644; NR_170706; NR_170707; XM_017005574; XM_017005584; NM_001385485; NM_001385536; NM_001385581; NM_001385589; NM_001385594; XM_011533301; XM_017005580; XM_017005588; NM_001267616; NM_001385495; NM_001385576; NR_169645; XM_017005596; XM_024453320; NM_001385565; NM_001385566; NM_001385590; NM_016300; NR_169632; XM_011533303; XM_017005590; XM_017005598; XM_024453322; NM_001267617; NM_001385484; NM_001385488; NM_001385517; NM_001385585; NM_001385592; NR_169647; XM_011533299; XM_017005607; XM_024453323; NM_001025069; NM_001385489; NM_001385492; NM_001385496; NM_001385567; NM_001385577; NM_001385584; NM_001385587; NM_001385591; NM_001385593; XM_017005591; NM_001267618; NM_001385486; NM_001385491; NM_001385564; NM_001385578; NM_001385595; NM_198399; NR_169633; XM_011533300; XM_011533302; XM_017005575; XM_017005579; XM_017005612; XM_024453324; NM_001025068; NM_001385497; NM_001385556; NM_001385562; NM_001385563; NM_001385574; NM_001385580; NM_001385588; NR_169646; NR_170705 |
| SLC13A2 | 9058 | NM_001145975; NM_001346683; NM_003984; NM_001145976; XM_006722165; XM_011525450; XM_011525453; XM_011525454; NM_001346684; XM_011525452; XM_011525451 |
| FGFR4 | 2264 | NM_213647; NM_022963; NM_002011; NM_001291980; NM_001354984 |
| CD247 | 919 | NM_001378516; NM_198053; XM_011510144; XM_011510145; NM_000734; NM_001378515 |
| RAB23 | 51715 | NM_183227; NM_001278666; NM_001278668; NM_016277; NM_001278667; NR_103822 |
| FBXL6 | 26233 | NM_024555; NM_012162 |
| EFNA2 | 1943 | NM_001405; XM_017026449; XM_017026450 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| GHRH | 2691 | NM_001184731; NM_021081 |
| | | Germ_Cell_Neoplasm |
| CCNB1 | 891 | NM_031966 |
| POMC | 5443 | NM_001319205; NM_001035256; NM_001319204; NM_000939 |
| NR4A2 | 4929 | XR_001738751; XM_011511246; XM_017004220; NM_173171; XM_005246621; XM_017004219; NM_173172; NM_173173; XM_006712553; XR_001738752; NM_006186; XR_427087 |
| CLDN6 | 9074 | NM_021195 |
| DBNDD1 | 79007 | NM_001288709; NM_001288708; NM_001371581; NM_001042610; NM_024043 |
| CAP2 | 10486 | NM_001363534; NM_006366; NM_001363533 |

-continued

| Gene | NCBI Gene ID | NCBI Accession Number(s) |
|---|---|---|
| ESM1 | 11082 | NM_001135604; NM_007036 |
| EPS8L1 | 54869 | NM_133180; NM_139204; XM_011527052; XM_005259020; NM_017729; XM_011527051; XM_011527050 |
| MEP1B | 4225 | XM_011526013; XM_011526014; NM_005925; NM_001308171 |
| PLIN1 | 5346 | NM_002666; XM_005254934; NM_001145311 |
| ZWINT | 11130 | XR_428692; NM_007057; NM_001005413; XM_017015605; XM_024447784; NM_032997; NM_001005414 |
| HAMP | 57817 | NM_021175 |
| EIF1AY | 9086 | NM_004681; NM_001278612 |
| MISP | 126353 | NR_135168; XM_011527686; XM_011527685; NM_173481 |
| MMP9 | 4318 | NM_004994 |
| CLEC1B | 51266 | NM_001099431; XM_017019395; XM_011520685; XM_017019396; XM_011520686; NM_016509; NM_001393342 |
| ALLC | 55821 | XM_017004495; XM_017004498; NM_018436; XM_017004496; XM_011510369; XM_011510370; XM_017004497; NM_199232 |
| PGR | 5241 | XM_011542869; NM_001271161; NR_073142; NM_000926; XM_006718858; NM_001202474; NM_001271162; NR_073141; NR_073143 |
| COL9A1 | 1297 | NM_001851; NR_165185; NM_078485; XM_017010246; XM_011535429; XM_017010247; NM_001377289; NM_001377290; NM_001377291 |
| DNM1 | 1759 | NM_001005336; NM_001374269; NM_004408; NM_001288738; NM_001288739; NM_001288737 |
| KERA | 11081 | NM_007035 |
| PLA2G2A | 5320 | NM_001161728; NM_000300; NM_001161729; NM_001161727; NM_001395463 |
| AURKB | 9212 | NM_001313950; NM_001313953; XM_017025309; XM_017025307; XM_017025308; XM_017025311; NM_001313952; NM_004217; NM_001313954; NR_132730; NR_132731; XM_017025310; NM_001284526; XM_011524072; NM_001256834; NM_001313951; NM_001313955 |
| APOBEC3B | 9582 | NM_004900; NM_001270411 |
| ADAMTS13 | 11093 | NM_139027; NM_139028; XM_017014235; NM_139026; XM_017014233; XR_001746171; NM_139025; XM_017014232; XM_011518176; XM_017014234; XM_011518178; XM_011518179; NR_024514 |
| PTH1R | 5745 | NM_001184744; XM_017006933; XM_011533968; NM_000316; XM_017006934; XM_011533967; XM_005265344; XM_017006932 |
| PTCH2 | 8643 | NM_001166292; NM_003738 |
| CYP46A1 | 10858 | NM_006668; XM_005267274; XM_011536365; XM_011536364; XM_017020933 |
| VRTN | 55237 | XM_011536911; NM_018228 |
| PLVAP | 83483 | NM_031310 |
| PTHLH | 5744 | NM_198965; NM_198966; XM_011520774; NM_002820; XM_017019675; NM_198964 |
| COL8A1 | 1295 | NM_020351; NM_001850 |
| DAZL | 1618 | NM_001351; NM_001190811 |
| NANOG | 79923 | NM_024865; NM_001297698 |
| CXorf36 | 79742 | XM_006724559; NM_176819; NM_024689; XM_005272670 |
| C9 | 735 | NM_001737 |
| FOXH1 | 8928 | NM_003923 |
| MDFI | 4188 | XM_005249117; XM_011514626; NM_005586; NM_001300805; XM_011514625; NM_001300804; XM_017010867; NM_001300806 |
| KLF9 | 687 | NM_001206 |
| EDIL3 | 10085 | NM_005711; NM_001278642 |
| LRRTM4 | 80059 | NM_001134745; NM_001330370; NM_001282924; NM_024993; NM_001282928; NR_146416 |
| PRND | 23627 | NM_012409 |
| GDF3 | 9573 | NM_020634 |
| CDKN2A | 1029 | XR_929159; XM_011517676; XM_011517675; NM_001363763; NM_001195132; NM_058195; NM_000077; NM_058196; NM_058197; XM_005251343 |
| PRM1 | 5619 | NM_002761 |
| LIN28A | 79727 | XM_011542148; NM_024674 |
| DPP4 | 1803 | NR_166823; NM_001379606; NM_001379605; NR_166824; NM_001935; NM_001379604; NR_166825; NR_166822 |
| IBSP | 3381 | NM_004967 |
| CYP17A1 | 1586 | NM_000102 |
| VENTX | 27287 | XM_017016073; NM_014468 |
| LEFTY2 | 7044 | NM_003240; NM_001172425; XM_011544266 |
| GCKR | 2646 | XM_017003797; XM_011532763; XR_001738699; XM_017003796; NM_001486 |
| AKR1C3 | 8644 | NM_003739; NM_016253; NM_001253909; NM_001253908 |
| GATA4 | 2626 | NM_001308093; NM_002052; NM_001308094; NM_001374273; NM_001374274 |
| PLP1 | 5354 | NM_001128834; NM_000533; NM_001305004; NM_199478 |
| ADAM11 | 4185 | XM_005257373; NM_001318933; NM_002390; XM_024450754 |
| PRM2 | 5620 | NM_001286358; NR_104428; NM_002762; NM_001286356; NM_001286359; NM_001286357 |
| MUC1 | 4582 | NM_001204292; NM_001204286; NM_001204291; NM_001204285; NM_001204287; NM_001204288; NM_001204289; NM_001204290; NM_001204295; NM_001204297; NM_001204296; NM_001018016; NM_001018017; NM_001044390; NM_001044391; NM_001044392; NM_001044393; NM_001204293; NM_001204294; NM_002456 |
| HAPLN1 | 1404 | XM_017009052; XM_017009051; NM_001884; XM_017009054; XM_017009053; XM_011543168 |

-continued

| Gene | NCBI Gene ID | NCBI Accession Number(s) |
|---|---|---|
| DEPDC1 | 55635 | NM_001114120; NM_017779 |
| SLPI | 6590 | NM_003064 |
| C3orf36 | 80111 | NM_025041; NR_161373 |
| PEG3 | 5178 | NM_001369718; NM_001146184; NM_001369719; NM_001369734; NM_001369739; NR_161475; NM_001369731; NM_001369720; NM_001369724; NM_001369732; NM_001369733; NM_001146187; NM_001369722; NM_001369723; NM_001369726; NM_001369728; NM_001369735; NM_001369736; NM_001369737; NM_001369738; NM_001146185; NM_001369717; NM_001369721; NM_001369725; NM_006210; NM_001369729; NM_001369730; NM_001369727; NR_161476; NM_001146186 |
| MLANA | 2315 | NM_005511 |
| TREM2 | 54209 | NM_001271821; NM_018965 |
| GDF2 | 2658 | NM_016204 |
| DPPA4 | 55211 | XM_011512954; XM_024453622; NM_001348929; NM_001348928; NM_018189 |
| CDH15 | 1013 | NM_004933 |
| RRM2 | 6241 | NR_161344; NM_001034; NR_164157; NM_001165931 |
| MYL7 | 58498 | XM_011515464; NM_021223; XM_011515465; XM_011515463; XM_017012478; XM_017012479; XM_024446851; XM_005249817 |
| PRR7 | 80758 | NM_001375594; NM_030567; NM_001174102; NM_001174101; NM_001375593 |
| PHC1 | 1911 | XM_017018958; XM_011520600; XM_017018955; XM_017018957; XM_011520599; XM_017018956; XM_011520603; XM_005253334; NM_004426 |
| | | Neuroendocrine_small_cell |
| CD34 | 947 | NM_001025109; NM_001773 |
| NCAM1 | 4684 | NM_001386289; NM_001386290; NM_001386291; NM_001386292; NM_001076682; NM_000615; NM_001242608; NM_181351; NM_001242607 |
| MOGAT2 | 80168 | XM_024448696; NM_025098; XM_011545267 |
| COL11A1 | 1301 | XM_017000337; XM_017000335; XM_017000336; NR_134980; NM_080629; XM_017000334; NM_001190709; NM_001854; NM_080630 |
| DTL | 51514 | XM_011509614; NM_001286229; NM_001286230; NM_016448 |
| MYOC | 4653 | NM_000261 |
| FOXA1 | 3169 | NM_004496; XM_017021246 |
| IBSP | 3381 | NM_004967 |
| GLP2R | 9340 | XM_011524077; NM_004246; XM_017025340; XM_005256861; XM_017025339; XM_017025341 |
| C14orf105 | 55195 | XM_006720188; XR_001750402; NM_001283056; XM_006720189; XR_001750401; NM_001283057; NM_001283058; NM_001283059; XM_005267810; NM_018168; XM_005267813; XM_005267806; XM_005267811; XR_001750400; XM_005267814; NM_001283060 |
| ZNF185 | 7739 | XM_005274744; XM_017029823; XM_017029829; NM_001178107; XM_005274735; XM_005274740; XM_005274741; XM_017029825; XM_017029831; NM_001178106; NM_001178113; XM_005274738; XM_005274731; XM_017029822; XM_017029826; XM_017029827; XM_017029832; XM_005274745; XM_017029824; NM_001178108; NM_001178110; XM_011531195; XM_017029828; NM_001178115; NM_007150; NM_001178114; XM_005274730; XM_017029821; XM_011531194; NM_001178109; NM_001395254; XM_005274746; XM_017029830; XM_017029833; NM_001388432; XM_005274742; XM_017029834; XM_017029835 |
| SYN2 | 6854 | XM_006713312; XR_001740240; XM_006713311; XM_006713313; NM_133625; NM_003178; XM_017007087 |
| KRT2 | 3849 | NM_000423 |
| ANGPTL4 | 51129 | NM_016109; NM_139314; XM_005272484; XM_005272485; NR_104213; NM_001039667 |
| GABRG3 | 2567 | XM_017022058; XM_017022060; XM_024449889; NM_033223; XM_011521430; NM_001270873; XM_011521431; XM_017022059 |
| SPP1 | 6696 | NM_001251829; NM_001040060; NM_001251830; NM_000582; NM_001040058 |
| SYT12 | 91683 | XM_011545346; XM_011545347; NM_177963; XM_017018547; NM_001177880; NM_001318775; XM_017018548; XM_006718737; XM_024448766; NM_001318773 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| DLL3 | 10683 | NM_016941; NM_203486 |
| SFRP5 | 6425 | NM_003015 |
| GABRD | 2563 | XM_011541194; XM_017000936; NM_000815 |
| CCNB1 | 891 | NM_031966 |
| PRL | 5617 | XM_011514753; NM_000948; NM_001163558; XM_011514754 |
| RETN | 56729 | NM_020415; NM_001385725; NM_001385727; NM_001385726; NM_001193374 |
| PPM1H | 57460 | XM_017019676; XM_011538578; NM_020700; XM_011538579 |
| ESM1 | 11082 | NM_001135604; NM_007036 |
| CELA3B | 23436 | NM_007352 |
| CHGA | 1113 | NM_001301690; NM_001275; XM_011536370 |
| GGCT | 79017 | NM_001199816; NM_001199817; NM_001199815; NM_024051; NR_037669 |
| ADH1B | 125 | NM_001286650; NM_000668 |
| AOC3 | 8639 | XR_934584; NM_001277732; NM_003734; NR_102422; XM_011525419; XR_001752673; XM_011525420; XM_024451015; NM_001277731 |
| AGL | 178 | NM_000646; XM_005270557; NM_000644; NM_000028; NM_000643; XM_017000501; NM_000642; NM_000645 |

-continued

| Gene | NCBI Gene ID | NCBI Accession Number(s) |
|---|---|---|
| CELSR3 | 1951 | NM_001407 |
| CLDN3 | 1365 | NM_001306 |
| STRA6 | 64220 | NM_022369; NM_001199042; XM_011521883; XM_011521885; NM_001142618; XM_017022479; NM_001142617; NM_001142619; NM_001142620; XM_011521884; XR_931877; XM_017022478; XM_017022480; NM_001199040; NM_001199041 |
| ALAS2 | 212 | NM_001037968; NM_001037967; NM_000032; NM_001037969 |
| CST1 | 1469 | NM_001898 |
| CA1 | 759 | NM_001128831; NM_001291967; NM_001164830; NM_001738; NM_001128830; NM_001128829; NM_001291968 |
| AOC1 | 26 | XM_017011946; NM_001091; XM_017011947; NM_001272072; XM_017011944; XM_017011945 |
| LIMS2 | 55679 | XM_006712627; XM_024452983; NM_017980; NM_001256542; XM_017004469; NM_001161403; XM_011511453; XM_024452984; NM_001136037; XM_024452986; XR_922961; NM_001161404; XM_006712628; XM_024452985; XM_005263710 |
| HSF2BP | 11077 | XM_017028269; XM_017028272; XM_011529446; XM_017028270; XM_017028271; XM_017028267; XM_017028268; XR_937435; XM_011529445; XM_011529443; XM_011529447; NM_007031 |
| CDK4 | 1019 | NM_000075; NM_052984 |
| HBB | 3043 | NM_000518 |
| HOXC10 | 3226 | NM_017409 |
| KRT1 | 3848 | NM_006121 |
| TTC22 | 55001 | XM_017001582; XM_011541671; NM_001114108; NM_017904 |
| TLN2 | 83660 | XM_017022669; XM_005254713; XM_005254715; XM_006720717; XM_017022667; XM_005254714; XM_005254708; XM_005254710; XR_001751405; NM_001394547; XM_005254712; NM_015059; XM_017022666; XM_024450087; XM_005254711; XM_017022665; XM_017022668 |
| S100A12 | 6283 | NM_005621 |
| KRT24 | 192666 | XM_017024299; NM_019016; XM_006721739; XM_011524460 |
| MET | 4233 | NM_001324402; NM_001324401; XM_006715990; NM_001127500; XM_011516223; NM_000245; XR_001744772; |
| DES | 1674 | NM_001927; NM_001382708; NM_001382710; NM_001382713; NM_001382709; NM_001382711; NM_001382712 |
| HOXC11 | 3227 | NM_014212 |
| GUCA2A | 2980 | NM_033553 |
| PTH1R | 5745 | NM_001184744; XM_017006933; XM_011533968; NM_000316; XM_017006934; XM_011533967; XM_005265344; XM_017006932 |
| ULBP2 | 80328 | NM_025217; XM_017011321 |
| TGM3 | 7053 | NM_003245 |
| CTRB2 | 440387 | NM_001025200 |
| CKM | 1158 | NM_001824 |
| ALDOC | 230 | XM_005257949; NM_005165; XM_011524556 |
| CCL23 | 6368 | NM_005064; XR_429910; NM_145898 |
| MMP11 | 4320 | NM_005940; NR_133013 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| HOXC13 | 3229 | NM_017410 |
| MAGEA3 | 4102 | XM_011531161; XM_005274676; XM_006724818; XM_011531160; NM_005362 |
| INS | 3630 | NM_001185098; NM_001185097; NM_000207; NM_001291897 |
| NKX6-1 | 4825 | NM_006168 |
| HINT1 | 3094 | NR_134495; NM_005340; NR_073488; NR_024610; NR_134494; NR_024611 |
| GRIN2D | 2906 | XM_011526872; NM_000836 |
| FCN3 | 8547 | NM_173452; NM_003665 |
| MGLL | 11343 | XM_017005665; NM_001256585; NM_001388313; NM_001388318; NM_001388317; XM_011512383; NM_001003794; XM_017005663; XM_024453334; NM_001388312; NM_001388315; NM_007283; XM_011512382; NM_001388314; NM_001388316 |
| FMO2 | 2327 | NM_001460; NR_160266; XR_921761; NM_001365900; XR_001737072; NM_001301347 |
| PCSK2 | 5126 | NM_002594; NM_001201529; NM_001201528 |
| MYL2 | 4633 | NM_000432 |
| SIM1 | 6492 | XM_011536072; NM_001374769; NM_005068 |
| EFNA3 | 1944 | NM_004952 |
| MT1M | 4499 | NM_176870 |
| CST4 | 1472 | NM_001899 |
| P2RY14 | 9934 | XM_011513340; NM_001081455; XM_005247922; NM_014879; XM_017007583; XM_005247923 |
| MMP14 | 4323 | NM_004995 |
| CDH19 | 28513 | XM_011525931.3; XM_017025711.2; XM_011525932.1 |
| COL10A1 | 1300 | XM_011535432; NM_000493; XM_011535433; XM_017010248; XM_006715333 |
| ETV4 | 2118 | NM_001261437; NM_001261439; NM_001986; NM_001369368; NM_001079675; NM_001261438; XM_024450644; NM_001369366; NM_001369367 |

-continued

| Gene | NCBI Gene ID | NCBI Accession Number(s) |
|---|---|---|
| SIX1 | 6495 | XM_017021602; NM_005982 |
| ABCA12 | 26154 | XM_011510951; NR_103740; NM_173076; NM_015657 |
| BARX2 | 8538 | XM_011543043; NM_003658; XM_011543044 |
| CRISP2 | 7180 | XM_011514841; XM_011514842; XR_002956303; NM_001142417; NM_001261822; NM_003296; XM_011514843; XR_926302; XM_005249350; XM_005249352; XM_005249349; XM_005249353; XR_002956302; XM_005249351; NM_001142435; XM_005249356; XR_002956301; NM_001142407; XR_002956300; XR_926303; NM_001142408 |
| IGFBP3 | 3486 | NM_000598; NM_001013398 |
| CA7 | 766 | NM_001365337; XM_011523312; NM_001014435; NM_005182 |
| PPEF1 | 5475 | NM_001377996; NM_001377994; NM_001389623; NM_001377986; NM_006240; NM_152224; NM_152226; NM_152225; NM_001378381; NM_001389624; NM_152223; NM_001377993; NM_001378382; XM_017029612; NM_001389621; NM_001377995; NM_001389620 |
| | | Clear_Cell_Renal_Cell_Carcinoma |
| NKX2-4 | 644524 | NM_033176 |
| LCN2 | 3934 | NM_005564 |
| HGFAC | 3083 | NM_001297439; NM_001528 |
| TNNI3 | 7137 | NM_000363 |
| NMRK2 | 27231 | NM_001289117; NM_001375468; NM_001375469; NM_170678; NM_001375467; NM_014446; XM_006722725; NR_110316 |
| NKAIN3 | 286183 | XM_017013359; XM_011517511; XM_017013360; XM_017013361; NM_001039769; NR_130764; NR_027378; XM_011517512; NM_173688; NM_001304533 |
| ARHGAP40 | 343578 | NM_001164431 |
| KRT7 | 3855 | XM_017019294; XR_001748700; NM_005556; XM_011538325; XR_001748699 |
| CST4 | 1472 | NM_001899 |
| SFTPC | 6440 | NM_001317779; NM_001385656; NM_001385658; NM_001385659; NM_001172410; NM_001385654; NM_001385655; NM_001317778; NM_001317780; NM_001385657; NM_001385660; NM_001385653; XM_011544613; NM_001172357; NM_003018 |
| DNTT | 1791 | NM_004088; NM_001017520 |
| LRRN4 | 164312 | XM_011529183; NM_152611 |
| NPBWR1 | 2831 | NM_005285 |
| CLDN3 | 1365 | NM_001306 |
| CXCL11 | 6373 | NM_001302123; NM_005409 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| HTR1F | 3355 | NM_001322208; XM_005264751; NM_000866; NM_001322210; NM_001322209; XM_011533664 |
| IFNG | 3458 | NM_000619 |
| GRIN2A | 2903 | XM_017023172; NM_001134407; XM_011522461; NM_001134408; NM_000833; XM_011522458; XM_017023173 |
| REN | 5972 | NM_000537 |
| HILPDA | 29923 | NM_013332; NM_001098786 |
| EGLN3 | 112399 | NM_001308103; NM_022073 |
| C14orf180 | 400258 | XM_005267638; NM_001286399; NM_001286400; XM_011536764; NM_001008404 |
| CIB4 | 130106 | XM_024452692; NM_001029881; XM_017003329; XM_017003331; XM_011532514; XM_017003330 |
| CTAGE9 | 643854 | NM_001145659 |
| IGFBP1 | 3484 | NM_000596; NM_001013029 |
| GDF6 | 392255 | NM_001001557 |
| APOB | 338 | NM_000384 |
| PCSK6 | 5046 | NM_001291309; NM_138322; NM_138325; NM_138320; NM_138324; NM_138319; NM_138321; NM_002570; NM_138323 |
| LOX | 4015 | NM_001317073; NM_001178102; NM_002317 |
| DAZ2 | 57055 | NM_001388495; NM_001389303; NM_001005785; NM_001388494; NM_001005786; NM_001388493; NM_020363 |
| DAZ4 | 57135 | XM_011531509; NM_020420; NM_001388484; NM_001005375; XM_011531510 |
| | | Papillary_Renal_Cell_Carcinoma |
| FABP7 | 2173 | NM_001319039; NM_001319041; NM_001319042; NM_001446 |
| KLK15 | 55554 | XM_011527088; XR_001753713; NM_001277081; NM_017509; NM_138563; XM_011527085; XM_011527087; XM_011527089; NM_023006; XM_006723265; NM_138564; XM_017026943; NM_001277082; NR_102274 |
| NDUFA4L2 | 56901 | NM_001394961; NM_001394960; NM_020142 |
| KISS1R | 84634 | NM_032551; XM_017027382 |
| EBF2 | 64641 | NM_022659 |
| FGG | 2266 | NM_000509; NM_021870 |
| MCHR1 | 2847 | NM_005297 |

-continued

| Gene | NCBI Gene ID | NCBI Accession Number(s) |
|---|---|---|
| STAP1 | 26228 | NM_001317769; NM_012108; XM_017008018 |
| CP | 1356 | XM_006713500; XM_006713501; XM_017005735; XM_017005734; XM_006713499; XM_011512435; XR_427361; NM_000096; NR_046371 |
| DAZ1 | 1617 | XM_011531482; NM_004081; XM_011531483; NM_001388496 |
| LOX | 4015 | NM_001317073; NM_001178102; NM_002317 |
| IGFBP1 | 3484 | NM_000596; NM_001013029 |
| RGS5 | 8490 | NM_003617; NM_001195303; NM_001254748; NM_001254749 |
| REN | 5972 | NM_000537 |
| FBN3 | 84467 | NM_032447; XM_017027374; XM_017027376; NM_001321431; XM_017027372; XM_017027373; XM_017027378; XM_017027375; XM_017027377; XM_017027379 |
| PTPRN | 5798 | NM_002846; NM_001199764; NM_001199763 |
| APOB | 338 | NM_000384 |
| GRIK3 | 2899 | NM_000831 |
| APLN | 8862 | NM_017413 |
| CA9 | 768 | XR_428428; NM_001216; XR_001746374 |
| CD36 | 948 | XM_024447002; NM_000072; NM_001289909; NM_001371081; NR_110501; NM_001001548; NM_001127443; XM_005250715; NM_001371074; NM_001001547; NM_001371075; NM_001127444; NM_001371077; NM_001371078; NM_001371079; NM_001371080; XM_024447003; NM_001289908; NM_001289911 |
| UBTFL1 | 642623 | NM_001143975 |
| SPARCL1 | 8404 | NM_001291976; NM_004684; NM_001291977; NM_001128310 |
| SLCO1C1 | 53919 | XR_001748769; XR_001748771; NM_001145946; XM_017019486; NM_001145945; XM_011520703; XR_001748768; XR_001748770; XM_005253394; XM_011520711; XM_024449024; XM_017019487; NM_017435; XM_005253396; NM_001145944; XM_024449025; XM_017019489; XM_011520704; XM_017019490 |
| CIB4 | 130106 | XM_024452692; NM_001029881; XM_017003329; XM_017003331; XM_011532514; XM_017003330 |
| TUBA3E | 112714 | NM_207312 |
| COX4I2 | 84701 | XM_005260580; XM_005260581; NM_032609; XM_005260579 |
| ERP27 | 121506 | NM_152321; NM_001300784 |
| CREB3L3 | 84699 | NM_001271997; NM_032607; NM_001271995; NM_001271996 |
| BAALC | 79870 | XR_001745601; NM_001024372; NM_001364874; NM_024812 |
| MEOX2 | 4223 | NM_005924 |
| CSPG4 | 1464 | NM_001897 |
| GRIN2A | 2903 | XM_017023172; NM_001134407; XM_011522461; NM_001134408; NM_000833; XM_011522458; XM_017023173 |
| LHX9 | 56956 | NM_001014434; NM_020204; XM_005245350; XM_011509781; XM_017001849; NM_001370213 |
| GABRQ | 55879 | NM_018558; XM_011531184 |
| AVPR1A | 552 | NM_000706 |
| COL25A1 | 84570 | XM_011532334; NM_001256074; XM_011532358; NM_032518; NM_198721; XM_011532333; XM_011532356; XM_017008736; XM_017008737; NR_045756; XM_011532338; XM_017008735; XM_011532335; XM_011532355 |
| ASB5 | 140458 | XM_005262759; XM_011531617; NM_080874; XM_011531616 |
| ADAMTSL1 | 92949 | XM_017015311; NM_052866; XM_011518063; XM_011518067; XM_017015313; NM_001040272; XM_011518064; XM_011518068; NM_139238; XM_017015310; XM_011518070; XM_017015312; XM_017015314; NM_139264 |
| FHL5 | 9457 | NM_001170807; NM_001322466; NM_001322467; NM_020482 |
| DEFB132 | 400830 | NM_207469 |
| CTAGE9 | 643854 | NM_001145659 |
| OPN4 | 94233 | NM_001030015; XM_017016955; XM_017016956; XM_017016957; NM_033282 |
| CXCL11 | 6373 | NM_001302123; NM_005409 |
| ACAN | 176 | XM_011521313; XM_011521314; NM_001135; NM_001369268; NM_013227 |
| B4GALNT1 | 2583 | XM_024448928; XR_002957307; XM_011538147; XM_024448929; NM_001276469; XM_017019141; NM_001276468; XM_005268773; XM_017019140; NM_001478; XM_017019142 |
| ADGRL4 | 64123 | NM_022159 |
| SMOC1 | 64093 | NM_001034852; NM_022137; XM_005267996; XM_005267995 |
| SLC38A8 | 146167 | NM_001080442; XM_017022946 |
| DNAAF3 | 352909 | NM_001256716; NM_001256714; NM_001256715; NM_001031802; NM_178837 |
| IGFBP6 | 3489 | NM_002178 |
| SLC47A2 | 146802 | NM_001099646; XM_017024221; XM_017024225; XM_017024222; XM_017024224; XM_017024226; XR_001752432; XM_017024223; NR_135624; NM_001256663; NM_152908; NR_135625; XR_001752433 |
| SFN | 2810 | NM_006142 |
| CPNE4 | 131034 | XM_017005695; NM_130808; XM_017005694; NM_001388327; XM_024453338; XM_011512408; XM_024453339; NM_001388326; NM_153429; XM_017005696; XM_024453340; NM_001289112 |
| CST6 | 10395 | NM_001316668; NM_182643; XM_005273374; NM_001348081; NM_001348083; NM_001348084; NM_001164271; NM_006094; NM_024767; NM_001348082 |
| CLDN3 | 1365 | NM_001306 |
| PIGR | 5284 | XM_011509629; NM_002644 |
| CPLX2 | 10814 | XM_005265798; XM_005265799; XM_017008964; NM_032282; NM_001008220; NM_006650; XM_011534419 |
| LRRN4 | 164312 | XM_011529183; NM_152611 |
| WFDC5 | 149708 | NM_001395506; NM_145652; XM_011528601; XM_011528602 |

-continued

| Gene | NCBI Gene ID | NCBI Accession Number(s) |
|---|---|---|
| NPBWR1 | 2831 | NM_005285 |
| PRKCG | 5582 | NM_002739; NM_001316329 |
| ARHGAP40 | 343578 | NM_001164431 |
| KRT23 | 25984 | NM_001282433; XM_005257200; XM_011524595; NM_015515; NM_173213 |
| HS3ST4 | 9951 | NM_006040 |
| SPAG6 | 9576 | NM_001253855; XM_005252646; XM_005252645; NM_172242; NM_001253854; NM_012443 |
| HGFAC | 3083 | NM_001297439; NM_001528 |
| CNTN6 | 27255 | NM_001289081; NM_001349352; NM_001349356; XM_017006174; NM_001349361; XM_011533591; NM_001349358; NM_014461; NM_001289080; NM_001349353; NM_001349359; XM_011533590; NM_001349350; NM_001349357; NM_001349354; XR_940415; NM_001349351; NM_001349355; NM_001349360; XM_017006171; XM_017006172; XM_017006177; NM_001349362 |
| LCN2 | 3934 | NM_005564 |
| AKR1B10 | 57016 | XR_927491; XM_011516416; XM_011516417; NM_020299 |
| SCEL | 8796 | XM_006719884; XM_011535281; XM_011535284; XM_011535285; XM_011535288; XM_011535289; NM_144777; XM_006719882; XM_011535291; XM_017020805; XM_006719885; XM_011535283; XM_011535287; XM_011535290; NM_003843; XM_005266578; NM_001160706; XM_011535282; XM_011535286 |
| NKX2-4 | 644524 | NM_033176 |
| | | Chromophobe_Renal_Cell_Carcinoma |
| REG1A | 5967 | NM_002909 |
| PADI3 | 51702 | NM_016233; XM_011541571; XM_017001463; XM_011541572 |
| MUC12 | 10071 | NM_001164462 |
| AVPR1B | 553 | NM_000707 |
| CTSE | 1510 | XM_011509245; NM_001910; NM_148964; XM_011509244; NM_001317331 |
| KRT6A | 3853 | NM_005554 |
| KRT6B | 3854 | NM_005555 |
| SLC17A2 | 10246 | XM_006714951; XM_017010160; XM_006714949; XM_006714950; NM_001286123; NM_005835; XM_017010159; NM_001286125 |
| HAVCR1 | 26762 | XM_017009339; XM_024446021; XM_024446023; XM_024446020; XM_024446024; NM_001308156; XM_024446019; XM_011534515; NM_001173393; NM_012206; NM_001099414; XM_024446022 |
| KRT6C | 286887 | NM_173086 |
| TMEM196 | 256130 | NM_001366626; NM_001366628; XM_017011929; NM_001366627; NM_152774; NM_001363562; XM_017011928; NM_001366625 |
| CDH6 | 1004 | NM_004932; NM_001362435; XM_017008910; XM_011513921; XR_001741972 |
| PSORS1C2 | 170680 | NM_014069 |
| LYZL1 | 84569 | XR_428650; XM_017016791; NM_032517; XM_005252627 |
| KRT33B | 3884 | NM_002279 |
| C4orf51 | 646603 | XM_024454188; XR_002959750; XR_002959751; XR_002959755; XR_002959756; XM_024454189; XR_002959749; XR_002959752; NM_001080531; XM_024454190; XR_002959748; XR_002959746; XR_002959747; XR_002959753; XR_002959754 |
| PSG5 | 5673 | NM_001130014; XM_011527132; NM_002781; XM_017027003 |
| UMODL1 | 89766 | XM_017028508; NM_001199527; XM_017028507; NM_001004416; NM_001199528; NM_173568; XM_011529797 |
| DEFB132 | 400830 | NM_207469 |
| PIP | 5304 | NM_002652 |
| DBX1 | 120237 | NM_001029865 |
| SLC6A2 | 6530 | XM_011523295; XM_011523297; XR_933403; XM_011523299; XM_011523300; NM_001172502; NM_001043; NM_001172501; XM_006721263; XM_011523298; NM_001172504; XM_011523296 |
| SPSB4 | 92369 | XM_017007509; XR_924215; XR_924216; NM_080862 |
| ATP6V0D2 | 245972 | NM_152565 |
| RGS8 | 85397 | XM_011510089; XM_017002634; NM_001387848; XM_017002631; NM_001387849; NM_001369564; NM_001387847; XM_017002632; NM_001102450; NM_033345; XM_011510090; XM_011510091 |
| FOXI1 | 2299 | XR_941092; NM_012188; NM_144769 |
| CLEC2L | 154790 | XM_017011770; NM_001353368; NM_001080511 |
| AMTN | 401138 | NM_001286731; NM_212557 |
| | | Glioblastoma |
| TCEAL2 | 140597 | NM_080390 |
| RBP1 | 5947 | NM_002899; NM_001130992; NM_001130993; NM_001365940 |
| CBLN1 | 869 | NM_004352 |
| FBXO17 | 115290 | NR_104026; NM_148169; NM_024907 |
| CLEC2B | 9976 | NM_005127 |
| ATOH8 | 84913 | XM_006712122; XM_011533139; XR_939732; XR_001739003; NM_032827; XR_939733; XR_939731 |
| TSTD1 | 100131187 | NM_001113207; NM_001113205; NM_001113206 |
| SNAP91 | 9892 | XM_017011576; XM_024446600; NM_001376676; NM_001376683; NM_001376689; NM_001376690; NM_001376698; NM_001376700; NM_001376710; NM_001376715; NM_001376739; NR_164846; XM_005248770; XM_006715615; XM_011536276; XM_017011575; XM_017011579; XM_017011580; XM_024446599; NR_026669; NM_001256717; NM_001376677; |

-continued

| Gene | NCBI Gene ID | NCBI Accession Number(s) |
|---|---|---|
| | | NM_001376687; NM_001376701; NM_001376706; NM_001376713; NM_001376716; NM_001376723; NM_001376736; XM_017011558; XM_017011564; XM_017011566; XM_017011570; NM_001376675; NM_001256718; NM_001376680; NM_001376688; NM_001376694; NM_001376707; NM_001376708; NM_001376711; NM_001376740; XM_017011567; XM_017011590; NM_001376678; NM_001376691; NM_001376705; NM_001376738; NR_164843; XM_011536266; XM_011536269; XM_011536271; XM_011536275; XM_017011562; XM_017011571; XM_017011574; XM_017011582; XM_017011583; XM_017011584; NM_001242792; NM_001363677; NM_001376686; NM_001376712; NM_001376719; NM_001376721; NM_001376731; NM_001376741; XM_011536273; XM_017011559; XM_017011565; XM_017011581; XM_017011585; XM_017011587; XM_017011589; NM_001242794; NM_001376679; NM_001376695; NM_001376696; NM_001376697; NM_001376702; NM_001376709; NM_001376717; NM_001376728; NR_164844; XM_017011569; XM_017011572; XM_017011573; XM_017011577; XM_017011586; NM_001242793; NM_001376681; NM_001376684; NM_001376685; NM_001376692; NM_001376693; NM_001376699; NM_001376703; NM_001376704; NM_001376714; NM_001376720; NM_001376726; NM_001376734; NM_001376737; NM_001376742; NM_014841; NR_164845; XM_011536265; XM_017011557; XM_017011560; NM_001376682; NM_001376718; NM_001376733; NM_001376735 |
| SNX22 | 79856 | NM_024798; XM_005254677; XM_017022581; NR_073534 |
| NDC80 | 10403 | NM_006101 |
| MEOX2 | 4223 | NM_005924 |
| LUZP2 | 338645 | NM_001252008; XM_017017648; XR_930864; NM_001252010; XM_011520056; XM_017017649; NM_001009909 |
| SUSD5 | 26032 | XM_005265034; XM_017006137; NM_015551 |
| ASF1B | 55723 | NM_018154 |
| CARD16 | 114769 | NM_001394580; NM_052889; XM_011542583; NM_001017534 |
| SH3GL2 | 6456 | NM_003026; XR_001746364; XM_011518005 |
| KLRC2 | 3822 | NM_002260 |
| AURKA | 6790 | NM_001323304; NM_001323303; NM_198435; NM_198437; XM_024451974; NM_198433; NM_198434; NM_198436; XM_017028034; XM_017028035; NM_001323305; NM_003600 |
| TNFAIP6 | 7130 | NM_007115 |
| FUT9 | 10690 | XM_011535383; XM_011535385; XM_017010188; NM_006581; XM_017010190 |
| TUBA1C | 84790 | NM_001303114; NM_032704; NM_001303116; NM_001303117; NM_001303115 |
| HDAC4 | 9759 | XM_011512219; XM_011512225; NM_001378415; XM_011512218; XM_017005394; XM_006712879; XM_011512224; XM_017005395; NM_001378416; NM_006037; XM_011512223; XM_011512227; NM_001378414; XM_011512220; XM_011512222; XM_011512230; XM_024453257; XM_011512217; XM_011512226; NM_001378417; XM_006712877; XM_006712880 |
| OPHN1 | 4983 | XM_006724653; XM_011530961; XM_005262270; XM_017029555; NM_002547 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| CRTAC1 | 55118 | NM_018058; XM_017016367; XM_005269938; XM_011539917; NM_001206528; XM_017016366 |
| SLC22A18 | 5002 | NM_002555; NM_183233; XM_011520142; NM_001315501; XM_011520141; NM_001315502 |
| SSTR1 | 6751 | NM_001049 |
| HMX1 | 3166 | NM_018942; NM_001306142 |
| GDF15 | 9518 | XM_024451789; NM_004864 |
| NALCN | 259232 | XM_017020537; XM_011521067; XM_011521069; NM_001350748; NM_052867; NM_001350751; NM_001350749; XM_017020536; XM_024449336; NM_001350750 |
| GABRG1 | 2565 | NM_173536; XM_017007990 |
| PHYHIPL | 84457 | XM_017016783; XM_017016782; XM_011540275; XM_011540276; NM_032439; NM_001143774 |
| TAGLN2 | 8407 | NM_003564; NM_001277223; NM_001277224 |
| PPM1L | 151742 | NM_001317911; NM_001317912; NR_134243; XM_011512440; NM_139245 |
| OCIAD2 | 132299 | NM_001014446; NM_152398; NM_001286773; NR_104589; NM_001286774 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| PDPN | 10630 | NM_001006625; NM_198389; NM_001385053; NM_001006624; XM_006710295; NM_006474; NM_013317; XM_024451404 |
| TOM1L1 | 10040 | XM_017024002; XR_002957936; NM_001321173; NM_001321175; NM_001321174; XR_243612; NM_001321176; NM_005486; XR_001752397 |
| NTNG2 | 84628 | XM_011519105; XM_011519099; XM_011519094; XM_011519097; XM_011519098; NM_032536; XM_011519096; XM_011519100; XM_011519108; XM_011519112; XM_011519104; XM_011519113; XM_017015213; XM_011519102; XM_011519106; XM_011519107; XM_017015216; |

-continued

| Gene | NCBI Gene ID | NCBI Accession Number(s) |
|---|---|---|
| | | XM_011519110; XM_017015212; XM_017015215; XM_006717304; XM_011519103; XM_011519109; XM_017015214 |
| PKIB | 5570 | XM_011535937; NM_181795; XM_011535930; XM_011535931; XM_011535935; XM_011535936; NM_001270393; NM_032471; XM_011535932; NM_001270395; XM_011535933; NM_001270394; NM_181794 |
| SHISA7 | 729956 | NM_001145176; NM_175908 |
| IL1RAP | 3556 | NM_001364880; NM_001167930; NM_001167931; NM_002182; NM_134470; NM_001167929; NM_001364879; NR_157353; NM_001167928; NM_001364881; NR_157352; XM_017006348 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| REPS2 | 9185 | XM_011545605; XM_024452479; XM_011545604; XM_005274625; XM_011545603; XM_005274626; XM_011545607; XM_024452478; XM_017029955; XM_017029956; NM_001080975; NM_004726; XM_017029958; XR_001755742; XM_011545606; XM_011545609; XM_017029957 |
| ATP6V1G2 | 534 | NM_130463; NM_138282; NM_001204078 |
| DIRAS3 | 9077 | NM_004675 |
| SOX8 | 30812 | NM_014587 |
| FCGBP | 8857 | NM_003890 |
| TIMP1 | 7076 | NM_003254; XM_017029766 |
| CSDC2 | 27254 | NM_014460 |
| DDIT4L | 115265 | NM_145244 |
| LGALS3 | 3958 | NM_001357678; NR_003225; NM_002306; NM_001177388 |
| G0S2 | 50486 | NM_015714 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |
| DSCAML1 | 57453 | XM_011542917; NM_020693; XM_011542920; NM_001367905; XM_011542918; XM_011542919; XM_011542921; XM_011542924; NM_001367904; XM_011542925 |
| | | Astrocytoma |
| RBP1 | 5947 | NM_002899; NM_001130992; NM_001130993; NM_001365940 |
| FBXO17 | 115290 | NR_104026; NM_148169; NM_024907 |
| HLF | 3131 | NM_002126; XM_011524705; XR_002957996; NM_001330375; XM_005257269 |
| CNTN3 | 5067 | XM_017006508; NM_020872; NM_001393376; XM_017006509; XM_011533768 |
| TMEM158 | 25907 | NM_015444 |
| CACNG2 | 10369 | XM_017028531; NM_006078; NM_001379051; NR_166440 |
| IRX2 | 153572 | NM_033267; XR_001742016; XM_024454379; NM_001134222; XM_011513979 |
| MEOX2 | 4223 | NM_005924 |
| LSP1 | 4046 | NM_001242932; NM_001013255; NM_001289005; NM_001013254; NM_002339; NM_001013253 |
| LUZP2 | 338645 | NM_001252008; XM_017017648; XR_930864; NM_001252010; XM_011520056; XM_017017649; NM_001009909 |
| ASF1B | 55723 | NM_018154 |
| LYZ | 4069 | NM_000239 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| CTSC | 1075 | NM_001114173; NM_148170; NM_001814 |
| GABBR1 | 2550 | XM_011514455; XM_006715047; XM_024446392; NM_001319053; NM_001470; XM_011514453; XR_001743302; NM_021903; XM_005248982; NM_021904; NM_021905; XR_001743303 |
| PBK | 55872 | NM_018492; NM_001278945; NM_001363040 |
| TUBA1C | 84790 | NM_001303114; NM_032704; NM_001303116; NM_001303117; NM_001303115 |
| PYGL | 5836 | NM_002863; NM_001163940 |
| MARCH4 | 57574 | NM_020814 |
| DPP10 | 57628 | XM_017004566; NM_001321908; NM_001321910; NM_001178034; NM_001004360; NM_001321905; NM_001321907; NM_001321909; NM_001321911; NM_001321912; XM_024453023; NM_001321906; NM_020868; NM_001178036; NM_001178037; NM_001321913; NM_001321914 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| RASL10A | 10633 | XM_011529821; NM_001007279; XM_011529822; XM_011529823; NM_006477 |
| UBE2T | 29089 | NM_001310326; NM_014176 |
| SSTR1 | 6751 | NM_001049 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; |

-continued

| Gene | NCBI Gene ID | NCBI Accession Number(s) |
|---|---|---|
| | | NM_152874; NM_152872; NR_028036; NM_152875; XM_011539767; NM_000043; NR_135313 |
| FAM155A | 728215 | XM_011521109; NM_001080396 |
| PHYHIPL | 84457 | XM_017016783; XM_017016782; XM_011540275; XM_011540276; NM_032439; NM_001143774 |
| PPM1L | 151742 | NM_001317911; NM_001317912; NR_134243; XM_011512440; NM_139245 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| MEGF11 | 84465 | NM_001385031; XM_017022673; NM_001385030; NM_001387150; NM_032445; NR_169554; NR_169555; NR_169556; NR_169557; NR_169558; XM_017022675; NM_001385029; XM_017022670; XM_017022674; NM_001387151; XM_017022671; XM_017022672; NM_001385028; NM_001385032; NM_001385033 |
| PLCB1 | 23236 | NM_015192; NM_182734 |
| STOX1 | 219736 | NM_001130162; NM_001130161; NM_001130160; NM_152709; XM_011539454; NM_001130159 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FKBP11 | 51303 | NM_001143782; NM_016594; NM_001143781 |
| GPX7 | 2882 | NM_015696 |
| GRID1 | 2894 | NM_017551; XM_011539720 |
| DNM3 | 26052 | XM_017000982; XM_017000983; XM_017000988; NM_001278252; XM_017000977; XM_017000989; NM_001350206; NM_015569; XM_017000979; XM_017000985; XM_017000991; XR_001737110; NM_001136127; NR_146559; XM_017000976; XM_017000978; XR_001737107; NM_001350204; XM_005245079; XM_017000987; XR_001737111; XM_017000980; XM_017000990; XM_017000992; XM_017000984; XM_017000986; XR_001737108; NM_001350205 |
| CLIC1 | 1192 | NM_001288; NM_001287593; NM_001287594 |
| ATP6V1G2 | 534 | NM_130463; NM_138282; NM_001204078 |
| RIMS2 | 9699 | XM_017014008; XM_017014028; XM_024447342; NM_001100117; NM_001348487; NM_001348496; NM_001348503; XM_005251106; XM_017014014; XM_017014019; XM_017014027; XM_024447344; XM_024447345; NM_001348489; NM_001348491; NM_001348505; NM_001348508; NM_001348509; XM_006716698; XM_017014021; NM_014677; XM_017014010; XM_017014022; XM_024447343; NM_001348499; NM_001395653; NM_001395654; XM_011517398; XM_017014009; XM_017014011; XM_017014016; XM_017014024; NM_001282881; NM_001348490; NM_001348497; NM_001348495; NM_001348498; NR_145710; XM_011517395; XM_017014007; NM_001282882; NM_001348484; NM_001348492; NM_001348494; NM_001348500; NM_001348501; NM_001348502; NM_001348504; XM_005251107; XM_017014012; XM_017014015; XM_017014034; XM_024447347; NM_001348488; NM_001348506; NR_145711; XM_017014006; XM_017014017; XM_017014023; XM_017014036; XM_024447346; NM_001348485; NM_001348486; NM_001348493; NM_001348507; NM_001395652 |
| TJP2 | 9414 | XM_011519206; NM_001369871; NM_001369872; XM_011519208; XM_011519209; NM_001369870; NM_004817; XM_011519207; NM_001369874; NM_001170630; NM_001369875; XM_011519204; NM_001170415; NM_001170416; NM_001170414; NM_001369873; NM_201629 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| RGS9 | 8787 | NM_001081955; NM_003835; NM_001165933 |
| FCGBP | 8857 | NM_003890 |
| APOC4-APOC2 | 100533990 | NR_037932 |
| TIMP1 | 7076 | NM_003254; XM_017029766 |
| NTSR2 | 23620 | NM_012344; XM_005246156; XM_006711877; XM_006711876; XM_017003738 |
| CA12 | 771 | NM_001218; NR_135511; NM_206925; NM_001293642 |
| JPH3 | 57338 | NM_001271604; NR_073379; NM_001271605; NM_020655 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| DDIT4L | 115265 | NM_145244 |
| RARRES2 | 5919 | XM_017012491; NM_002889 |
| MDK | 4192 | NM_001012334; XM_011520116; XM_017017764; NM_001270550; NM_001270551; NM_001012333; NM_001270552; NM_002391; NR_073039 |
| FPR1 | 2357 | NM_002029; NM_001193306 |
| CD58 | 965 | XM_017002869; NM_001779; NM_001144822; NR_026665 |
| POSTN | 10631 | NM_001135934; NM_001286665; NM_001286666; XM_017020355; NM_001330517; NM_006475; XM_005266232; NM_001286667; NM_001135936; XM_017020356; NM_001135935 |

-continued

| Gene | NCBI Gene ID | NCBI Accession Number(s) |
|---|---|---|
| DSCAML1 | 57453 | XM_011542917; NM_020693; XM_011542920; NM_001367905; XM_011542918; XM_011542919; XM_011542921; XM_011542924; NM_001367904; XM_011542925 |
| | | Oligodendroglioma |
| ZNF488 | 118738 | NM_153034; XM_006717617; XM_024447789; XM_017015643; NM_001346932; NM_001346933; NM_001346934; XM_011539244; NM_001346936; NM_001346935 |
| RBP1 | 5947 | NM_002899; NM_001130992; NM_001130993; NM_001365940 |
| WNT7B | 7477 | XM_011530366; NM_058238 |
| SLC7A14 | 57709 | NM_020949; NM_175917 |
| HLF | 3131 | NM_002126; XM_011524705; XR_002957996; NM_001330375; XM_005257269 |
| CACNG2 | 10369 | XM_017028531; NM_006078; NM_001379051; NR_166440 |
| SVOP | 55530 | NM_018711 |
| KCNK3 | 3777 | NM_002246; XM_005264293 |
| SUSD5 | 26032 | XM_005265034; XM_017006137; NM_015551 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| VIM | 7431 | XM_006717500; NM_003380 |
| CUX2 | 23316 | XM_011538069; XM_017019081; XM_017019080; XM_011538063; XM_011538070; NM_001370598; NM_015267 |
| HRH3 | 11255 | NM_007232; XM_005260266; XM_017027623 |
| MYH7 | 4625 | XM_017021340; NM_000257 |
| MYT1 | 4661 | NM_004535 |
| GPR158 | 57512 | NM_020752; XM_017016452; XR_930512 |
| PYGL | 5836 | NM_002863; NM_001163940 |
| ACSL6 | 23305 | NM_001205247; NM_001205248; NM_001205250; NM_001205251; NM_015256; NM_001009185 |
| CRTAC1 | 55118 | NM_018058; XM_017016367; XM_005269938; XM_011539917; NM_001206528; XM_017016366 |
| SPRY4 | 81848 | XM_011537685; NM_001293289; NM_001293290; NM_030964; XM_017009910; NM_001127496 |
| VSIG4 | 11326 | NM_007268; NM_001184830; NM_001184831; XM_017029251; NM_001100431; NM_001257403 |
| UPP1 | 7378 | XM_011515513; XM_011515512; NM_001287426; NR_109837; XM_005249838; NM_001287428; NM_001287430; XM_011515515; NM_001362774; NM_001287429; NM_181597; XM_011515514; NM_003364 |
| PDZD4 | 57595 | NM_001303513; NM_001303512; NM_001303516; NM_001303515; NM_001303514; NM_032512 |
| FAS | 355 | NR_028033; XM_011539765; XM_011539766; NR_028034; NR_135314; NR_135315; NM_152877; XM_011539764; XR_945732; XR_945733; NM_152873; NM_152876; XM_006717819; NM_001320619; NR_028035; NM_152871; NM_152874; NM_152872; NR_028036; NM_152875; XM_011539767; NM_000043; NR_135313 |
| FAM155A | 728215 | XM_011521109; NM_001080396 |
| KCNJ9 | 3765 | NM_004983 |
| LRRTM4 | 80059 | NM_001134745; NM_001330370; NM_001282924; NM_024993; NM_001282928; NR_146416 |
| CHGB | 1114 | NM_001819 |
| GABRA3 | 2556 | NM_000808; XM_006724811 |
| STOX1 | 219736 | NM_001130162; NM_001130161; NM_001130160; NM_152709; XM_011539454; NM_001130159 |
| BATF3 | 55509 | XR_921869; XR_001737289; XM_017001683; NM_018664 |
| CYTL1 | 54360 | NM_018659; XM_017008299 |
| ABCC8 | 6833 | XM_017018204; XM_017018202; XR_001747945; NM_001351296; NM_001351297; XR_001747946; XM_017018201; XR_002957189; NM_001287174; NR_147094; XM_024448668; NM_001351295; XM_017018199; XM_017018197; NM_000352 |
| PDPN | 10630 | NM_001006625; NM_198389; NM_001385053; NM_001006624; XM_006710295; NM_006474; NM_013317; XM_024451404 |
| FAM222A | 84915 | XM_006719654; XM_017020055; NM_032829; XM_024449229 |
| SCRT1 | 83482 | NM_031309; XM_024447291 |
| GPX7 | 2882 | NM_015696 |
| DIRAS3 | 9077 | NM_004675 |
| ATP6V1G2 | 534 | NM_130463; NM_138282; NM_001204078 |
| EIF3CL | 728689 | NM_001317857; NM_001099661; XM_017023620; XM_017023621; NM_001317856 |
| FCGR2A | 2212 | NM_001136219; NM_021642; XM_011509287; XM_024454040; XM_017000664; XM_017000665; XM_017000663; XR_001737042; XM_017000666; XM_011509290; XM_011509291; XM_024454041; NM_001375296; NM_001375297 |
| KCNIP2 | 30819 | XM_006717812; NM_173342; XM_005269729; XM_005269730; NM_014591; NM_173197; XM_011539731; NM_173191; NM_173195; XM_017016161; NM_173192; NM_173194; NM_173193 |
| PRLHR | 2834 | NM_004248 |
| FCGBP | 8857 | NM_003890 |
| KLHDC8A | 55220 | NM_001271863; NM_001271865; XM_024448121; NM_018203; NM_001271864 |
| FAM57B | 83723 | XM_017023754; XM_017023751; XM_024450465; XM_024450464; XM_017023752; XM_024450466; XM_017023750; XM_005255613; NM_001318504; NM_001352173; XM_005255614; XM_005255615; NM_031478 |
| BRINP1 | 1620 | NM_014618 |

-continued

| Gene | NCBI Gene ID | NCBI Accession Number(s) |
|---|---|---|
| CD58 | 965 | XM_017002869; NM_001779; NM_001144822; NR_026665 |
| RDH5 | 5959 | NM_001199771; NM_002905 |
| GFRA1 | 2674 | XM_011539634; NM_001348098; NM_001382557; NM_005264; NM_001382558; NM_001348099; NM_001382560; NM_001382559; NM_001145453; NM_001348096; NM_145793; NM_001382556; NM_001382561 |
| EPN2 | 22905 | NM_001102664; NM_148921; NM_014964 |
| | | Basal_Breast_Cancer |
| CDH6 | 1004 | NM_004932; NM_001362435; XM_017008910; XM_011513921; XR_001741972 |
| ESR1 | 2099 | XM_011535545; XM_017010378; XM_017010382; XR_001743223; XR_002956266; NM_001385568; XM_017010381; NM_001122741; NM_001328100; NM_001385570; XM_006715375; XM_017010383; NM_001385572; XM_011535547; XM_011535549; XM_017010377; NM_001385571; XM_017010380; NM_000125; NM_001122740; NM_001122742; NM_001291230; NM_001291241; XM_011535543; XM_017010379; NM_001385569 |
| SULT1C3 | 442038 | NM_001008743; XM_017004155; NM_001320878; XM_017004153; XM_017004154 |
| WNT10A | 80326 | XM_011511930; XM_011511929; NM_025216 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| CTCFL | 140690 | NM_001269041; NM_001269055; NM_001386993; NR_170377; NM_001269054; NM_080618; NR_072975; NM_001269042; NM_001269044; NM_001269047; NM_001269043; NM_001269045; NM_001269051; NM_001386994; NM_001269040; NM_001269048; NM_001269050; NM_001386997; NM_001269052; NM_001386995; NM_001386996; NM_001269046; NM_001269049 |
| UGT2B11 | 10720 | XM_011531550; XM_017007660; NM_001073 |
| KRT16 | 3868 | NM_005557 |
| TFF3 | 7033 | NM_003226 |
| CCL19 | 6363 | NM_006274 |
| DNALI1 | 7802 | NM_003462 |
| EN1 | 2019 | NM_001426 |
| S100B | 6285 | NM_006272; XM_017028424 |
| BPI | 671 | XM_024451972; NM_001725 |
| SERHL2 | 253190 | NM_014509; NR_104301; XR_244363; NR_104300; NM_001284334; XM_024452196; XM_017028739; XM_024452197; XR_001755198 |
| UBXN10 | 127733 | XM_005245742; NM_152376; XM_011540699 |
| SLC44A4 | 80736 | NM_001178045; NM_001178044; NM_025257 |
| ROPN1 | 54763 | NM_001394218; NM_001317775; NR_133919; NR_133916; NR_133917; NM_001394219; NM_001317774; NM_001394217; NM_017578; NR_133918; NR_172091 |
| SPINK8 | 646424 | NM_001080525; XM_017007046; XM_024453712; XR_002959568 |
| CT83 | 203413 | NM_001017978 |
| ACTL8 | 81569 | NM_030812; XM_011542212 |
| MIA | 8190 | NM_006533; NM_001202553 |
| ERBB4 | 2066 | XM_005246376; XM_017003577; XM_017003578; XM_005246377; NM_001042599; XM_017003581; XM_006712364; XM_017003582; XM_017003579; XM_017003580; NM_005235 |
| GABRP | 2568 | XM_005265872; NM_001291985; NM_014211; XM_024446012 |
| TMEM246 | 84302 | NM_001303107; NM_001303108; NM_032342; XM_024447701; NM_001371233 |
| C1orf64 | 149563 | NM_178840 |
| SPON1 | 10418 | NM_006108 |
| KRT6B | 3854 | NM_005555 |
| KRT79 | 338785 | NM_175834 |
| KCNT1 | 57582 | XM_017014932; XM_017014933; NM_020822; XM_017014931; XM_011518877; XM_011518878; XM_011518879; NM_001272003; XM_011518880; XM_011518881; XM_024447617; XM_024447618 |
| SHC4 | 399694 | NM_203349; XM_005254375 |
| HORMAD1 | 84072 | NM_001199829; NM_032132; XM_011510054 |
| LRRC31 | 79782 | XM_011513158; XM_011513159; XM_011513160; NM_001277127; NM_001277128; NM_024727; XM_017007204 |
| NRTN | 4902 | NM_004558 |
| C1QL4 | 338761 | NM_001008223; XM_011538270 |
| TLX1 | 3195 | NM_001195517; XM_011539744; XM_011539745; NM_005521 |
| CLDN8 | 9073 | NM_199328; NM_012132 |
| MGAM2 | 93432 | NM_001293626; NM_001008748; XM_011516692; XM_011516694; NR_003715; XM_024446997; XM_011516693; XR_927547; NR_003717 |
| ST6GALNAC1 | 55808 | NM_018414; XR_002958047; XM_017024842; XM_017024844; NM_001289107; XM_011524995; XM_011524996; XM_017024843; XR_001752559; NR_110309 |
| GFRA3 | 2676 | NM_001496 |
| MAGEA3 | 4102 | XM_011531161; XM_005274676; XM_006724818; XM_011531160; NM_005362 |
| PRR15 | 222171 | NM_001329997; NM_001329996; NM_175887; XM_011515198; XM_011515199 |
| IGF2 | 3481 | NM_001291862; NM_001291861; NM_000612; NM_001007139; NM_001127598 |
| LY6D | 8581 | NM_003695 |
| TPSG1 | 25823 | NM_012467; XM_011522447; XM_011522446 |
| TAT | 6898 | NM_000353 |
| SMOC1 | 64093 | NM_001034852; NM_022137; XM_005267996; XM_005267995 |

-continued

| Gene | NCBI Gene ID | NCBI Accession Number(s) |
|---|---|---|
| MT1H | 4496 | NM_005951 |
| REEP6 | 92840 | NM_138393; NM_001329556 |
| FOXA1 | 3169 | NM_004496; XM_017021246 |
| IL12RB2 | 3595 | NR_047584; XM_011541384; XM_005270827; XM_006710617; NM_001374259; XM_011541383; NM_001258215; NM_001258216; XM_017001204; NM_001258214; NM_001319233; XM_005270828; XM_017001203; NM_001559; NR_047583 |
| ART3 | 419 | NM_001377183; XM_017008210; XM_024454058; NM_001377173; NM_001377180; XM_024454052; XM_024454061; XM_024454062; XR_002959732; NM_001130017; NM_001377181; XM_017008208; XR_002959733; NM_001377174; XM_024454051; NM_001377179; XM_024454050; XM_024454053; XM_024454054; XM_024454059; XM_024454063; NM_001377177; NM_001377178; NM_001377182; XM_024454056; NM_001179; NM_001377176; XM_017008206; NM_001130016; NM_001377175; NM_001377184; NM_001377185 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| LOR | 4014 | NM_000427; XM_024447049 |
| GRIK1 | 2897 | NM_001320618; NM_001320616; XM_005260944; NM_001320630; NM_000830; XR_001754829; NM_001320621; NM_001393425; NM_001393426; NM_001330993; NM_001330994; NM_001393424; NM_175611 |
| FDCSP | 260436 | NM_152997 |
| PKP1 | 5317 | NM_000299; NM_001005337 |
| C6orf15 | 29113 | NM_014070 |
| AADAC | 13 | NM_001086; XM_005247104 |
| PGR | 5241 | XM_011542869; NM_001271161; NR_073142; NM_000926; XM_006718858; NM_001202474; NM_001271162; NR_073141; NR_073143 |
| ORM2 | 5005 | NM_000608 |
| ROPN1B | 152015 | XM_006713513; NM_001012337; XM_005247138; NM_001308313 |
| TBC1D9 | 23158 | NM_015130 |
| NPAS3 | 64067 | XM_005267991; NM_001394989; XM_011537069; XM_017021582; XM_017021584; XM_017021585; XM_017021587; NM_022123; XM_011537067; XM_011537071; NM_001165893; NM_001394988; NM_173159; XM_017021583; XM_017021586; XM_017021588; XM_005267992; NM_001164749 |
| HMGCS2 | 3158 | NM_001166107; XM_011541313; NM_005518 |
| NPR1 | 4881 | XM_017001374; XM_005245218; NM_000906 |
| ELOVL2 | 54898 | NM_017770; XM_011514717; XM_011514716; XM_017010985 |
| CA12 | 771 | NM_001218; NR_135511; NM_206925; NM_001293642 |
| CT62 | 196993 | NR_168259; NM_001102658; NR_168260 |
| | | Non_Basal_Breast_Cancer |
| CHODL | 140578 | XM_017028273; NM_001204174; NM_024944; XM_011529453; NM_001204176; NM_001204175; NM_001204177; XM_011529457; NM_001204178 |
| MSLN | 10232 | NM_001177355; NM_005823; NM_013404 |
| CST4 | 1472 | NM_001899 |
| CEACAM6 | 4680 | NM_002483; XM_011526990 |
| OVGP1 | 5016 | NM_002557 |
| FOLR1 | 2348 | NM_000802; NM_016729; NM_016730; NM_016725; NM_016724 |
| LRRTM1 | 347730 | NM_178839; XM_017003987; XM_017003986 |
| TTC6 | 319089 | XM_017021257; XM_011537431; XM_017021254; XM_024449560; XM_011537430; XM_011537432; XR_943762; NM_001310135; XM_017021256; NM_001368142; XM_017021255; XR_001750287; NM_001007795 |
| SPRR2A | 6700 | NM_005988 |
| NCAM2 | 4685 | XM_024452081; NM_001352594; XM_011529580; NM_001352592; NM_004540; XM_011529575; NM_001352597; XM_011529576; XM_011529582; NM_001352591; XM_011529581; XM_017028356; NM_001352595; XM_011529585; XM_017028357; NM_001352593; NM_001352596 |
| WNT10A | 80326 | XM_011511930; XM_011511929; NM_025216 |
| PKHD1L1 | 93035 | XM_017013970; XM_017013969; XM_011517371; XM_017013971; XM_017013972; XM_017013973; XM_017013974; NM_177531 |
| BCAS1 | 8537 | XM_005260591; XM_017028111; XM_005260595; NM_001366295; XM_005260590; XM_011529090; NM_001366298; XM_005260594; XM_005260589; XM_011529091; NM_001366297; NM_001316361; NM_003657; NM_001323347; NM_001366296 |
| SMYD1 | 150572 | NM_198274; NM_001330364 |
| DACT2 | 168002 | NM_001286350; NM_001286351; XM_011535507; NM_214462; NR_104425 |
| AKR7A3 | 22977 | XM_017000714; NM_012067; XM_011541046; XR_001737055 |
| HPX | 3263 | NM_000613 |
| S100B | 6285 | NM_006272; XM_017028424 |
| MAL | 4118 | NM_022438; NM_002371; NM_022440; NM_022439 |
| D4S234E | 27065 | NM_001287763; NM_001287764; NM_001040101; NR_167932; NM_001382227; NM_001382228; NR_167933; NM_014392 |
| SLC44A4 | 80736 | NM_001178045; NM_001178044; NM_025257 |
| SPINK8 | 646424 | NM_001080525; XM_017007046; XM_024453712; XR_002959568 |
| THSD4 | 79875 | NM_024817; NM_001286429; XM_017022584; NM_001394532; XM_017022586; XM_011522044; XM_017022585; XM_011522043; XM_017022582; XM_017022583 |
| TBX5 | 6910 | NM_181486; NM_080717; NM_000192; XM_017019912; NM_080718 |

-continued

| Gene | NCBI Gene ID | NCBI Accession Number(s) |
|---|---|---|
| NEK10 | 152110 | XM_006712998; XM_011533415; XM_017005765; XR_001740034; NM_001394966; XM_017005768; NM_001394968; XM_024453374; NM_001031741; NM_001394965; NM_001394967; NM_001394971; XM_006712997; XM_006713002; XM_011533413; XM_011533414; NM_001394970; NM_001394964; NM_001394969; XM_006712999; XM_017005762; XM_017005764; NM_001394963; NM_199347; XM_017005763; XM_017005773; XM_024453373; NM_001304384; XM_006713001; XM_017005774; NM_152534 |
| TFAP2B | 7021 | XM_017011235; XM_017011233; NM_003221; XM_011514837; XM_017011234 |
| MB | 4151 | NM_001382810; NM_001382809; NM_203378; NM_001362846; NM_001382812; NM_203377; NM_001382811; NM_005368; NM_001382813 |
| OCA2 | 4948 | XM_017022264; XM_017022257; XM_017022258; XM_017022262; XM_017022255; XM_017022263; XM_011521640; XM_017022256; XM_017022261; XR_001751294; NM_001300984; XM_017022265; NM_000275; XM_017022259; XM_017022260 |
| CCNA1 | 8900 | XM_011535294; XM_011535296; NM_001111047; XM_011535295; NM_001111046; NM_003914; NM_001111045 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| GABRP | 2568 | XM_005265872; NM_001291985; NM_014211; XM_024446012 |
| C1orf64 | 149563 | NM_178840 |
| MSMB | 4477 | NM_138634; NM_002443 |
| PSAT1 | 29968 | NM_021154; NM_058179 |
| CPA2 | 1358 | NM_001869 |
| SLC30A8 | 169026 | XM_024447083; NM_001172813; NM_001172814; NM_001172815; NM_001172811; NM_173851 |
| NRTN | 4902 | NM_004558 |
| ZG16B | 124220 | NM_145252 |
| ABCC11 | 85320 | XM_017023802; NM_001370496; NM_032583; XM_017023798; XM_011523397; XM_017023797; XM_017023800; XM_017023803; XM_017023799; XM_017023801; NM_001370497; XM_011523398; NM_145186; XM_024450475; XR_001752012; NM_033151 |
| MGAM2 | 93432 | NM_001293626; NM_001008748; XM_011516692; XM_011516694; NR_003715; XM_024446997; XM_011516693; XR_927547; NR_003717 |
| KCNH1 | 3756 | NM_172362; XM_017001246; NM_002238 |
| CALB2 | 794 | NM_007088; XR_002957842; NM_001740; NR_027910; NM_007087 |
| PGC | 5225 | NM_002630; NM_001166424 |
| FSIP1 | 161835 | XM_011521307; XM_017021972; XM_011521309; NM_152597; XM_011521305; NM_001324338; XM_011521311; XM_011521306 |
| HIF3A | 64344 | XM_017027133; XM_017027139; XM_024451649; XR_001753736; XR_935849; NM_022462; XM_017027132; XM_017027142; XM_005259152; XM_017027138; NM_152796; XM_005259156; XM_005259155; XM_017027136; XM_017027137; XR_002958343; XM_005259153; XM_017027135; XM_017027140; NM_152794; XM_017027134; XM_017027141; NM_152795 |
| HMP19 | 51617 | NM_015980 |
| PRR15 | 222171 | NM_001329997; NM_001329996; NM_175887; XM_011515198; XM_011515199 |
| SERTM1 | 400120 | NM_203451 |
| MMP3 | 4314 | NM_002422 |
| POU3F3 | 5455 | NM_006236 |
| PCK1 | 5105 | NM_002591; XM_024451888 |
| CHAD | 1101 | XM_011524214; NM_001267 |
| SLITRK6 | 84189 | NM_032229 |
| SOX10 | 6663 | NM_006941 |
| TAT | 6898 | NM_000353 |
| PIP | 5304 | NM_002652 |
| F2RL2 | 2151 | NM_001256566; NM_004101 |
| MT1H | 4496 | NM_005951 |
| FOXA1 | 3169 | NM_004496; XM_017021246 |
| KRT15 | 3866 | XM_017024614; XM_011524784; NM_002275 |
| TF | 7018 | NM_001063; NM_001354703; NM_001354704 |
| FAM196A | 642938 | XM_017016537; XM_017016538; XM_017016539; XM_005252694; XM_017016540; XM_017016541; XM_017016542; XM_017016543; NM_001039762 |
| MLPH | 79083 | XM_011511812; XM_006712737; XM_006712740; XM_006712739; NM_024101; NM_001281473; NM_001042467; NM_001281474; NR_104019; XM_017004893; XM_017004894 |
| PRSS33 | 260429 | NM_001385462; NM_001385463; NM_001385464; NM_152891; NR_169625 |
| SCX | 642658 | XM_006716616; NM_001080514; NM_001008271 |
| WNT6 | 7475 | NM_006522 |
| SIAH3 | 283514 | NM_198849 |
| ROPN1B | 152015 | XM_006713513; NM_001012337; XM_005247138; NM_001308313 |
| HOXC13 | 3229 | NM_017410 |
| NPR1 | 4881 | XM_017001374; XM_005245218; NM_000906 |
| RASGEF1C | 255426 | NM_175062; NM_001031799 |

-continued

| Gene | NCBI Gene ID | NCBI Accession Number(s) |
|---|---|---|
| LEMD1 | 93273 | XM_011510163; XM_011510162; XM_011510165; NM_001199052; XM_011510160; XM_011510161; XM_011510164; NR_037583; NM_001001552; NM_001199050; NM_001199051 |
| PRSS50 | 29122 | NM_013270 |
| | | Squamous_Cell_Carcinoma_of_the_Head_and_Neck |
| IGFBP6 | 3489 | NM_002178 |
| NLGN4Y | 22829 | XM_011531429; NM_001365586; XM_017030036; NM_001365591; XM_006724874; XM_011531427; XM_011531428; XM_017030041; NM_001164238; NM_001206850; NR_028319; XM_017030039; NR_046355; NM_014893; XM_011531430; NM_001365588; NM_001365592; NM_001394830; XM_017030040; NM_001365584; NM_001365590; XM_024452490; NM_001365593; NM_001394831 |
| SCGB1A1 | 7356 | NM_003357 |
| FGG | 2266 | NM_000509; NM_021870 |
| PLIN1 | 5346 | NM_002666; XM_005254934; NM_001145311 |
| AGER | 177 | XR_001743190; NM_001206940; XM_017010328; NM_001206936; NM_001206954; NM_172197; XR_001743189; NM_001136; NM_001206929; NM_001206932; NM_001206934; NR_038190; NM_001206966 |
| MMP13 | 4322 | NM_002427 |
| MYL1 | 4632 | NM_079422; NM_079420 |
| FCN3 | 8547 | NM_173452; NM_003665 |
| IRX4 | 50805 | NM_016358; NM_001278633; NM_001278632; NM_001278635; NM_001278634 |
| BPIFA1 | 51297 | NM_130852; NM_001243193; NM_016583 |
| PAX1 | 5075 | NM_006192; NM_001257096 |
| ADH1B | 125 | NM_001286650; NM_000668 |
| C4BPA | 722 | XM_005273252; NM_000715; XM_005273251 |
| CA4 | 762 | XM_017025012; XR_001752604; NM_000717; XM_005257639; XR_001752608; NR_137422; XR_001752605; XR_001752607; XR_001752610; XM_011525183; XR_001752606; XR_001752609 |
| F2RL2 | 2151 | NM_001256566; NM_004101 |
| HOXA13 | 3209 | NM_000522 |
| PCSK2 | 5126 | NM_002594; NM_001201529; NM_001201528 |
| BMP8A | 353500 | XM_017001198; XM_006710616; XM_011541381; XM_011541382; XR_946642; XR_946640; XR_946641; NM_181809 |
| TBX4 | 9496 | XM_011525490; XM_011525491; NM_001321120; XM_011525495; NM_018488 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PGC | 5225 | NM_002630; NM_001166424 |
| RPE65 | 6121 | XM_017002027; NM_000329 |
| GSTM5 | 2949 | NM_000851; XM_005270785; XM_005270784 |
| MYH7 | 4625 | XM_017021340; NM_000257 |
| ATP1A2 | 477 | NM_000702 |
| KIF18B | 146909 | XM_011524389; NM_001264573; NM_001265577; XM_011524386; NM_001080443; XM_011524390; XM_011524388; XM_011524385; XM_011524387; XM_011524391 |
| SCARA5 | 286133 | NM_173833 |
| FILIP1 | 27145 | NR_110608; XM_011535756; NM_001289987; NM_001300866; XM_005248713; NM_015687; XM_005248715 |
| DCD | 117159 | NM_001300854; NM_053283 |
| SLURP1 | 57152 | NM_020427 |
| DLX1 | 1745 | NM_178120; NM_001038493 |
| WT1 | 7490 | NM_000378; NR_160306; NM_001367854; NM_001198551; NM_001198552; NM_024424; NM_024426; NM_024425 |
| TCF21 | 6943 | NM_003206; NM_198392 |
| EN1 | 2019 | NM_001426 |
| KRT14 | 3861 | NM_000526 |
| RPS4Y1 | 6192 | NM_001008 |
| TBX5 | 6910 | NM_181486; NM_080717; NM_000192; XM_017019912; NM_080718 |
| CDKN2A | 1029 | XR_929159; XM_011517676; XM_011517675; NM_001363763; NM_001195132; NM_058195; NM_000077; NM_058196; NM_058197; XM_005251343 |
| ALDH1A2 | 8854 | NM_001206897; NM_170697; NM_170696; NM_003888 |
| CFTR | 1080 | NM_000492 |
| AMY1A | 276 | NM_004038; NM_001008221 |
| NAV3 | 89795 | XM_017020172; NM_001024383; NM_014903; XM_011538944 |
| HPN | 3249 | NM_002151; NM_182983; XM_017026732; NM_001384133; XM_017026731; NM_001375441 |
| MKRN3 | 7681 | NM_005664 |
| SCN7A | 6332 | NM_002976; XM_006712680; XM_006712682; XM_011511615; XM_017004667; NR_045628 |
| ACTC1 | 70 | NM_005159 |
| MYOG | 4656 | NM_002479 |

-continued

| Gene | NCBI Gene ID | NCBI Accession Number(s) |
|---|---|---|
| HOXB5 | 3215 | NM_002147 |
| PKMYT1 | 9088 | NM_001258451; NM_182687; NM_001258450; XM_011522735; XM_024450490; NM_004203; XM_011522734; XM_011522736 |
| HJURP | 55355 | XM_011511437; NM_001282962; NM_001282963; NM_018410 |
| HP | 3240 | NM_001126102; NM_005143; NM_001318138 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| DLL3 | 10683 | NM_016941; NM_203486 |
| CYP2B6 | 1555 | NM_000767 |
| SNTN | 132203 | NM_001080537; NM_001348756 |
| CRNN | 49860 | NM_016190 |
| HOXB8 | 3218 | NM_024016; XM_005257286; XM_017024564 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| EIF1AY | 9086 | NM_004681; NM_001278612 |
| IBSP | 3381 | NM_004967 |
| C7 | 730 | NM_000587 |
| COL10A1 | 1300 | XM_011535432; NM_000493; XM_011535433; XM_017010248; XM_006715333 |
| AJAP1 | 55966 | XM_011541787; NM_001042478; NM_018836; XM_011541786 |
| ADIPOQ | 9370 | NM_004797; NM_001177800 |
| | | Squamous_Cell_Lung_Carcinoma |
| C20orf85 | 128602 | NM_178456 |
| KLK10 | 5655 | XM_006723289; XM_005259061; NM_002776; NM_145888; NM_001077500; XM_017026993; XM_006723287; XM_005259062 |
| ACTC1 | 70 | NM_005159 |
| IGFBP6 | 3489 | NM_002178 |
| ADH1B | 125 | NM_001286650; NM_000668 |
| B4GALNT4 | 338707 | XM_017017654; XR_001747858; NM_178537 |
| C4BPA | 722 | XM_005273252; NM_000715; XM_005273251 |
| CENPM | 79019 | NM_001110215; NM_001304372; NM_024053; XM_011530368; NM_001304371; NM_001002876; NM_001304370; NM_001304373 |
| PRAME | 23532 | XM_011530034; NM_206954; NM_001318126; NM_001318127; NM_001291715; NM_001291719; NM_001291716; NM_006115; NM_001291717; NM_206953; NM_206956; NM_206955 |
| MYOG | 4656 | NM_002479 |
| CACNG1 | 786 | NM_000727 |
| HOXB5 | 3215 | NM_002147 |
| FABP4 | 2167 | NM_001442 |
| MMP11 | 4320 | NM_005940; NR_133013 |
| SCGB1A1 | 7356 | NM_003357 |
| RSPO1 | 284654 | XM_006710583; NM_001242909; NM_001242908; NM_001242910; NM_173640; NM_001038633 |
| LRRN4CL | 221091 | NM_203422 |
| ENDOU | 8909 | NM_001172439; NM_006025; NM_001172440 |
| MMP12 | 4321 | NM_002426 |
| GSTA1 | 2938 | XM_005249034; NM_001319059; NM_145740 |
| TNXB | 7148 | NM_001365276; NM_019105; NM_032470 |
| HP | 3240 | NM_001126102; NM_005143; NM_001318138 |
| KLHL41 | 10324 | NM_006063 |
| NEFL | 4747 | NM_006158 |
| TBX5 | 6910 | NM_181486; NM_080717; NM_000192; XM_017019912; NM_080718 |
| NKX2-1 | 7080 | NM_001079668; NM_003317 |
| CTSE | 1510 | XM_011509245; NM_001910; NM_148964; XM_011509244; NM_001317331 |
| KCNK10 | 54207 | NM_021161; NM_138317; XM_011536840; XM_024449628; NM_138318 |
| VPREB3 | 29802 | NM_013378 |
| TBX4 | 9496 | XM_011525490; XM_011525491; NM_001321120; XM_011525495; NM_018488 |
| TROAP | 10024 | XM_011537723; NM_005480; XR_944445; XM_011537724; XR_944446; NM_001100620; XM_006719181; NM_001278324 |
| PKNOX2 | 63876 | NR_168078; NM_001382330; NM_001382335; NR_168084; NM_001382328; NM_001382329; NM_001382341; NR_168083; NM_022062; NM_001382324; NM_001382326; NM_001382334; NM_001382336; NM_001382337; NM_001382340; NR_168079; NR_168080; NR_168081; NM_001382325; NM_001382323; NM_001382327; NM_001382332; NM_001382338; NM_001382339; NR_168076; NR_168077; NM_001382331; NM_001382333; NR_168082 |
| PAK7 | 57144 | XM_017027960; XM_017027964; XM_017027962; XM_017027963; XM_017027965; NM_177990; XM_017027961; NM_020341 |
| CASQ2 | 845 | NM_001232 |
| PGC | 5225 | NM_002630; NM_001166424 |
| AMY1C | 278 | NM_001346780; XM_017001058; NM_001008219 |
| COX6A2 | 1339 | NM_005205 |
| MUC7 | 4589 | NM_001145006; NM_152291; NM_001145007 |
| CLEC2L | 154790 | XM_017011770; NM_001353368; NM_001080511 |

-continued

| Gene | NCBI Gene ID | NCBI Accession Number(s) |
|---|---|---|
| POU6F2 | 11281 | NM_007252; NM_001370959; NM_001166018 |
| ZNF280B | 140883 | XR_002958666; NM_080764; XM_011529897; XR_002958668; XR_002958667; NR_130642; NR_130643 |
| CRNN | 49860 | NM_016190 |
| SNTN | 132203 | NM_001080537; NM_001348756 |
| GREM2 | 64388 | XM_005273226; XM_011544249; NM_022469 |
| OGN | 4969 | NM_033014; NM_014057; NM_024416 |
| MYH7 | 4625 | XM_017021340; NM_000257 |
| KIF18B | 146909 | XM_011524389; NM_001264573; NM_001265577; XM_011524386; NM_001080443; XM_011524390; XM_011524388; XM_011524385; XM_011524387; XM_011524391 |
| PLA2G4F | 255189 | NM_213600; XR_931785; NR_033151; XR_931786 |
| LGSN | 51557 | XM_017010931; XM_017010929; XM_011535889; XM_011535892; NM_016571; XM_017010930; NM_001143940 |
| AHSG | 197 | NM_001354571; NM_001354572; NM_001622; NM_001354573 |
| UBE2C | 11065 | NM_001281742; NM_001281741; NM_181802; NM_181803; NR_104036; NR_104037; NM_007019; NM_181800; NM_181801; NM_181799 |
| DES | 1674 | NM_001927; NM_001382708; NM_001382710; NM_001382713; NM_001382709; NM_001382711; NM_001382712 |
| RNF223 | 401934 | NM_001205252 |
| MYL1 | 4632 | NM_079422; NM_079420 |
| C1orf116 | 79098 | XM_011509973; NM_001083924; XM_005273259; XM_006711530; NM_023938 |
| BMP5 | 653 | XM_011514817; NM_001329756; XM_024446524; NM_001329754; NM_021073 |
| SCARA5 | 286133 | NM_173833 |
| FCN3 | 8547 | NM_173452; NM_003665 |
| HPN | 3249 | NM_002151; NM_182983; XM_017026732; NM_001384133; XM_017026731; NM_001375441 |
| LOR | 4014 | NM_000427; XM_024447049 |
| LDB3 | 11155 | NM_001171610; NM_001368064; NM_007078; NM_001080115; NM_001080114; NM_001368068; NM_001080116; NM_001171611; NM_001368067; NM_001368063; NM_001368065; NM_001368066 |
| DHRS7C | 201140 | NM_001220493; NM_001105571 |
| CRISP3 | 10321 | NM_001368123; NM_006061; NM_001190986 |
| LY6D | 8581 | NM_003695 |
| FOXM1 | 2305 | XM_011520932; XM_011520934; NM_001243088; XM_011520930; XM_011520933; XM_011520935; XR_931507; NM_202003; NM_202002; XM_005253676; XM_011520931; NM_001243089; NM_021953 |
| CNTNAP2 | 26047 | XM_017011950; NM_014141 |
| ANLN | 54443 | XM_017012355; NM_018685; NM_001284302; XM_006715746; XM_017012354; XM_017012356; NM_001284301; XM_006715747 |
| DCD | 117159 | NM_001300854; NM_053283 |
| C7 | 730 | NM_000587 |
| THBS4 | 7060 | XR_002956176; XM_017009798; NM_001306214; NM_003248; NM_001306213; XM_017009799; NM_001306212 |
| GPR87 | 53836 | NM_023915 |
| MYOT | 9499 | XM_017010060; XM_017010061; NM_001300911; NM_001135940; XM_017010062; NM_006790 |
| USP43 | 124739 | XM_011523640; XM_011523642; XM_011523641; XM_017024161; XM_017024160; XM_017024159; XM_011523639; NM_001267576; NM_153210; XM_017024162 |
| EMX1 | 2016 | XM_011532697; NM_001040404; NM_004097; XM_005264203 |
| SLURP1 | 57152 | NM_020427 |
| BPIFA1 | 51297 | NM_130852; NM_001243193; NM_016583 |
| KLK5 | 25818 | NM_001077492; XM_011526702; NM_001077491; XM_011526703; NM_012427 |
| GYLTL1B | 120071 | XM_011519891; NM_001300721; NM_001300722; XM_011519888; XM_006718141; XM_011519890; XM_006718140; XM_011519893; NM_152312; XM_005252787; XM_011519886; XM_011519889; XM_011519892; XM_017017173 |
| HAND2 | 9464 | NM_021973 |
| MYOC | 4653 | NM_000261 |
| MCEMP1 | 199675 | NM_174918 |
| DCC | 1630 | XM_011525843; XM_011525844; XM_017025570; NM_005215; XM_017025568; XM_017025569 |
| LRRC26 | 389816 | NM_001013653 |
| KLK13 | 26085 | NM_015596; NR_145464; NM_001348178; NR_145466; NR_145465; XR_935788; NR_145463; NM_001348177; NR_145467 |
| WT1 | 7490 | NM_000378; NR_160306; NM_001367854; NM_001198551; NM_001198552; NM_024424; NM_024426; NM_024425 |
| KRT4 | 3851 | NM_002272 |
| COL10A1 | 1300 | XM_011535432; NM_000493; XM_011535433; XM_017010248; XM_006715333 |
| DPP6 | 1804 | NM_001364499; NR_157196; NM_001364500; XM_017011812; NM_001290252; NM_001364498; NM_001364501; NM_001039350; NM_001936; NM_130797; NR_157195; NM_001290253; NM_001364502; NM_001364497 |
| MASP1 | 5648 | XM_011512989; XM_017006869; XM_017006870; XM_017006871; NM_001031849; XM_006713701; XM_011512990; NM_001879; NR_033519; XM_017006872; XM_011512991; NM_139125 |

-continued

| Gene | NCBI Gene ID | NCBI Accession Number(s) |
|---|---|---|
| SGCG | 6445 | NM_000231; NM_001378245; NM_001378244; NM_001378246 |
| SCN7A | 6332 | NM_002976; XM_006712680; XM_006712682; XM_011511615; XM_017004667; NR_045628 |
| FEZF1 | 389549 | NM_001024613; XM_011516202; NM_001160264; XM_005250337 |
| SLCO4C1 | 353189 | XM_011543372; XM_011543370; NM_180991 |
| AJAP1 | 55966 | XM_011541787; NM_001042478; NM_018836; XM_011541786 |
| AMN | 81693 | XM_024449714; XM_011537203; NM_030943; XM_011537202 |
| SDR16C5 | 195814 | NM_001318049; NM_001318050; NM_138969; XM_011517479 |
| AQP4 | 361 | NM_001317387; NM_001364287; NM_001364286; NM_001317384; XM_011525942; NM_001650; NM_001364289; NM_004028 |
| CPNE7 | 27132 | NM_153636; XM_017023139; XM_011523000; XM_017023138; XM_017023140; XM_017023141; XM_011523001; NM_014427 |
| TCF21 | 6943 | NM_003206; NM_198392 |
| PTGER3 | 5733 | XM_011541810; NM_198718; NM_000957; NM_198712; NM_198713; NM_198720; NM_198714; NM_198719; NM_198717; NM_001126044; NM_198715; NR_028292; XR_946714; NM_198716; NR_028293; NR_028294 |
| | | Cervical_Squamous_Cell_Carcinoma |
| SALL1 | 6299 | NM_001127892; NM_002968 |
| MEOX2 | 4223 | NM_005924 |
| BCHE | 590 | NR_137636; NM_000055; NR_137635 |
| SYCP2 | 10388 | XM_011528488; XM_011528487; XM_011528493; XM_017027590; XM_011528490; XM_017027586; XM_017027591; NM_014258; XM_011528489; XM_017027589; XM_017027587; XM_017027588; XM_017027592 |
| KDM5D | 8284 | XM_005262561; XR_002958832; XR_002958834; XR_002958837; XR_244571; NM_001146705; XM_011531468; XR_001756013; XM_024452495; XM_005262560; XM_024452496; XR_001756009; XR_001756011; XR_002958835; XR_001756010; NM_001146706; XR_002958836; XR_430568; NM_004653; XR_001756012; XR_002958833 |
| OLFM4 | 10562 | NM_006418 |
| SYNGR3 | 9143 | NM_004209 |
| SLC6A15 | 55117 | XM_011538525; NM_018057; NM_001146335; NM_182767 |
| ADAMTS20 | 80070 | XM_011538754; XM_017019979; NM_025003; NM_175851 |
| FA2H | 79152 | XM_011523319; XM_011523317; NM_024306 |
| PGR | 5241 | XM_011542869; NM_001271161; NR_073142; NM_000926; XM_006718858; NM_001202474; NM_001271162; NR_073141; NR_073143 |
| FOXL2 | 668 | NM_023067 |
| KRT81 | 3887 | NM_002281 |
| HOXA13 | 3209 | NM_000522 |
| KRT36 | 8689 | NM_003771 |
| KRT83 | 3889 | NM_002282 |
| RPS4Y1 | 6192 | NM_001008 |
| TBX5 | 6910 | NM_181486; NM_080717; NM_000192; XM_017019912; NM_080718 |
| ASF1B | 55723 | NM_018154 |
| E2F8 | 79733 | NM_001256372; XM_011520367; NM_001256371; NM_024680; XR_930907 |
| CASP14 | 23581 | NM_012114; XM_011527861 |
| MYOCD | 93649 | XM_005256863; NM_001378306; NM_001146312; NM_153604; NM_001146313; XM_017025342 |
| KIF4A | 24137 | NM_012310 |
| PDLIM3 | 27295 | NM_001114107; XR_938723; NM_001257963; XR_938724; NM_001257962; NR_047562; NM_014476; XR_001741206 |
| PAGE2B | 389860 | XM_017029513; XM_011530785; XM_011530786; XM_011530787; NM_001015038 |
| RPE65 | 6121 | XM_017002027; NM_000329 |
| POU6F2 | 11281 | NM_007252; NM_001370959; NM_001166018 |
| CDKN2A | 1029 | XR_929159; XM_011517676; XM_011517675; NM_001363763; NM_001195132; NM_058195; NM_000077; NM_058196; NM_058197; XM_005251343 |
| HOXB8 | 3218 | NM_024016; XM_005257286; XM_017024564 |
| ALDH1A2 | 8854 | NM_001206897; NM_170697; NM_170696; NM_003888 |
| HTR2B | 3357 | XM_005246520; NM_000867; XM_006712482; NM_001320758 |
| DDX3Y | 8653 | NR_136716; NR_136718; NR_136719; NR_136721; NM_001122665; NR_136720; NR_136723; NM_004660; NM_001324195; XR_001756014; NM_001302552; NR_136717; NR_136724; NR_136722 |
| NAV3 | 89795 | XM_017020172; NM_001024383; NM_014903; XM_011538944 |
| BARX1 | 56033 | NM_021570 |
| OR2B6 | 26212 | NM_012367 |
| SEMA3D | 223117 | XM_011515961; NM_152754; NM_001384901; NM_001384902; NM_001384900; NM_001384903 |
| DYNC1I1 | 1780 | NM_001135556; NM_004411; NM_001278422; NM_001278421; NM_001135557 |
| NAP1L2 | 4674 | NM_021963 |
| MYL1 | 4632 | NM_079422; NM_079420 |
| ANO1 | 55107 | XM_006718602; XM_006718605; XM_011545124; XM_011545129; XM_017017956; XM_006718604; NM_001378095; NM_001378096; XM_011545123; XM_011545127; XM_011545131; NM_001378097; NM_018043; NR_030691; NM_001378092; XM_011545126; NM_001378093; NM_001378094 |
| HOXA11 | 3207 | NM_005523 |
| CDC25C | 995 | XM_011543764; XM_011543760; XM_011543761; XM_011543763; NM_001364026; NM_001364027; XM_005272145; NM_001287582; |

-continued

| Gene | NCBI Gene ID | NCBI Accession Number(s) |
|---|---|---|
| | | NM_001287583; NM_001790; NM_022809; XM_006714739; XM_011543759; XM_011543762; NM_001318098; NM_001364028 |
| SLCO1A2 | 6579 | NM_001386879; NM_001386886; NM_001386908; NM_001386920; NM_001386926; NM_001386939; NM_001386959; NM_001386960; XM_011520819; NM_001386881; NM_001386929; NM_134431; NR_170340; NM_001386878; NM_001386946; NM_001386952; XM_024449138; NM_001386890; NM_001386922; NM_001386938; NM_001386947; NM_001386961; XM_011520821; NM_001386927; NM_001386940; NM_001386948; NM_001386949; NM_001386958; NM_001386880; NM_001386882; NM_001386937; NM_001386951; NM_001386962; NM_001386963; NM_001386887; NM_001386921; NM_001386954; NR_170341; NR_170343; NM_005075; XM_017019849; NM_001386919; NM_001386931; NM_001386953; NM_021094 |
| EIF1AY | 9086 | NM_004681; NM_001278612 |
| RBFOX3 | 146713 | XM_017024209; XM_017024211; XM_024450595; NM_001385812; NM_001385840; NM_001385844; NM_001385847; XM_011524366; XM_017024208; NM_001385805; NM_001385807; NM_001385843; NM_001385845; NM_001025448; NM_001082575; NM_001385804; NM_001385808; NM_001385813; NM_001385836; NM_001385817; NM_001385819; NM_001385823; NM_001385826; NM_001385827; NM_001385828; NM_001385829; NM_001385831; NM_001385833; NM_001385842; XM_011524360; XM_024450593; XM_024450596; NM_001350453; NM_001385809; NM_001385832; NM_001385834; NM_001385838; NM_001039904; XM_011524367; XM_024450592; NM_001385811; NM_001385824; NM_001385835; NM_001385837; NM_001385846; NM_001350451; NM_001385806; NM_001385810; NM_001385820; NM_001385825; NM_001385830; NM_001385839; NM_001385841; NM_001385814; NM_001385815; NM_001385816; NM_001385818; NM_001385821; NM_001385822 |
| RDM1 | 201299 | NM_001163124; NR_027996; NR_027999; XM_011524509; NM_001163122; NM_001163130; NM_001163121; NM_001163125; NR_027998; NM_001163120; NM_001034836; NM_001330194; NM_145654; NR_027997; NR_028000 |
| SCARA5 | 286133 | NM_173833 |
| KCNS1 | 3787 | XM_017027846; NM_002251; NM_001322799 |
| PIANP | 196500 | NM_001244014; NM_153685; NM_001244015; XM_011520926 |
| C1orf106 | 55765 | XM_011509754; XM_011509755; NM_001367289; NM_001367290; XM_011509756; NM_001142569; NM_018265 |
| HOXA10 | 3206 | NR_037939; NM_153715; NM_018951 |
| AIM1L | 55057 | NM_017977; XM_011541672; XM_011541673; XR_001737260; NM_001039775; XR_946681; XM_005245918 |
| LEFTY2 | 7044 | NM_003240; NM_001172425; XM_011544266 |
| IRX5 | 10265 | NM_005853; XM_011522809; NM_001252197 |
| TRDN | 10345 | NM_001251987; NM_001256020; NM_001256021; NM_006073; NM_001256022 |
| CNTNAP2 | 26047 | XM_017011950; NM_014141 |
| FOXA1 | 3169 | NM_004496; XM_017021246 |
| ADGRD1 | 283383 | NM_198827; XM_005253566; XM_011538204; XM_011538208; XM_011538212; NM_001330497; XM_011538205; XM_011538206; XM_011538207; XM_011538209; XM_011538210; XM_011538211 |
| PENK | 5179 | NM_006211; NM_001135690 |
| AKR1C2 | 1646 | NM_001354; NM_001321027; NM_001135241; NM_205845; NM_001393392 |
| MKRN3 | 7681 | NM_005664 |
| NMU | 10874 | NM_001292046; XM_011534368; XM_011534367; NM_001292045; NM_006681; NR_120489 |
| DIAPH3 | 81624 | XM_011535258; XM_006719876; XM_024449422; NM_001258367; NM_001258370; XR_941672; XM_011535265; XR_002957479; XR_002957480; NM_001258366; XM_017020789; XR_002957478; NM_001042517; NM_001258368; XM_011535263; XR_001749694; XR_002957477; NM_001258369; NM_030932 |
| MUC2 | 4583 | NM_002457 |
| ZIC5 | 85416 | NM_033132; NR_146224; NR_146225 |
| MYLPF | 29895 | NM_001324458; NM_013292; NM_001324459 |
| POLQ | 10721 | NM_199420; NM_006596 |
| SYNDIG1 | 79953 | XM_011529349; XM_011529352; XR_937144; NM_001323607; XM_017028064; XM_017028065; XM_017028066; XM_011529350; XM_011529348; XM_011529351; XM_011529356; XM_011529358; XM_017028068; XM_017028069; XM_011529347; XM_017028067; NM_001323606; NM_024893; NR_147606; XM_011529353; XM_011529354 |
| SMC1B | 27127 | NM_148674; XM_011530145; XR_244368; XM_011530144; NM_001291501 |
| WT1 | 7490 | NM_000378; NR_160306; NM_001367854; NM_001198551; NM_001198552; NM_024424; NM_024426; NM_024425 |
| EPHA7 | 2045 | NM_001288630; NM_001376467; NM_001288629; XM_017010366; NM_001376466; NM_001376471; NM_004440; XR_001743218; NM_001376465; NM_001376470; NR_164810; NM_001376468; NM_001376469 |
| TCF23 | 150921 | NM_175769; XM_005264159 |
| | | Colorectal_Adenocarcinoma |
| EFHC1 | 114327 | NR_033327; NM_001172420; NM_018100 |
| KCNN3 | 3782 | NM_001204087; NM_001365837; NM_001365838; NM_170782; NM_002249 |

-continued

| Gene | NCBI Gene ID | NCBI Accession Number(s) |
|---|---|---|
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |

-continued

| Gene | NCBI Gene ID | NCBI Accession Number(s) |
|---|---|---|
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |

-continued

| Gene | NCBI Gene ID | NCBI Accession Number(s) |
|---|---|---|
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |

-continued

| Gene | NCBI Gene ID | NCBI Accession Number(s) |
| --- | --- | --- |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |

-continued

| Gene | NCBI Gene ID | NCBI Accession Number(s) |
|---|---|---|
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456 |
| | | Stomach_Adenocarcinoma |
| EFHC1 | 114327 | NR_033327; NM_001172420; NM_018100 |
| KCNN3 | 3782 | NM_001204087; NM_001365837; NM_001365838; NM_170782; NM_002249 |
| USP49 | 25862 | NM_001286554; NM_018561; NM_001384542 |
| ACTL6B | 51412 | NR_134539; NM_016188 |
| RBM38 | 55544 | NM_017495; NM_001291780; XM_011528885; XM_005260446; NM_183425 |
| CNNM1 | 26507 | NM_001345888; XM_011539631; XR_002956974; NM_020348; NM_001345887; NM_001345889; NR_144311; XR_945667 |
| DRAP1 | 10589 | NM_006442 |
| CWF19L1 | 55280 | NM_001303406; NM_018294; NM_001303407; NM_001303404; NM_001303405 |
| ADAM12 | 8038 | XM_017016705; NM_001288973; NM_001288974; NM_001288975; XM_017016706; NM_003474; NM_021641; XM_024448210 |

-continued

| Gene | NCBI Gene ID | NCBI Accession Number(s) |
|---|---|---|
| TSPAN6 | 7105 | XM_011531018; NM_001278741; NM_001278743; NM_001278740; NM_001278742; NM_003270 |
| TAF6L | 10629 | NM_006473; XM_017017100; XM_005273714 |
| RHBDF1 | 64285 | XM_017023556; XM_017023557; XM_017023558; NM_022450; XM_005255494; XM_005255498; XM_006720921 |
| ZNF135 | 7694 | XM_017027242; NM_001289401; NM_007134; NM_001164530; XM_017027241; XM_006723362; XM_017027240; XM_005259211; NM_001164527; XM_006723363; NM_003436; NM_001164529; NM_001289402 |
| HOXD12 | 3238 | NM_021193 |
| FABP1 | 2168 | NM_001443 |
| PFN2 | 5217 | NM_053024; NM_002628 |
| GAST | 2520 | NM_000805 |
| PPM1G | 5496 | NM_177983 |
| ALDH8A1 | 64577 | NM_001193480; NM_022568; NM_170771 |
| NRSN2 | 80023 | XM_017028074; XM_017028076; NM_001323685; XM_011529360; NM_001323679; NM_001323684; NM_024958; NM_001323680; NR_136649; XM_017028075; XM_011529363; XM_006723630; NM_001323682; NM_001323683; XM_017028073; NM_001323681; XM_011529362 |
| DRD4 | 1815 | NM_000797 |
| GKN1 | 56287 | NM_019617 |
| PLA2G12A | 81579 | NM_030821 |
| VWF | 7450 | NM_000552 |
| A4GNT | 51146 | XM_017006543; NM_016161; XM_017006544 |
| ANGEL2 | 90806 | XM_005273345; XR_001737529; XM_005273344; XM_017002776; XR_001737527; NM_001300753; NM_001300757; NM_144567; XM_005273346; XM_017002778; XR_001737530; XR_001737531; XR_001737532; XM_005273347; XR_001737528; XR_247045; XM_017002774; XM_017002777; NR_125333; NM_001300758; NM_001300755; XM_017002775 |
| PTPRCAP | 5790 | NM_005608 |
| MAGEA10 | 4109 | NM_001251828; NM_021048; NM_001011543 |
| RGS12 | 6002 | XM_017008534; XM_017008531; NM_001394162; NM_002926; NM_198227; NM_198229; NM_198432; NM_198587; NM_001394158; NM_001394159; XM_017008529; XR_924987; NM_001394156; NM_001394163; XM_011513543; XR_002959745; NM_001394154; NM_001394161; NM_198230; XR_427479; NM_001394157; NM_198430; NM_001394155 |
| SRC | 6714 | XM_017028025; XM_017028026; XM_017028024; XM_011529013; NM_198291; XM_017028027; NM_005417 |
| SLC5A3 | 6526 | NM_006933 |
| HSPB7 | 27129 | NM_001349685; NM_001349688; NM_001349686; NM_001349683; NM_001349682; NM_001349689; NM_001349687; NM_014424 |
| ZC3H3 | 23144 | XM_006716536; XM_017013248; XM_011516944; XM_017013249; XR_928313; XM_011516943; NM_015117 |
| TSSC4 | 10078 | XM_011519830; NM_005706; NM_001297659; XM_006718118; NM_001297661; NM_001297660; NM_001297658 |
| ADAM15 | 8751 | NM_003815; NM_207191; NR_048577; NR_048578; NM_207197; NM_001261464; NM_207196; NM_207195; NR_048579; NM_001261466; NM_001261465; NM_207194 |
| CTF1 | 1489 | XM_011545759; NM_001330; XM_011545760; NR_165660; NM_001142544 |
| TMEM120B | 144404 | XM_024448851; XM_024448852; NM_001080825 |
| CA12 | 771 | NM_001218; NR_135511; NM_206925; NM_001293642 |
| DBN1 | 1627 | NM_001393631; XM_017009139; NM_004395; XM_011534447; NM_080881; XM_017009140; NM_001363541; NM_001364151; NM_001364152; NM_001393630 |
| CXCL5 | 6374 | NM_002994 |
| CSPG4 | 1464 | NM_001897 |
| FAHD2B | 151313 | XM_011510746; XM_011510747; XM_024452730; XM_024452731; XR_001738649; XR_002959246; XM_017003471; NM_001320849; XM_011510748; XM_011510745; XM_011510750; XM_017003470; XM_017003472; NM_001320848; NM_199336 |
| KIR3DL2 | 3812 | XM_017026784; XM_011526940; NM_006737; NM_001242867 |
| IGLL1 | 3543 | NM_001369906; NM_020070; NM_152855 |
| CFP | 5199 | XM_017029575; NM_001145252; NM_002621 |
| IL11 | 3589 | NM_000641; NM_001267718 |
| VEGFB | 7423 | NM_003377; NM_001243733 |
| PGA5 | 5222 | NM_014224 |
| AR | 367 | NM_001348064; NM_001011645; NM_001348061; NM_001348063; NM_000044 |
| GGA2 | 23062 | XM_024450200; XM_017023075; NM_015044; NM_138640 |
| LIPF | 8513 | NM_004190; NM_001198829; NM_001198830; NM_001198828; XM_011540311 |
| MYH11 | 4629 | XM_017023250; NM_002474; NM_022844; NM_001040113; NM_001040114; XM_011522502 |
| CETP | 1071 | XM_006721124; NM_000078; NM_001286085 |
| LRFN3 | 79414 | NM_024509 |
| CPSF4 | 10898 | XM_011515757; XM_017011701; XM_017011702; XM_011515755; NM_001318161; NM_001318160; NM_006693; NM_001081559; NM_001318162; XM_011515756; XM_017011700; XM_017011703 |

-continued

| Gene | NCBI Gene ID | NCBI Accession Number(s) |
|---|---|---|
| GSDMD | 79792 | NM_024736; XM_011517301; NM_001166237 |
| WT1 | 7490 | NM_000378; NR_160306; NM_001367854; NM_001198551; NM_001198552; NM_024424; NM_024426; NM_024425 |
| SATB2 | 23314 | NM_015265; NM_001172517; XM_024452767; XM_024452768; NM_001172509; NR_134967; XM_005246396; XM_011510840; XM_017003656 |
| PRLR | 5618 | XM_011514068; NM_001204315; XM_017009645; NM_001204318; XM_024446132; NM_001204317; NR_037910; NM_000949; NM_001204316; XM_006714484; XM_011514069; NM_001204314; XM_024446131 |
| HOXA7 | 3204 | NM_006896 |
| KLHL11 | 55175 | NM_018143; XR_001752552 |
| TJAP1 | 93643 | XM_006715254; XM_011514995; NM_001146017; NM_001146018; NM_001350570; NM_001394543; XM_006715257; XM_017011493; XR_926337; NM_001350565; NM_001350568; NM_001394542; NM_001394544; XM_006715250; XM_006715261; XM_006715268; XM_024446587; NM_001350562; XM_017011492; NM_001146020; NM_001350561; NM_001394538; NM_001394541; XM_017011489; XM_024446584; NM_001350566; NM_001350569; NM_080604; XM_006715262; XM_006715263; XM_006715266; XM_024446586; NM_001146016; NM_001350563; NM_001350564; NM_001394539; NM_001394545; XM_006715269; XM_011514996; XM_024446585; NM_001350567; XM_006715251; XM_006715265; XM_006715267; NM_001146019; NM_001394540; NR_146793 |
| L1TD1 | 54596 | NM_001164835; NM_019079 |
| PTPRD | 5789 | XM_006716835; XM_017014958; XM_017014963; XM_017014968; XM_017014976; XM_017014987; XM_017014988; XM_017014990; NM_001040712; NM_001377947; NM_130391; XM_006716827; XM_006716832; XM_017014970; XM_017014971; XM_017014983; XM_017014985; XM_017014989; NM_001378058; XM_017014960; XM_017014965; XM_017014967; XM_017014979; NM_001377958; XM_017014964; XM_017014974; XM_017014977; XM_017014978; XM_017014986; NM_001377946; NM_002839; NM_130392; XM_006716834; XM_006716837; XM_017014959; XM_017014966; XM_017014984; XM_017014993; XM_017014995; NM_130393; XM_006716833; XM_017014972; XM_017014980; XM_017014981; XM_017014991; XM_024447625; XM_024447627; XM_011517992; XM_017014961; XM_017014969; XM_017014982; XM_017014994; XM_017014992; NM_001171025; XM_006716817; XM_006716823; XM_006716825; XM_017014973; XM_017014975 |
| DAGLA | 747 | XM_017018239; XM_017018238; NM_006133; XM_017018240 |
| CSF1 | 1435 | NM_000757; NM_172210; XM_017000369; NM_172211; NM_172212 |
| C1orf61 | 10485 | NM_001320454; NR_135260; NR_168070; NR_168072; NR_135267; NR_168071; NR_168073; NM_001320455; NR_135265; NR_135264; NR_135266; NM_001320453; NM_006365; NR_135268; NR_135261; NR_135262; NR_135263 |
| FOXRED2 | 80020 | NM_001102371; NM_024955; NM_001363041; NM_001363042 |
| HSD17B6 | 8630 | XM_024449251; XM_011538927; XM_005269208; XM_011538925; XM_011538926; XM_024449250; XM_005269207; NM_003725; XM_005269209; XM_006719672; XM_024449249 |
| FAIM2 | 23017 | XM_005268730; NM_012306 |
| SORBS1 | 10580 | XM_017015501; XM_017015503; XM_017015510; XM_017015511; XM_017015512; XM_017015539; NM_001034957; NM_001290296; NM_001290297; NM_001290298; NM_001377208; NM_001377209; NM_001384448; NM_001384453; NM_001384456; NM_001384461; XM_006717589; XM_011539155; XM_017015500; XM_017015505; XM_017015509; XM_024447770; NM_001290294; NM_001384450; NM_001384460; NM_015385; NM_024991; XM_011539150; XM_017015506; XM_017015536; XM_024447769; NM_001377206; NM_001384452; NM_001384459; NM_001384463; XM_011539167; XM_017015514; XM_017015515; NM_001290295; NM_001377200; NM_001377207; NM_001384455; NM_001384464; XM_017015504; NM_001034954; NM_001034955; NM_001377201; NM_001384447; NM_001384449; NM_001384457; NM_001384458; NM_006434; XM_011539140; XM_017015502; XM_017015513; XM_017015523; XM_017015525; XM_017015537; XM_017015540; NM_001034956; NM_001377198; NM_001377205; NM_001384462; XM_017015507; XM_017015508; XM_017015517; XM_017015530; XM_017015532; XM_017015533; NM_001377199; NM_001377203; NM_001377204; NM_001384451; NM_001384454; NM_001384465; NM_001377197; NM_001377202 |
| ERF | 2077 | XM_017026469; NM_001308402; NM_001312656; NM_006494; XM_017026468; NM_001301035 |
| KIAA0907 | 22889 | NM_014949 |
| CD207 | 50489 | XM_011532876; XM_011532875; XM_011532874; NM_015717 |
| SF3A2 | 8175 | NM_007165 |
| AQP5 | 362 | NM_001651; XM_005268838 |
| GABRE | 2564 | XM_024452360; NM_021990; NM_021984; XM_011531140; XM_017029388; XM_017029389; NM_004961; NM_021987; XM_017029387 |
| RAB40AL | 282808 | NM_001031834 |
| F7 | 2155 | XM_011537476; XM_011537475; NM_001267554; XM_011537474; NR_051961; XM_006719963; NM_019616; NM_000131 |

-continued

| Gene | NCBI Gene ID | NCBI Accession Number(s) |
|---|---|---|
| ZNF467 | 168544 | NM_001329856; XM_005249959; XM_005249960; XM_017011799; NM_207336; XM_005249961; XM_011515858; XM_006715864; XM_011515857 |
| HTR2A | 3356 | NM_001378924; NM_000621; NM_001165947 |
| MAPRE3 | 22924 | XM_011532700; NM_001303050; XM_006711967; XM_017003597; NM_012326 |
| LY6G5C | 80741 | NM_025262; NM_001002849; NM_001002848 |
| DAZ4 | 57135 | XM_011531509; NM_020420; NM_001388484; NM_001005375; XM_011531510 |
| MTTP | 4547 | NM_001300785; NM_001386140; NM_000253 |
| CD7 | 924 | XM_011523608; XM_017025316; NM_006137; XR_001752681; XR_001752680 |
| ISG20 | 3669 | NM_002201; NM_001303234; NM_001303236; XM_005254899; XM_006720488; XM_017022148; NM_001303235; NM_001303237; XM_011521521; NR_130134; XM_017022147; NM_001303233 |
| ZSCAN2 | 54993 | XM_024449978; XM_017022393; XM_024449975; NM_017894; NM_181877; XM_024449977; XM_024449976; NM_001007072 |
| CCNL2 | 81669 | XM_024450050; NM_001350499; XR_001737454; XR_946769; NM_001350497; NM_001350500; NR_146722; NM_001320153; NM_001320155; NM_030937; XM_017002420; XR_001737453; XR_002957676; XR_002957678; XR_002957684; NM_001350498; NM_001144867; XR_001737452; XR_001737455; NM_001039577; NR_135154; XM_024450049; XR_001737450; XR_426630; NR_146723; XM_011542216; XR_002957683; NM_001144868 |
| MMP23B | 8510 | XM_017002617; XR_002957848; XM_017002615; NM_006983 |
| GPA33 | 10223 | XM_017000005; NM_005814 |
| ITPKA | 3706 | XM_011521522; NM_002220 |
| GPR162 | 27239 | NM_014449; NM_019858 |
| PGA3 | 643834 | NM_001079807 |
| RNF25 | 64320 | XM_017004695; NM_022453 |
| EPN1 | 29924 | NM_001130072; NM_001321263; NM_013333; NM_001130071 |
| PIK3C2G | 5288 | XM_017019472; XM_017019476; XM_017019470; XM_017019473; XR_931307; XM_017019475; NM_001288772; XM_011520696; XM_011520697; XM_017019471; NM_001288774; NM_004570; XM_017019474; XM_017019477; XM_011520700; XM_011520701; XM_017019478; XM_017019479 |
| CLCN4 | 1183 | NM_001256944; NM_001830 |
| FLOT2 | 2319 | XM_017024394; XM_024450667; XM_017024396; NM_004475; XM_017024395; XM_024450666; NM_001330170; XM_005257953 |
| CACNA1H | 8912 | XM_006720965; XM_017023820; XM_006720963; XM_006720967; XM_011522724; XR_002957850; XM_005255652; XM_017023821; XM_011522727; XM_017023819; NM_021098; XM_006720968; XM_006720964; NM_001005407 |
| ANXA10 | 11199 | XM_011531571; NM_007193 |
| NOTCH2NL | 388677 | NM_001395232; NM_001364006; NM_203458; NM_001395231 |
| ADRA1D | 146 | NM_000678 |
| SLC2A6 | 11182 | XR_001746173; XM_011518189; XM_017014238; NM_001145099; XM_017014237; XR_001746175; XR_001746172; XM_017014236; XR_001746174; NM_017585 |
| SIPA1 | 6494 | XR_247210; NM_153253; XM_005274189; NM_006747 |
| TMEM160 | 54958 | NM_017854 |
| PRDM16 | 63976 | NM_199454; NM_022114 |
| GTPBP6 | 8225 | XM_011546184; XM_011545637; NM_012227; XM_006724447; XM_006724868 |
| TP53I11 | 9537 | NM_001258321; XM_011520478; XM_017018580; NM_001076787; NM_001258323; NM_001318387; NM_001318388; XM_017018581; XM_024448777; NM_001258320; NM_001258324; NM_001318390; NM_006034; NR_134612; XM_011520476; XM_011520475; NM_001318385; NM_001318386; NM_001318389; XM_005253227; XM_011520477; NM_001258322; XM_005253229; NM_001318384 |
| PRRX2 | 51450 | XM_017014803; NM_016307 |
| ADAMTSL4 | 54507 | XM_011509650; XR_001737242; XM_011509648; NM_001378596; XM_011509645; XM_011509652; NM_001288607; XM_011509651; NM_019032; XM_011509649; XM_017001506; XM_011509644; XM_017001507; NM_001288608; XR_921844; NM_025008 |
| PALM | 5064 | XM_005259565; NM_002579; XM_005259566; XM_017026850; NM_001040134 |
| RNF31 | 55072 | NM_017999; NM_001310332 |
| CLPTM1 | 1209 | NM_001294; NM_001282175; NM_001199468; NM_001282176 |
| CDC14A | 8556 | NM_033313; NM_001319212; NM_033312; NM_001319211; NM_001319210; NM_003672 |
| NEBL | 10529 | XM_005252343; NM_001173484; NM_001377323; NM_001377327; XM_011519291; XR_001746996; XR_242691; NM_001377325; NM_001377324; NM_001377326; NM_213569; NM_001010896; NM_001377328; XM_005252344; NM_001377322; NM_001177483; XR_001746995; XM_005252342; XM_017015468; NM_006393; NM_016365 |
| AQP8 | 343 | NM_001169; XM_011545822; XM_011545823 |
| NOL6 | 65083 | NM_022917; NM_130793; XM_017015044; NM_139235 |
| LMF2 | 91289 | NM_001363816; XR_001755368; XR_938349; NM_033200; XM_017029077; XM_006724427; XM_006724426 |
| FBP2 | 8789 | NM_003837 |
| GTPBP2 | 54676 | XM_017010976; XM_024446478; XM_024446475; NM_001286216; XM_024446477; XM_024446476; NM_019096 |
| GNL3L | 54552 | NM_001184819; NM_019067 |
| FBLN1 | 2192 | NM_006485; NM_006486; NM_001996; NM_006487 |
| DDA1 | 79016 | NM_024050; XM_024451701 |
| ELOVL4 | 6785 | NM_022726 |

-continued

| Gene | NCBI Gene ID | NCBI Accession Number(s) |
| --- | --- | --- |
| ITGA10 | 8515 | XM_017002623; XR_001737503; XM_017002626; XM_017002628; NM_001303041; NM_001303040; XR_001737502; XM_017002622; XM_017002625; NM_003637; XR_001737501; XR_001737504; XM_005277436; XM_017002624; XM_011510083; XM_011510084; XM_017002627 |
| HOXB9 | 3219 | NM_024017 |
| PAX8 | 7849 | NM_013992; NM_013953; NM_013952; NM_003466; NM_013951 |
| GPR137 | 56834 | XM_017018016; NM_001378083; XR_002957154; NM_001378078; NM_001378081; NM_001378087; XM_011545168; XM_005274100; NM_001170881; NM_001378076; NM_001378079; NM_001378085; NM_001378088; NM_001378089; NM_020155; XM_005274102; NM_001170880; NM_001378077; NM_001378082; NR_165394; NR_165396; XM_024448611; NM_001378086; NR_165397; XM_005274104; XM_011545169; NM_001177358; NM_001170726; NM_001378080; NM_001378084; NR_165395 |
| APBB3 | 10307 | NM_133174; NM_133172; NM_133173; NM_133176; NM_133175; NM_006051 |
| SCGB2A1 | 4246 | NM_002407 |
| MAP4K2 | 5871 | XR_002957155; XM_017018093; XM_024448634; XM_017018095; XM_024448630; NM_001307990; XM_024448629; NM_004579; XM_024448631; XM_024448633; XM_011545204 |
| ZBTB10 | 65986 | NM_001277145; NM_023929; NM_001105539 |
| CLCA1 | 1179 | NM_001285 |
| GSTM1 | 2944 | XM_005270782; NM_146421; NM_000561 |
| CLDN5 | 7122 | NM_001363066; NM_001363067; NM_001130861; NM_003277 |
| MAPK3 | 5595 | XR_243293; NM_001109891; NM_001040056; NM_002746 |
| ZNF428 | 126299 | NM_182498 |
| LYL1 | 4066 | NM_005583 |
| GGT5 | 2687 | XM_017028769; NM_001302464; XM_011530137; XM_017028768; NM_001099781; XM_011530134; XM_011530133; XM_011530135; NM_001302465; XM_005261557; XM_011530136; NM_001099782; NM_004121; XM_005261558 |
| FAM124B | 79843 | NM_001122779; NM_024785 |
| MTG1 | 92170 | NM_138384 |
| ALPL | 249 | NM_001177520; NM_001369803; NM_001127501; NM_001369804; NM_001369805; XM_017000903; NM_000478 |
| SLC26A3 | 1811 | NM_000111 |
| TMEM127 | 55654 | NM_001193304; XM_017004452; NM_017849; NM_032218; XM_017004450 |
| EPOR | 2057 | NR_033663; NM_000121 |
| FBXO17 | 115290 | NR_104026; NM_148169; NM_024907 |
| GALNT14 | 79623 | NM_001253827; XR_001738942; XR_001738941; NM_001329095; XM_017004907; NM_001253826; XR_001738943; XM_017004906; NM_001329097; NM_001329096; NM_024572 |
| RAB11B | 9230 | NM_004218 |
| CCDC106 | 29903 | NM_001370468; NM_001370467; NM_001370469; NM_001370470; NM_013301; NM_001370471 |
| PCCA | 5095 | XM_017020609; XM_017020613; XM_017020616; NM_001178004; NR_148030; XM_017020611; XR_001749567; XR_001749568; XR_001749569; NM_001352606; NM_001352610; NM_001352611; NM_001352605; NR_148028; XM_017020615; NM_001352607; NM_001352609; XM_017020607; XR_001749574; XR_931615; NR_148029; XM_011521093; XM_017020605; NM_001352608; NM_001352612; XM_017020606; XR_001749577; NR_148027; XM_017020612; XR_001749576; NM_000282; NM_001127692; NR_148031 |
| GJC1 | 10052 | XM_024450525; XM_005256920; NM_005497; XM_024450526; XM_024450527; XR_934346; NM_001080383 |
| TMEM158 | 25907 | NM_015444 |
| PGC | 5225 | NM_002630; NM_001166424 |
| IFNA8 | 3445 | NM_002170 |
| HSPB6 | 126393 | NM_144617 |
| CLDN18 | 51208 | NM_001002026; NM_016369 |
| GATA4 | 2626 | NM_001308093; NM_002052; NM_001308094; NM_001374273; NM_001374274 |
| EPB41L2 | 2037 | XM_017010353; XR_001743213; XR_001743215; NM_001350314; XM_011535527; XM_017010352; NM_001135555; NM_001350302; XM_011535525; XM_017010351; XM_017010356; NM_001350305; NM_001350309; NR_146620; XM_017010364; XR_001743216; XR_001743217; NM_001199389; NM_001350301; NM_001350303; NM_001350308; NM_001350312; XM_011535524; NM_001135554; NM_001252660; NM_001350307; NM_001350315; NM_001199388; NM_001350310; NM_001350311; NM_001431; NM_001350306; NM_001350320; XM_011535528; XM_017010350; XM_024446349; NM_001350299; NM_001350304; NM_001350313 |
| TNNT2 | 7139 | XM_011509943; NM_001001430; XM_011509946; XM_017002217; XM_011509941; XM_024449450; XM_024449455; NM_001001432; XM_006711508; XM_011509939; XM_017002216; XM_006711509; XM_011509942; NM_000364; NM_001276346; NM_001276347; XM_011509944; NM_001001431; XM_011509938; XM_011509940; XM_024449454; NM_001276345 |
| ZNF557 | 79230 | NM_024341; NM_001044387; NM_001044388 |
| CDR2L | 30850 | NM_014603; XM_006721852 |
| LRRC37A2 | 474170 | XM_011524841; XM_011524849; XM_011524850; XM_011524844; XM_011524842; XM_024450774; XM_024450773; NM_001006607; XM_011524846; XM_024450775; NM_001385803; XM_011524843; XM_011524848 |

-continued

| Gene | NCBI Gene ID | NCBI Accession Number(s) |
|---|---|---|
| ZNF771 | 51333 | NM_016643; NM_001142305 |
| SERPIND1 | 3053 | NM_000185 |
| PAOX | 196743 | NM_152911; NM_207125; NM_207126; NR_109764; NM_207129; NM_207127; NR_109763; NR_109765; NM_207128; NR_109766 |
| PITX1 | 5307 | NM_002653 |
| RET | 5979 | NM_020975; NM_001355216; NM_020630; NM_020629; NM_000323 |
| CNGA3 | 1261 | XM_006712243; NM_001298; NM_001079878; XM_011510554 |
| PTGER1 | 5731 | NM_000955 |
| NOS1AP | 9722 | NM_001126060; NM_001164757; NM_014697 |
| SORL1 | 6653 | NM_003105 |
| KCNE2 | 9992 | NM_172201; NM_005136 |
| SNURF | 8926 | NM_022804; NM_005678; NM_001394334 |
| ZNF721 | 170960 | NM_133474 |
| SLC35E2 | 9906 | NM_182838; NR_173244; NR_173245; NM_001199787 |
| SELENBP1 | 8991 | NM_001258289; XR_002957987; XR_921993; NM_003944; XM_024450671; NM_032183; NM_001258288 |
| ARSB | 411 | XR_001742066; XM_011543393; XM_011543390; XM_017009471; XR_001742065; NM_198709; XM_011543392; XM_011543391; NM_000046 |
| ZNF148 | 7707 | NM_001348427; NM_001348436; NM_001348426; NM_001348430; NM_001348434; NM_001348425; NM_001348432; NM_001348431; NM_001348433; NM_001348424; NM_001348429; NM_021964; NM_001348428 |
| ACTG2 | 72 | NM_001199893; NM_001615 |
| CXXC1 | 30827 | XM_011525940; XM_017025718; XM_011525941; XM_017025719; NM_001101654; NM_014593 |
| SETD1A | 9739 | NM_014712; XM_006721106; XM_024450499; XM_005255723; XM_017023909 |
| EMD | 2010 | XM_024452349; NM_000117 |
| ADM2 | 79924 | NM_001369882; NM_001253845; NM_024866 |
| F2RL3 | 9002 | NM_003950; XM_005260139 |
| PSCA | 8000 | NR_033343; NM_005672 |
| CES3 | 23491 | NM_001185176; NM_001185177; NM_024922; NM_012122 |
| NOX1 | 27035 | NM_007052; NM_013955; XM_017029407; NM_001271815; NM_013954 |
| APIP | 51074 | XM_011520154; NM_015957; XM_017017875 |
| HARS2 | 23438 | NM_001363535; NM_001278731; NM_012208; NM_001278732; NM_001363536 |
| C12orf10 | 60314 | NM_021640 |
| SOX18 | 54345 | NM_018419 |
| MYO7A | 4647 | XM_011545044; XR_001747889; XM_017017783; NM_001369365; XM_011545046; XM_017017782; XM_017017786; NM_000260; XM_011545050; XM_017017788; XM_017017781; XR_001747886; XM_017017787; XR_001747885; NM_001127180; NM_001127179; XM_017017778; XM_017017785; XM_017017784; XM_017017779; XM_017017780; XR_001747887; XR_001747888 |
| SLC26A2 | 1836 | XM_017009191; NM_000112 |
| PNPLA6 | 10908 | NM_001166114; NM_006702; NM_001166112; NM_001166113; NM_001166111 |
| FAM3A | 60343 | XM_005274716; XM_005277879; XM_017029701; XM_024452419; NM_001171134; NM_001282311; XM_024452416; XR_002958798; XR_002958799; XR_002958803; NM_001171132; NM_001282312; NM_021806; XM_024452415; XR_002958801; NM_001363822; XR_002958800; XM_006724832; XM_006724833; XM_024452420; NM_001171133; XM_017029700; XM_017029702; XM_024452418; XR_002958802 |
| SLC29A1 | 2030 | XM_005248879; XM_005248882; NM_001078175; NM_001078177; NM_001078174; NM_001304466; NM_001304463; NM_004955; XM_005248880; XM_005248878; XM_011514341; NM_001372327; XM_024446348; NM_001304462; NM_001304465; XM_005248881; XM_005248876; NM_001078176 |
| ZNF205 | 7755 | NM_001042428; NM_001278158; XM_005255558; NM_003456. |

* * * * *